(12) United States Patent
Allen et al.

(10) Patent No.: US 9,174,992 B2
(45) Date of Patent: Nov. 3, 2015

(54) HETEROBICYCLIC COMPOUNDS

(71) Applicant: Amgen Inc., Thousand Oaks, CA (US)

(72) Inventors: Jennifer R. Allen, Newbury Park, CA (US); Albert Amegadzie, Moorpark, CA (US); Kristin L. Andrews, Thousand Oaks, CA (US); James Brown, Moorpark, CA (US); Jian J. Chen, Camarillo, CA (US); Ning Chen, Thousand Oaks, CA (US); Essa Hu Harrington, Camarillo, CA (US); Qingyian Liu, Camarillo, CA (US); Thomas T. Nguyen, Newbury Park, CA (US); Alexander J. Pickrell, Westlake Village, CA (US); Wenyuan Qian, Camarillo, CA (US); Shannon Rumfelt, Camarillo, CA (US); Robert M. Rzasa, Ventura, CA (US); Chester Chenguang Yuan, Newbury Park, CA (US); Wenge Zhong, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 72 days.

(21) Appl. No.: 13/780,557

(22) Filed: Feb. 28, 2013

(65) Prior Publication Data

US 2013/0225552 A1    Aug. 29, 2013

Related U.S. Application Data

(60) Provisional application No. 61/605,148, filed on Feb. 29, 2012.

(51) Int. Cl.
| | |
|---|---|
| *C07D 419/14* | (2006.01) |
| *C07D 419/12* | (2006.01) |
| *C07D 487/04* | (2006.01) |
| *C07D 498/04* | (2006.01) |
| *C07D 473/00* | (2006.01) |
| *C07D 471/04* | (2006.01) |
| *C07D 513/04* | (2006.01) |
| *C07D 417/12* | (2006.01) |
| *C07D 473/30* | (2006.01) |
| *C07D 473/34* | (2006.01) |
| *C07D 473/40* | (2006.01) |
| *C07D 519/00* | (2006.01) |

(52) U.S. Cl.
CPC ............ *C07D 487/04* (2013.01); *C07D 417/12* (2013.01); *C07D 471/04* (2013.01); *C07D 473/00* (2013.01); *C07D 473/30* (2013.01); *C07D 473/34* (2013.01); *C07D 473/40* (2013.01); *C07D 498/04* (2013.01); *C07D 513/04* (2013.01); *C07D 519/00* (2013.01)

(58) Field of Classification Search
CPC ............................. C07D 419/12; C07D 419/14
USPC .................... 514/210.18, 299–303, 311–314; 544/233, 235, 238–241, 405; 546/123
See application file for complete search history.

(56) References Cited

U.S. PATENT DOCUMENTS

| | | | |
|---|---|---|---|
| 4,107,288 A | 8/1978 | Oppenheim et al. | |
| 5,145,684 A | 9/1992 | Liversidge et al. | |
| 6,699,880 B1 * | 3/2004 | Yamakawa et al. ............ | 514/316 |
| 2003/0069249 A1 * | 4/2003 | Sun et al. ....................... | 514/248 |
| 2006/0019975 A1 | 1/2006 | Humphrey et al. | |

FOREIGN PATENT DOCUMENTS

| | | |
|---|---|---|
| EP | 0039051 A2 | 11/1981 |
| EP | 1849781 A1 | 10/2007 |
| EP | 2390254 A1 | 11/2011 |
| JP | 2012020973 A | 2/2012 |
| TW | 200848047 A | 12/2008 |
| WO | 9613262 A | 5/1996 |
| WO | 2004074278 A1 | 9/2004 |
| WO | 2005012485 | 2/2005 |
| WO | 2006114706 A1 | 11/2006 |
| WO | 2007085954 A2 | 8/2007 |
| WO | 2007100880 A1 | 9/2007 |
| WO | 2008137436 A1 | 11/2008 |
| WO | 2010009207 A1 | 1/2010 |

(Continued)

OTHER PUBLICATIONS

Berge et. al,; "Pharmaceutical Salts"; Journal of Pharmaceutical Sciences; 66; 1; 1-19; 1977.
Bundgaard et. al.; "Prodrug forms for the sulfonamide group. I. Evaluation of N-acyl derivatives, N-sulfonylamidines, N-sulfonylsulfilimines and sulfonylureas as possible prodrug derivatives"; International Journal of Pharmaceutics; 37; 87-95; 1987.
Bundgaard et. al.; "A Novel Solution-Stable, Water-Soluble Prodrug Type for Drugs Containing a Hydroxyl or NH Acidic Group" Journal of Medicinal Chemistry 32; 12; 2503-2507; 1989.
Fujishige et. al.;"Cloning and Characterization of a Novel Human Phosphodiesterase That Hydrolyzes Both cAMP and cGMP (PDE10A)"; The Journal of Biological Chemistry; 274; 26; 18438-18445; 1999.

(Continued)

*Primary Examiner* — Jeffrey S Lundgren
*Assistant Examiner* — Chris Simmons
(74) *Attorney, Agent, or Firm* — Elsa D. Lemoine

(57) ABSTRACT

Heterobicyclic compounds of Formula (I):

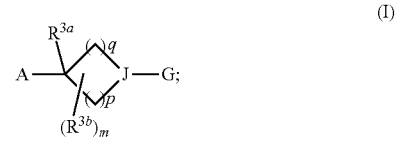

or a pharmaceutically-acceptable salt, tautomer, or stereoisomer thereof, as defined in the specification, and compositions containing them, and processes for preparing such compounds. Provided herein also are methods of treating disorders or diseases treatable by inhibition of PDE10, such as obesity, non-insulin dependent diabetes, schizophrenia, bipolar disorder, obsessive-compulsive disorder, Huntington's Disease, and the like.

17 Claims, No Drawings

(56) References Cited

FOREIGN PATENT DOCUMENTS

| WO | 2011029915 A1 | 3/2011 |
|----|---------------|--------|
| WO | 2011143129 A1 | 11/2011 |
| WO | 2011143365 A1 | 11/2011 |
| WO | 2011145718 A1 | 11/2011 |
| WO | 2012022045 A1 | 2/2012 |
| WO | 2012103806 A1 | 8/2012 |

OTHER PUBLICATIONS

Giedd et. al.; "MRI Assessment of Children With Obsessive-Compulsive Disorder or Tics associated with Streptococcal Infection"; Am J Psych; 157; 281-283; 2000.

Loughney et. al.; "Isolation and characterization of PDE10A, a novel human 3', 5'-cyclic nucleotide phosphodiesterase"; Gene; 234; 109-117; 1999.

Obeso et. al.; "The origin of motor fluctuations in Parkinson's disease"; Neurology; 62;S1; S17-S30; 2004.

Radchenko et. al.; "Cyclobutane-Derived Diamines: Synthesis and Molecular Structure"; Journal of Organic Chemistry; 75; 5941-5952; 2010.

Saxena et. al.; "Neuroimaging and frontal-subcortical circuitry in OCD"; British Journal of Psychiatry; 173; Suppl. 34; 26-37; 1998.

Soderling et. al.; "Isolation and characterization of a dual-substrate phosphodiesterase gene family:PDE10A"; Proc. Natl. Acad. Sci. USA; 96; 7071-7076; 1999.

Svensson et. al.; The Design and Bioactivation of Presystemically Stable Prodrugs; Drug Metabolism Reviews, 19 (2) 165-194; 1988.

International Search Report; PCT/US2013/028436.

* cited by examiner

HETEROBICYCLIC COMPOUNDS

CROSS-REFERENCE TO RELATED APPLICATIONS

This application claims the benefit of U.S. Provisional Application No. 61/605,148 filed Feb. 29, 2012 which is hereby incorporated by reference.

FIELD OF THE INVENTION

Provided herein are certain heterobicyclic compounds that are PDE10 inhibitors, pharmaceutical compositions containing such compounds, and processes for preparing such compounds. Provided herein also are methods of treating disorders or diseases treatable by inhibition of PDE10, such as obesity, non-insulin dependent diabetes, schizophrenia, bipolar disorder, obsessive-compulsive disorder, and the like.

BACKGROUND OF THE INVENTION

Neurotransmitters and hormones, as well as other types of extracellular signals such as light and odors, create intracellular signals by altering the amounts of cyclic nucleotide monophosphates (cAMP and cGMP) within cells. These intracellular messengers alter the functions of many intracellular proteins. Cyclic AMP regulates the activity of cAMP-dependent protein kinase (PKA). PKA phosphorylates and regulates the function of many types of proteins, including ion channels, enzymes, and transcription factors. Downstream mediators of cGMP signaling also include kinases and ion channels. In addition to actions mediated by kinases, cAMP and cGMP bind directly to some cellular proteins and directly regulate their activities.

Cyclic nucleotide monophosphates are produced from the actions of adenylyl cyclase and guanylyl cyclase, which convert ATP to cAMP and GTP to cGMP. Extracellular signals, often through the actions of G protein-coupled receptors, regulate the activities of the cyclases. Alternatively, the amount of cAMP and cGMP may be altered by regulating the activities of the enzymes that degrade cyclic nucleotide monophosphates. Cell homeostasis is maintained by the rapid degradation of cyclic nucleotide mono-phosphates after stimulus-induced increases. The enzymes that degrade cyclic nucleotide monophosphates are called 3',5'-cyclic nucleotide-specific phosphodiesterases (PDEs).

Eleven PDE gene families (PDE1-PDE11) have been identified based on their distinct amino acid sequences, catalytic and regulatory characteristics, and sensitivity to small molecule inhibitors. These families are coded for by 21 genes; and further multiple splice variants are transcribed from many of these genes. Expression patterns of each of the gene families are distinct. PDEs differ with respect to their affinity for cAMP and cGMP. Activities of different PDEs are regulated by different signals. For example, PDE1 is stimulated by $Ca^{2+}$/calmodulin. PDE2 activity is stimulated by cGMP. PDE3 is inhibited by cGMP. PDE4 is cAMP specific and is specifically inhibited by rolipram. PDE5 is cGMP-specific. PDE6 is expressed in retina.

PDE10 sequences were identified by using bioinformatics and sequence information from other PDE gene families (Fujishige et al., *J. Biol. Chem.* 274:18438-18445, 1999; Loughney et al., *Gene* 234:109-117, 1999; Soderling et al., *Proc. Natl. Acad. Sci. USA* 96:7071-7076, 1999). The PDE10 gene family is distinguished based on its amino acid sequence, functional properties and tissue distribution. The human PDE10 gene is large, over 200 kb, with up to 24 exons coding for each of the splice variants. The amino acid sequence is characterized by two GAF domains (which bind cGMP), a catalytic region, and alternatively spliced N and C termini. Numerous splice variants are possible because at least three alternative exons encode N termini and two exons encode C-termini. PDE10A1 is a 779 amino acid protein that hydrolyzes both cAMP and cGMP. The $K_m$ values for cAMP and cGMP are 0.05 and 3.0 micromolar, respectively. In addition to human variants, several variants with high homology have been isolated from both rat and mouse tissues and sequence banks.

PDE10 RNA transcripts were initially detected in human testis and brain. Subsequent immunohistochemical analysis revealed that the highest levels of PDE10 are expressed in the basal ganglia. Specifically, striatal neurons in the olfactory tubercle, caudate nucleus and nucleus accumbens are enriched in PDE10. Western blots did not reveal the expression of PDE10 in other brain tissues, although immunoprecipitation of the PDE10 complex was possible in hippocampal and cortical tissues. This suggests that the expression level of PDE10 in these other tissues is 100-fold less than in striatal neurons. Expression in hippocampus is limited to the cell bodies, whereas PDE10 is expressed in terminals, dendrites and axons of striatal neurons.

The tissue distribution of PDE10 indicates that PDE10 inhibitors can be used to raise levels of cAMP and/or cGMP within cells that express the PDE10 enzyme, for example, in neurons that comprise the basal ganglia and therefore would be useful in treating a variety of neuropsychiatric conditions involving the basal ganglia such as obesity, non-insulin dependent diabetes, schizophrenia, bipolar disorder, obsessive compulsive disorder, and the like.

Existing therapeutics for schizophrenia are efficacious only at treating positive symptoms of the disease. Negative symptoms, including flattened affect, social withdrawal as well as cognitive deficits are not ameliorated by current medications, which primarily target the mesolimbic dopamine system. Therefore, novel treatments for schizophrenia are needed to specifically improve negative symptoms and cognitive deficits associated with the disease. The present invention fulfills this need and related needs.

SUMMARY OF THE INVENTION

The present invention comprises a new class of heterobicyclic compounds useful in the treatment of diseases, such as PDE10-mediated diseases and other maladies, such as schizophrenia, bipolar disorder, or obsessive-compulsive disorder. Accordingly, the invention also comprises pharmaceutical compositions comprising the compounds, methods for the treatment of PDE10-mediated diseases and other maladies, such as schizophrenia, bipolar disorder, or obsessive-compulsive disorder, using the compounds and compositions of the invention, and intermediates and processes useful for the preparation of the compounds of the invention.

In one aspect, this invention is directed to a compound of Formula (I):

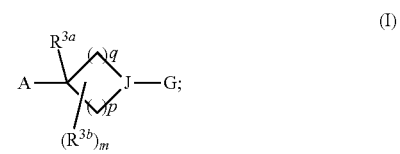

or a pharmaceutically-acceptable salt, tautomer, or stereoisomer thereof, wherein:

each p and q is independently 0, 1, 2, 3, 4, 5, or 6; wherein the sum of p and q is 1, 2, 3, 4, 5, or 6;

m is 0, 1, 2, 3, or 4;

A is a 9- to 10-membered heterocyclic ring having the formula:

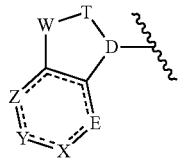

wherein the group —W-T-D< is selected from the group consisting of:

—N=CR$^5$—N<; NR$^7$—N=C<; —NR$^7$—(C=O)—N<; NR$^7$—CR$^6$R$^7$—(C=O)—N<; —NR$^7$—(SO$_2$)—N<; —CR$^5$=CR$^5$—N<; —CR$^8$=N—N<; —CR$^6$R$^7$—(C=O)—N<; —CR$^6$R$^7$—NR$^7$—(C=O)—N<; —CR$^6$R$^7$—O—(C=O)—N<; —CR$^6$R$^7$—(SO$_2$)—N<; —O—(C=O)—N<; and —O—CR$^6$R$^7$—(C=O)—N<;

J is independently N or CR$^{3c}$; wherein each E, X, Y, and Z is independently N or CR$^4$; wherein 0, 1, 2, or 3 of E, X, Y, and Z are N;

(a) when J is N, then G is R$^1$ or (C=O)R$^1$; wherein R$^1$ is carbon-linked;

(b) when J is CR$^{3c}$; then G is R$^1$, —NR$^1$R$^2$; —NH(C=O)R$^1$; —OR$^1$, —(C=O)R$^1$; or —CHR$^1$R$^2$; wherein R$^1$ is carbon-linked or nitrogen-linked;

R$^1$ is a carbon-linked or nitrogen-linked saturated, partially-saturated or unsaturated 5- or 6-membered monocyclic ring, or a saturated, partially-saturated or unsaturated 9- or 10-membered bicyclic ring, wherein each said ring contains 0, 1, 2, 3, or 4 N atoms and 0, 1, or 2 O or S atoms; wherein each $^{R1}$ is independently substituted by 0, 1, 2 or 3$^{R9}$ groups;

R$^2$ is independently H, OH, C$_{1-4}$alk, a carbon-linked or nitrogen-linked saturated, partially-saturated or unsaturated 5- or 6-membered monocyclic ring, wherein each said ring contains 0, 1, 2, 3, or 4 N atoms and 0, 1, or 2 O or S atoms; wherein each R$^2$C$_{1-4}$alk or monocyclic ring is independently substituted by 0, 1, 2 or 3 R$^9$ groups;

each R$^{3a}$ and R$^{3c}$ is independently H, F, OH, C$_{1-4}$alk, or C$_{1-4}$haloalk; R$^{3b}$ is independently F, Cl, Br, CN, OH, OC$_{1-4}$alk, C$_{1-4}$alk, C$_{1-4}$haloalk, or oxo;

R$^4$ is halo, R$^{4a}$, —SR$^{4a}$, —OR$^{4a}$, —NHR$^{4a}$, or —N(C$_{1-4}$alk)R$^{4a}$, wherein —R$^{4a}$ is H, C$_{1-4}$alk, a saturated, partially-saturated or unsaturated 3-, 4-, 5- or 6-membered monocyclic ring, wherein each said ring contains 0, 1, 2, 3, or 4 N atoms and 0, 1, or 2 O or S atoms; wherein each R$^4$C$_{1-4}$alk or monocyclic ring is independently substituted by 0, 1, 2 or 3 R$^9$ groups;

each R$^5$ is independently R$^{5a}$, —OR$^{5b}$, —NHR$^{5a}$, or —N(C$_{1-4}$alk)R$^{5a}$, wherein R$^{5a}$ is H, C$_{1-4}$alk, a saturated, partially-saturated or unsaturated 3-, 4-, 5- or 6-membered monocyclic ring, wherein each said ring contains 0, 1, 2, 3, or 4 N atoms and 0, 1, or 2 O or S atoms; R$^{5b}$ is C$_{1-4}$alk, a saturated, partially-saturated or unsaturated 3-, 4-, 5- or 6-membered monocyclic ring, wherein each said ring contains 0, 1, 2, 3, or 4 N atoms and 0, 1, or 2 O or S atoms; wherein each R$^5$C$_{1-4}$alk or monocyclic ring is independently substituted by 0, 1, 2 or 3 R$^9$ groups;

each R$^6$ and R$^7$ is independently H, halo, OH, C$_{1-4}$alk, OC$_{1-4}$alk, a saturated, partially-saturated or unsaturated 3-, 4-, 5- or 6-membered monocyclic ring, wherein each said ring contains 0, 1, 2, 3, or 4 N atoms and 0, 1, or 2 O or S atoms; wherein each R$^6$ and R$^7$ C$_{1-4}$alk or monocyclic ring is independently substituted by 0, 1, 2 or 3 R$^9$ groups;

or R$^6$ and R$^7$ may optionally form a saturated or partially-saturated 3-, 4-, 5- or 6-membered monocyclic ring, wherein each said ring contains 0, 1, 2, 3, or 4 N atoms and 0, 1, or 2 O or S atoms; wherein said monocyclic ring is independently substituted by 0, 1, 2 or 3 R$^9$ groups;

R$^8$ is R$^{8a}$, —O—R$^{8a}$, —NHR$^{8a}$, or —N(C$_{1-4}$alk)R$^{8a}$, wherein R$^{8a}$ is H, C$_{1-4}$alk, a saturated, partially-saturated or unsaturated 3-, 4-, 5- or 6-membered monocyclic ring, wherein each said ring contains 0, 1, 2, 3, or 4 N atoms and 0, 1, or 2 O or S atoms; wherein each R$^8$C$_{1-14}$alk or monocyclic ring is independently substituted by 0, 1, 2 or 3 R$^9$ groups;

R$^9$ is independently F, Cl, Br, C$_{1-6}$alk, C$_{1-4}$haloalk, —OR$^a$, OR$^c$, —OC$_{1-4}$haloalk, CN, R$^b$, R$^c$, —C(=O)R$^b$, —C(=O)R$^c$, —C(=O)OR$^a$, —C(=O)NR$^a$R$^a$, —C(=O)NR$^a$R$^c$, —C(=NR$^a$)NR$^a$R$^a$, —OC(=O)R$^b$, —OC(=O)NR$^a$R$^a$, —OC$_{1-6}$alkNR$^a$R$^a$, —OC$_{1-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R)S(=O)$_2$NR$^a$R$^a$, —NR$^a$C$_{1-6}$alkNR$^a$R$^a$, —NR$^a$C$_{1-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo;

R$^{10}$ is halo, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{1-6}$alkNR$^a$R$^a$, —OC$_{1-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{1-6}$alkNR$^a$R$^a$, —NR$^a$C$_{1-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo;

R$^a$ is independently H or R$^b$;

R$^b$ is independently phenyl, benzyl, or C$_{1-6}$alk, wherein said phenyl, benzyl, and C$_{1-6}$alk are substituted by 0, 1, 2 or 3 substituents which are C$_{1-4}$alk, C$_{1-3}$haloalk, —OH, —OC$_{1-4}$alk, —NH$_2$, —NHC$_{1-4}$alk, —OC(=O)C$_{1-4}$alk, or —N(C$_{1-4}$alk)C$_{1-4}$alk; and R$^c$ is independently a carbon-linked or nitrogen-linked saturated, partially-saturated or unsaturated 3-, 4-, 5-, 6-, or 7-membered monocyclic ring or a saturated, partially-saturated or unsaturated 6-, 7-, 8-, 9-, 10-, 11-, or 12-membered bicyclic ring, said ring contains 0, 1, 2, 3, or 4 N atoms and 0, 1, or 2 atoms which are O or S; R$^c$ is independently substituted by 0, 1, 2 or 3 R$^{10}$ groups.

In one embodiment of compound of Formula (I) has the structure shown below:

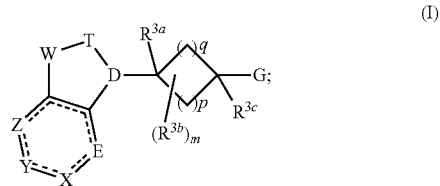

(I)

wherein E, X, Y, Z, G, the group —W-T-D<, R$^{3a}$, R$^{3b}$, R$^{3c}$, m, p and q are as defined above.

In another embodiment, the compound of Formula (I) has the structure shown below:

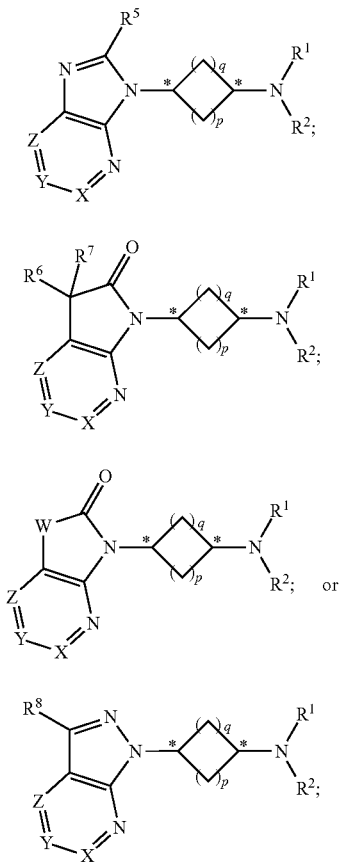

(IA)

(IB)

(IC)

(ID)

wherein relative stereochemistry at *C is cis or trans.

In another embodiment, the group

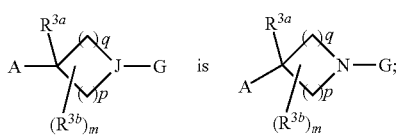

and the sum of p and q is 2 or 4.

In another embodiment, the group

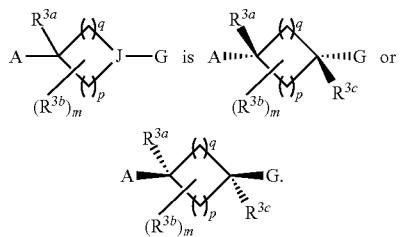

In another embodiment, the group

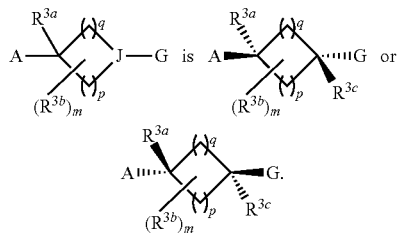

In another embodiment, E, X, Y, and Z is independently N or $CR^4$; wherein 1 or 2 of E, X, Y, and Z are N; selected from the group consisting of

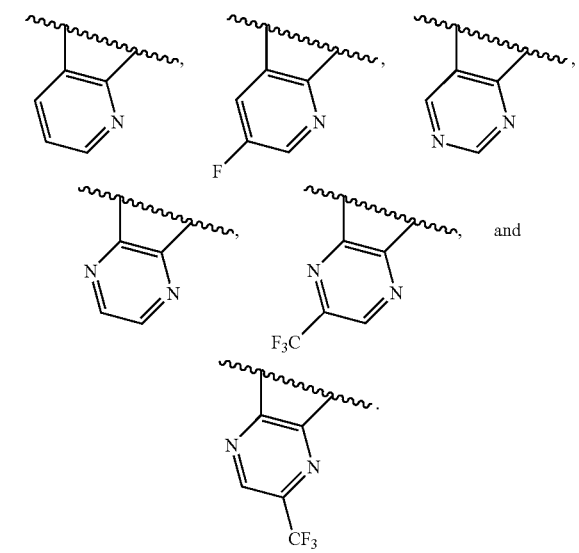

and

In another embodiment, the group —W-T-D< is selected from the group consisting of —N=$CR^5$—N<; $NR^7$—N=C<; —$NR^7$—(C=O)—N<; $NR^7$—$CR^6R^7$—(C=O)—N<; and —$NR^7$—($SO_2$)—N<.

In another embodiment, the group —W-T-D< is selected from the group consisting of —$CR^5$=$CR^5$—N<; —$CR^8$=N—N<; —$CR^6R^7$—(C=O)—N<; —$CR^6R^7$—$NR^7$—(C=O)—N<; —$CR^6R^7$—O—(C=O)—N<; and —$CR^6R^7$—($SO_2$)—N<.

In another embodiment, the group —W-T-D< is selected from the group consisting of —O—(C=O)—N<; and —O—$CR^6R^7$—(C=O)—N<.

In another embodiment, the group —W-T-D< is —$CR^5$=$CR^5$—N<.

In another embodiment, the group —W-T-D< is —N=$CR^5$—N<.

In another embodiment, J is $CR^3$; and each $R^5$ is independently H, $C_{1-4}$alk, —O—$C_{1-4}$alk, or a saturated 3-, 4-, 5- or 6-membered monocyclic ring, wherein each said ring contains 0, 1, 2, 3, or 4 N atoms and 0, 1, or 2 O or S atoms; wherein said monocyclic ring is independently substituted by 0, 1, 2 or 3 $R^9$ groups.

In another embodiment, J is N; and each $R^5$ is independently H, $C_{1-4}$alk, —O—$C_{2-4}$alk, or a saturated 3-, 4-, 5- or 6-membered monocyclic ring, wherein each said ring contains 0, 1, 2, 3, or 4 N atoms and 0, 1, or 2 O or S atoms; wherein said monocyclic ring is independently substituted by 0, 1, 2 or 3 $R^9$ groups.

In another embodiment, the group —W-T-D< is —CR⁶R⁷—(C=O)—N<.

In another embodiment, each R⁶ and R⁷ is independently R⁶ and R⁷ is independently H, halo, OH, O—C₁₋₄alk, C₁₋₄alk or a saturated 3-, 4-, 5- or 6-membered monocyclic ring; or unsaturated 5- or 6-membered monocyclic ring; wherein each said ring contains 0, 1, or 2 N atoms and 0, 1, or 2 O or S atoms; wherein said R⁷C₁₋₄alk or monocyclic ring is independently substituted by 0, 1, 2 or 3 R⁹ groups.

In another embodiment, each R⁶ and R⁷ is independently H, OH, F, methyl, ethyl, propyl, isopropyl, cyclopropyl, phenyl or methoxy. Preferably, each R⁶ and R⁷ is independently H, F, or methyl.

In another embodiment, R⁶ and R⁷ form a saturated 3-, 4-, 5- or 6-membered monocyclic ring, wherein each said ring contains 0, 1, 2, 3, or 4 N atoms and 0, 1, or 2 O or S atoms; wherein said monocyclic ring is independently substituted by 0, 1, 2 or 3 R⁹ groups.

In another embodiment, the group —W-T-D< is —NR⁷—(C=O)—N<.

In another embodiment, R⁷ is H, C₁₋₄alk or a saturated 3-, 4-, 5- or 6-membered monocyclic ring; or unsaturated 5- or 6-membered monocyclic ring; wherein each said ring contains 0, 1, or 2 N atoms and 0, 1, or 2 O or S atoms; wherein said R⁷C₁₋₄alk or monocyclic ring is independently substituted by 0, 1, 2 or 3 R⁹ groups.

In another embodiment, the group —W-T-D< is —O—(C=O)—N<.

In another embodiment, the group —W-T-D< is NR⁷—N—C<.

In another embodiment, the group —W-T-D< is —CR⁸=N—N<.

In another embodiment, R⁸ is independently H, C₁₋₄alk, —OC₁₋₄alk, —NH(C₁₋₄alk), —N(C₁₋₄alk)(C₁₋₄alk), or a saturated 3-, 4-, 5- or 6-membered monocyclic ring; or unsaturated 5- or 6-membered monocyclic ring; wherein each said ring contains 0, 1, or 2 N atoms and 0, 1, or 2 O or S atoms; wherein said R⁸C₁₋₄alk or monocyclic ring is independently substituted by 0, 1, 2 or 3 R⁹ groups.

In another embodiment, R⁸ is NH₂ or CF₃.

In another embodiment, the group —W-T-D< is —NR⁷—CR⁶R⁷—(C=O)—N<.

In another embodiment, the group —W-T-D< is —O—CR⁶R⁷—(C=O)—N<.

In another embodiment, the group —W-T-D< is —CR⁶R⁷—O—(C=O)—N<,

In another embodiment, the group —W-T-D< is —CR⁶R⁷—NR⁷—(C=O)—N<.

In another embodiment, the group —W-T-D< is —CR⁶R⁷—(SO₂)—N<.

In another embodiment, the group —W-T-D< is —NR⁷—(SO₂)—N<.

In another embodiment, each R⁵ and R⁷ is cyclopropyl.
In another embodiment, the sum of p and q is 1.
In another embodiment, the sum of p and q is 2.
In another embodiment, the sum of p and q is 3.
In another embodiment, the sum of p and q is 4.
In another embodiment, J is N.
In another embodiment, J is N and G is R¹.
In another embodiment, J is CR³ᶜ, and G is R¹, —NR¹R²; —NH(C=O)R¹; or —OR¹.
In another embodiment, the ring containing p and q is piperidinyl.
In another embodiment, the ring containing p and q is azetidinyl.
In another embodiment, the group

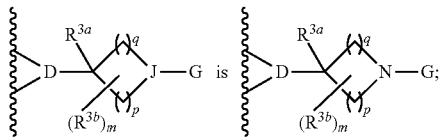

and the sum of p and q is 2 or 4.

In another embodiment, the group

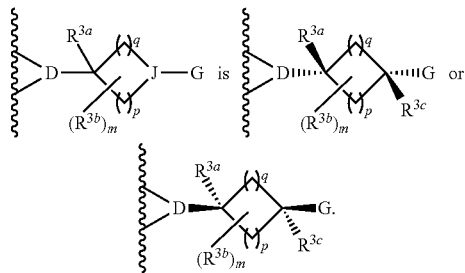

In another embodiment, the group

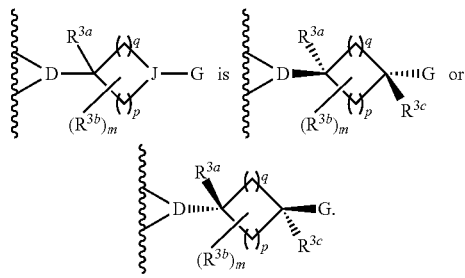

In another embodiment, R¹ is a saturated, partially-saturated or unsaturated 5- or 6-membered monocyclic ring; wherein each said ring contains 0, 1, 2, 3, or 4 N atoms and 0, 1, or 2 O or S atoms; wherein each R¹ is independently substituted by 0, 1, 2 or 3 R⁹ groups.

In another embodiment, R¹ is unsaturated 6-membered monocyclic ring; wherein each said ring contains 0, 1, 2, 3, or 4 N atoms and 0, 1, or 2 O or S atoms; wherein each R¹ is independently substituted by 0, 1, 2 or 3 R⁹ groups.

In another embodiment, R¹ is a saturated, partially-saturated or unsaturated 9- or 10-membered bicyclic ring, wherein each said ring contains 0, 1, 2, 3, or 4 N atoms and 0, 1, or or S atoms; wherein each R¹ is independently substituted by 0, 1, 2 or 3 R⁹ groups.

In another embodiment, R¹ is unsaturated 9- or 10-membered bicyclic ring, wherein each said ring contains 0, 1, 2, 3, or 4 N atoms and 0, 1, or 2 O or S atoms; wherein each R¹ is independently substituted by 0, 1, 2 or 3 R⁹ groups.

In another embodiment, R¹ is phenyl, oxazolyl, pyridothiazolyl, pyridooxazolyl, pyridimidazolyl, pyrazimidazolyl, pyrimidimidazolyl, pyridinyl, pyrazinyl, pyrimidinyl, thiazolyl, pyrazolyl, triazolyl, imidazolyl, benzimidazolyl, benzoxazolyl, benzthiazolyl, quinolinyl, isoquinolinyl, quinazolinyl, quinaxolinyl, naphthyridinyl, pyridimidazolyl, pyridopyrazolyl, or thiazolo[5,4-b]pyridinyl.

In another embodiment, R¹ is thiazolyl, oxazolyl, benzoxazolyl, quinazolinyl, quinolinyl, pyridinyl, benzimidazolyl, benzthiazolyl, 1,5-naphthyridinyl, 1,6-naphthyridinyl, 1,7-naphthyridinyl, or 1,8-naphthyridinyl.

In another embodiment, $R^1$ is:

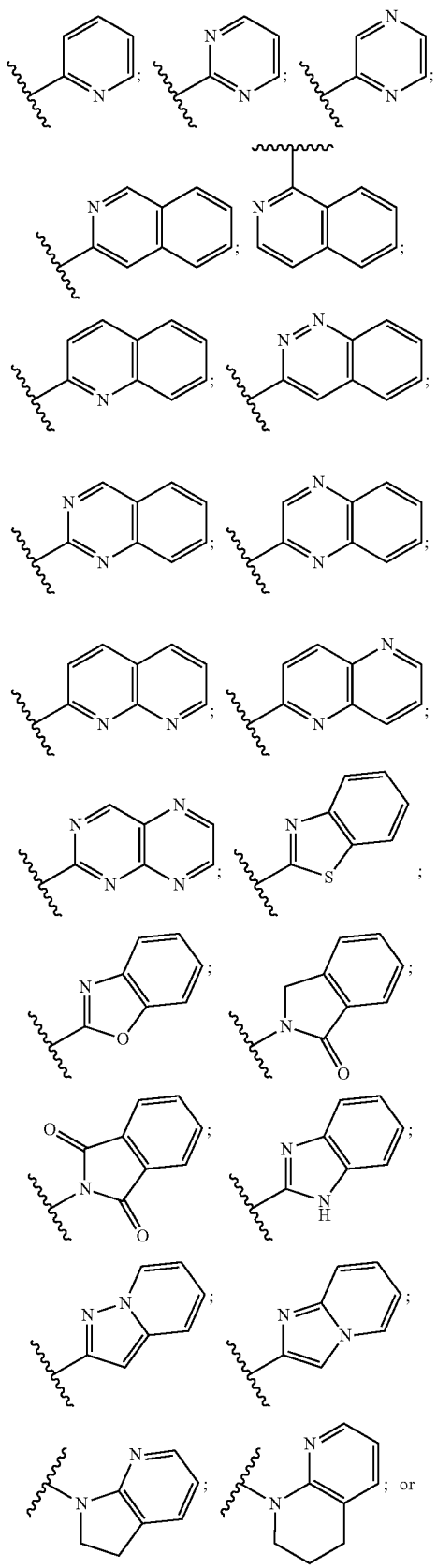

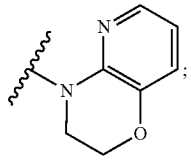

wherein each $R^1$ is independently substituted by 0, 1, 2 or 3 $R^9$ groups.

In another embodiment, $R^2$ is H, OH, or methyl. Preferably, $R^2$ is H.

In another embodiment, $R^2$ is pyridinyl.

In another embodiment, each $R^{3a}$ and $R^{3b}$ is H, OH, F, or CN.

In another embodiment, m is 0.

In another embodiment, $R^{3a}$ and $R^{3c}$ is H and m is 0.

In another embodiment, $R^9$ is F, Br, Cl, methyl, ethyl, —OCH$_2$F, —OCHF$_2$, —OCF$_3$, CN, CF$_3$, methoxy, —C(=O)CH$_3$, —C(=O)—NH—CH$_3$, —NH—C(=O)CH$_3$, cyclopropyl, or phenyl.

In another embodiment, G is $R^1$.

In another embodiment, J is —CH or —CCH$_3$ and G is —NR$^1$R$^2$.

In another embodiment, J is —CH or —CCH$_3$ and G is —NR$^1$R$^2$; wherein $R^1$ is unsaturated 9- or 10-membered bicyclic ring, wherein each said ring contains 0, 1, 2, 3, or 4 N atoms and 0, 1, or 2 O or S atoms; wherein each $R^1$ is independently substituted by 0, 1, 2 or 3 $R^9$ groups, and $R^2$ is H.

In another embodiment, J is —CH or —CCH$_3$ and G is —NR$^1$R$^2$; wherein $R^1$ is benzimidazolyl, benzoxazolyl, benzthiazolyl, and $R^2$ is H.

In another embodiment, J is —CH or —CCH$_3$ and G is —NR$^1$R$^2$; wherein $R^1$ is quinolinyl, isoquinolinyl, quinazolinyl, quinaxolinyl, naphthyridinyl, pyridimidazolyl, pyridopyrazolyl, or thiazolo[5,4-b]pyridinyl and $R^2$ is H.

In another embodiment of compound of Formula (I), the following compounds are excluded:

(1H-Benzo[d]imidazol-2-yl)(4-(2-methoxy-3H-imidazo[4,5-b]pyridine-3-yl)piperidin-1-yl)methanone;

2-(4-(2-Methoxy-3H-imidazo[4,5-b]pyridin-3-yl)piperidin-1-yl)benzo[d]thiazole;

Benzo[d]thiazol-2-yl(4-(2-methoxy-3H-imidazo[4,5-b]pyridine-3-yl)piperidin-1-yl)methanone;

3-(1-(1-H-Benzo[d]imidazol-2-yl)piperidin-4-yl)-2-methoxy-3H-imidazo[4,5-b]pyridine;

2-(3-(2-Methoxy-3H-imidazo[4,5-b]pyridin-3-yl)azetidin-1-yl)quinoline;

2-Methoxy-3-(1-(4-methylpyrimidin-2-yl)azetidin-3-yl)-3H-imidazo[4,5-b]pyridine;

2-Methoxy-3-(1-(5-methylpyrimidin-2-yl)azetidin-3-yl)-3H-imidazo[4,5-b]pyridine;

2-(3-(2-Methoxy-3H-imidazo[4,5-b]pyridin-3-yl)azetidin-1-yl)quinazoline;

2-Methoxy-3-(1-(4-(6-methylpyridin-3-yl)pyrimidin-2-yl)azetidin-3-yl)-3H-imidazo[4,5-b]pyridine;

2-(3-(2-Methoxy-3H-imidazo[4,5-b]pyridin-3-yl)azetidin-1-yl)benzo[d]thiazole;

3-(1H-benzo[d]imidazol-2-yl)azetidin-3-yl)-2-methoxy-3H-imidazo[4,5-b]pyridine;

N-(4-(2-methoxy-3H-imidazo[4,5-b]pyridin-3-yl)cyclohexyl)-1,3-benzothiazol-2-amine;

N-(4-(2-methoxy-3H-imidazo[4,5-b]pyridin-3-yl)cyclohexyl)-1H-benzimidazol-2-amine;

N-(3-(2-methoxy-3H-imidazo[4,5-b]pyridin-3-yl)cyclobutyl)-1,3-benzothiazol-2-amine;

1H-benzimidazol-2-yl(3-(2-methoxy-3H-imidazo[4,5-b]pyridin-3-yl)cyclobutyl)methanol;
N-(cis-3-(2-methoxy-3H-imidazo[4,5-b]pyridin-3-yl)cyclobutyl)-1,3-benzothiazol-2-amine;
N-(trans-3-(2-methoxy-3H-imidazo[4,5-b]pyridin-3-yl)cyclobutyl)-1,3-benzothiazol-2-amine; and
N-(trans-3-(2-methoxy-3H-imidazo[4,5-b]pyridin-3-yl)cyclobutyl)-3,4-dihydro-2-quinoxalinamine.

In a second aspect, this invention is directed to a pharmaceutical composition comprising a compound of Formula (I), a pharmaceutically acceptable salt, tautomer, or a stereoisomer thereof; as in any one of the preceding embodiments, and a pharmaceutically acceptable excipient.

In a third aspect, this invention is directed to a method of treating conditions that may be treated with PDE10 inhibitors comprising the step of administering a compound, or a pharmaceutically-acceptable salt thereof, as in any one of the preceding embodiments.

In one embodiment, in the method above, said condition is selected from the group consisting of psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

In one embodiment, in the method above, said condition is selected from the group consisting of schizophrenia, Huntington's disease, bipolar disorder, and obsessive-compulsive disorder.

In one embodiment, in the method above, said condition is schizophrenia.

In one embodiment, in the method above, said condition is Huntington's disease.

In another embodiment, in the method above, said compound of Formula (I), a pharmaceutically-acceptable salt, tautomer, or stereoisomer thereof, as in any one of the preceding embodiments, is administered in combination with another anti-psychotic agent. In one embodiment, the antipychotic agent is selected from the group consisting of Clozaril, Zyprexa, Risperidone, and Seroquel.

In a fourth aspect, this invention is directed to a method of making a compound of Formula (I), a pharmaceutically-acceptable salt, tautomer, or stereoisomer thereof, as in any one of the preceding embodiments.

In a fifth aspect, this invention is directed to said compound of Formula (I), a pharmaceutically-acceptable salt, tautomer, or stereoisomer thereof, as in any one of the preceding embodiments, selected from the group consisting of:
N-(trans-3-(2-ethyl-3H-imidazo[4,5-b]pyridin-3-yl)cyclobutyl)benzo[d]thiazol-2-amine;
N-(trans-3-(2-cyclopropyl-3H-imidazo[4,5-b]pyridin-3-yl)cyclobutyl)benzo[d]thiazol-2-amine;
N-(Trans-3-(2-cyclopropyl-3h-imidazo[4,5-b]pyridin-3-yl)cyclobutyl)-1,5-naphthyridin-2-amine;
N-(Trans-3-(2-cyclopropyl-3h-imidazo[4,5-b]pyridin-3-yl)cyclobutyl)thiazolo[5,4-b]pyridin-2-amine;
N-(Trans-3-(2-methoxy-3H-imidazo[4,5-b]pyridin-3-yl)cyclobutyl)benzo[d]thiazol-2-amine;
N-(Trans-3-(2-cyclopropyl-3h-imidazo[4,5-b]pyridin-3-yl)cyclobutyl)quinolin-2-amine;
N-(Trans-3-(2-cyclopropyl-3H-imidazo[4,5-b]pyridin-3-yl)cyclobutyl)-6-fluoroquinolin-2-amine;
N-(Trans-3-(2-cyclopropyl-3H-imidazo[4,5-b]pyridin-3-yl)cyclobutyl)quinazolin-2-amine;
N-(Cis-3-(2-methoxy-3H-imidazo[4,5-b]pyridin-3-yl)cyclobutyl)benzo[d]thiazol-2-amine;
N-(trans-3-(2-(trifluoromethyl)-3H-imidazo[4,5-b]pyridin-3-yl)cyclobutyl)benzo[d]thiazol-2-amine;
N-(Trans-3-(2-cyclopropyl-3h-imidazo[4,5-b]pyridin-3-yl)cyclobutyl)-1,8-naphthyridin-2-amine;
N-(Trans-3-(2-(trifluoromethyl)-3H-imidazo[4,5-b]pyridin-3-yl)cyclobutyl)quinazolin-2-amine;
N-(trans-3-(8-cyclopropyl-9H-purin-9-yl)cyclobutyl)quinazolin-2-amine;
N-(trans-3-(3H-imidazo[4,5-b]pyridin-3-yl)cyclobutyl)benzo[d]thiazol-2-amine;
N-(Trans-3-(2-cyclopropyl-3H-imidazo[4,5-b]pyridin-3-yl)cyclobutyl)benzo[d]oxazol-2-amine;
N-(Trans-3-(2-cyclopropyl-3h-imidazo[4,5-b]pyridin-3-yl)cyclobutyl)-1,7-naphthyridin-2-amine;
7-Chloro-N-(trans-3-(2-(tetrahydro-2H-pyran-4-yl)-3H-imidazo[4,5-b]pyridin-3-yl)cyclobutyl)quinoxalin-2-amine;
N-(Trans-3-(2-cyclopropyl-3H-imidazo[4,5-b]pyridin-3-yl)cyclobutyl)-1,7-naphthyridin-2-amine;
7-Chloro-N-(trans-3-(2-methoxy-3H-imidazo[4,5-b]pyridin-3-yl)cyclobutyl)quinoxalin-2-amine;
7-Chloro-N-(trans-3-(2-cyclopropyl-3H-imidazo[4,5-b]pyridin-3-yl)cyclobutyl)quinolin-2-amine;
N-(Trans-3-(6-chloro-9H-purin-9-yl)cyclobutyl)quinazolin-2-amine;
N-(Trans-3-(3H-imidazo[4,5-b]pyridin-3-yl)cyclobutyl)quinazolin-2-amine;
9-(Trans-3-(quinazolin-2-ylamino)cyclobutyl)-8-(trifluoromethyl)-9H-purin-6-ol;
N-(Trans-3-(6-morpholino-9H-purin-9-yl)cyclobutyl)quinazolin-2-amine;
Methyl 4-(9-(trans-3-(quinazolin-2-ylamino)cyclobutyl)-8-(trifluoromethyl)-9H-purin-6-yl)benzoate;
Methyl 4-(9-(trans-3-(quinazolin-2-ylamino)cyclobutyl)-9H-purin-6-yl)benzoate;
N-(Trans-3-(2-cyclopropyl-3H-imidazo[4,5-b]pyridin-3-yl)cyclobutyl)thiazolo[4,5-b]pyridin-2-amine;
7-Chloro-N-(trans-3-(2-methoxy-3H-imidazo[4,5-b]pyridin-3-yl)cyclobutyl)quinazolin-2-amine;
6-((trans-3-(3,3-dimethyl-2-oxo-2,3-dihydro-1H-pyrrolo[2,3-b]pyridin-1-yl)cyclobutyl)amino)-N-methylnicotinamide;
1-(trans-3-(benzo[d]thiazol-2-ylamino)cyclobutyl)-3,3-dimethyl-1H-pyrrolo[2,3-b]pyridin-2(3H)-one;
1'-(Trans-3-(benzo[d]thiazol-2-ylamino)cyclobutyl)spiro[cyclopropane-1,3'-pyrrolo[2,3-b]pyridin]-2'(1'H)-one;
1-(trans-3-((6-fluorobenzo[d]thiazol-2-yl)amino)cyclobutyl)-3,3-dimethyl-1H-pyrrolo[2,3-b]pyridin-2(3H)-one;
1'-(trans-3-(1,3-benzothiazol-2-ylamino)cyclobutyl)-5'-fluorospiro[cyclopropane-1,3'-pyrrolo[2,3-b]pyridin]-2'(1'H)-one;
5-(trans-3-(benzo[d]thiazol-2-ylamino)cyclobutyl)-7,7-dimethyl-5H-pyrrolo[2,3-b]pyrazin-6(7H)-one;
1'-(trans-3-(benzo[d]thiazol-2-ylamino)cyclobutyl)spiro[cyclobutane-1,3'-pyrrolo[2,3-b]pyridin]-2'(1'H)-one;
1'-(Trans-3-(benzo[d]thiazol-2-ylamino)cyclobutyl)spiro[cyclopentane-1,3'-pyrrolo[2,3-b]pyridin]-2'(1'H)-one;
1'-(Trans-3-(benzo[d]thiazol-2-ylamino)cyclobutyl)-2,3,5,6-tetrahydrospiro[pyran-4,3'-pyrrolo[2,3-b]pyridin]-2'(1'H)-one;
3,3-Dimethyl-1-trans-3-(5-methylpyridin-2-yl)amino)cyclobutyl-1H-pyrrolo[2,3-b]pyridin-2(3H)-one;
1-(Trans-3-((5-methoxypyridin-2-yl)amino)cyclobutyl)-3,3-dimethyl-1H-pyrrolo[2,3-b]pyridin-2(3H)-one;

1-(Trans-3-((5-bromopyridin-2-yl)amino)cyclobutyl)-3,3-dimethyl-1H-pyrrolo[2,3-b]pyridin-2(3H)-one;
1-(Trans-3-((5-cyclopropylpyridin-2-yl)amino)cyclobutyl)-3,3-dimethyl-1H-pyrrolo[2,3-b]pyridin-2(3H)-one;
1-(Trans-3-((5-chloropyridin-2-yl)amino)cyclobutyl)-3,3-dimethyl-1H-pyrrolo[2,3-b]pyridin-2(3H)-one;
1-(trans-3-((5-acetylpyridin-2-yl)amino)cyclobutyl)-3,3-dimethyl-1H-pyrrolo[2,3-b]pyridin-2(3H)-one;
1-(trans-3-(benzo[d]thiazol-2-ylamino)cyclobutyl)-1H-pyrrolo[2,3-b]pyridin-2(3H)-one;
1-(Trans-3-((3-methoxypyridin-2-yl)amino)cyclobutyl)-3,3-dimethyl-1H-pyrrolo[2,3-b]pyridin-2(3H)-one;
1-(Trans-3-((5-trifluoromethylpyridin-2-yl)amino)cyclobutyl)-3,3-dimethyl-1H-pyrrolo[2,3-b]pyridin-2(3H)-one;
1-(trans-3-((5-ethylpyrimidin-2-yl)amino)cyclobutyl)-3,3-dimethyl-1H-pyrrolo[2,3-b]pyridin-2(3H)-one;
1-(trans-3-((5-methylpyrimidin-2-yl)amino)cyclobutyl)-3,3-dimethyl-1H-pyrrolo[2,3-b]pyridin-2(3H)-one;
5-(trans-3-((5-chloropyridin-2-yl)cyclobutyl)-7,7-dimethyl-5H-pyrrolo[2,3-b]pyrazin-6(7H)-one;
1-(trans-3-(bis(5-methoxypyridin-2-yl)amino)cyclobutyl)-3,3-dimethyl-1H-pyrrolo[2,3-b]pyridin-2(3H)-one;
1-(Trans-3-((4-methylpyridin-2-yl)amino)cyclobutyl)-3,3-dimethyl-1H-pyrrolo[2,3-b]pyridin-2(3H)-one;
1-(Trans-3-((3-fluoropyridin-2-yl)amino)cyclobutyl)-3,3-dimethyl-1H-pyrrolo[2,3-b]pyridin-2(3H)-one;
1-(Trans-3-((3-methylpyridin-2-yl)amino)cyclobutyl)-3,3-dimethyl-1H-pyrrolo[2,3-b]pyridin-2(3H)-one;
1-(Trans-3-((5-fluoropyridin-2-yl)amino)cyclobutyl)-3,3-dimethyl-1H-pyrrolo[2,3-b]pyridin-2(3H)-one;
3,3-Dimethyl-1-trans-3-(thiazol-2-ylamino)cyclobutyl)-1H-pyrrolo[2,3-b]pyridine-2(3H)-one;
N-(6-((Trans-3-(3,3-dimethyl-2-oxo-2,3-dihydro-1H-pyrrolo[2,3-b]pyridine-1-yl)cyclobutyl)amino)pyridine-3-yl)acetamide;
1-(trans-3-((3-chloropyridin-2-yl)amino)cyclobutyl)-3,3-dimethyl-1H-pyrrolo[2,3-b]pyridin-2(3H)-one;
1-(trans-3-((4-methoxypyrimidin-2-yl)amino)cyclobutyl)-3,3-dimethyl-1H-pyrrolo[2,3-b]pyridin-2(3H)-one;
1-(Trans-3-((5-cyanopyridin-2-yl)amino)cyclobutyl)-3,3-dimethyl-1H-pyrrolo[2,3-b]pyridin-2(3H)-one;
1-(trans-3-((5-bromopyrimidin-2-yl)amino)cyclobutyl)-3,3-dimethyl-1H-pyrrolo[2,3-b]pyridin-2(3H)-one;
1-(trans-3-((5-chloropyrimidin-2-yl)amino)cyclobutyl)-3,3-dimethyl-1H-pyrrolo[2,3-b]pyridin-2(3H)-one;
1-(trans-3-((pyrimidin-2-yl)amino)cyclobutyl)-3,3-dimethyl-1H-pyrrolo[2,3-b]pyridin-2(3H)-one;
1-(trans-3-((4-methylpyrimidin-2-yl)amino)cyclobutyl)-3,3-dimethyl-1H-pyrrolo[2,3-b]pyridin-2(3H)-one;
1-(trans-3-((4-chloropyrimidin-2-yl)amino)cyclobutyl)-3,3-dimethyl-1H-pyrrolo[2,3-b]pyridin-2(3H)-one;
3,3-Dimethyl-1-trans-3-(pyrazin-2-ylamino)cyclobutyl)-1H-pyrrolo[2,3-b]pyridine-2(3H)-one;
1-(trans-3-((6-chloropyridin-2-yl)amino)cyclobutyl)-3,3-dimethyl-1H-pyrrolo[2,3-b]pyridin-2(3H)-one;
1-(trans-3-((4-(trifluoromethyl)pyrimidin-2-yl)amino)cyclobutyl)-3,3-dimethyl-1H-pyrrolo[2,3-b]pyridin-2(3H)-one;
3,3-Dimethyl-1-(trans-3-(pyridazin-3-ylamino)cyclobutyl)-1H-pyrrolo[2,3-b]pyridine-2(3H)-one;
3,3-Dimethyl-1-(trans-3-((4-phenylthiazol-2-yl)amino)cyclobutyl)-1H-pyrrolo[2,3-b]pyridine-2(3H)-one;
1-(trans-3-((5-(trifluoromethyl)pyrimidin-2-yl)amino)cyclobutyl)-3,3-dimethyl-1H-pyrrolo[2,3-b]pyridin-2(3H)-one;
1-(trans-3-((5-fluoropyrimidin-2-yl)amino)cyclobutyl)-3,3-dimethyl-1H-pyrrolo[2,3-b]pyridin-2(3H)-one;
1-(trans-3-((2-chloropyrimidin-4-yl)amino)cyclobutyl)-3,3-dimethyl-1H-pyrrolo[2,3-b]pyridin-2(3H)-one;
7,7-Dimethyl-5-(trans-3-((5-methylpyridin-2-yl)amino)cyclobutyl)-5H-pyrrolo[2,3-b]pyrazin-6(7H)-one;
5-(trans-3-((5-methoxypyridin-2-yl)amino)cyclobutyl)-7,7-dimethyl-5H-pyrrolo[2,3-b]pyrazin-6(7H)-one;
7,7-Dimethyl-5-(trans-4-((5-methylpyridin-2-yl)amino)cyclohexyl)-5H-pyrrolo[2,3-b]pyrazin-6(7H)-one;
5-(trans-3-((5-fluoropyridin-2-yl)amino)cyclobutyl)-7,7-dimethyl-5H-pyrrolo[2,3-b]pyrazin-6(7H)-one;
3,3-Dimethyl-1-(trans-4-((5-methylpyridin-2-yl)amino)cyclohexyl)-1H-pyrrolo[2,3-b]pyridin-2(3H)-one;
5-(trans-3-((5-cyclopropylpyridin-2-yl)amino)cyclobutyl)-7,7-dimethyl-5H-pyrrolo[2,3-b]pyrazin-6(7H)-one;
1-(trans-3-((5-cyclopropylpyrimidin-2-yl)amino)cyclobutyl)-3,3-dimethyl-1H-pyrrolo[2,3-b]pyridin-2(3H)-one;
3,3-Dimethyl-1-(trans-3-((5-(prop-1-en-2-yl)pyrimidin-2-yl)amino)cyclobutyl)-1H-pyrrolo[2,3-b]pyridin-2(3H)-one;
1-(Cis-3-(benzo[d]thiazol-2-ylamino)cyclobutyl)-3,3-dimethyl-1H-pyrrolo[2,3-b]pyridin-2(3H)-one;
1-(trans-3-((5-isopropylpyrimidin-2-yl)amino)cyclobutyl)-3,3-dimethyl-1H-pyrrolo[2,3-b]pyridin-2(3H)-one;
1-(trans-3-((5-methoxypyrimidin-2-yl)amino)cyclobutyl)-3,3-dimethyl-1H-pyrrolo[2,3-b]pyridin-2(3H)-one;
5-(trans-3-((5-acetylpyridin-2-yl)amino)cyclobutyl)-7,7-dimethyl-5H-pyrrolo[2,3-b]pyrazin-6(7H)-one;
3-(trans-3-(benzo[d]thiazol-2-ylamino)cyclobutyl)-1-cyclopropyl-1H-imidazo[4,5-b]pyridin-2(3H)-one;
3-(trans-3-(benzo[d]thiazol-2-ylamino)cyclobutyl)-6-fluoro-1-methyl-1H-imidazo[4,5-b]pyridin-2(3H)-one;
3-(trans-3-(benzo[d]thiazol-2-ylamino)cyclobutyl)-1-cyclopropyl-6-fluoro-1H-imidazo[4,5-b]pyridin-2(3H)-one;
3-(trans-3-(benzo[d]thiazol-2-ylamino)cyclobutyl)-1-methyl-1H-imidazo[4,5-b]pyridin-2(3H)-one;
3-(trans-3-(benzo[d]thiazol-2-ylamino)cyclobutyl)-1-cyclopentyl-1H-imidazo[4,5-b]pyridin-2(3H)-one;
1-(trans-3-(benzo[d]thiazol-2-ylamino)cyclobutyl)-3-cyclopropyl-1H-imidazo[4,5-b]pyrazin-2(3H)-one;
9-(trans-3-(benzo[d]thiazol-2-ylamino)cyclobutyl)-7-cyclopropyl-7H-purin-8(9H)-one;
3-(trans-3-((6-fluorobenzo[d]thiazol-2-yl)amino)cyclobutyl)-1H-imidazo[4,5-b]pyridin-2(3H)-one;
9-(trans-3-(benzo[d]thiazol-2-ylamino)cyclobutyl)-7-methyl-7H-purin-8(9H)-one;
3-(trans-3-(benzo[d]thiazol-2-ylamino)cyclobutyl)-1H-imidazo[4,5-b]pyridin-2(3H)-one;
1-(trans-3-(benzo[d]thiazol-2-ylamino)cyclobutyl)-3-methyl-1H-imidazo[4,5-b]pyrazin-2(3H)-one;
3-(trans-3-(quinolin-2-ylamino)cyclobutyl)-1H-imidazo[4,5-b]pyridin-2(3H)-one;
9-(trans-3-(benzo[d]thiazol-2-ylamino)cyclobutyl)-7H-purin-8(9H)-one;
3-(trans-3-((4-fluorobenzo[d]thiazol-2-yl)amino)cyclobutyl)-1H-imidazo[4,5-b]pyridin-2(3H)-one;
3-(trans-3-((5-fluorobenzo[d]thiazol-2-yl)amino)cyclobutyl)-1H-imidazo[4,5-b]pyridin-2(3H)-one;
3-(trans-3-(benzo[d]thiazol-2-ylamino)cyclobutyl)oxazolo[4,5-b]pyridin-2(3H)-one;
3-trans-3-((7-fluoroquinolin-2-yl)amino)cyclobutyl)-1H-imidazo[4,5-b]pyridin-2(3H)-one;
3-(trans-3-(quinazolin-2-ylamino)cyclobutyl)-1H-imidazo[4,5-b]pyridin-2(3H)-one;
3-(cis-3-(benzo[d]thiazol-2-ylamino)cyclobutyl)-1H-imidazo[4,5-b]pyridin-2(3H)-one;
3-(trans-4-(benzo[d]thiazol-2-ylamino)cyclohexyl)-1H-imidazo[4,5-b]pyridin-2(3H)-one;

3-trans-3-((7-methoxyquinolin-2-yl)amino)cyclobutyl)-1H-imidazo[4,5-b]pyridin-2(3H)-one;
3-(cis-3-(benzo[d]thiazol-2-yl(methyl)amino)cyclobutyl)-1-methyl-1H-imidazo[4,5-b]pyridin-2(3H)-one;
3-(trans-4-((5-fluorobenzo[d]thiazol-2-yl)amino)cyclohexyl)-1H-imidazo[4,5-b]pyridin-2(3H)-one;
3-(trans-4-(quinolin-2-ylamino)cyclohexyl)-1H-imidazo[4,5-b]pyridin-2(3H)-one;
3-(trans-3-((7-fluoroquinazolin-2-yl)amino)cyclobutyl)-1H-imidazo[4,5-b]pyridin-2(3H)-one;
3-(trans-4-(quinazolin-2-ylamino)cyclohexyl)-1H-imidazo[4,5-b]pyridin-2(3H)-one;
3-(trans-4-((7-fluoroquinolin-2-yl)amino)cyclohexyl)-1H-imidazo[4,5-b]pyridin-2(3H)-one;
3-(trans-4-((7-chloroquinazolin-2-yl)amino)cyclohexyl)-1H-imidazo[4,5-b]pyridin-2(3H)-one;
N-(trans-3-(3-amino-1H-pyrazolo[3,4-b]pyridin-1-yl)cyclobutyl)benzo[d]thiazol-2-amine;
N-(trans-3-(3-cyclopropyl-1H-pyrazolo[3,4-b]pyridin-1-yl)cyclobutyl)benzo[d]thiazol-2-amine;
N-(trans-3-(3-(trifluoromethyl)-1H-pyrazolo[3,4-b]pyridin-1-yl)cyclobutyl)benzo[d]thiazol-2-amine;
1-(4-((1-(trans-3-(benzo[d]thiazol-2-ylamino)cyclobutyl)-1H-pyrazolo[3,4-b]pyridin-3-yl)amino)piperidin-1-yl)ethanone;
3-(1-(1H-benzo[d]imidazole-2-carbonyl)azetidin-3-yl)-1H-imidazo[4,5-b]pyridin-2(3H)-one;
1'-(1-(benzo[d]thiazole-2-carbonyl)azetidin-3-yl)spiro[cyclopropane-1,3'-pyrrolo[2,3-b]pyridin]-2'(1'H)-one;
3,3-dimethyl-1-(1-picolinoylpiperidin-4-yl)-1H-pyrrolo[2,3-b]pyridin-2(3H)-one;
3,3-dimethyl-1-(1-(pyridin-2-yl)piperidin-4-yl)-1H-pyrrolo[2,3-b]pyridin-2(3H)-one;
3,3-dimethyl-1-(5-methylpyridin-2-yl)piperidin-4-yl)-1H-pyrrolo[2,3-b]pyridin-2(3H)-one;
(1H-Benzo[d]imidazol-2-yl)(4-(2-methoxy-3H-imidazo[4,5-b]pyridine-3-yl)piperidin-1-yl)methanone;
2-(4-(2-Methoxy-3H-imidazo[4,5-b]pyridin-3-yl)piperidin-1-yl)benzo[d]thiazole;
Benzo[d]thiazol-2-yl(4-(2-methoxy-3H-imidazo[4,5-b]pyridine-3-yl)piperidin-1-yl)methanone;
3-(1-(1-H-Benzo[d]imidazol-2-yl)piperidin-4-yl)-2-methoxy-3H-imidazo[4,5-b]pyridine;
2-(3-(2-Methoxy-3H-imidazo[4,5-b]pyridin-3-yl)azetidin-1-yl)quinoline;
2-Methoxy-3-(1-(4-methylpyrimidin-2-yl)azetidin-3-yl)-3H-imidazo[4,5-b]pyridine;
2-Methoxy-3-(1-(5-methylpyrimidin-2-yl)azetidin-3-yl)-3H-imidazo[4,5-b]pyridine;
2-(3-(2-Methoxy-3H-imidazo[4,5-b]pyridin-3-yl)azetidin-1-yl)quinazoline;
2-Methoxy-3-(1-(4-(6-methylpyridin-3-yl)pyrimidin-2-yl)azetidin-3-yl)-3H-imidazo[4,5-b]pyridine;
2-(3-(2-Methoxy-3H-imidazo[4,5-b]pyridin-3-yl)azetidin-1-yl)benzo[d]thiazole;
3-(1-(1H-benzo[d]imidazol-2-yl)azetidin-3-yl)-2-methoxy-3H-imidazo[4,5-b]pyridine;
N-(4-(2-methoxy-3H-imidazo[4,5-b]pyridin-3-yl)cyclohexyl)-1,3-benzothiazol-2-amine;
N-(4-(2-methoxy-3H-imidazo[4,5-b]pyridin-3-yl)cyclohexyl)-1H-benzimidazol-2-amine;
N-(3-(2-methoxy-3H-imidazo[4,5-b]pyridin-3-yl)cyclobutyl)-1,3-benzothiazol-2-amine;
1H-benzimidazol-2-yl(3-(2-methoxy-3H-imidazo[4,5-b]pyridin-3-yl)cyclobutyl)methanol;
N-(cis-3-(2-methoxy-3H-imidazo[4,5-b]pyridin-3-yl)cyclobutyl)-1,3-benzothiazol-2-amine;
N-(trans-3-(2-methoxy-3H-imidazo[4,5-b]pyridin-3-yl)cyclobutyl)-1,3-benzothiazol-2-amine;
N-(trans-3-(2-methoxy-3H-imidazo[4,5-b]pyridin-3-yl)cyclobutyl)-3,4-dihydro-2-quinoxalinamine:
4-(trans-3-(benzo[d]thiazol-2-ylamino)cyclobutyl)-2H-pyrido[3,2-b][1,4]oxazin-3(4H)-one;
7,7-dimethyl-5-(trans-3-(thiazolo[5,4-b]pyridin-2-ylamino)cyclobutyl)-5h-pyrrolo[2,3-b]pyrazin-6(7H)-one;
3-(cis-3-(benzo[d]thiazol-2-ylamino)cyclobutyl)-1-methyl-1H-imidazo[4,5-b]pyridin-2(3H)-one; 7,7-dimethyl-5-(cis-3-((5-methylpyridin-2-yl)amino)cyclobutyl)-5H-pyrrolo[2,3-b]pyrazin-6(7H)-one;
5-((3r)-1-(1,3-benzothiazol-2-yl)-3-pyrrolidinyl)-7,7-dimethyl-5,7-dihydro-6H-pyrrolo[2,3-b]pyrazin-6-one;
5-((3s)-1-(1,3-benzothiazol-2-yl)-3-pyrrolidinyl)-7,7-dimethyl-5,7-dihydro-6H-pyrrolo[2,3-b]pyrazin-6-one;
3-(trans-3-(benzo[d]oxazol-2-ylamino)cyclobutyl)-1-methyl-1H-imidazo[4,5-b]pyridin-2(3H)-one;
3-(trans-3-((5-fluorobenzo[d]thiazol-2-yl)amino)cyclobutyl)-1-methyl-1H-imidazo[4,5-b]pyridin-2(3H)-one;
1-methyl-3-(trans-3-((1-methyl-1H-benzo[d]imidazol-2-yl)oxy)cyclobutyl)-1H-imidazo[4,5-b]pyridin-2(3H)-one;
1-methyl-3-(trans-3-((1-methyl-1H-benzo[d]imidazol-2-yl)amino)cyclobutyl)-1H-imidazo[4,5-b]pyridin-2(3H)-one;
3-(trans-3-((5-chloropyridin-2-yl)amino)cyclobutyl)-1-methyl-1H-imidazo[4,5-b]pyridin-2(3H)-one;
7-(trans-3-(1,3-benzothiazol-2-ylamino)cyclobutyl)-5,5-dimethyl-5,7-dihydro-6H-pyrrolo[2,3-d]pyrimidin-6-one;
1-methyl 2-((trans-3-(3-cyclopropyl-2-oxo-2,3-dihydro-1H-imidazo[4,5-b]pyrazin-1-yl)cyclobutyl)amino)-1,3-thiazole-5-carboxylate;
2-((trans-3-(3-cyclopropyl-2-oxo-2,3-dihydro-1H-imidazo[4,5-b]pyrazin-1-yl)cyclobutyl)amino)-1,3-thiazole-5-carboxylic acid;
5,5-dimethyl-7-(trans-3-(1,5-naphthyridin-2-ylamino)cyclobutyl)-5,7-dihydro-6H-pyrrolo[2,3-d]pyrimidin-6-one;
N-(1-cyanocyclopropyl)-2-((trans-3-(3-cyclopropyl-2-oxo-2,3-dihydro-1H-imidazo[4,5-b]pyrazin-1-yl)cyclobutyl)amino)-1,3-thiazole-5-carboxamide;
1-cyclopropyl-3-(trans-3-((5-(4-morpholinylcarbonyl)-1,3-thiazol-2-yl)amino)cyclobutyl)-1,3-dihydro-2H-imidazo[4,5-b]pyrazin-2-one;
3-(trans-3-((6-fluorobenzo[d]thiazol-2-yl)amino)cyclobutyl)-1-methyl-1H-imidazo[4,5-b]pyridin-2(3H)-one;
5-(trans-3-((5-fluorobenzo[d]thiazol-2-yl)amino)cyclobutyl)-7,7-dimethyl-5H-pyrrolo[2,3-b]pyrazin-6(7H)-one;
5-(trans-3-((5-fluoro-1,3-benzothiazol-2-yl)amino)cyclobutyl)-7,7-dimethyl-5,7-dihydro-6H-pyrrolo[2,3-b]pyrazin-6-one;
1-(trans-3-(1,3-benzothiazol-2-ylamino)cyclobutyl)-3-methyl-1,3-dihydro-2H-benzimidazol-2-one;
7-(trans-3-((6-fluoro-1,3-benzothiazol-2-yl)amino)cyclobutyl)-5,5-dimethyl-2-(methylsulfanyl)-5,7-dihydro-6H-pyrrolo[2,3-d]pyrimidin-6-one;
7-(trans-3-((6-fluoro-1,3-benzothiazol-2-yl)amino)cyclobutyl)-5,5-dimethyl-5,7-dihydro-6H-pyrrolo[2,3-d]pyrimidin-6-one;
5-(trans-3-((5-methoxypyrazin-2-yl)amino)cyclobutyl)-7,7-dimethyl-5H-pyrrolo[2,3-b]pyrazin-6(7H)-one:
5-(trans-3-((5-bromopyridin-2-yl)amino)cyclobutyl)-7,7-dimethyl-5H-pyrrolo[2,3-b]pyrazin-6(7H)-one;
7,7-dimethyl-5-(trans-3-((1-methyl-1H-benzo[d]imidazol-2-yl)amino)cyclobutyl)-5H-pyrrolo[2,3-b]pyrazin-6(7H)-one;
5-(trans-3-((1,8-naphthyridin-2-yl)amino)cyclobutyl)-7,7-dimethyl-5H-pyrrolo[2,3-b]pyrazin-6(7H)-one;

5-(trans-3-((1,5-naphthyridin-2-yl)amino)cyclobutyl)-7,7-dimethyl-5H-pyrrolo[2,3-b]pyrazin-6(7H)-one;
5-(trans-3-((5-(1H-pyrazol-1-yl)pyridin-2-yl)amino)cyclobutyl)-7,7-dimethyl-5H-pyrrolo[2,3-b]pyrazin-6(7H)-one triacetate;
N-(trans-3-(1H-pyrrolo[2,3-b]pyridin-1-yl)cyclobutyl)benzo[d]thiazol-2-amine;
3,3-dimethyl-1-(trans-3-(quinazolin-2-ylamino)cyclobutyl)-1H-pyrrolo[2,3-b]pyridin-2(3H)-one; 5-(trans-3-((5-(difluoromethoxy)-2-pyridinyl)amino)cyclobutyl)-7,7-dimethyl-5,7-dihydro-6H-pyrrolo[2,3-b]pyrazin-6-one;
3,3-dimethyl-1-(trans-3-(2-quinazolinylamino)cyclobutyl)-1,3-dihydro-2H-pyrrolo[2,3-b]pyridin-2-one; 1-(trans-3-(1,3-benzoxazol-2-ylamino)cyclobutyl)-3,3-dimethyl-1,3-dihydro-2H-pyrrolo[2,3-b]pyridin-2-one;
5-(trans-3-((5,6-di fluoro-1,3-benzothiazol-2-yl)amino)cyclobutyl)-7,7-dimethyl-5,7-dihydro-6H-pyrrolo[2,3-b]pyrazin-6-one;
5-(trans-3-((4,6-difluoro-1,3-benzothiazol-2-yl)amino)cyclobutyl)-7,7-dimethyl-5,7-dihydro-6H-pyrrolo[2,3-b]pyrazin-6-one;
5-(trans-3-((6-methoxy-1,3-benzothiazol-2-yl)amino)cyclobutyl)-7,7-dimethyl-5,7-dihydro-6H-pyrrolo[2,3-b]pyrazin-6-one;
7,7-dimethyl-5-(trans-3-([1,3]thiazolo[5,4-b]pyridin-2-ylamino)cyclobutyl)-5,7-dihydro-6H-pyrrolo[2,3-b]pyrazin-6-one:
1-methyl-3-(trans-3-([1,3]thiazolo[5,4-b]pyridin-2-ylamino)cyclobutyl)-1,3-dihydro-2H-imidazo[4,5-b]pyridin-2-one;
1-cyclopropyl-3-(trans-3-((7-fluoro-2-quinazolinyl)amino)cyclobutyl)-1,3-dihydro-2H-imidazo[4,5-b]pyrazin-2-one;
5-(trans-3-((7-fluoro-2-quinazolinyl)amino)cyclobutyl)-7,7-dimethyl-5,7-dihydro-6H-pyrrolo[2,3-b]pyrazin-6-one;
1-cyclopropyl-3-(trans-3-((6-fluoro-1,3-benzoxazol-2-yl)amino)cyclobutyl)-1,3-dihydro-2H-imidazo[4,5-b]pyrazin-2-one;
5-(trans-3-((6-fluoro-1,3-benzoxazol-2-yl)amino)cyclobutyl)-7,7-dimethyl-5,7-dihydro-6H-pyrrolo[2,3-b]pyrazin-6-one;
1-cyclopropyl-3-(trans-3-([1.3]thiazolo[5,4-b]pyridin-2-ylamino)cyclobutyl)-1,3-dihydro-2H-imidazo[4,5-b]pyrazin-2-one;
1-cyclopropyl-3-(trans-3-((6-fluoro-1,3-benzothiazol-2-yl)amino)cyclobutyl)-1,3-dihydro-2H-imidazo[4,5-b]pyrazin-2-one;
1 (r)-1-(trans-3-(benzo[d]thiazol-2-ylamino)cyclobutyl)-3-hydroxy-3-methyl-1H-pyrrolo[2,3-b]pyridin-2(3H)-one;
(s)-1-(trans-3-(benzo[d]thiazol-2-ylamino)cyclobutyl)-3-hydroxy-3-methyl-1H-pyrrolo[2,3-b]pyridin-2(3H)-one;
5-((1R,2S)-2-(3-methoxyphenyl)cyclopropyl)-7,7-dimethyl-5,7-dihydro-6H-pyrrolo[2,3-b]pyrazin-6-one;
5-((1S,2R)-2-(3-methoxyphenyl)cyclopropyl)-7,7-dimethyl-5,7-dihydro-6H-pyrrolo[2,3-b]pyrazin-6-one;
(3R)-1-(trans-3-(1,3-benzothiazol-2-ylamino)cyclobutyl)-3-hydroxy-3-methyl-1,3-dihydro-2H-pyrrolo[2,3-b]pyridin-2-one, (3s)-1-(trans-3-(1,3-benzothiazol-2-yl-amino)cyclobutyl)-3-hydroxy-3-methyl-1,3-dihydro-2H-pyrrolo[2,3-b]pyridin-2-one;
1-cyclopropyl-3-(trans-3-(quinazolin-2-ylamino)cyclobutyl)-1H-imidazo[4,5-b]pyridin-2(3H)-one;
1-cyclopropyl-3-(trans-3-((5-fluorobenzo[d]thiazol-2-yl)amino)cyclobutyl)-1H-imidazo[4,5-b]pyridin-2(3H)-one;
1-cyclopropyl-3-(trans-3-((6-fluorobenzo[d]thiazol-2-yl)amino)cyclobutyl)-1H-imidazo[4,5-b]pyridin-2(3H)-one;

7,7-dimethyl-5-(3-(quinolin-2-ylamino)cyclobutyl)-5H-pyrrolo[2,3-b]pyrazin-6(7H)-one;
3,3-dimethyl-1-(1-(quinazolin-2-yl)piperidin-4-yl)-1H-pyrrolo[2,3-b]pyridin-2(3H)-one;
1-(1-(benzo[d]thiazol-2-yl)piperidin-4-yl)-3,3-dimethyl-1H-pyrrolo[2,3-b]pyridin-2(3H)-one;
7,7-dimethyl-5-(trans-3-(2-quinolinylamino)cyclobutyl)-5,7-dihydro-6H-pyrrolo[2,3-b]pyrazin-6-one;
3,3-dimethyl-1-(1-(2-quinazolinyl)-4-piperidinyl)-1,3-dihydro-2H-pyrrolo[2,3-b]pyridin-2-one;
1-(1-(1,3-benzothiazol-2-yl)-4-piperidinyl)-3,3-dimethyl-1,3-dihydro-2H-pyrrolo[2,3-b]pyridin-2-one;
3,3-dimethyl-1-(1-(2-quinolinyl)-4-piperidinyl)-1,3-dihydro-2H-pyrrolo[2,3-b]pyridin-2-one;
1-(1-(6-fluoro-1,3-benzothiazol-2-yl)-4-piperidinyl)-3,3-dimethyl-1,3-dihydro-2H-pyrrolo[2,3-b]pyridin-2-one;
5-(trans-3-((6-fluoro-2-quinolinyl)amino)cyclobutyl)-7,7-dimethyl-5,7-dihydro-6H-pyrrolo[2,3-b]pyrazin-6-one;
1-(1-(7-fluoro-2-quinolinyl)-4-piperidinyl)-3,3-dimethyl-1,3-dihydro-2H-pyrrolo[2,3-b]pyridin-2-one;
1-(1-(6-fluoro-2-quinolinyl)-4-piperidinyl)-3,3-dimethyl-1,3-dihydro-2H-pyrrolo[2,3-b]pyridin-2-one;
5-(trans-3-((7-fluoro-2-quinolinyl)amino)cyclobutyl)-7,7-dimethyl-5,7-dihydro-6H-pyrrolo[2,3-b]pyrazin-6-one:
5-(trans-3-(1,3-benzothiazol-2-yloxy)cyclobutyl)-7,7-dimethyl-5,7-dihydro-6H-pyrrolo[2,3-b]pyrazin-6-one;
5-(1-(1,3-benzothiazol-2-yl)-4-piperidinyl)-7,7-dimethyl-5,7-dihydro-6H-pyrrolo[2,3-b]pyrazin-6-one;
5-(1-(6-fluoro-2-quinolinyl)-4-piperidinyl)-7,7-dimethyl-5,7-dihydro-6H-pyrrolo[2,3-b]pyrazin-6-one; and
5-(1-(7-chloro-2-quinazolinyl)-4-piperidinyl)-7,7-dimethyl-5,7-dihydro-6H-pyrrolo[2,3-b]pyrazin-6-one.
5-(1-(6-fluoro-2-quinazolinyl)-piperidinyl)-7,7-dimethyl-5,7-dihydro-6H-pyrrolo[2,3-b]pyrazin-6-one;
7,7-dimethyl-5-(1-(6-(trifluoromethyl)-1,3-benzothiazol-2-yl)-4-piperidinyl)-5,7-dihydro-6H-pyrrolo[2,3-b]pyrazin-6-one;
3,3-dimethyl-1-(trans-3-((5-methylthiazol-2-yl)amino)cyclobutyl)-1H-pyrrolo[2,3-b]pyridin-2(3H)-on;
6-fluoro-1-methyl-3-(trans-3-(quinazolin-2-ylamino)cyclobutyl)-1H-imidazo[4,5-b]pyridin-2(3H)-one;
5-(trans-3-((5-bromopyridin-2-yl)amino)cyclobutyl)-7,7-dimethyl-5H-pyrrolo[2,3-b]pyrazin-6(7H)-one;
1-(trans-3-(benzo[d]thiazol-2-ylamino)cyclobutyl)-3,3,5-trifluoro-1H-pyrrolo[2,3-b]pyridin-2(3H)-one;
6-fluoro-3-(trans-3-((6-fluorobenzo[d]thiazol-2-yl)amino)cyclobutyl)-1-methyl-1H-imidazo[4,5-b]pyridin-2(3H)-one;
6-fluoro-3-(trans-3-((5-fluorobenzo[d]thiazol-2-yl)amino)cyclobutyl)-1-methyl-1H-imidazo[4,5-b]pyridin-2(3H)-one;
1-(trans-3-(benzo[d]thiazol-2-ylamino)cyclobutyl)-5-chloro-3,3-difluoro-1H-pyrrolo[2,3-b]pyridin-2(3H)-one;
1-(trans-3-(benzo[d]thiazol-2-ylamino)cyclobutyl)-3,3-difluoro-1H-pyrrolo[2,3-b]pyridin-2(3H)-one;
1-cyclopropyl-3-(trans-3-((6-fluorobenzo[d]thiazol-2-yl)amino)cyclobutyl)-1H-imidazo[4,5-b]pyrazin-2(3H)-one;
1-(trans-3-(1,3-benzothiazol-2-ylamino)cyclobutyl)-3,3-difluoro-1,3-dihydro-2H-pyrrolo[2,3-b]pyridin-2-one;
5-(cis-3-(benzo[d]thiazol-2-ylamino)cyclobutyl)-7,7-dimethyl-5H-pyrrolo[2,3-b]pyrazin-6(7H)-one;
1-(cis-3-(benzo[d]thiazol-2-ylamino)cyclobutyl)-3-methyl-1H-imidazo[4,5-b]pyrazin-2(3H)-one;
n-(cis-3-(7,7-dimethyl-6-oxo-6,7-dihydro-5H-pyrrolo[2,3-b]pyrazin-5-yl)cyclobutyl)-1H-benzo[d]imidazole-2-carboxamide;

7,7-dimethyl-5-(cis-4-((5-methylpyridin-2-yl)amino)cyclohexyl)-5H-pyrrolo[2,3-b]pyrazin-6(7H)-one;
1-cyclopropyl-3-(trans-3-(quinazolin-2-ylamino)cyclobutyl)-1H-imidazo[4,5-b]pyrazin-2(3H)-one;
1-(trans-3-(benzo[d]oxazol-2-ylamino)cyclobutyl)-3-cyclopropyl-1H-imidazo[4,5-b]pyrazin-2(3H)-one;
1-(trans-3-((5-chloropyridin-2-yl)amino)cyclobutyl)-3-cyclopropyl-1H-imidazo[4,5-b]pyrazin-2(3H)-one;
1-(trans-3-((5-chloro-2-pyridinyl)amino)cyclobutyl)-3-cyclopropyl-1,3-dihydro-2H-imidazo[4,5-b]pyrazin-2-one;
1-cyclopropyl-3-(trans-3-((5-fluoro-1,3-benzothiazol-2-yl)amino)cyclobutyl)-1,3-dihydro-2H-imidazo[4,5-b]pyrazin-2-one;
1-cyclopropyl-3-(trans-3-(1,8-naphthyridin-2-ylamino)cyclobutyl)-1,3-dihydro-2H-imidazo[4,5-b]pyrazin-2-one;
1-cyclopropyl-3-(trans-3-((6-methoxy-1,3-benzothiazol-2-yl)amino)cyclobutyl)-1,3-dihydro-2H-imidazo[4,5-b]pyrazin-2-one;
1-cyclopropyl-3-(trans-3-(2-quinolinylamino)cyclobutyl)-1,3-dihydro-2H-imidazo[4,5-b]pyrazin-2-one;
1-cyclopropyl-3-(trans-3-((1-methyl-1H-benzimidazol-2-yl)amino)cyclobutyl)-1,3-dihydro-2H-imidazo[4,5-b]pyrazin-2-one;
1-cyclopropyl-3-(trans-4-(1,5-naphthyridin-2-ylamino)cyclohexyl)-1,3-dihydro-2H-imidazo[4,5-b]pyrazin-2-one;
1-(trans-3-((6-chlorobenzo[d]oxazol-2-yl)amino)cyclobutyl)-3-cyclopropyl-1H-imidazo[4,5-b]pyrazin-2(3H)-one;
1-(trans-3-(1,3-benzothiazol-2-ylamino)cyclobutyl)-5-bromo-3-cyclopropyl-1,3-dihydro-2H-imidazo[4,5-b]pyrazin-2-one; and
5-bromo-3-cyclopropyl-1-(trans-3-((7-fluoro-2-quinazolinyl)amino)cyclobutyl)-1,3-dihydro-2H-imidazo[4,5-b]pyrazin-2-one.

Representative embodiments of compounds of the Invention are shown in Tables 1-6 below:

Table 1 shows embodiments of examples of compounds of Formula (I), wherein the group —W-T-D< is —N=CR$^5$—N<; E is N; G is —NR$^1$R$^2$; and R$^{3a}$, R$^{3b}$, and R$^{3c}$ are hydrogens; as shown in compounds of Formula (IA) below:

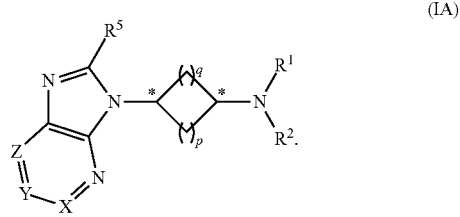

(IA)

TABLE 1

Examples of embodiments of compounds of Formula (IA)

| Ex. # | =X—Y=Z— | R$^1$ | R$^2$ | R$^5$ | P | q | Relative stereochemistry at *C |
|---|---|---|---|---|---|---|---|
| 1 | =CH—CH=CH— | benzothiazol-2-yl | H | ethyl | 1 | 1 | trans |
| 2 | =CH—CH=CH— | benzothiazol-2-yl | H | cyclopropyl | 1 | 1 | trans |
| 3 | =CH—CH=CH— | 1,5-naphthyridin-2-yl | H | cyclopropyl | 1 | 1 | trans |
| 4 | =CH—CH=CH— | thiazolo[5,4-b]pyridin-2-yl | H | cyclopropyl | 1 | 1 | trans |

TABLE 1-continued

Examples of embodiments of compounds of Formula (IA)

| Ex. # | =X—Y=Z— | R¹ | R² | R⁵ | P | q | Relative stereo-chemistry at *C |
|---|---|---|---|---|---|---|---|
| 5 | =CH—CH=CH— | benzothiazol-2-yl | H | —OCH₃ | 1 | 1 | trans |
| 6 | =CH—CH=CH— | quinolin-2-yl | H | cyclopropyl | 1 | 1 | trans |
| 7 | =CH—CH=CH— | 6-fluoroquinolin-2-yl | H | cyclopropyl | 1 | 1 | trans |
| 8 | =CH—CH=CH— | quinazolin-2-yl | H | cyclopropyl | 1 | 1 | trans |
| 9 | =CH—CH=CH— | benzothiazol-2-yl | H | —OCH₃ | 1 | 1 | cis |
| 10 | =CH—CH=CH— | benzothiazol-2-yl | H | —CF₃ | 1 | 1 | trans |
| 11 | =CH—CH=CH— | 1,8-naphthyridin-2-yl | H | cyclopropyl | 1 | 1 | trans |
| 12 | =CH—CH=CH— | quinazolin-2-yl | H | —CF₃ | 1 | 1 | trans |
| 13 | =CH—N=CH— | quinazolin-2-yl | H | cyclopropyl | 1 | 1 | trans |

TABLE 1-continued

Examples of embodiments of compounds of Formula (IA)

| Ex. # | =X—Y=Z— | R¹ | R² | R⁵ | P | q | Relative stereo-chemistry at *C |
|---|---|---|---|---|---|---|---|
| 14 | =CH—CH=CH— | benzothiazol-2-yl | H | H | 1 | 1 | trans |
| 15 | =CH—CH=CH— | benzoxazol-2-yl | H | cyclopropyl | 1 | 1 | trans |
| 16 | =CH—CH=CH— | 1,7-naphthyridin-2-yl | H | cyclopropyl | 1 | 1 | trans |
| 17 | =CH—CH=CH— | 7-chloroquinoxalin-2-yl | H | tetrahydropyran-4-yl | 1 | 1 | trans |
| 18 | =CH—CH=CH— | 2,6-naphthyridin-2-yl | H | cyclopropyl | 1 | 1 | trans |
| 19 | =CH—CH=CH— | 7-chloroquinoxalin-2-yl | H | —OCH₃ | 1 | 1 | trans |
| 20 | =CH—CH=CH— | 7-chloroquinolin-2-yl | H | cyclopropyl | 1 | 1 | trans |
| 21 | =CH—N=CCl— | quinazolin-2-yl | H | H | 1 | 1 | trans |

TABLE 1-continued
Examples of embodiments of compounds of Formula (IA)
| Ex. # | =X—Y=Z— | R¹ | R² | R⁵ | p | q | Relative stereo-chemistry at *C |
|---|---|---|---|---|---|---|---|
| 22 | =CH—CH=CH— | 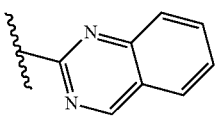 [SMILES: *c1ncc2ccccc2n1] | H | H | 1 | 1 | trans |
| 23 | =CH—N=C(OH)— | 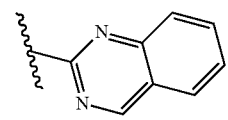 [SMILES: *c1ncc2ccccc2n1] | H | —CF₃ | 1 | 1 | trans |
| 24 | =CH—N=C(morpholino)— | 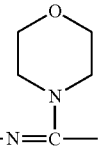 | H | H | 1 | 1 | trans |
| 25 | =CH—N=C(C₆H₄-CO₂CH₃)— | 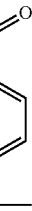 | H | —CF₃ | 1 | 1 | trans |
| 26 | =CH—N=C(C₆H₄-CO₂CH₃)— | 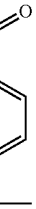 | H | H | 1 | 1 | trans |
| 27 | =CH—CH=CH— | 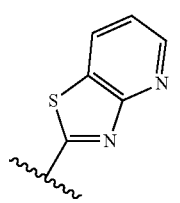 [SMILES: *c1nc2ncccc2s1] | H | cyclo-propyl | 1 | 1 | trans |
| 28 | =CH—CH=CH— | 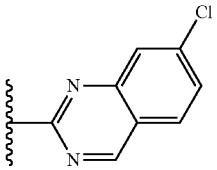 [SMILES: *c1ncc2ccc(Cl)cc2n1] | H | —OCH₃ | 1 | 1 | trans |

And are named as follows.

| Ex. # | Chemical name |
|---|---|
| 1 | N-(trans-3-(2-ethyl-3H-imidazo[4,5-b]pyridin-3-yl)cyclobutyl)benzo[d]thiazol-2-amine\ |
| 2 | N-(trans-3-(2-cyclopropyl-3H-imidazo[4,5-b]pyridin-3-yl)cyclobutyl)benzo[d]thiazol-2-amine |
| 3 | N-(Trans-3-(2-cyclopropyl-3h-imidazo[4,5-b]pyridin-3-yl)cyclobutyl)-1,5-naphthyridin-2-amine |
| 4 | N-(Trans-3-(2-cyclopropyl-3h-imidazo[4,5-b]pyridin-3-yl)cyclobutyl)thiazolo[5,4-b]pyridin-2-amine |
| 5 | N-(Trans-3-(2-methoxy-3H-imidazo[4,5-b]pyridin-3-yl)cyclobutyl)benzo[d]thiazol-2-amine |
| 6 | N-(Trans-3-(2-cyclopropyl-3h-imidazo[4,5-b]pyridin-3-yl)cyclobutyl)quinolin-2-amine |
| 7 | N-(Trans-3-(2-cyclopropyl-3H-imidazo[4,5-b]pyridin-3-yl)cyclobutyl)-6-fluoroquinolin-2-amine |
| 8 | N-(Trans-3-(2-cyclopropyl-3H-imidazo[4,5-b]pyridin-3-yl)cyclobutyl)quinazolin-2-amine |
| 9 | N-(Cis-3-(2-methoxy-3H-imidazo[4,5-b]pyridin-3-yl)cyclobutyl)benzo[d]thiazol-2-amine |
| 10 | N-(trans-3-(2-(trifluoromethyl)-3H-imidazo[4,5-b]pyridin-3-yl)cyclobutyl)benzo[d]thiazol-2-amine |
| 11 | N-(Trans-3-(2-cyclopropyl-3h-imidazo[4,5-b]pyridin-3-yl)cyclobutyl-1,8-naphthyridin-2-amine |
| 12 | N-(Trans-3-(2-(trifluoromethyl)-3H-imidazo[4,5-b]pyridin-3-yl)cyclobutyl)quinazolin-2-amine |
| 13 | N-(trans-3-(8-cyclopropyl-9H-purin-9-yl)cyclobutyl)quinazolin-2-amine |
| 14 | N-(trans-3-(3H-imidazo[4,5-b]pyridin-3-yl)cyclobutyl)benzo[d]thiazol-2-amine |
| 15 | N-(Trans-3-(2-cyclopropyl-3H-imidazo[4,5-b]pyridin-3-yl)cyclobutyl)benzo[d]oxazol-2-amine |
| 16 | N-(Trans-3-(2-cyclopropyl-3h-imidazo[4,5-b]pyridin-3-yl)cyclobutyl)-1,7-naphthyridin-2-amine |
| 17 | 7-Chloro-N-(trans-3-(2-(tetrahydro-2H-pyran-4-yl)-3H-imidazo[4,5-b]pyridin-3-yl)cyclobutyl)quinoxalin-2-amine |
| 18 | N-(Trans-3-(2-cyclopropyl-3H-imidazo[4,5-b]pyridin-3-yl)cyclobutyl)-1,7-naphthyridin-2-amine |
| 19 | 7-Chloro-N-(trans-3-(2-methoxy-3H-imidazo[4,5-b]pyridin-3-yl)cyclobutyl)quinoxalin-2-amine |
| 20 | 7-Chloro-N-(trans-3-(2-cyclopropyl-3H-imidazo[4,5-b]pyridin-3-yl)cyclobutyl)quinolin-2-amine |
| 21 | N-(Trans-3-(6-chloro-9H-purin-9-yl)cyclobutyl)quinazolin-2-amine |
| 22 | N-(Trans-3-(3H-imidazo[4,5-b]pyridin-3-yl)cyclobutyl)quinazolin-2-amine |
| 23 | 9-(Trans-3-(quinazolin-2-ylamino)cyclobutyl)-8-(trifluoromethyl)-9H-purin-6-ol |
| 24 | N-(Trans-3-(6-morpholino-9H-purin-9-yl)cyclobutyl)quinazolin-2-amine |
| 25 | Methyl 4-(9-(trans-3-(quinazolin-2-ylamino)cyclobutyl)-8-(trifluoromethyl)-9H-purin-6-yl)benzoate |
| 26 | Methyl 4-(9-(trans-3-(quinazolin-2-ylamino)cyclobutyl)-9H-purin-6-yl)benzoate |
| 27 | N-(Trans-3-(2-cyclopropyl-3H-imidazo[4,5-b]pyridin-3-yl)cyclobutyl)thiazolo[4,5-b]pyridin-2-amine |
| 28 | 7-Chloro-N-(trans-3-(2-methoxy-3H-imidazo[4,5-b]pyridin-3-yl)cyclobutyl)quinazolin-2-amine |

Table 2 shows examples of embodiments of compounds of Formula (I), wherein the group —W-T-D< is —CR$^6$R$^7$—(C=O)—N<; E is N; G is —NR$^1$R$^2$; and R$^{3a}$, R$^{3b}$, and R$^{3c}$ are hydrogens; as shown in compounds of Formula (IB) below:

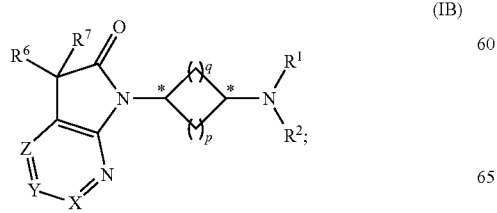

(IB)

TABLE 2

Examples of embodiments of compounds of Formula (IB)

| Ex. # | =X—Y=Z— | R¹ | R² | R⁶ | R⁷ | p | q | Relative stereochemistry at *C |
|---|---|---|---|---|---|---|---|---|
| 29 | =CH—CH=CH— | 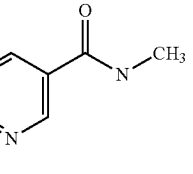 | H | —CH₃ | —CH₃ | 1 | 1 | trans |
| 30 | =CH—CH=CH— | 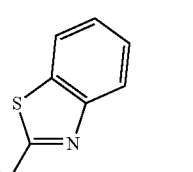 | H | —CH₃ | —CH₃ | 1 | 1 | trans |
| 31 | =CH—CH=CH— | 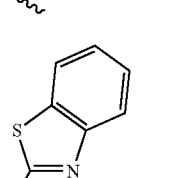 | H | R⁶ and R⁷ combined to form a cyclopropyl ring | | 1 | 1 | trans |
| 32 | =CH—CH=CH— | 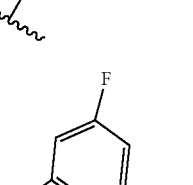 | H | —CH₃ | —CH₃ | 1 | 1 | trans |
| 33 | =CH—CF=CH— | 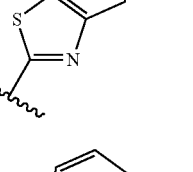 | H | R⁶ and R⁷ combined to form a cyclopropyl ring | | 1 | 1 | trans |
| 34 | =CCH—CH=N— | 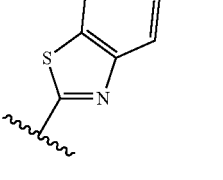 | H | —CH₃ | —CH₃ | 1 | 1 | trans |
| 35 | =CH—CH=CH— | 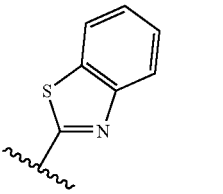 [SMILES: *c1nc2ccccc2s1] | H | R⁶ and R⁷ combined to form a cyclobutyl ring | | 1 | 1 | trans |

TABLE 2-continued

Examples of embodiments of compounds of Formula (IB)

| Ex. # | =X—Y=Z— | R¹ | R² | R⁶ | R⁷ | p | q | Relative stereochemistry at *C |
|---|---|---|---|---|---|---|---|---|
| 36 | =CH—CH=CH— | 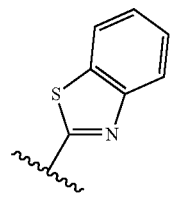 | H | R⁶ and R⁷ combined to form a cyclopentyl ring | | 1 | 1 | trans |
| 37 | =CH—CH=CH— | 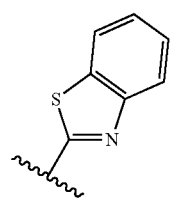 [SMILES: *c1nc2ccccc2s1] | H | R⁶ and R⁷ combined to 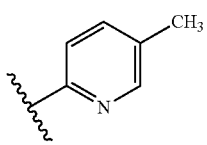 [SMILES: *c1ccc(C)cn1] form a ring | | 1 | 1 | trans |
| 38 | =CH—CH=CH— | 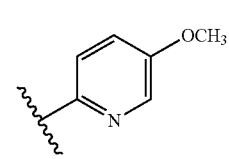 [SMILES: *c1ccc(OC)cn1] | H | —CH₃ | —CH₃ | 1 | 1 | trans |
| 39 | =CH—CH=CH— | 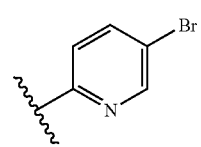 [SMILES: *c1ccc(Br)cn1] | H | —CH₃ | —CH₃ | 1 | 1 | trans |
| 40 | =CH—CH=CH— | 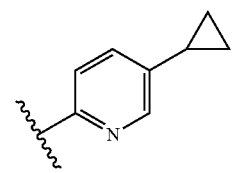 [SMILES: *c1ccc(C2CC2)cn1] | H | —CH₃ | —CH₃ | 1 | 1 | trans |
| 41 | =CH—CH=CH— | 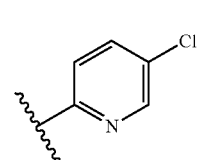 | H | —CH₃ | —CH₃ | 1 | 1 | trans |
| 42 | =CH—CH=CH— | 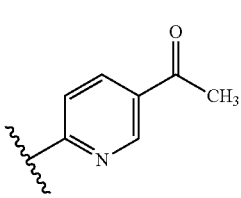 [SMILES: *c1ccc(C(C)=O)cn1] | H | —CH₃ | —CH₃ | 1 | 1 | trans |
| 43 | =CH—CH=CH— |  | H | —CH₃ | —CH₃ | 1 | 1 | trans |

TABLE 2-continued
Examples of embodiments of compounds of Formula (IB)
| Ex. # | =X—Y=Z— | R¹ | R² | R⁶ | R⁷ | p | q | Relative stereo-chemistry at *C |
|---|---|---|---|---|---|---|---|---|
| 44 | =CH—CH=CH— | 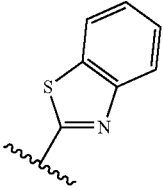 [SMILES: *c1nc2ccccc2s1] | H | H | H | 1 | 1 | trans |
| 45 | =CH—CH=CH— | 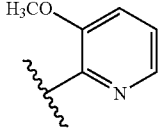 | H | —CH₃ | —CH₃ | 1 | 1 | trans |
| 46 | =CH—CH=CH— | 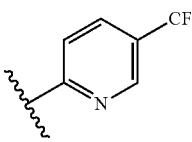 | H | —CH₃ | —CH₃ | 1 | 1 | trans |
| 47 | =CH—CH=CH— | 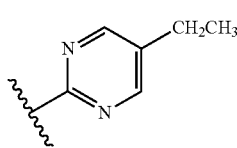 [SMILES: *c1ncc(CC)cn1] | H | —CH₃ | —CH₃ | 1 | 1 | trans |
| 48 | =CH—CH=CH— | 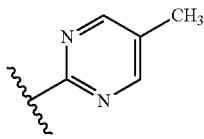 [SMILES: *c1ncc(C)cn1] | H | —CH₃ | —CH₃ | 1 | 1 | trans |
| 49 | =CH—CH=N— | 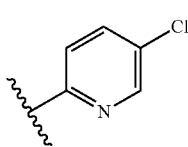 [SMILES: *c1ccc(Cl)cn1] | H | —CH₃ | —CH₃ | 1 | 1 | trans |
| 50 | =CH—CH=CH— | 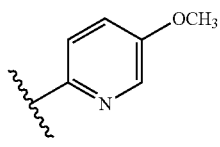 [SMILES: *c1ccc(OC)cn1] | 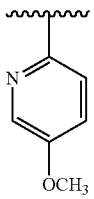 | —CH₃ | —CH₃ | 1 | 1 | trans |
| 51 | =CH—CH=CH— | 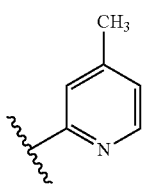 | H | —CH₃ | —CH₃ | 1 | 1 | trans |
| 52 | =CH—CH=CH— | 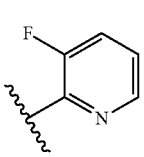 | H | —CH₃ | —CH₃ | 1 | 1 | trans |

TABLE 2-continued

Examples of embodiments of compounds of Formula (IB)

| Ex. # | =X—Y=Z— | R¹ | R² | R⁶ | R⁷ | p | q | Relative stereochemistry at *C |
|---|---|---|---|---|---|---|---|---|
| 53 | =CH—CH=CH— | 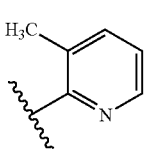 3-methylpyridin-2-yl | H | —CH₃ | —CH₃ | 1 | 1 | trans |
| 54 | =CH—CH=CH— | 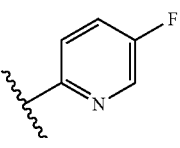 5-fluoropyridin-2-yl | H | —CH₃ | —CH₃ | 1 | 1 | trans |
| 55 | =CH—CH=CH— | 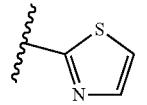 [SMILES: *c1nccs1] thiazol-2-yl | H | —CH₃ | —CH₃ | 1 | 1 | trans |
| 56 | =CH—CH=CH— | 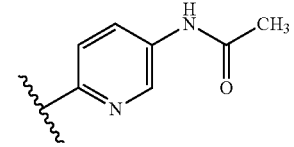 [SMILES: *c1ccc(NC(C)=O)cn1] 5-acetamidopyridin-2-yl | H | —CH₃ | —CH₃ | 1 | 1 | trans |
| 57 | =CH—CH=CH— | 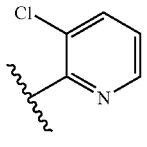 3-chloropyridin-2-yl | H | —CH₃ | —CH₃ | 1 | 1 | trans |
| 58 | =CH—CH=CH— | 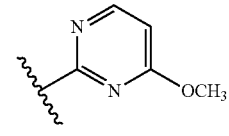 [SMILES: *c1nccc(OC)n1] 4-methoxypyrimidin-2-yl | H | —CH₃ | —CH₃ | 1 | 1 | trans |
| 59 | =CH—CH=CH— | 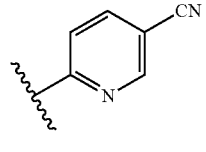 5-cyanopyridin-2-yl | H | —CH₃ | —CH₃ | 1 | 1 | trans |
| 60 | =CH—CH=CH— | 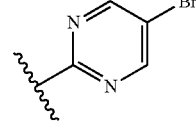 5-bromopyrimidin-2-yl | H | —CH₃ | —CH₃ | 1 | 1 | trans |
| 61 | =CH—CH=CH— | 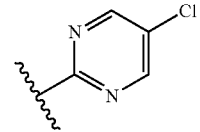 [SMILES: *c1ncc(Cl)cn1] 5-chloropyrimidin-2-yl | H | —CH₃ | —CH₃ | 1 | 1 | trans |
| 62 | =CH—CH=CH— | 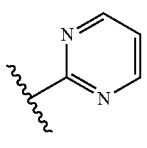 pyrimidin-2-yl | H | —CH₃ | —CH₃ | 1 | 1 | trans |

TABLE 2-continued

Examples of embodiments of compounds of Formula (IB)

| Ex. # | =X—Y=Z— | R¹ | R² | R⁶ | R⁷ | p | q | Relative stereochemistry at *C |
|---|---|---|---|---|---|---|---|---|
| 63 | =CH—CH=CH— | 4-methylpyrimidin-2-yl | H | —CH₃ | —CH₃ | 1 | 1 | trans |
| 64 | =CH—CH=CH— | 4-chloropyrimidin-2-yl | H | —CH₃ | —CH₃ | 1 | 1 | trans |
| 65 | =CH—CH=CH— | pyrazin-2-yl | H | —CH₃ | —CH₃ | 1 | 1 | trans |
| 66 | =CH—CH=CH— | 6-chloropyridin-2-yl | H | —CH₃ | —CH₃ | 1 | 1 | trans |
| 67 | =CH—CH=CH— | 4-(trifluoromethyl)pyrimidin-2-yl | H | —CH₃ | —CH₃ | 1 | 1 | trans |
| 68 | =CH—CH=CH— | pyridazin-3-yl | H | —CH₃ | —CH₃ | 1 | 1 | trans |
| 69 | =CH—CH=CH— | 4-phenylthiazol-2-yl | H | —CH₃ | —CH₃ | 1 | 1 | trans |
| 70 | =CH—CH=CH— | 5-(trifluoromethyl)pyrimidin-2-yl | H | —CH₃ | —CH₃ | 1 | 1 | trans |
| 71 | =CH—CH=CH— | 5-fluoropyrimidin-2-yl | H | —CH₃ | —CH₃ | 1 | 1 | trans |

TABLE 2-continued
Examples of embodiments of compounds of Formula (IB)
| Ex. # | =X—Y=Z— | R¹ | R² | R⁶ | R⁷ | p | q | Relative stereo-chemistry at *C |
|---|---|---|---|---|---|---|---|---|
| 72 | =CH—CH=CH— | 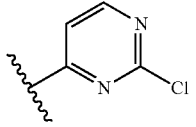 [SMILES: *c1ccnc(Cl)n1] | H | —CH₃ | —CH₃ | 1 | 1 | trans |
| 73 | =CH—CH=N— | 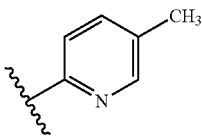 [SMILES: *c1ccc(C)cn1] | H | —CH₃ | —CH₃ | 1 | 1 | trans |
| 74 | =CH—CH=N— | 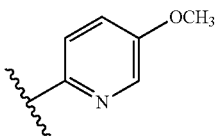 [SMILES: *c1ccc(OC)cn1] | H | —CH₃ | —CH₃ | 1 | 1 | trans |
| 75 | =CH—CH=N— | 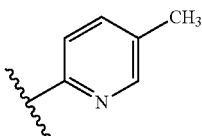 [SMILES: *c1ccc(C)cn1] | H | —CH₃ | —CH₃ | 2 | 2 | trans |
| 76 | =CH—CH=N— | 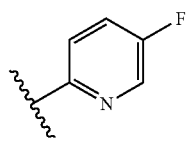 | H | —CH₃ | —CH₃ | 1 | 1 | trans |
| 77 | =CH—CH=CH— | 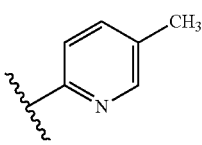 [SMILES: *c1ccc(C)cn1] | H | —CH₃ | —CH₃ | 2 | 2 | trans |
| 78 | =CH—CH=N— | 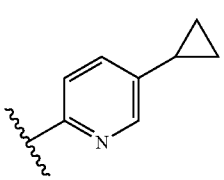 [SMILES: *c1ccc(C2CC2)cn1] | H | —CH₃ | —CH₃ | 1 | 1 | trans |
| 79 | =CH—CH=CH— | 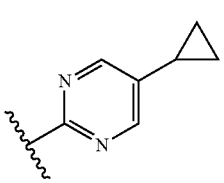 [SMILES: *c1ncc(C2CC2)cn1] | H | —CH₃ | —CH₃ | 1 | 1 | trans |
| 80 | =CH—CH=CH— | 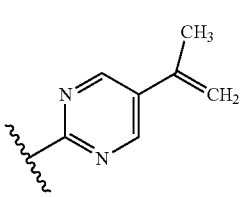 [SMILES: *c1ncc(C(=C)C)cn1] | H | —CH₃ | —CH₃ | 1 | 1 | trans |

TABLE 2-continued

Examples of embodiments of compounds of Formula (IB)

| Ex. # | =X—Y=Z— | R¹ | R² | R⁶ | R⁷ | p | q | Relative stereochemistry at *C |
|---|---|---|---|---|---|---|---|---|
| 81 | =CH—CH=CH— | 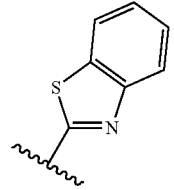 [SMILES: *c1nc2ccccc2s1] | H | —CH₃ | —CH₃ | 1 | 1 | cis |
| 82 | =CH—CH=CH— | 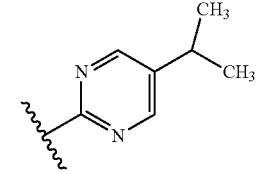 [SMILES: *c1ncc(C(C)C)cn1] | H | —CH₃ | —CH₃ | 1 | 1 | trans |
| 83 | =CH—CH=CH— | 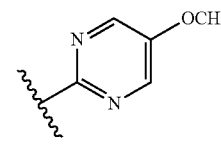 | H | —CH₃ | —CH₃ | 1 | 1 | trans |
| 84 | =CH—CH=N— | 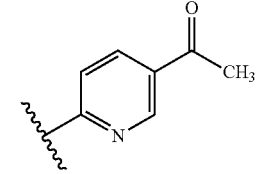 [SMILES: *c1ccc(C(C)=O)cn1] | H | —CH₃ | —CH₃ | 1 | 1 | trans |

| Ex. # | Chemical name |
|---|---|
| 29 | 6-((trans-3-(3,3-dimethyl-2-oxo-2,3-dihydro-1H-pyrrolo[2,3-b]pyridin-1-yl)cyclobutyl)amino)-N-methylnicotinamide |
| 30 | 1-(trans-3-(benzo[d]thiazol-2-ylamino)cyclobutyl)-3,3-dimethyl-1H-pyrrolo[2,3-b]pyridin-2(3H)-one |
| 31 | 1'-(Trans-3-(benzo[d]thiazol-2-ylamino)cyclobutyl)spiro[cyclopropane-1,3'-pyrrolo[2,3-b]pyridin]-2'(1'H)-one |
| 32 | 1-(trans-3-((6-fluorobenzo[d]thiazol-2-yl)amino)cyclobutyl)-3,3-dimethyl-1H-pyrrolo[2,3-b]pyridin-2(3H)-one |
| 33 | 1'-(trans-3-(1,3-benzothiazol-2-ylamino)cyclobutyl)-5'-fluorospiro[cyclopropane-1,3'-pyrrolo[2,3-b]pyridin]-2'(1'H)-one |
| 34 | 5-(trans-3-(benzo[d]thiazol-2-ylamino)cyclobutyl)-7,7-dimethyl-5H-pyrrolo[2,3-b]pyrazin-6(7H)-one |
| 35 | 1'-(trans-3-(benzo[d]thiazol-2-ylamino)cyclobutyl)spiro[cyclobutane-1,3'-pyrrolo[2,3-b]pyridin]-2'(1'H)-one |
| 36 | 1'-(Trans-3-(benzo[d]thiazol-2-ylamino)cyclobutyl)spiro[cyclopentane-1,3'-pyrrolo[2,3-b]pyridin]-2'(1'H)-one |
| 37 | 1'-(Trans-3-(benzo[d]thiazol-2-ylamino)cyclobutyl)-2,3,5,6-tetrahydrospiro[pyran-4,3'-pyrrolo[2,3-b]pyridin]-2'(1'H)-one |
| 38 | 3,3-Dimethyl-1-(trans-3-(5-methylpyridin-2-yl)amino)cyclobutyl-1H-pyrrolo[2,3-b]pyridin-2(3H)-one |
| 39 | 1-(Trans-3-((5-methoxypyridin-2-yl)amino)cyclobutyl-3,3-dimethyl-1H-pyrrolo[2,3-b]pyridin-2(3H)-one |
| 40 | 1-(Trans-3-((5-bromopyridin-2-yl)amino)cyclobutyl)-3,3-dimethyl-1H-pyrrolo[2,3-b]pyridin-2(3H)-one |
| 41 | 1-(Trans-3-((5-cyclopropylpyridin-2yl)amino)cyclobutyl)-3,3-dimethyl-1H-pyrrolo[2,3-b]pyridin-2(3H)-one |
| 42 | 1-(Trans-3-((5-chloropyridin-2-yl)amino)cyclobutyl)-3,3-dimethyl-1H-pyrrolo[2,3-b]pyridin-2(3H)-one |
| 43 | 1-(trans-3-((5-acetylpyridin-2-yl)amino)cyclobutyl)-3,3-dimethyl-1H-pyrrolo[2,3-b]pyridin-2(3H)-one |
| 44 | 1-(trans-3-(benzo[d]thiazol-2-ylamino)cyclobutyl)-1H-pyrrolo[2,3-b]pyridin-2(3H)-one |
| 45 | 1-(Trans-3-((3-methoxypyridin-2-yl)amino)cyclobutyl)-3,3-dimethyl-1H-pyrrolo[2,3-b]pyridin-2(3H)-one |
| 46 | 1-(Trans-3-((5-trifluoromethylpyridin-2-yl)amino)cyclobutyl)-3,3-dimethyl-1H-pyrrolo[2,3-b]pyridin-2(3H)-one |
| 47 | 1-(trans-3-((5-ethylpyrimidin-2-yl)amino)cyclobutyl)-3,3-dimethyl-1H-pyrrolo[2,3-b]pyridin-2(3H)-one |
| 48 | 1-(trans-3-((5-methylpyrimidin-2-yl)amino)cyclobutyl)-3,3-dimethyl-1H-pyrrolo[2,3-b]pyridin-2(3H)-one |
| 49 | 5-(trans-3-((5-chloropyridin-2-yl)cyclobutyl)-7,7-dimethyl-5H-pyrrolo[2,3-b]pyrazin-6(7H)-one |
| 50 | 1-(trans-3-(bis(5-methoxypyridin-2-yl)amino)cyclobutyl)-3,3-dimethyl-1H-pyrrolo[2,3-b]pyridin-2(3H)-one |
| 51 | 1-(Trans-3-((4-methylpyridin-2-yl)amino)cyclobutyl)-3,3-dimethyl-1H-pyrrolo[2,3-b]pyridin-2(3H)-one |
| 52 | 1-(Trans-3-((3-fluoropyridin-2-yl)amino)cyclobutyl)-3,3-dimethyl-1H-pyrrolo[2,3-b]pyridin-2(3H)-one |
| 53 | 1-(Trans-3-((3-methylpyridin-2-yl)amino)cyclobutyl)-3,3-dimethyl-1H-pyrrolo[2,3-b]pyridin-2(3H)-one |
| 54 | 1-(Trans-3-((5-fluoropyridin-2-yl)amino)cyclobutyl)-3,3-dimethyl-1H-pyrrolo[2,3-b]pyridin-2(3H)-one |
| 55 | 3,3-Dimethyl-1-(trans-3-(thiazol-2-ylamino)cyclobutyl)-1H-pyrrolo[2,3-b]pyridine-2(3H)-one |
| 56 | N-(6-((Trans-3-(3,3-dimethyl-2-oxo-2,3-dihydro-1H-pyrrolo[2,3-b]pyridine-1-yl)cyclobutyl)amino)pyridine-3-yl)acetamide |
| 57 | 1-(trans-3-((3-choloropyridin-2-yl)amino)cyclobutyl-3,3-dimethyl-1H-pyrrolo[2,3-b]pyridin-2(3H)-one |
| 58 | 1-(trans-3-((4-methoxypyrimidin-2-yl)amino)cyclobutyl)-3,3-dimethyl-1H-pyrrolo[2,3-b]pyridin-2(3H)-one |

| Ex. # | Chemical name |
|---|---|
| 59 | 1-(Trans-3-((5-cyanopyridin-2-yl)amino)cyclobutyl)-3,3-dimethyl-1H-pyrrolo[2,3-b]pyridin-2(3H)-one |
| 60 | 1-(trans-3-((5-bromopyrimidin-2-yl)amino)cyclobutyl)-3,3-dimethyl-1H-pyrrolo[2,3-b]pyridin-2(3H)-one |
| 61 | 1-(trans-3-((5-chloropyrimidin-2-yl)amino)cyclobutyl)-3,3-dimethyl-1H-pyrrolo[2,3-b]pyridin-2(3H)-one |
| 62 | 1-(trans-3-((pyrimidin-2-yl)amino)cyclobutyl)-3,3-dimethyl-1H-pyrrolo[2,3-b]pyridin-2(3H)-one |
| 63 | 1-(trans-3-((4-methylpyrimidin-2-yl)amino)cyclobutyl)-3,3-dimethyl-1H-pyrrolo[2,3-b]pyridin-2(3H)-one |
| 64 | 1-(trans-3-((4-chloropyrimidin-2-yl)amino)cyclobutyl)-3,3-dimethyl-1H-pyrrolo[2,3-b]pyridin-2(3H)-one |
| 65 | 3,3-Dimethyl-1-(trans-3-(pyrazin-2-ylamino)cyclobutyl)-1H-pyrrolo[2,3-b]pyridine-2(3H)-one |
| 66 | 1-(trans-3-((6-chloropyridin-2-yl)amino)cyclobutyl)-3,3-dimethyl-1H-pyrrolo[2,3-b]pyridin-2(3H)-one |
| 67 | 1-(trans-3-((4-trifluoromethyl)pyrimidin-2-yl)amino)cyclobutyl)-3,3-dimethyl-1H-pyrrolo[2,3-b]pyridin-2(3H)-one |
| 68 | 3,3-Dimethyl-1-(trans-3-(pyridazin-3-ylamino)cyclobutyl)-1H-pyrrolo[2,3-b]pyridine-2(3H)-one |
| 69 | 3,3-Dimethyl-1-(trans-3-((4-phenylthiazol-2-yl)amino)cyclobutyl)-1H-pyrrolo[2,3-b]pyridine-2(3H)-one |
| 70 | 1-(trans-3-((5-(trifluoromethyl)pyrimidin-2-yl)amino)cyclobutyl)-3,3-dimethyl-1H-pyrrolo[2,3-b]pyridin-2(3H)-one |
| 71 | 1-(trans-3-((5-fluoropyrimidin-2-yl)amino)cyclobutyl)-3,3-dimethyl-1H-pyrrolo[2,3-b]pyridin-2(3H)-one |
| 72 | 1-(trans-3-((2-cholropyrimidin-4-yl)amino)cyclobutyl)-3,3-dimethyl-1H-pyrrolo[2,3-b]pyridin-2(3H)-one |
| 73 | 7,7-Dimethyl-5-(trans-3-((5-methylpyridin-2-yl)amino)cyclobutyl)-5H-pyrrolo[2,3-b]pyrazin-6(7H)-one |
| 74 | 5-(trans-3-((5-methoxypyridin-2-ylamino)cyclobutyl)-7,7-dimethyl-5H-pyrrolo[2,3-b]pyrazin-6(7H)-one |
| 75 | 7,7-Dimethyl-5-(trans-4-((5-methylpyridin-2-yl)amino)cyclohexyl)-5H-pyrrolo[2,3-b]pyrazin-6(7H)-one |
| 76 | 5-(trans-3-((5-fluoropyridin-2-yl)amino)cyclobutyl)-7,7-dimethyl-5H-pyrrolo[2,3-b]pyrazin-6(7H)-one |
| 77 | 3,3-Dimethyl-1-(trans-4-((5-methylpyridin-2-yl)amino)cyclohexyl)-1H-pyrrolo[2,3-b]pyridin-2(3H)-one |
| 78 | 5-(trans-3-((5-cyclopropylpyridin-2-yl)amino)cyclobutyl)-7,7-dimethyl-5H-pyrrolo[2,3-b]pyrazin-6(7H)-one |
| 79 | 1-(trans-3-((5-cyclopropylpyrimidin-2-yl)amino)cyclobutyl)-3,3-dimethyl-1H-pyrrolo[2,3-b]pyridin-2(3H)-one |
| 80 | 3,3-Dimethyl-1-(trans-3-((5-(prop-1-en-2-yl)pyrimidin-2-yl)amino)cyclobutyl)-1H-pyrrolo[2,3-b]pyridin-2(3H)-one |
| 81 | 1-(Cis-3-(benzo[d]thiazol-2-ylamino)cyclobutyl)-3,3-dimethyl-1H-pyrrolo[2,3-b]pyridin-2(3H)-one |
| 82 | 1-(trans-3-((5-isopropylpyrimidin-2-yl)amino)cyclobutyl)-3,3-dimethyl-1H-pyrrolo[2,3-b]pyridin-2(3H)-one |
| 83 | 1-(trans-3-((5-methoxypyrimidin-2-yl)amino)cyclobutyl)-3,3-dimethyl-1H-pyrrolo[2,3-b]pyridin-2(3H)-one |
| 84 | 5-(trans-3-((5-acetylpyridin-2-yl)amino)cyclobutyl)-7,7-dimethyl-5H-pyrrolo[2,3-b]pyrazin-6(7H)-one |

Table 3 shows examples of embodiments of compounds of Formula (I), wherein the group —W-T-D< is —NR$^7$—(C=O)—N< or —O—(C=O)—N<; E is N; G is —NR$^1$R$^2$; and R$^{3a}$, R$^{3b}$, and R$^{3c}$ are hydrogens; as shown in compounds of Formula (IC) below:

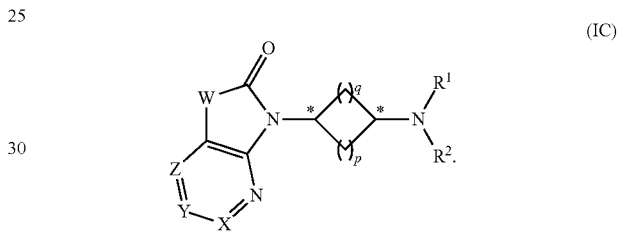

(IC)

TABLE 3

Examples of embodiments of compounds of Formula (IC)

| Ex # | =X—Y=Z— | R$^1$ | R$^2$ | W | P | q | Relative stereochemistry at *C |
|---|---|---|---|---|---|---|---|
| 85 | =CH—CH=CH— | benzo[d]thiazol-2-yl | H | cyclopropyl-N | 1 | 1 | trans |
| 86 | =CH—CF=CH— | benzo[d]thiazol-2-yl | H | N(CH$_3$) | 1 | 1 | trans |
| 87 | =CH—CF=CH— | benzo[d]thiazol-2-yl | H | cyclopropyl-N | 1 | 1 | trans |

TABLE 3-continued

Examples of embodiments of compounds of Formula (IC)

| Ex # | =X—Y=Z— | R¹ | R² | W | P | q | Relative stereochemistry at *C |
|---|---|---|---|---|---|---|---|
| 88 | =CH—CH=CH— | benzothiazole | H | N(CH₃) | 1 | 1 | trans |
| 89 | =CH—CH=CH— | benzothiazole | H | N-cyclopentyl | 1 | 1 | trans |
| 90 | =CH—CH=N— | benzothiazole | H | N-cyclopropyl | 1 | 1 | trans |
| 91 | =CH—N=CH— | benzothiazole | H | N-cyclopropyl | 1 | 1 | trans |
| 92 | =CH—CH=CH— | F-benzothiazole | H | NH | 1 | 1 | trans |
| 93 | =CH—N=CH— | benzothiazole | H | N(CH₃) | 1 | 1 | trans |
| 94 | =CH—CH=CH— | benzothiazole | H | NH | 1 | 1 | trans |

TABLE 3-continued

Examples of embodiments of compounds of Formula (IC)

| Ex # | =X—Y=Z— | R¹ | R² | W | P | q | Relative stereo-chemistry at *C |
|---|---|---|---|---|---|---|---|
| 95 | =CH—CH=N— | benzothiazol-2-yl | H | N(CH₃) | 1 | 1 | trans |
| 96 | =CH—CH=CH— | quinolin-2-yl | H | NH | 1 | 1 | trans |
| 97 | =CH—N=CH— | benzothiazol-2-yl | H | NH | 1 | 1 | trans |
| 98 | =CH—CH=CH— | 7-fluorobenzothiazol-2-yl | H | NH | 1 | 1 | trans |
| 99 | =CH—CH=CH— | 5-fluorobenzothiazol-2-yl | H | NH | 1 | 1 | trans |
| 100 | =CH—CH=CH— | benzothiazol-2-yl | H | —O— | 1 | 1 | trans |
| 101 | =CH—CH=CH— | 7-fluoroquinolin-2-yl | H | NH | 1 | 1 | trans |

TABLE 3-continued

Examples of embodiments of compounds of Formula (IC)

| Ex # | =X—Y=Z— | R¹ | R² | W | P | q | Relative stereo-chemistry at *C |
|---|---|---|---|---|---|---|---|
| 102 | =CH—CH=CH— | quinazolin-2-yl | H | NH | 1 | 1 | trans |
| 103 | =CH—CH=CH— | benzothiazol-2-yl | H | NH | 1 | 1 | cis |
| 104 | =CH—CH=CH— | benzothiazol-2-yl | H | NH | 2 | 2 | trans |
| 105 | =CH—CH=CH— | 7-OCH₃-quinolin-2-yl | H | NH | 1 | 1 | trans |
| 106 | =CH—CH=CH— | benzothiazol-2-yl | H | N-CH₃ | 1 | 1 | cis |
| 107 | =CH—CH=CH— | 6-F-benzothiazol-2-yl | H | NH | 2 | 2 | trans |
| 108 | =CH—CH=CH— | quinolin-2-yl | H | NH | 2 | 2 | trans |

TABLE 3-continued

Examples of embodiments of compounds of Formula (IC)

| Ex # | =X—Y=Z— | R¹ | R² | W | P | q | Relative stereo-chemistry at *C |
|---|---|---|---|---|---|---|---|
| 109 | =CH—CH=CH— | 7-fluoroquinazolin-2-yl | H | NH (cyclobutyl linker) | 1 | 1 | trans |
| 110 | =CH—CH=CH— | quinazolin-2-yl | H | NH (cyclobutyl linker) | 2 | 2 | trans |
| 111 | =CH—CH=CH— | 7-fluoroquinolin-2-yl | H | NH (cyclobutyl linker) | 2 | 2 | trans |
| 112 | =CH—CH=CH— | 7-chloroquinazolin-2-yl | H | NH (cyclobutyl linker) | 2 | 2 | trans |

And are named as follows:

| Ex. # | Chemical name |
|---|---|
| 85 | 3-(trans-3-(benzo[d]thiazol-2-ylamino)cyclobutyl)-1-cyclopropyl-1H-imidazo[4,5-b]pyrdin-2(3H)-one |
| 86 | 3-(trans-3-(benzo[d]thiazol-2-ylamino)cyclobutyl)-6-fluoro-1-methyl-1H-imidazo[4,5-b]pyridin-2(3H)-one |
| 87 | 3-(trans-3-(benzo[d]thiazol-2-ylamino)cyclobutyl)-1-cyclopropyl-6-fluoro-1H-imidazo[4,5-b]pyridin-2(3H)-one |
| 88 | 3-(trans-3-(benzo[d]thiazol-2-ylamino)cyclobutyl)-1-methyl-1H-imidazo[4,5-b]pyridin-2(3H)-one |
| 89 | 3-(trans-3-(benzo[d]thiazol-2-ylamino)cyclobutyl)-1-cyclopentyl-1H-imidazo[4,5-b]pyridin-2(3H)-one |
| 90 | 1-(trans-3-(benzo[d]thiazol-2-ylamino)cyclobutyl)-3-cyclopropyl-1H-imidazo[4,5-b]pyrazin-2(3H)-one |
| 91 | 9-(trans-3-(benzo[d]thiazol-2-ylamino)cyclobutyl)-7-cyclopropyl-7H-purin-8(9H)-one |
| 92 | 3-(trans-3-((6-fluorobenzo[d]thiazol-2-yl)amino)cyclobutyl)-1H-imidazo[4,5-b]pyridin-2(3H)-one |
| 93 | 9-(trans-3-(benzo[d]thiazol-2-ylamino)cyclobutyl)-7-methyl-7H-purin-8(9H)-one |
| 94 | 3-(trans-3-(benzo[d]thiazol-2-ylamino)cyclobutyl)-1H-imidazo[4,5-b]pyridin-2(3H)-one |
| 95 | 1-(trans-3-(benzo[d]thiazol-2-ylamino)cyclobutyl)-3-methyl-1H-imidazo[4,5-b]pyrazin-2(3H)-one |
| 96 | 3-(trans-3-(quinolin-2-ylamino)cyclobutyl)-1H-imidazo[4,5-b]pyridin-2(3H)-one |
| 97 | 9-(trans-3-(benzo[d]thiazol-2-ylamino)cyclobutyl)-7H-purin-8(9H)-one |
| 98 | 3-(trans-3-((4-fluorobenzo[d]thiazol-2-yl)amino)cyclobutyl-1H-imidazo[4,5-b]pyridin-2(3H)-one |
| 99 | 3-(trans-3-((5-fluorobenzo[d]thiazol-2-yl)amino)cyclobutyl)-1H-imidazo[4,5-b]pyridin-2(3H)-one |
| 100 | 3-(trans-3-(benzo[d]thiazol-2-ylamino)cyclobutyl)oxazolo[4,5-b]pyridin-2(3H)-one |
| 101 | 3-(trans-3-((7-fluoroquinolin-2-yl)amino)cyclobutyl)-1H-imidazo[4,5-b]pyridin-2(3H)-one |

| Ex. # | Chemical name |
|---|---|
| 102 | 3-(trans-3-(quinazolin-2-ylamino)cyclobutyl)-1H-imidazo[4,5-b]pyridin-2(3H)-one |
| 103 | 3-(cis-3-(benzo[d]thiazol-2-ylamino)cyclobutyl)-1H-imidazo[4,5-b]pyridin-2(3H)-one |
| 104 | 3-(trans-4-(benzo[d]thiazol-2-yl)amino)cyclohexyl)-1H-imidazo[4,5-b]pyridin-2(3H)-one |
| 105 | 3-(trans-3-((7-methoxyquinolin-2-yl)amino)cyclobutyl)-1H-imidazo[4,5-b]pyridin-2(3H)-one |
| 106 | 3-(cis-3-(benzo[d]thiazol-2-yl(methyl)amino)cyclobutyl)-1-methyl-1H-imidazo[4,5-b]pyridin-2(3H)-one |
| 107 | 3-(trans-4-((5-fluorobenzo[d]thiazol-2-yl)amino)cyclohexyl)-1H-imidazo[4,5-b]pyridin-2(3H)-one |
| 108 | 3-(trans-4-(quinolin-2-ylamino)cyclohexyl)-1H-imidazo[4,5-b]pyridin-2(3H)-one |
| 109 | 3-(trans-3-((7-fluoroquinazolin-2-yl)amino)cyclobutyl)-1H-imidazo[4,5-b]pyridin-2(3H)-one |
| 110 | 3-(trans-4-(quinazolin-2-ylamino)cyclohexyl)-1H-imidazo[4,5-b]pyridin-2(3H)-one |
| 111 | 3-(trans-4-((7-fluoroquinolin-2-yl)amino)cyclohexyl)-1H-imidazo[4,5-b]pyridin-2(3H)-one |
| 112 | 3-(trans-4-((7-chloroquinazolin-2-yl)amino)cyclohexyl)-1H-imidazo[4,5-b]pyridin-2(3H)-one |

Table 4 shows examples of embodiments of compounds of Formula (I), wherein the group —W-T-D< is —$CR^8$=N—N<; E is N; G is —$NR^1R^2$; and $R^{3a}$, $R^{3b}$, and $R^{3c}$ are hydrogens; as shown in compounds of Formula (ID) below:

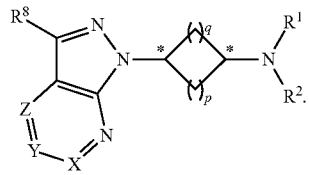

(ID)

TABLE 4

Examples of embodiments of compounds of Formula (ID)

| Ex. # | =X—Y=Z— | $R^1$ | $R^2$ | $R^8$ | p | q | Relative stereochemistry at *C |
|---|---|---|---|---|---|---|---|
| 113 | =CH—CH=CH— | 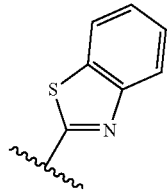 [SMILES: *c1nc2ccccc2s1] | H | —$NH_2$ | 1 | 1 | trans |
| 114 | =CH—CH=CH— | 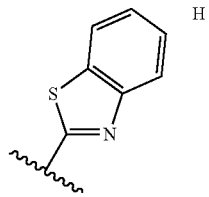 | H | Cyclopropyl | 1 | 1 | trans |

TABLE 4-continued

Examples of embodiments of compounds of Formula (ID)

| Ex. # | =X—Y=Z— | R¹ | R² | R⁸ | p | q | Relative stereo-chemistry at *C |
|---|---|---|---|---|---|---|---|
| 115 | =CH—CH=CH— | benzo[d]thiazol-2-yl | H | —CF₃ | 1 | 1 | trans |
| 116 | =CH—CH=CH— | benzo[d]thiazol-2-yl | H | 1-acetyl-piperidin-4-ylamino | 1 | 1 | trans |

And are named as follows:

| Ex. # | Chemical name |
|---|---|
| 113 | N-(trans-3-(3-amino-1H-pyrazolo[3,4-b]pyridin-1-yl)cyclobutyl)benzo[d]thiazol-2-amine |
| 114 | N-(trans-3-(3-cyclopropyl-1H-pyrazolo[3,4-b]pyridin-1-yl)cyclobutyl)benzo[d]thiazol-2-amine |
| 115 | N-(trans-3-(3-(trifluoromethyl)-1H-pyrazolo[3,4-b]pyridin-1-yl)cyclobutyl)benzo[d]thiazol-2-amine |
| 116 | 1-(4-((1-(trans-3-(benzo[d]thiazol-2-ylamino)cyclobutyl)-1H-pyrazolo[3,4-b]pyridin-3-yl)amino)piperidin-1-yl)ethanone |

Table 5 shows examples of embodiments of compounds of Formula (I), wherein the group —W-T-D< is —W—C (=O)—N<; =X—Y=Z— is =CH—CH=CH—; E is N; J is N; and R³ᵃ, R³ᵇ, and R³ᶜ are hydrogens; as shown in compounds of Formula (IE) below:

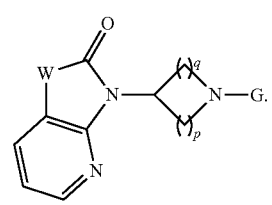

(IE)

TABLE 5

Examples of embodiments of compounds of Formula (IE)

| Ex # | G | W | p | q | Name |
|---|---|---|---|---|---|
| 117 | 1H-benzo[d]imidazol-2-ylcarbonyl | NH | 1 | 1 | 3-(1-(1H-benzo[d]imidazole-2-carbonyl)azetidin-3-yl)-1H-imidazo[4,5-b]pyridin-2(3H)-one |
| 118 | benzo[d]thiazol-2-ylcarbonyl | spirocyclopropane | 1 | 1 | 1'-(1-(benzo[d]thiazole-2-carbonyl)azetidin-3-yl)spiro[cyclopropane-1,3'-pyrrolo[2,3-b]pyridin-2'(1'H)-one |
| 119 | picolinoyl | 3,3-dimethyl | 2 | 2 | 3,3-dimethyl-1-(1-picolinoylpiperidin-4-yl)-1H-pyrrolo[2,3-b]pyridin-2(3H)-one |
| 120 | pyridin-2-yl | 3,3-dimethyl | 2 | 2 | 3,3-dimethyl-1-(1-(pyridin-2-yl)piperidin-4-yl)-1H-pyrrolo[2,3-b]pyridin-2(3H)-one |

TABLE 5-continued

Examples of embodiments of compounds of Formula (IE)

| Ex # | G | W | p | q | Name |
|---|---|---|---|---|---|
| 121 | 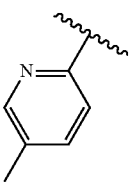 [SMILES: *c1ccc(C)cn1] | 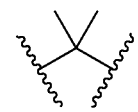 [SMILES: *C(*)(C)C] | 2 | 2 | 3,3-dimethyl-1-(1-(5-methylpyridin-2-yl)piperidin-4-yl)-1H-pyrrolo[2,3-b]pyridin-2(3H)-one |

Table 6 shows examples of embodiments of compounds of Formula (I), wherein the group —W-T-D< is —N=C(OCH$_3$)—N<; =X—Y=Z— is =CH—CH=CH—; E is N; and $R^{3a}$, $R^{3b}$, and $R^{3c}$ are hydrogens; as shown in compounds of Formula (IF) below:

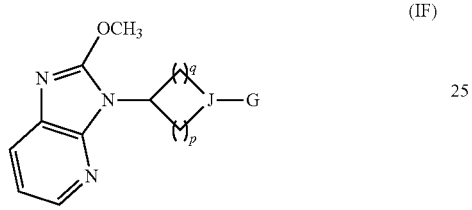

(IF)

TABLE 6

Examples of embodiments of compounds of Formula (IF)

| Ex. # | G | J | p | q | Chemical Name |
|---|---|---|---|---|---|
| 122 | 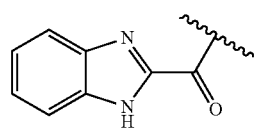 [SMILES: *C(=O)c1nc2ccccc2[nH]1] |  | 2 | 2 | (1H-Benzo[d]imidazol-2-yl)(4-(2-methoxy-3H-imidazo[4,5-b]pyridine-3-yl)piperidin-1-yl)methanone |
| 123 | 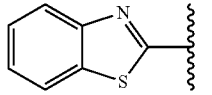 |  | 2 | 2 | 2-(4-(2-Methoxy-3H-imidazo[4,5-b]pyridin-3-yl)piperidin-1-yl)benzo[d]thiazole |
| 124 | 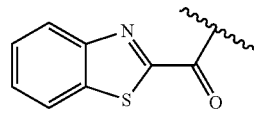 [SMILES: *C(=O)c1nc2ccccc2s1] |  | 2 | 2 | Benzo[d]thiazol-2-yl(4-(2-methoxy-3H-imidazo[4,5-b]pyridine-3-yl)piperidin-1-yl)methanone |
| 125 | 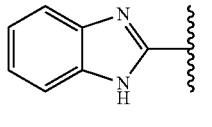 |  | 2 | 2 | 3-(1-(1-H-Benzo[d]imidazol-2-yl)piperidin-4-yl)-2-methoxy-3H-imidazo[4,5-b]pyridine |
| 126 | 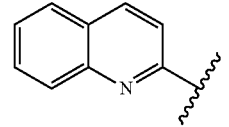 [SMILES: *c1ccc2ccccc2n1] |  | 1 | 1 | 2-(3-(2-Methoxy-3H-imidazo[4,5-b]pyridin-3-yl)azetidin-1-yl)quinoline |

TABLE 6-continued

Examples of embodiments of compounds of Formula (IF)

| Ex. # | G | J | p | q | Chemical Name |
|---|---|---|---|---|---|
| 127 | 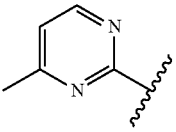 [SMILES: *c1nccc(C)n1] |  | 1 | 1 | 2-Methoxy-3-(1-(4-methylpyrimidin-2-yl)azetidin-3-yl)-3H-imidazo[4,5-b]pyridine |
| 128 | 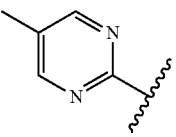 [SMILES: *c1ncc(C)cn1] |  | 1 | 1 | 2-Methoxy-3-(1-(5-methylpyrimidin-2-yl)azetidin-3-yl)-3H-imidazo[4,5-b]pyridine |
| 129 | 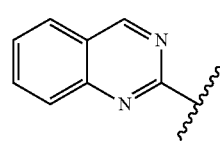 [SMILES: *c1ncc2ccccc2n1] |  | 1 | 1 | 2-(3-(2-Methoxy-3H-imidazo[4,5-b]pyridin-3-yl)azetidin-1-yl)quinazoline |
| 130 | 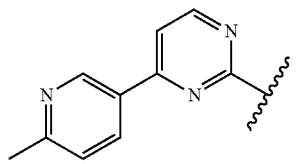 [SMILES: *c1nccc(-c2ccc(C)nc2)n1] |  | 1 | 1 | 2-Methoxy-3-(1-(4-(6-methylpyridin-3-yl)pyrimidin-2-yl)azetidin-3-yl)-3H-imidazo[4,5-b]pyridine |
| 131 | 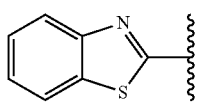 |  | 1 | 1 | 2-(3-(2-Methoxy-3H-imidazo[4,5-b]pyridin-3-yl)azetidin-1-yl)benzo[d]thiazole |
| 132 | 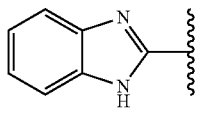 |  | 1 | 1 | 3-(1-(1H-benzo[d]imidazol-2-yl)azetidin-3-yl)-2-methoxy-3H-imidazo[4,5-b]pyridine |
| 133 | 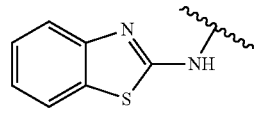 [SMILES: *Nc1nc2ccccc2s1] |  | 2 | 2 | N-(4-(2-methoxy-3H-imidazo[4,5-b]pyridin-3-yl)cyclohexyl)-1,3-benzothiazol-2-amine |
| 134 | 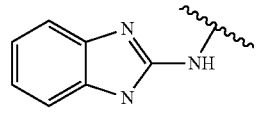 |  | 2 | 2 | N-(4-(2-methoxy-3H-imidazo[4,5-b]pyridin-3-yl)cyclohexyl)-1H-benzimidazol-2-amine |
| 135 | 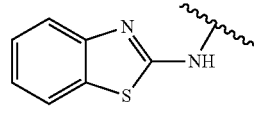 [SMILES: *Nc1nc2ccccc2s1] |  | 1 | 1 | N-(3-(2-methoxy-3H-imidazo[4,5-b]pyridin-3-yl)cyclobutyl)-1,3-benzothiazol-2-amine |
| 136 | 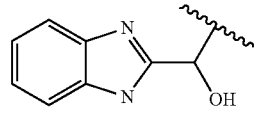 [SMILES: *C(O)c1nc2ccccc2[nH]1] |  | 1 | 1 | 1H-benzimidazol-2-yl(3-(2-methoxy-3H-imidazo[4,5-b]pyridin-3-yl)cyclobutyl)methanol |
| 137 | 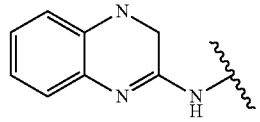 [SMILES: *NC1=Nc2ccccc2NC1] |  | 1 | 1 | N-(trans-3-(2-methoxy-3H-imidazo[4,5-b]pyridin-3-yl)cyclobutyl)-3,4-dihydro-2-quinoxalinamine |

Any combination of two or more of the embodiments described herein is considered within the scope of the present invention.

The compounds of this invention may have in general several asymmetric centers and are typically depicted in the form of mixtures of enantiomers, partially racemic mixtures, separate enantiomers, mixtures of diastereomers, or separate diastereomers.

The present invention includes all pharmaceutically acceptable isotopically-labelled compounds of the present invention wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2$H and $^3$H, carbon, such as $^{11}$C, $^{13}$C and $^{14}$C, chlorine, such as $^{38}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the present invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Specific embodiments of the present invention include the compounds exemplified in the Examples below and their pharmaceutically acceptable salts, complexes, solvates, polymorphs, stereoisomers, metabolites, prodrugs, and other derivatives thereof, Unless otherwise specified, the following definitions apply to terms found in the specification and claims:

"$C_{\alpha-\beta}$alk" means an alkyl group comprising a minimum of α and a maximum of β carbon atoms in a branched, cyclical or linear relationship or any combination of the three, wherein α and β represent integers. The alkyl groups described in this section may also contain one or two double or triple bonds. A designation of $C_0$alk indicates a direct bond. Examples of $C_{1-6}$alkyl include, but are not limited to the following:

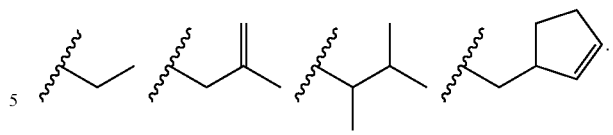

The terms "oxo" and "thioxo" represent the groups =O (as in carbonyl) and =S (as in thiocarbonyl), respectively.

"Halo" or "halogen" means a halogen atoms selected from F, Cl, Br and I.

"$C_{\alpha-\beta}$haloalk" means an alk group, as described above, wherein any number—at least one—of the hydrogen atoms attached to the alk chain are replaced by F, Cl, Br or I.

The term "carbon-linked" means a substituent is linked to another group through a carbon atom. Examples of "carbon-linked" substituents include, but are not limit to the following:

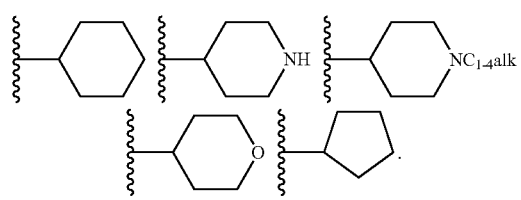

The term "nitrogen-linked" means a substituent is linked to another group through a nitrogen atom. Examples of "nitrogen-linked" substituents include, but are not limited to the following:

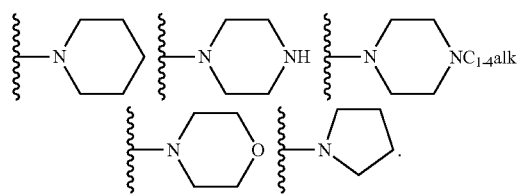

The group $NR^aR^a$ and the like include substituents where the two $R^a$ groups together form a ring, optionally including a N, O or S atom, and include groups such as:

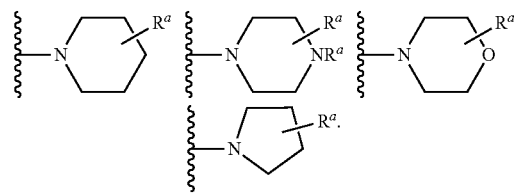

The group $N(C_{\alpha-\beta}alk)C_{\alpha-\beta}alk$, wherein α and β are as defined above, include substituents where the two $C_{\alpha-\beta}alk$ groups together form a ring, optionally including a N, O or S atom, and include groups such as:

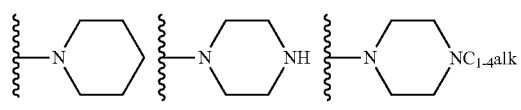

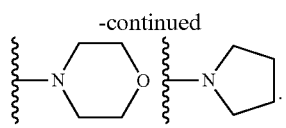

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially-saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups can be removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

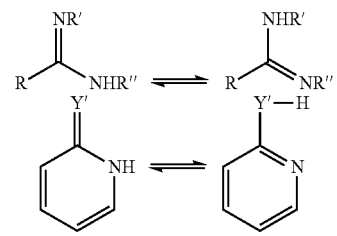

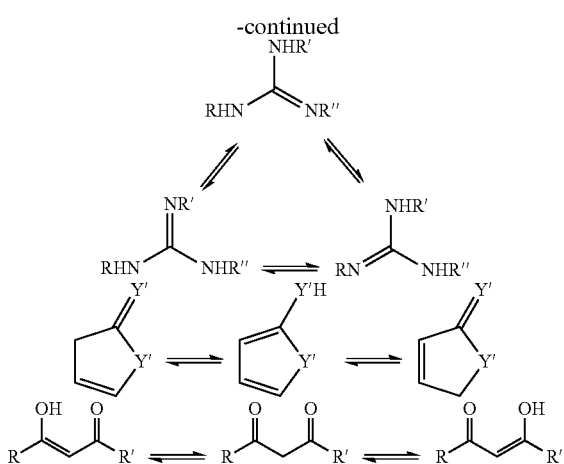

and though one form is named, described, displayed and/or claimed herein, all the tautomeric forms are intended to be inherently included in such name, description, display and/or claim. For example, compounds of Formula (IC) of the invention is designated as:

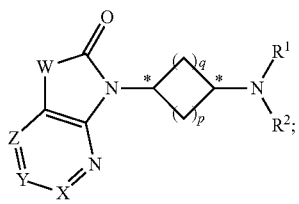

and those skilled in the art understand that such designation includes the tautomers below:

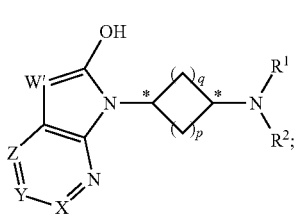

wherein W' is N or $CR^7$ or $NR^7$.

Prodrugs of the compounds of Formula (I) are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from the group consisting of . . . and . . . "; "is . . . or . . . "; and "selected from . . . is . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Sulfonyl" means a —$SO_2R$ radical where R is alkyl, haloalkyl, aryl, aralkyl, heteroaryl, heteroaralkyl, heterocyclyl, heterocyclylalkyl, each as defined herein, e.g., methylsulfonyl, phenylsulfonyl, benzylsulfonyl, pyridinylsulfonyl, and the like.

The phrase in the definition of groups $R^1$ and $R^2$ in the claims and in the specification of this Application ". . . wherein the aforementioned rings are optionally substituted with $R^a$, $R^b$, or $R^c$ independently selected from . . . " and similar phrases used for others groups [e.g., $Ar^1$ and $Ar^2$ groups] in the claims and in the specification with respect to the compound of Formula (I) and (IA)-(IF), means that the rings can be mono-, di-, or trisubstituted unless indicated otherwise.

"Treating" or "treatment" of a condition or disease includes: preventing the disease, i.e. causing the clinical symptoms of the disease not to develop in a mammal that may be exposed to or predisposed to the disease but does not yet experience or display symptoms of the disease; inhibiting the disease, i.e., arresting or reducing the development of the disease or its clinical symptoms; or relieving the disease, i.e., causing regression of the disease or its clinical symptoms.

A "therapeutically effective amount" means the amount of a compound of Formula (I) that, when administered to a mammal for treating a disease, is sufficient to effect such treatment for the disease. The "therapeutically effective amount" will vary depending on the compound, the disease and its severity and the age, weight, etc., of the mammal to be treated.

GENERAL SYNTHETIC SCHEMES

In general, as appreciated to one of ordinary skill in the art, there are many different synthetic strategies for preparing compounds of Formula (I), as defined in the above summary of the invention.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of Formula (I) can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula (I), including (IA), (B), (IC), (ID), (IE), and (IF):

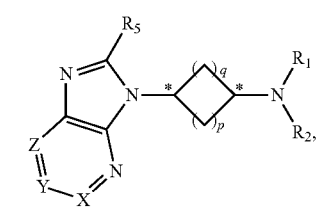

(IA)

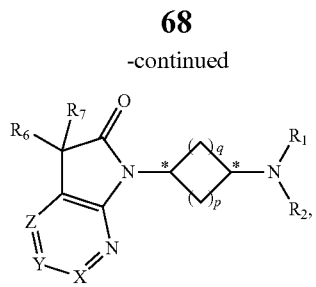

(IB)

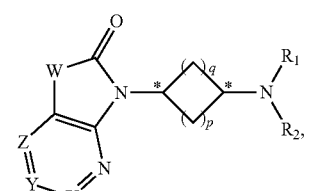

(IC)

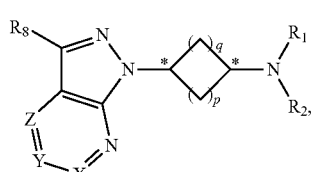

(ID)

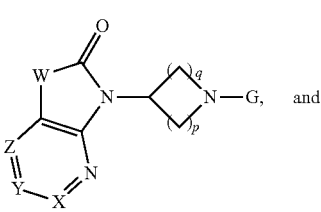

(IE)

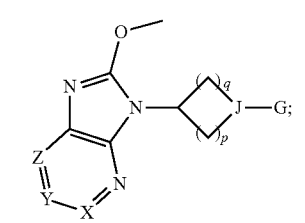

(IF)

as defined above, can be prepared according to according to the following General Schemes 1-11.

General Schemes 1 and 2: Preparation of Compounds of Formula (IA).

Compounds of Formula (IA): as defined above, can be prepared according to the following General Schemes 1a, 1b, and 2.

GENERAL SCHEME 1a

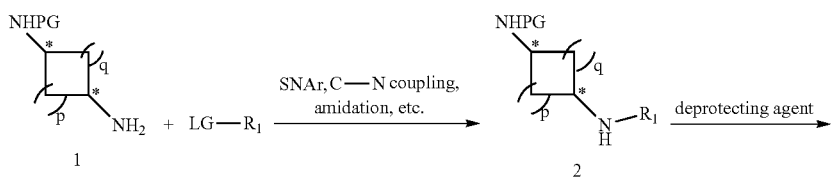

* can be cis or trans

-continued

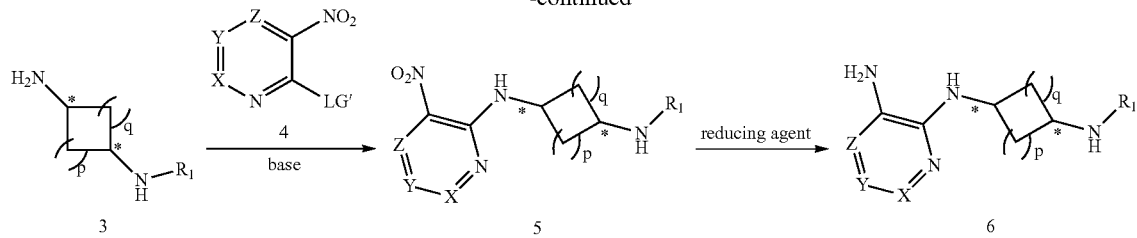

GENERAL SCHEME 1b

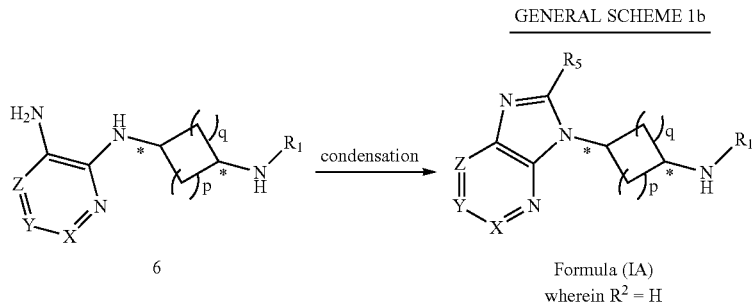

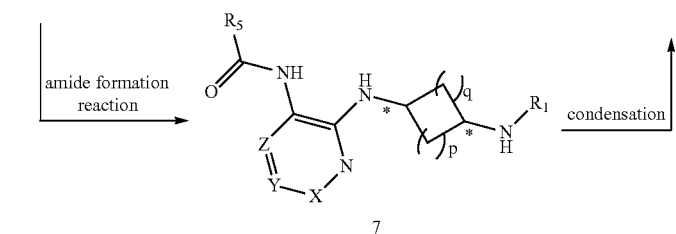

In General Scheme 1a, compound 1, wherein PG is an amine protecting group, such as tert-Butyloxycarbonyl (Boc) or Carbobenzyloxy (Cbz), is generally commercially available or can be synthesized via selective synthetic methods such as the methods described in *J. Org. Chem.* 2010, 75, 5941-5952. Compound 1, which can be cis or trans isomers, or mixtures thereof, can be reacted with $R^1$-LG, wherein LG is a leaving group such as halogen, sulfonate or perfluorosulfonate, in a suitable solvent such as DMSO or dioxane at ambient or more preferably at elevated temperature in the presence of a mild base, such as $Cs_2CO_3$, $K_2CO_3$, or amine base, such as triethylamine, to provide compound 2. Compound 2 is then reacted with an amine deprotecting agent, such as concentrated, strong acid (such as HCl or $CF_3COOH$), or hydrogenolysis condition, to afford compound 3, which can subsequently react with suitably substituted heterocyclic compounds 4 via a direct SNAr reaction or a metal-catalyzed C—N coupling reaction, wherein LG' is a leaving group such as halogen, sulfonate or perfluorosulfonate, to provide compound 5. Such SNAr reaction . . . C—N coupling . . . (copy from later section?) Compound 5 is then reacted with a nitro group reducing agent, such as $Fe/NH_4Cl$, $H_2/Pd$—C, or the like, to provide compound 6.

In General Scheme 1b, compound 6 can then be reacted under a coupling reaction condition with an appropriate acid, such as HATU coupling, or acid chloride containing $R^5$, wherein $R^5$ is an alkyl or aryl group, to give amide 7, which can be reacted under condensation or dehydration conditions to provide a compound of Formula (IA), wherein $R^5$ is an alkyl or aryl group. Compound 6 can be treated under condensation condition, such as with an orthocarbonate reagent under acidic condition, to provide a compound of Formula (IA), wherein $R^5$ is an alkoxy group.

Alternatively, as shown in General Scheme 2 below, compound 1, as described above in Scheme 1a, can be reacted in under coupling reaction condition, with a suitably substituted heterocyclic compound 4, as described above in Scheme 1a, in the presence of a solvent, such as DMSO, DMF, or dioxane, at ambient or more preferably at elevated temperature, in the presence of a mild base, such as $Cs_2CO_3$ or $K_2CO_3$, or amine base, such as triethylamine, to provide compound 8. Compound 8 can then be reacted with a reducing agent, such as $Fe/NH_4Cl$, $H_2/Pd$—C, or other appropriate reagents, to convert the nitro group to amino group and produce compound 9. Compound 9 can then be reacted under a coupling reaction condition with an appropriate acid, such as HATU coupling, or acid chloride containing $R^5$, wherein $R^5$ is an alkyl or aryl group, to give amide 10, which can be reacted under condensation or dehydration conditions to provide a compound of Formula (IA), wherein $R^5$ is an alkyl or aryl group. Compound 9 can be treated under condensation condition, such as with an orthocarbonate reagent under acidic condition, to provide compound 11, which can then be reacted with a amine deprotecting group, an amine deprotecting agent, such as concentrated, strong acid (such as HCl or $CF_3COOH$), or hydrogenolysis condition, followed by reaction with a reagent of formula $R^1$-LG, wherein LG is a leaving group, such as halogen, sulfonate or perfluorosulfonate, to provide a compound of Formula (IA), wherein $R^5$ is an alkoxy group.

GENERAL SCHEME 2:
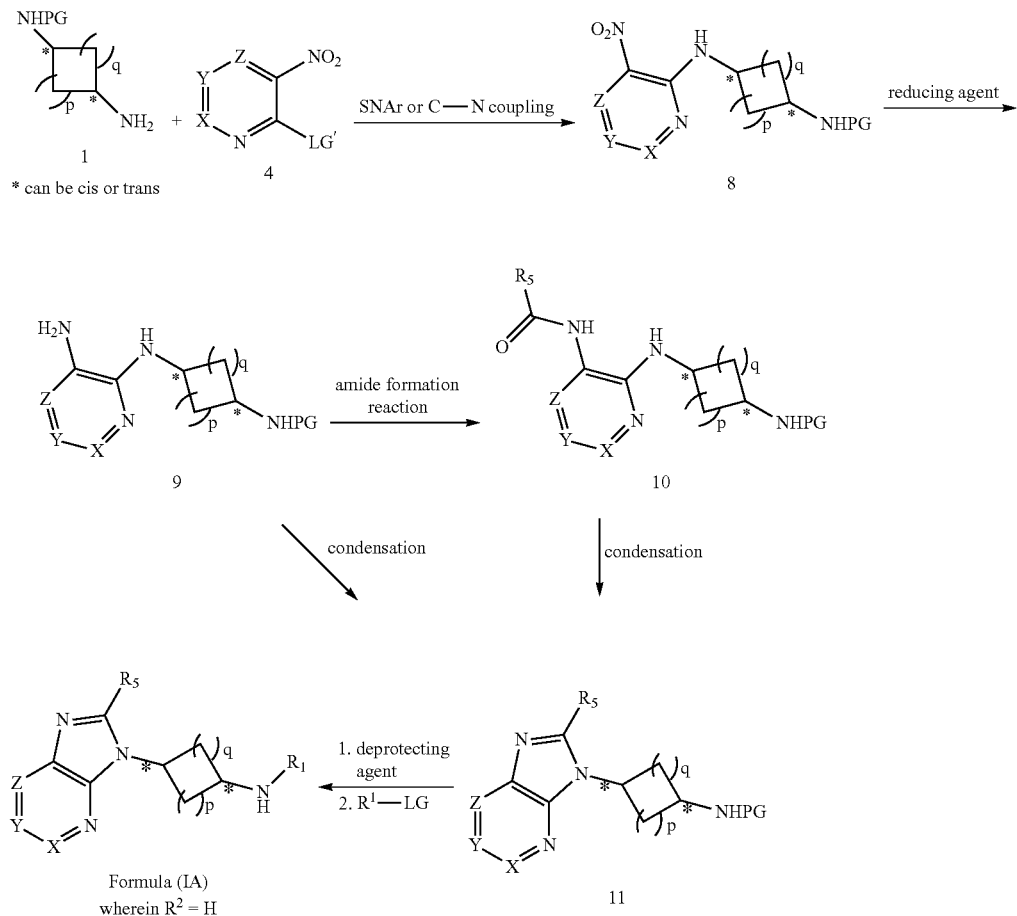
General Schemes 3, 4, and 5: Preparation of Compounds of Formula (IB).
Compounds of Formula (IB), as defined above, can be prepared according to the following General Schemes 3, 4, and 5.
GENERAL SCHEME 3
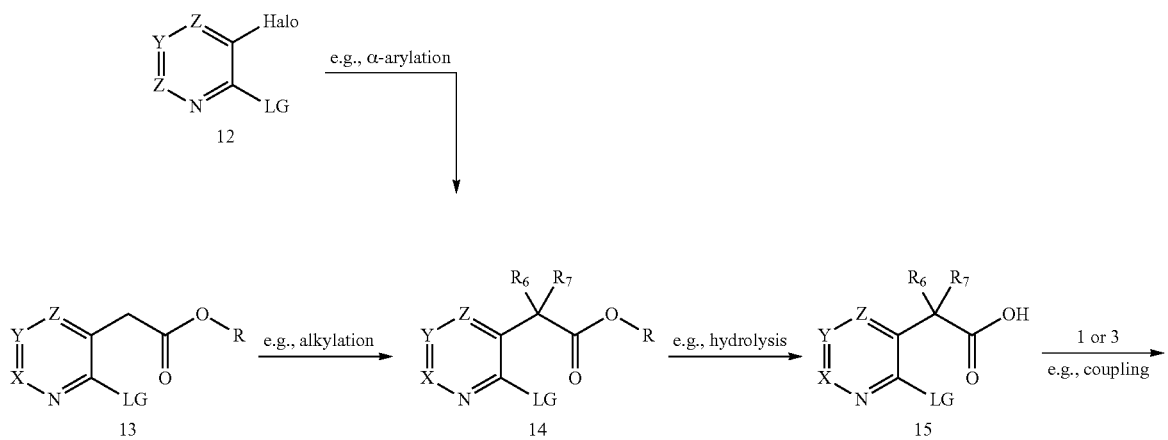
LG = leaving group
e.g., F, Cl, Br, etc.

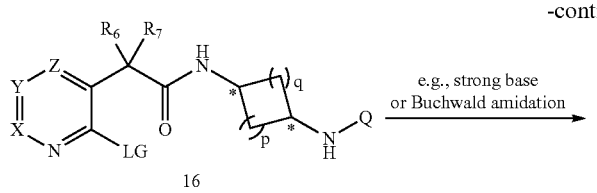

Q = R¹ or protecting group
(e.g., Boc or Cbz)

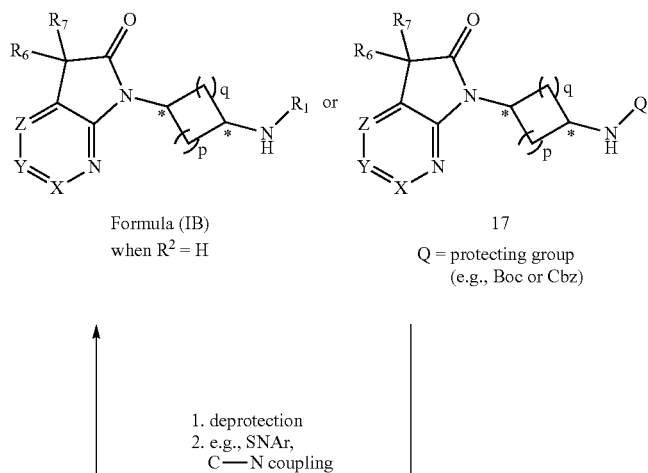

Formula (IB)
when R² = H

17
Q = protecting group
(e.g., Boc or Cbz)

1. deprotection
2. e.g., SNAr,
   C—N coupling

In General Scheme 3, compound of Formula (IB) can be prepared from compound 14. Compound 14, wherein LG is a leaving group such as halogen, sulfonate or perfluorosulfonate, and R is a $C_{1-6}$alkyl or benzyl, can be prepared under several reaction conditions, for example from compound 12 or compound 13. Compound 12 is generally commercially available or can be synthesized via selective synthetic methods as described in this invention as heterocyclic halide, preferably chloride, which can be converted to compound 14 by metal-catalyzed α-arylation reactions with suitably substituted acetates, such as tert-butyl isobutyrate. Compound 13 is generally commercially available heteroaryl substituted acetates, which can be converted to compound 14 by metal-catalyzed α-arylation, or under basic alkylation condition reactions, such as with the use of LiHMDS, with a suitably substituted alkylating or arylating agent containing $R^6$ and $R^7$, such as methyliodide or phenylbromide. Once formed, compound 14 can be reacted under hydrolysis reaction condition, to provide compound 15, which can then be reacted with compound 1 or compound 3, as defined in above Scheme 1a, to provide compound 16, wherein Q is an amine protecting group, such as Boc or Cbz, or $R^1$. When Q is an amine protecting group, compound 16 can then be reacted with a strong base, such as LiHMDS, at ambient or elevated temperatures to provide compound 17, wherein Q is a protecting group. Such protecting group can then be removed with a deprotecting agent, and the deprotected compound 17 may be reacted with $R^1$-LG under general coupling conditions, such as SNAr or C—N coupling, to provide a compound of Formula (IB). When Q is $R^1$, compound 16 can then be reacted with a strong base, such as LiHMDS, at ambient or elevated temperatures to provide compound 17, which is a compound of Formula (IB), as defined above. Alternatively, compound 16 may be reacted under Buchwald amidation conditions or similar conditions to provide compound 17.

Alternatively, as shown in General Scheme 4 below, compound of Formula (IB) can be prepared from compound 19. Compound 19 wherein LG is a leaving group such as halogen, sulfonate or perfluorosulfonate, can be prepared under several reaction conditions, for example from compound 12, as described above in General Scheme 3, or compound 18. Compound 12 can be converted to compound 19 by metal-catalyzed α-arylation reactions with a suitably substituted acetonitrile, such as 2,3-dichloropyrazine. Compound 18 is generally commercially available heteroaryl substituted acetonitrile, or can be prepared using the methods described in this invention, which can be converted to compound 19 by metal-catalyzed α-alkylation or arylation, or under basic condition reactions, such as NaH or NaHMDS, with a suitably substituted alkylating or arylating agent containing $R^6$ and $R^7$, such as 1-bromo-2-chloroethane or phenylbromide. Once formed, compound 19 can be reacted with compound 1, as defined in above Scheme 1a, in the presence of a strong base, such as LiHMDS or NaOtBu, at ambient or elevated temperatures, or under metal-catalyzed amination conditions, after acidic work up or acid treatment of reaction mixture at ambient or elevated temperature, to provide compound 17, wherein Q is a protecting group such as Carbobenzyloxy (Cbz) or H wherein tert-Butyloxycarbonyl (Boc) is the protecting group for 1. Such protecting group can then be removed with a deprotecting agent, and the deprotected compound 17 may then be reacted with $R^1$-LG under general coupling conditions, such as SNAr or C—N coupling, to provide a compound of Formula (IB). Alternatively, compound 19 can then be reacted with compound 3 in the presence of a strong base, such as LiHMDS, or under Buchwald conditions, at ambient or elevated temperatures to provide compound of Formula (IB), as defined above.

GENERAL SCHEME 4

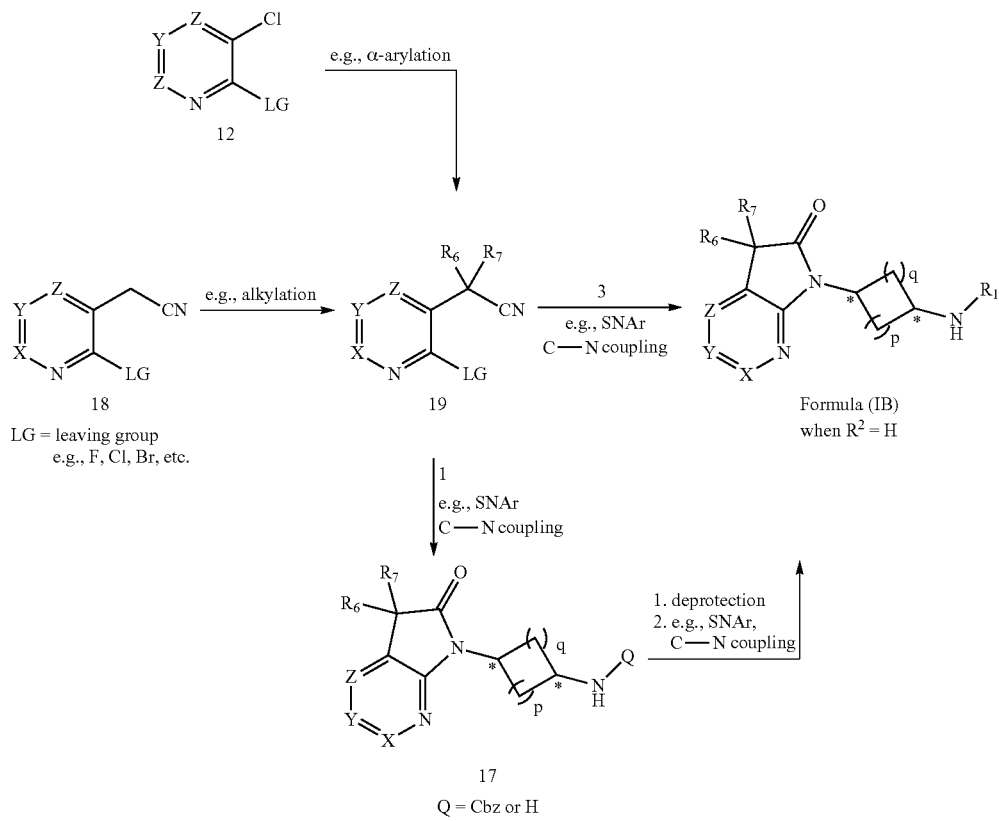

General Scheme 5 below describes a modified method of preparation for compounds of Formula (IB) of General Scheme 3, wherein $R^6$ is OH. In General Scheme 5, compound 12a is a generally commercially available heteroaryl bromide, which can be treated with a metal halide reagent, such as isopropyl MgCl, LiCl, or other reagents such as butyl lithium, sec-butyl lithium, or ten-butyl lithium, to form the reactive nucleophile via metal-halo exchange at ambient or lowered temperature (e.g., −78° C.), followed by treatment with suitably $R^7$-substituted α-keto acetates to provide compound 14a. Compound 14a is then reacted under hydrolysis condition to form compound 15a, which can then be converted to a compound of Formula (IB), wherein $R^6$ is hydroxy group, according to methods outlined in General Scheme 3 above.

GENERAL SCHEME 5

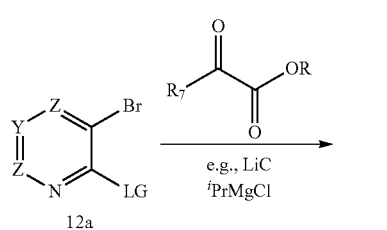

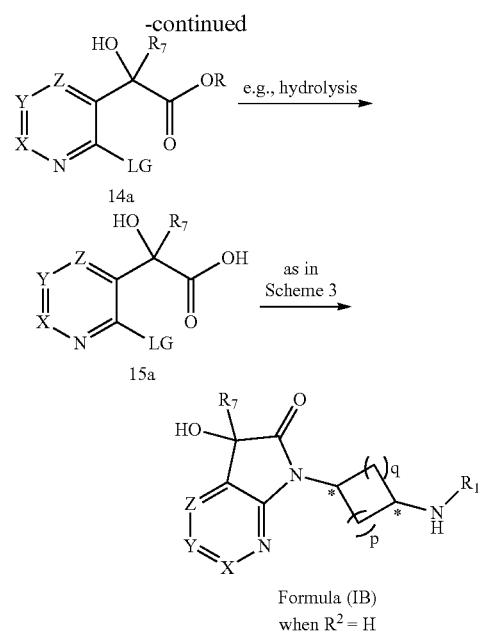

The above General Schemes 1, 2, 3, 4, and 5 provide methods of synthesis of compounds of Formulae (IA) and (IB) wherein in the final products, $R^2$ is H. Such compounds can be further reacted with R²-LG, wherein LG is a leaving group such as halogen, sulfonate or perfluorosulfonate, in sequential manner or together under more forcing conditions such as in the presence of strong bases and/or at more elevated temperatures, to form compounds of Formulae (IA) and (IB) wherein in the final products, R² is other than H.

In an alternate embodiment, reaction with R²-LG, wherein LG is a leaving group such as halogen, sulfonate or perfluorosulfonate, can be performed earlier in the methods, for example to compound 1 or compound 3, or any suitable compounds which may be ultimately converted to compounds of Formulae (IA) and (IB), wherein R² is other than H.

General Schemes 6, 7, and 8: Preparation of Compounds of Formula (IC).

Compounds of Formula (IC), as defined above, can be prepared according to the following General Schemes 6, 7, and 8.

In General Scheme 6, compound of Formula (IC), wherein the group —W-T-D< is —NR⁷—(C=O)—N<, E is N; G is —NR¹R², and R³ᵃ, R³ᵇ, and R³ᶜ are hydrogens, can be prepared by reacting compound 6, which can be prepared according to the above General Scheme 1a, with a cyclizating agent, such as CDI, triphosgene, optionally in the presence of a base, such as triethylamine, or orthoformate in the presence of an acid such as propionic acid, at ambient or elevated temperature to provide a compound of Formula (IC), wherein R² is H. Alternatively, compound of Formula (IC) can be prepared by reacting compound 9, which can be prepared according to the above General Scheme 2, with a cyclizating agent, such as CDI, triphosgene, optionally in the presence of a base, such as triethylamine, or orthoformate in the presence of an acid such as propionic acid, at ambient or elevated temperature to provide compound 20, wherein PG is an amine protecting group, such as Boc or Cbz, which can be deprotected with a deprotecting agent, such as hydrochloric acid, trifluoroacetic acid, or under hydrogenolysis condition, followed by reaction with a reagent of formula R¹-LG, wherein LG is a leaving group, such as halogen, sulfonate or perfluorosulfonate, to provide a compound of Formula (IC), wherein R² is H. Such compounds of Formula (IC), wherein R² is H, can be further reacted with R²-LG, wherein LG is a leaving group such as halogen, sulfonate or perfluorosulfonate, in the presence of a strong base and/or at more elevated temperatures, to form a compound of Formula (IC) wherein in the final products, R² is other than H.

GENERAL SCHEME 6

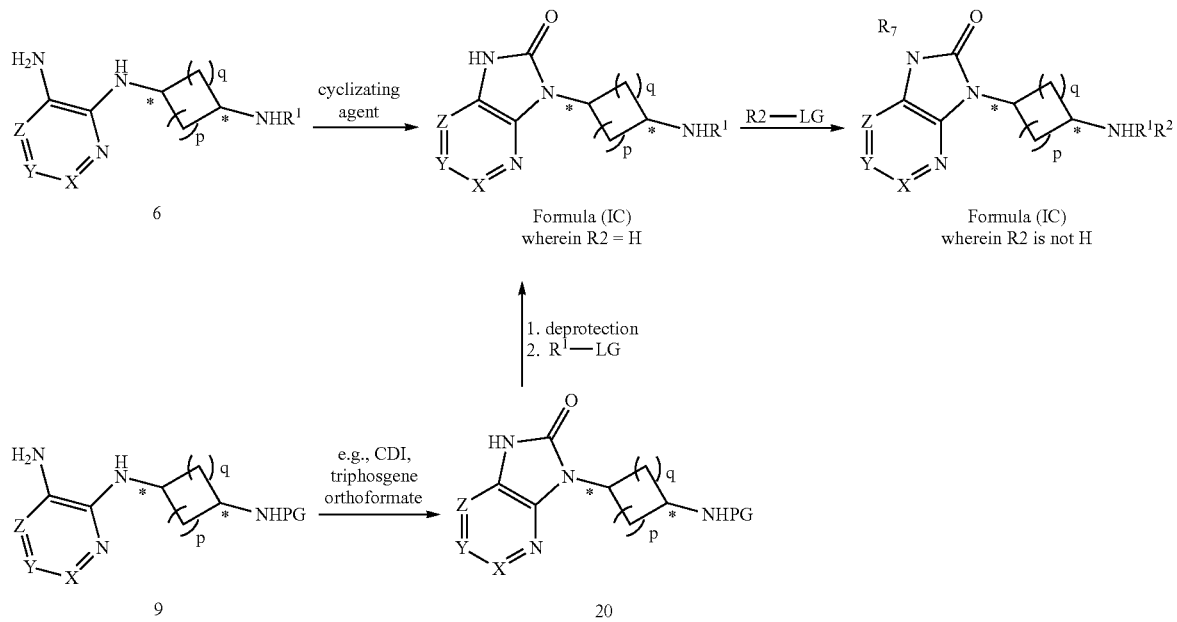

GENERAL SCHEME 7

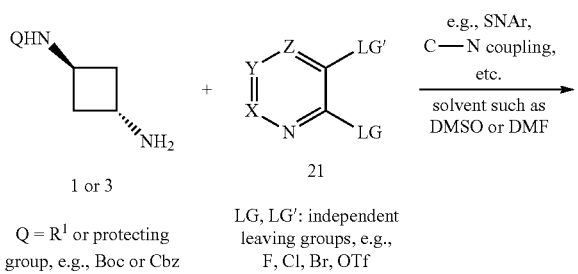

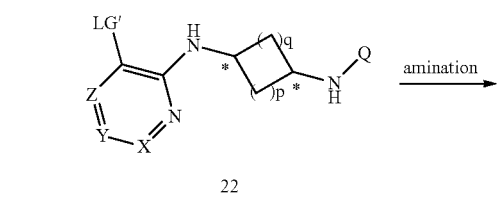

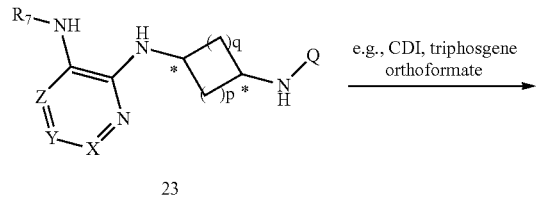

-continued

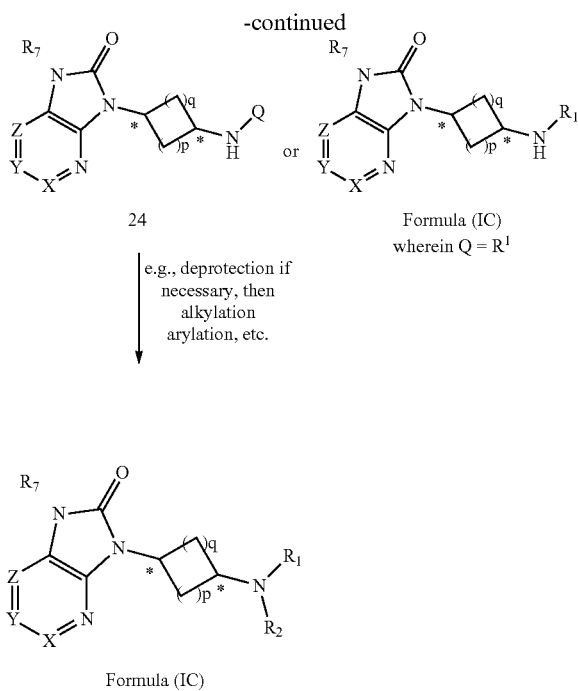

Alternatively, as shown in the above General Scheme 7, compound of Formula (IC) wherein the group —W-T-D< is —NR$^7$—(C=O)—N<, E is N; G is —NR$^1$R$^2$, and R$^{3a}$, R$^{3b}$, and R$^{3c}$ are hydrogens, can be prepared by reacting compound 1 or compound 3, as described in General Scheme 1a above, with compound 21, wherein each LG and LG' is independently a leaving group such as halogen, sulfonate or perfluorosulfonate, in the presence of a strong base, such as LiHMDS, at ambient or elevated temperatures, or under metal-catalyzed amination conditions, to provide compound 22, wherein Q is a protecting group or R$^1$ as defined herein, and LG' is a leaving group, such as halogen, sulfonate or perfluorosulfonate. Compound 22 can then be reacted with an amine reagent, such as R$^7$—NH$_2$, under metal catalyzed amination condition to provide compound 23. Compound 23 can then be reacted with a cyclizating agent, such as CDI, triphosgene, optionally in the presence of a base, such as triethylamine, or orthoformate in the presence of an acid such as propionic acid, at ambient or elevated temperature to provide compound 24, wherein Q is an amine protecting group, or provide a compound of Formula (IC) wherein Q is R$^1$. When Q is an amine protecting group, such protecting group of compound 24 can then be reacted with a deprotecting agent, such as hydrochloric acid, trifluoroacetic acid, or under hydrogenolysis condition, followed by reaction with a reagent of formula R$^1$-LG, wherein LG is a leaving group, such as halogen, sulfonate or perfluorosulfonate, to provide a compound of Formula (IC), wherein both R$^2$ is H. Such compound of Formula (IC) can be further reacted with R$^2$-LG, wherein LG is a leaving group such as halogen, sulfonate or perfluorosulfonate, in the presence of a strong base and/or at more elevated temperatures, to form a compound of Formula (IC), wherein in the final products, R$^2$ is other than H.

In an alternative embodiment, as described in General Scheme 8 below, compound of Formula (IC) wherein the group —W-T-D< is —O—(C=O)—N<, —O—CR$^6$R$^7$—(C=O)—N<, or —NR$^7$—CR$^6$R$^7$—(C=O)—N<, E is N; G is —NR$^1$R$^2$, and R$^{3a}$, R$^{3b}$, and R$^{3c}$ are hydrogens, can be prepared. In General Scheme 8, commercially available compound 25 is reacted with compound 26, wherein PG is an amine protecting group, and LG is a leaving group such as halogen, sulfonate or perfluorosulfonate, which can be accessed by methods described herein, in the presence of a base, such as LiHMDS or triethylamine, at ambient or elevated temperature, in suitable solvent, such as THF or DMF, to provide compound 27, wherein PG is an amine protecting group. Such protecting group of compound 27 can further be reacted according to method of General Scheme 7 above, with a deprotecting agent, such as hydrochloric acid, trifluoroacetic acid, or under hydrogenolysis condition, to provide a compound of Formula (IC), wherein both R$^1$ and R$^2$ are H. Such compound of Formula (IC) can be further reacted with R$^1$-LG, optionally followed by R$^2$-LG, wherein LG is a leaving group such as halogen, sulfonate or perfluorosulfonate, in the presence of a strong base and/or at more elevated temperatures, to form a compound of Formula (IC), wherein in the final products, R$^1$, R$^2$, or both R$^1$ and R$^2$ are independently other than H.

GENERAL SCHEME 8

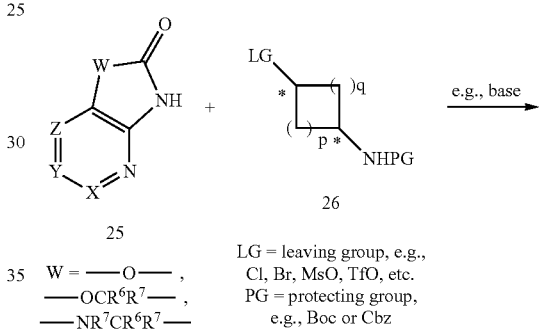

LG = leaving group, e.g., Cl, Br, MsO, TfO, etc.
PG = protecting group, e.g., Boc or Cbz

W = —O—,
—OCR$^6$R$^7$—,
—NR$^7$CR$^6$R$^7$—

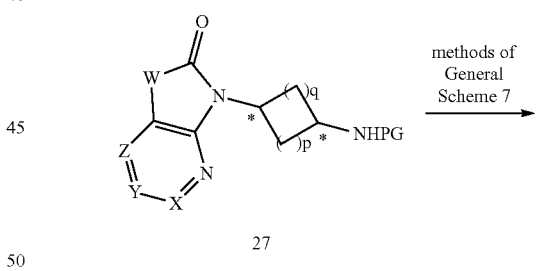

methods of General Scheme 7

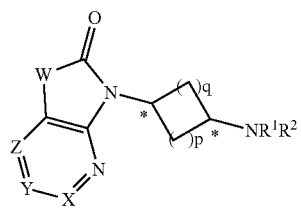

Formula (IC)
wherein
W = —O—,
—OCR$^6$R$^7$—,
—NR$^7$CR$^6$R$^7$—

GENERAL SCHEME 9: PREPARATION OF COMPOUNDS OF FORMULA (ID).

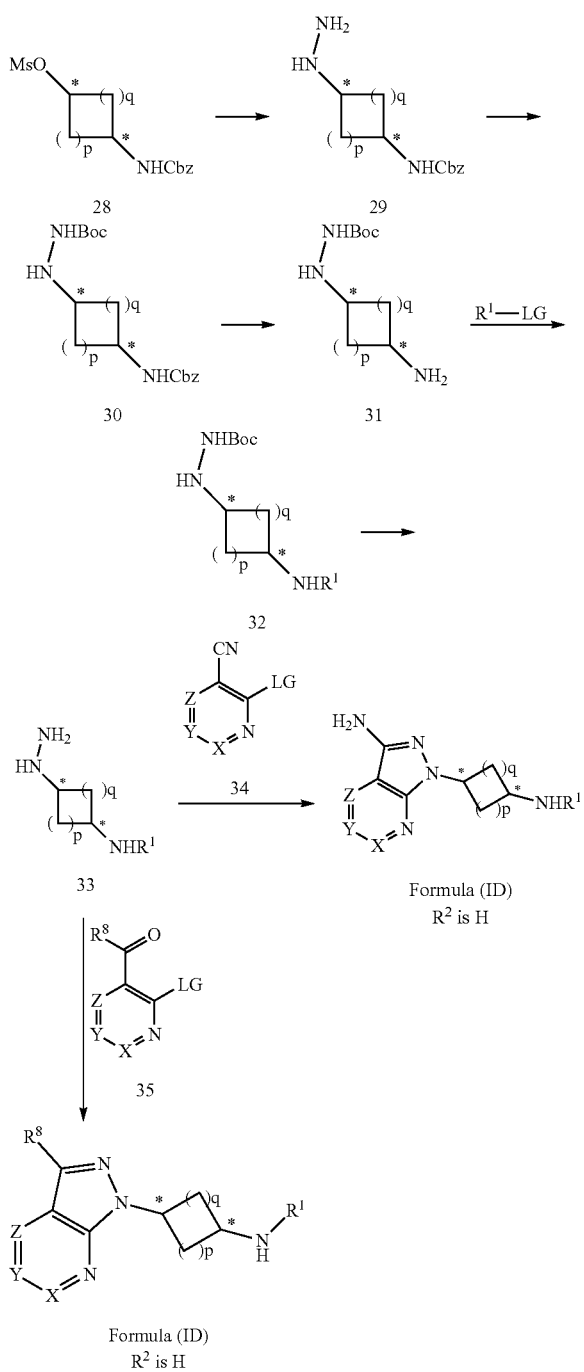

Formula (ID)
R² is H

In General Scheme 9 above, compound of Formula (ID) can be prepared from compound 28, which can be prepared according to methods described herein. Compound 28 can be reacted with hydrazine to provide compound 29, which can be reacted with an amine protecting group to provide compound 30. Compound 30 can then be selectively deprotected under standard hydrogenation conditions to provide compound 31. Reaction of compound 31 with various R¹-LG reagents under general SNAr or C—N coupling conditions provides compound 32, which can be further deprotected by reaction with a deprotecting agent, such as hydrochloric acid, trifluoroacetic acid, to provide compound 33, which then can be treated with a commercially available heteroaryl nitrile compound 34 or a readily available heteroaryl ketone compound 35 to provide a compound of Formula (ID) wherein R² is H. Such compounds of formula (ID), wherein R² is H, can be further reacted with R²-LG, wherein LG is a leaving group such as halogen, sulfonate or perfluorosulfonate, in the presence of a strong base and/or at more elevated temperatures, to form a compound of Formula (ID) wherein in the final products, R² is other than H. SNAr reactions are reactions in which a nucleophile such as an amine or alcohol reacts with an electrophile, such as aryl or heteroaryl halides or sulfonates or perfluorosulfonates, usually in the presence of a base, such as triethylamine or $K_2CO_3$, at ambient or elevated temperature in suitable solvents, such as THF, DMF, or DMSO. C—N coupling conditions are reactions that form a new C—N bond by directly joining together a nitrogen-containing group, such as an amino group or amido group as a formal nucleophile and a formal electrophile such as aryl or heteroaryl halides or sulfonates or perfluorosulfonates. It is appreciated by one skilled in the art that such C—N coupling reactions can also take place in an intramolecular fashion to form a new ring structure. Such C—N coupling reactions are catalyzed by metal-based catalysts such as a palladium- or copper-based catalyst and usually are conducted in the presence of a base such as LiHMDS or triethylamine at ambient or elevated temperatures in suitable organic solvents such as dioxane, THF, or DMF. (Do you want to move this to Scheme 1?)

GENERAL SCHEME 10: PREPARATION OF COMPOUNDS OF FORMULA (IE).

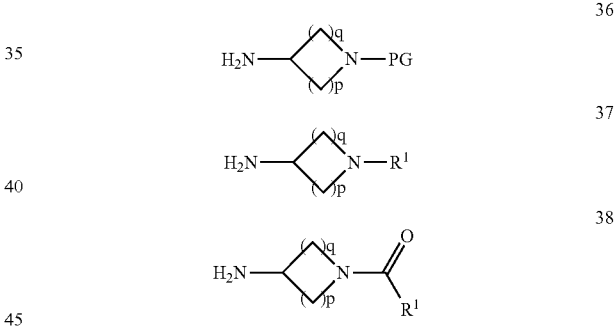

In General Scheme 10 above, compound of Formula (IE) can be prepared according to methods of General Schemes 3 to 7, wherein compound 1 or 3 is replaced with compounds 36, 37, or 38.

Preparation of Compounds of Formula (IF).

Compound of Formula (IF), wherein J is N, can be prepared according to methods of General Schemes 1 and 2, wherein compound 1 or 3 is replaced with compounds 36, 37, or 38.

General Scheme 11 describes preparation of a compound of Formula (IF), wherein J is CH and G is —(C=O)R¹ or —(CHOH)R¹. In General Scheme 12, compound 39, wherein P is $N(OCH_3)(CH_3)$ or OR, wherein R is simple alkyl such as methyl or ethyl, which is commercially available or can be prepared according to procedures described herein, may be converted to compound 40, wherein P is $N(OCH_3)(CH_3)$ or OR, wherein R is simple alkyl such as methyl or ethyl, which is commercially available or can be prepared according to procedures described herein, according to methods analogous to General Schemes 1 and 2, wherein reactions or transformations involving compound 1 or 3 can be conducted with compound 39. Treatment of compound 40 with a $R^1$-derived organ metallic reagent, such as M-$R^1$, provides a compound of Formula (IF) wherein G is —(C=O)$R^1$, which can be further reacted with a reducing agent, such as NaBH$_4$, to provide a compound of Formula (IF) wherein G is —(CHOH) $R^1$.

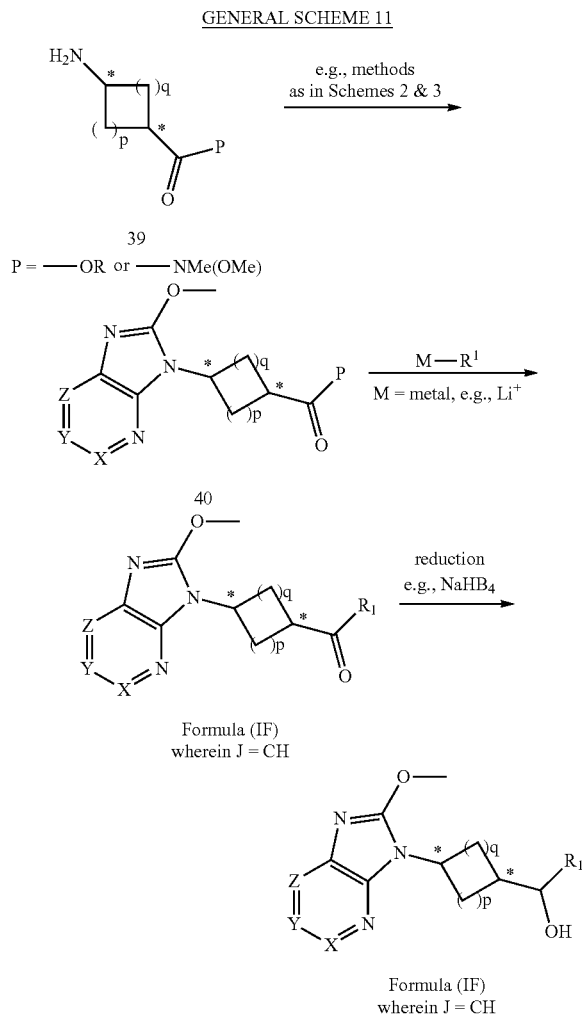

UTILITY AND METHODS OF USE

Provided herein are methods for treating a disorder or disease by inhibiting PDE10 enzyme. The methods, in general, comprise the step of administering a therapeutically effective amount of a compounds of the present invention, or an individual stereoisomer, a mixture of stereoisomers, or a pharmaceutically acceptable salt thereof, to a patient in need thereof to treat the disorder or disease.

In certain embodiments, this invention provides a use of a compound as described herein in the manufacture of a medicament for treating a disorder or disease treatable by inhibition of PDE10.

The compounds of the present invention inhibit PDE10 enzyme activity, and hence raise the levels of cAMP or cGMP within cells that express PDE10. Accordingly, inhibition of PDE10 enzyme activity would be useful in the treatment of diseases caused by deficient amounts of cAMP or cGMP in cells. PDE10 inhibitors would also be of benefit in cases wherein raising the amount of cAMP or cGMP above normal levels results in a therapeutic effect. Inhibitors of PDE10 may be used to treat disorders of the peripheral and central nervous system, cardiovascular diseases, cancer, gastro-enterological diseases, endocrinological diseases and urological diseases.

Indications that may be treated with PDE10 inhibitors, either alone or in combination with other drugs, include, but are not limited to, those diseases thought to be mediated in part by the basal ganglia, prefrontal cortex, and hippocampus. These indications include psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Psychoses are disorders that affect an individual's perception of reality. Psychoses are characterized by delusions and hallucinations. The compounds of the present invention are suitable for use in treating patients suffering from all forms of psychoses, including, but not limited to, schizophrenia, late-onset schizophrenia, schizoaffective disorders, prodromal schizophrenia, and bipolar disorders. Treatment can be for the positive symptoms of schizophrenia as well as for the cognitive deficits and negative symptoms. Other indications for PDE10 inhibitors include psychoses resulting from drug abuse (including amphetamines and PCP), encephalitis, alcoholism, epilepsy, Lupus, sarcoidosis, brain tumors, multiple sclerosis, dementia with Lewy bodies, or hypoglycemia. Other psychiatric disorders, like posttraumatic stress disorder (PTSD), and schizoid personality may also be treated with PDE10 inhibitors.

Accordingly, the compounds of the present invention have utility in treating a variety of neurological and psychiatric disorders associated with inhibition of PDE10, including one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, Parkinson's disease, Huntington's disease, Pick's disease, Creutzfeldt-Jacob disease, perinatal hypoxia, other general medical conditions or substance abuse); delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); bipolar disorders, mood disorders including depressive disorders; depression including unipolar depression, seasonal depression and post-partum depression, premenstrual syndrome (PMS) and premenstrual dysphoric, disorder (PDD), mood disorders due to a general medical condition, and substance-induced mood disorder; learning disorders, pervasive developmental disorder including autistic disorder, attention disorders including attention-deficit hyperactivity disorder (ADHD) and conduct disorder; NMDA receptor-related disorders such as autism, depression, benign forgetfulness, childhood learning disorders and closed head injury; movement disorders, including akinesias and akinetic-rigid syndromes (including Parkinson's disease, drug-induced parkinsonism, postencephalitic parkinsonism, progressive I supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and; intention tremor), chorea (such as Sydenham's chorea, Huntington's disease, benign hereditary chorea, neuroacanthocytosis, symptomatic chorea, drug-induced chorea and hemiballism), myoclonus (including generalized myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); urinary incontinence; neuronal damage including ocular damage, retinopathy or macular degeneration of the eye, tinnitus, hearing impairment and loss, and brain edema; emesis; and sleep disorders including insomnia and narcolepsy.

Obsessive-compulsive disorder (OCD) has been linked to deficits in the frontal-striatal neuronal pathways (Saxena et al., Br. J. Psychiatry Suppl, 35:26-37, 1998). Neurons in these pathways project to striatal neurons that express PDE10. PDE10 inhibitors cause cAMP to be elevated in these neurons; elevations in cAMP result in an increase in CREB phosphorylation and thereby improve the functional state of these neurons. The compounds of the present invention are therefore suitable for use in the indication of OCD. OCD may result, in some cases, from streptococcal infections that cause autoimmune reactions in the basal ganglia (Giedd et al., Am J Psychiatry. 157:281-283, 2000). Because PDE10 inhibitors may serve a neuroprotective role, administration of PDE10 inhibitors may prevent the damage to the basal ganglia after repeated streptococcal infections and thereby prevent the development of OCD.

In the brain, the level of cAMP or cGMP within neurons is believed to be related to the quality of memory, especially long term memory. Without wishing to be bound to any particular mechanism, it is proposed that, since PDE10 degrades cAMP or cGMP, the level of this enzyme affects memory in animals, for example, in humans. A compound that inhibits cAMP phosphodiesterase (PDE) can thereby increase intracellular levels of cAMP, which in turn activate a protein kinase that phosphorylates a transcription factor (cAMP response binding protein). The phosphorylated transcription factor then binds to a DNA promoter sequence to activate genes that are important in long term memory. The more active such genes are, the better is long-term memory. Thus, by inhibiting a phosphodiesterase, long term memory can be enhanced.

Dementias are diseases that include memory loss and additional intellectual impairment separate from memory. The compounds of the present invention are suitable for use in treating patients suffering from memory impairment in all forms of dementia. Dementias are classified according to their cause and include: neurodegenerative dementias (e.g., Alzheimer's, Parkinson's disease, Huntington's disease, Pick's disease), vascular (e.g., infarcts, hemorrhage, cardiac disorders), mixed vascular and Alzheimer's, bacterial meningitis, Creutzfeld-Jacob Disease, multiple sclerosis, traumatic (e.g., subdural hematoma or traumatic brain injury), infectious (e.g., HIV), genetic (down syndrome), toxic (e.g., heavy metals, alcohol, some medications), metabolic (e.g., vitamin B12 or folate deficiency), CNS hypoxia, Cushing's disease, psychiatric (e.g., depression and schizophrenia), and hydrocephalus.

The condition of memory impairment is manifested by impairment of the ability to learn new information and/or the inability to recall previously learned information. The present invention includes methods for dealing with memory loss separate from dementia, including mild cognitive impairment (MCI) and age-related cognitive decline. The present invention includes methods of treatment for memory impairment as a result of disease. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. The compounds of the present invention are suitable for use in the treatment of memory impairment due to, for example, Alzheimer's disease, multiple sclerosis, amylolaterosclerosis (ALS), multiple systems atrophy (MSA), schizophrenia, Parkinson's disease, Huntington's disease, Pick's disease, Creutzfeld-Jakob disease, depression, aging, head trauma, stroke, spinal cord injury, CNS hypoxia, cerebral senility, diabetes associated cognitive impairment, memory deficits from early exposure of anesthetic agents, multiinfarct dementia and other neurological conditions including acute neuronal diseases, as well as HIV and cardiovascular diseases.

The compounds of the present invention are also suitable for use in the treatment of a class of disorders known as polyglutamine-repeat diseases. These diseases share a common pathogenic mutation. The expansion of a CAG repeat, which encodes the amino acid glutamine, within the genome leads to production of a mutant protein having an expanded polyglutamine region. For example, Huntington's disease has been linked to a mutation of the protein huntingtin. In individuals who do not have Huntington's disease, huntingtin has a polyglutamine region containing about 8 to 31 glutamine residues. For individuals who have Huntington's disease, huntingtin has a polyglutamine region with over 37 glutamine residues. Aside from Huntington's disease (HD), other known polyglutamine-repeat diseases and the associated proteins include dentatorubral-pallidoluysian atrophy, DRPLA (atrophin-1); spinocerebellar ataxia type-1 (ataxin-1); spinocerebellar ataxia type-2 (ataxin-2); spinocerebellar ataxia type-3 (also called Machado-Joseph disease or MJD) (ataxin-3); spinocerebellar ataxia type-6 (alpha 1a-voltage dependent calcium channel); spinocerebellar ataxia type-7 (ataxin-7); and spinal and bulbar muscular atrophy (SBMA, also know as Kennedy disease).

The basal ganglia are important for regulating the function of motor neurons; disorders of the basal ganglia result in movement disorders. Most prominent among the movement disorders related to basal ganglia function is Parkinson's disease (Obeso et al., Neurology. 62(1 Suppl 1):S17-30, 2004). Other movement disorders related to dysfunction of the basal ganglia include tardive dyskinesia, progressive supranuclear palsy and cerebral palsy, corticobasal degeneration, multiple system atrophy, Wilson disease, dystonia, tics, and chorea. The compounds of the invention are also suitable for use to treat movement disorders related to dysfunction of basal ganglia neurons.

PDE10 inhibitors are useful in raising cAMP or cGMP levels and prevent neurons from undergoing apoptosis. PDE10 inhibitors may be anti-inflammatory by raising cAMP in glial cells. The combination of anti-apoptotic and anti-inflammatory properties, as well as positive effects on synaptic plasticity and neurogenesis, make these compounds useful to treat neurodegeneration resulting from any disease or injury, including stroke, spinal cord injury, Alzheimer's disease, multiple sclerosis, amylolaterosclerosis (ALS), and multiple systems atrophy (MSA).

Autoimmune diseases or infectious diseases that affect the basal ganglia may result in disorders of the basal ganglia including ADHD, OCD, tics, Tourette's disease, Sydenham chorea. In addition, any insult to the brain can potentially damage the basal ganglia including strokes, metabolic abnormalities, liver disease, multiple sclerosis, infections, tumors, drug overdoses or side effects, and head trauma. Accordingly, the compounds of the invention can be used to stop disease progression or restore damaged circuits in the brain by a combination of effects including increased synaptic plasticity, neurogenesis, anti-inflammatory, nerve cell regeneration and decreased apoptosis.

The growth of some cancer cells is inhibited by cAMP and cGMP. Upon transformation, cells may become cancerous by expressing PDE10 and reducing the amount of cAMP or cGMP within cells. In these types of cancer cells, inhibition of PDE10 activity inhibits cell growth by raising cAMP. In some cases, PDE10 may be expressed in the transformed, cancerous cell but not in the parent cell line. In transformed renal carcinoma cells, PDE10 is expressed and PDE10 inhibitors reduce the growth rate of the cells in culture. Similarly, breast cancer cells are inhibited by administration of PDE10 inhibitors. Many other types of cancer cells may also be sensitive to growth arrest by inhibition of PDE10. Therefore, compounds disclosed in this invention can be used to stop the growth of cancer cells that express PDE10.

The compounds of the invention are also suitable for use in the treatment of diabetes and related disorders such as obesity, by focusing on regulation of the cAMP signaling system. By inhibiting PDE-10, especially PDE-100A, intracellular levels of cAMP are increased, thereby increasing the release of insulin-containing secretory granules and, therefore, increasing insulin secretion. See, for example, WO 2005/012485, which is hereby incorporated by reference in its entirety. The compounds of Formula (I) can also be used to treat diseases disclosed in US Patent application publication No. 2006/019975, the disclosure of which is incorporated herein by reference in its entirety.

Testing

The PDE10 inhibitory activities of the compounds of the present invention can be tested, for example, using the in vitro and in vivo assays described in the Biological Examples below.

Administration and Pharmaceutical Compositions

In general, the compounds of Formula (I) can be administered in a therapeutically effective amount by any of the accepted modes of administration for agents that serve similar utilities. The actual amount of a compound of this invention, i.e., the active ingredient, depends upon numerous factors, such as the severity of the disease to be treated, the age and relative health of the subject, the potency of the compound used, the route and form of administration, and other factors.

Therapeutically effective amounts of compounds of Formula (I) may range from approximately 0.1-1000 mg per day; preferably 0.5 to 250 mg/day, more preferably 3.5 mg to 70 mg per day.

In general, compounds of Formula (I) can be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors, such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area, i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, Gennaro, A. R. (Mack Publishing Company, 18th ed., 1995).

The level of the compound of Formula (I) in a formulation can vary within the full range employed by those skilled in the art. Typically, the formulation contains, on a weight percent (wt %) basis, from about 0.01-99.99 wt % of a compound of Formula (I) based on the total formulation, with the balance being one or more suitable pharmaceutical excipients. Preferably, the compound of Formula (I) is present at a level of about 1-80 wt %.

The compound of Formula (I) can be administered as the sole active agent or in combination with other pharmaceutical agents such as other agents used in the treatment of psychoses, especially schizophrenia and bipolar disorder, obsessive-compulsive disorder, Parkinson's disease, Alzheimer's disease, cognitive impairment and/or memory loss, e.g., nicotinic α-7 agonists, PDE4 inhibitors, other PDE10 inhibitors, calcium channel blockers, muscarinic m1 and m2 modulators, adenosine receptor modulators, ampakines, NMDA-R modulators, mGluR modulators, dopamine modulators, serotonin modulators, canabinoid modulators, and cholinesterase inhibitors (e.g., donepezil, rivastigimine, and galanthanamine). In such combinations, each active ingredient can be administered either in accordance with their usual dosage range or a dose below their usual dosage range, and can be administered either simultaneously or sequentially.

Accordingly, the pharmaceutical compositions of the present invention also include those that contain one or more other active ingredients, in addition to a compound of the present invention.

The above combinations include combinations of a compound of Formula (I) not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of Formula (I) is used contemporaneously with one or more other drugs, a pharmaceutical composition containing such other drugs in addition to the compound of the present invention is preferred. Accordingly, the pharmaceutical compositions of the present invention also include those that also contain one or more other active ingredients, in addition to a compound of the present invention. The weight ratio of the compound of the present invention to the second active ingredient may be varied and will depend upon the effective dose of each ingredient. Generally, an effective dose of each will be used.

Drugs suitable in combination with the compounds of Formula (I) include, but are not limited to, other suitable schizophrenia drugs such as Clozaril, Zyprexa, Risperidone, and Seroquel; bipolar disorder drugs, including, but not limited to, Lithium, Zyprexa, and Depakote; Parkinson's disease drugs, including, but not limited to, Levodopa, Parlodel, Permax, Mirapex, Tasmar, Contan, Kemadin, Artane, and Cogentin; agents used in the treatment of Alzheimer's disease, including, but not limited to, Reminyl, Cognex, Aricept, Exelon, Akatinol, Neotropin, Eldepryl, Estrogen and Cliquinol; agents used in the treatment of dementia, including, but not limited to, Thioridazine, Haloperidol, Risperidone, Cognex, Aricept, and Exelon: agents used in the treatment of epilepsy, including, but not limited to, Dilantin, Luminol, Tegretol, Depakote, Depakene, Zarontin, Neurontin, Barbita, Solfeton, and Felbatol; agents used in the treatment of multiple sclerosis, including, but not limited to, Detrol, Ditropan XL, OxyContin, Betaseron, Avonex, Azothioprine, Methotrexate, and Copaxone; agents used in the treatment of Huntington's disease, including, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone; agents useful in the treatment of diabetes, including, but not limited to, PPAR ligands (e.g. agonists, antagonists, such as Rosiglitazone, Troglitazone and Pioglitazone), insulin secretagogues (e.g., sulfonylurea drugs, such as Glyburide, Glimepiride, Chlorpropamide, Tolbutamide, and Glipizide, and non-sulfonyl secretagogues), α-glucosidase inhibitors (such as Acarbose, Miglitol, and Voglibose), insulin sensitizers (such as the PPAR-γ agonists, e.g., the glitazones; biguanides, PTP-1B inhibitors, DPP-IV inhibitors, and 11beta-HSD inhibitors), hepatic glucose output lowering compounds (such as glucagon antagonists and metaformin, e.g., Glucophage and Glucophage XR), insulin and insulin derivatives (both long and short acting forms and formulations of insulin); and anti-obesity drugs, including, but not limited to, β-3 agonists, CB-1 agonists, neuropeptide Y5 inhibitors, Ciliary Neurotrophic Factor and derivatives (e.g., Axokine), appetite suppressants (e.g., Sibutramine), and lipase inhibitors (e.g., Orlistat).

In one embodiment, the compound of Formula (I) may be administered in combination with anti-Alzheimer's agents, beta-secretase inhibitors, gamma-secretase inhibitors, HMG-CoA reductase inhibitors, NSAID's including ibuprofen, vitamin E, and anti-amyloid antibodies. In another embodiment, the compound of the present invention may be administered in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, PDE10 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazopam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazopam, thioridazine, thiothixene, tracazolate, kanylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof.

In another embodiment, the compound of Formula (I) may be administered in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the compound of Formula (I) may be administered in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the compound of the present invention may be administered in combination with acetophenazine, alentemol, aripiprazole, amisulpride, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the compound of Formula (I) may be administered in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, adrenoreceptor antagonists, neurokinin-1 receptor antagonists, atypical anti-depressants, benzodiazepines, 5-HTA agonists or antagonists, especially 5-HTA partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide, venlafaxine; duloxetine; aprepitant; bupropion, lithium, nefazodone, trazodone and viloxazine; alprazolam, chlordiazepoxide, clonazepam, chlorazepate, diazopam, halazepam, lorazepam, oxazopam and prazepam; buspirone, flesinoxan, gepirone and ipsapirone, and pharmaceutically acceptable salts thereof.

The compounds of Formula (I) may be administered orally, parentally, by inhalation spray, rectally, or topically in dosage unit formulations containing conventional pharmaceutically acceptable carriers, adjuvants, and vehicles, for the treatment of PDE10-related diseases, such as acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating PDE10-receptor-mediated diseases, cancer, and/or hyperglycemia with the compounds of Formula (I) and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of Formula (I) can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of Formula (I) are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinylpyrrolidine, and/or polyvinyl alcohol, and tableted or encapsulated for conventional administration. Alternatively, the compounds of Formula (I) may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate optically active acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of Formula (I) may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of Formula (I) in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of Formula (I) are to be construed as encompassed within the scope of the present invention.

The compounds of the present invention can be used in the form of salts derived from inorganic or organic acids. The organic salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of inorganic acids that may be employed to from pharmaceutically acceptable acid addition salts include hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$-$C_4$) alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

EXAMPLES

Synthetic Examples

The following preparations of compounds of Formula (I) and intermediate compounds are given to enable those skilled in the art to more clearly understand and to practice the present invention. They should not be considered as limiting the scope of the invention, but merely as being illustrative and representative thereof.

Unless otherwise noted, all materials were obtained from commercial suppliers and used without further purification. All parts are by weight and temperatures are in degrees centigrade unless otherwise indicated. All microwave assisted reactions were conducted with a Smith Synthesizer™ from Biotage™. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography. Unless otherwise stated, reactions were run at room temperature.

The following abbreviations are used:
HATU: O-(7-Azobenzotriazol-1-yl)-1,1,3,3-tetramethyluronium hexafluorophosphate.
HBTU: 1-[bis(dimethylamino)methylene]-1H-benzotriazolium 3-oxide hexafluorophosphate Representative Intermediate Compound (I.C.) #1-84 were used in the preparation of compounds of Formula (I):

| I.C.# | INTERMEDIATE COMPOUND NAME |
|---|---|
| 1 | 2-chloro-1,8-naphthyridine |
| 2 | 2-chloro-1,6-naphthyridine |
| 3 | 2-chloro-1,5-naphthyridine |
| 4 | 2-chloro-1,7-naphthyridine |
| 5 | 2-chlorothiazolo[5,4-b]pyridine |
| 6 | 2-chlorothiazolo[4,5-b]pyridine |
| 7 | 2-chloro-5-fluorobenzo[d]thiazole |
| 8 | 2,7-dichloroquinazoline |
| 9 | 2,7-dichloroquinoline |
| 10 | tert-butyl (trans-3-(benzo[d]thiazol-2-ylamino)cyclobutyl)carbamate |
| 11 | trans-3-(benzo[d]thiazol-2-ylamino)cyclobutane-1,3-diamine |
| 12 | trans-3-(2-cyclopropyl-3h-imidazo[4,5-b]pyridin-3-yl)cyclobutanamine |
| 13 | 2-(2-chloro-5-fluoropyridin-3-yl)acetonitrile |
| 14 | 2-(2-chloropyridin-3-yl)acetonitrile |
| 15 | 1-(2-chloro-5-fluoropyridin-3-yl)cyclopropanecarbonitrile |
| 16 | 1-(2-chloropyridin-3-yl)cyclopropanecarbonitrile |
| 17 | 4-(2-chloropyridin-3-yl)tetrahydro-2H-pyran-4-carbonitrile |

-continued

| I.C.# | INTERMEDIATE COMPOUND NAME |
|---|---|
| 18 | 1-(2-chloropyridin-3-yl)cyclopentanecarbonitrile |
| 19 | 1-(2-chloropyridin-3-yl)cyclobutanecarbonitrile |
| 20 | 1-(2-chloro-5-fluoropyridin-3-yl)cyclopropanecarboxylic acid |
| 21 | 1-(2-chloropyridin-3-yl)cyclopropanecarboxylic acid |
| 22 | 2-(2-chloro-5-fluoropyridin-3-yl)-2-methylpropanenitrile |
| 23 | 2-(2-chloro-5-fluoropyridin-3-yl)-2-methylpropanoic acid |
| 24 | 2-(2-chloropyridin-3-yl)-2-methylpropanenitrile |
| 25 | 2-(2-chloropyridin-3-yl)-2-methylpropanoic acid |
| 26 | 1-(trans-3-aminocyclobutyl)-3,3-dimethyl-1H-pyrrolo[2,3-b]pyridin-2(3h)-one hydrochloride |
| 27 | trans-N$^1$-(benzo[d]thiazol-2-yl)-N$^3$-(3-chloropyrazin-2-yl)cyclobutane-1,3-diamine |
| 28 | 2-bromo-5-(2-methyl-1,3-dioxolan-2-yl)pyridine |
| 29 | 2-(3-chloropyrazin-2-yl)-2-methylpropanoic acid |
| 30 | 5-(trans-3-aminocyclobutyl)-7,7-dimethyl-5h-pyrrolo[2,3-b]pyrazin-6(7H)-one |
| 31 | trans-N$^1$-(5-methylpyridin-2-yl)cyclohexane-1,4-diamine dihydrochloride |
| 32 | cis-N$^1$-(benzo[d]thiazol-2-yl)cyclobutane-1,3-diamine |
| 33 | trans-N$^1$-(benzo[d]thiazol-2-yl)-n$^3$-(3-bromopyridin-2-yl)cyclobutane-1,3-diamine |
| 34 | methyl (2-chloro-5-fluoropyridin-3-yl)carbamate |
| 35 | tert-butyl (2-chloro-5-fluoropyridin-3-yl)carbamate |
| 36 | tert-butyl (2-chloro-5-fluoropyridin-3-yl)(methyl)carbamate |
| 37 | methyl (2-chloro-5-fluoropyridin-3-yl)(methyl)carbamate |
| 38 | 2-chloro-5-fluoro-n-methylpyridin-3-amine |
| 39 | 2-chloro-N-cyclopropyl-5-fluoropyridin-3-amine |
| 40 | methyl (2-chloropyridin-3-yl)(methyl)carbamate |
| 41 | 3-chloro-N-cyclopropylpyrazin-2-amine |
| 42 | trans-N$^1$-(benzo[d]thiazol-2-yl)-N$^3$-(5-bromopyrimidin-4-yl)cyclobutane-1,3-diamine |
| 43 | 3-(trans-3-aminocyclobutyl)-1H-imidazo[4,5-b]pyridin-2(3H)-one dihydrochloride |
| 44 | trans-N$^1$-(benzo[d]thiazol-2-yl)-N$^3$-(3-chloropyrazin-2-yl)cyclobutane-1,3-diamine |
| 45 | N$^4$-(trans-3-(benzo[d]thiazol-2-ylamino)cyclobutyl)pyrimidine-4,5-diamine |
| 46 | 2-chloro-4-fluorobenzo[d]thiazole |
| 47 | benzyl (cis-3-hydroxycyclobutyl)carbamate |
| 48 | 7-fluoroquinolin-2-yl trifluoromethanesulfonate |
| 49 | 3-(trans-4-aminocyclohexyl)-1h-imidazo[4,5-b]pyridin-2(3H-one dihydrochloride |
| 50 | 7-methoxyquinolin-2-yl trifluoromethanesulfonate |
| 51 | quinolin-2-yl trifluoromethanesulfonate |
| 52 | N-(trans-3-hydrazinylcyclobutyl)benzo[d]thiazol-2-amine dihydrochloride |
| 53 | cyclopropyl(2-fluoropyridin-3-yl)methanone |
| 54 | 2,2,2-trifluoro-1-(2-fluoropyridin-3-yl)ethanone |
| 55 | tert-butyl 3-(2-methoxy-3H-imidazo[4,5-b]pyridin-3-yl)azetidine-1-carboxylate |
| 56 | tert-butyl 3-(2'-oxospiro[cyclopropane-1,3'-pyrrolo[2,3-b]pyridin]-1'(2'H)-yl)azetidine-1-carboxylate |
| 57 | 3,3-dimethyl-1-(piperdin-4-yl)-1H-pyrrolo[2,3-b]pyridin-2(3h)-one dihydrochloride |
| 58 | (3-nitro-pyridin-2-yl)-piperidin-4-yl-amine hydrochloride |
| 59 | 2-chloro-4-(6-methylpyridin-3-yl)pyrimidine |
| 60 | cis-N1-(benzo[d]thiazol-2-yl)cyclobutane-1,3-diamine dihydrochloride |
| 61 | cis-N1-(5-methylpyridin-2-yl)cyclobutane-1,3-diamine dihydrochloride |
| 62 | 7-(trans-3-aminocyclobutyl)-5,5-dimethyl-5h-pyrrolo[2,3-d]pyrimidin-6(7H)-one hydrochloride |
| 63 | tert-butyl (trans-3-(5,5-dimethyl-2-(methylthio)-6-oxo-5H-pyrrolo[2,3-d]pyrimidin-7(6H)-yl)cyclobutyl)carbamate |
| 64 | tert-butyl (cis-3-(benzo[d]thiazol-2-ylamino)cyclobutyl)carbamate |
| 65 | tert-butyl (cis-3-aminocyclobutyl)carbamate |
| 66 | tert-butyl (cis-3-azidocyclobutyl)carbamate |
| 67 | trans-3-((tert-butoxycarbonyl)amino)cyclobutyl methanesulfonate |
| 68 | tert-butyl (trans-3-((1-methyl-1H-benzo[d]imidazol-2-yl)oxy)cyclobutyl)carbamate |
| 69 | tert-butyl (trans-3-hydroxycyclobutyl)carbamate |
| 70 | trans-3-((tert-butoxycarbonyl)amino)cyclobutyl 4-nitrobenzoate |
| 71 | tert-butyl (cis-3-hydroxycyclobutyl)carbamate |
| 72 | trans-N$^1$-(6-fluorobenzo[d]thiazol-2-yl)cyclobutane-1,3-diamine |
| 73 | trans-N$^1$-(5-fluorobenzo[d]thiazol-2-yl)cyclobutane-1,3-diamine |
| 74 | methyl (2-bromophenyl)(methyl)carbamate |
| 75 | benzyl(trans)-3-(1-cyclopropyl-2-oxo-1H-imidazo[4,5-b]pyridin-3(2h)-yl)cyclobutyl)carbamate |
| 76 | 2-(methylsulfonyl)thiazolo[5,4-b]pyridine |
| 77 | tert-butyl (trans-3-(1-cyclopropyl-2-oxo-1H-imidazo[4,5-b]pyridin-3(2h)-yl)cyclobutyl)carbamate |
| 78 | 7,7-dimethyl-5-(piperidin-4-yl)-5h-pyrrolo[2,3-b]pyrazin-6(7H)-one hydrochloride |
| 79 | 1-(trans-3-aminocyclobutyl)-3-cyclopropyl-1H-imidazo[4,5-b]pyrazin-2(3H)-one hydrochloride |
| 80 | cis-3-((tert-butoxycarbonyl)amino)cyclobutyl methanesulfonate |
| 81 | cis-N$^1$-(benzo[d]thiazol-2-yl)-N$^3$-(3-chloropyrazin-2-yl)cyclobutane-1,3-diamine |
| 82 | 1-(trans-3-aminocyclobutyl)-5-bromo-3-cyclopropyl-1h-imidazo[4,5-b]pyrazin-2(3H)-one hydrochloride |

| I.C.# | INTERMEDIATE COMPOUND NAME |
|---|---|
| 83 | 5-(trans-3-aminocyclobutyl)-7,7-dimethyl-5H-pyrrolo[2,3-b]pyrazin-6(7H)-one dihydrochloride |
| 84 | 3-(trans-3-aminocyclobutyl)-1-methyl-1H-imidazo[4,5-b]pyridin-2(3H-one hydrochloride | tert-Butyl(trans-3-aminocyclobutyl)carbamate and tert-Butyl(cis-3-aminocyclobutyl)carbamate, which were used as starting materials in the following synthesis of one or more intermediate compounds, were synthesized according to published literature procedures, specifically Radchenko, D. S., Pavlenko, S. O., et al., J. Org. Chem. 2010, 75, 5941-5952.

2-chlorobenzothiazole is available commercially, for example from Bosche Scientific Intermediate 1

2-chloro-1,8-naphthyridine

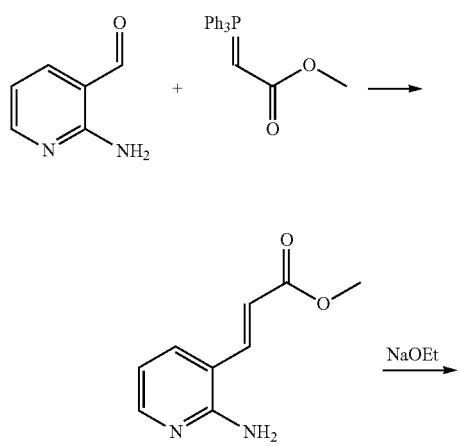

Step 1: (E)-methyl 3-(2-aminopyridin-3-yl)acrylate ((Carbomethyloxymethylene)triphenylphosphorane) (7.8 g, 23.33 mmol) and 2-amino-3-formylpyridine (2.81 g, 23.01 mmol) were suspended in methanol (90 mL) and heated at reflux. Once the mixture came to a boil, all of the solids dissolved. The mixture was evaporated to dryness under reduced pressure. The thick yellow oil was purified using silica chromatography (0-50% ethyl acetate in dichloromethane gradient) to give the desired (E)-methyl 3-(2-aminopyridin-3-yl)acrylate (3.50 g, 19.64 mmol, 85% yield) as a yellow solid.

Step 2: 1,8-naphthyridin-2-ol (E)-Methyl 3-(2-aminopyridin-3-yl)acrylate (3.50 g, 19.64 mmol) was dissolved in ethanol (80 mL) and treated with sodium ethoxide (21 wt. % solution in denatured ethanol, ml, 26.8 mmol). The solution was heated at reflux for 2 hours then evaporated to dryness under reduced pressure. Saturated ammonium chloride (100 mL) and water (100 mL) were added to the crude and it was stirred for 10 minutes. The solid product was filtered off and dried by toluene azeotrope to give 1,8-naphthyridin-2-ol (2.80 g, 19.16 mmol, 83% yield) as a white powder.

Step 3: 2-chloro-1,8-naphthyridine 1,8-Naphthyridin-2-ol (2.80 g, 19.16 mmol) was suspended in phosphorus oxychloride (100 ml, 1092 mmol) and heated at gentle reflux. The chlorination was followed by LC/MS and once the conversion was complete the reaction was evaporated to dryness and the residue partitioned between water (400 mL) and ethyl acetate (2×400 mL). The aqueous was extracted with additional ethyl acetate (2×400 mL). The combined organic layers were dried with magnesium sulfate and evaporated to dryness under reduced pressure. The crude compound was used without further purification.

Intermediate 2

2-chloro-1,6-naphthyridine

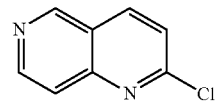

2-Chloro-1,6-naphthyridine was synthesized analogous to intermediate 1 using commercial 4-amino-3-formylpyridine in place of 2-amino-3-formylpyridine.

Intermediate 3

2-xhloro-1,5-naphthyridine

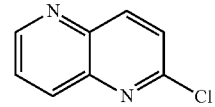

2-Chloro-1,5-napthyridine was synthesized analogous to intermediate 1 using commercially available 3-aminopicolinaldehyde in place of 2-amino-3-formylpyridine.

Intermediate 4

2-chloro-1,7-naphthyridine

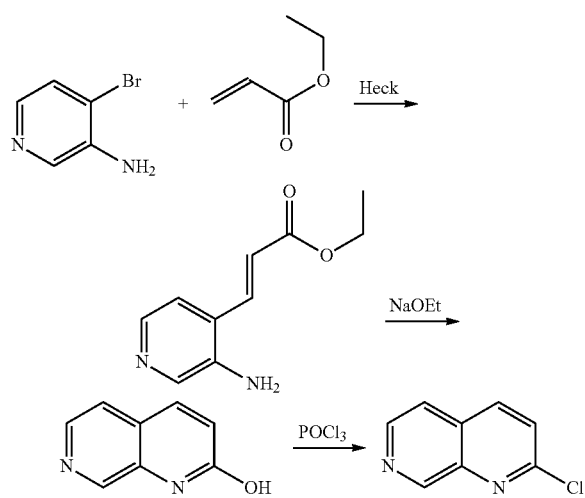

Step 1: ethyl 3-(3-aminopyridin-4-yl)acrylate

3-Amino-4-bromopyridine (1.440 ml, 8.32 mmol), palladium (ii) acetate (0.195 g, 0.869 mmol), and tri(o-tolyl)phosphine (0.302 g, 0.992 mmol) were suspended in a mixture of triethylamine (5.0 ml, 35.9 mmol) and acetonitrile (5 mL) in a microwave vial under argon. Ethyl acrylate (1.1 ml, 10.12 mmol) was added and the cap sealed. It was heated in an oil bath to 105° C. After 2 hours the vial was opened and the reaction mixture partitioned between water (100 mL), saturated ammonium chloride (50 mL) and ethyl acetate (200 mL). The organic was dried with magnesium sulfate and evaporated to dryness under reduced pressure. Purification using silica chromatography (dichloromethane to ethyl acetate gradient) gave the desired (E)-ethyl 3-(3-aminopyridin-4-yl)acrylate (0.462 g, 2.404 mmol, 28.9% yield).

Steps 2-3

The acrylate intermediate was cyclized and chlorinated using the method described in steps 2 and 3 for Intermediate 1.

Intermediate 5

2-chlorothiazolo[5,4-b]pyridine

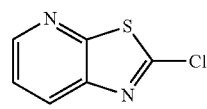

3-Amino-2-bromopyridine (1.14 g, 6.59 mmol) and ethyl potassium xanthate (2.324 g, 14.50 mmol) were dissolved in dry dimethylformamide (4 mL) and heated at 130° C. for 15 hours. The reaction was cooled and diluted with water (150 mL). 5 N Hydrochloric acid (4 mL) was added and the mixture stirred. The intermediate precipitated as a light yellow solid and was filtered off. The solids were suspended in warm ethyl acetate (200 mL) and dried with magnesium sulfate. The filter cake was washed with additional warm ethyl acetate (200 mL). The organic was evaporated to dryness under reduced pressure and suspended in dichloromethane (50 mL). Sulfuryl chloride (20 ml, 247 mmol) was added and the mixture stirred at room temperature. After 1 hour, the mixture was evaporated to dryness under reduced pressure and the residue partitioned between ethyl acetate (200 mL), ice (~50 mL), water (100 mL) and saturated sodium bicarbonate (60 mL). The organic phase was dried with magnesium sulfate and evaporated to dryness under reduced pressure. Purification using silica chromatography (dichloromethane to ethyl acetate gradient) gave the desired 2-chlorothiazolo[5,4-b]pyridine (0.120 g, 0.703 mmol, 10.7% yield).

Intermediate 6

2-chlorothiazolo[4,5-b]pyridine

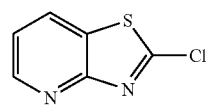

2-Chlorothiazolo[4,5-b]pyridine was synthesized analogous to intermediate 5 using 2-amino-3-bromopyridine instead of 3-amino-2-bromopyridine.

Intermediate 7

2-chloro-5-fluorobenzo[d]thiazole

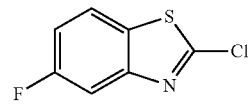 [SMILES: Fc1ccc2sc(Cl)nc2c1]

2-Chloro-5-fluorobenzo[d]thiazole was synthesized analogous to intermediate 5 using 2,5-difluoroaniline instead of 3-amino-2-bromopyridine.

Intermediate 8

2,7-dichloroquinazoline

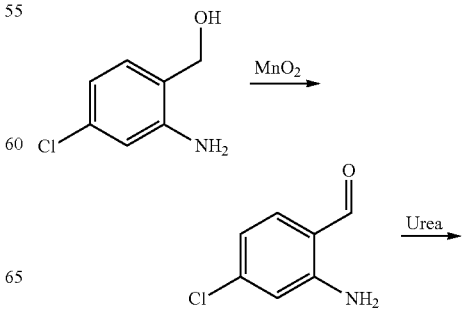

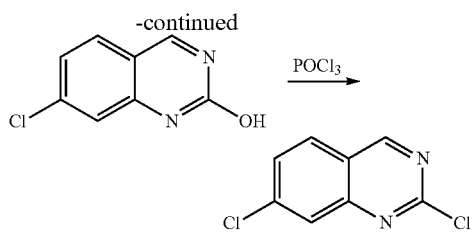

Step 1: 2-amino-4-chlorobenzaldehyde (2-amino-4-chlorophenyl)methanol (10.08 g, 64.0 mmol) was suspended in chloroform (250 mL) and treated with manganese dioxide (15.87 g, 183 mmol). The mixture was stirred vigorously and heated at reflux. The oxidation was followed by TLC and found to be complete after 1 hour. The suspension was filtered through a pad of CELITE™ and evaporated to dryness under reduced pressure. Further drying under high vacuum gave a dark red solid which was used in the next step without further purification.

Step 2: 2-hydroxy-7-chloroquinazoline

Urea (115 g, 1915 mmol) was melted in a 500 mL 3 neck flask under nitrogen and heated at 160° C. The crude aminobenzaldehyde from step 1 (8.4 g) was added, one of the necks of the flask was opened to the atmosphere and the temperature of the oil bath raised to 190° C. When the bath temperature reached 175° C., a white precipitate was observed. The mixture was cooled and water (400 mL) was added. It was stirred for 15 minutes then filtered through a sintered glass frit. The collected solids were dried by azeotroping with toluene at reduced pressure (3×300 mL) then further dried under high vacuum at 70° C. The crude material was used without further purification.

Step 3: 2,7-dichloroquinazoline

The crude material was treated with phosphorus oxychloride (150 ml, 1639 mmol) and heated at reflux. It was allowed to stir for 2 hours. The mixture was filtered through a pad of CELITE™ and the solids washed with chloroform (2×100 mL). The combined organic was evaporated to dryness under reduced pressure. The thick brown oil was cooled in an ice bath and ethyl acetate (500 mL) and ice (about 200 mL) were added. The mixture was stirred for another 20 minutes then water (100 mL) was added and the phases separated. The organic was dried with magnesium sulfate and evaporated to dryness under reduced pressure. It was dry loaded on silica gel and purified (0 to 30% ethyl acetate in dichloromethane gradient) to give 2,7-dichloroquinazoline (4.38 g, 22.01 mmol, 34.4% yield) as a light yellow solid.

Intermediate 9

2,7-dichloroquinoline

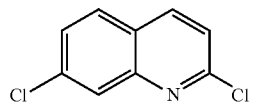 [SMILES: Clc1ccc2ccc(Cl)nc2c1]

7-Chloroquinoline (2.2 g, 13.45 mmol) was dissolved in chloroform (100 mL) and treated with 3-chloroperoxybenzoic acid (3.32 g, 13.45 mmol). The reaction was stirred at 45° C. for 30 minutes after which the oxidation was deemed complete. Water (100 mL), 1 N sodium hydroxide (50 mL) and dichloromethane (200 mL) were added and the phases mixed and separated. The organic was dried with magnesium sulfate and evaporated to dryness under reduced pressure. The crude N-oxide was treated with phosphorus oxychloride (20 ml, 218 mmol) and heated at 110° C. After 5 minutes the chlorination was deemed complete and the solution evaporated to dryness under reduced pressure. The crude product was partitioned between water (50 mL), 1 N sodium hydroxide (50 mL) and ethyl acetate (200 mL). The organic phase was dried with magnesium sulfate and evaporated to dryness under reduced pressure. Purification using silica chromatography (hexane to ethyl acetate gradient) gave the desired 2,7-dichloroquinoline (0.98 g, 4.95 mmol, 36.8% yield).

Intermediate 10 tert-butyl(trans-3-(benzo[d]thiazol-2-ylamino)cyclobutyl carbamate

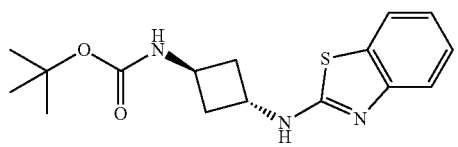 [SMILES: CC(C)(C)OC(=O)N[C@H]1C[C@H](Nc2nc3ccccc3s2)C1]

Tert-butyl(trans-3-aminocyclobutyl)carbamate (1.48 g, 7.95 mmol), 2-chlorobenzothiazole (1.6 ml, 12.93 mmol), 4-dimethylaminopyridine (0.051 g, 0.417 mmol), and diisopropylethylamine (3.0 ml, 17.25 mmol) were suspended in dry dimethylsulfoxide (5 mL) under nitrogen. The mixture was heated at 110° C. for 2 hours then cooled to room temperature. Then, the mixture was partitioned between 30% saturated ammonium chloride (300 mL) and ethyl acetate (300 mL). The organic was dried with magnesium sulfate and evaporated to dryness under reduced pressure. The crude product was triturated with 1:1 dichloromethane:hexane (50 mL total) at 40° C. The mixture was filtered through a sintered glass frit and the solids washed with additional 1:1 dichloromethane:hexane (10 mL) before drying under high vacuum to give tert-butyl(trans-3-(benzo[d]thiazol-2-ylamino)cyclobutyl)carbamate (2.063 g, 6.46 mmol, 81% yield) as an off white solid.

Intermediate 11 trans-N$^1$-(benzo[d]thiazol-2-yl)cyclobutane-1,3-diamine

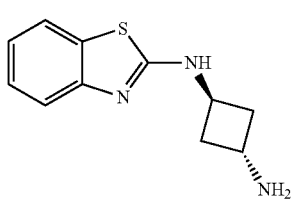 [SMILES: N[C@H]1C[C@H](Nc2nc3ccccc3s2)C1]

Tert-butyl(trans-3-(benzo[d]thiazol-2-ylamino)cyclobutyl)carbamate (Intermediate 10) (720 mg, 2.262 mmol) was dissolved in dichloromethane (30 mL) and treated with trifluoroacetic acid (2 mL). The solution was stirred at room temperature for 15 minutes then evaporated to dryness under reduced pressure and further dried under high vacuum. 2 N Hydrochloric acid (50 mL) and diethyl ether (100 mL) were added and the phases mixed and separated. The organic was discarded. The aqueous layer was saturated with sodium chloride and the pH adjusted to >10 using 5N sodium hydroxide. Ethyl acetate (200 mL) was added and the phases mixed and separated. The aqueous was extracted with ethyl acetate one more time (200 mL) and the combined organic layers dried with magnesium sulfate before evaporating to dryness under reduced pressure. The crude trans-N-(benzo[d]thiazol-2-yl)cyclobutane-1,3-diamine (459 mg, 2.10 mmol, 92.4% yield) was used without further purification.

Intermediate 12 trans-3-(2-cyclopropyl-3H-imidazo[4,5-b]pyridin-3-yl)cyclobutanamine

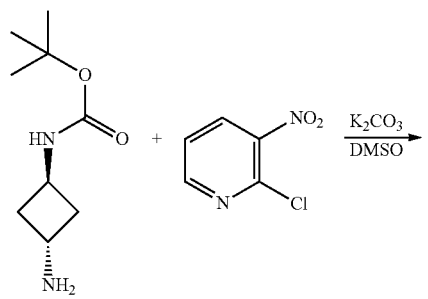

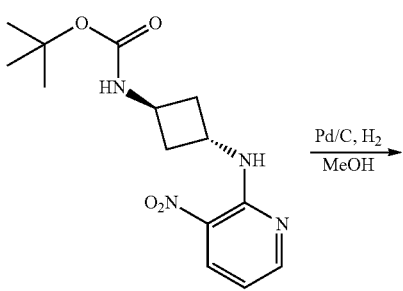

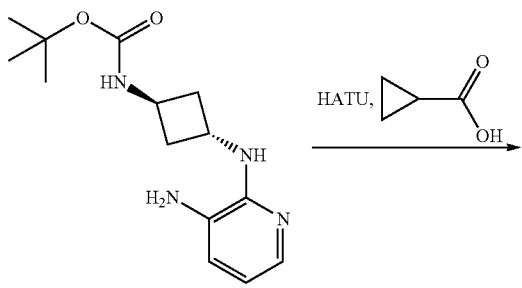

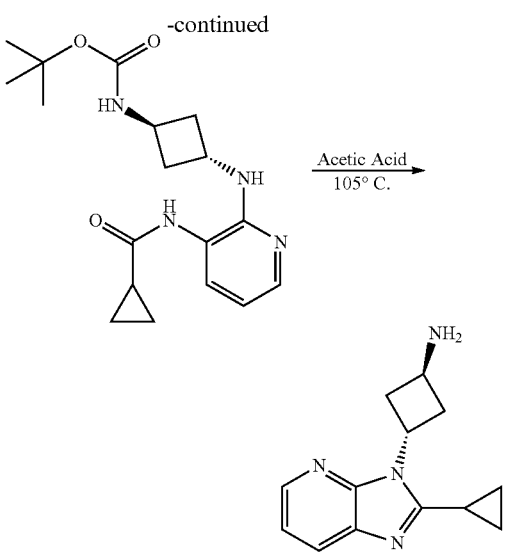

Step 1: tert-butyl(trans-3-((3-nitropyridin-2-yl)amino)cyclobutyl) carbamate

Tert-butyl(trans-3-aminocyclobutyl)carbamate (1.38 g, 7.41 mmol), 2-chloro-3-nitropyridine (1.25 g, 7.88 mmol) and potassium carbonate (0.655 ml, 10.85 mmol) were combined in dry dimethylsulfoxide (20 mL) and heated at 110° C. After 2 hours the reaction was cooled and partitioned between ethyl acetate (300 mL) and water (300 mL). The organic was dried with magnesium sulfate and evaporated to dryness under reduced pressure. Purification using silica chromatography (dichloromethane to ethyl acetate gradient) gave the desired tert-butyl(trans-3-((3-nitropyridin-2-yl)amino)cyclobutyl)carbamate (1.45 g, 4.70 mmol, 63.5% yield).

Step 2: tert-butyl(trans-3-((3-aminopyridin-2-yl)amino)cyclobutyl) carbamate

Tert-butyl(trans-3-((3-nitropyridin-2-yl)amino)cyclobutyl)carbamate (1.45 g, 4.70 mmol) was dissolved in methanol (150 mL) and placed under argon. palladium, 10% wt. on activated carbon (0.144 g, 0.135 mmol) was added and the reaction hydrogenated under a hydrogen balloon for 40 minutes. The mixture was filtered through a pad of CELITE™ and evaporated to dryness under reduced pressure. The crude amine was used without further purification.

Step 3: tert-butyl(trans-3-((3-(cyclopropanecarboxamido)pyridin-2-yl)amino)cyclobutyl)carbamate The crude amine from step 2 was dissolved in dry dimethylformamide (10 mL) and treated with cyclopropanecarboxylic acid (0.400 ml, 5.02 mmol), HATU (1.90 g, 5.00 mmol), and triethylamine (1.0 ml, 7.19 mmol). The reaction was stirred for 35 minutes. Water (200 mL) and ethyl acetate (300 mL) were added and the phases mixed and separated. The organic was washed with 10% saturated ammonium chloride (200 mL) followed by brine (200 mL) before drying with magnesium sulfate and evaporating to dryness under reduced pressure. Purification using silica chromatography (0-7% methanol in dichloromethane gradient) gave the desired tert-butyl(trans-3-((3-(cyclopropanecarboxamido)pyridin-2-yl)amino)cyclobutyl)carbamate (1.27 g, 3.67 mmol, 78% yield).

Step 4: trans-3-(2-cyclopropyl-3H-imidazo[4,5-b]pyridin-3-yl)cyclobutanamine

Tert-butyl(trans-3-((3-(cyclopropanecarboxamido)pyridin-2-yl)amino)cyclobutyl)carbamate (1.27 g, 3.67 mmol, was dissolved in acetic acid (300 mL) and heated at 105° C. After 4½ hours, trifluoroacetic acid (1 mL) was added and the reaction stirred at 105° C. After heating for an additional 5 hours, the reaction was evaporated to dryness under reduced pressure. The crude product was free based by partitioning between dichloromethane and saturated aqueous sodium bicarbonate. The organic was dried with magnesium sulfate and evaporated to dryness under reduced pressure. The crude was purified using silica chromatography (0-10% methanol in dichloromethane gradient) to give trans-3-(2-cyclopropyl-3H-imidazo[4,5-b]pyridin-3-yl)cyclobutanamine (0.579 g, 2.54 mmol, 53.9% yield).

Intermediate 13

(2-chloro-5-fluoropyridin-3-yl)acetonitrile

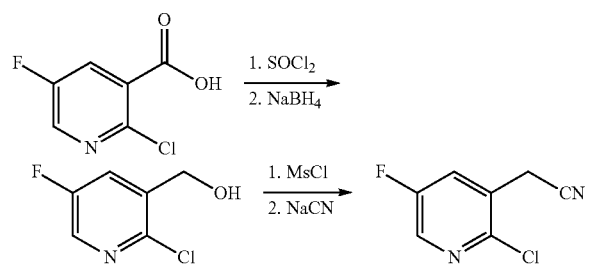

Step 1: (2-chloro-5-fluoropyridin-3-yl)methanol

2-Chloro-5-fluoronicotinic acid (4.50 g, 25.6 mmol) was dissolved in dichloromethane (100 mL) and dry dimethylformamide (1 mL) and cooled in an ice bath. Thionyl chloride (20 ml, 274 mmol) was added slowly and the reaction stirred for 20 minutes then it was removed from the ice bath. After another 15 minutes the solution was evaporated to dryness under reduced pressure. The crude acid chloride was further dried under high vacuum then dissolved in dry tetrahydrofuran (20 mL) and slowly added to an ice cooled solution of sodium borohydride (2.5 g, 66.1 mmol) in water (100 mL with about 80 mL of ice) over 40 minutes. The reaction was stirred for an additional 15 minutes. Ethyl acetate (400 mL) and additional water (100 mL) were added and the phases stirred. Sodium hydroxide (5 N, 40 mL) was added to make the aqueous layer basic. The mixed phases were stirred for 2 hours then the layers were separated. The organic layer was dried with magnesium sulfate before evaporating to dryness under reduced pressure. Purification using silica chromatography (hexane to ethyl acetate gradient) gave the desired (2-chloro-5-fluoropyridin-3-yl)methanol (1.42 g, 8.79 mmol, 34.3% yield) as a brown oil that solidified on standing.

Step 2: (2-chloro-5-fluoropyridin-3-yl)acetonitrile (2-chloro-5-fluoropyridin-3-yl)methanol (1.42 g, 8.79 mmol) was dissolved in dichloromethane (100 mL) and treated with triethylamine (1.5 ml, 10.78 mmol). The solution was cooled in an ice bath and methanesulfonyl chloride (0.75 ml, 9.69 mmol) was added dropwise. After stirring for 5 minutes, saturated sodium bicarbonate (100 mL) was added and the phases mixed and separated. The organic was dried with magnesium sulfate and evaporated under reduced pressure to about 5 mL to give the crude mesylate which was not purified further. It was dissolved in dimethylformamide (10 mL) and treated with an aqueous solution of sodium cyanide (0.5 g, 10.20 mmol) (10 mL). Catalytic potassium iodide (0.056 ml, 1.054 mmol) was added and the reaction heated at 60° C. for 15 minutes. The reaction was cooled and water (100 mL), saturated sodium bicarbonate (20 mL) and ethyl acetate (200 mL) were added. The phases mixed and separated and the organic dried with magnesium sulfate and evaporated to dryness under reduced pressure. Purification using silica chromatography (hexane to ethyl acetate gradient) gave impure material which was recolumned (dichloromethane isocratic) to give 2-(2-chloro-5-fluoropyridin-3-yl)acetonitrile (0.571 g, 3.35 mmol, 38.1% yield).

Intermediate 14

(2-chloropyridin-3-yl)acetonitrile

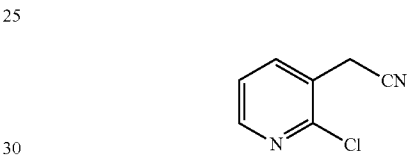

(2-Chloropyridin-3-yl)acetonitrile was synthesized analogous to intermediate 13 using 2-chloronicotinic acid as a starting material in place of 2-chloro-5-fluoronicotinic acid.

Intermediate 15

1-(2-chloro-5-fluoropyridin-3-yl)cyclopropanecarbonitrile

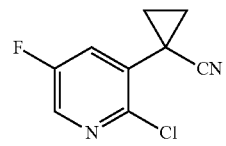

Sodium hydride (60% in oil, 0.620 g, 15.5 mmol) was washed with hexanes (2×10 mL) under nitrogen. Dry dimethylformamide (5 mL) was added and the suspension cooled in an acetone/ice bath. A solution of 2-(2-chloro-5-fluoropyridin-3-yl)acetonitrile (0.571 g, 3.35 mmol) in dry dimethylformamide (10 mL) was added slowly and the reaction stirred for minutes. 1-Bromo-2-chloroethane (0.300 ml, 3.60 mmol) was added. After stirring in the cold bath for 5 minutes, the orange mixture was removed from the cold bath and heated at 50° C. After 45 minutes the mixture was cooled and carefully quenched by addition of saturated ammonium chloride (10 mL) then partitioned between 10% saturated ammonium chloride (200 mL) and ethyl acetate (300 mL). The organic was dried with magnesium sulfate and evaporated to dryness under reduced pressure. The crude product was purified using silica chromatography (hexane to ethyl acetate gradient) to give the desired 1-(2-chloro-5-fluoropyridin-3-yl)cyclopropanecarbonitrile (0.400 g, 2.034 mmol, 60.8% yield).

Intermediate 16

1-(2-chloropyridin-3-yl)cyclopropanecarbonitrile

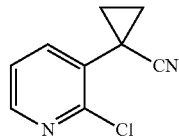 [SMILES: N#CC1(c2cccnc2Cl)CC1]

1-(2-Chloropyridin-3-yl)cyclopropanecarbonitrile was synthesized analogous to 1-(2-chloro-5-fluoropyridin-3-yl)cyclopropanecarbonitrile (Intermediate 15) using (2-chloropyridin-3-yl)acetonitrile as a reactant in place of 2-(2-chloro-5-fluoropyridin-3-yl)acetonitrile.

Intermediate 17

4-(2-chloropyridin-3-yl)tetrahydro-2H-pyran-4-carbonitrile

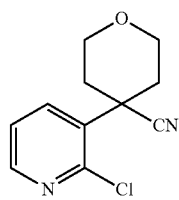 [SMILES: N#CC1(c2cccnc2Cl)CCOCC1]

Intermediate 17 was synthesized using the method for intermediate 15 substituting chloroethyl ether for 1-bromo-2-chloroethane.

Intermediate 18

1-(2-chloropyridin-3-yl)cyclopentanecarbonitrile

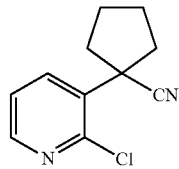 [SMILES: N#CC1(c2cccnc2Cl)CCCC1]

2-(2-Chloropyridin-3-yl)acetonitrile (0.280 g, 1.835 mmol) was dissolved in dry tetrahydrofuran (1.5 mL) under nitrogen and cooled in an ice bath. 1,4-Dibromobutane (0.220 ml, 1.842 mmol) was added followed by dropwise addition of sodium bis(trimethylsilyl)amide (1.0 M in tetrahydrofuran, 4.5 ml, 4.50 mmol). The mixture was stirred for 20 minutes then quenched by addition of saturated ammonium chloride (10 mL). Water (100 mL) and ethyl acetate (200 mL) were added and the phases mixed and separated. The organic was dried with magnesium sulfate and evaporated to dryness under reduced pressure. Purification using silica chromatography (hexane to ethyl acetate gradient) gave the desired 1-(2-chloropyridin-3-yl)cyclopentanecarbonitrile (0.252 g, 1.219 mmol, 66.4% yield).

Intermediate 19

1-(2-chloropyridin-3-yl)cyclobutanecarbonitrile

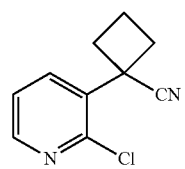 [SMILES: N#CC1(c2cccnc2Cl)CCC1]

Intermediate 19 was synthesized using the method analogous to intermediate 18 substituting 1,3-dibromopropane for 1,4-dibromobutane.

Intermediate 20

1-(2-chloro-5-fluoropyridin-3-yl) Cyclopropanecarboxylic Acid

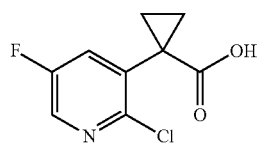 [SMILES: O=C(O)C1(c2cc(F)cnc2Cl)CC1]

1-(2-chloro-5-fluoropyridin-3-yl)cyclopropanecarbonitrile (intermediate 16, 0.400 g, 2.034 mmol) was dissolved in a mixture of water (6 mL) and concentrated sulfuric acid (6 mL). The reaction was heated at 105° C. and stirred for 3½ hours. The reaction was cooled and ice (~200 mL) and ethyl acetate (200 mL) were added. The pH was carefully adjusted to about 9 and the phases separated. The organic was discarded and the aqueous was reacidified to about pH 1 using 5 N hydrochloric acid. It was extracted with ethyl acetate (2×300 mL). The combined organic layers were dried with magnesium sulfate and evaporated to dryness under reduced pressure. The crude 1-(2-chloro-5-fluoropyridin-3-yl)cyclopropanecarboxylic acid (0.402 g, 1.864 mmol, 92% yield) was used without further purification.

Intermediate 21

1-(2-chloropyridin-3-yl)cyclopropanecarboxylic acid

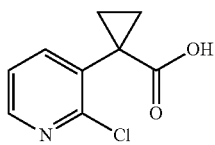 [SMILES: O=C(O)C1(c2cccnc2Cl)CC1]

Intermediate 21 was synthesized analogous to intermediate 20 using intermediate 16 in place of intermediate 15.

Intermediate 22

2-(2-chloro-5-fluoropyridin-3-yl)-2-methylpropanenitrile

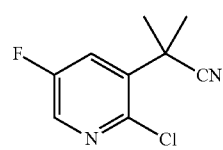

Intermediate 22 was synthesized analogous to intermediate 15 using 3 equivalents of methyl iodide in place of 1-bromo-2-chloroethane.

Intermediate 23

2-(2-chloro-5-fluoropyridin-3-yl)-2-methylpropanoic acid

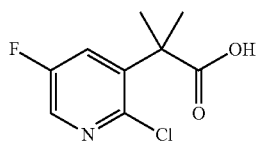

Intermediate 23 was synthesized analogous to intermediate 20 using intermediate 22 in place of intermediate 16.

Intermediate 24

2-(2-chloropyridin-3-yl)-2-methylpropanenitrile

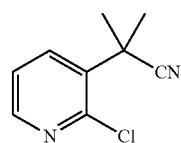

Intermediate 24 was synthesized analogous to intermediate 16 using 3 equivalents of methyl iodide in place of 1-bromo-2-chloroethane.

Intermediate 25

2-(2-chloropyridin-3-yl)-2-methylpropanoic acid

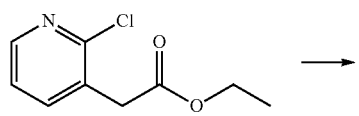

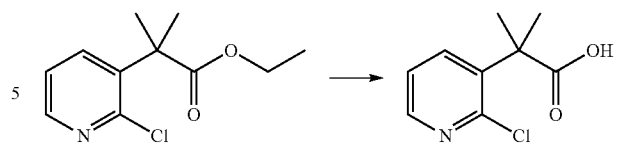

Step 1: ethyl 2-(2-chloropyridin-3-yl)-2-methylpropanoate

Ethyl 2-(2-chloropyridin-3-yl)acetate (1.3306 g, 6.67 mmol) was dissolved in dry tetrahydrofuran (18 mL) under nitrogen. The reaction mixture was cooled to −78° C. and lithium bis(trimethylsilyl)amide (1.0 M solution in tetrahydrofuran, 20.00 mL, 20.00 mmol) was added dropwise. After stirring for 10 minutes, iodomethane (1.248 mL, 20.00 mmol) was added. After 1 h, the cooling bath was removed and the mixture was allowed to warm to room temperature. The reaction was stirred for another hour then the mixture was diluted with water (20 mL) and extracted with EtOAc (3×100 mL). The combined organic layer was washed with saturated ammonium chloride (100 mL) and dried over sodium sulfate before evaporating to dryness under reduced pressure. The crude ethyl 2-(2-chloropyridin-3-yl)-2-methylpropanoate (1.43 g, 6.32 mmol, 95% yield) was used without further purification.

Step 2: 2-(2-chloropyridin-3-yl)-2-methylpropanoic acid

Ethyl 2-(2-chloropyridin-3-yl)-2-methylpropanoate (1.43 g, 6.28 mmol) was suspended in concentrated hydrochloric acid (36.5-38.0%, 21.20 mL, 251 mmol) under nitrogen and heated at 105° C. for 20 hours. Additional concentrated hydrochloric acid (15 mL) was added and the reaction heated for another 12 hours. The mixture was concentrated in vacuo and the product was obtained as a brown solid.

Intermediate 26

1-(trans-3-aminocyclobutyl)-3,3-dimethyl-1H-pyrrolo[2,3-b]Pyridin-2(3H)-One Hydrochloride

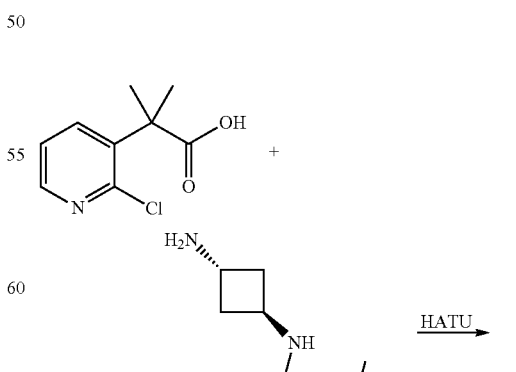

113

-continued

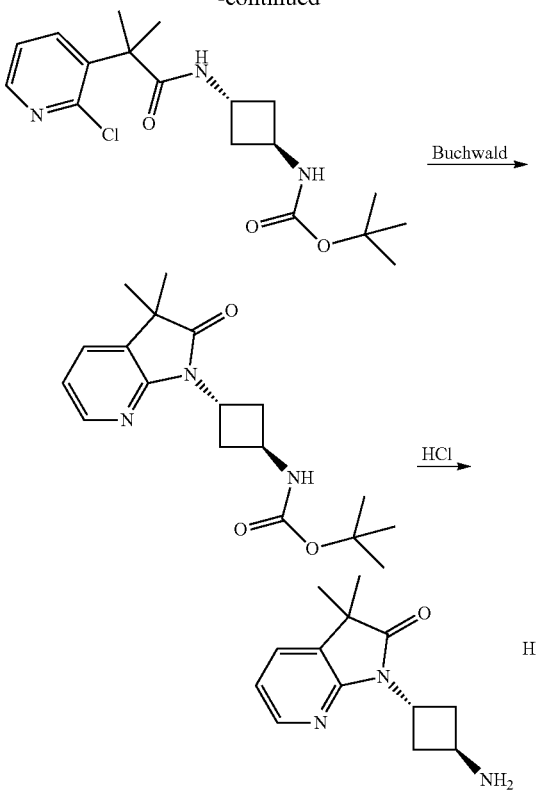

Step 1: tert-butyl(trans-3-(2-(2-chloropyrdin-3-yl)-2-methylpropanamido)cyclobutyl)carbamate 2-(2-Chloropyridin-3-yl)-2-methylpropanoic acid hydrochloride (intermediate 25, 992 mg, 4.20 mmol), tert-butyl (trans-3-aminocyclobutyl)carbamate (939 mg, 5.04 mmol), hatu (2077 mg, 5.46 mmol) and triethylamine (2.4 ml, 16.81 mmol) were dissolved in dichloromethane (8.4 mL). The reaction mixture was stirred at room temperature for 21 hours then diluted with water and extracted with dichloromethane. The organic was washed with saturated ammonium chloride and dried over magnesium sulfate. Evaporation under reduced pressure and purification using silica chromatography (0% to 100% ethyl acetate in hexane gradient) gave tert-butyl(trans-3-(2-(2-chloropyridin-3-yl)-2-methylpropanamido)cyclobutyl)carbamate (1327 mg, 3.61 mmol, 86% yield) as white solid.

Step 2: tert-butyl(trans-3-(3,3-dimethyl-2-oxo-2,3-dihydro-1H-pyrrolo[2,3-b]pyridin-1-yl)cyclobutyl) carbamate Tert-butyl(trans-3-(2-(2-chloropyridin-3-yl)-2-methylpropanamido)cyclobutyl)carbamate (1074 mg, 2.92 mmol), sodium t-butoxide (561 mg, 5.84 mmol), and chloro(2-dicyclohexylphosphino-2',6'-di-1-propoxy-1,1'-biphenyl)[2-(2-aminoethyl-phenyl)]palladium(ii) methyl tert-butyl ether adduct (143 mg, 0.175 mmol) were sealed in a round-bottomed flask under nitrogen. Dry dioxane (5 mL) was added and the reaction heated at 80° C. After 2 hours, the mixture was cooled and partitioned between ethyl acetate, water, and saturated ammonium chloride. The organic was dried with magnesium sulfate and evaporated to dryness to give tert-butyl(trans-3-(3,3-dimethyl-2-oxo-2,3-dihydro-1H-pyrrolo[2,3-b]pyridin-1-yl)cyclobutyl)carbamate (980 mg, 2.96 mmol, quantitative) as light-yellow solid.

Step 3: 1-(trans-3-aminocyclobutyl)-3,3-dimethyl-1H-pyrrolo[2,3-b]pyridin-2(3H)-one hydrochloride To the product from step 2 was added ethyl acetate (10 mL) followed by 4 M hydrogen chloride in 1,4-dioxane (3649 µl, 14.60 mmol). After stirring at room temperature for 3 hours, the precipitate was collected by filtration, washed with additional ethyl acetate, and dried to give 1-(trans-3-aminocyclobutyl)-3,3-dimethyl-1H-pyrrolo[2,3-b]pyridin-2(3H)-one hydrochloride (680 mg, 2.54 mmol, 87% yield) as tan solid.

Intermediate 27 trans-N1-(benzo[d]thiazol-2-yl)-$N^3$-(3-chloropyrazin-2-yl)cyclobutane-1,3-diamine

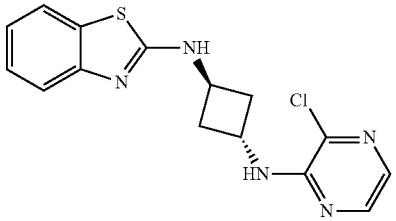 [SMILES: Clc1nccnc1N[C@H]1C[C@H](Nc2nc3ccccc3s2)C1]

Trans-$N^1$-(benzo[d]thiazol-2-yl)cyclobutane-1,3-diamine (intermediate 11, 0.058 g, 0.264 mmol) and 2,3-dichloropyrazine (0.035 ml, 0.336 mmol) were suspended in isopropanol (1 mL) in a microwave vial. The mixture was heated at 150° C. for 90 minutes. The mixture was evaporated to dryness under reduced pressure and purified using silica chromatography (hexane to ethyl acetate gradient) to give trans-$N^1$-(benzo[d]thiazol-2-yl)-$N^3$-(3-chloropyrazin-2-yl) cyclobutane-1,3-diamine (0.0594 g, 0.179 mmol, 67.7% yield) as an oil.

Intermediate 28

2-bromo-5-(2-methyl-1,3-dioxolan-2-yl)pyridine

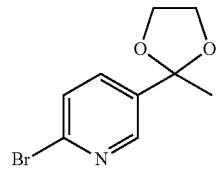

A mixture of 5-acetyl-2-bromopyridine (0.6 g, 3.00 mmol), ethylene glycol (0.535 ml, 9.60 mmol), p-toluenesulfonic acid monohydrate (0.171 g, 0.900 mmol), and toluene (12.00 ml) was stirred at 140° C. for 5 hours. The reaction mixture was washed with saturated sodium bicarbonate and brine. The aqueous layer was back extracted with ethyl acetate and the combined organics dried with magnesium sulfate and concentrated to give crude 2-bromo-5-(2-methyl- 1,3-dioxolan-2-yl)pyridine (0.575 g, 2.356 mmol, 79% yield) as an orange oil. It was used without further purification.

Intermediate 29

2-(3-chloropyrazin-2-yl)-2-methylpropanoic acid

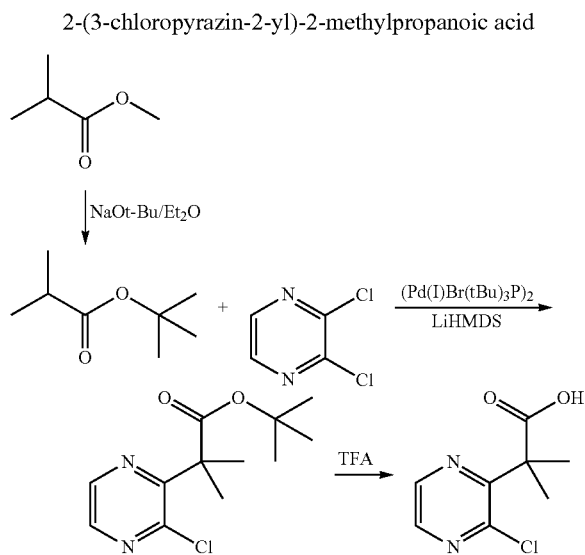

Step 1: tert-butyl 2-(3-chloropyrazin-2-yl)-2-methylpropanoate

Sodium tert-butoxide (7.2 g, 74.9 mmol) was suspended in diethyl ether (2500 mL) under argon. Methyl isobutyrate (6.0 ml, 58.7 mmol) was added and the mixture stirred at room temperature for 3 hours. The suspension was filtered through a pad of neutral alumina and concentrated under reduced pressure to ~50 mL. The crude product was placed under argon and bromo[tri-tert-butylphosphine]dipalladium(I) dimer (0.282 g, 0.363 mmol) was added. The solution was cooled in an ice/acetone bath and lithium bis(trimethylsilyl) amide (1.0 M solution in tetrahydrofuran, 55 ml, 55.0 mmol) was added. The solution was stirred for minutes. 2,3-Dichloropyrazine (5.0 ml, 48.0 mmol) was added neat and after another 5 minutes the mixture was heated at 50° C. for 40 hours. The mixture was cooled and partitioned between water (400 mL), saturated ammonium chloride (100 mL) and ethyl acetate (400 mL). The organic was dried with magnesium sulfate and evaporated to dryness under reduced pressure. The crude product was purified using silica chromatography (hexane to ethyl acetate gradient) to give tert-butyl 2-(3-chloropyrazin-2-yl)-2-methylpropanoate (8.51 g, 33.1 mmol, 69.0% yield).

Step 2: 2-(3-chloropyrazin-2-yl)-2-methylpropanoic acid

The tert-butyl ester from step 1 was dissolved in a mixture of dichloromethane (40 mL) and trifluoroacetic acid (20 mL) and heated at reflux. After 4 hours the solution was evaporated to dryness under reduced pressure and purified using silica chromatography (0-10% methanol in dichloromethane gradient) to give 2-(3-chloropyrazin-2-yl)-2-methylpropanoic acid (5.70 g, 28.4 mmol, 59.2% yield) as a tan solid.

Intermediate 30

5-(trans-3-aminocyclobutyl)-7,7-dimethyl-5H-pyrrolo[2,3-b]pyrazin-6(7H)-one

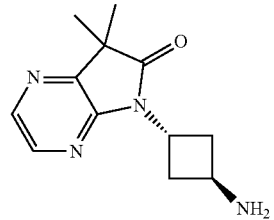 [SMILES: CC1(C)C(=O)N([C@H]2C[C@H](N)C2)c2nccnc21]

2-(3-Chloropyrazin-2-yl)-2-methylpropanoic acid (intermediate 29, 0.302 g, 1.505 mmol) was dissolved in dichloromethane (20 mL) and treated with thionyl chloride (5.0 ml, 68.5 mmol). The solution was heated at reflux for 30 minutes then evaporated to dryness under reduced pressure. Carbon tetrachloride (20 ml) was added to the crude residue and it was evaporated to dryness once more. It was dried under high vacuum for 20 minutes. The crude acid chloride was dissolved in dichloromethane (6 mL) and added slowly to an ice cooled solution of tert-butyl(trans-3-aminocyclobutyl)carbamate (0.280 g, 1.505 mmol) and diisopropylethylamine (2.5 ml, 14.37 mmol) in dichloromethane (10 mL). The solution was stirred for 15 minutes after which the mixture was evaporated to dryness under reduced pressure and the crude dissolved in dry tetrahydrofuran (10 mL). Sodium t-butoxide (1.45 g, 15.09 mmol) was added and the reaction stirred at room temperature. After 30 minutes the reaction was partitioned between water (300 mL) and ethyl acetate (300 mL). The organic was washed with 20% saturated ammonium chloride (200 mL) then dried with magnesium sulfate and evaporated to dryness under reduced pressure. Purification using silica chromatography (hexane to ethyl acetate gradient) gave the desired tert-butyl(trans-3-(7,7-dimethyl-6-oxo-6,7-dihydro-5H-pyrrolo[2,3-b]pyrazin-5-yl)cyclobutyl)carbamate (0.462 g, 1.390 mmol, 92% yield). It was dissolved in dichloromethane (10 mL) and treated with trifluoroacetic acid (5 mL). The solution was stirred for 15 minutes. The dark solution was evaporated to dryness under reduced pressure and further dried under high vac. The crude amine was combined with purified using silica chromatography (1-20% (2N ammonia in methanol) in dichloromethane gradient) to give 5-(trans-3-aminocyclobutyl)-7,7-dimethyl-5H-pyrrolo[2,3-b]pyrazin-6(7H)-one (0.294 g, 1.27 mmol, 91% yield).

Intermediate 31 trans-$N^1$-(5-methylpyridin-2-yl)cyclohexane-1,4-diamine dihydrochloride

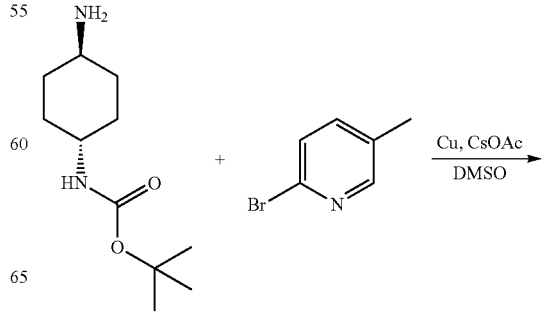

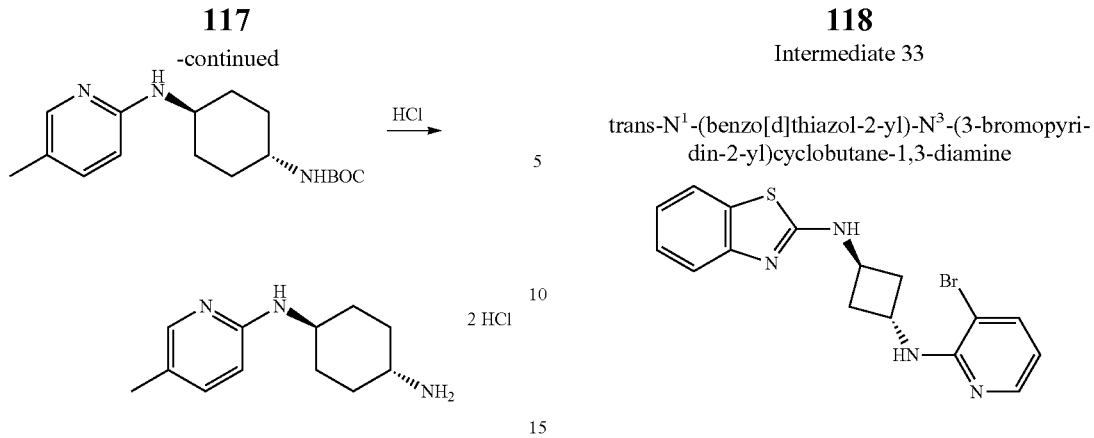

Step 1: tert-butyl(trans-4-((5-methylpyridin-2-yl)amino) cyclohexyl)carbamate Tert-butyl trans-4-aminocyclohexylcarbamate (1.9965 g, 9.32 mmol), 2-bromo-5-methylpyridine (1.923 g, 11.18 mmol), copper (0.047 g, 0.745 mmol), and cesium acetate (11.09 g, 57.8 mmol) were suspended in dry DMSO (11.65 ml) and stirred at 100° C. for 22 hours. The reaction was allowed to cool to room temperature. The reaction mixture was diluted with 1N sodium hydroxide and extracted with ethyl acetate. The organic extract was washed with water, brine, dried over magnesium sulfate and concentrated in vacuo. The crude product was adsorbed onto a plug of silica gel and chromatographed through a Biotage SNAP HP-silica gel column (100 g), eluting with a gradient of 10% to 100% EtOAc in hexane, to provide tert-butyl(trans-4-((5-methylpyridin-2-yl)amino)cyclohexyl)carbamate (0.9695 g, 3.17 mmol, 34.1% yield).

Step 2: trans-$N^1$-(5-methylpyridin-2-yl)cyclohexane-1,4-diamine dihydrochloride Tert-butyl(trans-4-((5-methylpyridin-2-yl)amino)cyclohexyl)carbamate (0.9695 g, 3.17 mmol) and hydrogen chloride (4.0 M solution in 1,4-dioxane, 11.02 ml, 31.7 mmol) to stir at room temperature. After 3½ hours the mixture was evaporated to dryness under reduced pressure. The crude trans-$N^1$-(5-methylpyridin-2-yl)cyclohexane-1,4-diamine dihydrochloride was used without further purification.

Intermediate 32 cis-$N^1$-(benzo[d]thiazol-2-yl)cyclobutane-1,3-diamine

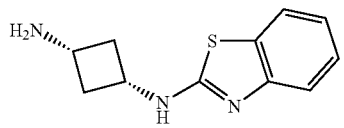 [SMILES: N[C@H]1C[C@@H](Nc2nc3ccccc3s2)C1]

Intermediate 32 was synthesized analogous to intermediate 11 using tert-butyl(cis-3-aminocyclobutyl)carbamate in place of tert-butyl(trans-3-aminocyclobutyl)carbamate.

Intermediate 33 trans-$N^1$-(benzo[d]thiazol-2-yl)-$N^3$-(3-bromopyridin-2-yl)cyclobutane-1,3-diamine Tert-butyl(trans-3-(benzo[d]thiazol-2-ylamino)cyclobutyl)carbamate (intermediate 10, 1.16 g, 3.63 mmol) was dissolved in a mixture of dichloromethane (50 mL) and trifluoroacetic acid (10 mL). The solution was stirred for 20 minutes then evaporated to dryness under reduced pressure and further dried under high vacuum at 60° C. The crude amine was treated with cesium carbonate (2.85 g, 8.75 mmol) and dissolved in dry dimethylsulfoxide (5 mL). 3-Bromo-2-fluoropyridine (0.400 ml, 3.89 mmol) was added in one portion and the reaction heated at 110° C. After 2½ hours, another portion of 3-bromo-2-fluoropyridine (0.100 mL) was added and the reaction heated for another 12 hours. Additional 3-bromo-2-fluoropyridine (0.100 mL) was added and the heating continued for another 2 hours. The reaction was cooled and partitioned between 20% saturated sodium bicarbonate (200 mL) and ethyl acetate (200 mL). The organic phase was dried with magnesium sulfate and evaporated to dryness under reduced pressure. Purification using silica chromatography (hexane to ethyl acetate gradient) gave the desired trans-$N^1$-(benzo[d]thiazol-2-yl)-$N^3$-(3-bromopyridin-2-yl)cyclobutane-1,3-diamine (0.869 g, 2.316 mmol, 63.8% yield) as a yellow oil that solidified on standing.

Intermediate 34 methyl (2-chloro-5-fluoropyridin-3-yl)carbamate

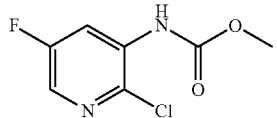

2-Chloro-5-fluoronicotinic acid (1.52 g, 7.36 mmol) was dissolved in a mixture of dry dimethylformamide (2 mL) and triethylamine (1.6 ml, 11.50 mmol) under nitrogen. The solution was cooled to −10° C. and diphenylphosphoryl azide (2.4 ml, 11.14 mmol) was added dropwise over 10 minutes. The reaction was stirred for 15 minutes then removed from the cold bath. After another 15 minutes the solution was diluted with ethyl acetate (200 mL) then washed with water (2×200 mL) before drying with brine (200 mL). The crude intermediate was dried further with magnesium sulfate then evaporated to dryness under reduced pressure using a 40° C. water bath. Toluene (100 mL) was added to the crude oil and the solution heated at 80° C. After 20 minutes methanol (80 mL) was added. The solution was stirred for another another 20 minutes then the mixture was evaporated to dryness under reduced pressure. The crude product was purified using silica chromatography (hexane to ethyl acetate gradient) to give the desired methyl (2-chloro-5-fluoropyridin-3-yl)carbamate (0.903 g, 4.41 mmol, 60.0% yield) as a clear oil.

Intermediate 35 tert-butyl(2-chloro-5-fluoropyridin-3-yl) carbamate

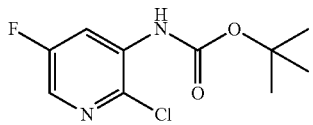 [SMILES: CC(C)(C)OC(=O)Nc1cc(F)cnc1Cl]

2-Chloro-5-fluoronicotinic acid (7.03 g, 40.0 mmol) was dissolved in a mixture of toluene (100 mL), tert-butanol (20 ml, 209 mmol), and triethylamine (6.8 ml, 48.9 mmol). Diphenylphosphoryl azide (9 ml, 41.8 mmol) was added slowly and the reaction heated at 90° C. After 2 hours the reaction was cooled and concentrated under reduced pressure. The residue was partitioned between water (100 mL), saturated sodium bicarbonate (70 mL) and ethyl acetate (300 mL). The organic was dried with magnesium sulfate and evaporated to dryness under reduced pressure. Purification using silica chromatography (hexane to ethyl acetate gradient) gave the desired tert-butyl (2-chloro-5-fluoropyridin-3-yl)carbamate (4.97 g, 20.15 mmol, 50.3% yield) as a thick oil.

Intermediate 36 tert-butyl(2-chloro-5-fluoropyridin-3-yl)(methyl) carbamate

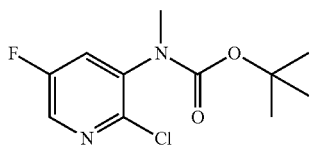 [SMILES: CN(C(=O)OC(C)(C)C)c1cc(F)cnc1Cl]

Tert-butyl (2-chloro-5-fluoropyridin-3-yl)carbamate (Intermediate 35) (1.05 g, 4.26 mmol) was dissolved in dry tetrahydrofuran (20 mL) and cooled in an ice bath under nitrogen. Sodium hydride (60% dispersion in mineral oil, 0.18 g, 4.50 mmol) was added in one portion and the mixture stirred for 20 minutes. Iodomethane (0.300 ml, 4.83 mmol) was added dropwise and the reaction stirred for another 2 hours. Dry dimethylformamide (5 mL) was added and the reaction stirred for 14 hours. The reaction was quenched by addition of saturated ammonium chloride (10 mL) then partitioned between water (300 mL) and ethyl acetate (300 mL). The organic was dried with magnesium sulfate and evaporated to dryness under reduced pressure. Purification using silica chromatography (hexane to ethyl acetate gradient) gave the desired tert-butyl (2-chloro-5-fluoropyridin-3-yl)methyl) carbamate (0.920 g, 3.53 mmol, 83% yield) as a light yellow oil that solidified on standing.

Intermediate 37 methyl (2-chloro-5-fluoropyridin-3-yl)(methyl)carbamate

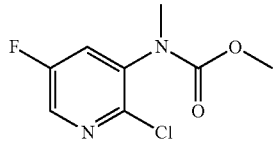

Intermediate 37 was synthesized analogous to intermediate 36 using intermediate 34 in place of intermediate 35.

Intermediate 38

2-chloro-5-fluoro-N-methylpyridin-3-amine

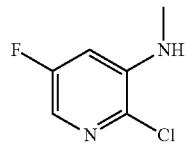

Tert-butyl (2-chloro-5-fluoropyridin-3-yl)(methyl)carbamate (Intermediate 36) (0.920 g, 3.53 mmol) was dissolved in trifluoroacetic acid (20 mL) and heated at 50° C. for 90 minutes. The solution was allowed to cool to room temperature and stir for another 14 hours. The reaction mixture was evaporated to dryness under reduced pressure and water (80 mL), saturated sodium bicarbonate (50 mL) and ethyl acetate (100 mL) were added. The phases were mixed and separated and the organic phase was dried with magnesium sulfate before evaporating to dryness under reduced pressure. Purification using silica chromatography (0-10% methanol in dichloromethane gradient) gave 2-chloro-5-fluoro-N-methylpyridin-3-amine as an oil.

Intermediate 39

2-chloro-N-cyclopropyl-5-fluoropyridin-3-amine

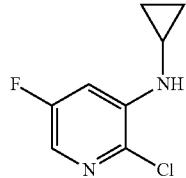 [SMILES: Fc1cnc(Cl)c(NC2CC2)c1]

Tert-butyl (2-chloro-5-fluoropyridin-3-yl)carbamate (Intermediate 36) (0.500 g, 2.027 mmol) was dissolved in dichloromethane (5 mL) and treated with trifluoroacetic acid (0.5 mL). The mixture was stirred at 45° C. for 1 hour then cooled to room temperature. The solution was evaporated to dryness under reduced pressure and the crude amine partitioned between 50% saturated sodium bicarbonate (80 mL) and ethyl acetate (60 mL). The organic was dried with magnesium sulfate and evaporated to dryness under reduced pressure. The solid amine intermediate was combined with anhydrous cupric acetate (0.375 g, 2.065 mmol), sodium carbonate (1.00 g, 9.43 mmol), 2,2'-bipyridyl (0.325 g, 2.081 mmol) and cyclopropylboronic acid (0.305 g, 3.55 mmol). 1,2-Dichloroethane (5 mL) was added and the mixture heated at 70° C. in air. After 2 hours, the mixture was cooled and diluted with ethyl acetate (300 mL). It was washed with a mixture of saturated ammonium chloride (50 mL), water (100 mL), and ammonium hydroxide (20 mL) before drying with magnesium sulfate and evaporating to dryness under reduced pressure. Purification using silica chromatography (hexane to ethyl acetate gradient) gave 2-chloro-N-cyclopropyl-5-fluoropyridin-3-amine (0.270 g, 1.447 mmol, 71.4% yield).

Intermediate 40 methyl (2-chloropyridin-3-yl)(methyl)carbamate

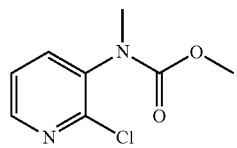

Sodium azide (8 g, 123 mmol) was dissolved in water (100 mL) and cooled in an ice bath. A solution of 2-chloronicotinyl chloride (10 g, 56.8 mmol) in acetone (300 mL, required mild heating to dissolve) was added dropwise via a pressure equalized addition funnel over 40 minutes. Once the acid chloride was added the mixture was stirred for an additional 10 minutes. The mixture was diluted with water (300 mL) and extracted with diethyl ether (2×300 mL). The combined organic was dried with magnesium sulfate and carefully concentrated under reduced pressure (bath temp 40° C.) to about 100 mL. Toluene (200 mL) and methanol (80 mL) were added and the solution heated at 75° C. After 45 minutes the mixture was evaporated to dryness under reduced pressure. The crude methyl carbamate was dissolved in dry dimethylformamide (10 mL) and added dropwise to an ice cooled suspension of sodium hydride (60% in oil, 2.0 g, 50.0 mmol) in dry dimethylformamide (20 mL) under nitrogen. The mixture was stirred for 15 minutes then iodomethane (3.2 ml, 51.5 mmol) was added. The mixture was stirred vigorously for 20 minutes then water (200 mL) and ethyl acetate (300 mL) were added carefully and the phases mixed and separated. The organic was dried with magnesium sulfate and evaporated to dryness under reduced pressure. Purification using silica chromatography (hexane to ethyl acetate gradient) gave the desired methyl (2-chloropyridin-3-yl)(methyl)carbamate (5.80 g, 28.9 mmol, 50.9% yield) as a clear oil.

Intermediate 41

3-chloro-N-cyclopropylpyrazin-2-amine

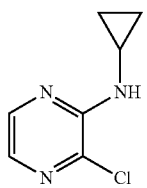 [SMILES: Clc1nccnc1NC1CC1]

2,3-Dichloropyrazine (1.013 ml, 9.73 mmol) and cyclopropylamine (3 ml, 42.8 mmol) were combined in a microwave vial and heated at 130° C. for 30 minutes. The reaction mixture was partitioned between water (100 mL) and ethyl acetate (200 mL). The organic was dried with magnesium sulfate and evaporated to dryness under reduced pressure. Purification using silica chromatography (dichloromethane to ethyl acetate gradient) gave the desired 3-chloro-N-cyclopropylpyrazin-2-amine (1.45 g, 8.55 mmol, 88% yield) as an oil.

Intermediate 42 trans-N1-(benzo[d]thiazol-2-yl)-N3-(5-bromopyrimidin-4-yl)cyclobutane-1,3-diamine

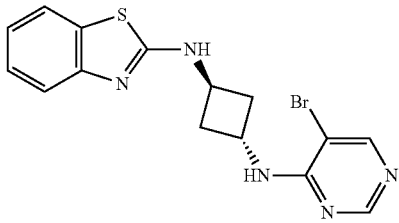 [SMILES: Brc1cncnc1N[C@H]1C[C@H](Nc2nc3ccccc3s2)C1]

Intermediate 42 was synthesized analogous to intermediate 33 using 5-bromo-4-chloropyrimidine in place of 3-bromo-2-chloropyridine.

Intermediate 43

3-(trans-3-aminocyclobutyl)-1H-imidazo[4,5-b]pyridin-2(3H)-one dihydrochloride

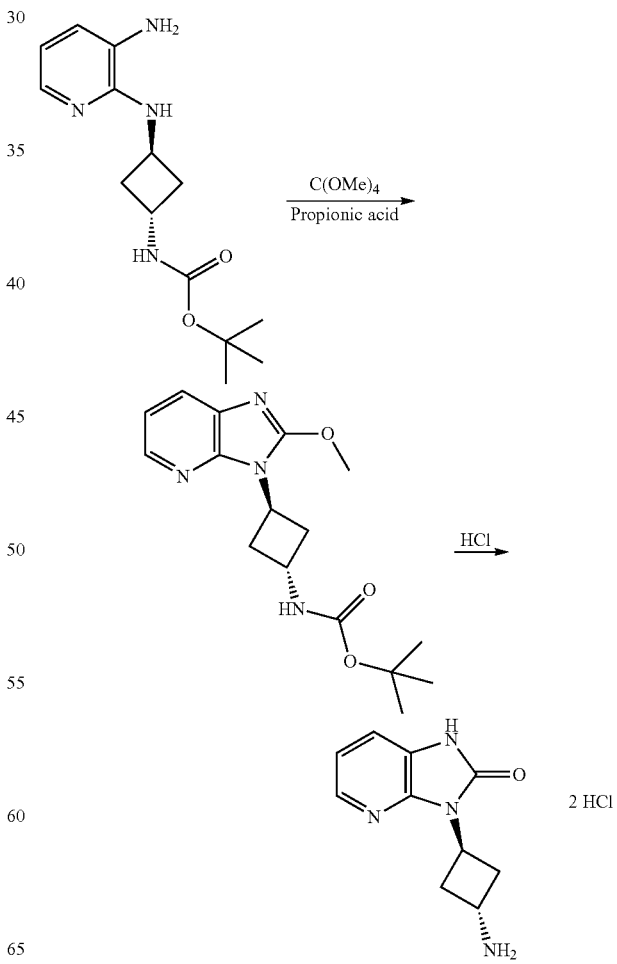

Step 1: tert-butyl(trans-3-(2-methoxy-3H-imidazo[4,5-b]pyridin-3-yl)cyclobutyl)carbamate To a glass microwave vial was added tert-butyl(trans-3-((3-aminopyridin-2-yl)amino)cyclobutyl)carbamate (intermediate 12, step 2, 1.7367 g, 6.24 mmol), tetramethyl orthocarbonate (16.66 ml, 125 mmol), and propionic acid (0.233 ml, 3.12 mmol). The reaction mixture was heated at 100° C. for 5 hours then was allowed to cool to room temperature. The reaction mixture was diluted with water and extracted with ethyl acetate. The organic extract was washed with water, brine, and dried over magnesium sulfate before evaporating to dryness under reduced pressure. The crude product was adsorbed onto a plug of silica gel and chromatographed through a Biotage SNAP HP-silica gel column (50 g), eluting with a gradient of 10% to 100% ethyl acetate in hexane, to provide tert-butyl(trans-3-(2-methoxy-3H-imidazo[4,5-b]pyridin-3-yl)cyclobutyl)carbamate (0.968 g, 3.04 mmol, 48.7% yield).

Step 2: 3-(trans-3-aminocyclobutyl)-1H-imidazo[4,5-b]pyridin-2(3H)-one dihydrochloride Tert-butyl(trans-3-(2-methoxy-3H-imidazo[4,5-b]pyridin-3-yl)cyclobutyl)carbamate (0.9680 g, 3.04 mmol) and hydrogen chloride (4.0M solution in 1,4-dioxane, 7.60 ml, 30.4 mmol) were combined at room temperature and stirred for 75 minutes. The mixture was evaporated to dryness under reduced pressure and the crude 3-(trans-3-aminocyclobutyl)-1H-imidazo[4,5-b]pyridin-2(3H)-one dihydrochloride (0.780 g, 2.82 mmol, 93.5% yield) used without further purification.

Intermediate 44 trans-N$^1$-(benzo[d]thiazol-2-yl)-N$^3$-(3-chloropyrazin-2-yl)cyclobutane-1,3-diamine

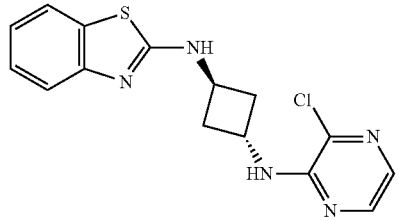 [SMILES: Clc1nccnc1N[C@H]1C[C@H](Nc2nc3ccccc3s2)C1]

Intermediate 44 was synthesized analogous to intermediate 33 using 2,3-dichloropyrazine in place of 3-bromo-2-fluoropyridine.

Intermediate 45

N$^4$-(trans-3-(benzo[d]thiazol-2-ylamino)cyclobutyl)pyrimidine-4,5-diamine

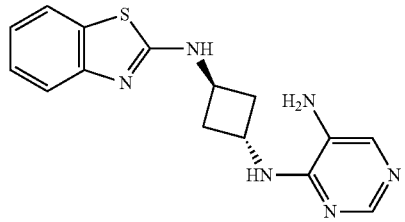 [SMILES: Nc1cncnc1N[C@H]1C[C@H](Nc2nc3ccccc3s2)C1]

Trans-N$^1$-(benzo[d]thiazol-2-yl)-N$^3$-(5-iodopyrimidin-4-yl)cyclobutane-1,3-diamine (synthesized analogous to intermediate 33 using 5-iodo-4-chloropyrimidine in place of 3-bromo-2-chloropyridine, 0.130 g, 0.307 mmol), copper (0.010 g, 0.157 mmol), and cesium acetate (0.250 g, 1.302 mmol) were suspended in dry dimethylsulfoxide (2 mL) in a microwave vessel. Ammonia (2.0 M solution in methanol, 1.0 ml, 2.000 mmol) was added and the mixture sealed under argon. It was heated at 80° C. in an oil bath for 4½ hours then cooled to 60° C. and stirred for another 14 hours. The reaction mixture was partitioned between ethyl acetate (200 mL), water (200 mL), and ammonium hydroxide (30 mL). The organic was dried with magnesium sulfate and evaporated to dryness under reduced pressure. Purification using silica chromatography (0-10% (2 N ammonia in methanol) in dichloromethane gradient) gave the desired N$^4$-(trans-3-(benzo[d]thiazol-2-ylamino)cyclobutyl)pyrimidine-4,5-diamine (0.033 g, 0.106 mmol, 34.4% yield).

Intermediate 46

2-chloro-4-fluorobenzo[d]thiazole

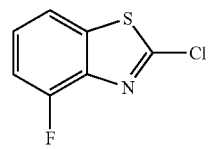 [SMILES: Fc1cccc2sc(Cl)nc12]

4-Fluorobenzo[d]thiazol-2-amine (0.9908 g, 5.89 mmol), copper (II) chloride (1.188 g, 8.84 mmol), and tert-butyl nitrite (1.051 ml, 8.84 mmol) were suspended in acetonitrile and heated at 65° C. After 4½ hours the reaction was allowed to cool to room temperature. The mixture was concentrated under reduced pressure then diluted with 1N hydrochloric acid and extracted with ethyl acetate. The organic extract was washed with water, brine, dried over magnesium sulfate and concentrated in vacuo to give 2-chloro-4-fluorobenzo[d]thiazole (0.8483 g, 4.52 mmol, 77% yield). It was used without further purification.

Intermediate 47 benzyl (cis-3-hydroxycyclobutyl)carbamate

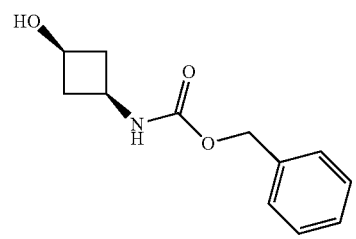 [SMILES: O=C(N[C@H]1C[C@@H](O)C1)OCc1ccccc1]

Intermediate 47 was synthesized analogous to tert-butyl (cis-3-hydroxycyclobutyl)carbamate following the procedure in Radchenko, D. S., Pavlenko, S. O., et al J. Org. Chem. 2010, 75, 5941-5952 using benzyl alcohol in place of tert-butanol.

Intermediate 48

7-fluoroquinolin-2-yl trifluoromethanesulfonate

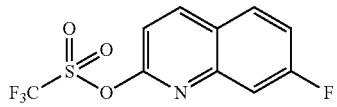 [SMILES: O=S(=O)(Oc1ccc2ccc(F)cc2n1)C(F)(F)F]

To an ice cooled solution of 7-fluoroquinolin-2(1H)-one (1.60 g, 9.81 mmol) in pyridine (40 mL) was added trifluoromethanesulfonic anhydride (2.2 mL, 13.10 mmol) via syringe. After complete addition the reaction was allowed to warm to room temperature. After 1 hour, the solvent was removed in vacuo and the residue was azeotroped with toluene. The residue was stirred vigorously over diethyl ether, filtered and washed with additional diethyl ether. The filtrate was concentrated to dryness to give 2.50 g (86%) of 7-fluoroquinolin-2-yl trifluoromethanesulfonate as an orange oil.

Intermediate 49

3-(trans-4-aminocyclohexyl)-1H-imidazo[4,5-]pyridin-2(3H)-one dihydrochloride

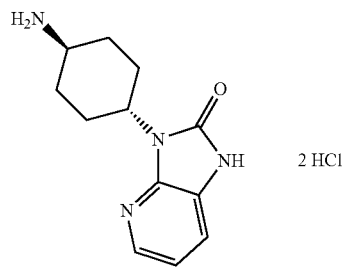 [SMILES: N[C@H]1CC[C@H](n2c(=O)[nH]c3cccnc32)CC1]

Intermediate 49 was synthesized analogous to intermediate 43 using tert-butyl trans-(4-aminocyclohexyl)carbamate in place of tert-butyl trans-(3-aminocyclobutyl)carbamate.

Intermediate 50

7-methoxyquinolin-2-yl trifluoromethanesulfonate

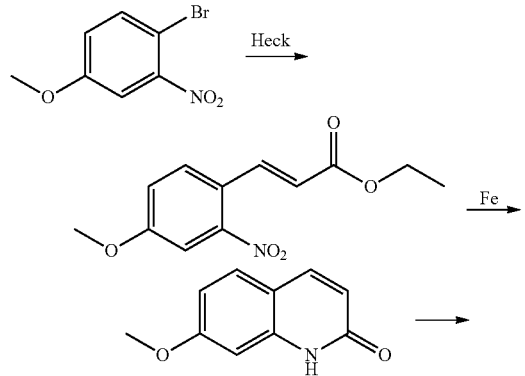

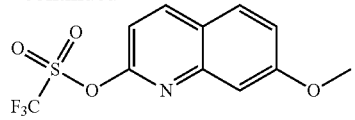

Step 1: (E)-ethyl 3-(4-methoxy-2-nitrophenyl)acrylate

4-Bromo-3-nitroanisole (10.00 g, 43.1 mmol), ethyl acrylate (5.62 mL, 51.7 mmol), tris(dibenzylideneacetone)dipalladium (0) (0.789 g, 0.862 mmol), tri-tert-butylphosphonium tetrafluoroborate (0.500 g, 1.724 mmol), and N,N-dicyclohexylmethylamine (10.10 mL, 51.7 mmol) were mixed in 1,4-dioxane (170 mL) and placed under an argon atmosphere. The reaction mixture was stirred at room temperature for 22 hours. The reaction mixture was diluted with water and extracted twice with ethyl acetate. The combined organic layers were separated, washed with brine, dried over magnesium sulfate, and concentrated. The resulting crude product was purified via silica gel flash column chromatography eluting with 0 to 20% ethyl acetate in hexanes to yield (E)-ethyl 3-(4-methoxy-2-nitrophenyl)acrylate (5.05 g, 20 mmol, 46.5% yield) as an orange solid.

Step 2: 7-methoxyquinolin-2(1H)-one (E)-Ethyl 3-(4-methoxy-2-nitrophenyl)acrylate (20.00 g, 80 mmol) and iron powder (3.39 mL, 478 mmol) were mixed in acetic acid (300 mL). The reaction mixture was stirred at room temperature for 4 days. The reaction mixture was filtered through CELITE™. The filtrate was partitioned between ethyl acetate and saturated sodium bicarbonate. The aqueous layer was separated and extracted once more with ethyl acetate. The combined organic layers were washed with brine, dried over magnesium sulfate, and concentrated. The resulting crude product was diluted with dichloromethane and filtered. The filtrate was diluted with hexanes and partially concentrated. The resulting precipitate was filtered off to yield 7-methoxyquinolin-2(1H)-one (13.16 g, 75 mmol, 94% yield) as a light yellow solid.

Step 3: 7-methoxyquinolin-2-yl trifluoromethanesulfonate 7-methoxyquinolin-2(1H)-one (prepared in step 2) was used as starting material to synthesize Intermediate 50 according to method analogous to intermediate 48 in place of 7-fluoroquinolin-2(1H)-one.

Intermediate 51 quinolin-2-yl trifluoromethanesulfonate

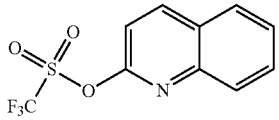 [SMILES: O=S(=O)(Oc1ccc2ccccc2n1)C(F)(F)F]

Intermediate 51 was synthesized analogous to intermediate 48 using quinolin-2(1H)-one in place of 7-fluoroquinolin-2(1H)-one.

Intermediate 52

N-(trans-3-hydrazinylcyclobutyl)benzo[d]thiazol-2-amine dihydrochloride

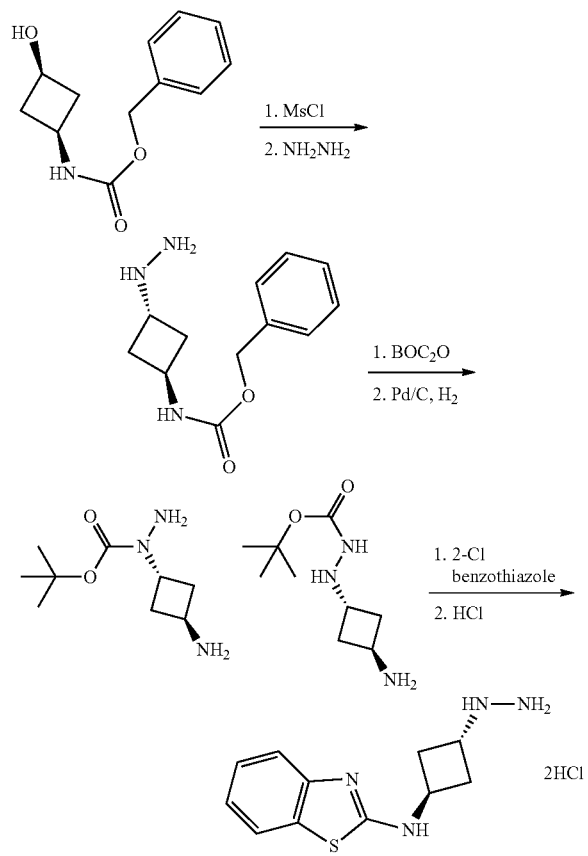

Step 1: benzyl (trans-3-hydrazinylcyclobutyl)carbamate

Benzyl (cis-3-hydroxycyclobutyl)carbamate (intermediate 47, 3.26 g, 14.73 mmol) was suspended in a mixture of diisopropylethylamine (4 ml, 23.00 mmol) and dichloromethane (100 mL) and cooled in an acetone/ice bath under nitrogen. Methanesulfonyl chloride (1.3 ml, 16.80 mmol) was added slowly and the solution stirred for minutes. The reaction was partitioned between water (200 mL), saturated ammonium chloride (50 mL) and dichloromethane (100 mL). The aqueous was extracted with additional dichloromethane (100 mL) and the organic layers combined. They were dried with magnesium sulfate and evaporated to dryness under reduced pressure using a 40° C. water bath. The crude solid mesylate was suspended in ethanol (10 mL) and treated with hydrazine (anhydrous, 4 ml, 127 mmol). The slurry was heated at 80° C. As the mixture warmed it became homogeneous. After 2 hours additional hydrazine (2 mL) was added and the flask was fitted with a reflux condenser. The bath temperature was raised to 95° C. After an additional 3 hours the solution was evaporated to dryness under reduced pressure to give benzyl (trans-3-hydrazinylcyclobutyl)carbamate as a thick white oil. It was further dried under high vacuum at 50° C. for 20 minutes then used without further purification.

Step 2: mixture of tert-butyl 2-(trans-3-aminocyclobutyl) hydrazinecarboxylate and tert-butyl 1-(trans-3-aminocyclobutyl)hydrazinecarboxylate The crude benzyl (trans-3-hydrazinylcyclobutyl)carbamate from step 1 was dissolved in a mixture of tetrahydrofuran (200 mL) and saturated sodium bicarbonate (50 mL). Di-tert-butyl dicarbonate (4.90 ml, 22.91 mmol) was added and the reaction stirred for 15 minutes. Water (400 mL) and ethyl acetate (500 mL) were added and the phases mixed and separated. The organic was washed with brine (300 mL) then dried with magnesium sulfate and evaporated to dryness under reduced pressure. Purification using silica chromatography (hexane to ethyl acetate gradient, visualized in an iodine chamber) gave tert-butyl(trans-3-(((benzyloxy)carbonyl)amino)cyclobutyl)hydrazinecarboxylate (4.48 g, 13.36 mmol, 91% yield, mixture of N1 and N2 protected isomers) as a thick, colorless oil. The intermediate (4.48 g, 13.36 mmol, mixture of N1 and N2 isomers) was dissolved in methanol (150 mL) under argon. Palladium (10% wt. on activated carbon, 0.842 g, 0.791 mmol) was added and the suspension was stirred under a hydrogen balloon for 12 hours. The mixture was filtered through a pad of CELITE™ and the filtrate evaporated to dryness under reduced pressure. The crude amine was used without further purification.

Step 3: N-(trans-3-hydrazinylcyclobutyl)benzo[d]thiazol-2-amine dihydrochloride

The crude amine mixture was treated with 2-chlorobenzothiazole (2.3 ml, 13.56 mmol), cesium carbonate (1.228 ml, 15.35 mmol), and dry N-methylpyrrolidinone (10 mL). The mixture was heated at 100° C. After 3 hours the reaction was cooled and water (300 mL) and ethyl acetate (300 mL) were added. The phases were mixed and separated and the organic dried with magnesium sulfate before evaporating to dryness under reduced pressure. Purification using silica chromatography (0-10% methanol in dichloromethane gradient) gave tert-butyl 1-(trans-3-(benzo[d]thiazol-2-ylamino)cyclobutyl)hydrazinecarboxylate (2.24 g, 6.70 mmol, 50.1% yield) as a white solid. It was dissolved in a hydrogen chloride solution (4 N in dioxane, 15 ml, 60.0 mmol) and stirred for 1 hour at 40° C. The solution was evaporated to dryness under reduced pressure and further dried under high vacuum. The product was assumed to be the dihydrochloride salt and was used without further purification.

Intermediate 53 cyclopropyl(2-fluoropyridin-3-yl)methanone

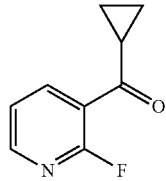 [SMILES: O=C(c1cccnc1F)C1CC1]

Diisopropylamine (0.9 mL, 6.42 mmol) and lithium chloride (0.120 g, 2.83 mmol) were dissolved in dry tetrahydrofuran (1 mL) under nitrogen and cooled in a dry ice bath. A solution of butyllithium (2.5 M in hexanes, 2.6 mL, 6.50 mmol) was added slowly and the reaction stirred for 10 minutes. 2-Fluoropyridine (0.5 mL, 5.81 mmol) was added dropwise and the mixture stirred for 1 hour. Cyclopropanecarboxaldehyde (0.5 mL, 6.69 mmol) was added slowly. After 30 minutes, the mixture was quenched by addition of saturated ammonium chloride (5 mL). Water (200 mL) and ethyl acetate (300 mL) were added and the phases mixed and separated. The organic was dried with magnesium sulfate and evaporated to dryness under reduced pressure. Purification using silica chromatography (hexane to ethyl acetate gradient) gave cyclopropyl(2-fluoropyridin-3-yl)methanol (0.415 g, 2.482 mmol, 42.7% yield). The alcohol was dissolved in chloroform (150 mL) and treated with manganese (IV) oxide (3.0 g, 34.5 mmol). The suspension was heated at gentle reflux for 14 hours. The crude product was purified using silica chromatography (hexane to ethyl acetate gradient) to give cyclopropyl(2-fluoropyridin-3-yl)methanone (0.270 g, 1.635 mmol, 28.1% yield) as a clear oil.

Intermediate 54

2,2,2-trifluoro-1-(2-fluoropyridin-3-yl)ethanone

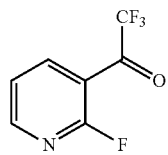 [SMILES: O=C(c1cccnc1F)C(F)(F)F]

Lithium chloride (0.500 g, 11.79 mmol) and diisopropylamine (1.8 mL, 12.84 mmol) were combined under nitrogen with dry tetrahydrofuran (10 mL) and cooled in a dry ice bath. N-Butyllithium (2.5 M solution in hexane, 5.0 mL, 12.50 mmol) was added and the mixture stirred for 10 minutes. 2-Fluoropyridine (0.800 mL, 9.30 mmol) was added dropwise and the reaction stirred. After 10 minutes, additional dry tetrahydrofuran (5 mL) was added to help with stirring. The mixture was stirred for 90 minutes then ethyl trifluoroacetate (1.7 mL, 14.30 mmol) was added dropwise. After 60 minutes the reaction was quenched by addition of hydrochloric acid (5N in 2-propanol, 5 mL, 10 mmol). The mixture was warmed to room temperature and water (150 mL) and ethyl acetate (200 ml) were added. The phases were mixed and separated and the organic dried with magnesium sulfate. Purification using silica chromatography (hexane to ethyl acetate gradient) gave the desired 2,2,2-trifluoro-1-(2-fluoropyridin-3-yl) ethanone (0.812 g, 4.21 mmol, 45.2% yield).

Intermediate 55 tert-butyl 3-(2-methoxy-3H-imidazo[4,5-b]pyridin-3-yl)azetidine-1-carboxylate

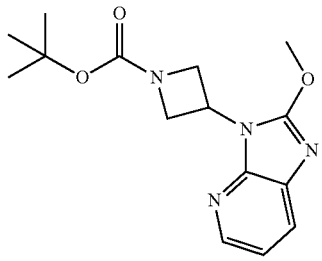 [SMILES: COc1nc2cccnc2n1C1CN(C(=O)OC(C)(C)C)C1]

Intermediate 55 was synthesized analogous to tert-butyl (trans-3-(2-methoxy-3H-imidazo[4,5-b]pyridin-3-yl)cyclobutyl)carbamate (intermediate 43, step 1) using tert-butyl 3-aminoazetidine-1-carboxylate in place of tert-butyl(trans-3-aminocyclobutyl)carbamate.

intermediate 56 tert-butyl 3-(2'-oxospiro[cyclopropane-1,3'-pyrrolo [2,3-b]pyridin]-1'(2'H)-yl)azetidine-1-carboxylate

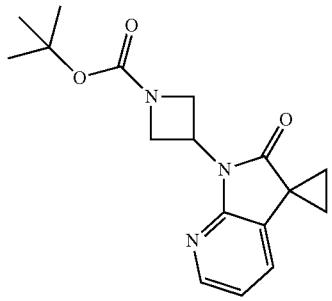 [SMILES: CC(C)(C)OC(=O)N1CC(N2C(=O)C3(CC3)c3cccnc32)C1]

Intermediate 56 was synthesized analogous to tert-butyl (trans-3-(3,3-dimethyl-2-oxo-2,3-dihydro-1H-pyrrolo[2,3-b]pyridin-1-yl)cyclobutyl)carbamate (intermediate 26, step 2) using intermediate 21 in place of intermediate 25 and tert-butyl 3-aminoazetidine-1-carboxylate in place of tert-butyl(trans-3-aminocyclobutyl)carbamate.

Intermediate 57

3,3-dimethyl-1-(piperdin-4-yl)-1H-pyrrolo[2,3-b]pyridin-2(3H)-one dihydrochloride

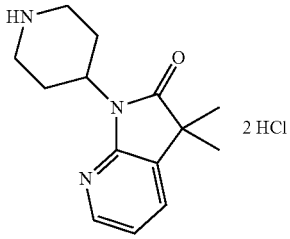 [SMILES: CC1(C)C(=O)N(C2CCNCC2)c2ncccc21]

Intermediate 57 was synthesized analogous to intermediate 26 using tert-butyl 4-aminopiperidine-1-carboxylate in place of tert-butyl(trans-3-aminocyclobutyl)carbamate.

Intermediate 58

3-nitro-N-(piperidin-4-yl)pyridin-2-amine hydrochloride

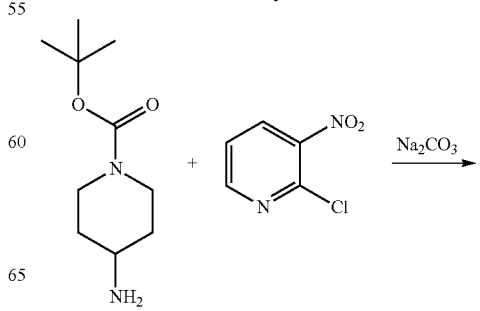

Step 1: tert-butyl 4-((3-nitropyridin-2-yl)amino)piperidine-1-carboxylate

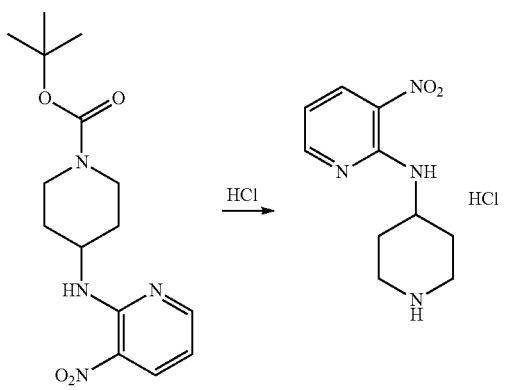

2-Chloro-3-nitro-pyridine (5 g, 33.3 mmol), anhydrous N,N-dimethylformamide (50 mL), 4-amino-piperidine-1-carboxylic acid tert-butyl ester (6.7 g, 33.3 mmol) and anhydrous sodium carbonate (7.1 g, 66.6 mmol) were combined with stirring under nitrogen. The reaction mixture was heated at 90° C. overnight. Then it was poured into water and the resulting yellow solid was filtered off and found to be tert-butyl 4-((3-nitropyridin-2-yl)amino)piperidine-1-carboxylate (8.5 g, 26.4 mmol, 79.4% yield).

Step 2: 3-nitro-N-(piperidin-4-yl)pyridin-2-amine hydrochloride

A mixture of tert-butyl 4-((3-nitropyridin-2-yl)amino)piperidine-1-carboxylate (8.5 g, 26.4 mmol) in hydrogen chloride (4 M solution in methanol, 50 mL) was stirred at room temperature for 3 hours. It was concentrated under reduced pressure to give crude 3-nitro-N-(piperidin-4-yl)pyridin-2-amine hydrochloride (6 g, 23.2 mmol, 88% yield) which was used without further purification.

Intermediate 59

2-chloro-4-(6-methylpyridin-3-yl)pyrimidine

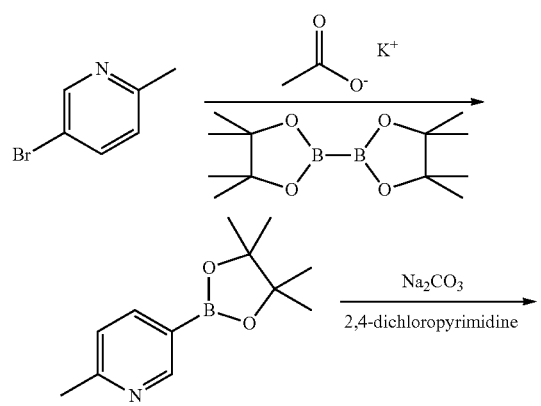

Step 1: 2-methyl-5-(4,4,5,5-tetramethyl-1,3,2-dioxaborolan-2-yl)pyridine

5-Bromo-2-methylpyridine (0.50 g, 2.89 mmol), potassium acetate (0.57 g, 5.80 mmol), 4,4,5,5,4',4',5',5'-octamethyl-[2,2']bi[[1,3,2]dioxaborolanyl](0.75 g, 2.89 mmol) and 1,1'-bis(diphenylphosphino)ferrocene-palladium(ii) dichloride (0.100 g, 0.15 mmol) in dioxane (20 mL) was stirred and heated at 100° C. for 8 hours. The mixture was filtered through CELITE™ and washed with dichloromethane. The organic layer was dried over sodium sulfate and concentrated in vacuo to give crude 2-methyl-5-(4,4,5,5-tetramethyl-1,3,2-dioxaborolan-2-yl)pyridine (650 mg, 2.89 mmol, 100% yield).

Step 2: 2-chloro-4-(6-methylpyridin-3-yl)pyrimidine

2-Methyl-5-(4,4,5,5-tetramethyl-1,3,2-dioxaborolan-2-yl)pyridine (0.65 g, 2.89 mmol), sodium carbonate (0.610 g, 5.80 mmol), 2,4-dichloropyrimidine (0.430 g, 2.89 mmol) and 1,1'-bis(diphenylphosphino)ferrocene-palladium(ii) dichloride (0.100 g, 0.15 mmol) in a mixture of dioxane (20 mL) and water (4 mL) was stirred and heated at 40° C. for 10 hours. The mixture was filtered through CELITE™ and washed with dichloromethane. The filtrate was evaporated in vacuo and the residue was purified by column chromatography on silica gel (10% to 30% ethyl acetate in petroleum ether) to give 2-chloro-4-(6-methylpyridin-3-yl)pyrimidine (280 mg, 1.36 mmol, 47% yield).

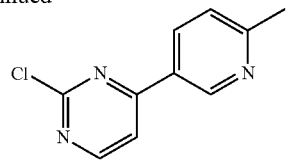

Intermediate 60 cis-N1-(benzo[d]thiazol-2-yl)cyclobutane-1,3-diamine dihydrochloride

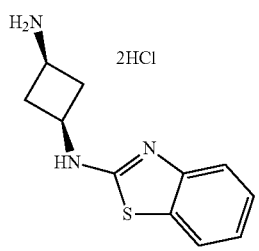 [SMILES: N[C@H]1C[C@@H](Nc2nc3ccccc3s2)C1]

A solution of tert-butyl(cis-3-(benzo[d]thiazol-2-ylamino)cyclobutyl)carbamate (0.40 g, 1.252 mmol) in Dioxane (5 mL) was treated with hydrogen chloride, 4N in 1,4-dioxane (6.26 ml, 25.05 mmol). The resulting solution was stirred at room temperature for 2 h and concentrated to give the desired product cis —N1-(benzo[d]thiazol-2-yl)cyclobutane-1,3-diamine dihydrochloride (0.301 g, 1.030 mmol, 82% yield).

117243-44-1. The product was used in next step without further purification. m/z: 220.1 (M+1) (−2HCl)

Intermediate 61 cis-N1-(5-methylpyridin-2-yl)cyclobutane-1,3-diamine dihydrochloride

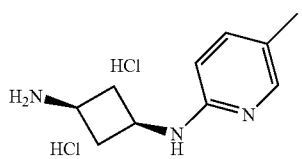

A mixture of tert-butyl(cis-3-aminocyclobutyl)carbamate (1.3 g, 6.98 mmol), 2-bromo-5-methylpyridine (1.321 g, 7.68 mmol), copper powder (3.98 μl, 0.558 mmol), and cesium acetate (6.70 g, 34.9 mmol) in DMSO (8 mL) was heated to 100° C. in a sealed microwave vial for 4 h. The reaction was cooled to room temperature, diluted with water and extracted with EtOAc. The EtOAc extract was concentrated and crude material purified with ISCO using 40 g Grace column, eluting with 0% to 60% EtOAc/hexane to give the boc protected intermediate. To this was added hydrogen chloride, 4N in 1,4-dioxane (17.45 ml, 69.8 mmol) and solution stirred for 2 h and concentrated to give the desired product cis-NI-(5-methylpyridin-2-yl)cyclobutane-1,3-diamine dihydrochloride (0.420 g, 33.9% yield). m/z: 178.1 (M+1-2HCl).

Intermediate 62

7-(trans-3-aminocyclobutyl)-5,5-dimethyl-5H-pyrrolo[2,3-d]pyrimidin-6(7H)-one hydrochloride

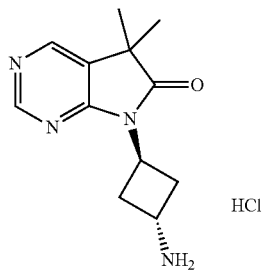 [SMILES: CC1(C)C(=O)N([C@H]2C[C@H](N)C2)c2ncncc21 ; Cl]

To a solution of tert-butyl(trans-3-(5,5-dimethyl-2-(methylthio)-6-oxo-5H-pyrrolo[2,3-d]pyrimidin-7(6H)-yl)cyclobutyl)carbamate, INTERMEDIATE 63, (0.9 g, 2.378 mmol) in dry tetrahydrofuran (10 mL) was added cautiously palladium 10 wt. % on activated carbon (0.051 ml, 0.476 mmol) followed by triethylsilane (3.04 ml, 19.02 mmol). The mixture was stirred for 15 minutes under nitrogen atmosphere, filtered, and filtrate concentrated to give tert-butyl (trans-3-(5,5-dimethyl-6-oxo-5H-pyrrolo[2,3-d]pyrimidin-7 (6H)-yl)cyclobutyl)carbamate. The crude tert-butyl(trans-3-(5,5-dimethyl-6-oxo-5H-pyrrolo[2,3-d]pyrimidin-7(6H)-yl) cyclobutyl)carbamate was redissolved in dioxane (10 mL) and treated with 4N HCl in dioxane (10 mL). After 30 minutes the reaction mixture was evaporated to dryness under reduced pressure to give the desired crude product 7-(trans-3-aminocyclobutyl)-5,5-dimethyl-5H-pyrrolo[2,3-d]pyrimidin-6 (7H)-one hydrochloride (0.55 g, 2.047 mmol, 86% yield). The product was used in next step without further purification. m/z: 233.0 (M+1-HCl).

Intermediate 63 tert-butyl(trans-3-(5,5-dimethyl-2-(methylthio)-6-oxo-5H-pyrrolo[2,3-d]pyrimidin-7(6H)-yl)cyclobutyl)carbamate

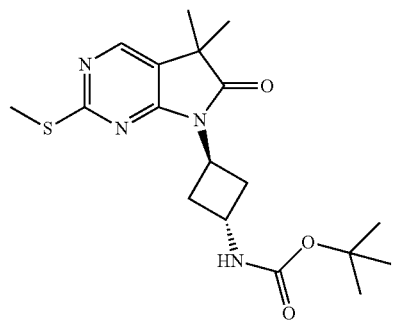 [SMILES: CSc1ncc2c(n1)N([C@H]1C[C@H](NC(=O)OC(C)(C)C)C1)C(=O)C2(C)C]

A microwave vial containing a mixture of ethyl 2-(4-chloro-2-(methylthio)pyrimidin-5-yl)-2-methylpropanoate (2.08 g, 7.57 mmol), tert-butyl(trans-3-aminocyclobutyl)carbamate (1.551 g, 8.33 mmol), tris(dibenzylideneacetone) dipalladium (0) (0.520 g, 0.568 mmol), dicyclohexyl(2',4',6'-triisopropyl-3,6-dimethoxy-[1,1'-biphenyl]-2-yl)phosphine (0.731 g, 1.363 mmol) and sodium tert-butoxide (2.317 ml, 18.93 mmol) in dioxane (15 mL) was purged with argon and capped. The reaction mixture was heated at 100° C. for 3 hours, cooled, and partitioned between water (200 mL) and ethyl actate (200 mL). The organic was isolated and concentrated under reduced pressure. Purification using the ISCO eluting with 0-70% EtOAc/hexane to give the desired product tert-butyl(trans-3-(5,5-dimethyl-2-(methylthio)-6-oxo-5H-pyrrolo[2,3-d]pyrimidin-7(6H)-yl)cyclobutyl)carbamate (0.9 g, 2.378 mmol, 31.4% yield). m/z: 379.2 (M+1).

Intermediate 64 tert-butyl(cis-3-(benzo[d]thiazol-2-ylamino)cyclobutyl)carbamate

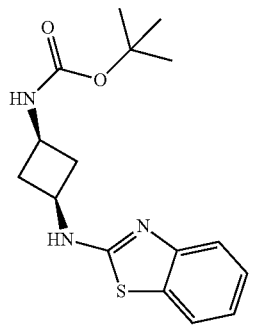 [SMILES: CC(C)(C)OC(=O)N[C@H]1C[C@@H](Nc2nc3ccccc3s2)C1]

A mixture of tert-butyl(cis-3-aminocyclobutyl)carbamate (1.26 g, 6.77 mmol), 2-chlorobenzothiazole (0.965 mL, 6.77 mmol) and N,N-diisopropylethylamine (2.354 mL, 13.53 mmol) in DMSO (5 mL) was heated to 110° C. in a sealed microwave vial for 4 h, cooled to room temperature, diluted with water and extracted with EtOAc. EtOAc extract was concentrated and crude material purified with ISCO using silica gel column eluting with 0-80% EtOAc/hexane to give the desired product tert-butyl(cis-3-(benzo[d]thiazol-2-ylamino)cyclobutyl)carbamate (1.5 g, 4.70 mmol, 69.4% yield). m/z: 320.1 (M+1).

Intermediate 65 tert-butyl(cis-3-aminocyclobutyl)carbamate

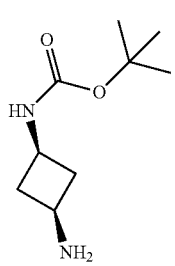

A mixture of tert-butyl(cis-3-azidocyclobutyl)carbamate (7.0 g, 33.0 mmol) and palladium 10% on activated carbon (3.51 ml, 33.0 mmol) in a three necked 1000 mL flask was flushed with nitrogen and 2M ammonia in methanol solution (200 mL) was added. The flask was evacuated and a balloon filled with hydrogen was introduced. The mixture was stirred at room temperature for 18 h, filtered, and the filtrate was evaporated under reduced pressure to give the desired product tert-butyl(cis-3-aminocyclobutyl)carbamate (6.1 g, 99% yield). $^1$H NMR (400 MHz, CHLOROFORM-d) δ ppm 4.64 (br. s., 1 H), 3.72 (d, J=6.85 Hz, 1 H), 3.12 (t, J=7.73 Hz, 1 H), 2.71 (d, J=7.24 Hz, 2 H), 1.51 (q, J=9.85 Hz, 2 H), 1.43 (br. s., 11 H).

Intermediate 66 tert-butyl(cis-3-azidocyclobutyl)carbamate

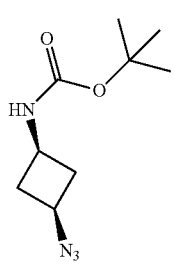

To a solution of cis-3-((tert-butoxycarbonyl)amino)cyclobutyl methanesulfonate (29 g, 109 mmol) in DMF (100 mL) was added sodium azide (5.68 mL, 162 mmol) portionwise and the mixture stirred at 85° C. for 18 h. After cooling, the reaction mixture was diluted with water (200 mL) and extracted with EtOAc (3×100 mL). The combined organic was washed with water (2×100 mL) and brine, dried over Na$_2$SO$_4$ and evaporated in vacuo to give the desired product tert-butyl(cis-3-azidocyclobutyl)carbamate (22 g, 104 mmol, 95% yield) that was used in the next step without further purification. $^1$H NMR (400 MHz, CHLOROFORM-d) δ ppm 4.68 (br. s., 1 H), 3.87 (br. s., 1 H), 3.44-3.68 (m, 1 H), 2.75 (d, J=6.85 Hz, 2 H), 1.90 (q, J=9.19 Hz, 2 H), 1.44 (s, 10 H).

Intermediate 67 trans-3-((tert-butoxycarbonyl)amino)cyclobutyl methanesulfonate

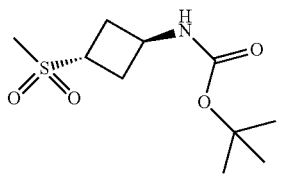 [SMILES: CC(C)(C)OC(=O)N[C@H]1C[C@H](S(C)(=O)=O)C1]

A solution of tert-butyl(trans-3-hydroxycyclobutyl)carbamate (20.05 g, 107 mmol) and triethylamine, anhydrous (22.34 mL, 161 mmol) in DCM (200 mL) was cooled to −30° C. and methanesulfonyl chloride (9.94 mL, 129 mmol) was added dropwise over 20 min period. The mixture was stirred at room temperature for 12 h, washed with 200 mL water, then 200 mL 10% aq. citric acid followed by brine, dried over Na2SO4 and evaporated to give the desired product trans-3-((tert-butoxycarbonyl)amino)cyclobutyl methanesulfonate (29 g, 109 mmol, 102% yield), which was used in the next step without further purification. $^1$H NMR (400 MHz, CHLOROFORM-d) δ ppm 5.03-5.25 (m, 1 H), 4.73 (br. s., 1 H), 4.27 (br. s., 1 H), 3.00 (s, 3 H), 2.67 (ddd, J=13.60, 8.51, 4.50 Hz, 2 H), 2.44 (dt, J=12.86, 6.19 Hz, 2 H), 1.33-1.53 (m, 9 H).

Intermediate 68 tert-butyl(trans-3-((1-methyl-1H-benzo[d]imidazol-2-yl)oxy)cyclobutyl)carbamate

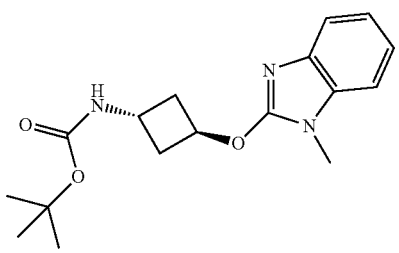 [SMILES: Cn1c(O[C@H]2C[C@H](NC(=O)OC(C)(C)C)C2)nc2ccccc21]

Sodium hydride, 60% in oil (0.141 mL, 6.70 mmol) was added portionwise to a solution of tert-butyl(trans-3-hydroxycyclobutyl)carbamate (0.57 g, 3.04 mmol) and 2-chloro-1-methyl-1H-benzoimidazole (0.558 g, 3.35 mmol) in DMF (3 mL). The reaction mixture was stirred at room temperature for 3 h, diluted with water and extracted with EtOAc. EtOAc extract was concentrated and residue purified with ISCO eluting with 0-40% EtOAc/hexanes to give the desired product tert-butyl(trans-3-((1-methyl-1H-benzo[d]imidazol-2-yl)oxy)cyclobutyl)carbamate (0.388 g, 1.222 mmol, 40.2% yield). m/z: 318.2 (M+1)

Intermediate 69 tert-butyl(trans-3-hydroxycyclobutyl)carbamate

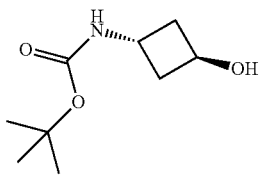

To a mixture of potassium carbonate (5.24 mL, 87 mmol) and water (100 mL) and MeOH (400 mL), was added trans-3-((tert-butoxycarbonyl)amino)cyclobutyl 4-nitrobenzoate (17.1 g, 50.8 mmol). The resulting mixture was heated to 100° C. for 2 h, cooled, and filtered. The filtrate was evaporated under vacuum to give the desired product tert-butyl(trans-3-hydroxycyclobutyl)carbamate (4.4 g, 23.50 mmol, 46.2% yield) as a white solid. $^1$H NMR (400 MHz, CHLOROFORM-d) δ ppm 4.73 (br. s., 1 H), 4.39-4.58 (m, 1 H), 4.22 (br. s., 1 H), 2.10-2.48 (m, 5 H), 1.44 (s, 9 H).

Intermediate 70 trans-3-((tert-butoxycarbonyl)amino)cyclobutyl 4-nitrobenzoate

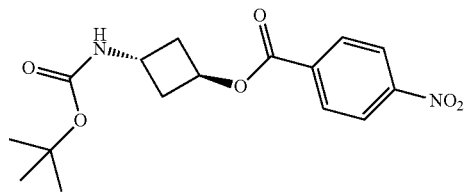 [SMILES: CC(C)(C)OC(=O)N[C@H]1C[C@H](OC(=O)c2ccc([N+](=O)[O-])cc2)C1]

To a solution of racemic (2:1) in favor of trans tert-butyl (3-hydroxycyclobutyl)carbamate (16.8 g, 90 mmol) and 4-nitrobenzoic acid (10.97 ml, 102 mmol) in THF (300 mL) were added triphenyl phosphorus (30.0 ml, 130 mmol) and (E)-diisopropyl diazene-1,2-dicarboxylate (25 ml, 124 mmol) dropwise at 0° C. The resulting mixture was stirred at room temperature for 18 h. The reaction was concentrated and the crude material purified by flash silica gel chromatography on ISCO eluting with 0-40% EtOAc/hexanes to give a mixture cis and trans products. The mixture of isomers was purified by chiral separation to give the desired trans isomer trans-3-((tert-butoxycarbonyl)amino)cyclobutyl 4-nitrobenzoate (17.4 g, 51.7 mmol, 87% yield).

Intermediate 71 tert-butyl(cis-3-hydroxycyclobutyl)carbamate

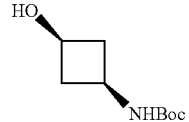 [SMILES: CC(C)(C)OC(=O)N[C@H]1C[C@@H](O)C1]

tert-Butyl (3-oxocyclobutyl)carbamate (43.2 g, 233 mmol) was charged into a 2 L 3-necked flask equipped with a thermometer and an addition funnel. THF (0.7 L) was added and the mixture was cooled to −73° C. internal temperature. Lithium borohydride, 2M in THF (140 mL, 280 mmol) was added over 30 minutes via the addition funnel, during which time the temperature did not exceed −72° C. After stirring for an additional 1 h at that temperature, TLC analysis indicated reaction was complete. Saturated aqueous ammonium chloride (0.3 L) was added and the mixture was warmed to 0° C. After gas evolution ceased, EtOAc (0.3 L) and water (0.3 L) were added and the mixture was stirred vigorously for 1 h. The layers were then separated and the aqueous layer was extracted with EtOAc (1×). The combined extracts were dried over anhydrous magnesium sulfate, filtered, and concentrated in vacuo to give a yellow solid. This solid was suspended in 3:1 EtOAc/hexane and heated to boiling. The remaining solid was filtered off and additional hexane (100 mL) was added to the filtrate. The filtrate was then cooled in the freezer overnight. The resulting solid was collected by filtration and washed with cold 1:1 EtOAc/hexane solution, then dried to give tert-butyl(cis-3-hydroxycyclobutyl)carbamate (25.8 g, 59.0% yield) as a white solid. $^1$H NMR (400 MHz, DMSO-d$_6$) δ ppm 1.36 (s, 9 H) 1.68 (qd, J=8.54, 2.93 Hz, 2 H) 2.33-2.45 (m, 2 H) 3.34-3.44 (m, 1 H) 3.65-3.76 (m, 1 H) 4.98 (d, J=5.67 Hz, 1 H) 7.03 (d, J=7.82 Hz, 1 H).

Intermediate 72 trans-N1-(6-fluorobenzo[d]thiazol-2-yl)cyclobutane-1,3-diamine

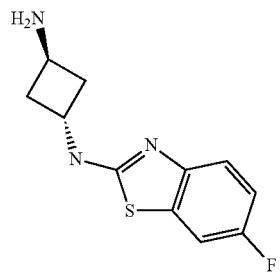 [SMILES: N[C@H]1C[C@H](Nc2nc3ccc(F)cc3s2)C1]

Intermediate 72 was synthesized analogous to intermediate 11 using 2-chloro-6-fluorobenzo[d]thiazole in place of 2-chlorobenzothiazole.

Intermediate 73 trans-N1-(5-fluorobenzo[d]thiazol-2-yl)cyclobutane-1,3-diamine

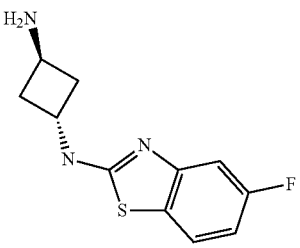 [SMILES: N[C@H]1C[C@H](Nc2nc3cc(F)ccc3s2)C1]

Intermediate 73 was synthesized analogous to intermediate 11 using intermediate 7 in place of 2-chlorobenzothiazole.

Intermediate 74 methyl (2-bromophenyl)(methyl)carbamate

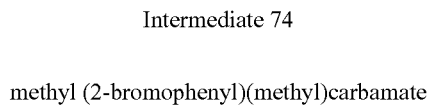

2-Bromo-N-methylaniline (1.00 g, 5.37 mmol) and diisopropylethylamine (2.0 ml, 11.50 mmol) were dissolved in dichloromethane (50 mL) and cooled in an ice bath. Methyl chloroformate (1.0 ml, 12.94 mmol) was added dropwise and the reaction stirred overnight. The reaction mixture was partitioned between water (200 mL) and ethyl acetate (200 mL). The organic was dried with magnesium sulfate and evaporated to dryness under reduced pressure. The crude was used without further purification.

Intermediate 75 benzyl(trans-3-(1-cyclopropyl-2-oxo-1H-imidazo[4,5-b]pyridin-3(2H)-yl)cyclobutyl)carbamate

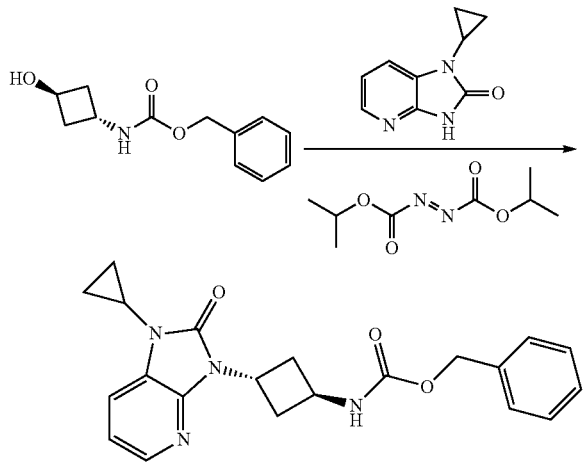

1-Cyclopropyl-1H-imidazo[4,5-b]pyridin-2(3H)-one (0.740 g, 4.22 mmol), benzyl (trans-3-hydroxycyclobutyl) carbamate (0.934 g, 4.22 mmol), and triphenylphosphine (1.661 g, 6.33 mmol) were mixed in THF (15 mL) under an argon atmosphere and cooled to 0° C. Diisopropyl azodicarboxylate (1.244 mL, 6.33 mmol) was added dropwise via syringe, and the reaction mixture was warmed to room temperature and stirred for 1 h. The reaction mixture was diluted with saturated aqueous sodium bicarbonate and extracted with EtOAc. The organic layer was separated, washed with saturated aqueous sodium chloride, dried over magnesium sulfate, filtered, and concentrated in vacuo. The resulting crude product was purified by silica gel column chromatography eluting with EtOAc in hexanes to yield benzyl (trans-3-(1-cyclopropyl-2-oxo-1H-imidazo[4,5-b]pyridin-3(2H)-yl)cyclobutyl)carbamate (1.244 g, 3.29 mmol, 78% yield) as an off-white solid. M+1: 379.2.

Intermediate 76

2-(methylsulfonyl)thiazolo[5,4-b]pyridine

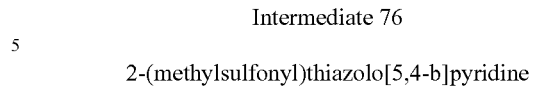

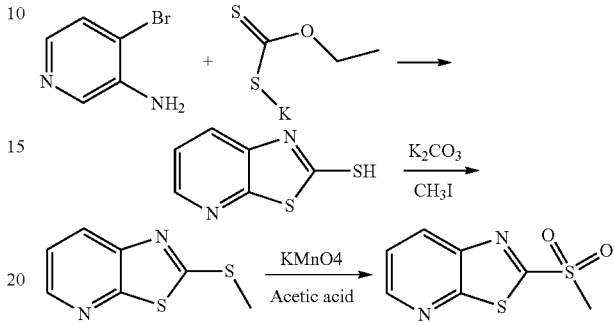

Step 1: thiazolo[5,4-b]pyridine-2-thiol

In a round-bottomed flask, 3-amino-2-bromopyridine (1.14 g, 6.59 mmol), potassium ethylxanthate (2.32 g, 14.5 mmol) and dry dimethylformamide (4 mL) were mixed. The reaction mixture was heated to 130° C. overnight. After cooling to room temperature, the reaction mixture was diluted with water (150 mL). 5 N Hydrochloric acid (4 mL) was added and the mixture was stirred for 10 minutes. The precipitate formed was collected by filtration and dried in a vacuum oven at 80° C. overnight to give thiazolo[5,4-b]pyridine-2-thiol (1.07 g, 6.36 mmol, 97% yield) as tan solid. $^1$H NMR (300 MHz, DMSO-d) δ ppm 7.43 (dd, J=8.18, 4.82 Hz, 1 H) 7.63 (dd, J=8.18, 1.32 Hz, 1 H) 8.34-8.47 (m, 1 H). ESI (M+1) 168.9.

Step 2: 2-(methylthio)thiazolo[5,4-b]pyridine

To the suspension of thiazolo[5,4-b]pyridine-2-thiol (168 mg, 1.0 mmol) in THF (3.3 ml) was added potassium carbonate (193 mg, 1.4 mmol), followed by iodomethane (68.2 µl, 1.1 mmol) dropwise. The reaction mixture was stirred at room temperature for 16 h. Additional iodomethane were mixed in (40 uL) and stirred at room temperature for another 3 h. LCMS showed reaction was complete. The crude reaction mixture was suspended in ethyl acetate and washed with water, then brine, dried over sodium sulfate, filtered, and concentrated to give 2-(methylthio)thiazolo[5,4-b]pyridine (182 mg, 1.0 mmol, 100% yield) as a tan solid.
$^1$H NMR (300 MHz, CHLOROFORM-d) δ ppm 2.80 (s, 3 H) 7.35 (dd, J=8.18, 4.68 Hz, 1 H) 8.06 (dd, J=8.18, 1.61 Hz, 1 H) 8.39-8.49 (m, 1 H). ESI (M+1) 182.9.

Step 3: 2-(methylsulfonyl)thiazolo[5,4-b]pyridine

To a stirred, room temperature solution of 2-(methylthio) thiazolo[5,4-b]pyridine (182 mg, 1.0 mmol) in acetic acid (10 mL) was added a solution of potassium permanganate (47.3 mg, 0.3 mmol) in water (6 mL) dropwise. The reaction mixture was stirred at room temperature for 16 h. LCMS showed incomplete conversion. Additional KMnO$_4$ (158 mg) was mixed in and stirred for another 5 h. LCMS showed complete conversion. The reaction mixture was quenched with aqueous sodium sulfite. The resulting mixture was vigorously stirred at room temperature overnight. The resulting solution was partitioned between EtOAc and saturated Na$_2$CO$_3$. The aqueous layer was extracted with ethyl acetate, dried (Na$_2$SO$_4$), and concentrated. To the residue was added aq. Na$_2$CO$_3$ until the pH reaches 7. The precipitate formed was collected by filtration, dried to give 2-(methylsulfonyl)thiazolo[5,4-b]pyridine (43 mg, 0.201 mmol, 20.10% yield) as a tan solid. $^1$H NMR (300 MHz, CHLOROFORM-d) δ ppm 3.42 (s, 3 H) 7.62 (dd, J=8.40, 4.60 Hz, 1 H) 8.47 (dd, J=8.33, 1.46 Hz, 1 H) 8.75-8.84 (m, 1H). EST (M+1) 214.9.

Intermediate 77 tert-butyl(trans-3-(1-cyclopropyl-2-oxo-1H-imidazo [4,5-b]pyridin-3(2H)-yl)cyclobutyl)carbamate

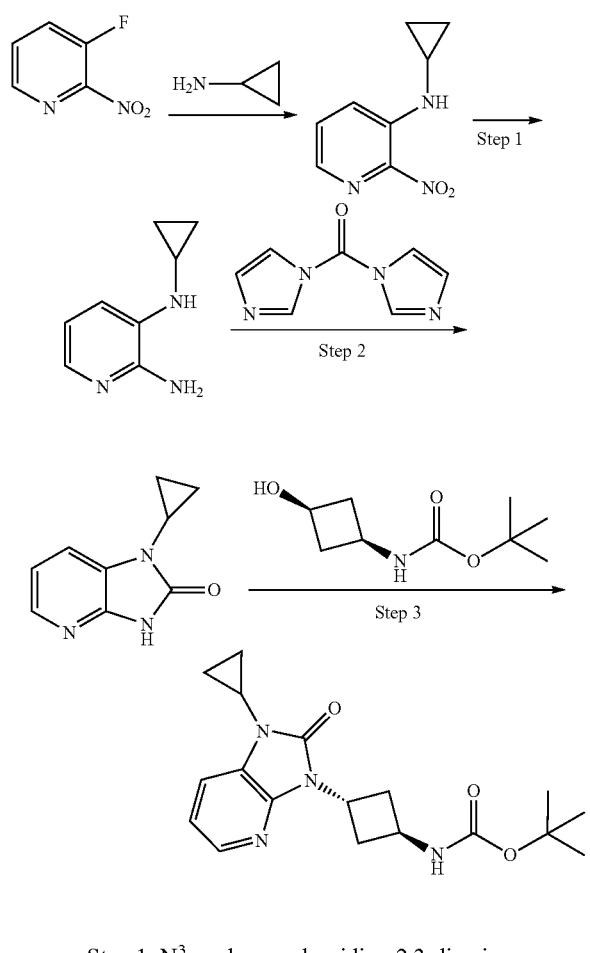

Step 1. N$^3$-cyclopropylpyridine-2,3-diamine

A mixture of 3-fluoro-2-nitropyridine (FSSI, 2.5 g, 17.59 mmol), triethylamine (Aldrich, 2.94 ml, 21.11 mmol), cyclopropylamine (Alfa Aesar, Avocado, Lancaster, 1.481 ml, 21.11 mmol) in DMF (35.2 ml) was heated to 50° C. for 1 h. The reaction mixture was diluted with EtOAc and washed with alternating water and brine washes. The organic layer was dried with sodium sulfate and rotovapped to afford 2.7 g of orange oil. M+1: 179.9.

The dried organic layer was an oil, which was then solubilized in 180 mL of MeOH (~0.1 M) and hydrogenated via H-Cube at 30° C., 1 mL/min flow rate, full H$_2$ mode, to afford the title compound. The collected fractions were advanced to the next step. M+1: 150.1.

Step 2.
1-cyclopropyl-1H-imidazo[4,5-b]pyridin-2(3H)-one

To a solution of N$^3$-cyclopropylpyridine-2,3-diamine (1.0 g, 6.70 mmol) in dioxane (13.41 ml) was added 1,1'-carbonyldiimidazole (Acros Organics, 1.630 g, 10.05 mmol). The resulting mixture was heated to 60° C. for 2 h. The reaction mixture was diluted with EtOAc and washed with water. The organic layer was loaded onto a Biotage samplet and purified (0-100% EtOAc/hexane, 25G biotage column) to afford product that solidified upon rotovap. Material was advanced to the next step. M+1: 176.0.

Step 3. tert-butyl(trans-3-(1-cyclopropyl-2-oxo-1H-imidazo[4,5-b]pyridin-3(2H)-yl)cyclobutyl)carbamate To a solution of tert-butyl(cis-3-hydroxycyclobutyl)carbamate (Intermediate 71) (0.502 g, 2.68 mmol), triphenylphosphine (Sigma-Aldrich, 0.932 ml, 4.02 mmol), 1-cyclopropyl-1H-imidazo[4,5-b]pyridin-2(3H)-one (0.47 g, 2.68 mmol) in THF (10.73 ml) cooled to 0° C. was added diisopropyl azodicarboxylate (Sigma-Aldrich, 0.791 ml, 4.02 mmol) dropwise. The ice bath was removed after 1 h of stirring to allow the mixture to warm to room temperature. After an additional 3 h stirring, the reaction mixture was diluted with EtOAc and washed with saturated NaHCO$_3$ solution. The organic layer was directly loaded onto a Biotage samplet. Purification (0-100% EtOAc/hexane) produced the title compound that solidified upon drying, which was advanced to next step directly without further purification. M+1: 345.0.

Intermediate 78

7,7-dimethyl-5-(piperidin-4-yl)-5H-pyrrolo[2,3-b] pyrazin-6(7H)-one hydrochloride

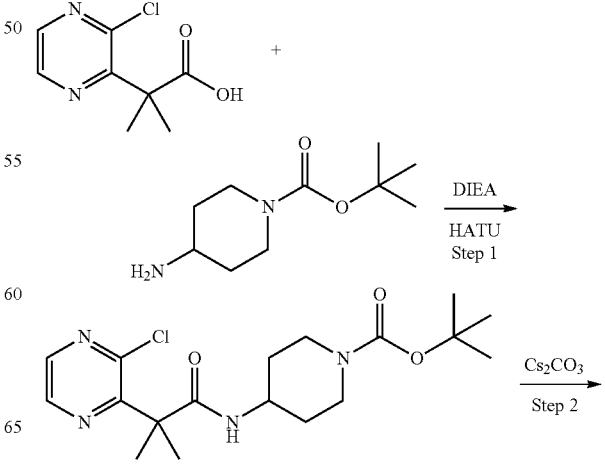

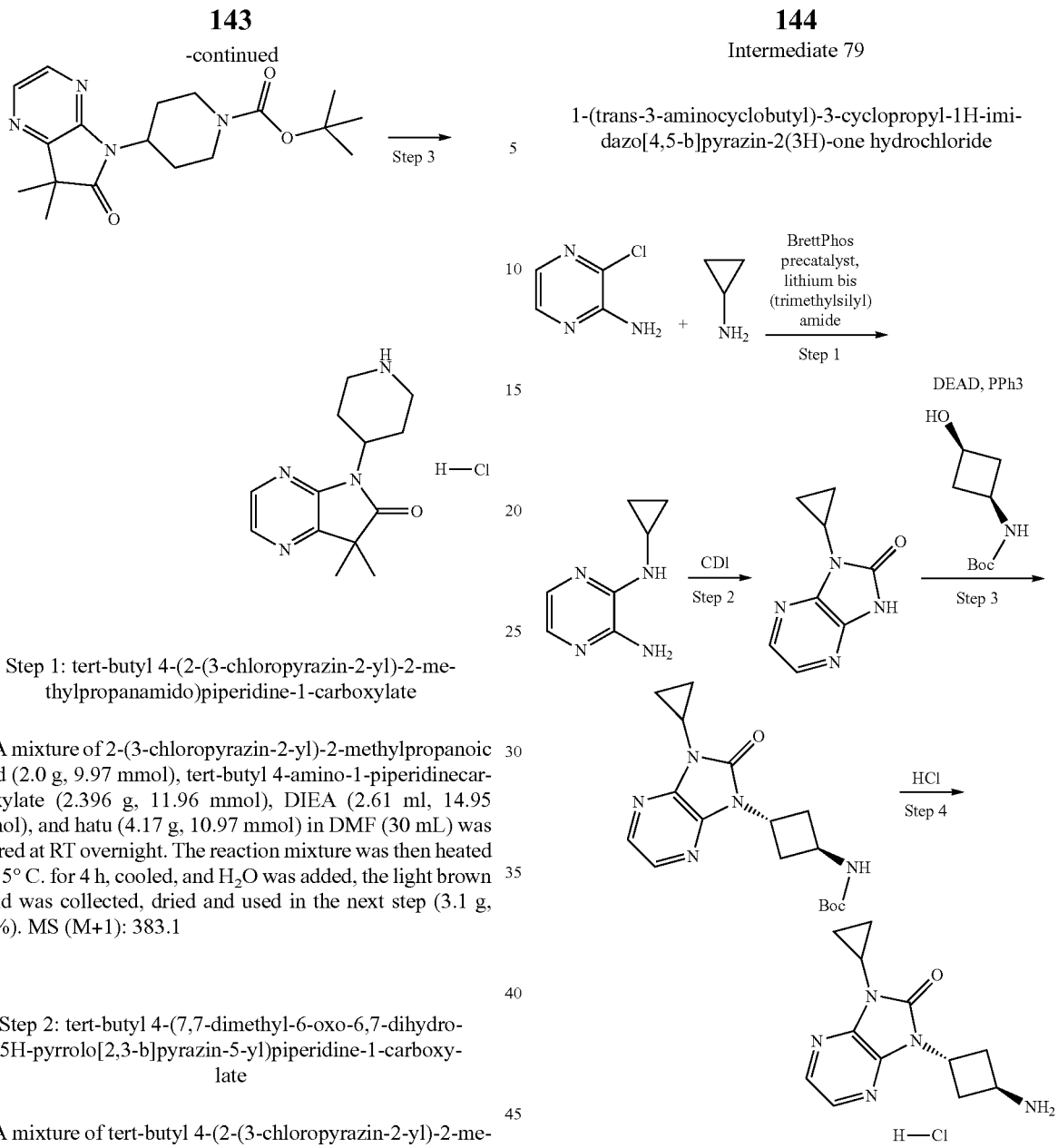

Step 1: tert-butyl 4-(2-(3-chloropyrazin-2-yl)-2-methylpropanamido)piperidine-1-carboxylate A mixture of 2-(3-chloropyrazin-2-yl)-2-methylpropanoic acid (2.0 g, 9.97 mmol), tert-butyl 4-amino-1-piperidinecarboxylate (2.396 g, 11.96 mmol), DIEA (2.61 ml, 14.95 mmol), and hatu (4.17 g, 10.97 mmol) in DMF (30 mL) was stirred at RT overnight. The reaction mixture was then heated to 55° C. for 4 h, cooled, and H$_2$O was added, the light brown solid was collected, dried and used in the next step (3.1 g, 81%). MS (M+1): 383.1

Step 2: tert-butyl 4-(7,7-dimethyl-6-oxo-6,7-dihydro-5H-pyrrolo[2,3-b]pyrazin-5-yl)piperidine-1-carboxylate A mixture of tert-butyl 4-(2-(3-chloropyrazin-2-yl)-2-methylpropanamido)piperidine-1-carboxylate (2.8 g, 7.31 mmol) and cesium carbonate (7.15 g, 21.94 mmol) in DMSO (25 mL) was stirred at RT overnight. H$_2$O was added, extracted with EtOAc (3×). The extracts were dried over MgSO$_4$, concentrated, purified by ISCO (30% EtOAc/Hexanes) to give the title compound (2.15 g, 85%). MS (M+1): 347.1

Step 3: 7,7-dimethyl-5-(piperidin-4-yl)-5H-pyrrolo[2,3-b]pyrazin-6(7H)-one hydrochloride To a stirred cooled (0° C.) solution of tert-butyl 4-(7,7-dimethyl-6-oxo-6,7-dihydro-5H-pyrrolo[2,3-b]pyrazin-5-yl)piperidine-1-carboxylate (0.700 g, 2.021 mmol) in EtOAc (15 mL) was added hydrogen chloride (2.53 ml, 10.10 mmol). The mixture was then stirred at room temperature over the weekend, concentrated to dryness and used in the next step (570 mg, 100%). MS (M+1): 283.1

Intermediate 79

1-(trans-3-aminocyclobutyl)-3-cyclopropyl-1H-imidazo[4,5-b]pyrazin-2(3H)-one hydrochloride

Step 1: N$^2$—cyclopropylpyrazine-2,3-diamine

To a 250 mL round bottomed flask was added 2-amino-3-chloropyrazine (2.2204 g, 17.14 mmol, Synthetech, Inc.) and BrettPhos precatalyst (0.411 g, 0.514 mmol, Sigma-Aldrich Chemical Company, Inc.), and the reaction mixture were placed under vacuum. The round bottomed flask was flushed with argon. This process was repeated 3 times. Cyclopropylamine (1.803 ml, 25.7 mmol, Fluka Chemie GmbH) was added followed by a dropwise addition of lithium bis(trimethylsilyl)amide, 1.0 m solution in tetrahydrofuran (42.8 ml, 42.8 mmol, Sigma-Aldrich Chemical Company, Inc.). The reaction mixture was then heated to 45° C. for 2 h. The reaction mixture was then diluted with saturated NH$_4$Cl and extracted with CH$_2$Cl$_2$. The organic extract was washed with water, saturated NaCl, dried over MgSO$_4$, filtered and concentrated in vacuo. The crude product was adsorbed onto a plug of silica gel and chromatographed through a Biotage SNAP HP-silica gel column (50 g), eluting with a gradient of 10% to 60% Acetone in DCM, to provide the title compound (0.7993 g, 5.32 mmol, 31.1% yield). LCMS showed product peak at 0.629 min (m+1=151.1) with purity at 80-90%. $^1$H NMR (400 MHz, DMSO-d$_6$) δ ppm 0.31-0.38 (m, 2 H) 0.59-0.66 (m, 2 H) 2.64 (tq, J=6.85, 3.52 Hz, 1 H) 5.79 (s, 2 H) 6.25 (d, J=2.15 Hz, 1 H) 7.08 (d, J=3.13 Hz, 1 H) 7.20 (d, J=3.13 Hz, 1 H).

Step 2:
1-cyclopropyl-1H-imidazo[4,5-b]pyrazin-2(3H)-one

To a solution of N$^2$-cyclopropylpyrazine-2,3-diamine (2.0003 g, 13.32 mmol) in THF (66.6 ml) at 50° C. was added CDI (8.64 g, 53.3 mmol, Fluka) and stirred. The reaction flask was place in an ice bath until temperature reached 0° C. The flask was raised and water (10 mL) was added dropwise to quench. (Note: if exothermic reaction was detected then flask was placed back into ice bath until it stopped.) The reaction mixture was diluted with water and extracted with EtOAc. The organic extract was washed with water, saturated NaCl, dried over MgSO$_4$, filtered and concentrated in vacuo. NMR showed product and imidazole. The crude product was adsorbed onto a plug of silica gel and chromatographed through a Biotage SNAP HP-silica gel column (100 g), eluting with a gradient of 1% to 6% MeOH in CH$_2$Cl$_2$, to provide the title compound (0.9715 g, 5.51 mmol, 41.4% yield). LCMS showed product peak at 1.00 min (m+1=177.1) $^1$H NMR (400 MHz, DMSO-d) δ ppm 0.94-1.02 (m, 2 H) 1.02-1.08 (m, 2 H) 2.89-3.00 (m, 1 H) 7.84-7.89 (m, 1 H) 7.89-7.94 (m, 1 H) 11.87 (s, 1 H).

Step 3: tert-butyl(trans-3-(3-cyclopropyl-2-oxo-2,3-dihydrop-1H-imidazo[4,5-b]pyrazin-1-yl)cyclobutyl)carbamate To a cooled solution (0° C.) of tert-butyl(cis-3-hydroxycyclobutyl)carbamate (Intermediate 71) (1.032 g, 5.51 mmol), 1-cyclopropyl-1H-imidazo[4,5-b]pyrazin-2(3H)-one (0.9715 g, 5.51 mmol), and triphenylphosphine (1.917 ml, 8.27 mmol, Sigma Aldrich) in THF (30.5 ml) was added diethyl azodicarboxylate, 40 wt. % solution in toluene (3.26 ml, 8.27 mmol, Chem Impex International) dropwise. After 10 mins, the round bottomed flask was removed from the ice bath and allowed to warm to room temperature to stir. Solvent was evaporated in vacuo. The crude product was adsorbed onto a plug of silica gel and chromatographed through a Biotage SNAP HP-silica gel column (50 g), eluting with a gradient of 10% to 100% EtOAc in hexane, to provide the title compound (2.240 g, 6.49 mmol, 118% yield). LCMS showed product peak at 2.007 min (m+1=346.0). NMR showed biproduct from DEAD reagent. The product was carried on assuming 100% yield without further purification.

Step 4: 1-(trans-3-aminocyclobutyl)-3-cyclopropyl-1H-imidazo[4,5-b]pyrazin-2(3H)-one hydrochloride To a round bottomed flask was added tert-butyl(trans-3-(3-cyclopropyl-2-oxo-2,3-dihydro-1H-imidazo[4,5-b]pyrazin-1-yl)cyclobutyl)carbamate (1.905 g, 5.52 mmol) and hydrogen chloride, 4.0M solution in 1,4-dioxane (1.915 ml, 55.2 mmol) to stir at room temperature. The reaction was monitored by TLC until completion (10% MeOH/90% DCM). The reaction mixture was filtered and solids were washed with diethyl ether and dried in a vacuum oven to give the title compound (1.0201 g, 3.62 mmol, 65.6% yield). LCMS showed product peak at 0.997 min (m+1=246.1). $^1$H NMR (400 MHz, DMSO-d$_6$) δ ppm 0.94-1.06 (m, 4 H) 2.52-2.60 (m, 2 H) 2.90-2.99 (m, 1 H) 3.16 (ddd, J=14.52, 8.66, 7.34 Hz, 2 H) 3.96-4.08 (m, 1 H) 5.21-5.33 (m, 1 H) 7.92-8.01 (m, 2 H) 8.34 (br. s., 3 H).

Intermediate 80 cis-3-((tert-butoxycarbonyl)amino)cyclobutyl methanesulfonate

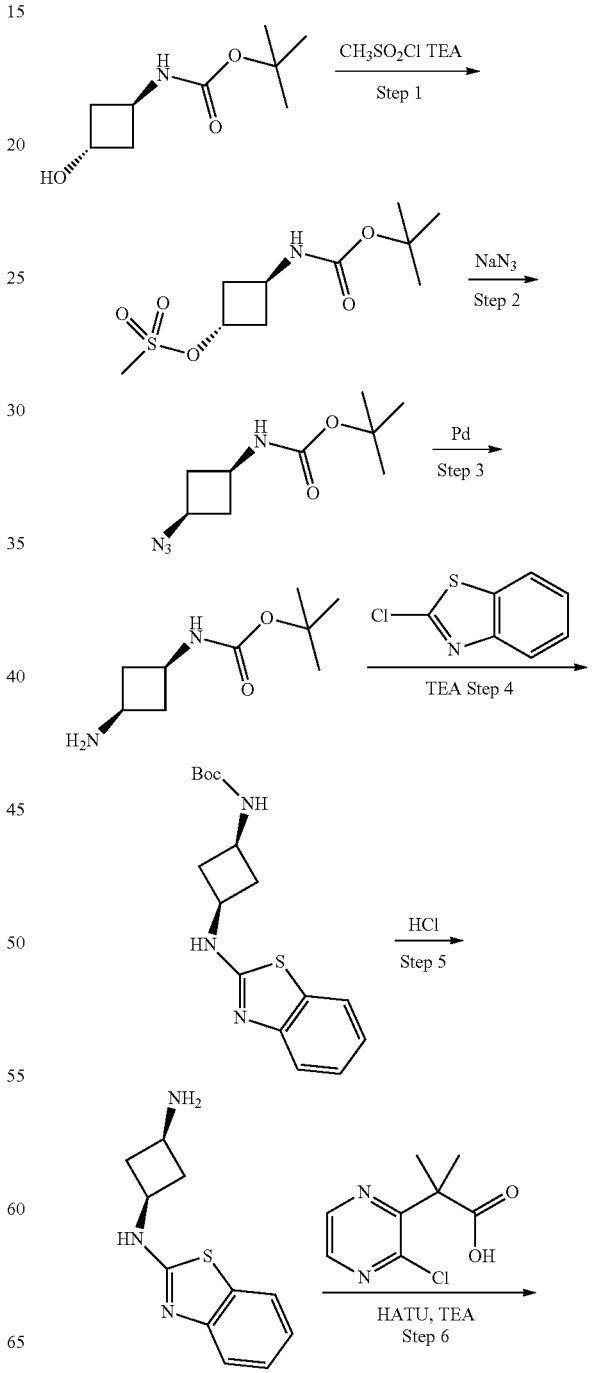

-continued

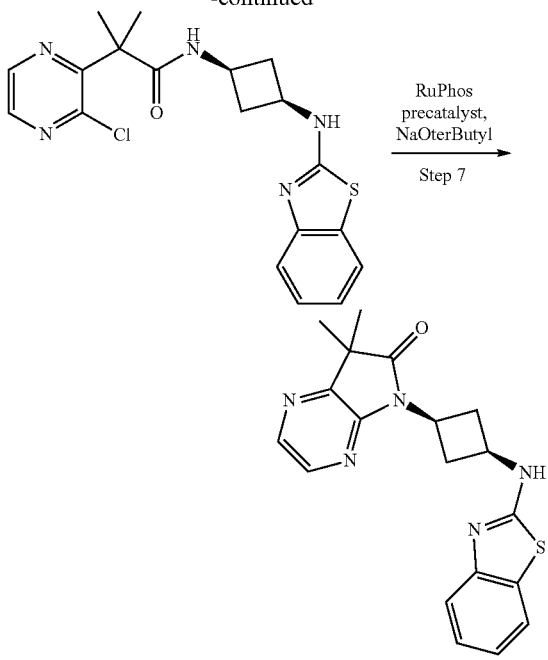

Step 1: (trans)-3-((tert-butoxycarbonyl)amino)cyclobutyl methanesulfonate

A solution of tert-butyl(trans-3-hydroxycyclobutyl)carbamate (20.05 g, 107 mmol, Pharmacore) and triethylamine, anhydrous (22.34 mL, 161 mmol, Sigma-Aldrich Chemical Company, Inc.) in DCM (200 mL) was cooled to −30° C. and methanesulfonyl chloride (9.94 mL, 129 mmol, Sigma-Aldrich Chemical Company, Inc.) was added dropwise over 20 min period. The mixture was stirred at room temperature for 12 h, washed with 200 mL water, then 200 mL 10% aq. citric acid followed by brine, dried over $Na_2SO_4$ and evaporated to give the title compound (29 g, 109 mmol, 102% yield), which was used in the next step without further purification.

Step 2: tert-butyl(cis-3-azidocyclobutyl)carbamate

To a solution of trans-3-((tert-butoxycarbonyl)amino)cyclobutyl methanesulfonate (29 g, 109 mmol) in DMF (100 mL) was added sodium azide (5.68 mL, 162 mmol, Sigma-Aldrich Chemical Company, Inc.) portionwise and the mixture stirred at 85° C. for 18 h. The reaction was diluted with water (200 mL) after cooling and extracted with EtOAc (3×100 mL). The combined organic was washed with water (2×100 mL) and brine, dried over $Na_2SO_4$ and evaporated in vacuo to give the title compound (22 g, 104 mmol, 95% yield) that was used in the next step without further purification.

Step 3: tert-butyl(cis-3-aminocyclobutyl)carbamate

A mixture of tert-butyl(cis-3-azidocyclobutyl)carbamate (7.0 g, 33.0 mmol) and palladium 10% on activated carbon (3.51 ml, 33.0 mmol, Sigma-Aldrich Chemical Company, Inc.) in three necked 1000 mL flask was flushed with $N_2$ and closed tightly and 2M ammonia in methanol solution (200 mL) was added. The flask was evacuated and a balloon filled with hydrogen was introduced. The mixture was stirred for 18 h, filtered, and the filtrate was evaporated under reduced pressure to give the title compound, which was used in the next step without further purification.

Step 4: tert-butyl(cis-3-(benzo[d]thiazol-2-ylamino)cyclobutyl) carbamate

To a round bottomed flask was added tert-butyl(cis-3-aminocyclobutyl)carbamate (0.5314 g, 2.85 mmol), 2-chlorobenzo[d]thiazole (0.557 ml, 4.28 mmol, Alfa Aesar), and hunig's base (0.993 ml, 5.71 mmol, Sigma-Aldrich Chemical Company, Inc.) in DMSO (2.85 ml) at 90° C. to stir for 2 hours. The reaction mixture was diluted with water and extracted with $CH_2Cl_2$. The organic extract was washed with water, saturated NaCl, dried over $MgSO_4$, filtered and concentrated in vacuo. The crude product was adsorbed onto a plug of silica gel and chromatographed through a Biotage SNAP HP-silica gel column (50 g), eluting with a gradient of 10% to 100% EtOAc in hexane, to provide the title compound. LCMS showed product peak at 1.692 min (m+1=320.0). $^1$H NMR (400 MHz, DMSO-$d_6$) δ ppm 1.40 (s, 9 H) 1.80-1.94 (m, 2 H) 2.57-2.70 (m, 2 H) 3.70 (sxt, J=7.94 Hz, 1 H) 3.86-3.99 (m, 1 H) 7.02 (td, J=7.63, 1.17 Hz, 1 H) 7.18-7.27 (m, 2 H) 7.39 (d, J=7.43 Hz, 1 H) 7.67 (dd, J=7.82, 0.78 Hz, 1 H) 8.28 (d, J=6.65 Hz, 1 H)

Step 5: tert-butyl(cis-3-(benzo[d]thiazol-2-ylamino)cyclobutyl)carbamate

To a round bottomed flask was added tert-butyl(cis-3-(benzo[d]thiazol-2-ylamino)cyclobutyl)carbamate (0.8080 g, 2.53 mmol) and hydrogen chloride, 4.0M solution in 1,4-dioxane (6.32 ml, 25.3 mmol) to stir at room temperature. LCMS showed product peak at 0.387 min (m+1=220.0). Solvent was evaporated. Product was carried to future reaction without further purification assuming 100% yield.

Step 6: N-(cis-3-(benzo[d]thiazol-2-ylamino)cyclobutyl)-2-(3-chloropyrazin-2-yl2-methylpropanamide To a round bottomed flask was added cis-$N^1$-(benzo[d]thiazol-2-yl)cyclobutane-1,3-diamine (0.3010 g, 1.030 mmol), 2-(3-chloropyrazin-2-yl)-2-methylpropanoic acid (Intermediate 29, 0.248 g, 1.236 mmol), HATU (0.509 g, 1.339 mmol, GenScript Corp), and triethylamine (0.573 ml, 4.12 mmol, Sigma-Aldrich Chemical Company, Inc.) in DCM (2.060 ml) to stir at rt for 4 hours. The reaction mixture was diluted with water and extracted with $CH_2Cl_2$. The organic extract was washed with water, saturated $NaHCO_3$, saturated NaCl, dried over $MgSO_4$, filtered and concentrated in vacuo. The crude product (592.4 mg) was adsorbed onto a plug of silica gel and chromatographed through a Biotage SNAP HP-silica gel column (50 g), eluting with a gradient of 10% to 100% EtOAc in hexane, to provide the title compound (0.3181 g, 0.791 mmol, 77% yield). LCMS showed product peak at 1.536 min (m+1=401.9).

$^1$H NMR (400 MHz, DMSO-$d_6$) δ ppm 1.52 (s, 4 H) 1.88-2.03 (m, 1 H) 2.60-2.69 (m, 1 H) 3.87-4.03 (m, 1 H) 6.97-7.07 (m, 1 H) 7.18-7.26 (m, 1 H) 7.39 (d, J=7.43 Hz, 1 H) 7.63-7.71 (m, 1 H) 7.76 (d, J=6.65 Hz, 1 H) 8.27 (d, J=6.26 Hz, 1 H) 8.45 (d, J=2.54 Hz, 1 H) 8.68 (d, J=2.54 Hz, 1 H)

Step 7: 5-(cis-3-(benzo[d]thiazol-2-ylamino)cyclobutyl)-7,7-dimethyl-5H-pyrrolo[2,3-b]pyrazin-6(7H)-one To a glass microwave reaction vessel was added N-(cis-3-(benzo[d]thiazol-2-ylamino)cyclobutyl)-2-(3-chloropyrazin-2-yl)-2-methylpropanamide (0.3181 g, 0.791 mmol), RuPhos Precatalyst (0.035 g, 0.047 mmol, Strem Chemicals, Inc.), and sodium tert-butoxide (0.152 g, 1.583 mmol, Sigma-Aldrich Chemical Company, Inc.) in dry dioxane (0.791 ml) to stir at 80° C. for 5 h. The crude product was purified by reverse-phase preparative HPLC using 0.1% TFA in CH$_3$CN/ H$_2$O, gradient 10% to 90% over 12 mins. The collected fractions were evaporated and the residue was taken up in DCM and filtered through a Silicycle Si-Carbonate cartridge to remove any salts to give the title compound (139.2 mg, 0.381 mmol, 48.1% yield). LCMS showed product peak at 1.607 min (m+1=366.0). $^1$H NMR (400 MHz, DMSO-d$_6$) δ ppm 1.35 (s, 6 H) 2.74 (qd, J=7.86, 2.64 Hz, 2 H) 3.00 (qd, J=9.13, 2.74 Hz, 2 H) 4.12-4.27 (m, 1 H) 4.55-4.69 (m, 1 H) 7.04 (td, J=7.58, 1.08 Hz, 1 H) 7.24 (td, J=7.68, 1.27 Hz, 1 H) 7.36-7.44 (m, 1 H) 7.69 (dd, J=7.83, 0.78 Hz, 1 H) 8.15-8.23 (m, 2 H) 8.49 (d, J=6.65 Hz, 1 H)

Intermediate 81 cis-N$^1$-(benzo[d]thiazol-2-yl)-N$^3$-(3-chloropyrazin-2-yl)cyclobutane-1,3-diamine

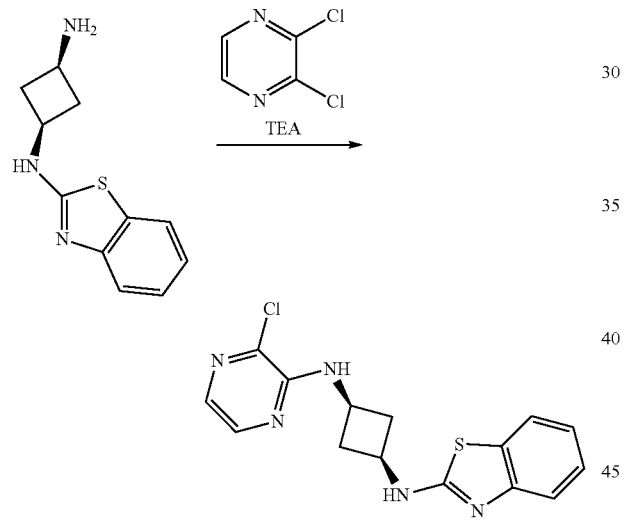

To a round bottomed flask was added cis-N$^1$-(benzo[d] thiazol-2-yl)cyclobutane-1,3-diamine (0.5306 g, 1.816 mmol), 2,3-dichloropyrazine (0.271 g, 1.816 mmol, Pfaltz & Bauer, Inc.), and triethylamine (0.758 ml, 5.45 mmol, Sigma-Aldrich Chemical Company, Inc.) to stir at 75° C. in DMSO (1.816 ml) to stir for 6 h. The reaction mixture was diluted with water and extracted with CH$_2$Cl$_2$. The organic extract was washed with water, saturated NaCl, dried over MgSO$_4$, filtered and concentrated in vacuo. The crude product was adsorbed onto a plug of silica gel and chromatographed through a Biotage SNAP HP-silica gel column (50 g), eluting with a gradient of 10% to 100% EtOAc in hexane, to provide the title compound (0.1952 g, 0.588 mmol, 32.4% yield). LCMS showed product peak at 1.625 min (m+1=332.0). $^1$H NMR (400 MHz, DMSO-d$_6$) δ ppm 2.06-2.20 (m, 2 H) 2.75-2.87 (m, 2 H) 3.98-4.11 (m, 1 H) 4.11-4.22 (m, 1 H) 7.03 (td, J=7.53, 1.17 Hz, 1 H) 7.19-7.28 (m, 2 H) 7.40 (d, J=7.24 Hz, 1 H) 7.60 (d, J=2.54 Hz, 1 H) 7.69 (dd, J=7.82, 0.78 Hz, 1 H) 8.05 (d, J=2.74 Hz, 1 H) 8.32 (d, J=6.65 Hz, 1 H)

Intermediate 82

1-(trans-3-aminocyclobutyl)-5-bromo-3-cyclopropyl-1H-imidazo[4,5-b]pyrazin-2(3H)-one hydrochloride

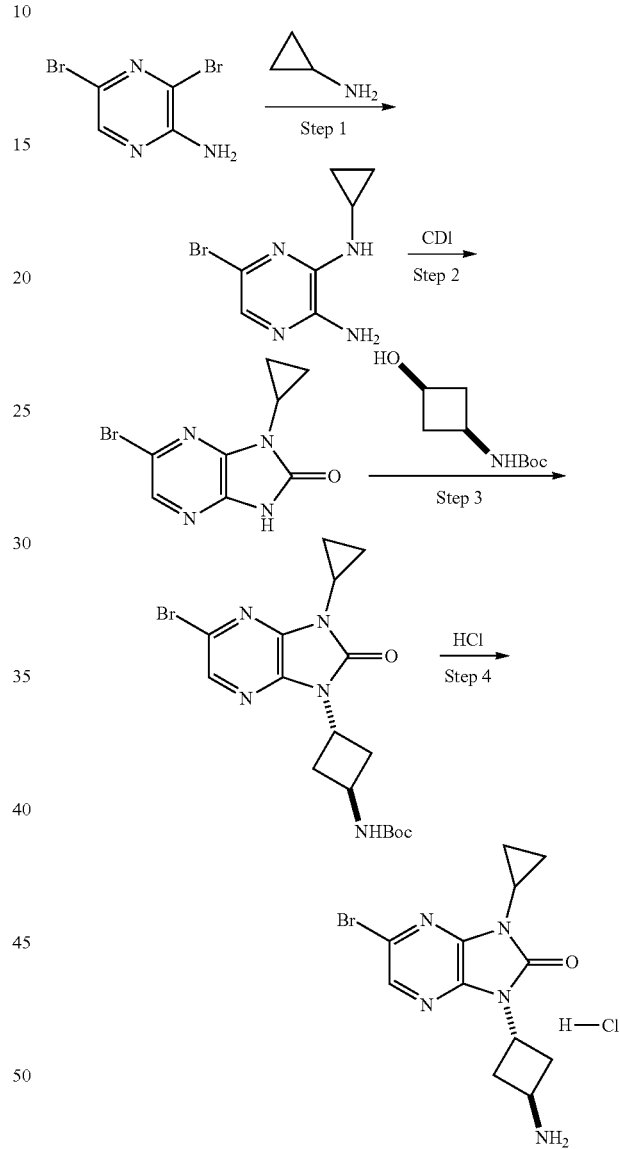

STEP 1: 6-bromo-N$^2$-cyclopropylpyrazine-2,3-diamine

A glass microwave reaction vessel was charged with 2-amino-3,5-dibromopyrazine (1.00 g, 3.95 mmol) and cyclopropylamine (1.40 ml, 19.96 mmol). The reaction mixture was sealed under argon and heated in an Initiator microwave reactor (Personal Chemistry, Biotage AB, Inc., Upssala, Sweden) at 120° C. for 20 min. Additional cyclopropylamine (1.0 mL) was added and the reaction was heated at 120° C. for 30 min in the microwave. Excess cyclopropylamine was removed in vacuo and the residue was dissolved in MeOH and evaporated onto silica gel and purified by flash chromatography (Isco (40 gram)) eluting with EtOAc:hexanes (0:1→1:2) to give 740 mg (82%) of a golden-brown tar. ESI MS 228.9 [M+1].

Step 2: 6-bromo-1-cyclopropyl-1H-imidazo[4,5-b]pyrazin-2(3H)-one

To a heated (50° C.) solution of 6-bromo-$N^2$-cyclopropylpyrazine-2,3-diamine (0.740 g, 3.23 mmol) in THF (20 mL) was added 1,1'-carbonyldiimidazole (1.00 g, 6.17 mmol) in one portion. The reaction was then heated at 66° C. for 3 h. Additional 1,1'-carbonyldiimidazole (1.00 g, 6.17 mmol) was added and the reaction was heated at 50° C. overnight. The reaction was cooled to room temperature and carefully quenched with water (slight exotherm) until gas evolution ceased. The solution was diluted with EtOAc and the layer were separated. The organic layer was washed with water (1×) and brine (1×). The solution was evaporated onto silica gel and purified by flash chromatography (ISCO(40 gram)) eluting with EtOAc:hexanes (0:1→2:3) to give 467 mg (57%) of a yellow crystalline solid. ESI MS 256.9 [M+1].

Step 3: tert-butyl(trans-3-(5-bromo-3-cyclopropyl-2-oxo-2,3-dihydro-1H-imidazo[4,5-b]pyrazin-1-yl)cyclobutyl)carbamate To a cooled (0° C.) solution of tert-butyl(trans-3-hydroxycyclobutyl)carbamate (0.250 g, 1.335 mmol), 6-bromo-1-cyclopropyl-1H-imidazo[4,5-b]pyrazin-2(3H)-one (0.334 g, 1.309 mmol) and triphenylphosphine (0.520 g, 1.983 mmol) in THF (10 ml) was added DIAD (0.400 ml, 2.032 mmol) dropwise via syringe. After 10 min the reaction was allowed to warm to room temperature and stirred overnight. The reaction mixture was concentrated in vacuo and the residue was dissolved in MeOH/EtOAc, evaporated onto silica gel and purified by flash chromatography (Isco (25 gram)) eluting with EtOAc:hexanes (0:1-1:1) to give a light-yellow solid. ESI MS 445.9, 447.8 [M+Na].

Step 4: 1-(trans-3-aminocyclobutyl)-5-bromo-3-cyclopropyl-1H-imidazo[4,5-b]pyrazin-2(3H)-one hydrochloride To a room temperature slurry of tert-butyl(trans-3-(5-bromo-3-cyclopropyl-2-oxo-2,3-dihydro-1H-imidazo[4,5-b]pyrazin-1-yl)cyclobutyl)carbamate (0.556 g, 1.31 mmol) in dioxane (10 mL) was added hydrogen chloride, 4.0M solution in 1,4-dioxane (5.0 mL, 20.00 mmol). After stirring overnight the reaction was filtered and the precipitate was washed with Et$_2$O to give 430 mg of a white amorphous solid. ESI MS 323.9, 325.9 [M+1].

Intermediate 83

5-(trans-3-aminocyclobutyl)-7,7-dimethyl-5H-pyrrolo[2,3-b]pyrazin-6(7H)-one dihydrochloride

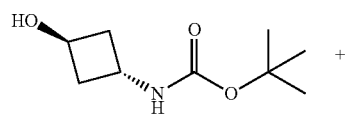
+

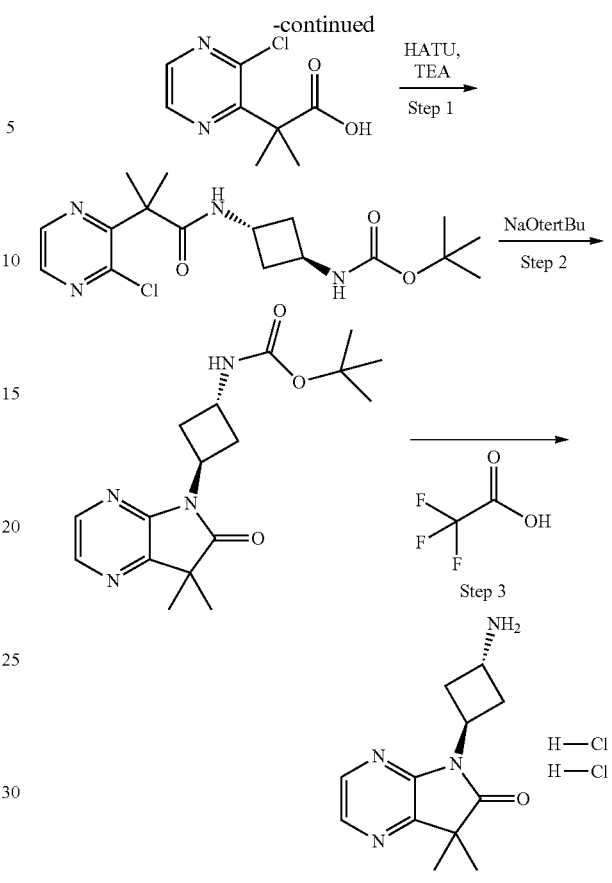

Step 1: tert-butyl(trans-3-(2-(3-chloropyrazin-2-yl)-2-methylpropanamido)cyclobutyl)carbamate To a round bottomed flask was added tert-butyl(trans-3-aminocyclobutyl)carbamate (1.847 g, 9.92 mmol), 2-(3-chloropyrazin-2-yl)-2-methylpropanoic acid (1.99 g, 9.92 mmol), HATU (4.90 g, 12.89 mmol), and triethylamine (5.52 ml, 39.7 mmol) in DCM (25 ml) to stir at room temperature for 16 h. The reaction mixture was diluted with water and extracted with CH$_2$Cl$_2$. The organic extract was washed with water, saturated NaCl solution, dried over MgSO$_4$, filtered and concentrated in vacuo. The crude product was purified by chromatography through a Redi-Sep pre-packed silica gel column (40 g), eluting with a gradient of 10% to 70% EtOAc in hexane, to provide the title compound (2.73 g, 7.40 mmol, 74.6% yield) as off-white solid.

Step 2: tert-butyl(trans-3-(7,7-dimethyl-6-oxo-6,7-dihydro-5H-pyrrolo[2,3-b]pyrazin-5-yl)cyclobutyl)carbamate To the solution of tert-butyl((1R,3R)-3-(2-(3-chloropyrazin-2-yl)-2-methylpropanamido)cyclobutyl)carbamate (2.73 g, 7.40 mmol) in THF (25 ml) was added sodium tert-butoxide (1.42 g, 14.8 mmol) under nitrogen. The reaction mixture was stirred at room temperature for 1.5 h. The reaction was partitioned between water and ethyl acetate. The organic was washed with saturated sodium chloride then dried (Na$_2$SO$_4$) and concentrated to give the title compound (2.3 g, 6.92 mmol, 93% yield) as off-white solid.

Step 3: 5-(trans-3-aminocyclobutyl)-7,7-dimethyl-5H-pyrrolo[2,3-b]pyrazin-6(7H)-one dihydrochloride tert-Butyl((1R,3R)-3-(7,7-dimethyl-6-oxo-6,7-dihydro-5H-pyrrolo[2,3-b]pyrazin-5-yl)cyclobutyl)carbamate (2.3 g, 6.92 mmol) was dissolved in dichloromethane (23 mL) and treated with trifluoroacetic acid (10.3 ml, 138 mmol). The solution was stirred for 1.5 h. The orange solution was evaporated to dryness under reduced pressure and azeotroped with DCM (2×). The crude amine was dissolved in DCM and treated with 1N HCl in ether (20 mL) dropwise. The precipitate formed was collected by filtration, washed with ether, dried in vacuum oven at 80° C. to give the title compound (1.89 g, 6.19 mmol, 89% yield) as off-white solid.

Intermediate 84

3-(trans-3-aminocyclobutyl)-1-methyl-1H-imidazo[4,5-b]pyridin-2(3H)-one hydrochloride

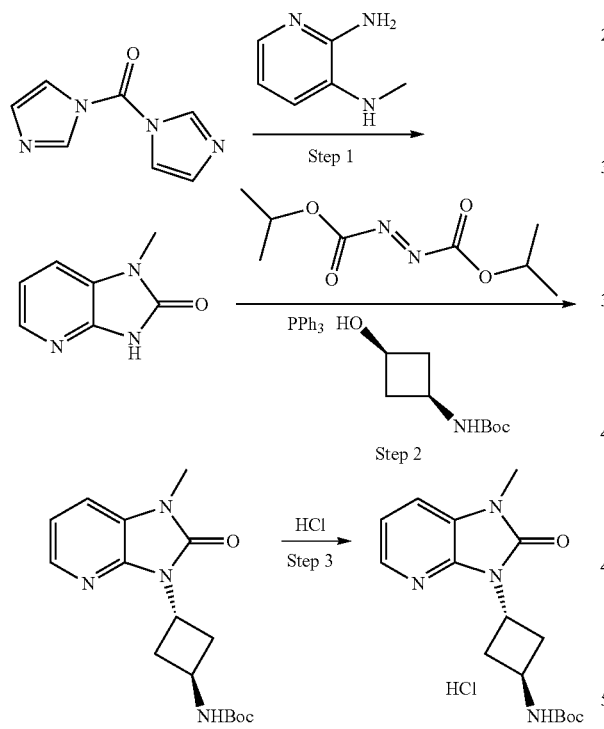

Step 1: 1-methyl-1H-imidazo[4,5-b]pyridin-2(3H)-one $N^3$-methylpyridine-2,3-diamine (14.9 g, 121 mmol) and 1,1'-carbonyldiimidazole reagent grade (39.3 g, 242 mmol) were mixed in THF (250 mL). The reaction mixture was stirred at 60° C. for 1 h. The reaction mixture was diluted with saturated NaHCO$_3$ and extracted three times with EtOAc. The combined organic layers were washed with brine, dried over MgSO$_4$, filtered, and concentrated. The resulting dark brown solid was slurried for 1 h in EtOH. The suspension was cooled in an ice bath and filtered to give product as a light brown solid (5.64 g). The filtrate was concentrated and purified via silica gel flash column chromatography eluting with 0 to 10% MeOH in DCM. The isolated product was slurried in DCM and filtered to yield another crop of product as a light brown solid. (1.78 g). The filtrate was diluted with hexanes, and the resulting precipitate was filtered to yield the third batch of the title compound as a brown solid (1.56 g, total yield 50%).

Step 2: tert-butyl(trans-3-(1-methyl-2-oxo-1H-imidazo[4,5-b]pyridin-3(2H)-yl)cyclobutyl)carbamate 1-Methyl-1H-imidazo[4,5-b]pyridin-2(3H)-one (9.63 g, 64.6 mmol), tert-butyl(trans-3-hydroxycyclobutyl)carbamate (Intermediate 69, 12.1 g, 64.6 mmol), and triphenylphosphine (25.4 g, 97 mmol) were mixed in THF (250 mL) under an argon atmosphere at 0° C. Diisopropyl azodicarboxylate (19.0 mL, 97 mmol) was added dropwise via syringe, and the reaction mixture was warmed to room temperature and stirred for 18 h. The reaction mixture was diluted with saturated NaHCO$_3$ and extracted with EtOAc (3×). The organic layer was separated, washed with brine, dried over MgSO$_4$, filtered, and concentrated. The resulting crude product was purified via silica gel flash column chromatography eluting with 0 to 100% EtOAc in hexanes to yield the title compound as a yellow solid and used in the next step without further purification.

Step 3: 3-(trans-3-aminocyclobutyl)-1-methyl-1H-imidazo[4,5-b]pyridin-2(3H)-one hydrochloride Hydrogen chloride, 4.0M solution in 1,4-dioxane (130 mL, 519 mmol) was added to a stirred solution of the tert-butyl (trans-3-(1-methyl-2-oxo-1H-imidazo[4,5-b]pyridin-3(2H)-yl)cyclobutyl)carbamate product of step 2 (33.1 g, 104 mmol) in 1,4-dioxane (400 mL). The reaction mixture was stirred at room temperature for 21 h. The precipitate was filtered and washed with ether to yield the title compound (13.4 g, 51% yield) as an off-white solid.

Representative compounds of Formula (I), as shown above in Tables 1-5 as Examples 1-231, were prepared as follows by using the above Intermediates Compounds 1-83. Examples 1-2, 4-5, 7, 10, 13-14, 19-20, 23-26 were prepared according to Methods A1-A14 as follows:

Method A1

Example 1

N-(trans-3-(2-ethyl-3H-imidazo[4,5-b]pyridin-3-yl)cyclobutyl)benzo[d]thiazol-2-amine

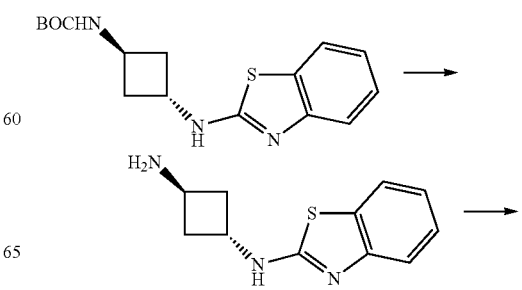

-continued

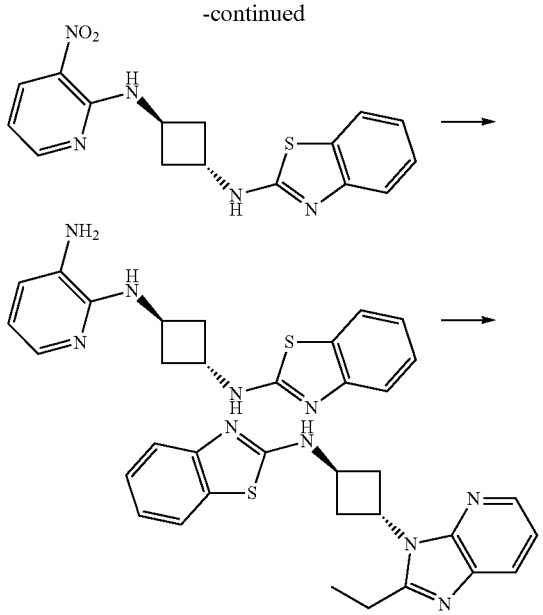

Step 1: trans-N¹-(benzo[d]thiazol-2-yl)cyclobutane-1,3-diamine

Tert-butyl(trans-3-(benzo[d]thiazol-2-ylamino)cyclobutyl)carbamate (intermediate 10, 720 mg, 2.262 mmol) was dissolved in dichloromethane (30 mL) and treated with trifluoroacetic acid (2 mL). The solution was stirred at room temperature for 15 minutes then evaporated to dryness under reduced pressure and further dried under high vacuum. The crude amine salt was used without further purification.

Step 2: trans-N¹-(benzo[d]thiazol-2-yl)-N3-(3-nitro-pyridin-2-yl)cyclobutane-1,3-diamine The crude amine from step 1, cesium carbonate (2.500 g, 1.535 mmol), 2-chloro-3-nitropyridine (394 mg, 2.488 mmol), and dry dimethylsulfoxide (5 mL) were added and the reaction mixture was stirred at 120° C. for 2 hours. The reaction was cooled and partitioned between water (100 mL), saturated sodium bicarbonate (20 mL) and ethyl acetate. The organic phase was dried with magnesium sulfate and evaporated to dryness under reduced pressure. Purification using silica chromatography (dichloromethane to ethyl acetate gradient) gave the desired trans-N¹-(benzo[d]thiazol-2-yl)-N³-(3-nitropyridin-2-yl)cyclobutane-1,3-diamine (580 mg, 1.699 mmol, 75% yield) as light-yellow solid.

Step 3: N²-(trans-3-(benzo[d]thiazol-2-ylamino)cyclobutyl)pyridine-2,3-diamine

Trans-N¹-(benzo[d]thiazol-2-yl)-N³-(3-nitropyridin-2-yl)cyclobutane-1,3-diamine (580 mg, 1.699 mmol), ammonium chloride (46 mg, 0.849 mmol) and iron dust (0.036 mL, 5.10 mmol) were suspended in a mixture of water (1.000 mL) and ethanol (3 mL). The reaction mixture was stirred at 50° C. for 16 hours then cooled and partitioned between water (100 mL) and ethyl acetate (100 mL). The organic phase was dried with sodium sulfate and evaporated to dryness under reduced pressure. Purification using silica chromatography (hexane to ethyl acetate gradient) gave N2-(trans-3-(benzo[d]thiazol-2-ylamino)cyclobutyl)pyridine-2,3-diamine (370 mg, 1.188 mmol, 69.9% yield) as light-yellow solid.

Step 4: N-(trans-3-(2-ethyl-3H-imidazo[4,5-b]pyridin-3-yl)cyclobutyl)benzo[d]thiazol-2-amine N²-(Trans-3-(benzo[d]thiazol-2-ylamino)cyclobutyl)pyridine-2,3-diamine (0.075 g, 0.241 mmol) was suspended in dichloromethane (20 mL) and treated with propionyl chloride (0.03 ml, 0.357 mmol). Triethylamine (0.050 ml, 0.359 mmol) was added and the reaction stirred for 1 hour. The mixture was evaporated to dryness under reduced pressure and the crude redissolved in propionic acid (5 mL). The solution was heated at 100° C. for 16 hours. The mixture was evaporated to dryness under reduced pressure and purified using silica chromatography (0-10% methanol in dichloromethane gradient) followed by reverse phase HPLC gave the desired N-(trans-3-(2-ethyl-3H-imidazo[4,5-b]pyridin-3-yl)cyclobutyl)benzo[d]thiazol-2-amine (0.045 g, 0.129 mmol, 53.5% yield). M+1: 350.1. ¹H NMR (400 MHz, CHLOROFORM-d) δ ppm 1.31 (t, J=7.53 Hz, 3 H) 2.46 (br. s., 1 H) 2.52-2.68 (m, 2 H) 2.79 (q, J=7.63 Hz, 2 H) 3.61-3.84 (m, 2 H) 4.47-4.68 (m, 1 H) 5.12 (quin, J=8.20 Hz, 1 H) 7.03 (t, J=7.53 Hz, 1 H) 7.12 (dd, J=7.92, 4.79 Hz, 1 H) 7.18-7.32 (m, 1 H) 7.52 (dd, J=21.91, 8.00 Hz. 2 H) 7.88 (dd, J=8.02, 1.37 Hz. 1 H) 8.26 (dd, J=4.69, 1.37 Hz. 1 H).

Method A2

Example 2

N-(trans-3-(2-cyclopropyl-3H-imidazo[4,5-b]pyridin-3-yl)cyclobutyl)benzo[d]thiazol-2-amine

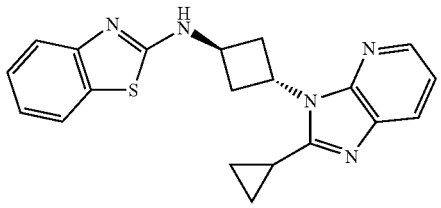 [SMILES: c1ccc2sc(N[C@H]3C[C@H](n4c(C5CC5)nc5cccnc54)C3)nc2c1]

Trans-3-(2-cyclopropyl-3H-imidazo[4,5-b]pyridin-3-yl)cyclobutanamine (intermediate 12, 0.185 g, 0.810 mmol), 2-chlorobenzo[d]thiazole (0.150 ml, 1.152 mmol), and potassium carbonate (0.400 g, 2.89 mmol) were combined with dry dimethylsulfoxide (2 mL) and sealed in a vial under argon. The reaction was heated in the microwave to 130 for 40 minutes then partitioned between water (100 mL), saturated sodium bicarbonate (50 mL) and ethyl acetate (200 mL). The organic phase was dried with magnesium sulfate and evaporated to dryness under reduced pressure. Purification using silica chromatography (0-5% methanol in dichloromethane gradient) gave the desired N-(trans-3-(2-cyclopropyl-3H-imidazo[4,5-b]pyridin-3-yl)cyclobutyl)benzo[d]thiazol-2-amine (0.0502 g, 0.139 mmol, 17.14% yield). M+1: 357.2. ¹H NMR (400 MHz, CHLOROFORM-d) δ ppm 1.10-1.29 (m, 4 H) 1.97-2.13 (m, 1 H) 2.57-2.85 (m, 2 H) 3.72-3.94 (m, 2 H) 4.82 (td, J=7.38, 4.21 Hz, 1 H) 5.59 (quin, J=8.51 Hz, 1 H) 6.93 (d, J=9.19 Hz, 1 H) 7.17 (dd, J=7.92, 4.79 Hz, 1 H) 7.47 (dd, J=8.41, 4.30 Hz, 1 H) 7.90 (m, J=8.02 Hz, 1 H) 7.99 (d, J=8.41 Hz, 1H) 8.13 (d, J=9.19 Hz, 1 H) 8.32 (m, J=3.70 Hz, 1 H) 8.57-8.81 (m, 1 H).

Method A3

Example 4

N-(trans-3-(2-cyclopropyl-3H-imidazo[4,5-b]pyridin-3-yl)cyclobutyl)thiazolo[5,4-b]pyridin-2-amine

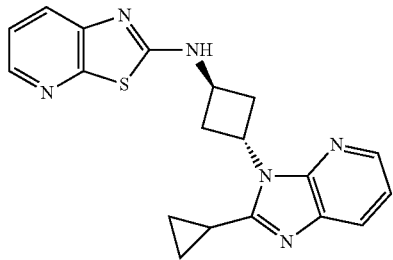 [SMILES: c1cnc2sc(N[C@H]3C[C@H](n4c(C5CC5)nc5cccnc54)C3)nc2c1]

Step 1: tert-butyl(trans-3-(thiazolo[5,4-b]pyridin-2-ylamino)cyclobutyl)carbamate Tert-butyl(trans-3-aminocyclobutyl)carbamate (0.150 g, 0.805 mmol) and intermediate 5 (0.120 g, 0.703 mmol) were dissolved in dry dimethylsulfoxide (3 mL) and cesium carbonate (0.123 ml, 1.535 mmol) was added. The reaction was heated at 70° C. After minutes the reaction was cooled and partitioned between water (100 mL) and ethyl acetate (200 mL). The organic phase was dried with magnesium sulfate and evaporated to dryness under reduced pressure. Purification using silica chromatography (dichloromethane to ethyl acetate gradient) gave the desired tert-butyl(trans-3-(thiazolo[5,4-b]pyridin-2-ylamino)cyclobutyl)carbamate (0.150 g, 0.468 mmol, 66.6% yield)

The tert-butyl(trans-3-(thiazolo[5,4-b]pyridin-2-ylamino)cyclobutyl)carbamate was reacted according to steps 1 to 4 of Example 1 using cyclopropanecarbonyl chloride in place of propionyl chloride in step 4. M+1: 363.1. $^1$H NMR (400 MHz, CHLOROFORM-d) δ ppm 1.10 (m, J=8.12, 2.64 Hz, 2 H) 1.23 (m, J=4.79, 2.45 Hz, 2 H) 1.88-2.05 (m, 1 H) 2.74 (ddt, J=11.15, 8.71, 2.89, 2.89 Hz, 2 H) 3.82 (m, J=13.89 Hz, 2 H) 4.67-4.89 (m, 1 H) 5.40-5.73 (m, 1 H) 7.06-7.28 (m, 2 H) 7.75 (dd, J=8.02, 1.17 Hz, 1 H) 7.89 (dd, J=8.02, 1.17 Hz, 1 H) 8.22 (dd, J=4.69, 1.17 Hz, 1 H) 8.30 (dd, J=4.69, 1.17 Hz, 1 H).

Method A4

Example 5

N-(trans-3-(2-methoxy-3H-imidazo[4,5-b]pyridin-3-yl)cyclobutyl)benzo[d]thiazol-2-amine

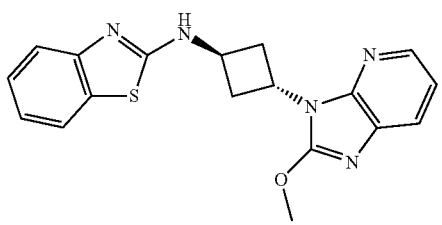 [SMILES: COc1nc2cccnc2n1[C@H]1C[C@H](Nc2nc3ccccc3s2)C1]

N$^2$-(3-(Thiazolo[4,5-b]pyridin-2-ylamino)cyclobutyl)pyridine-2,3-diamine (mixture of cis and trans cyclobutyl isomers) was synthesized according to example 1 using a commercial mixture of cis/trans tert-butyl 3-aminocyclobutylcarbamate.

N$^2$-(3-(thiazolo[4,5-b]pyridin-2-ylamino)cyclobutyl)pyridine-2,3-diamine (1.08 g, 3.46 mmol), tetramethyl orthocarbonate (9.22 ml, 69.2 mmol) and propionic acid (0.129 ml, 1.73 mmol) were combined under nitrogen. The reaction mixture was stirred at 100° C. for 2 hours. The reaction mixture was diluted with water (400 mL) and extracted with dichloromethane (2×400 mL). The organic phase was washed with saturated ammonium chloride (400 mL) and dried over magnesium sulfate before concentrating in vacuo to give the crude material as an off-white solid. Purification using silica chromatography (hexane to ethyl acetate gradient) gave 3-(2-(methoxy-3H-imidazo[4,5-b]pyridin-3-yl)cyclobutyl)benzo[d]thiazol-2-amine (880 mg, 25.0 mmol, 72.5% yield) as white solid. The material was separated by chiral prep. HPLC (Column: Chiralcel OD-H 250*30 mm, 5 u; Mobile phase: 85% hexane in EtOH (0.05% diethyl amine); Flow rate: 30 mL/minute) to give N-(cis-3-(2-methoxy-3H-imidazo[4,5-b]pyridin-3-yl)cyclobutyl)benzo[d]thiazol-2-amine (0.342 g, 0.97 mmol, 42% yield) and N-(trans-3-(2-methoxy-3H-imidazo[4,5-b]pyridin-3-yl)cyclobutyl)benzo[d]thiazol-2-amine (0.187 g, 0.53 mmol, 23% yield) as solid. ESI-MS (M+1): 352.

TRANS ISOMER—$^1$H NMR (CDCl$_3$, 400 MHz): δ (ppm) 2.66-2.59 (m, 2H) 3.58-3.50 (m, 2 H) 4.26 (s, 3 H); 4.63-4.61 (m, 1 H); 5.46-5.41 (m, 1 H); 6.28 (brs, 1H); 7.16-7.11 (m, 2 H); 7.33-7.31 (m, 1 H); 7.66-7.61 (m, 2 H); 7.79-7.77 (m, 1 H); 8.21-8.19 (m, 1 H).

CIS ISOMER—$^1$H NMR (CDCl$_3$, 400 MHz): δ (ppm) 3.16-3.12 (m, 4 H); 4.21 (s, 3 H); 4.37-4.33 (m, 1 H); 4.92-4.84 (m, 1 H); 6.94 (brs, 1H); 7.17-7.08 (m, 2 H); 7.32-7.29 (m, 1 H); 7.62-7.58 (m, 2 H); 7.80-7.78 (m, 1 H); 8.22-8.20 (m, 1 H).

Method A5

Example 7

N-(trans-3-(2-cyclopropyl-3H-imidazo[4,5-b]pyridin-3-yl)cyclobutyl)-6-fluoroquinolin-2-amine

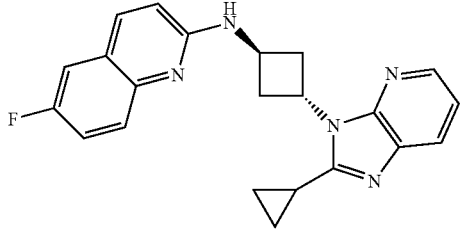 [SMILES: Fc1ccc2nc(N[C@H]3C[C@H](n4c(C5CC5)nc5cccnc54)C3)ccc2c1]

Trans-3-(2-cyclopropyl-3H-imidazo[4,5-b]pyridin-3-yl)cyclobutanamine (intermediate 12, 0.145 g, 0.635 mmol), 2-chloro-6-fluoroquinoline (0.115 g, 0.635 mmol), cesium carbonate (0.123 ml, 1.535 mmol), chloro(2-dicyclohexylphosphino-3,6-dimethoxy-2'-4'-6'-triisopropyl-1,1'-biphenyl)]2-(2-aminoethyl)phenyl)palladium(II) (0.011 g, 0.014 mmol), and 2-(dicyclohexylphosphino)-3,6-dimethoxy-2'-4'-6'-tri-isopropyl-1,1' biphenyl (0.009 g, 0.017 mmol) were suspended in dioxane in a microwave vessel. The reaction was heated in the microwave to 130° C. for 50 minutes. The crude was partitioned between water (100 mL) and ethyl acetate (100 mL). The organic phase was dried with magnesium sulfate and evaporated to dryness under reduced pressure. Purification using silica chromatography (0-6% methanol in dichloromethane gradient) followed by reverse phase HPLC gave the desired N-(trans-3-(2-cyclopropyl-3H-imidazo[4,5-b]pyridin-3-yl)cyclobutyl)-6-fluoroquinolin-2-amine (0.038 g, 0.102 mmol, 16.02% yield). M+1: 374.1. $^1$H NMR (300 MHz, CHLOROFORM-d) δ ppm 0.97-1.21 (m, 4 H) 1.86-2.08 (m, 1 H) 2.48-2.78 (m, 2 H) 3.62-3.84 (m, 2 H) 4.65-4.84 (m, 1 H) 5.53 (quin, J=8.29 Hz, 1 H) 6.76 (d, J=9.21 Hz, 1 H) 7.09 (dd, J=7.97, 4.90 Hz, 1 H) 7.25 (dd, J=8.48, 2.78 Hz, 1 H) 7.32 (td, J=8.70, 2.78 Hz, 1 H) 7.70 (dd, J=9.06, 4.82 Hz, 1 H) 7.82 (dd, J=7.89, 1.46 Hz, 1 H) 7.90 (d, J=9.21 Hz, 1 H) 8.22 (dd, J=4.82, 1.32 Hz, 1 H).

Method A6

Example 10

N-(trans-3-(2-(trifluoromethyl)-3H-imidazo[4,5-b]pyridin-3-yl)cyclobutyl)benzo[d]thiazol-2-amine

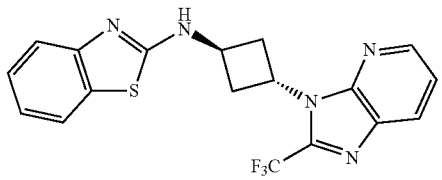 [SMILES: FC(F)(F)c1nc2cccnc2n1[C@H]1C[C@H](Nc2nc3ccccc3s2)C1]

N$^2$-(Trans-3-(benzo[d]thiazol-2-ylamino)cyclobutyl)pyridine-2,3-diamine (intermediate from step 3 of example 1, 0.100 g, 0.321 mmol) was dissolved in dichloromethane (20 mL) and treated with trifluoroacetic anhydride (0.050 ml, 0.357 mmol). The solution was stirred for 90 minutes. Acetic acid (60 mL) was added and the temperature raised to 105° C. After 30 minutes the solution was evaporated to dryness under reduced pressure. The crude was dissolved in methanol (40 mL) and treated with cesium carbonate (0.86 g) then stirred for 20 minutes and evaporated to dryness under reduced pressure. Ethyl acetate (100 mL) and water (70 mL) were added and the phases mixed and separated. The organic phase was dried with magnesium sulfate and evaporated to dryness under reduced pressure. Purification using silica chromatography (0-10% methanol in dichloromethane gradient) gave the N-(trans-3-(2-(trifluoromethyl)-3H-imidazo[4,5-b]pyridin-3-yl)cyclobutyl)benzo[d]thiazol-2-amine (0.0497 g, 0.128 mmol, 39.7% yield) as a white solid.

M+1: 389.7. $^1$H NMR (400 MHz, CHLOROFORM-d) δ ppm 2.67-2.77 (m, 2 H) 3.80-3.92 (m, 2 H) 4.63-4.74 (m, 1 H) 5.49 (quin, J=8.36 Hz, 1 H) 7.11 (t, J=7.63 Hz, 1 H) 7.32 (t, J=7.73 Hz, 1 H) 7.41 (dd, J=8.12, 4.79 Hz, 1 H) 7.54 (d, J=8.02 Hz, 1 H) 7.62 (d, J=8.02 Hz, 1H) 8.19 (d, J=8.22 Hz, 1 H) 8.60 (d, J=4.70 Hz, 1 H).

Method A7

Example 13

N-(trans-3-(8-cyclopropyl-9H-purin-9-yl)cyclobutyl)quinazolin-2-amine

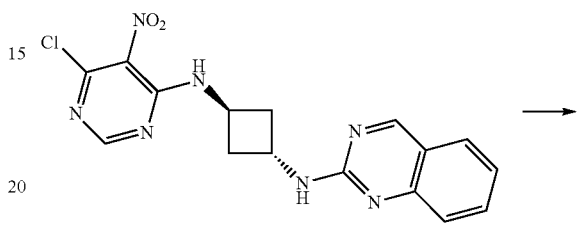

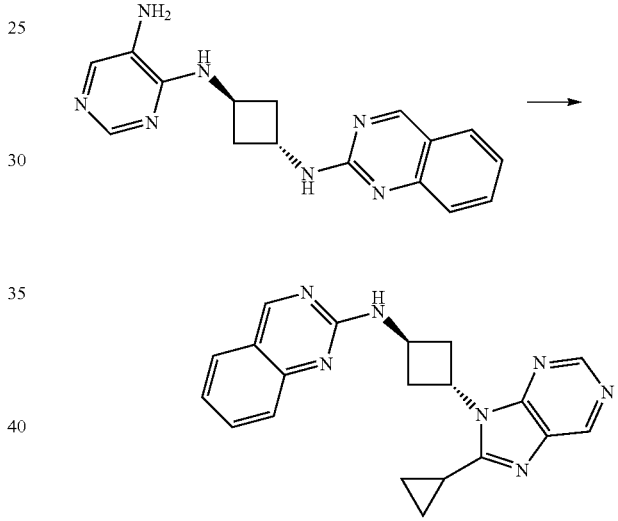

Step 1: trans-N-(6-chloro-5-nitropyrimidin-4-yl)-N$^3$-(quinazolin-2-yl)cyclobutane-1,3-diamine Tert-butyl(trans-3-(quinazolin-2-ylamino)cyclobutyl)carbamate, which was synthesized analagous to intermediate 10, (1.71 g, 5.44 mmol) was dissolved in dichloromethane (20 mL) and treated with trifluoroacetic acid (5 mL). The solution was stirred at room temperature for 20 minutes after which the solution was evaporated to dryness under reduced pressure. The crude oil was further dried under high vacuum then dissolved in dry dimethylsulfoxide (40 mL). 4,6-Dichloro-5-nitropyrimidine (1.5 g, 7.73 mmol) was added followed by potassium carbonate (1.8 g, 13.02 mmol) and the reaction heated at 60° C. After 2 hours the mixture was cooled and diluted with water (300 mL). The product precipitated out and was filtered off using a sintered glass frit. It was dried on the frit and used without purification.

Step 2: N⁴-(trans-3-(quinazolin-2-ylamino)cyclobutyl)pyrimidine-4,5-diamine

Trans-N¹-(6-chloro-5-nitropyrimidin-4-yl)-N³-(quinazolin-2-yl)cyclobutane-1,3-diamine (1.08 g, 2.90 mmol) was dissolved in dichloromethane (50 mL) and treated with palladium (10% wt. on activated carbon, 0.210 g, 0.197 mmol). Ethanol (100 mL) was added and the resulting suspension stirred under a hydrogen balloon. After 1 hour potassium acetate (2.4 g) was added and the reaction stirred for an additional 14 hours.

It was filtered through a pad of celite and washed with dichloromethane/methanol (1:1). The filtrate was evaporated to dryness under reduced pressure and purified using the silica chromatography (0-8% (2 N ammonia in methanol) in dichloromethane gradient) to give N⁴-(trans-3-(quinazolin-2-ylamino)cyclobutyl)pyrimidine-4,5-diamine (0.045 g, 0.146 mmol, 5.04% yield) and 6-chloro-N⁴-(trans-3-(quinazolin-2-ylamino)cyclobutyl)pyrimidine-4,5-diamine (0.080 g, 0.234 mmol, 8.06% yield)

Step 3: N-(trans-3-(8-cyclopropyl-9H-purin-9-yl)cyclobutyl) quinazolin-2-amine N⁴-(Trans-3-(quinazolin-2-ylamino)cyclobutyl)pyrimidine-4,5-diamine (0.045 g, 0.146 mmol) and triethylamine (0.50 ml, 3.59 mmol) were dissolved in dry tetrahydrofuran (10 mL) and treated with cyclopropanecarbonyl chloride (0.050 ml, 0.546 mmol). The reaction was stirred at room temperature for 14 hours. The mixture was evaporated to dryness under reduced pressure and the residue dissolved in acetic acid (20 mL). It was sealed in a microwave vessel and heated at 125° C. for 20 minutes then to 145° C. for 1 hour. The solution was evaporated to dryness under reduced pressure. Purification using silica chromatography (0-4% methanol in dichloromethane gradient) gave the desired N-(trans-3-(8-cyclopropyl-9H-purin-9-yl)cyclobutyl)quinazolin-2-amine (0.025 g, 0.070 mmol, 47.8% yield). M+1: 358.1. ¹H NMR (400 MHz, CHLOROFORM-d) δ ppm 1.15-1.24 (m, 2 H) 1.24-1.33 (m, 2 H) 2.02-2.12 (m, 1 H) 2.69-2.80 (m, 2 H) 3.68-3.81 (m, 2 H) 4.89 (m, J=7.70, 7.70, 4.10 Hz, 1 H) 5.54 (quin, J=8.36 Hz, 1 H) 5.92 (br. s, 1 H) 7.23-7.35 (m, 1 H) 7.59-7.67 (m, 1 H) 7.67-7.76 (m, 2 H) 8.95 (s, 1 H) 8.91 (s, 1 H) 9.03 (s, 1 H).

Method A8

Example 14

N-(trans-3-(3H-imidazo[4,5-b]pyridin-3-yl)cyclobutyl)benzo[d]thiazol-2-amine

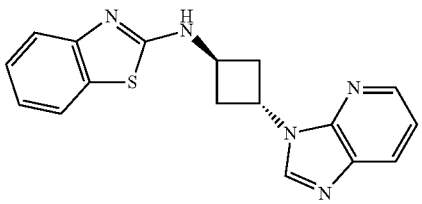 [SMILES: c1ccc2sc(N[C@H]3C[C@H](n4cnc5cccnc54)C3)nc2c1]

N²-(Trans-3-(benzo[d]thiazol-2-ylamino)cyclobutyl)pyridine-2,3-diamine (intermediate from step 3 in example 1, 0.100 g, 0.321 mmol) was dissolved in acetic acid (10 mL) and treated with ethyl orthoformate (2.0 ml, 12.02 mmol). The solution was heated at 90° C. for 20 minutes and the solution evaporated to dryness under reduced pressure. Purification using the silica chromatography (0-10% methanol in dichloromethane gradient) gave the desired N-(trans-3-(3H-imidazo[4,5-b]pyridin-3-yl)cyclobutyl)benzo[d]thiazol-2-amine (0.061 g, 0.190 mmol, 59.1% yield) as an off-white solid. M+1: 322.1. ¹H NMR (400 MHz, CHLOROFORM-d) δ ppm 2.82 (ddd, J=13.89, 8.51, 4.01 Hz, 2 H) 3.20-3.32 (m, 2 H) 4.61 (tt, J=7.73, 4.01 Hz, 1 H) 5.37 (quin, J=7.68 Hz, 1 H) 7.06-7.15 (m, 1 H) 7.23-7.34 (m, 2 H) 7.61 (d, J=8.02 Hz, 1 H) 7.58 (d, J=8.22 Hz, 1 H) 8.10 (dd, J=8.12, 1.27 Hz, 1 H) 8.19 (s, 1 H) 8.41 (dd, J=4.69, 1.37 Hz, 1 H).

Method A9

Example 19

7-chloro-N-(trans-3-(2-methoxy-3H-imidazo[4,5-b]pyridin-3-yl)cyclobutyl)quinoxalin-2-amine

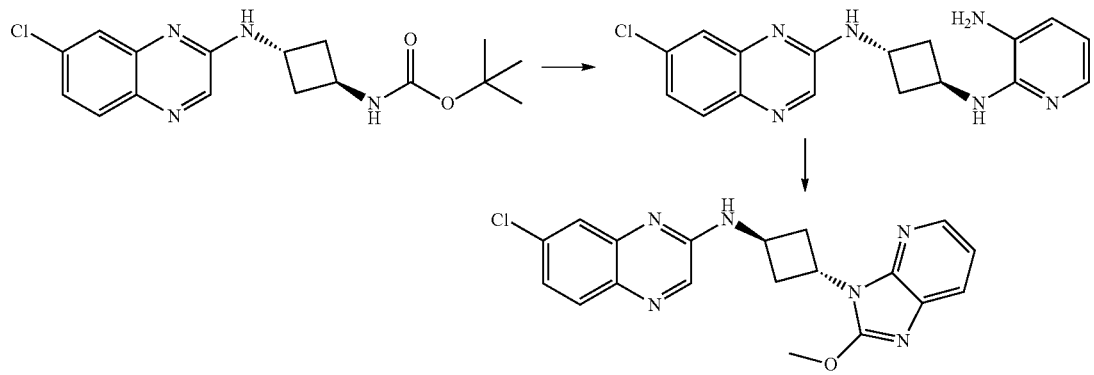

Tert-butyl(trans-3-(7-chloroquinoxalin-2-yl)amino)cyclobutyl)carbamate, which was made analogous to intermediate 10 using 2,7-dichloroquinoxaline in place of 2-chlorobenzo[d]thiazole, was used to synthesize N2-(trans-3-((7-chloroquinoxalin-2-yl)amino)cyclobutyl)pyridine-2,3-diamine following the procedure from example 1.

N²-(trans-3-((7-chloroquinoxalin-2-yl)amino)cyclobutyl)pyridine-2,3-diamine (118 mg, 0.346 mmol), tetramethyl orthocarbonate (922 μl, 6.92 mmol) and propionic acid (12.91 μl, 0.173 mmol) were combined under nitrogen. The reaction mixture was stirred at 100° C. for 2 hours. The reaction mixture was diluted with water and extracted with dichloromethane. The organic extract was washed with saturated ammonium chloride and dried over magnesium sulfate. The solution was concentrated in vacuo to give the crude material as a off-white solid. It was absorbed onto a plug of silica gel and purified by chromatography through a Redi-Sep pre-packed silica gel column (4 g), eluting with a hexane to ethyl acetate gradient, to provide 7-chloro-N-(trans-3-(2-methoxy-3H-imidazo[4,5-b]pyridin-3-yl)cyclobutyl)quinoxalin-2-amine (85 mg, 0.223 mmol, 64.5% yield). M+1: 380.9.

$^1$H NMR (300 MHz, CHLOROFORM-d) δ ppm 2.43-2.75 (m, 2 H) 3.38-3.62 (m, 2 H) 4.27 (s, 3 H) 4.81 (br. s., 1 H) 5.31-5.60 (m, 2 H) 7.13 (dd, J=7.82, 5.04 Hz, 1 H) 7.34 (dd, J=8.77, 2.19 Hz, 1 H) 7.70 (d, J=2.19 Hz, 1 H) 7.74-7.89 (m, 2 H) 8.18 (dd, J=4.97, 1.32 Hz, 1 H) 8.22 (s, 1 H).

Method A10

Example 20

7-chloro-N-(trans-3-(2-cyclopropyl-3H-imidazo[4,5-b]pyridin-3-yl)cyclobutyl)quinolin-2-amine

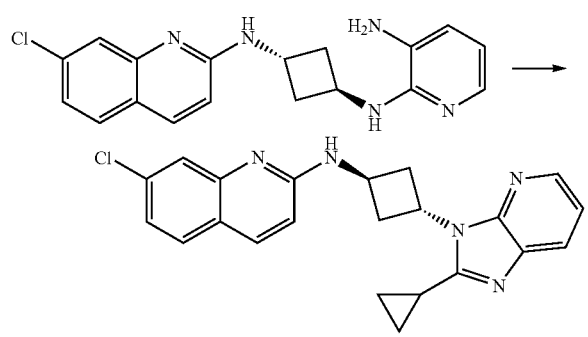

N$^2$-(Trans-3-((7-chloroquinolin-2-yl)amino)cyclobutyl)pyridine-2,3-diamine (0.240 g, 0.706 mmol), which was synthesized analogous to N$^2$-(trans-3-(benzo[d]thiazol-2-ylamino)cyclobutyl)pyridine-2,3-diamine (example 1 step 3) using intermediate 9 instead of 2-chlorobenzo[d]thiazole, was dissolved in dry dimethylformamide (3 mL) and treated with cyclopropanecarboxylic acid (0.100 ml, 1.256 mmol) and HATU (0.269 g, 0.706 mmol). Once all of the reagents dissolved n,n-diisopropylethylamine (1.0 ml, 5.75 mmol) was added and the reaction was allowed to stir at room temperature for 12 hours. Water (100 mL) and ethyl acetate (100 mL) were added and the phases mixed and separated. The organic phase was dried with magnesium sulfate and evaporated to dryness under reduced pressure. Purification using silica chromatography (0-10% methanol in dichloromethane gradient) gave the intermediate amide. It was dissolved in acetic acid (150 mL) and heated at 100° C. for 37 hours. The solution was evaporated to dryness under reduced pressure and further dried under high vac. The crude product was purified using reverse phase HPLC. Free basing and drying under high vacuum gave 7-chloro-N-(trans-3-(2-cyclopropyl-3H-imidazo[4,5-b]pyridin-3-yl)cyclobutyl)quinolin-2-amine (0.110 g, 0.282 mmol, 39.9% yield) as a tan solid. M+1: 390. $^1$H NMR (400 MHz, CHLOROFORM-d) δ ppm 1.03-1.18 (m, 2 H) 1.18-1.29 (m, 2 H) 1.99-2.10 (m, 1 H) 2.56-2.69 (m, 2 H) 3.78 (dtd, J=10.95, 8.17, 8.17, 2.64 Hz, 2 H) 4.68-4.84 (m, 1 H) 5.50 (br. s., 1 H) 5.57 (quin, J=8.60 Hz, 1 H) 6.67 (d, J=9.00 Hz, 1 H) 7.10-7.23 (m, 2 H) 7.52 (d, J=8.41 Hz, 1 H) 7.66-7.75 (m, 1 H) 7.84 (d, J=8.80 Hz, 1 H) 7.86-7.95 (m, 1 H) 8.26-8.38 (m, 1 H).

Method A11

Example 23

9-(trans-3-(quinazolin-2-ylamino)cyclobutyl)-8-(trifluoromethyl)-9H-purin-6-ol

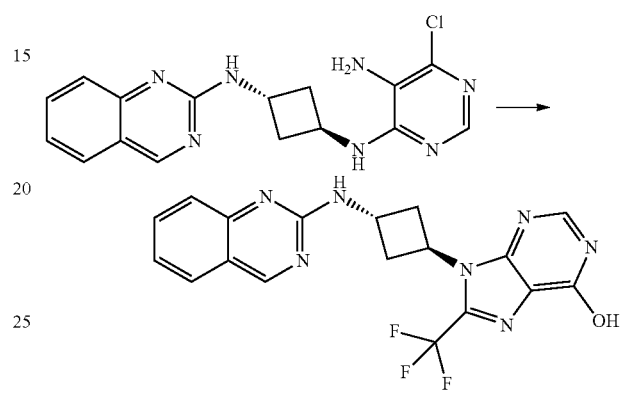

6-Chloro-N$^4$-(trans-3-(quinazolin-2-ylamino)cyclobutyl)pyrimidine-4,5-diamine (from Example 13, step 2) (0.150 g, 0.439 mmol) was dissolved in dichloromethane (30 mL) and treated with trifluoroacetic anhydride (0.070 ml, 0.500 mmol). The reaction was stirred at room temperature for 30 minutes then additional trifluoroacetic anhydride (0.070 mL) was added along with triethylamine (0.100 ml, 0.719 mmol). The reaction was stirred for another 2 hours. Acetic acid (60 mL) was added and the solution heated at 105° C. The dichloromethane was allowed to evaporate off and the solution heated for 16 hours. The mixture was evaporated to dryness under reduced pressure and purified using silica chromatography (0-15% (2N ammonia in methanol) in dichloromethane gradient) to give 9-(trans-3-(quinazolin-2-ylamino)cyclobutyl)-8-(trifluoromethyl)-9H-purin-6-ol (0.105 g, 0.262 mmol, 59.6% yield). M+1: 402. $^1$H NMR (400 MHz, CHLOROFORM-d) δ ppm 2.68-2.81 (m, 2 H) 3.57-3.71 (m, 2 H) 4.80-4.92 (m, 1 H) 5.46 (quin, J=8.41 Hz, 1 H) 7.31 (t, J=7.43 Hz, 1 H) 7.62 (d, J=8.80 Hz, 1 H) 7.74 (m, J=7.24 Hz, 1 H) 8.09 (s, 1 H) 9.03 (s, 1 H).

Method A12

Example 24

N-(trans-3-(6-morpholino-9H-purin-9-yl)cyclobutyl)quinazolin-2-amine

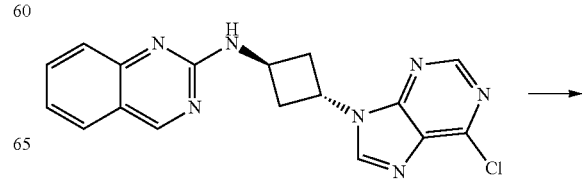

-continued

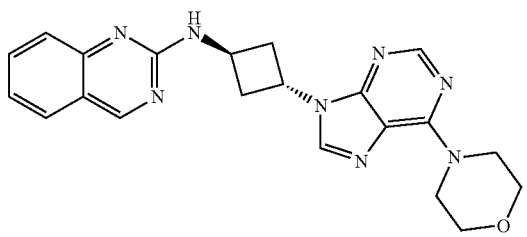

N-(Trans-3-(6-chloro-9H-purin-9-yl)cyclobutyl)quinazolin-2-amine (example 21, 0.0681 g, 0.194 mmol) was dissolved in morpholine (2.0 ml, 22.97 mmol) and heated in the microwave to 100° C. for 20 minutes. The solution was evaporated to dryness under reduced pressure and further dried under high vac. Purification using silica chromatography (0-10% methanol in dichloromethane gradient) gave the desired N-(trans-3-(6-morpholino-9H-purin-9-yl)cyclobutyl)quinazolin-2-amine (0.038 g, 0.094 mmol, 48.8% yield) as an off white solid. M+1: 403.2. $^1$H NMR (400 MHz, CHLOROFORM-d) δ ppm 2.80 (ddd, J=13.30, 8.31, 4.79 Hz, 2 H) 3.02-3.20 (m, 2 H) 3.85 (t, J=4.69 Hz, 4 H) 4.33 (br. s., 4 H) 4.78-4.94 (m, 1 H) 5.30 (quin, J=7.60 Hz, 1 H) 5.93 (br. s., 1 H) 7.23-7.34 (m, 1 H) 7.62 (d, J=8.22 Hz, 1 H) 7.66-7.75 (m, 2 H) 7.96 (s, 1 H) 8.37 (s, 1 H) 9.02 (s, 1 H).

Method A13

Example 25 methyl 4-(9-(trans-3-(quinazolin-2-ylamino)cyclobutyl)-8-(trifluoromethyl)-9H-purin-6-yl)benzoate Step 1: methyl 4-(5-amino-6-((trans-3-(quinazolin-2-ylamino)cyclobutyl)amino)pyrimidin-4-yl)benzoate 6-chloro-N$^4$-(trans-3-(quinazolin-2-ylamino)cyclobutyl) pyrimidine-4,5-diamine (from example 13 step 2, 0.045 g, 0.132 mmol), tetrakis(triphenylphosphine)palladium (0.015 g, 0.013 mmol), (4-methoxycarbonylphenyl)boronic acid (0.036 g, 0.197 mmol), and potassium carbonate (0.073 g, 0.527 mmol) were combined with dioxane (2 mL) and water (0.5 mL) and sealed in a vial under argon. The reaction was heated at 120° C. for 25 minutes in the microwave. The crude product was partitioned between water (100 mL) and ethyl acetate (100 mL) and the organic phase dried with magnesium sulfate. Purification using silica chromatography (0-8% (2N ammonia in methanol) in dichloromethane) gave the desired methyl 4-(5-amino-6-((trans-3-(quinazolin-2-ylamino)cyclobutyl)amino)pyrimidin-4-yl)benzoate (0.039 g, 0.088 mmol, 67.1% yield) as a yellow oil.

Step 2: methyl 4-(9-(trans-3-(quinazolin-2-ylamino)cyclobutyl)-8-(trifluoromethyl)-9H-purin-6-yl)benzoate Methyl 4-(5-amino-6-((trans-3-(quinazolin-2-ylamino)cyclobutyl)amino) pyrimidin-4-yl)benzoate (0.039 g, 0.088 mmol) was dissolved in dry tetrahydrofuran and treated with triethylamine (0.100 ml, 0.719 mmol). Trifluoroacetic acid anhydride (0.025 ml, 0.179 mmol) was added and the reaction stirred. After 5 minutes the reaction was evaporated to dryness under reduced pressure and the crude dissolved in acetic acid (50 mL). It was heated at reflux. After an hour the solution was evaporated to dryness under reduced pressure. Purification using silica chromatography (0-3% methanol in dichloromethane gradient) gave the desired methyl 4-(9-(trans-3-(quinazolin-2-ylamino)cyclobutyl)-8-(trifluoromethyl)-9H-purin-6-yl)benzoate. M+1: 520.1. $^1$H NMR (400 MHz, CHLOROFORM-d) δ ppm 2.68-2.78 (m, 2 H) 3.69-

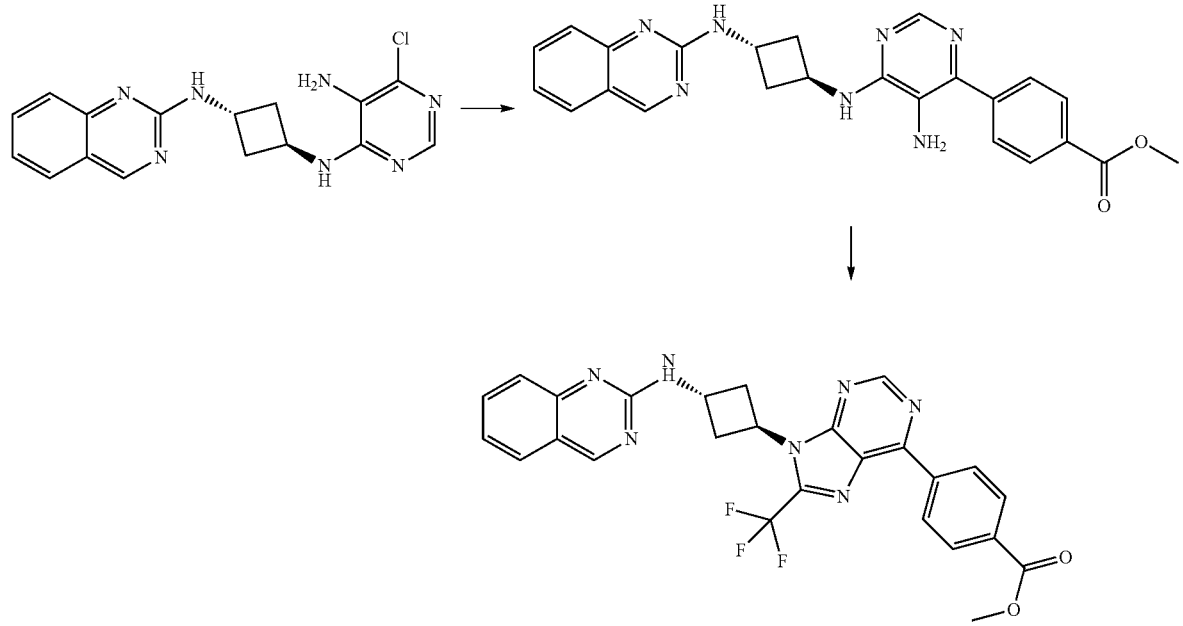 [SMILES: Nc1c(Cl)ncnc1N[C@H]1C[C@H](Nc2ncc3ccccc3n2)C1 ; COC(=O)c1ccc(-c2ncnc(N[C@H]3C[C@H](Nc4ncc5ccccc5n4)C3)c2N)cc1 ; COC(=O)c1ccc(-c2ncnc3c2nc(C(F)(F)F)n3[C@H]2C[C@H](Nc3ncc4ccccc4n3)C2)cc1]

3.81 (m, 2 H) 3.90 (s, 3 H) 4.87-4.96 (m, 1 H) 5.50 (quin, J=8.31 Hz, 1 H) 7.19-7.25 (m, 1 H) 7.55 (d, J=8.22 Hz, 1 H) 7.61-7.69 (m, 2 H) 8.16 (d, J=8.41 Hz, 2 H) 8.83 (d, J=8.41 Hz, 2 H) 8.96 (s, 1 H) 9.13 (s, 1 H).

Method A14

Example 26 methyl 4-(9-(trans-3-(quinazolin-2-ylamino)cyclobutyl)-9H-purin-6-yl)benzoate

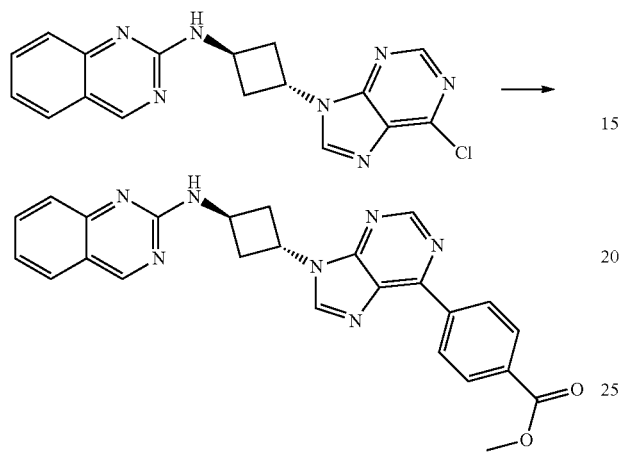

N-(Trans-3-(6-chloro-9H-purin-9-yl)cyclobutyl)quinazolin-2-amine (example 21, 0.110 g, 0.313 mmol), tetrakis(triphenylphosphine)palladium (0.018 g, 0.016 mmol), (4-methoxycarbonylphenyl)boronic acid (0.073 g, 0.406 mmol), and cesium carbonate (0.357 g, 1.094 mmol) were suspended in a mixture of dioxane (1.25 mL) and water (0.15 mL) and heated in the microwave to 120° C. for 25 minutes. The crude was partitioned between ethyl acetate (200 mL) and water (200 mL). The organic phase was dried with magnesium sulfate and evaporated to dryness under reduced pressure. Purification using silica chromatography (0-3% methanol in dichloromethane gradient) gave the desired methyl 4-(9-(trans-3-(quinazolin-2-ylamino)cyclobutyl)-9H-purin-6-yl)benzoate (0.0531 g, 0.118 mmol, 37.6% yield). M+1: 452.1. $^1$H NMR (400 MHz, CHLOROFORM-d) δ ppm 2.89 (ddd, J=13.60, 8.51, 4.89 Hz, 2 H) 3.15-3.33 (m, 2 H) 3.98 (s, 3 H) 4.89-5.00 (m, 1 H) 5.44 (quin, J=7.34 Hz, 1 H) 7.30-7.35 (m, 1 H) 7.65 (d, J=8.41 Hz, 1 H) 7.69-7.81 (m, 2 H) 8.24 (d, J=8.41 Hz, 2 H) 8.45 (s, 1 H) 8.84 (d, J=8.41 Hz, 2 H) 9.01-9.14 (m, 2 H).

Examples 3, 5-6, 8-9, 11-12, 15-18, 21-22, and 27-28 were prepared analogous to the above Methods A1-A14 as follows:

TABLE 7

Preparation of Examples 3, 5-6, 8-9, 11-12, 15-18, 21-22, and 27-28

| Ex. # | Method | Reagents | M + 1 | NMR |
|---|---|---|---|---|
| 3 | A2 | Intermediate 12, intermediate 3 | 357.2 | $^1$H NMR (400 MHz, CHLOROFORM-d) δ ppm 1.10-1.29 (m, 4 H) 1.97-2.13 (m, 1 H) 2.57-2.85 (m, 2 H) 3.72-3.94 (m, 2 H) 4.82 (td, J = 7.38, 4.21 Hz, 1 H) 5.59 (quin, J = 8.51 Hz, 1 H) 6.93 (d, J = 9.19 Hz, 1 H) 7.17 (dd, J = 7.92, 4.79 Hz, 1 H) 7.47 (dd, J = 8.41, 4.30 Hz, 1 H) 7.90 (m, J = 8.02 Hz, 1 H) 7.99 (d, J = 8.41 Hz, 1 H) 8.13 (d, J = 9.19 Hz, 1 H) 8.32 (m, J = 3.70 Hz, 1 H) 8.57-8.81 (m, 1 H) |
| 5 | A4 | 2-chlorobenzo[d]thiazole | 352 | $^1$H NMR (CDCl$_3$, 400 MHz): δ (ppm) 2.66-2.59 (m, 2H) 3.58-3.50 (m, 2 H) 4.26 (s, 3 H); 4.63-4.61 (m, 1 H); 5.46-5.41 (m, 1 H); 6.28 (brs, 1H); 7.16-7.11 (m, 2 H); 7.33-7.31 (m, 1 H); 7.66-7.61 (m, 2 H); 7.79-7.77 (m, 1 H); 8.21-8.19 (m, 1 H) |
| 6 | A2 | Intermediate 12, 2-chloroquinoline | 356.1 | $^1$H NMR (400 MHz, CHLOROFORM-d) δ ppm 0.99-1.18 (m, 2 H) 1.18-1.36 (m, 2 H) 1.97-2.16 (m, 1 H) 2.55-2.78 (m, 2 H) 3.73-3.92 (m, 2 H) 4.76 (br. s., 1 H) 5.59 (quin, J = 8.51 Hz 1 H) 5.74 (br. s., 1 H) 6.71 (d, J = 9.00 Hz, 1 H) 7.11-7.35 (m, 2 H) 7.57 (t, J = 7.63 Hz, 1 H) 7.63 (d, J = 7.83 Hz, 1 H) 7.71 (d, J = 8.41 Hz, 1 H) 7.93 (d, J = 9.00 Hz, 1 H) 7.89 (d, J = 8.02 Hz, 1 H) 8.31 (d, J = 4.69 Hz, 1 H) |
| 8 | A2 | Intermediate 12, 2-chloroquinazoline | 357 | $^1$H NMR (400 MHz, CHLOROFORM-d) δ ppm 1.10-1.20 (m, 2 H) 1.20-1.30 (m, 2 H) 2.03-2.13 (m, 1 H) 2.73 (ddt, J = 11.15, 8.66, 2.91, 2.91 Hz, 2 H) 3.76-3.87 (m, 2 H) 4.91-5.02 (m, 1 H) 5.62 (quin, J = 8.51 Hz, 1 H) 7.16 (dd, J = 8.02, 4.69 Hz, 1 H) 7.31 (t, J = 7.43 Hz, 1 H) 7.64-7.79 (m, 3 H) 7.90 (dd, J = 7.92, 1.27 Hz, 1 H) 8.32 (dd, J = 4.79, 1.27 Hz, 1 H) 9.08 (s, 1 H) |

TABLE 7-continued

Preparation of Examples 3, 5-6, 8-9, 11-12, 15-18, 21-22, and 27-28

| Ex. # | Method | Reagents | M + 1 | NMR |
|---|---|---|---|---|
| 9 | A4 | 2-chlorobenzo[d]thiazole, tetramethyl orthocarbonate | 352 | $^1$H NMR (CDCl$_3$, 400 MHz); δ (ppm) 8.22-8.20 (m, 1 H); 7.80-7.78 (m, 1 H); 7.62-7.58(m, 2 H); 7.32-7.29 (m, 1 H); 7.17-7.08 (m, 2 H); 6.94 (brs, 1H); 4.92-4.84 (m, 1 H); 4.37-4.33 (m, 1 H); 4.21 (s, 3 H); 3.16-3.12 (m, 4 H). |
| 11 | A2 | Intermediate 10, intermediate 1 | 357 | $^1$H NMR (400 MHz, CHLOROFORM-d) δ ppm 0.97-1.14 (m, 4 H) 2.09-2.24 (m, 1 H) 2.58-2.77 (m, 2 H) 3.52-3.77 (m, 2 H) 4.88-5.11 (m, 1 H) 5.44-5.77 (m, 1 H) 7.03 (d, J = 9.00 Hz, 1 H) 7.16 (dd, J = 8.02, 4.89 Hz, 1 H) 7.36 (dd, J = 7.63, 5.67 Hz, 1 H) 7.76 (m, J = 8.02 Hz, 1 H) 7.96 (m, J = 9.00 Hz, 1 H) 8.23 (d, J = 4.69 Hz, 1 H) 8.40 (m, J = 7.82 Hz, 1 H) 8.53 (d, J = 5.48 Hz, 1 H) |
| 12 | A6 | 2-chloroquinazoline, trifluoroacetic anhydride | 385.1 | $^1$H NMR (400 MHz, CHLOROFORM-d) δ ppm 2.67-2.79 (m, 2 H) 3.82-3.94 (m, 2 H) 4.88-4.98 (m, 1 H) 5.55 (quin, J = 8.46 Hz, 1 H) 5.69 (d, J = 4.89 Hz, 1 H) 7.24-7.31 (m, 1 H) 7.37 (dd, J = 8.22, 4.69 Hz, 1 H) 7.60-7.66 (m, 1 H) 7.67-7.74 (m, 2 H) 8.18 (dd, J = 8.22, 1.37 Hz, 1 H) 8.60 (dd, J = 4.70, 1.17 Hz, 1 H) 9.03 (s, 1 H) |
| 15 | A2 | Intermediate 12 2-chlorobenzo[d]oxazole | 346.1 | $^1$H NMR (300 MHz, CHLOROFORM-d,) δ ppm 1.12-1.31 (m, 4 H) 2.06-2.16 (m, 1 H) 2.70-2.82 (m, 2 H) 3.65-3.81 (m, 2 H) 4.71-4.81 (m, 1 H) 5.60 (quin, J = 8.51 Hz, 1 H) 7.00-7.09 (m, 1 H) 7.13-7.22 (m, 2H) 7.25-7.33 (m, 1 H) 7.36 (d, J = 7.75 Hz, 1 H) 7.89 (dd, J = 7.97, 1.39 Hz, 1 H) 8.30 (dd, J = 4.82, 1.46 Hz, 1 H) |
| 16 | A2 | Intermediate 12, intermediate 4 | 356.9 | $^1$H NMR (400 MHz, CHLOROFORM-d) δ ppm 1.07-1.19 (m, 2 H) 1.19-1.29 (m, 2 H) 2.01-2.11 (m, 1 H) 2.59-2.74 (m, 2 H) 3.75-3.87 (m, 2 H) 4.85 (m, J = 7.30, 3.20 Hz, 1 H) 5.52-5.69 (m, 2 H) 6.89 (d, J = 8.80 Hz, 1 H) 7.17 (dd., J = 7.82, 4.89 Hz, 1 H) 7.44 (d, J = 5.48 Hz, 1 H) 7.90 (d, J = 8.02 Hz, 1 H) 7.85 (d, J = 9.00 Hz, 1 H) 8.36 (d, J = 5.48 Hz, 1 H) 8.31 (d, J = 4.89 Hz, 1 H) 9.11 (s, 1 H) |
| 17 | A1 | Intermediate 8, tetrahydro-2H-pyran-4-carbonyl chloride | 435 | $^1$H NMR (300 MHz, CHLOROFORM-d) δ ppm 1.88 (d, J = 14.47 Hz, 2 H) 2.10-2.24 (m, 2 H) 2.60-2.70 (m, 2 H) 3.10-3.25 (m, 1 H) 3.62 (td, J = 11.80, 1.97 Hz, 2 H) 3.84-3.95 (m, 2 H) 4.10-4.17 (m, 2 H) 5.30-5.40 (m, 2 H) 7.23 (dd, J = 8.11, 4.90 Hz, 1 H) 7.36 (dd, J = 8.77, 2.19 Hz, 1 H) 7.71 (d, J = 2.19 Hz, 1 H) 7.82 (d, J = 8.77 Hz, 1 H) 8.01 (dd, J = 8.04, 1.46 Hz, 1 H) 8.26 (s, 1 H) 8.38 (dd, J = 4.75, 1.53 Hz, 1 H). |
| 18 | A2 | Intermediate 12, intermediate 2 | 357 | $^1$H NMR (400 MHz, CHLOROFORM-d) δ ppm 1.09-1.17 (m, 2 H) 1.22-1.29 (m, 2 H) 2.02-2.11 (m, 0 H) 2.62-2.73 (m, 2 H) 3.76-3.88 (m, 2 H) 4.82-4.92 (m, 1 H) 5.58 (quin, J = 8.46 Hz, 1 H) 5.97 (br. s., 1 H) 6.77 (d, J = 9.00 Hz, 1 H) 7.17 (dd, J = 7.82, 4.89 Hz, 1 H) 7.49 (d, J = 5.87 Hz, 1 H) 7.94 (d, J = 9.00 Hz, 1 H) 7.90 (d, J = 8.02 Hz, 1 H) 8.31 (d, J = 4.69 Hz, 1 H) 8.54 (d, J = 5.87 Hz, 1 H) 8.92 (s, 1 H) |
| 21 | A8 | 6-chloro-N$^4$-(trans-3-(quinazolin-2-ylamino)cyclobutyl)pyrimidine-4,5-diamine (Method A7, step 2) | 352.1 | $^1$H NMR (400 MHz, CHLOROFORM-d) δ ppm 2.79-2.94 (m, 2 H) 3.15-3.26 (m, 2 H) 4.83-4.99 (m, 1 H) 5.34-5.45 (m, 1 H) 7.26-7.34 (m, 1 H) 7.62 (d, J = 8.80 Hz, 1H) 7.68-7.77 (m, 2 H) 8.45 (s, 1 H) 8.77 (s, 1 H) 9.02 (s, 1 H) |

TABLE 7-continued

Preparation of Examples 3, 5-6, 8-9, 11-12, 15-18, 21-22, and 27-28

| Ex. # | Method | Reagents | M + 1 | NMR |
|---|---|---|---|---|
| 22 | A8 | 2-chloroquinazoline | 317.1 | $^1$H NMR (400 MHz, CHLOROFORM-d) δ ppm 2.83 (ddd, J = 13.55, 8.46, 4.79 Hz, 2 H) 3.09-3.25 (m, 2 H) 4.83-5.00 (m, 1 H) 5.43 (quin, J = 7.34 Hz, 1 H) 5.97 (d, J = 5.67 Hz, 1 H) 7.16-7.34 (m, 2 H) 7.62 (d, J = 8.00 Hz, 1 H) 7.66-7.78 (m, 2 H) 8.10 (dd, J = 8.02, 1.17 Hz, 1 H) 8.31 (s, 1 H) 8.42 (dd, J = 4.69, 1.17 Hz, 1 H) 9.03 (s, 1 H) |
| 27 | A3 | Intermediate 6, cyclopropane-carbonyl chloride | 363.1 | $^1$H NMR (400 MHz, CHLOROFORM-d,) δ ppm 1.09-1.32 (m, 4 H) 2.12 (m, J = 5.28, 5.28 Hz, 1 H) 2.72-2.85 (m, 2 H) 3.74 (m, J = 5.53, 2.81, 2.81 Hz, 2 H) 4.57-4.74 (m, 1 H) 5.63 (quin, J = 8.22 Hz, 1 H) 6.95-7.08 (m, 1 H) 7.20 (dd, J = 7.53, 4.99 Hz, 1 H) 7.91 (dd J = 10.07, 8.51 Hz, 2 H) 8.33 (dd, J = 14.28, 4.69 Hz, 2 H) |
| 28 | A9 | Intermediate 8 | 381 | $^1$H NMR (400 MHz, CHLOROFORM-d) δ ppm 2.44-2.67 (m, 2 H) 3.37-3.66 (m, 2 H) 4.26 (s, 3 H) 4.67-4.90 (m, 1 H) 5.45 (s, 1 H) 5.73-5.93 (m, 1 H) 7.11 (dd, J = 7.82, 4.89 Hz, 1 H) 7.19 (dd, J = 8.41, 1.96 Hz, 1 H) 7.50-7.67 (m, 2 H) 7.76 (dd, J = 7.82, 1.37 Hz, 1 H) 8.18 (dd, J = 4.89, 1.37 Hz, 1 H) 8.96 (s, 1 H) |

Examples 29-30, 34-35, 43-44, 47, 50, 73, 79, and 82 were prepared according to Methods B1-B11 as follows:

Method B1

Example 29

6-((trans-3-(3,3-dimethyl-2-oxo-2,3-dihydro-1H-pyrrolo[2,3-b]pyridin-1-yl)cyclobutyl)amino)-N-methylnicotinamide

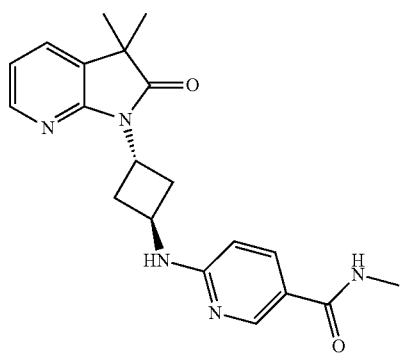 [SMILES: CNC(=O)c1ccc(N[C@H]2C[C@H](N3C(=O)C(C)(C)c4cccnc43)C2)nc1]

Intermediate 26 (100 mg, 0.373 mmol), cesium acetate (516 mg, 2.69 mmol), 6-bromo-n-methylnicotinamide (120 mg, 0.560 mmol), and copper (1.899 mg, 0.030 mmol) were weighed into a microwave vial. The vial was evacuated and flushed with nitrogen. DMSO (467 µl) was then added and the mixture was heated at 100° C. for 20 h. The mixture was diluted with ethyl acetate and washed with aqueous ammonium hydroxide. The aqueous layer was back extracted with ethyl acetate and the combined organics dried with magnesium sulfate and evaporated to dryness under reduced pressure. The crude product was purified by silica chromatography, eluting with a gradient of hexane/ethyl acetate (50-100%) to provide 6-((trans-3-(3,3-dimethyl-2-oxo-2,3-dihydro-1H-pyrrolo[2,3-b]pyridin-1-yl)cyclobutyl)amino)-N-methylnicotinamide (50 mg, 0.137 mmol, 36.6% yield) as off-white solid. M+1: 366. $^1$H NMR (300 MHz, CHLOROFORM-d) δ ppm 1.38 (s, 6 H) 2.28-2.40 (m, 2 H) 3.00 (d, J=4.82 Hz, 3 H) 3.39-3.54 (m, 2 H) 4.50 (br. s., 1 H) 5.28 (quin, J=8.59 Hz, 1 H) 5.38 (br. d, J=4.80 Hz, 1 H) 5.98 (br. s., 1 H) 6.34 (d, J=8.77 Hz, 1 H) 6.96 (dd, J=7.31, 5.26 Hz, 1 H) 7.43 (dd, J=7.16, 1.61 Hz, 1 H) 7.91 (dd, J=8.70, 2.41 Hz, 1 H) 8.18 (dd, J=5.26, 1.61 Hz, 1 H) 8.51 (d, J=2.05 Hz, 1 H)

Method B2

Example 30

1-(trans-3-(benzo[d]thiazol-2-ylamino)cyclobutyl)-3,3-dimethyl-1H-pyrrolo[2,3-b]pyridin-2(3H)-one Intermediates 25 and 11 ⟶

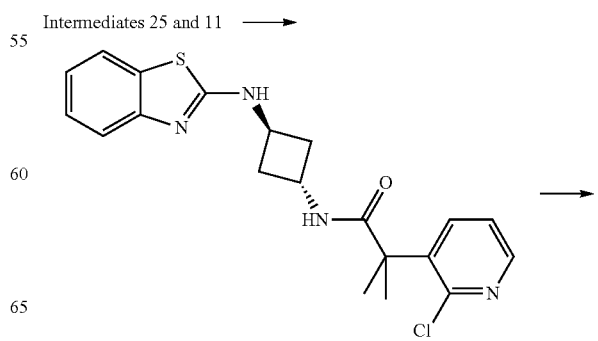

-continued

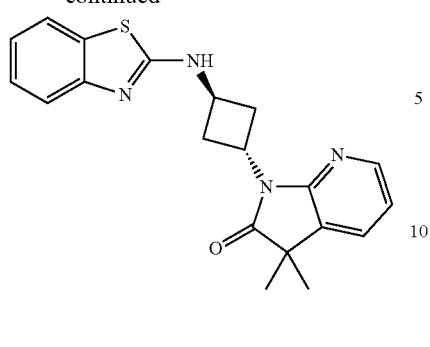

Step 1: N-(trans-3-(benzo[d]thiazol-2-ylamino)cyclobutyl)-2-(2-chloropyridin-3-yl)-2-methylpropanamide Intermediate 25 (216 mg, 1.083 mmol), intermediate 11 (198 mg, 0.903 mmol), HBTU (376 mg, 0.993 mmol) and triethylamine (377 µl, 2.71 mmol) were dissolved in dichloromethane (20 mL). The reaction mixture was stirred at room temperature for 14 hours. The reaction mixture was diluted with water and extracted with dichloromethane. The organic extract was washed with saturated ammonium chloride and dried over magnesium sulfate. The solution was concentrated in vacuo to give the crude material as a tan solid. The crude material was absorbed onto a plug of silica gel and purified by silica chromatography (hexane to ethyl acetate gradient) to provide N-(trans-3-(benzo[d]thiazol-2-ylamino)cyclobutyl)-2-(2-chloropyridin-3-yl)-2-methylpropanamide (220 mg, 0.549 mmol, 60.8% yield) as white solid.

Step 2: 1-(trans-3-(benzo[d]thiazol-2-ylamino)cyclobutyl)-3,3-dimethyl-1H-pyrrolo[2,3-b]pyridin-2(3H)-one N-(Trans-3-(benzo[d]thiazol-2-ylamino)cyclobutyl)-2-(2-chloropyridin-3-yl)-2-methylpropanamide (0.086 g, 0.216 mmol), sodium t-butoxide (0.040 g, 0.416 mmol), and chloro(2-dicyclohexylphosphino-2',6'-di-1-propoxy-1,1'-biphenyl)[2-(2-aminoethyl-phenyl)]palladium(ii), methyl t-butyl ether adduct (0.010 g, 0.012 mmol) were sealed in a microwave vessel under argon. Dry, sparged dioxane (0.5 mL) was added and the reaction heated at 80° C. After 35 minutes the mixture was cooled and partitioned between ethyl acetate (100 mL), water (100 mL) and saturated sodium bicarbonate (10 mL). The organic phase was dried with magnesium sulfate and evaporated to dryness under reduced pressure. Purification using silica chromatography (dichloromethane to ethyl acetate gradient) followed by reverse phase HPLC gave 1-(trans-3-(benzo[d]thiazol-2-ylamino) cyclobutyl)-3,3-dimethyl-1H-pyrrolo[2,3-b]pyridin-2(3H)-one (0.0481 g, 0.126 mmol, 58.6% yield) as an off white solid. M+1: 365.1. $^1$H NMR (300 MHz, CHLOROFORM-d) δ ppm 1.39 (s, 6 H) 2.45 (m, J=3.36 Hz, 2 H) 3.38-3.63 (m, 2 H) 4.51-4.72 (m, 1 H) 5.30 (quin, J=8.66 Hz, 1 H) 5.59-5.80 (m, 1 H) 6.97 (dd, J=7.16, 5.26 Hz, 1 H) 7.04-7.16 (m, 1 H) 7.21-7.35 (m, 1 H) 7.43 (dd, J=7.31, 1.61 Hz, 1 H) 7.59 (dd, J=10.52, 8.33 Hz, 2 H) 8.19 (dd, J=5.19, 1.53 Hz, 1 H).

Method B3

Example 34

5-(trans-3-(benzo[d]thiazol-2-ylamino)cyclobutyl)-7,7-dimethyl-5H-pyrrolo[2,3-b]pyrazin-6(7H)-one

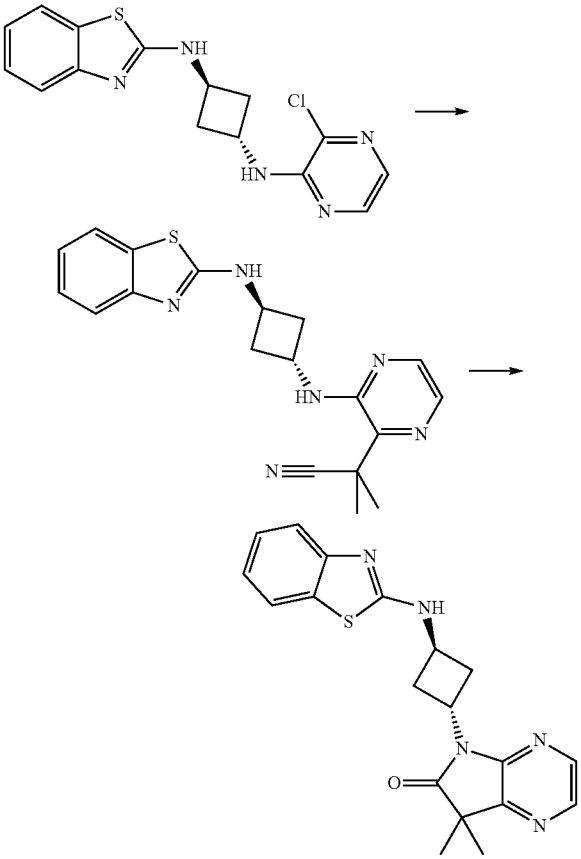

Step 1: 2-(3-((trans-3-(benzo[d]thiazol-2-ylamino) cyclobutyl) amino)pyrazin-2-yl)-2-methylpropanenitrile Dibromobis(tri-tert-butylphosphine)dipalladium(I) (0.031 g, 0.040 mmol) was sealed in a microwave vessel under argon. Diisopropylamine (0.200 ml, 1.427 mmol) was added and the mixture cooled in a dry ice bath. A nitrogen needle was added followed by dropwise addition of butyllithium solution (2.5 m in hexanes, 0.500 ml, 1.250 mmol). The mixture was stirred for 5 minutes then isobutyronitrile (0.100 ml, 1.114 mmol) was added. The reaction was removed from the cold bath and allowed to slowly warm to room temperature. A solution of trans-$N^1$-(benzo[d]thiazol-2-yl)-$N^3$-(3-chloropyrazin-2-yl)cyclobutane-1,3-diamine (intermediate 27, 0.150 g, 0.452 mmol) in dry, sparged dioxane (1.5 mL) was added and the nitrogen needle removed. The reaction was heated at 95° C. for 14 hours. The crude was partitioned between water (100 mL), saturated ammonium chloride (10 mL) and ethyl acetate (200 mL). The organic phase was dried with magnesium sulfate and evaporated to dryness under reduced pressure. Purification using silica chromatography (dichloromethane to ethyl acetate gradient) gave the desired 2-(3-((trans-3-(benzo[d]thiazol-2-ylamino)cyclobutyl)amino)pyrazin-2-yl)-2-methylpropanenitrile (0.067 g, 0.184 mmol, 40.7% yield).

Step 2: 5-(trans-3-(benzo[d]thiazol-2-ylamino)cyclobutyl)-7,7-dimethyl-5H-pyrrolo[2,3-b]pyrazin-6(7H)-one 2-(3-((Trans-3-(benzo[d]thiazol-2-ylamino)cyclobutyl)amino)pyrazin-2-yl)-2-methylpropanenitrile (0.067 g, 0.184 mmol) was dissolved in a mixture of water (3 mL) and concentrated sulfuric acid (2 mL) and heated at 100° C. After 35 minutes the heat was turned off and the reaction allowed to cool in the oil bath over 90 minutes. Water (100 mL), ice (about 100 mL), and ethyl acetate (200 mL) were added followed by 5 N sodium hydroxide (15 mL). The phases were mixed and separated and the organic dried with magnesium sulfate before evaporating to dryness under reduced pressure. Purification using silica chromatography (dichloromethane to ethyl acetate gradient) gave the desired 5-(trans-3-(benzo[d]thiazol-2-ylamino)cyclobutyl)-7,7-dimethyl-5H-pyrrolo[2,3-b]pyrazin-6(7H)-one (0.061 g, 0.167 mmol, 91% yield) as a white solid. M+1: 366.2. $^1$H NMR (400 MHz, CHLOROFORM-d) δ ppm 1.45 (s, 6 H) 2.42-2.58 (m, 2 H) 3.45 (s, 2 H) 4.53-4.68 (m, 1 H) 5.31 (quin, J=8.46 Hz, 1 H) 6.53 (br. s, 1 H) 7.04-7.15 (m, 1 H) 7.30 (t, J=7.24 Hz, 1 H) 7.59 (d, J=8.22 Hz, 1 H) 7.61 (d, J=8.02 Hz, 1 H) 8.09 (d, J=3.33 Hz, 1 H) 8.13 (d, J=3.30 Hz, 1 H).

Method B4

Example 35

1'-(trans-3-(benzo[d]thiazol-2-ylamino)cyclobutyl)spiro[cyclobutane-1,3'-pyrrolo[2,3-b]pyridin]-2'(1'H)-one

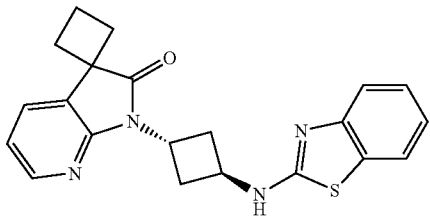 [SMILES: O=C1N([C@H]2C[C@H](Nc3nc4ccccc4s3)C2)c2ncccc2C12CCC2]

1-(2-Chloropyridin-3-yl)cyclobutanecarbonitrile (intermediate 19, 0.070 g, 0.363 mmol), (trans)-N$^1$-(benzo[d]thiazol-2-yl)cyclobutane-1,3-diamine (intermediate 11, 0.080 g, 0.363 mmol), [dicyclohexyl(2',4',6'-triisopropyl-3,6-dimethoxy-[1,1'-biphenyl]-2-yl)phosphine]2-(2-aminoethyl)phenyl)palladium(II) chloride (0.015 g, 0.018 mmol), and sodium t-butoxide (0.096 ml, 0.780 mmol) were combined under argon in a ROUND BOTTOMED FLASK. Dry, sparged dioxane (0.8 mL) was added and the reaction heated at 90° C. After 25 minutes water (150 mL), saturated ammonium chloride (20 mL) and ethyl acetate (200 mL) were added and the phases mixed and separated. The organic phase was dried with magnesium sulfate and evaporated to dryness under reduced pressure. The crude intermediate was dissolved in a mixture of water (5 mL) and concentrated sulfuric acid (5 mL) and heated at 100° C. After 5 hours the reaction was allowed to cool to room temperature. Water (100 mL) and ethyl acetate (100 mL) were added and the phases mixed and separated. The organic phase was discarded. Ice (100 mL) was added to the aqueous along with additional ethyl acetate (200 mL). The pH was adjusted to about 9 using 10 N sodium hydroxide and the phases mixed and separated. The aqueous was extracted with an additional portion of ethyl acetate (100 mL) then the combined organics were dried with magnesium sulfate and evaporated to dryness under reduced pressure. Purification using silica chromatography (dichloromethane to ethyl acetate gradient) gave the desired 1'-(trans-3-(benzo[d]thiazol-2-ylamino)cyclobutyl)spiro[cyclobutane-1,3'-pyrrolo[2,3-b]pyridin]-2'(1'H)-one (0.041 g, 0.109 mmol, 30.0% yield). M+1: 377.1. $^1$H NMR (400 MHz, CHLOROFORM-d) δ ppm 2.17-2.55 (m, 6 H) 2.61-2.78 (m, 2 H) 3.42-3.58 (m, 2 H) 4.53-4.67 (m, 1 H) 5.29 (quin, J=8.46 Hz, 1 H) 6.38 (br. s., 1 H) 6.99 (dd, J=7.24, 5.28 Hz, 1 H) 7.08 (td, J=7.58, 1.08 Hz, 1 H) 7.24-7.33 (m, 1 H) 7.54-7.64 (m, 2 H) 7.70 (dd, 1=7.24, 1.56 Hz, 1 H) 8.17 (dd, J=5.28, 1.56 Hz, 1 H).

Method B5

Example 43

1-(trans-3-((5-acetylpyridin-2-yl)amino)cyclobutyl)-3,3-dimethyl-1H-pyrrolo[2,3-b]pyridin-2(3H)-one

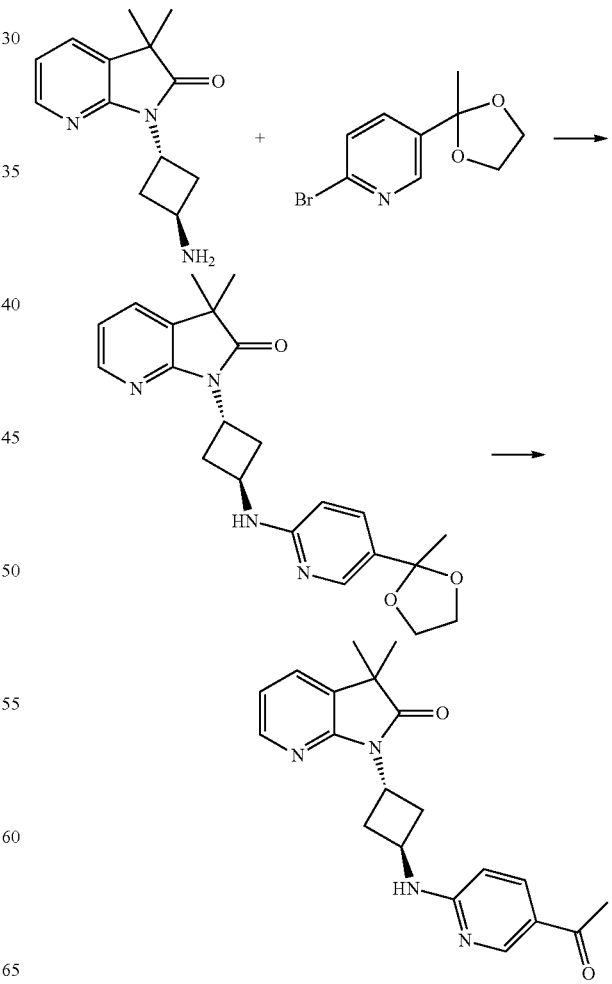

Step 1: 3,3-dimethyl-1-(trans-3-((5-(2-methyl-1,3-diOXOLAN-2-yl)pyridin-2-yl)amino)cyclobutyl)-1H-pyrrolo[2,3-b]pyridin-2(3H)-one 3,3-Dimethyl-1-(trans-3-((5-(2-methyl-1,3-dioxolan-2-yl)pyridin-2-yl)amino)cyclobutyl)-1H-pyrrolo[2,3-b]pyridin-2(3H)-one was synthesized analogous to example 29 using intermediate 28 in place of 6-bromo-N-methylnicotinamide.

Step 2: 1-(trans-3-((5-acetylpyridin-2-yl)amino)cyclobutyl)-3,3-dimethyl-1H-pyrrolo[2,3-b]pyridin-2(3H)-one 3,3-Dimethyl-1-(trans-3-((5-(2-methyl-1,3-dioxolan-2-yl)pyridin-2-yl)amino)cyclobutyl)-1H-pyrrolo[2,3-b]pyridin-2(3H)-one (68 mg, 0.172 mmol) was dissolved in dioxane (345 µl). Aqueous hydrochloric acid (2 M, 862 µl, 1.724 mmol) was added and the reaction mixture heated at 80° C. for 3 h. The reaction mixture was partitioned between ethyl acetate and saturated sodium bicarbonate. The aqueous layer was back extracted with ethyl acetate and the combined organic layer was dried with sodium sulfate and concentrated. The crude product was purified silica chromatography eluting with a gradient of ethyl acetate in hexane (0-70%) to give 1-(trans-3-((5-acetylpyridin-2-yl)amino)cyclobutyl)-3,3-dimethyl-1H-pyrrolo[2,3-b]pyridin-2(3H)-one (30 mg, 0.086 mmol, 49.7% yield) as white solid. M+1: 351.
$^1$H NMR (300 MHz, CHLOROFORM-d) δ ppm 1.39 (s, 6 H) 2.28-2.42 (m, 2 H) 2.51 (s, 3 H) 3.39-3.57 (m, 2 H) 4.51-4.63 (m, 1 H) 5.28 (quin, J=8.30 Hz, 1 H) 5.43 (br. d, J=4.70 Hz, 1 H) 6.35 (d, J=8.77 Hz, 1 H) 6.97 (dd, J=7.31, 5.26 Hz, 1 H) 7.44 (dd, J=7.23, 1.53 Hz, 1 H) 8.04 (dd, J=8.77, 2.34 Hz, 1 H) 8.18 (dd, J=5.26, 1.61 Hz, 1 H) 8.73 (d, J=2.19 Hz, 1 H)

Method B6

Example 44

1-(trans-3-(benzo[d]thiazol-2-ylamino)cyclobutyl)-1H-pyrrolo[2,3-b]pyridin-2(3H)-one

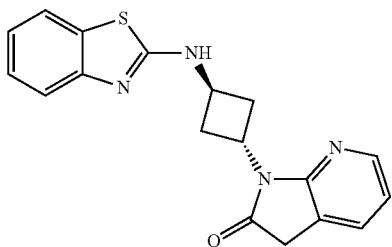 [SMILES: O=C1Cc2cccnc2N1[C@H]1C[C@H](Nc2nc3ccccc3s2)C1]

Sodium tert-butoxide (0.844 mL, 6.89 mmol), [dicyclohexyl(2',4',6'-triisopropyl-3,6-dimethoxy-[1,1'-biphenyl]-2-yl)phosphine]2-(2-aminoethyl)phenyl)palladium(II) chloride (125 mg, 0.157 mmol), trans-N$^1$-(benzo[d]thiazol-2-yl)cyclobutane-1,3-diamine (intermediate 11, 687 mg, 3.13 mmol), methyl 2-(2-chloropyridin-3-yl)acetate (640 mg, 3.45 mmol) and dry dioxane (5 mL) were sealed in a microwave vessel under argon. The mixture was stirred for 4 hours at room temperature. The reaction mixture was diluted with water (mL) and extracted with ethyl acetate. The organic extract was washed with water and dried over magnesium sulfate. Evaporation in vacuo gave the crude material as a tan solid. The crude material was absorbed onto a plug of silica gel and purified by chromatography through a Redi-Sep pre-packed silica gel column (12 g, hexane to ethyl acetate gradient), to provide methyl 2-(2-((trans-3-(benzo[d]thiazol-2-ylamino)cyclobutyl)amino)pyridin-3-yl)acetate (210 mg, 0.570 mmol, 18.19% yield) and 1-(trans-3-(benzo[d]thiazol-2-ylamino)cyclobutyl)-1H-pyrrolo[2,3-b]pyridin-2(3H)-one (24 mg, 0.071 mmol, 2.277% yield) as white solid. M+1: 337.
$^1$H NMR (400 MHz, MeOH) δ ppm 2.44-2.53 (m, 2 H) 3.48-3.57 (m, 2 H) 3.62 (s, 2 H) 4.62-4.70 (m, 1 H) 5.30 (quin, J=8.66 Hz, 1 H) 7.03-7.13 (m, 2 H) 7.25-7.31 (m, 1 H) 7.48 (d, J=8.02 Hz, 1 H) 7.61-7.66 (m, 2 H) 8.22 (d, J=4.69 Hz, 1 H)

Method B7

Example 47

1-(trans-3-((5-ethylpyrimidin-2-yl)amino)cyclobutyl)-3,3-dimethyl-1H-pyrrolo[2,3-b]pyridin-2(3H)-one

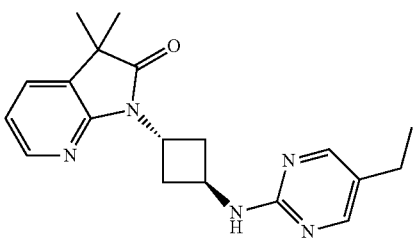 [SMILES: CCc1cnc(N[C@H]2C[C@H](N3C(=O)C(C)(C)c4cccnc43)C2)nc1]

1-(Trans-3-aminocyclobutyl)-3,3-dimethyl-1H-pyrrolo[2,3-b]pyridin-2(3H)-one hydrochloride (intermediate 26, 100 mg, 0.329 mmol), 2-chloro-5-ethylpyrimidine (0.047 mL, 0.329 mmol), and potassium carbonate (0.079 mL, 1.315 mmol) were mixed in DMSO (0.7 mL) in a microwave vial. The reaction mixture was stirred at 80° C. for 16 hours. The temperature was increased to 100° C. and the reaction stirred for another 9 hours. The reaction mixture was diluted with water and extracted with ethyl acetate. The organic layer was separated, washed with brine, dried over magnesium sulfate, and concentrated. The resulting crude product was purified via silica gel flash column chromatography eluting with 0 to 100% ethyl acetate in hexanes to yield 1-(trans-3-((5-ethylpyrimidin-2-yl)amino)cyclobutyl)-3,3-dimethyl-1H-pyrrolo[2,3-b]pyridin-2(3H)-one as an off-white solid. M+1: 338.1. $^1$H NMR (400 MHz, DMSO-d$_6$) δ ppm 1.14 (t, J=7.63 Hz, 3 H) 1.31 (s, 6 H) 2.26-2.37 (m, 2 H) 2.43 (q, J=7.63 Hz, 2 H) 3.15-3.26 (m, 2 H) 4.47-4.62 (m, 1 H) 5.16 (quin, J=8.20 Hz, 1 H) 7.07 (dd, J=7.24, 5.28 Hz, 1 H) 7.48 (d, J=6.46 Hz, 1 H) 7.75 (dd, J=7.24, 1.76 Hz, 1 H) 8.21 (dd, J=5.28, 1.56 Hz, 2 H)

Method B8

Example 50

1-(trans-3-(BIS(5-methoxypyridin-2-yl)amino)cyclobutyl)-3,3-dimethyl-1H-pyrrolo[2,3-b]pyridin-2(3H)-one

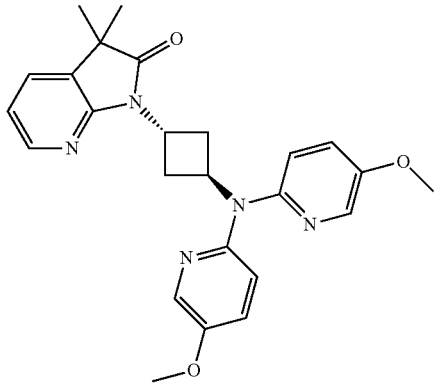 [SMILES: COc1ccc(N(c2ccc(OC)cn2)[C@H]2C[C@H](N3C(=O)C(C)(C)c4cccnc43)C2)nc1]

To a 10 mL microwave tube was added sodium tert-butoxide (0.105 mL, 0.856 mmol), [dicyclohexyl(2',4',6'-triisopropyl-3,6-dimethoxy-[1,1'-biphenyl]-2-yl)phosphine]2-(2-aminoethyl)phenyl)palladium(II) chloride (15.54 mg, 0.019 mmol), 2-chloro-5-methoxy-pyridine (61.5 mg, 0.428 mmol), 1-(trans-3-aminocyclobutyl)-3,3-dimethyl-1H-pyrrolo[2,3-b]pyridin-2(3H)-one (intermediate 26, 90 mg, 0.389 mmol) and dry dioxane (1 mL) and it was sealed under argon. The mixture was stirred at 110° C. for 2 hours. The vial was opened and the reaction mixture evaporated to dryness under reduced pressure. Purification using reverse phase HPLC gave 1-(trans-3-(bis(5-methoxypyridin-2-yl)amino)cyclobutyl)-3,3-dimethyl-1H-pyrrolo[2,3-b]pyridin-2(3H)-one (62 mg, 0.139 mmol, 35% yield). M+1: 446.1. $^1$H NMR (300 MHz, CHLOROFORM-d) δ ppm 1.35 (s, 6 H) 2.47-2.61 (m, 2 H) 3.20-3.33 (m, 2 H) 3.83 (s, 6 H) 4.97-5.14 (m, 1 H) 5.20-5.33 (m, 1 H) 6.83 (d, J=8.77 Hz, 2 H) 6.92 (dd, j=7.16, 5.26 Hz, 1 H) 7.17 (dd, J=8.84, 3.14 Hz, 2 H) 7.39 (dd, J=7.16, 1.61 Hz, 1H) 8.10 (d, J=2.92 Hz, 2 H) 8.17 (dd, J=5.26, 1.61 Hz, 1 H).

Method B9

Example 73

7,7-dimethyl-5-(trans-4-((5-methylpyridin-2-yl)amino) cyclohexyl)-5H-pyrrolo[2,3-b]pyrazin-6(7H)-one

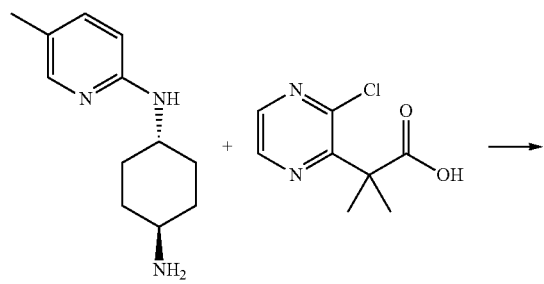

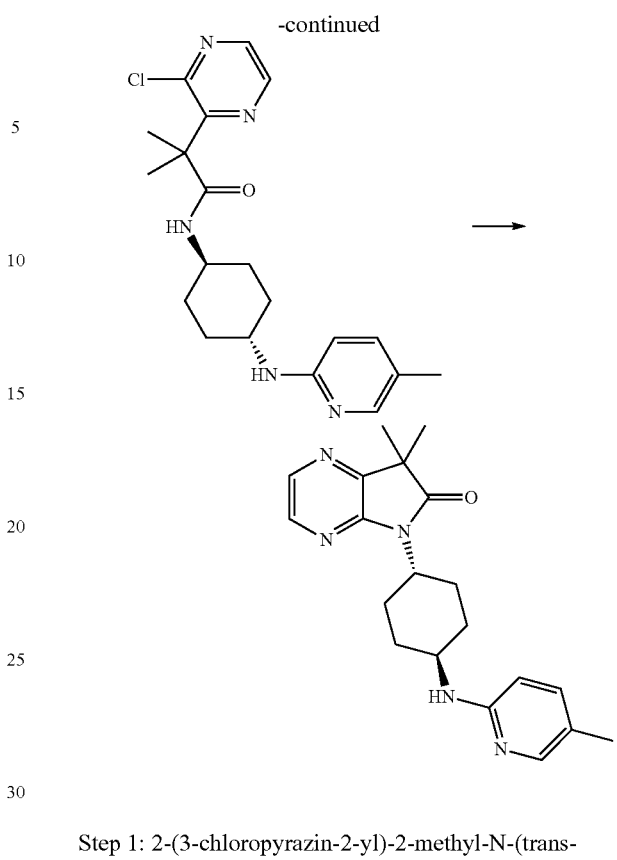

Step 1: 2-(3-chloropyrazin-2-yl)-2-methyl-N-(trans-4-((5-methylpyridin-2-yl)amino)cyclohexyl)propanamide To a round bottom flask was added trans-$N^1$-(5-methylpyridin-2-yl)cyclohexane-1,4-diamine dihydrochloride (intermediate 31, 0.2108 g, 0.758 mmol), 2-(3-chloropyrazin-2-yl)-2-methylpropanoic acid (intermediate 29, 0.182 g, 0.909 mmol), HATU (0.375 g, 0.985 mmol), and triethylamine (0.422 ml, 3.03 mmol) in dichloromethane (1.515 ml) to stir at room temperature. After 4 hours the solvent was evaporated off. The crude product was adsorbed onto a plug of silica gel and chromatographed through a Biotage SNAP HP-silica gel column (25 g), eluting with a gradient of 0% to 5% methanol in dichloromethane, to provide 2-(3-chloropyrazin-2-yl)-2-methyl-N-(trans-4-((5-methylpyridin-2-yl)amino)cyclohexyl)propanamide (0.2148 g, 0.554 mmol, 73.1% yield).

Step 2: 7,7-dimethyl-5-(trans-4-((5-methylpyridin-2-yl)amino) cyclohexyl)-5H-pyrrolo[2,3-b]pyrazin-6(7H)-one To a glass microwave vial was added 2-(3-chloropyrazin-2-yl)-2-methyl-N-(trans-4-((5-methylpyridin-2-yl)amino) cyclohexyl)propanamide (0.2148 g, 0.554 mmol), RuPhos precatalyst (0.024 g, 0.033 mmol), and sodium tert-butoxide (0.106 g, 1.107 mmol) in dry dioxane (0.554 ml). The mixture was sealed and stirred at 80° C. for 3 hours. The mixture was allowed to cool to room temperature then the crude product was adsorbed onto a plug of silica gel and chromatographed through a Biotage SNAP HP-silica gel column (25 g), eluting with a gradient of 0% to 5% methanol in dichloromethane, to provide 7,7-dimethyl-5-(trans-4-((5-methylpyridin-2-yl)amino)cyclohexyl)-5H-pyrrolo[2,3-b]pyrazin-6(7H)-one (0.0178 g, 0.051 mmol, 9.15% yield). M+1: 324. $^1$H NMR (400 MHz, CHLOROFORM-d) δ ppm 1.38 (s, 6 H) 1.50-1.72

(m, 3 H) 2.18 (s, 3 H) 2.23-2.35 (m, 2 H) 3.37-3.48 (m, 2 H) 4.36-4.46 (m, 1 H) 4.71-4.77 (m, 1 H) 5.27 (quin, J=8.90 Hz, 1 H) 6.26 (d, J=8.00 Hz, 1 H) 6.92-6.99 (m, 1 H) 7.42 (d, J=5.87 Hz, 1 H) 7.90-7.97 (m, 1 H) 8.15-8.20 (m, 1 H)

Method B10

Example 79

1-(trans-3-((5-cyclopropylpyrimidin-2-yl)amino)cyclobutyl)-3,3-dimethyl-1H-pyrrolo[2,3-b]pyridin-2(3H)-one

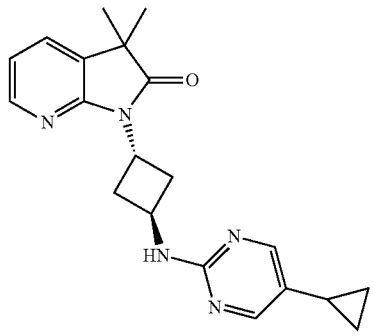 [SMILES: CC1(C)C(=O)N([C@H]2C[C@H](Nc3ncc(C4CC4)cn3)C2)c2ncccc21]

1-(Trans-3-((5-bromopyrimidin-2-yl)amino)cyclobutyl)-3,3-dimethyl-1H-pyrrolo[2,3-b]pyridin-2(3H)-one (example 60, 95 mg, 0.245 mmol), cyclopropyl boronic acid (31.5 mg, 0.367 mmol), and bis(di-tert-butyl(4-dimethylaminophenyl)phosphine)dichloropalladium(II) (17.33 mg, 0.024 mmol) were mixed in 1,4-dioxane (1 msL) under an argon atmosphere. Aqueous sodium carbonate (2 M, 0.367 mL, 0.734 mmol) was added via syringe and the reaction mixture was stirred at 80° C. for 18 hrs. The reaction mixture was diluted with water and extracted with ethyl acetate. The organic layer was separated, washed with brine, dried over magnesium sulfate, and evaporated to dryness under reduced pressure. The resulting crude product was purified via silica gel flash column chromatography eluting with 0 to 100% ethyl acetate in hexanes to yield 1-(trans-3-((5-cyclopropylpyrimidin-2-yl)amino)cyclobutyl)-3,3-dimethyl-1H-pyrrolo[2,3-b]pyridin-2(3H)-one as a light yellow solid. M+1: 350.1. $^1$H NMR (400 MHz, DMSO-$d_6$) δ ppm 0.59-0.66 (m, 2 H) 0.78-0.94 (m, 2 H) 1.31 (s, 6 H) 1.75 (tt, J=8.44, 5.16 Hz, 1 H) 2.25-2.37 (m, 2 H) 3.18 (m, 2 H) 4.47-4.57 (m, 1 H) 5.16 (quin, J=8.41 Hz, 1 H) 7.07 (dd, J=7.24, 5.28 Hz, 1 H) 7.51 (br. d, J=6.50 Hz, 1 H) 7.76 (dd, J=7.24, 1.56 Hz, 1 H) 8.12 (s, 2 H) 8.21 (dd, J=5.28, 1.56 Hz, 1 H).

Method B11

Example 82

1-(trans-3-((5-isopropylpyrimidin-2-yl)amino)cyclobutyl)-3,3-dimethyl-1H-pyrrolo[2,3-b]pyridin-2(3H)-one

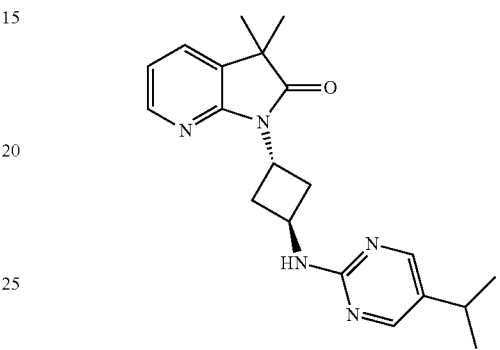

Palladium (10 wt. % on activated carbon, 3.53 mg, 3.32 µmol) was added to a mixture of 3,3-dimethyl-1-(-3-((5-(prop-1-en-2-yl)pyrimidin-2-yl)amino)cyclobutyl)-1H-pyrrolo[2,3-b]pyridin-2(3H)-one (example 80, 58 mg, 0.166 mmol) in ethanol (1 mL) and ethyl acetate (0.5 mL) under an argon atmosphere. The reaction mixture was placed under a hydrogen atmosphere (balloon) and stirred at room temperature for 6 hours. The reaction mixture was filtered through celite, and the filtrate was concentrated to yield 1-(trans-3-((5-isopropylpyrimidin-2-yl)amino)cyclobutyl)-3,3-dimethyl-1H-pyrrolo[2,3-b]pyridin-2(3H)-one as a yellow solid. M+1: 352.3. $^1$H NMR (400 MHz, DMSO-$d_6$) δ ppm 1.19 (d, J=6.85 Hz, 6 H) 1.31 (s, 6 H) 2.23-2.39 (m, 2 H) 2.76 (spt, J=6.94 Hz, 1 H) 3.14-3.26 (m, 2 H) 4.47-4.59 (m, 1 H) 5.16 (quin, J=8.51 Hz, 1 H) 7.08 (dd, J=7.24, 5.28 Hz, 1 H) 7.53 (br. d, J=6.50 Hz, 1 H) 7.76 (dd, J=7.24, 1.57 Hz, 1 H) 8.21 (dd, J=5.28, 1.56 Hz, 1 H) 8.24 (s, 2 H)

Examples 31-33, 36-42, 45-46, 48-49, 51-72, 74-78, and 80-81 were prepared analogous to the above Methods B1-B11 as follows:

TABLE 2

Preparation of Examples 31-33, 36-42, 45-46, 48-49, 51-72, 74-78, and 80-81

| Ex. # | Method | Reagents | M + 1 | NMR |
|---|---|---|---|---|
| 31 | B2 | Intermediate 21 intermediate 11 | 363 | $^1$H NMR (400 MHz, CHLOROFORM-d) δ ppm 1.54 (q, J = 4.11 Hz, 2 H) 1.81 (q, J = 3.91 Hz, 2 H) 2.43-2.60 (m, 2 H) 3.46-3.62 (m, 2 H) 4.54-4.68 (m, 1 H) 5.39 (quin, J = 8.51 Hz, 1 H) 6.86-6.99 (m, 1 H) 7.02-7.15 (m, 2 H) 7.30 (t, J = 7.73 Hz, 1 H) 7.60 (d, J = 8.02 Hz, 1 H) 7.58 (d, J = 8.41 Hz, 1 H) 8.19 (d, J = 5.28 Hz, 1 H) |
| 32 | B1 | Intermediate 26, 6-fluoro-2-bromobenzo[d]thiazole | 383 | $^1$H NMR (400 MHz, CHLOROFORM-d) δ ppm 1.64 (m, 2 H) 1.85 (m, 2 H) 2.58 (m, 2 H) 3.43-3.56 (m, 2 H) 3.72 (d, J = 10.76 Hz, 1 H) 4.56 (m, 1 H) 5.34 (quin, J = 8.20 Hz, 1 H) 6.99 (d, J = 5.09 Hz, 1 H) 7.16 (t, J = 7.34 Hz, 1 H) 7.28-7.39 (m, 1 H) 7.55 |

TABLE 2-continued

Preparation of Examples 31-33, 36-42, 45-46, 48-49, 51-72, 74-78, and 80-81

| Ex. # | Method | Reagents | M + 1 | NMR |
|---|---|---|---|---|
| | | | | (d, J = 7.82 Hz, 1 H) 7.61 (d, J = 7.43 Hz, 1 H) 8.05 (s, 1 H) |
| 33 | B2 | Intermediate 11, intermediate 20 | 381 | $^1$H NMR (400 MHz, CHLOROFORM-d) δ ppm 1.47-1.55 (m, 2 H) 1.68-1.76 (m, 2 H) 2.40-2.51 (m, 2 H) 3.31-3.43 (m, 2 H) 3.60 (br. d, J = 10.80 Hz, 1 H) 4.39-4.48 (m, 1 H) 5.22 (quin, J = 8.12 Hz, 1 H) 6.87 (dd, J = 7.04, 2.15 Hz, 1 H) 7.04 (t, J = 7.34 Hz, 1 H) 7.19-7.26 (m, 1 H) 7.42 (d, J = 7.82 Hz, 1 H) 7.49 (d, J = 7.43 Hz, 1 H) 7.90-7.96 (m, 1 H) |
| 36 | B4 | Intermediate 11, intermediate 18 | 391.1 | $^1$H NMR (400 MHz, CHLOROFORM-d) δ ppm 1.77-1.87 (m, 2 H) 1.89-2.02 (m, 2 H) 2.05-2.25 (m, 4 H) 2.41-2.51 (m, 2 H) 3.44-3.57 (m, 2 H) 4.47-4.63 (m, 1 H) 5.30 (quin, J = 8.51 Hz, 1 H) 6.94 (dd, J = 7.14, 5.38 Hz, 1 H) 7.03-7.15 (m, 1 H) 7.30 (t, J = 7.63 Hz, 1 H) 7.41 (d, J = 7.24 Hz, 1 H) 7.54 (d, J = 8.22 Hz, 1 H) 7.60 (d, J = 7.82 Hz, 1 H) 8.17 (d, J = 5.28 Hz, 1 H) |
| 37 | B4 | Intermediate 11, intermediate 17 | 407.1 | $^1$H NMR (400 MHz, CHLOROFORM-d) δ ppm 1.73-1.83 (m, 2 H) 1.95 (ddd, J = 13.69, 6.36, 3.42 Hz, 2 H) 2.44-2.54 (m, 2 H) 3.42-3.55 (m, 2 H) 3.85-3.96 (m, 2 H) 4.23 (ddd, J = 11.69, 7.97, 3.42 Hz, 2 H) 4.53-4.67 (m, 1 H) 5.33 (quin, J = 8.51 Hz, 1 H) 6.94-7.11 (m, 2 H) 7.25-7.32 (m, 1 H) 7.59 (dd, J = 7.53, 4.99 Hz, 2 H) 7.65 (dd, J = 7.34, 1.47 Hz, 1 H) 8.22 (dd, J = 5.18, 1.47 Hz, 1 H) |
| 38 | B1 | Intermediate 26, 2-bromo-5-methylpyridine | 323 | $^1$H NMR (400 MHz, CHLOROFORM-d) δ ppm 1.38 (s, 6 H) 2.18 (s, 3 H) 2.24-2.36 (m, 2 H) 3.30-3.54 (m, 2 H) 4.35-4.16 (m, 1 H) 4.74 (br. s., 1 H) 5.27 (quin, J = 8.51 Hz, 1 H) 6.26 (d, J = 8.02 Hz, 1 H) 6.90-6.99 (m, 1 H) 7.22-7.34 (m, 1 H) 7.42 (d, J = 5.87 Hz, 1 H) 7.94 (s, 1 H) 8.17 (s, 1 H) |
| 39 | B1 | Intermediate 26, 2-bromo-5-methoxypyridine | 339 | $^1$H NMR (400 MHz, CHLOROFORM-d) δ ppm 1.38 (s, 6 H) 2.24-2.34 (m, 2 H) 3.36-3.48 (m, 2 H) 3.78 (s, 3 H) 4.34-4.43 (m, 1 H) 4.62 (br. s., 1 H) 5.27 (quin, J = 8.40 Hz, 1 H) 6.31 (d, J = 8.61 Hz, 1 H) 6.90-7.02 (m, 1 H) 7.13 (d, J = 9.19 Hz, 1 H) 7.42 (d, J = 6.85 Hz, 1 H) 7.79-7.90 (m, 1 H) 8.11-8.22 (m, 1 H) |
| 40 | B1 | Intermediate 26, 2,5-dibromopyridine | 388.9 | $^1$H NMR (300 MHz, CHLOROFORM-d) δ ppm 1.38 (s, 6 H) 2.24-2.36 (m, 2 H) 3.37-3.50 (m, 2 H) 4.35-4.47 (m, 1 H) 4.93 (br. d, J = 5.10 Hz, 1 H) 5.26 (quin, J = 8.40 Hz, 1 H) 6.24 (d, J = 8.92 Hz, 1 H) 6.96 (dd, J = 7.16, 5.26 Hz, 1 H) 7.43 (dd, J = 7.31, 1.61 Hz, 1 H) 7.51 (dd, J = 8.92, 2.48 Hz, 1 H) 8.13 (d, J = 2.34 Hz, 1 H) 8.17 (dd, J = 5.26, 1.61 Hz, 1 H) |
| 41 | B1 | Intermediate 26, 2-bromo-5-cyclopropylpyridine | 349 | $^1$H NMR (300 MHz, CHLOROFORM-d) δ ppm 0.52-0.62 (m, 2 H) 0.80-0.93 (m, 2 H) 1.38 (s, 6 H) 1.78 (tt, J = 8.51, 5.15 Hz, 1 H) 2.23-2.36 (m, 2 H) 3.35-3.48 (m, 2 H) 4.35-4.46 (m, 1 H) 4.81 (br. s, 1 H) 5.27 (quin, J = 8.55 Hz, 1 H) 6.26 (d, J = 8.48 Hz, 1 H) 6.95 (dd, J = 7.16, 5.26 Hz, 1 H) 7.16 (dd, J = 8.55, 2.41 Hz, 1 H) 7.42 (dd, J = 7.31, 1.61 Hz, 1 H) 7.95 (d, J = 2.34 Hz, 1 H) 8.17 (dd, J = 5.19, 1.68 Hz, 1 H) |
| 42 | B1 | Intermediate 26, 2-bromo-5 chloropyridine | 343 | $^1$H NMR (300 MHz, CHLOROFORM-d) δ ppm 1.38 (s, 6 H) 2.24-2.36 (m, 2 H) 3.37-3.50 (m, 2 H) 4.36-4.48 (m, 1 H) 4.91 (br. d, J = 5.00 Hz, 1 H) 5.26 (quin, J = 8.40 Hz, 1 H) 6.28 (d, J = 8.77 Hz, 1 H) 6.96 (dd, J = 7.16, 5.26 Hz, 1 H) 7.34-7.48 (m, 2 H) 8.05 (d, J = 2.19 Hz, 1 H) 8.17 (dd, J = 5.26, 1.61 Hz, 1 H) |

TABLE 2-continued

Preparation of Examples 31-33, 36-42, 45-46, 48-49, 51-72, 74-78, and 80-81

| Ex. # | Method | Reagents | M + 1 | NMR |
|---|---|---|---|---|
| 45 | B1 | Intermediate 26, 2-bromo-3-methoxypyridine | 339 | $^1$H NMR (400 MHz, CHLOROFORM-d) δ ppm 1.37 (s, 6 H) 2.27-2.37 (m, 2 H) 3.49-3.60 (m, 2 H) 4.65-4.76 (m, 1 H) 5.21 (br. d, J = 5.50 Hz, 1 H) 5.28 (quin, J = 8.75 Hz, 1 H) 6.52 (dd, J = 7.73, 5.18 Hz, 1 H) 6.83 (dd, J = 7.73, 1.08 Hz, 1 H) 6.94 (dd, J = 7.24, 5.28 Hz, 1 H) 7.41 (dd, J = 7.24, 1.56 Hz, 1 H) 7.73 (dd, J = 5.18, 1.27 Hz, 1 H) 8.17 (dd, J = 5.28, 1.57 Hz, 1 H) |
| 46 | B1 | Intermediate 26, 2-bromo-5-trifluoromethylpyridine | 377.1 | $^1$H NMR (300 MHz, CHLOROFORM-d) δ ppm 1.39 (s, 6 H) 2.27-2.41 (m, 2 H) 3.40-3.54 (m, 2 H) 4.43-4.61 (m, 1 H) 5.18-5.38 (m, 2 H) 6.35 (d, J = 8.77 Hz, 1 H) 6.97 (dd, J = 7.31, 5.26 Hz, 1 H) 7.43 (dd, J = 7.23, 1.53 Hz, 1 H) 7.62 (dd, J = 8.84, 2.27 Hz, 1 H) 8.18 (dd, J = 5.26, 1.46 Hz, 1 H) 8.36 (s, 1 H) |
| 48 | B7 | Intermediate 26, 2-chloro-5-methylpyrimidine | 324.2 | $^1$H NMR (400 MHz, DMSO-$d_6$) δ ppm 1.30 (s, 6 H) 2.06 (s, 3 H) 2.25-2.35 (m, 2 H) 3.13-3.24 (m, 2 H) 4.46-4.58 (m, 1 H) 5.15 (quin, J = 8.46 Hz, 1 H) 7.06 (dd, J = 7.24, 5.28 Hz, 1 H) 7.44 (br. d, J = 6.50 Hz, 1 H) 7.74 (dd, J = 7.24, 1.57 Hz, 1 H) 8.15 (s, 2 H) 8.20 (dd, J = 5.28, 1.56 Hz, 1 H) |
| 49 | B1 | Intermediate 30, 2-bromo-5-chloropyridine | 344 | $^1$H NMR (300 MHz, CHLOROFORM-d) δ ppm 1.44 (s, 6 H) 2.25-2.39 (m, 2 H) 3.31-3.45 (m, 2 H) 4.36-4.47 (m, 1 H) 4.87 (br. d, J = 5.40 Hz, 1 H) 5.26 (quin, J = 8.59 Hz, 1 H) 6.28 (d, J = 8.77 Hz, 1 H) 7.40 (dd, J = 8.84, 2.56 Hz, 1 H) 8.04-8.13 (m, 3 H) |
| 51 | B1 | Intermediate 26, 2 bromo-4-methylpyridine | 323 | $^1$H NMR (400 MHz, CHLOROFORM-d) δ ppm 1.38 (s, 6 H) 2.25 (s, 3 H) 2.26-2.35 (m, 2 H) 3.38-3.49 (m, 2 H) 4.37-4.47 (m, 1 H) 4.83 (br. d, J = 4.50 Hz, 1 H) 5.27 (quin, J = 8.51 Hz, 1 H) 6.13 (s, 1 H) 6.45 (d, J = 5.09 Hz, 1 H) 6.95 (dd, J = 7.24, 5.28 Hz, 1 H) 7.42 (dd, J = 7.24, 1.56 Hz, 1 H) 7.96 (d, J = 5.09 Hz, 1 H) 8.18 (dd, J = 5.28, 1.37 Hz, 1 H) |
| 52 | B1 | Intermediate 26, 2-bromo-3-fluoropyridine | 327 | $^1$H NMR (300 MHz, CHLOROFORM-d) δ ppm 1.38 (s, 6 H) 2.29-2.41 (m, 2 H) 3.45-3.60 (m, 2 H) 4.68-4.80 (m, 1 H) 4.91 (br. s, 1 H) 5.28 (quin, J = 8.66 Hz, 1 H) 6.53 (ddd, J = 8.04, 4.82, 3.51 Hz, 1 H) 6.94 (dd, J = 7.31, 5.26 Hz, 1 H) 7.14 (ddd, J = 11.29, 7.86, 1.46 Hz, 1 H) 7.42 (dd, J = 7.31, 1.61 Hz, 1 H) 7.86-7.94 (m, 1 H) 8.18 (dd, J = 5.26, 1.61 Hz, 1 H) |
| 53 | B1 | Intermediate 26, 2-bromo-3-methylpyridine | 323 | $^1$H NMR (300 MHz, CHLOROFORM-d) δ ppm 1.38 (s, 6 H) 2.14 (s, 3 H) 2.24-2.37 (m, 2 H) 3.48-3.63 (m, 2 H) 4.40 (br. d, J = 4.10 Hz, 1 H) 4.64-4.77 (m, 1 H) 5.28 (quin, J = 8.70 Hz, 1 H) 6.53 (dd, J = 7.09, 5.04 Hz, 1 H) 6.94 (dd, J = 7.16, 5.26 Hz, 1 H) 7.19-7.26 (m, 1 H) 7.41 (dd, J = 7.16, 1.61 Hz, 1 H) 8.03 (dd, J = 4.97, 1.17 Hz, 1 H) 8.17 (dd, J = 5.26, 1.46 Hz, 1 H) |
| 54 | B1 | Intermediate 26, 2-bromo-5-fluoropyridine | 327 | $^1$H NMR (300 MHz, CHLOROFORM-d) δ ppm 1.38 (s, 6 H) 2.24-2.37 (m, 2 H) 3.36-3.49 (m, 2 H) 4.34-4.47 (m, 1 H) 4.95 (br. s, 1 H) 5.27 (quin, J = 8.50 Hz, 1 H) 6.30 (dd, J = 8.92, 3.36 Hz, 1 H) 6.95 (dd, J = 7.31, 5.26 Hz, 1 H) 7.19-7.25 (m, 1 H) 7.42 (dd, J = 7.31, 1.61 Hz, 1 H) 7.97 (d, J = 3.07 Hz, 1 H) 8.17 (dd, J = 5.26, 1.61 Hz, 1 H) |
| 55 | B7 | Intermediate 26, 2-chlorothiazole | 315.2 | $^1$H NMR (400 MHz, CHLOROFORM-d) δ ppm 1.38 (s, 6 H) 2.35-2.47 (m, 2 H) 3.40-3.51 (m, 2 H) 4.35-4.46 (m, 1 H) 5.29 (quin, J = 8.56 Hz, 1 H) 5.87 (br. s, 1 H) 6.53 (d, J = 3.72 Hz, 1 H) 6.96 (dd, J = 7.24, |

TABLE 2-continued

Preparation of Examples 31-33, 36-42, 45-46, 48-49, 51-72, 74-78, and 80-81

| Ex. # | Method | Reagents | M + 1 | NMR |
|---|---|---|---|---|
| | | | | 5.28 Hz, 1 H) 7.19 (d, J = 3.72 Hz, 1 H) 7.43 (dd, J = 7.24, 1.37 Hz, 1 H) 8.18 (dd, J = 5.18, 1.47 Hz, 1 H) |
| 56 | B1 | Intermediate 26, 5-acetamido-2-bromopyridine | 366 | $^1$H NMR (300 MHz, CHLOROFORM-d) δ ppm 1.38 (s, 6 H) 2.16 (s, 3 H) 2.22-2.36 (m, 2 H) 3.37-3.51 (m, 2 H) 4.35-4.49 (m, 1 H) 4.87 (br. d, J = 5.40 Hz, 1 H) 5.27 (quin, J = 8.60 Hz, 0 H) 6.32 (d, J = 8.92 Hz, 1 H) 6.95 (m, J = 7.16, 5.26 Hz, 1 H) 7.00 (br. s, 1 H) 7.42 (dd, J = 7.23, 1.53 Hz, 1 H) 7.77 (dd, J = 8.77, 2.63 Hz, 1 H) 8.03 (d, J = 2.48 Hz, 1 H) 8.17 (dd, J = 5.26, 1.61 Hz, 1 H) |
| 57 | B1 | Intermediate 26, 2-bromo-3-chloropyridine | 343 | $^1$H NMR (400 MHz, CHLOROFORM-d) δ ppm 1.38 (s, 6 H) 2.30-2.40 (m, 2 H) 3.48-3.59 (m, 2 H) 4.67-4.77 (m, 1 H) 5.23-5.35 (m, 2 H) 6.54 (dd, J= 7.73, 4.99 Hz, 1 H) 6.95 (dd, J = 7.04, 5.28 Hz, 1 H) 7.39-7.48 (m, 2 H) 8.04 (dd, J = 4.89, 1.37 Hz, 1 H) 8.18 (dd, J = 5.18, 1.47 Hz, 1 H) |
| 58 | B7 | Intermediate 26, 2-chloro-4-methoxypyrimidine | 340.2 | $^1$H NMR (400 MHz, DMSO-$d_6$) δ ppm 1.31 (s, 6 H) 2.30-2.42 (m, 2 H) 3.15-3.27 (m, 2 H) 3.84 (s, 3 H) 4.51-4.64 (m, 1 H) 5.17 (quin, J = 8.46 Hz, 1 H) 6.05 (d, J = 5.48 Hz, 1 H) 7.07 (dd, J = 7.24, 5.28 Hz, 1 H) 7.63 (br. s, 1 H) 7.75 (dd, J = 7.24, 1.57 Hz, 1 H) 8.04 (d, J = 5.67 Hz, 1 H) 8.21 (dd, J = 5.28, 1.57 Hz, 1 H) |
| 59 | B1 | Intermediate 26, 2-bromo-5-cyanopyridine | 334 | $^1$H NMR (300 MHz, CHLOROFORM-d) δ ppm 1.37 (s, 6 H) 2.29-2.44 (m, 2 H) 3.35-3.50 (m, 2 H) 4.50-4.65 (m, 1 H) 5.27 (quin, J = 8.66 Hz, 1 H) 6.50 (d, J = 8.33 Hz, 1 H) 6.98 (t, J = 6.28 Hz, 1 H) 7.37-7.63 (m, 2 H) 8.16 (d, J = 4.97 Hz, 1 H) 8.33 (s, 1 H) |
| 60 | B7 | Intermediate 26, 5-bromo-2-chloropyrimidine | 388.1 | $^1$H NMR (400 MHz, DMSO-$d_6$) δ ppm 1.31 (s, 6 H) 2.35 (br. s., 2 H) 3.19 (br. s., 2 H) 4.47-4.58 (m, 1 H) 5.16 (quin, J = 8.46 Hz, 1 H) 7.08 (dd, J = 7.24, 5.28 Hz, 1 H) 7.76 (dd, J = 7.24, 1.56 Hz, 1 H) 8.05 (d, J = 6.46 Hz, 1 H) 8.21 (dd, J = 5.28, 1.57 Hz, 1 H) 8.42 (s, 2 H) |
| 61 | B7 | Intermediate 26, 2,5-dichloropyrimidine | 344.1 | $^1$H NMR (400 MHz, DMSO-$d_6$) δ ppm 1.30 (s, 6 H) 2.29-2.40 (m, 2 H) 3.15-3.25 (m, 2 H) 4.48-4.58 (m, 1 H) 5.15 (quin, J = 8.46 Hz, 1 H) 7.06 (dd, J = 7.24, 5.28 Hz, 1 H) 7.75 (dd, J = 7.24, 1.37 Hz, 1 H) 8.01 (d, J = 6.46 Hz, 1 H) 8.19 (dd, J = 5.28, 1.56 Hz, 1 H) 8.36 (s, 2 H) |
| 62 | B7 | Intermediate 26, 2-chloropyrimidine | 310.3 | $^1$H NMR (400 MHz, DMSO-$d_6$) δ ppm 1.30 (s, 6 H) 2.28-2.38 (m, 2 H) 3.14-3.25 (m, 2 H) 4.51-4.64 (m, 1 H) 5.16 (quin, J = 8.41 Hz, 1 H) 6.59 (t, J = 4.79 Hz, 1 H) 7.07 (dd, J = 7.04, 5.28 Hz, 1 H) 7.68 (br. d, J = 6.50 Hz, 1 H) 7.75 (dd, J = 7.24, 1.37 Hz, 1 H) 8.20 (dd, J = 5.28, 1.37 Hz, 1 H) 8.29 (d, J = 4.69 Hz, 2 H) |
| 63 | B7 | Intermediate 26, 2-chloro-4-methylpyrimidine | 324.2 | $^1$H NMR (400 MHz, DMSO-$d_6$) δ ppm 1.30 (s, 6 H) 2.25 (s, 3 H) 2.27-2.37 (m, 2 H) 3.14-3.25 (m, 2 H) 4.50-4.61 (m, 1 H) 5.15 (quin, J = 8.36 Hz, 1 H) 6.48 (d, J = 4.89 Hz, 1 H) 7.06 (dd, J = 7.04, 5.28 Hz, 1 H) 7.58 (d, J = 6.46 Hz, 1 H) 7.74 (dd, J = 7.14, 1.27 Hz, 1 H) 8.14 (d, J = 4.89 Hz, 1 H) 8.20 (dd, J = 5.18, 1.27 Hz, 1 H) |
| 64 | B7 | Intermediate 26, 2,4-dichloropyrimidine | 344.3 | $^1$H NMR (400 MHz, CHLOROFORM-d) δ ppm 1.38 (s, 6 H) 2.31-2.41 (m, 2 H) 3.40-3.53 (m, 2 H) 4.65-4.78 (m, 1 H) 5.26 (quin, J = 8.61 Hz, 1 H) 6.59 (d, J = 5.28 Hz, 1 H) 6.95 (dd, J = 7.24, 5.28 Hz, 1 H) 7.42 (dd, J = 7.24, 1.56 Hz, 1 H) 8.09-8.24 (m, 2 H) |

TABLE 2-continued

Preparation of Examples 31-33, 36-42, 45-46, 48-49, 51-72, 74-78, and 80-81

| Ex. # | Method | Reagents | M + 1 | NMR |
|---|---|---|---|---|
| 65 | B7 | Intermediate 26, 2-chloropyrazine | 310.3 | $^1$H NMR (400 MHz, CHLOROFORM-d) δ ppm 1.39 (s, 6 H) 2.29-2.39 (m, 2 H) 3.44-3.55 (m, 2 H) 4.51-4.62 (m, 1 H) 5.03 (br. d, J = 4.30 Hz, 1 H) 5.29 (quin, J = 8.56 Hz, 1 H) 6.97 (dd, J = 7.04, 5.48 Hz, 1 H) 7.44 (d, J = 7.24 Hz, 1 H) 7.84-7.89 (m, 2 H) 7.99-8.04 (m, 1 H) 8.18 (d, J = 5.28 Hz, 1 H) |
| 66 | B1 | Intermediate 26, 2-bromo-6-chloropyridine | 343 | $^1$H NMR (300 MHz, CHLOROFORM-d) δ ppm 1.38 (s, 6 H) 2.22-2.38 (m, 2 H) 3.35-3.49 (m, 2 H) 4.35-4.50 (m, 1 H) 5.03 (br. d, J = 4.50 Hz, 1 H) 5.26 (quin, J = 8.50 Hz, 1 H) 6.19 (d, J = 8.18 Hz, 1 H) 6.61 (d, J = 7.45 Hz, 1 H) 6.96 (dd, J = 7.31, 5.26 Hz, 1 H) 7.34-7.45 (m, 2 H) 8.17 (dd, J = 5.26, 1.61 Hz, 1 H) |
| 67 | B7 | Intermediate 26, 2-chloro-4-(trifluoromethyl)pyrimidine | 378.2 | $^1$H NMR (400 MHz, DMSO-d$_6$) δ ppm 1.32 (s, 6 H) 2.33-2.44 (m, 2 H) 3.17-3.30 (m, 2 H) 4.53-4.69 (m, 1 H) 5.18 (quin, J = 8.46 Hz, 1 H) 7.01 (d, J = 4.89 Hz, 1 H) 7.08 (dd, J = 7.24, 5.28 Hz, 1 H) 7.76 (dd, J = 7.24, 1.56 Hz, 1 H) 8.21 (dd, J = 5.28, 1.56 Hz, 1 H) 8.65 (d, J = 3.72 Hz, 1 H) |
| 68 | B7 | Intermediate 26, 3-chloropyridazine | 310.3 | $^1$H NMR (400 MHz, CHLOROFORM-d) δ ppm 1.39 (s, 6 H) 2.32-2.43 (m, 2 H) 3.42-3.54 (m, 2 H) 4.53-4.63 (m, 1 H) 5.30 (quin, J = 8.56 Hz, 1 H) 5.42 (br. d, J = 3.50 Hz, 1 H) 6.62 (d, J = 9.00 Hz, 1 H) 6.96 (t, J = 6.26 Hz, 1 H) 7.20 (dd, J = 9.00, 4.50 Hz, 1 H) 7.43 (d, J = 7.24 Hz, 1 H) 8.18 (d, J = 5.28 Hz, 1 H) 8.58 (d, J = 4.50 Hz, 1 H) |
| 69 | B7 | Intermediate 26, 2-chloro-4-phenylthiazole | 391.1 | $^1$H NMR (400 MHz, DMSO-d$_6$) δ ppm 1.32 (s, 6 H) 2.34-2.43 (m, 2 H) 3.25-3.34 (m, 2 H) 4.31-4.44 (m, 1 H) 5.21 (quin, J = 8.41 Hz, 1 H) 7.09 (dd, J = 7.24, 5.28 Hz, 1 H) 7.25-7.32 (m, 1 H) 7.35-7.43 (m, 2 H) 7.77 (dd, J = 7.24, 1.56 Hz, 1 H) 7.83-7.88 (m, 2 H) 8.21-8.26 (m, 2 H) |
| 70 | B7 | Intermediate 26, 2-chloro-5-(trifluoromethyl)pyrimidine | 378.2 | $^1$H NMR (400 MHz, DMSO-d$_6$) δ ppm 1.31 (s, 6 H) 2.34-2.44 (m, 2 H) 3.18-3.29 (m, 2 H) 4.60-4.72 (m, 1 H) 5.17 (quin, J = 8.36 Hz, 1 H) 7.07 (dd, J = 7.24, 5.28 Hz, 1 H) 7.75 (dd, J = 7.24, 1.56 Hz, 1 H) 8.20 (dd, J = 5.18, 1.47 Hz, 1 H) 8.60-8.70 (m, 3 H) |
| 71 | B7 | Intermediate 26, 2-chloro-5-fluoropyrimidine | 328.1 | $^1$H NMR (400 MHz, DMSO-d$_6$) δ ppm 1.31 (s, 6 H) 2.28-2.37 (m, 2 H) 3.15-3.26 (m, 2 H) 4.44-4.58 (m, 1 H) 5.16 (quin, J = 8.36 Hz, 1 H) 7.08 (dd, J = 7.24, 5.28 Hz, 1 H) 7.76 (dd, J = 7.24, 1.56 Hz, 1 H) 7.81 (br. d, J = 6.30 Hz, 1 H) 8.21 (dd, J = 5.28, 1.57 Hz, 1 H) 8.40 (d, J = 0.78 Hz, 2 H) |
| 72 | B7 | Intermediate 26, 2,4-dichloropyrimidine | 344.1 | $^1$H NMR (400 MHz, CHLOROFORM-d) δ ppm 1.39 (s, 6 H) 2.31-2.42 (m, 2 H) 3.40-3.53 (m, 2 H) 4.47-4.65 (m, 1 H) 5.27 (quin, J = 8.41 Hz, 1 H) 5.75 (br. s, 1 H) 6.22 (d, J = 5.67 Hz, 1 H) 6.98 (dd, J = 7.14, 5.38 Hz, 1 H) 7.45 (dd, J = 7.24, 1.37 Hz, 1 H) 8.03-8.13 (m, 1 H) 8.18 (dd, J = 5.18, 1.47 Hz, 1 H) |
| 73 | B9 | Intermediate 30, 2-bromo-5-methylpyridine | 324 | $^1$H NMR (300 MHz, CHLOROFORM-d) δ ppm 1.44 (s, 6 H) 2.19 (s, 3 H) 2.27-2.40 (m, 2 H) 3.30-3.44 (m, 2 H) 4.33-4.50 (m, 1 H) 5.07 (br. s, 1 H) 5.26 (quin, J = 8.48 Hz, 1 H) 6.29 (d, J = 8.48 Hz, 1 H) 7.32 (dd, J = 8.55, 2.27 Hz, 1 H) 7.88-7.95 (m, 1 H) 8.06-8.12 (m, 2 H) |

TABLE 2-continued

Preparation of Examples 31-33, 36-42, 45-46, 48-49, 51-72, 74-78, and 80-81

| Ex. # | Method | Reagents | M + 1 | NMR |
|---|---|---|---|---|
| 74 | B1 | Intermediate 30, 2-bromo-5-methoxypyridine | 340 | $^1$H NMR (300 MHz, CHLOROFORM-d) δ ppm 1.44 (s, 21 H) 2.23-2.39 (m, 2 H) 3.27-3.45 (m, 2 H) 3.78 (s, 3 H) 4.31-4.46 (m, 1 H) 4.59 (br. d, J = 4.50 Hz, 1 H) 5.26 (quin, J = 8.59 Hz, 1 H) 6.31 (d, J = 8.92 Hz, 1 H) 7.13 (dd, J = 8.92, 2.92 Hz, 1 H) 7.86 (d, J = 2.92 Hz, 1 H) 8.06-8.12 (m, 2 H) |
| 75 | B9 | Intermediate 31, intermediate 29 | 352.1 | 1H NMR (400 MHz, DMSO-d6) δ ppm 1.20-1.40 (m, 9 H) 1.72 (d, J = 10.76 Hz, 2 H) 2.02-2.14 (m, 5 H) 2.36-2.48 (m, 2 H) 3.64-3.77 (m, 1 H) 4.18-4.32 (m, 1 H) 6.42 (d, J = 8.41 Hz, 1 H) 7.22 (d, J = 7.43 Hz, 1 H) 7.79 (s, 1 H) 8.11-8.21 (m, 2 H) |
| 76 | B1 | Intermediate 30, 2-bromo-5-fluoropyridine | 328 | $^1$H NMR (300 MHz, CHLOROFORM-d) δ ppm 1.44 (s, 6 H) 2.25-2.39 (m, 2 H) 3.31-3.45 (m, 2 H) 4.35-4.46 (m, 1 H) 4.76 (br. d, J = 4.70 Hz, 1 H) 5.26 (quin, J = 8.48 Hz, 1 H) 6.29 (dd, J = 8.99, 3.43 Hz, 1 H) 7.17-7.25 (m, 1 H) 7.99 (d, J = 3.07 Hz, 1 H) 8.05-8.13 (m, 2 H) |
| 77 | B9 | Intermediate 31, intermediate 25 | 351.0 | 1H NMR (400 MHz, CHLOROFORM-d) δ ppm 1.30-1.47 (m, 8 H) 1.78 (d, J = 12.13 Hz, 2 H) 2.19 (br. s., 3 H) 2.26 (d, J = 12.13 Hz, 2 H) 2.60-2.77 (m, 2 H) 4.39 (t, J = 10.76 Hz, 1 H) 6.40 (d, J = 8.41 Hz, 1 H) 6.93 (br. s., 1 H) 7.31 (br. s., 1 H) 7.41 (d, J = 7.04 Hz, 1 H) 7.89 (br. s., 1 H) 8.16 br. s., 1 H) |
| 78 | B1 | Intermediate 30, 2-bromo-5-cyclopropylpyridine | 350 | $^1$H NMR (300 MHz, CHLOROFORM-d) δ ppm 0.51-0.62 (m, 2 H) 0.81-0.93 (m, 2 H) 1.44 (s, 6 H) 1.78 (tt, J = 8.42, 5.17 Hz, 1 H) 2.24-2.37 (m, 2 H) 3.30-3.44 (m, 2 H) 4.35-4.46 (m, 1 H) 4.72 (br. d, J = 4.70 Hz, 1 H) 5.26 (quin, J = 8.37 Hz, 1 H) 6.25 (d, J = 8.48 Hz, 1 H) 7.16 (dd, J = 8.48, 2.34 Hz, 1 H) 7.96 (d, J = 2.34 Hz, 1 H) 8.04-8.14 (m, 2 H) |
| 80 | B10 | Example 60, isopropenylboronic acid pinacol ester | 350.1 | $^1$H NMR (400 MHz, CHLOROFORM-d) δ ppm 1.38 (s, 6 H) 2.09 (s, 3 H) 2.30-2.42 (m, 2 H) 3.41-3.56 (m, 2 H) 4.62-4.79 (m, 1 H) 4.98 (s, 1 H) 5.21-5.36 (m, 2 H) 5.50 (br. d, J = 4.70 Hz, 1 H) 6.92-6.98 (m, 1 H) 7.42 (d, J = 7.24 Hz, 1 H) 8.18 (d, J = 5.10 Hz, 1 H) 8.43 (s, 2 H) |
| 81 | B2 | Intermediate 32, intermediate 25 | 365.1 | 1H NMR (400 MHz, CHLOROFORM-d) δ ppm, 1.39 (s, 6 H) 2.89-3.04 (m, 2 H), 3.05-3.18 (m, 2 H), 4.26 (br. s., 1 H), 4.88 (quin, J = 8.46 Hz, 1 H) 6.51 (br. s., 1 H), 6.99 (dd, J = 7.24, 5.28 Hz, 1 H), 7.05-7.15 (m, 1 H), 7.19-7.35 (m, 1 H), 7.45 (dd, J = 7.24, 1.57 Hz, 1 H), 7.57 (dd, J = 12.42, 7.92 Hz, 2 H), 8.23 (dd, J = 5.28, 1.37 Hz, 1 H). |
| 83 | B7 | Intermediate 26, 2-chloro-5-methoxypyrimidine | 340.1 | $^1$H NMR (400 MHz, DMSO-d$_6$) δ ppm 1.31 (s, 6 H) 2.24-2.36 (m, 2 H) 3.13-3.26 (m, 2 H) 3.76 (s, 3 H) 4.42-4.54 (m, 1 H) 5.16 (quin, J = 8.36 Hz, 1 H) 7.08 (dd, J = 7.24, 5.28 Hz, 1 H) 7.36 (d, J = 6.46 Hz, 1 H) 7.76 (dd, J = 7.24, 1.57 Hz, 1 H) 8.15 (s, 2 H) 8.21 (dd, J = 5.09, 1.57 Hz, 1 H) |
| 84 | B5 | Intermediate 30, intermediate 28 | 352 | $^1$H NMR (300 MHz, CHLOROFORM-d) δ ppm 1.45 (s, 6 H) 2.32-2.44 (m, 2 H) 2.51 (s, 3 H) 3.36-3.52 (m, 2 H) 4.49-4.67 (m, 1 H) 5.28 (quin, J = 8.50 Hz, 1 H) 5.41 (br. d, J = 5.10 Hz, 1 H) 6.35 (d, J = 8.77 Hz, 1 H) 8.04 (dd, J = 8.77, 2.34 Hz, 1 H) 8.07-8.14 (m, 2 H) 8.73 (d, J = 1.90 Hz, 1 H) |

Examples 85-87, 92, 97, 100, 103, and 106 were prepared according to Methods C1-C8 as follows:

Method C1

Example 85

3-(trans-3-(benzo[d]thiazol-2-ylamino)cyclobutyl)-1-cyclopropyl-1H-imidazo[4,5-b]pyridin-2(3H)-one

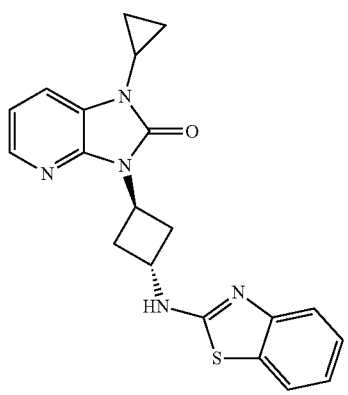 [SMILES: O=c1n(C2CC2)c2cccnc2n1[C@H]1C[C@H](Nc2nc3ccccc3s2)C1]

Trans-N$^1$-(benzo[d]thiazol-2-yl)-N$^3$-(3-bromopyridin-2-yl)cyclobutane-1,3-diamine (intermediate 33, 0.362 g, 0.965 mmol), sodium tert-butoxide (0.232 g, 2.411 mmol), and chloro(2-dicyclohexylphosphino-3,6-dimethoxy-2'-4'-6'-tri-1-1,1'-biphenyl)]2-(2-aminoethyl)phenyl)palladium(ii) (0.058 g, 0.072 mmol) were placed in a microwave vessel under argon. Dry, sparged dioxane (1.5 mL) was added followed by cyclopropylamine (0.170 ml, 2.424 mmol). The mixture was sealed under argon and stirred at room temperature for 15 minutes then heated in a 90° C. oil bath for 30 minutes. The reaction was cooled and opened. The reaction mixture was diluted with ethyl acetate (10 mL) and washed with water (10 mL). The organic phase was dried with magnesium sulfate and evaporated to dryness under reduced pressure. The crude was further dried under high vacuum to give a solid foam. It was dissolved in dry tetrahydrofuran (10 mL) and added to an ice cooled solution of triphosgene (0.112 g) in dry tetrahydrofuran (10 mL) and dichloromethane (10 mL). Triethylamine (6 mL) was added and the reaction stirred for 20 minutes. Water (50 mL) was added and the reaction stirred for 10 minutes. The phases were separated and the organic dried with magnesium sulfate before evaporating to dryness under reduced pressure. The crude product was purified using silica chromatography (20-100% ethyl acetate in hexane gradient) followed by reverse phase HPLC to give 3-(trans-3-(benzo[d]thiazol-2-ylamino)cyclobutyl)-1-cyclopropyl-1H-imidazo[4,5-b]pyridin-2(3H)-one (48.8 mg, 0.129 mmol, 13.40% yield). M+1: 378. $^1$H NMR (400 MHz, CHLOROFORM-d) δ ppm 0.95-1.07 (m, 2 H) 1.07-1.20 (m, 2 H) 2.43-2.63 (m, 2 H) 2.83-3.02 (m, 1 H) 3.45-3.66 (m, 2 H) 4.50-4.72 (m, 1 H) 5.37 (quin, J=8.36 Hz, 1 H) 6.08 (br. s., 1 H) 7.01 (dd, J=7.43, 5.48 Hz, 1 H) 7.08 (t, J=7.53 Hz, 1 H) 7.23-7.32 (m, 1 H) 7.36 (d, J=7.63 Hz, 1 H) 7.59 (dd, J=10.86, 8.31 Hz, 2 H) 8.05 (d, J=4.89 Hz, 1 H).

Method C2

Example 86

3-(trans-3-(benzo[d]thiazol-2-ylamino)cyclobutyl)-6-fluoro-1-methyl-1H-imidazo[4,5-b]pyridin-2(3H)-one

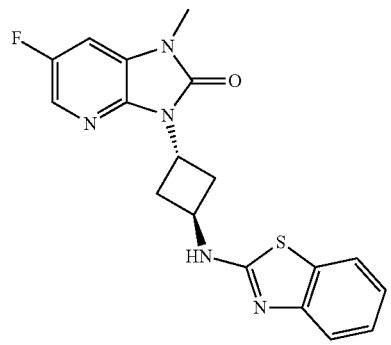 [SMILES: Cn1c(=O)n([C@H]2C[C@H](Nc3nc4ccccc4s3)C2)c2ncc(F)cc21]

Methyl (2-chloro-5-fluoropyridin-3-yl)(methyl)carbamate (intermediate 37, 0.310 g, 1.418 mmol), trans-N$^1$-(benzo[d]thiazol-2-yl)cyclobutane-1,3-diamine (intermediate 11, 0.311 g, 1.418 mmol), chloro(2-dicyclohexylphosphino-3,6-dimethoxy-2'-4'-6'-tri-1-1,1'-biphenyl)]2-(2-aminoethyl) phenyl)palladium(ii) (0.085 g, 0.106 mmol), and sodium t-butoxide (0.341 g, 3.55 mmol) were scaled in a microwave vial under argon. Dry, sparged dioxane (1.5 mL) was added and the suspension heated at 50° C. After 20 minutes the vial was opened and the crude partitioned between 10% saturated ammonium chloride (100 mL) and ethyl acetate (200 mL). The organic phase was dried with magnesium sulfate and evaporated to dryness under reduced pressure. The crude was purified using silica chromatography (dichloromethane to ethyl acetate gradient) then triturated with diethyl ether. Filtration gave the desired 3-(trans-3-(benzo[d]thiazol-2-ylamino)cyclobutyl)-6-fluoro-1-methyl-1H-imidazo[4,5-b]pyridin-2(3H)-one (0.295 g, 0.799 mmol, 56.3% yield) as a free flowing cream colored solid. M+1: 370.1. $^1$H NMR (400 MHz, CHLOROFORM-d) δ ppm 2.44-2.59 (m, 2 H) 2.63 (s, 3 H) 3.46-3.56 (m, 2 H) 4.50-4.59 (m, 1 H) 5.31 (quin, J=8.20 Hz, 1 H) 7.03 (dd, J=8.02, 2.54 Hz, 1 H) 7.09 (td, J=7.58, 1.08 Hz, 1 H) 7.30 (td, J=7.73, 1.17 Hz, 1 H) 7.52 (dd, J=8.02, 0.39 Hz, 1 H) 7.60 (dd, J=7.82, 0.78 Hz, 1 H) 7.95 (t, J=2.15 Hz, 1 H).

Method C3

Example 87

3-(trans-3-(benzo[d]thiazol-2-ylamino)cyclobutyl)-6-fluoro-1-cyclopropyl-1H-imidazo[4,5-b]pyridin-2(3H)-one -continued

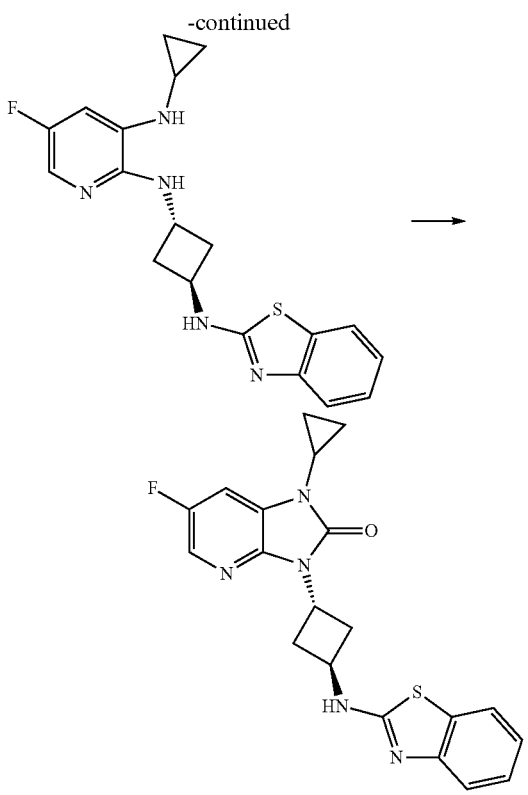

Step 1: N²-(trans-3-(benzo[d]thiazol-2-ylamino)cyclobutyl)-N-cyclopropyl-5-fluoropyridine-2,3-diamine 2-Chloro-N-cyclopropyl-5-fluoropyridin-3-amine (intermediate 39, 0.230 g, 1.232 mmol), trans-N¹-(benzo[d]thiazol-2-yl)cyclobutane-1,3-diamine (intermediate 11, 0.270 g, 1.232 mmol), chloro(2-dicyclohexylphosphino-3,6-dimethoxy-2'-4'-6'-triisopropyl-1,1'-biphenyl) 2-(2-aminoethyl)phenyl)palladium(II) (0.049 g, 0.062 mmol), and sodium t-butoxide (0.296 g, 3.08 mmol) were sealed in a microwave vial under argon. Dry, sparged dioxane (1 mL) was added and the reaction heated at 80° C. After 45 minutes the vial was opened and the crude and dry loaded on silica gel. Purification using silica chromatography (hexane to ethyl acetate gradient) gave N²-(trans-3-(benzo[d]thiazol-2-ylamino)cyclobutyl)-N³-cyclopropyl-5-fluoropyridine-2,3-diamine (0.304 g, 0.824 mmol, 66.8% yield).

Step 2: 3-(trans-3-(benzo[d]thiazol-2-ylamino)cyclobutyl)-1-cyclopropyl-6-fluoro-1H-imidazo[4,5-b]pyridin-2(3H)-one N²-(Trans-3-(benzo[d]thiazol-2-ylamino)cyclobutyl)-N³-cyclopropyl-5-fluoropyridine-2,3-diamine (0.051 g, 0.138 mmol) was dissolved in a mixture of dichloromethane (10 mL) and N,N-diisopropylethylamine (0.100 ml, 0.575 mmol) and cooled in an ice bath under nitrogen. Triphosgene (0.041 g, 0.138 mmol) was added in one portion. The reaction allowed to stir in the ice bath and warm to room temperature over 14 hours. Water (5 mL) and dichloromethane (10 mL) were added and the reaction stirred vigorously. The phases were separated and the organic dried with magnesium sulfate before evaporating to dryness under reduced pressure. Purification using silica chromatography (first column 0-10% methanol in dichloromethane gradient, repurify using hexane to ethyl acetate gradient) gave 3-(trans-3-(benzo[d]thiazol-2-ylamino)cyclobutyl)-1-cyclopropyl-6-fluoro-1H-imidazo[4,5-b]pyridin-2(3H)-one (0.017 g, 0.043 mmol, 31.1% yield). M+1: 396. ¹H NMR (400 MHz, CHLOROFORM-d) δ ppm 0.97-1.04 (m, 2 H) 1.10-1.17 (m, 2 H) 2.47-2.58 (m, 2 H) 2.88 (tt, J=6.92, 3.55 Hz, 1 H) 3.45-3.58 (m, 2 H) 4.55-4.65 (m, 1 H) 5.33 (quin, J=8.46 Hz, 1 H) 6.16 (br. s., 1 H) 7.05-7.12 (m, 1 H) 7.17 (dd, J=8.22, 2.35 Hz, 1 H) 7.25-7.35 (m, 1 H) 7.57 (d, J=8.02 Hz, 1 H) 7.60 (d, J=7.82 Hz, 1 H) 7.93 (t, J=2.15 Hz, 1 H).

Method C4

Example 92

3-(trans-3-((6-fluorobenzo[d]thiazol-2-yl)amino)cyclobutyl)-1H-imidazo[4,5-b]pyridin-2(3H)-one

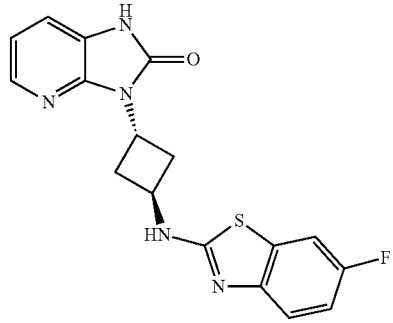 [SMILES: O=c1[nH]c2cccnc2n1[C@H]1C[C@H](Nc2nc3ccc(F)cc3s2)C1]

To a glass microwave reaction vessel was added 3-(trans-3-aminocyclobutyl)-1H-imidazo[4,5-b]pyridin-2(3H)-one (intermediate 43, 0.1288 g, 0.465 mmol), 2-chloro-6-fluorobenzo[d]thiazole (0.087 g, 0.465 mmol), and diisopropylethylamine (0.283 ml, 1.627 mmol) in dry dimethylsulfoxide (1.549 ml). The vial was sealed and heated at 90° C. for 14 hours. It was allowed to cool to room temperature and the crude product purified by reverse-phase preparative HPLC (Phenomenex Gemini column, 10 micron, C18, 100 Å, 150×30 mm, 0.1% TFA in acetonitrile/water, gradient 10% to 90% over 12 min) to give the desired 3-(trans-3-((6-fluorobenzo[d]thiazol-2-yl)amino)cyclobutyl)-1H-imidazo[4,5-b]pyridin-2(3H)-one (26.2 mg, 0.074 mmol, 15.86% yield). M+1: 355.99. ¹H NMR (400 MHz, DMSO-d₆) δ ppm 2.37-2.47 (m, 2 H) 3.25-3.34 (m, 1 H) 4.55 (d, J=5.28 Hz, 1 H) 5.20 (quin, J=8.41 Hz, 1 H) 6.99-7.12 (m, 2 H) 7.32 (dd, J=7.63, 1.17 Hz, 1 H) 7.41 (dd, J=8.80, 4.89 Hz, 1 H) 7.64 (dd, J=8.80, 2.74 Hz, 1 H) 8.00 (dd, J=5.18, 1.27 Hz, 1 H) 8.56 (d, J=6.06 Hz, 1 H) 11.15 (s, 1 H).

Method C5

Example 97

9-(trans-3-(benzo[d]thiazol-2-ylamino)cyclobutyl)-7H-purin-8(9H)-one

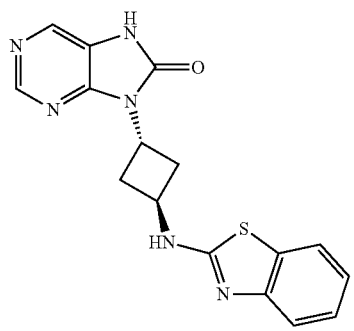 [SMILES: O=c1[nH]c2cncnc2n1[C@H]1C[C@H](Nc2nc3ccccc3s2)C1]

N[4]-((1R,3R)-3-(Benzo[d]thiazol-2-ylamino)cyclobutyl) pyrimidine-4,5-diamine (intermediate 45, 0.033 g, 0.106 mmol) and triethylamine (0.25 ml, 1.797 mmol) were dissolved in dichloromethane (10 mL) and treated with triphosgene (0.038 g, 0.127 mmol). The solution was stirred for 30 minutes. Water (5 mL) was added and the reaction stirred vigorously for 10 minutes. Saturated sodium bicarbonate (20 mL), water (100 mL), and dichloromethane (100 mL) were added and the phases mixed and separated. The organic phase was dried with magnesium sulfate and evaporated to dryness under reduced pressure. Purification using silica chromatography (0-10% (2N ammonia in methanol) in dichloromethane gradient) gave the desired 9-(trans-3-(benzo[d]thiazol-2-ylamino)cyclobutyl)-7H-purin-8(9H)-one (0.020 g, 0.059 mmol, 56.0% yield). M+1: 338.9. ¹H NMR (400 MHz, MeOH) δ ppm 2.47-2.67 (m, 2 H) 3.42-3.60 (m, 2 H) 4.62-4.71 (m, 1 H) 5.28 (quin, J=8.36 Hz, 1 H) 7.00-7.14 (m, 1 H) 7.26 (t, J=7.63 Hz, 1 H) 7.46 (d, J=8.02 Hz, 1 H) 7.60 (d, J=7.82 Hz, 1 H) 8.22 (s, 1 H) 8.64 (s, 1 H).

Method C6

Example 100

3-(trans-3-(benzo[d]thiazol-2-ylamino)cyclobutyl oxazolo[4,5-b]pyridin-2(3H)-one

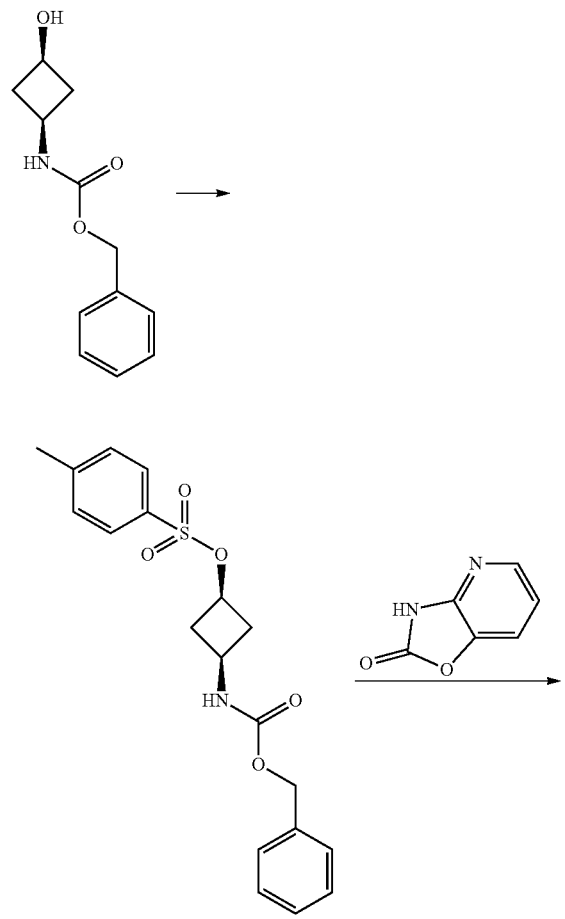

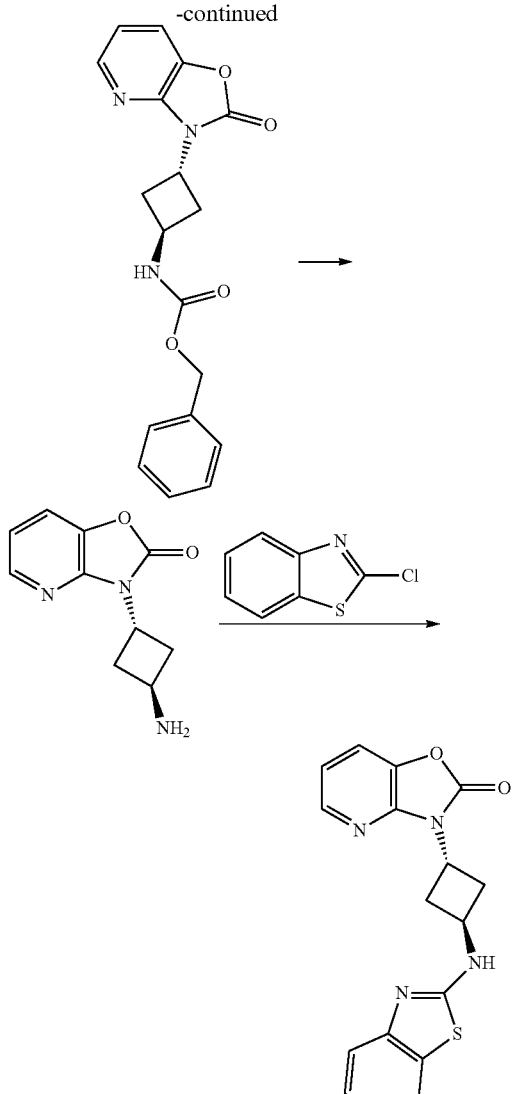

Step 1: (cis)-3-(((benzyloxy)carbonyl)amino)cyclobutyl 4-methylbenzenesulfonate

A solution of benzyl (cis-3-hydroxycyclobutyl)carbamate (intermediate 47, 0.3 g, 1.356 mmol), p-toluenesulfonyl chloride (0.284 g, 1.492 mmol), and triethylamine (0.567 ml, 4.07 mmol) in dichloromethane (2.71 ml) was stirred at room temperature for 14 hours. The mixture was diluted with dichloromethane and washed with saturated sodium bicarbonate solution. The organic layer was dried over sodium sulfate, rotovapped, and advanced to next step directly.

Step 2: benzyl (trans-3-(2-oxooxazolo[4,5-b]pyridin-3(2H)-yl)cyclobutyl)carbamate To a solution of cis-3-(((benzyloxy)carbonyl)amino)cyclobutyl 4-methylbenzenesulfonate (0.25 g, 0.666 mmol) in dry dimethylformamide (1.332 ml) was added oxazolo[4,5-b]pyridin-2(3H)-one (0.091 g, 0.666 mmol) and potassium carbonate (0.230 g, 1.665 mmol). The resulting mixture was heated at 50° C. for 14 hours, 100° C. for 3 hours, then 110° C. for an additional 20 hours. The mixture was diluted with dichloromethane and washed with water and brine then dried with magnesium sulfate and evaporated to dryness under reduced pressure. The crude was advanced directly to next step.

Step 3: 3-(trans-3-aminocyclobutyl)oxazolo[4,5-b]pyridin-2(3H)-one

To a solution of benzyl (trans-3-(2-oxooxazolo[4,5-b]pyridin-3(2H)-yl)cyclobutyl)carbamate (0.225 g, 0.666 mmol) in acetic acid (1 mL) was added hydrogen bromide (33 wt. % in acetic acid, 2 ml, 36.8 mmol). The resulting mixture was stirred at room temperature for 1 hour. The mixture was quenched with addition of 1N sodium hydroxide solution and rotovapped and dried by vacuum pump overnight.

Step 4: 3-(trans-3-(benzo[d]thiazol-2-ylamino)cyclobutyl)oxazolo[4,5-b]pyridin-2(3H)-one The crude solid was suspended in dry dimethylsulfoxide (3 ml) and diisopropylethylamine (0.465 ml, 2.66 mmol) and 2-chlorobenzothiazole (0.113 g, 0.666 mmol) were added. The resulting mixture was heated at 120° C. for 4 hours. The reaction mixture was diluted with dichloromethane and washed with water and brine. The residue was concentrated, solubilized with methanol and purified by Gilson HPLC (Gemini-NX 10 u C18 column, 100×50 mm, solvets: ACN/0.1% TFA and water/0.1% TFA). The recovered fractions were dried by Genevac. The remaining solvents were removed by azeotroping with methanol and dried by vacuum pump to give 3-(trans-3-(benzo[d]thiazol-2-ylamino)cyclobutyl)oxazolo[4,5-b]pyridin-2(3H)-one (20.2 mg, 0.06 mmol, 9% yield). M+1: 338.9. $^1$H NMR (300 MHz, MeOH) δ ppm 2.67-2.84 (m, 2 H); 3.49-3.68 (m, 2 H); 4.63-4.78 (m, 1 H); 5.16-5.34 (m, 1 H); 7.13-7.26 (m, 1 H); 7.32-7.43 (m, 1 H); 7.46-7.66 (m, 3 H); 7.77-7.88 (m, 1 H); 8.12-8.23 (m, 1 H).

Method C7

Example 103

3-(cis-3-(benzo[d]thiazol-2-ylamino)cyclobutyl)-1H-imidazo[4,5-b]pyridin-2(3H)-one

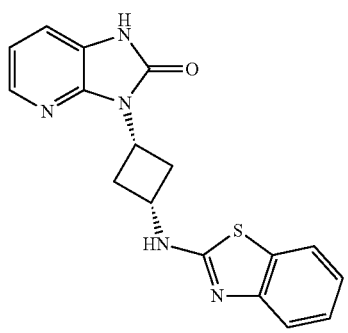 [SMILES: O=c1[nH]c2cccnc2n1[C@H]1C[C@@H](Nc2nc3ccccc3s2)C1]

To a 50-mL round-bottomed flask with N-(cis-3-(2-methoxy-3H-imidazo[4,5-b]pyridin-3-yl)cyclobutyl)benzo[d]thiazol-2-amine (example 9, 100 mg, 0.285 mmol) was added hydrogen chloride (1 M in diethyl ether, 1.0 mL, 1.0 mmol). The solution was stirred for minutes then concentrated under reduced pressure. The crude was diluted with saturated sodium bicarbonate solution and extracted with dichloromethane (10 mL). The organic extract was dried over sodium sulfate then concentrated in vacuo to give the crude material as a off-white oil. The crude material was absorbed onto a plug of silica gel and purified by chromatography through a Redi-Sep pre-packed silica gel column (4 g, hexane to ethyl acetate gradient) to provide 3-(cis-3-(benzo[d]thiazol-2-ylamino)cyclobutyl)-1H-imidazo[4,5-b]pyridin-2(3H)-one (40 mg, 0.119 mmol, 83% yield) as light-yellow solid. M+1: 338. $^1$H NMR (300 MHz, DMSO-$d_6$) δ ppm 2.67-2.80 (m, 2 H) 3.02-3.16 (m, 2 H) 4.12-4.26 (m, 1 H) 4.62-4.77 (m, 1 H) 6.93-7.10 (m, 2 H) 7.22 (td, J=7.20, 1.30 Hz, 1 H) 7.30 (dd, J=7.75, 1.32 Hz, 1 H) 7.37-7.43 (m, 1 H) 7.67 (dd, J=7.75, 0.73 Hz, 1 H) 7.98 (dd, J=5.19, 1.39 Hz, 1 H) 8.50 (d, J=6.72 Hz, 1 H).

Method C8

Example 106

3-(cis-3-(benzo[d]thiazol-2-yl(methyl)amino)cyclobutyl)-1-methyl-1H-imidazo[4,5-b]pyridin-2(3H)-one

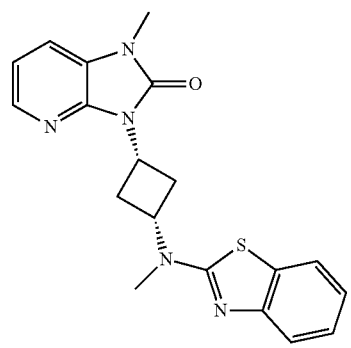 [SMILES: Cn1c(=O)n([C@H]2C[C@@H](N(C)c3nc4ccccc4s3)C2)c2ncccc21]

A glass microwave reaction vessel was charged with 3-(cis-3-(benzo[d]thiazol-2-ylamino)cyclobutyl)-1H-imidazo[4,5-b]pyridin-2(3H)-one (example 103, 60 mg, 0.178 mmol) and sodium hydride (60% oil dispersion, 12.80 mg, 0.533 mmol) in dry dimethylsulfoxide (0.5 mL). To the reaction mixture was added iodomethane (0.014 mL, 0.231 mmol) and the resulting mixture was stirred for 2 hours. The reaction mixture was diluted with water and extracted with ethyl acetate. The organic extract was washed with brine and dried over magnesium sulfate before concentrating in vacuo to give the crude material as a off-white solid. The crude material was absorbed onto a plug of silica gel and purified by chromatography through a Redi-Sep pre-packed silica gel column (12 g, hexane to ethyl acetate gradient) to provide 3-(cis-3-(benzo[d]thiazol-2-yl(methyl)amino)cyclobutyl)-1-methyl-1H-imidazo[4,5-b]pyridin-2(3H)-one (42 mg, 0.115 mmol, 64.6% yield) as white solid. M+1: 365.9. $^1$H NMR (400 MHz, DMSO-$d_6$) δ ppm 2.58-2.71 (m, 2 H) 3.35 (d, J=1.96 Hz, 6 H) 3.38-3.48 (m, 2 H) 4.62 (quin, J=8.41 Hz, 1 H) 4.84 (quin, J=8.66 Hz, 1 H) 7.00-7.09 (m, 1 H) 7.11 (dd, J=7.73, 5.18 Hz, 1 H) 7.22-7.33 (m, 1 H) 7.47 (d, J=7.82 Hz, 1 H) 7.52 (dd, J=7.73, 1.27 Hz, 1 H) 7.76 (d, J=7.82 Hz, 1 H) 8.04 (dd, J=5.18, 1.27 Hz, 1 H).

Examples 88-91, 93-96, 98-99, 101-102, 104-105, and 107-112 were prepared according to methods analogous to the above Methods C1-C8 as follows:

TABLE 3

Preparation of Examples 88-91, 93-96, 98-99, 101-102, 104-105, and 107-112

| Ex. # | Method | Reagent | M + 1 | NMR |
|---|---|---|---|---|
| 88 | C2 | Intermediate 11, intermediate 40 | 352.1 | $^1$H NMR (400 MHz, CHLOROFORM-d) δ ppm 2.51-2.62 (m, 2 H) 3.43 (s, 3 H) 3.48-3,63 (m, 2 H) 4.56-4.69 (m, 1 H) 5.40 (quin, J = 8.41 Hz, 1 H) 6.25-6.54 (m, 1 H) 7.03 (dd J = 7.73, 5.18 Hz 1 H) 7.07-7.14 (m, 1 H) 7.17 (dd, J = 7.63, 1.17 Hz, 1 H) 7.28-7.37 (m, 1 H) 7.58 (d, J = 8.02 Hz, 1 H) 7.61 (d, J = 7.82 Hz, 1 H) 8.07 (dd, J = 5.09, 1.17 Hz 1 H) |
| 89 | C1 | Intermediate 33, cyclopentylamine | 406.1 | $^1$H NMR (400 MHz, CHLOROFORM-d) δ ppm 1.65-2.12 (m, 9 H) 2.65-2.81 (m, 2 H) 3.45-3.58 (m, 2 H) 4.61-4.70 (m, 1 H) 4.87 (quin, J = 8.71 Hz, 1 H) 5.35-5.50 (m, 1 H) 6.99 (dd, J = 7.63, 5.28 Hz, 1 H) 7.19-7.30 (m, 1 H) 7.41 (t, J = 7.82 Hz, 1 H) 7.58 (d, J = 8.22 Hz, 1 H) 7.61 (d, J = 8.02 Hz, 1 H) 8.04 (d, J = 5.28 Hz, 1 H) |
| 90 | C3 | Intermediate 11, Intermediate 41 | 379.1 | $^1$H NMR (400 MHz, CHLOROFORM-d) δ ppm 2.42 (s, 4 H) 2.51-2.62 (m, 2 H) 3.00 (quin, J = 5.38 Hz, 1 H) 3.42-3.54 (m, 2 H) 4.50-4.60 (m, 2 H) 5.30 (quin, J = 8.46 Hz, 1 H) 7.05-7.13 (m, 1 H) 7.27-7.33 (m, 1 H) 7.53 (d, J = 8.02 Hz, 1 H) 7.60 (d, J = 8.02 Hz, 1 H) 7,94-7.99 (m, 2 H) |
| 91 | C1 | Intermediate 42, cyclopropylamine | 379.1 | $^1$H NMR (400 MHz, CHLOROFORM-d) δ ppm 1.01-1.07 (m, 2 H) 1.13-1.19 (m, 2 H) 2.52-2.62 (m, 2 H) 2.95 (tt, J = 6.94, 3.62 Hz, 1 H) 3,44-3.55 (m, 2 H) 4.59-4.68 (m, 1 H) 5.31 (quin, J = 8.41 Hz, 1 H) 7.06-7.14 (m, 1 H) 7.28-7.34 (m, 1 H) 7.58 (d, J = 8.02 Hz, 1 H) 7.61 (d, J = 7.82 Hz, 1 H) 8.36 (s, 1 H) 8.71 (s, 1 H) |
| 93 | C1 | Intermediate 42, methylamine | 353.1 | $^1$H NMR (400 MHz, CHLOROFORM-d) δ ppm 2.49-2.65 (m, 2 H) 3.42-3.60 (m, 5 H) 4.50-4.66 (m, 1 H) 5.32 (quin, J = 8.26 Hz, 1 H) 7.05-7.16 (m 1 H) 7.23-7.38 (m, 1 H) 7.53 (d, J = 7.63 Hz, 1 H) 7.60 (d, J = 7.04 Hz, 1 H) 8.22 (s, 1 H) 8.71 (s, 1 H) |
| 94 | C4 | Intermedate 43, 2-chlorobenzo[d]thiazole | 338 | $^1$H NMR (300 MHz, DMSO-d$_6$) δ ppm 2.51-2.61 (m, 2 H) 3.26-3.63 (m, 2 H), 4.48-4,66 (m, 1 H) 5.11-5.30 (m, 1 H) 6.89-7.11 (m, 2 H) 7.16-7.28 (m, 1 H) 7.28-7.37 (m, 1 H) 7.37-7.48 (m, 1 H) 7.63-7.73 (m, 1 H) 7.93-8.05 (m, 1 H) 8.48-8.61 (m, 1 H) |
| 95 | C1 | Intermediate 44, methylamine | 353.1 | $^1$H NMR (400 MHz, CHLOROFORM-d) δ ppm 2.48-2.65 (m, 2 H) 3.41-3.56 (m, 5 H) 4.56-4.71 (m, 1 H) 5.35 (quin, J = 8.36 Hz, 1 H) 5.96 (hr. s., 1 H) 7.10 (t, J = 7.24 Hz, 1 H) 7.28-7.37 (m, 1 H) 7.60 (dd, J = 11.74, 8.02 Hz, 2 H) 7.95 (s, 2 H) |
| 96 | C4 | Intermediate 43, 2-chloroquinoline | 332.0 | $^1$H NMR (400 MHz, DMSO-d6) δ 2.53-2.60 (m, 2 H) 3.63 (d, J = 8.61 Hz, 2 H) 4.63 (d, J = 6.65 Hz, 1 H) 5.31 (quin, J = 9.00 Hz, 1 H) 7.06 (dd, J = 7.63, 5.28 Hz, 1 H) 7.15 (d, J = 9.39 Hz, 1 H) 7.29-7.40 (m, 1 H) 7.52 (t, J = 7.63 Hz, 1 H) 7.79 (t, J = 7.63 Hz, 1 H) 7.94 (d, J = 7.83 Hz, 2 H) 8.01 (dd, J = 5.09, 1.17 Hz, 1 H) 8.35 (d, J = 9.39 Hz, 1 H) 11.21 (s, 1 H) |
| 98 | C4 | Intermediate 43, intermediate 46 | 356.0 | $^1$H NMR (400 MHz, DMSO-d$_6$) δ 2.40-2.49 (m, 2 H) 3.33-3.42 (m, 2 H) 4.57 (br. s., 1 H) 5.21 (quin, J = 8.46 Hz, 1 H) 6.98-7.06 (m, 2 H) 7.06-7.15 (m, 1 H) 7.32 (dd, J = 7.73, 1.08 Hz, 1 H) 7.54 (d, J = 7.82 Hz, 1 H) 8.01 (dd, J = 5.09, 1.17 Hz, 1 H) 8.80 (d, J = 6.06 Hz, 1 H) 11.16 (s, 1 H) |
| 99 | C4 | Intermedate 43, intermediate 7 | 356.1 | $^1$H NMR (400 MHz, DMSO-d$_6$) δ ppm 2.69-2.88 (m, 2 H) 3.52-3.78 (m, 2 H) 4.46-4.61 (m, 1 H) 5.18 (quin, J = 8.56 Hz, 1 H) 6.79-6.95 (m, 1 H) 7.07-7.17 (m, 1 H) 7.23 (dd, J = 10.47, 2.25 Hz, 1 H) 7.62-7.74 (m, 1 H) 7.74-7.86 (m, 1 H) 8.62-8.81 (m, 1 H) |
| 101 | C4 | Intermedate 43, intermediate 48 | 350.0 | 1H NMR (400 MHz, DMSO-d6) δ ppm 2.30-2.41 (m, 2 H) 3.33-3,44 (m, 2 H) |

TABLE 3-continued

Preparation of Examples 88-91, 93-96, 98-99, 101-102, 104-105, and 107-112

| Ex. # | Method | Reagent | M + 1 | NMR |
|---|---|---|---|---|
| | | | | 4.69 (br. s., 1 H) 5.25 (quin, J = 8.56 Hz, 1 H) 6.77 (d, J = 9.00 Hz, 1 H) 6.97-7.07 (m, 2 H) 7.20 (dd, J = 11.44, 2.25 Hz, 1 H) 7.32 (dd, J = 7.63, 1.17 Hz, 1 H) 7.69 (dd, J = 8.51, 6.75 Hz, 1 H) 7.75 (d, J = 5.87 Hz, 1 H) 7.91 (d, J = 9.00 Hz, 1 H) 8.02 (dd, J = 5.28, 1.17 Hz, 1 H) 11.14 (s, 1 H) |
| 102 | C4 | Intermediate 43, 2-chloroquinazoline | 333.0 | 1H NMR (400 MHz, DMSO-d6) δ ppm 2.39-2.49 (m, 1 H) 3.27-3.39 (m, 3 H) 4.69 (br. s., 1 H) 5.25 (quin, J = 8.41 Hz, 1 H) 7.03 (dd, J = 7.63, 5.28 Hz, 1 H) 7.24 (t, J = 7.43 Hz, 1 H) 7.31 (dd, J = 7.63, 1.17 Hz, 1 H) 7.49 (d, J = 8.41 Hz, 1 H) 7.65-7.75 (m, 1 H) 7.81 (d, J = 8.02 Hz, 1 H) 7.95-8.06 (m, 1 H) 9.15 (s, 1 H) 11.13 (s, 1 H) |
| 104 | C4 | Intermediate 49, 2-chlorobenzo[d]thiazole | 365.9 | 1H NMR (400 MHz, DMSO-d6) δ ppm 1.38-1.54 (m, 2 H) 1.79 (d, J = 10.56 Hz, 2 H) 2.22 (d, J = 10.76 Hz, 2 H) 2.54-2.65 (m, 2 H) 3.75-3.87 (m, 1 H) 4.26-4.38 (m, 1 H) 6.97-7.06 (m, 2 H) 7.19-7.27 (m, 1 H) 7.30 (dd, J = 7.63, 1.37 Hz, 1 H) 7.43 (d, J = 7.43 Hz, 1 H) 7.67 (dd, J = 7.82, 0.78 Hz, 1 H) 7.98 (dd, J = 5.18, 1.47 Hz, 1 H) 8.04 (d, J = 7.43 Hz, 1 H) 11.09 (s, 1 H) |
| 105 | C4 | Intermediate 43, intermediate 50 | 362.0 | 1H NMR (400 MHz, CHLOROFORM-d) δ ppm 2.71-2.83 (m, 1 H) 3.38-3.51 (m, 1 H) 3.98 (s, 2 H) 4.69-4.80 (m, 1 H) 5.33-5.46 (m, 1 H) 6.61 (d, J = 9.39 Hz, 1 H) 6.96-7.03 (m, 1 H) 7.21-7.26 (m, 1 H) 7.57 (d, J = 9.00 Hz, 1 H) 8.04 (d, J = 7.24 Hz, 1 H) |
| 107 | C4 | Intermediate 49, intermediate 7 | 383.9 | 1H NMR (400 MHz, DMSO-d6) δ ppm 1.39-1.54 (m, 2 H) 1.79 (d, J = 10.95 Hz, 2 H) 2.21 (d, J = 10.95 Hz, 2 H) 2.56-2.63 (m, 3 H) 3.82 (dd, J = 7.34, 3.81 Hz, 1 H) 4.32 (tt, J = 12.28, 3.96 Hz, 1 H) 6.87 (td, J = 9.00, 2.54 Hz, 1 H) 7.01 (dd, J = 7.73, 5.18 Hz, 1 H) 7.24 (dd, J = 10.56, 2.54 Hz, 1 H) 7.30 (dd. J = 7.82, 1.37 Hz, 1 H) 7.67 (dd, J = 8.61, 5.67 Hz, 1 H) 7.98 (dd, J = 5.28, 1.37 Hz, 1 H) 8.23 (d. J = 7.43 Hz, 1 H) 11.09 (s, 1 H) |
| 108 | C4 | Intermediate 49, intermediate 51 | 360.0 | 1H NMR (400 MHz, DMSO-d6) δ ppm 1.41 (q, J = 11.54 Hz, 2 H) 1.78 (d, J = 9.98 Hz, 2 H) 2.19 (d, J = 12.32 Hz, 2 H) 2.53-2.69 (m, 2 H) 4.00-4.10 (m, 1 H) 4.26-4.38 (m, 1 H) 6.75 (d, J = 8.80 Hz, 1 H) 6.94 (d, J = 6.26 Hz, 1 H) 7.00 (dd, J = 7.63, 5.28 Hz, 1 H) 7.13 (t, J = 6.94 Hz, 1 H) 7.29 (dd, J = 7.73, 1.27 Hz, 1 H) 7.39-7.49 (m, 1 H) 7.49-7.56 (m, 1 H) 7.59 (d, J = 8.02 Hz, 1 H) 7.83 (d, J = 8.61 Hz, 1 H) 7.98 (dd, J = 5.28. 1,37 Hz, 1 H) 11.08 (s, 1 H) |
| 109 | C4 | Intermediate 43, 2-chloro-7-fluoroquinazoline | 350.9 | 1H NMR (400 MHz, DMSO-d6) δ ppm 2.40-2.49 (m, 1 H) 3.25-3.31 (m, 1 H) 3.34-3.40 (m, 1 H) 4.69 (br. s., 1H ) 5.24 (quin, J = 8.46 Hz, 1 H) 7.03 (dd, J = 7.63, 5.28 Hz, 1 H) 7.12 (td, J = 8.75, 2.25 Hz, 1 H) 7.20 (d, J = 10.37 Hz, 1h) 7.31 (d, J = 6.65 Hz, 1 H) 7.91 (dd, J = 8.61, 6.85 Hz, 1 H) 8.01 (d, J = 4.30 Hz, 1 H) 8.16 (d, J = 4.69 Hz, 1 H) 9.14 (br. s., 1 H) 11.13 (s, 1 H) |
| 110 | C4 | Intermediate 49, 2-chloroquinazoline | 361.0 | 1H NMR (400 MHz, DMSO-d6) δ ppm 1.44-1.60 (m, 2 H) 1.79 (d, J = 10.37 Hz, 2 H) 2.14 (d, J = 11.15 Hz, 2 H) 2.55-2.66 (m, 3 H) 4.22-4.38 (m, 1 H) 7.02 (dd, J = 7.63, 5.28 Hz, 1 H) 7.24 (t, J = 7.43 Hz, 1 H) 7.31 (dd, J = 7.73, 1.47 Hz, 1 H) 7.66-7.75 (m, 1 H) 7.81 (d, J = 8.22 Hz, 1 H) 7.99 (dd, J = 5.18, 1.47 Hz, 1 H) 9.14 (br. s., 1 H) 11.10 (s, 1 H) |
| 111 | C4 | Intermediate 49, intermediate 48 | 378.0 | 1H NMR (400 MHz, DMSO-d6) δ ppm 1.43 (q, J = 11.48 Hz, 2 H) 1.79 (d, J = 11.15 Hz, 2 H) 2.19 (d, J = 10.37 Hz, 2 H) 2.60 (d, J = 12.91 Hz, 2 H) 4.06 (t, J = 7.14 Hz, 1 H) 4.28-4.40 (m, 1 H) 6.74 (d, J = 9.00 Hz, 1 H) 6.97-7.06 (m, 2 H) 7.13 (d, J = 7.43 Hz, |

TABLE 3-continued

Preparation of Examples 88-91, 93-96, 98-99, 101-102, 104-105, and 107-112

| Ex. # | Method | Reagent | M + 1 | NMR |
|---|---|---|---|---|
| 112 | C4 | Intermediate 49, intermediate 8 | 395.0 | 1 H) 7.24 (dd, J = 11.64, 2.25 Hz, 1 H) 7.31 (dd, J = 7.63, 1.37 Hz, 1 H) 7.67 (dd, J = 8.61, 6.85 Hz, 1 H) 7.86 (d, J = 8.80 Hz, 1 H) 7.99 (dd, J = 5.28, 1.37 Hz, 1 H) 11.10 (s, 1 H) 1H NMR (400 MHz, DMSO-d6) δ ppm 1.45-1.61 (m, 2 H) 1.79 (d, J = 10.56 Hz, 2 H) 2.13 (d, J = 9.98 Hz, 2 H) 2.55-2.66 (m, 4 H) 4.23-4.37 (m, 1 H) 7.02 (dd, J = 7.63, 5.28 Hz, 1 H) 7.24 (dd, J = 8.61, 1.96 Hz, 1 H) 7.31 (dd, J = 7.63, 1.37 Hz, 1 H) 7.59 (br. s., 1 H) 7.84 (d, J = 8.61 Hz, 1 H) 7.98 (dd, J = 5.28, 1.37 Hz, 1 H) 9.13 (br, s., 1 H) 11.10 (s, 1 H) |

Examples 113-116 were prepared according to Methods D1-D3 as follows:

Method D1

Example 113

N-(trans-3-(3-amino-1H-pyrazolo[3,4-b]pyridin-1-yl)cyclobutyl)benzo[d]thiazol-2-amine

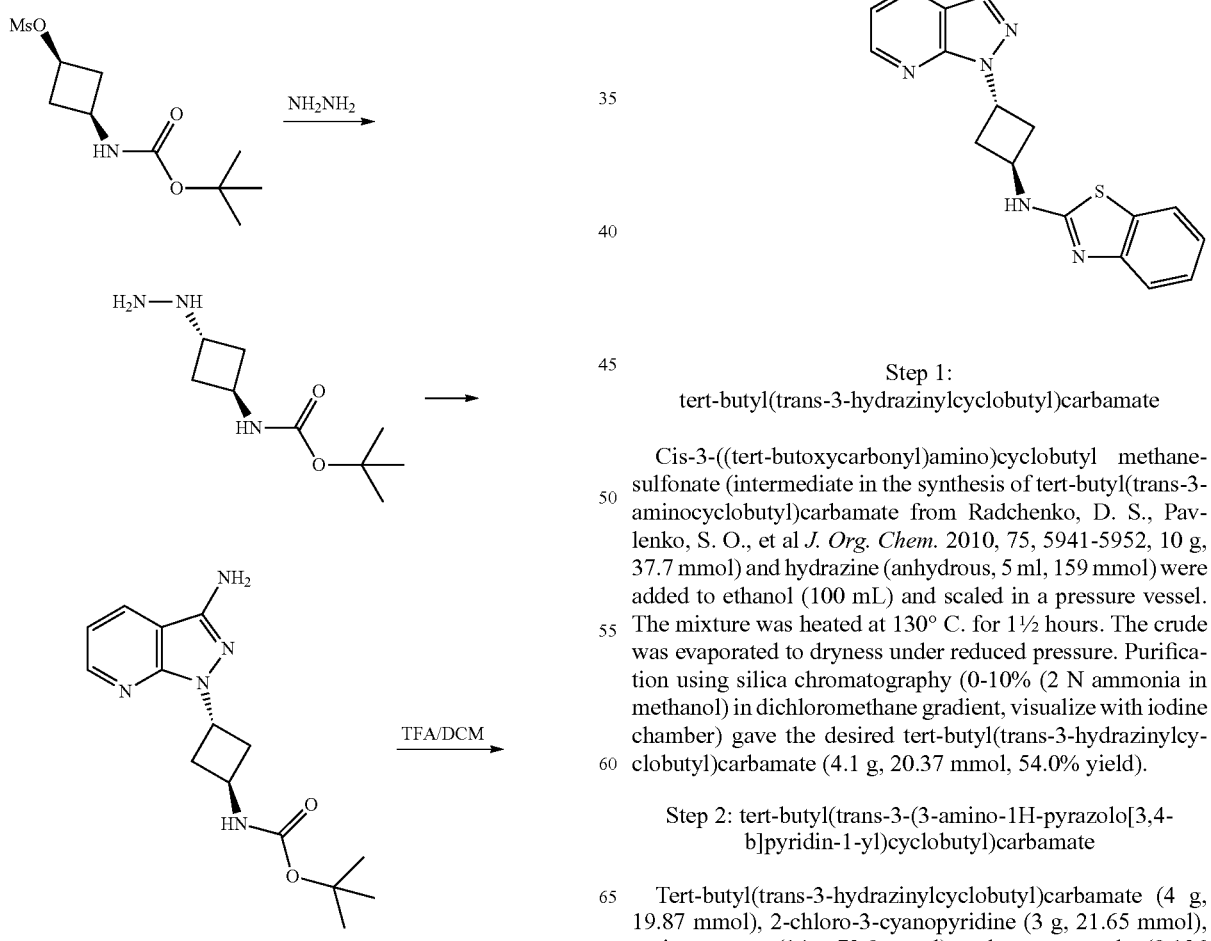

Step 1: tert-butyl(trans-3-hydrazinylcyclobutyl)carbamate

Cis-3-((tert-butoxycarbonyl)amino)cyclobutyl methanesulfonate (intermediate in the synthesis of tert-butyl(trans-3-aminocyclobutyl)carbamate from Radchenko, D. S., Pavlenko, S. O., et al *J. Org. Chem.* 2010, 75, 5941-5952, 10 g, 37.7 mmol) and hydrazine (anhydrous, 5 ml, 159 mmol) were added to ethanol (100 mL) and sealed in a pressure vessel. The mixture was heated at 130° C. for 1½ hours. The crude was evaporated to dryness under reduced pressure. Purification using silica chromatography (0-10% (2 N ammonia in methanol) in dichloromethane gradient, visualize with iodine chamber) gave the desired tert-butyl(trans-3-hydrazinylcyclobutyl)carbamate (4.1 g, 20.37 mmol, 54.0% yield).

Step 2: tert-butyl(trans-3-(3-amino-1H-pyrazolo[3,4-b]pyridin-1-yl)cyclobutyl)carbamate Tert-butyl(trans-3-hydrazinylcyclobutyl)carbamate (4 g, 19.87 mmol), 2-chloro-3-cyanopyridine (3 g, 21.65 mmol), cesium acetate (14 g, 72.9 mmol), and copper powder (0.126 g, 1.987 mmol) were placed under nitrogen. Dry dimethylsulfoxide (20 mL) was added and the mixture stirred at 100° C. After 1 hour the mixture was cooled and diluted with ethyl acetate (300 mL). The mixture was filtered through a pad of celite and the filtrate washed with 10% saturated sodium bicarbonate (500 mL) before drying with magnesium sulfate and evaporating to dryness under reduced pressure. Purification using silica chromatography (10% (2 N ammonia in methanol) in dichloromethane) gave the desired tert-butyl (trans-3-(3-amino-1H-pyrazolo[3,4-b]pyridin-1-yl)cyclobutyl)carbamate (2.72 g, 8.97 mmol, 45.1% yield).

Step 3: N-(trans-3-(3-amino-1H-pyrazolo[3,4-b]pyridin-1-yl)cyclobutyl) benzo[d]thiazol-2-amine Tert-butyl(trans-3-(3-amino-1H-pyrazolo[3,4-b]pyridin-1-yl)cyclobutyl)carbamate (0.505 g, 1.665 mmol) was dissolved in dichloromethane (30 mL) and treated with trifluoroacetic acid (5 mL). The solution was stirred for 20 minutes after which the solution was evaporated to dryness under reduced pressure and further dried under high vacuum. The crude amine was dissolved in dry dimethylsulfoxide (10 mL) and treated with cesium carbonate (1.25 g, 3.84 mmol). 2-Chlorobenzothiazole (0.265 ml, 1.857 mmol) was added and the reaction was heated at 85° C. After 16 hours the reaction was cooled, diluted with water (200 mL), ammonium hydroxide (20 mL) and extracted with ethyl acetate (200 mL). The organic phase was dried with magnesium sulfate and evaporated to dryness under reduced pressure. Purification using silica chromatography (0-10% methanol in dichloromethane gradient) followed by reverse phase HPLC gave N-(trans-3-(3-amino-1H-pyrazolo[3,4-b]pyridin-1-yl)cyclobutyl)benzo[d]thiaz δ 1-2-amine (0.076 g, 0.226 mmol, 13.57% yield). M+1: 337.1. $^1$H NMR (400 MHz, MeOH) δ ppm 2.54-2.69 (m, 2 H) 3.03-3.18 (m, 2 H) 4.57 (tt, J=7.80, 3.84 Hz, 1 H) 4.83 (s, 2 H) 5.55 (quin, J=7.68 Hz, 1 H) 6.97-7.13 (m, 2 H) 7.21-7.30 (m, 1 H) 7.46 (d, J=8.02 Hz, 1 H) 7.59 (d, J=7.63 Hz, 1 H) 8.13 (dd, J=8.02, 1.37 Hz, 1 H) 8.38 (dd, J=4.69, 1.37 Hz, 1 H).

Method D2

Example 114

N-(trans-3-(3-cyclopropyl-1H-pyrazolo[3,4-b]pyridin-1-yl)cyclobutyl)benzo[d]thiazol-2-amine

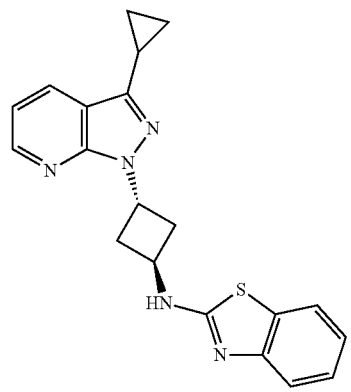 [SMILES: c1ccc2sc(N[C@H]3C[C@H](n4nc(C5CC5)c5cccnc54)C3)nc2c1]

Cyclopropyl(2-fluoropyridin-3-yl)methanone (intermediate 53, 0.270 g, 1.635 mmol), N-(trans-3-hydrazinylcyclobutyl)benzo[d]thiazol-2-amine dihydrochloride (intermediate 52, 0.502 g, 1.635 mmol), and potassium acetate (0.462 ml, 7.39 mmol) were suspended in a mixture of dry dioxane (5 mL), dry ethanol (5 mL), and dry toluene (5 mL) and heated at 105° C. for 30 minutes. The temperature was lowered to 90° C. and additional potassium acetate (1.2 g, 6.6 eq) was added. The mixture was stirred for another 90 minutes. After another 3 hours the reaction was evaporated to dryness under reduced pressure. Purification using silica chromatography (0-10% (2 N ammonia in methanol) in dichloromethane gradient) followed by repurification using reverse phase HPLC and free basing (ethyl acetate/saturated sodium bicarbonate) gave the desired N-(trans-3-(3-cyclopropyl-1H-pyrazolo[3,4-b]pyridin-1-yl)cyclobutyl)benzo[d]thiazol-2-amine (0.170 g, 0.470 mmol, 28.8% yield) as a white solid. M+1: 362.1. $^1$H NMR (400 MHz, CHLOROFORM-d) δ ppm 0.87-1.20 (m, 4 H) 2.12-2.22 (m, 1 H) 2.49-2.71 (m, 2 H) 3.00-3.26 (m, 2 H) 4.36-4.58 (m, 1 H) 5.63 (quin, J=7.24 Hz, 1 H) 6.61 (br. s., 1 H) 6.89-7.12 (m, 2 H) 7.21 (br. s., 1 H) 7.53 (m, J=7.80 Hz, 2 H) 7.94 (dd, J=7.82, 1.17 Hz, 1 H) 8.39 (dd, J=4.40, 1.08 Hz, 1 H).

Example 115

N-(trans-3-(3-(trifluoromethyl)-1H-pyrazolo[3,4-b]pyridin-1-yl)cyclobutyl)benzo[d]thiazol-2-amine

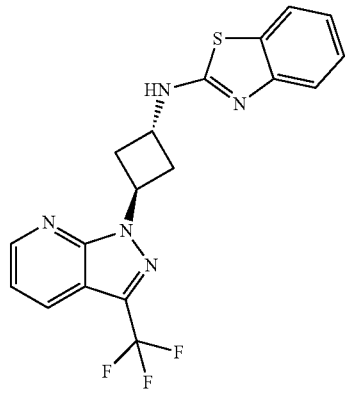 [SMILES: FC(F)(F)c1nn([C@H]2C[C@H](Nc3nc4ccccc4s3)C2)c2ncccc12]

Example 15 was prepared according to Method D2 of Example 114, wherein intermediate 54 was used in place of intermediate 53. M+1: 390. $^1$H NMR (400 MHz, CHLOROFORM-d) δ ppm 2.71-2.85 (m, 2 H) 3.20-3.35 (m, 2 H) 4.60 (tt, J=7.97, 4.16 Hz, 1 H) 5.85 (quin, J=7.48 Hz, 1 H) 7.11 (t, J=7.63 Hz, 1 H) 7.24-7.37 (m, 2 H) 7.57 (d, J=8.02 Hz, 1 H) 7.61 (d, J=7.82 Hz, 1 H) 8.19 (d, J=8.02 Hz, 1 H) 8.61 (dd, J=4.50, 1.17 Hz, 1 H).

Method D3

Example 116

1-(4-((1-(trans-3-(benzo[d]thiazol-2-ylamino)cyclobutyl)-1H-pyrazolo[3,4-b]pyridin-3-yl)amino)piperidin-1-yl)ethanone

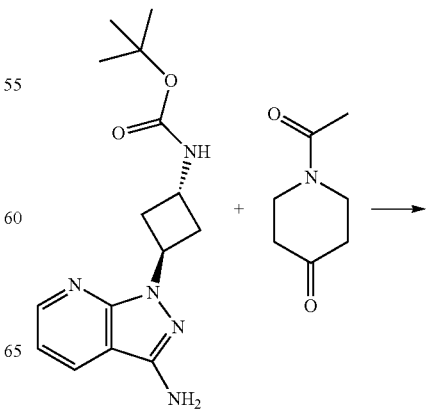

Step 1: tert-butyl(trans-3-(3-((1-acetylpiperidin-4-yl)amino)-1H-pyrazolo[3,4-b]pyridin-1-yl)cyclobutyl)carbamate

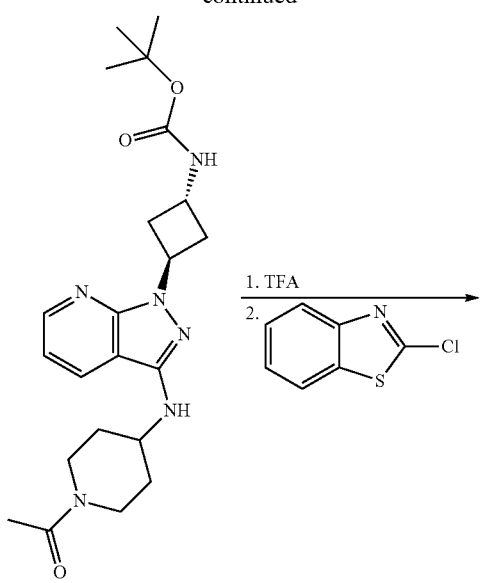

Tert-butyl(trans-3-(3-amino-1H-pyrazolo[3,4-b]pyridin-1-yl)cyclobutyl)carbamate (from example 113, step 2, 0.210 g, 0.692 mmol) was dissolved in methanol (4 mL) and acetic acid (3 drops). 1-Acetyl-4-piperidone (0.100 ml, 0.812 mmol) was added and the mixture heated at 60° C. for 1 hour. The solution was cooled and sodium cyanoborohydride (0.065 g, 1.034 mmol) was added. The reaction was stirred for 14 hours at room temperature. Saturated sodium bicarbonate (10 mL), water (50 mL) and ethyl acetate (100 mL) were added and the mixture stirred for 20 minutes. The phases were separated and the organic dried with magnesium sulfate before evaporating to dryness under reduced pressure. Purification using silica chromatography (0-10% methanol in dichloromethane gradient) gave the desired tert-butyl(trans-3-(3-((1-acetylpiperidin-4-yl)amino)-1H-pyrazolo[3,4-b]pyridin-1-yl)cyclobutyl)carbamate (0.134 g, 0.313 mmol, 45.2% yield).

Step 2: 1-(4-((1-(trans-3-(benzo[d]thiazol-2-ylamino)cyclobutyl)-1H-pyrazolo[3,4-b]pyridin-3-yl)amino)piperidin-1-yl)ethanone tert-Butyl(trans-3-(3-((1-acetylpiperidin-4-yl)amino)-1H-pyrazolo[3,4-b]pyridin-1-yl)cyclobutyl)carbamate was treated as in example 113 step 3 to give 1-(4-((1-(trans-3-(benzo[d]thiazol-2-ylamino)cyclobutyl)-1H-pyrazolo[3,4-b]pyridin-3-yl)amino)piperidin-1-yl)ethanone. M+1: 462.2. $^1$H NMR (400 MHz, CHLOROFORM-d) δ ppm 1.56 (t, J=12.03 Hz, 2 H) 2.14 (s, 3 H) 2.24 (d, J=12.91 Hz, 1 H) 2.33 (d, J=12.52 Hz, 1 H) 2.86 (d, J=5.09 Hz, 2 H) 2.99 (t, J=12.23 Hz, 1 H) 3.10-3.23 (m, 2 H) 3.26-3.38 (m, 1 H) 3.82-3.94 (m, 1 H) 3.94-4.06 (m, 1 H) 4.42-4.57 (m, 2 H) 5.59 (quin, J=6.99 Hz, 1 H) 6.90-7.03 (m, 1 H) 7.25-7.36 (m, 1 H) 7.48 (t, J=7.82 Hz, 1 H) 7.56-7.69 (m, 2 H) 7.96 (d, J=8.02 Hz, 1 H) 8.35-8.44 (m, 1 H).

Examples 117-121 were prepared according to Methods E1-E4 as follows:

Method E1

Example 117

3-(1-(1H-benzo[d]imidazole-2-carbonyl)azetidin-3-yl)-1H-imidazo[4,5-b]pyridin-2(3H)-one

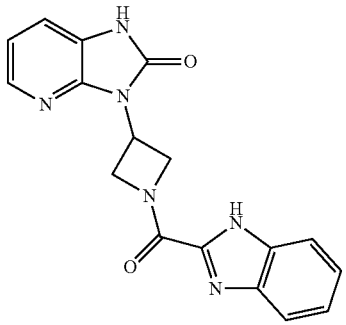 [SMILES: O=C(c1nc2ccccc2[nH]1)N1CC(n2c(=O)[nH]c3cccnc32)C1]

A mixture of tert-butyl 3-(2-methoxy-3H-imidazo[4,5-b]pyridin-3-yl)azetidine-1-carboxylate (intermediate 55, 450 mg, 1.479 mmol), trifluoroacetic acid (3.29 mL, 44.4 mmol) and dichloromethane (3 mL) was stirred at room temperature for 2 hours. The reaction mixture was concentrated under reduced pressure and dried under high vacuum. The crude 3-(azetidin-3-yl)-1H-imidazo[4,5-b]pyridin-2(3H)-one (250 mg, 0.598 mmol), 1H-benzimidazole-2-carboxylic acid (97 mg, 0.598 mmol), HBTU (227 mg, 0.598 mmol), triethylamine (0.416 mL, 2.99 mmol) and dry dimethylformamide (2 mL) were added to a 50 mL round bottom flask. The reaction mixture was stirred at room temperature for 12 hours. The reaction mixture was diluted with water and extracted with ethyl acetate. The organic extract was washed with saturated ammonium chloride and dried over magnesium sulfate before concentrating in vacuo to give the crude material as a tan solid. The crude material was absorbed onto a plug of silica gel and purified by chromatography through a Redi-Sep pre-packed silica gel column (12 g, hexane to ethyl acetate gradient) to provide 3-(1-(1H-benzo[d]imidazole-2-carbonyl)azetidin-3-yl)-1H-imidazo[4,5-b]pyridin-2(3H)-one (16 mg, 0.048 mmol, 8.01% yield) as off-white solid. M+1=335.1 $^1$H NMR (400 MHz, DMSO-d$_6$) δ ppm 4.42 (t, J=9.29 Hz, 1 H) 4.66 (dd, J=10.27, 6.16 Hz, 1 H) 4.97-5.03 (m, 1 H) 5.21-5.36 (m, 2 H) 6.92 (dd, J=7.82, 5.28 Hz, 1 H) 7.12-7.18 (m, 1 H) 7.18-7.25 (m, 2 H) 7.44 (d, J=7.82 Hz, 1 H) 7.62 (d, J=8.22 Hz, 1 H) 7.84 (dd, J=5.28, 1.37 Hz, 1 H) 11.13 (br. s., 1 H) 13.16 (br. s., 1 H)

Method E2

Example 118

1'-(1-(benzo[d]thiazole-2-carbonyl)azetidin-3-yl) spiro[cyclopropane-1,3'-pyrrolo[2,3-b]pyridin-]-2' (1'H)-one

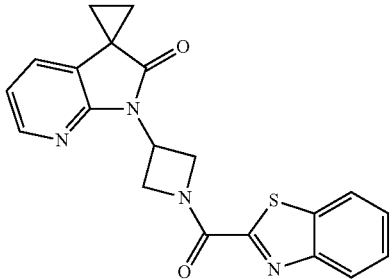 [SMILES: O=C(c1nc2ccccc2s1)N1CC(N2C(=O)C3(CC3)c3cccnc32)C1]

Tert-butyl 3-(2'-oxospiro[cyclopropane-1,3'-pyrrolo[2,3-b]pyridin]-1'(2H)-yl)azetidine-1-carboxylate (intermediate 56, 0.203 g, 0.644 mmol) was dissolved in dichloromethane (10 mL) and treated with trifluoroacetic acid (2 mL). The solution was stirred for 30 minutes after which the mixture was evaporated to dryness under reduced pressure and further dried under high vacuum. The crude amine was dissolved in dichloromethane (30 mL) and treated with N,N-diisopropylethylamine (0.5 ml, 2.87 mmol). 1,3-Benzothiazole-2-carbonyl chloride (0.150 g, 0.759 mmol) was added and the reaction stirred for 30 minutes. The mixture was evaporated to dryness under reduced pressure and the crude purified using silica chromatography (dichloromethane to ethyl acetate gradient) to give 1'-(1-(benzo[d]thiazole-2-carbonyl)azetidin-3-yl)spiro[cyclopropane-1,3'-pyrrolo[2,3-b]pyridin]-2'(1'H)-one (0.169 g, 0.449 mmol, 69.7% yield). $^1$H NMR (400 MHz, CHLOROFORM-d) δ ppm 1.54-1.62 (m, 2 H) 1.78-1.89 (m, 3 H) 4.60 (dd, J=10.56, 7.43 Hz, 1 H) 5.04-5.13 (m, 1 H) 5.14-5.24 (m, 1 H) 5.50-5.61 (m, 2 H) 6.93 (dd, J=7.24, 5.28 Hz, 1 H) 7.11 (dd, J=7.34, 1.27 Hz, 1 H) 7.43-7.55 (m, 2 H) 7.97 (d, J=7.24 Hz, 1 H) 8.05 (d, J=7.82 Hz, 1 H) 8.14 (dd, J=5.28, 1.37 Hz, 1 H)

Example 119

3,3-dimethyl-1-(1-picolinoylpiperidin-4-yl)-1H-pyrrolo[2,3-b]pyridin-2(3H)-one

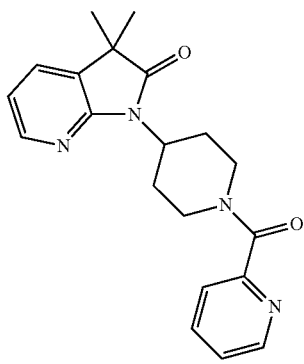 [SMILES: CC1(C)C(=O)N(C2CCN(C(=O)c3ccccn3)CC2)c2ncccc21]

Compound of Example 119 was prepared according to the above Method E1 of Example 117, wherein intermediate 57 was used in place of 3-(azetidin-3-yl)-1H-imidazo[4,5-b]pyridin-2(3H)-one, and picolinic acid was used in place of 1H-benzimidazole-2-carboxylic acid. (46% yield) M+1: 351.0. $^1$H NMR (400 MHz, CHLOROFORM-d) δ ppm 1.37 (s, 6 H) 1.65 (d, J=11.93 Hz, 1 H) 1.82 (d, J=10.76 Hz, 1 H) 2.68-2.86 (m, 2 H) 2.86-2.99 (m, 1 H) 3.23 (td, J=13.20, 1.96 Hz, 1 H) 4.13 (d, J=13.69 Hz, 1 H) 4.59 (tt, J=12.08, 3.96 Hz, 1 H) 4.95 (d, J=12.91 Hz, 1 H) 6.94 (dd, J=7.14, 5.38 Hz, 1 H) 7.34 (dd, J=6.65, 5.09 Hz, 1 H) 7.42 (dd, J=7.24, 1.56 Hz, 1 H) 7.68 (d, J=7.83 Hz, 1 H) 7.81 (td, J=7.73, 1.56 Hz, 1 H) 8.14 (dd, J=5.09, 1.37 Hz, 1 H) 8.61 (d, J=4.50 Hz, 1 H).

Method E3

Example 120

3,3-dimethyl-1-(1-(pyridin-2-yl)piperidin-4-yl)-1H-pyrrolo[2,3-b]pyridin-2(3H)-one

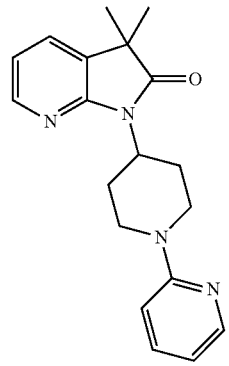 [SMILES: CC1(C)C(=O)N(C2CCN(c3ccccn3)CC2)c2ncccc21]

A mixture of 3,3-dimethyl-1-(piperidin-4-yl)-1H-pyrrolo[2,3-b]pyridin-2(3H)-one dihydrochloride (intermediate 57, 0.1167 g, 0.367 mmol), N-ethyl-N-isopropylpropan-2-amine (0.192 ml, 1.100 mmol), and 2-fluoropyridine (0.189 ml, 2.200 mmol) was stirred at 150° C. for 90 minutes. The mixture was filtered and was purified by reverse phase HPLC (10-55% in 30 min, acetonitrile in water with 0.1% trifluoroacetic acid). The collected fractions were neutralized with solid sodium carbonate and extracted with dichloromethane three times. The organic phase was dried over sodium sulfate and concentrated in vacuo to give 3,3-dimethyl-1-(1-(pyridin-2-yl)piperidin-4-yl)-1H-pyrrolo[2,3-b]pyridin-2(3H)-one (0.055 g, 0.171 mmol, 46.5% yield). M+1: 323.1. $^1$H NMR (400 MHz, CHLOROFORM-d) δ ppm 1.37 (s, 6 H) 1.72-1.84 (m, 2 H) 2.71-2.85 (m, 2 H) 2.95 (td, J=12.86, 1.86 Hz, 2 H) 4.43-4.65 (m, 3 H) 6.60 (dd, J=6.65, 5.28 Hz, 1 H) 6.71 (d, J=8.61 Hz, 1 H) 6.92 (dd, J=7.24, 5.28 Hz, 1 H) 7.41 (dd, J=7.24, 1.37 Hz, 1 H) 7.47 (ddd, J=8.71, 7.14, 1.96 Hz, 1 H) 8.12 (dd, J=5.18, 1.47 Hz, 1 H) 8.19 (dd, J=4.99, 1.08 Hz, 1 H)

213

Method E4

Example 121

3,3-dimethyl-1-(1-(5-methylpyridin-2-yl)piperidin-4-yl)-1H-pyrrolo[2,3-b]pyridin-2(3H)-one

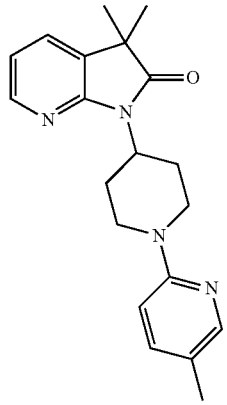 [SMILES: Cc1ccc(N2CCC(N3C(=O)C(C)(C)c4cccnc43)CC2)nc1]

A mixture of 3,3-dimethyl-1-(piperidin-4-yl)-1H-pyrrolo[2,3-b]pyridin-2(3H)-one dihydrochloride (intermediate 57, 0.2000 g, 0.628 mmol), cesium acetate (0.869 g, 4.52 mmol), 2-bromo-5-methylpyridine (0.119 g, 0.691 mmol), and dry dimethylsulfoxide (1.0 mL) was heated at 100° C. for 14 hours. Additional 2-bromo-5-methylpyridine (0.119 g, 0.691 mmol) and copper (7.99 mg, 0.126 mmol) were added to the mixture and the reaction was continued for an additional 14 hours. The mixture was diluted with ethyl acetate and ammonium hydroxide and the phases separated. The aqueous layer was extracted with ethyl acetate. The combined organic layers were dried over sodium sulfate and concentrated in vacuo. The crude product was purified by silica gel chromatography (0-100% ethyl acetate in hexane gradient) to give 3,3-dimethyl-1-(1-(5-methylpyridin-2-yl)piperidin-4-yl)-1H-pyrrolo[2,3-b]pyridin-2(3H)-one (0.052 g, 0.155 mmol, 24.6% yield). M+1: 337.0. $^1$H NMR (400 MHz, CHLOROFORM-d) δ ppm 1.37 (s, 6 H) 1.72-1.84 (m, 2 H) 2.20 (s, 3 H) 2.72-3.01 (m, 4 H) 4.40 (d, J=12.52 Hz, 2 H) 4.54 (tt, J=11.93, 3.91 Hz, 1 H) 6.66 (d, J=8.61 Hz, 1 H) 6.92 (dd, J=7.24, 5.28 Hz, 1 H) 7.31 (dd, J=8.61, 1.76 Hz, 1 H) 7.41 (dd, J=7.24, 1.37 Hz, 1 H) 8.02 (s, 1 H) 8.12 (dd, J=5.18, 1.27 Hz, 1 H).

Examples 122-123, 126, 133, and 136-137 were prepared according to Methods F1-F6 as follows:

Method F1

Example 122

(1H-benzo[d]imidazol-2-yl)(4-(2-methoxy-3H-imidazo[4,5-b]pyridine-3-yl)piperidin-1-yl)methanone

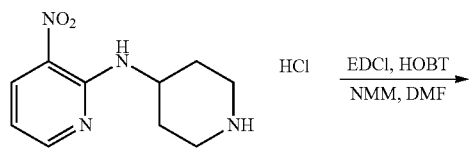

214

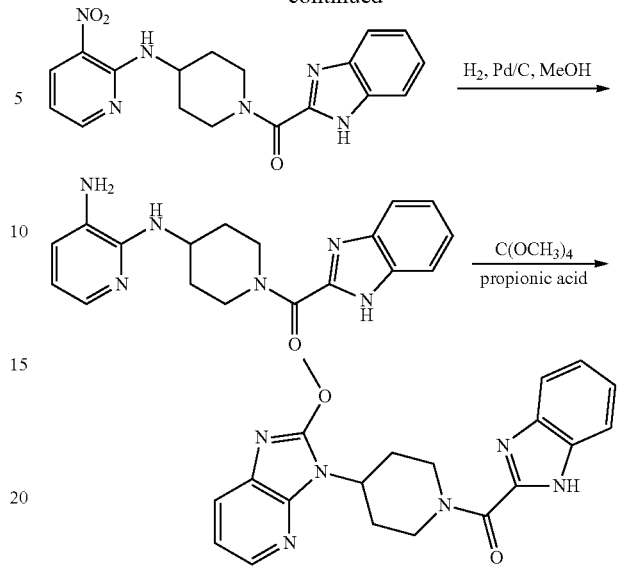

Step 1: (1H-benzo[d]imidazol-2-yl)(4-((3-nitro-pyridin-2-yl)amino)piperidin-1-yl)methanone A mixture of 3-nitro-N-(piperidin-4-yl)pyridin-2-amine hydrochloride (intermediate 58, 580 mg, 2.3 mmol), 1H-benzo[d]imidazole-2-carboxylic acid (365 mg, 2.3 mmol), 1H-benzo[d][1,2,3]triazol-1-ol (365 mg, 2.7 mmol), 1-(3-dimethylaminopropyl)-3-ethylcarbodiimide hydrochloride (516 mg, 2.7 mmol) and N-methylmorpholine (455 mg, 4.6 mmol) in dry dimethylformamide (15 mL) was stirred at room temperature overnight. The mixture was diluted with water (60 mL), and extracted with ethyl acetate (2×50 mL). The organic layer was washed with brine, dried over sodium sulfate and concentrated to give the crude compound which was purified by silica chromatography to afford (1H-benzo[d]imidazol-2-yl)(4-((3-nitro-pyridin-2-yl)amino)piperidin-1-yl)methanone (600 mg, 1.64 mmol, 72.8% yield).

Step 2: (4-((3-aminopyridin-2-yl)amino)piperidin-1-yl)(1H-benzo[d]imidazol-2-yl)methanone A mixture of (H-benzo[d]imidazol-2-yl)-4-((3-nitro-pyridin-2-yl)amino)piperidin-1-yl)methanone (600 mg, 1.64 mmol) and palladium on carbon (50% by wt., 300 mg) in methanol (10 mL) was stirred under hydrogen at 30 psi for 2 hours. The mixture was filtered through a pad of CELITE™ and the filtrate was concentrated to give (4-((3-aminopyridin-2-yl)amino)piperidin-1-yl)(1H-benzo[d]imidazol-2-yl)methanone (520 mg, 1.55 mmol, 94.4% yield) which was used in the next step without further purification.

Step 3: (1H-benzo[d]imidazol-2-yl)(4-(2-methoxy-3H-imidazo[4,5-b]pyridin-3-yl)piperidin-1-yl)methanone (4-((3-Amino-pyridin-2-yl)amino)piperidin-1-yl)(1H-benzo[d]imidazol-2-yl)methanone (520 mg, 1.55 mmol) was combined with tetramethylorthocarbonate (2 mL) and propionic acid (8 mg) and heated at 90° C. for 2 hours. After that, the reaction solution was concentrated under reduced pressure and the residue was purified by silica chromatography to give (1H-benzo[d]imidazol-2-yl)(4-(2-methoxy-3H-imidazo

[4,5-b]pyridin-3-yl)piperidin-1-yl)methanone (57 mg, 0.15 mmol, 9.8% yield). M+1: 377.

Method F2

Example 123

2-(4-(2-methoxy-3H-imidazo[4,5-b]pyridine-3-yl)piperidin-1-yl)benzo[d]thiazole

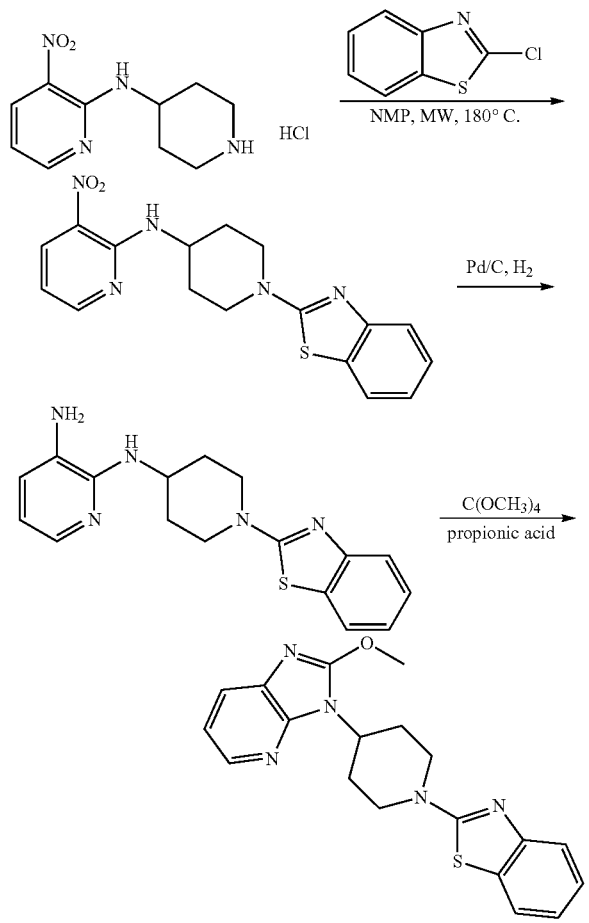

Step 1: N-(1-(benzo[d]thiazol-2-yl)piperidin-4-yl)-3-nitropyridin-2-amine

A mixture of 3-nitro-N-(piperidin-4-yl)pyridine-2-amine hydrochloride (intermediate 58, 500 mg, 2.24 mmol) and 2-chloro-benzo[d]thiazole (379 mg, 2.24 mmol) in N-methylpyrrolidine (5 mL) was heated at 180° C. in microwave for 2 hours. The mixture was diluted with water (60 mL) and extracted with ethyl acetate (2×50 mL). The organic layer was dried over sodium sulfate and concentrated under reduced pressure. Purification by silica chromatography gave N-(1-(benzo[d]thiazol-2-yl)piperidin-4-yl)-3-nitropyridin-2-amine (270 mg, 0.76 mmol, 33.8% yield).

Step 2: $N^2$-(1-(benzo[d]thiazol-2-yl)piperidin-4-yl)pyridine-2,3-diamine

A mixture of N-(1-(benzo[d]thiazol-2-yl)piperidin-4-yl)-3-nitropyridin-2-amine (270 mg, 0.76 mmol) and palladium on activated carbon (50% by wt, 0.15 g) in methanol (10 mL) was stirred under hydrogen at 30 psi for 2 hours. The mixture was filtered through a pad of CELITE™ and the filtrate was concentrated to give $N^2$-(1-(benzo[d]thiazol-2-yl)piperidin-4-yl)pyridine-2,3-diamine (200 mg, 0.61 mmol, 81.3% yield) which was used in the next step without further purification.

Step 3: 2-(4-(2-methoxy-3H-imidazo[4,5-b]pyridine-3-yl)piperidin-1-yl)benzo[d]thiazole $N^1$-(1-(Benzo[d]thiazol-2-yl)piperidin-4-yl)pyridine-2,3-diamine (200 mg, 0.61 mmol) was combined with tetramethylorthocarbonate (2 mL) and propionic acid (8 mg) and heated at 90° C. for 2 hours. After that, the reaction solution was concentrated under reduced pressure and the residue was purified by silica chromatography to give 2-(4-(2-methoxy-3H-imidazo[4,5-b]pyridine-3-yl)piperidin-1-yl)benzo[d]thiazole (30 mg, 0.082 mmol, 13.4% yield). M+1: 366.

Method F3

Example 126

2-(3-(2-methoxy-3H-imidazo[4,5-b]pyridin-3-yl)azetidin-1-yl)quinoline

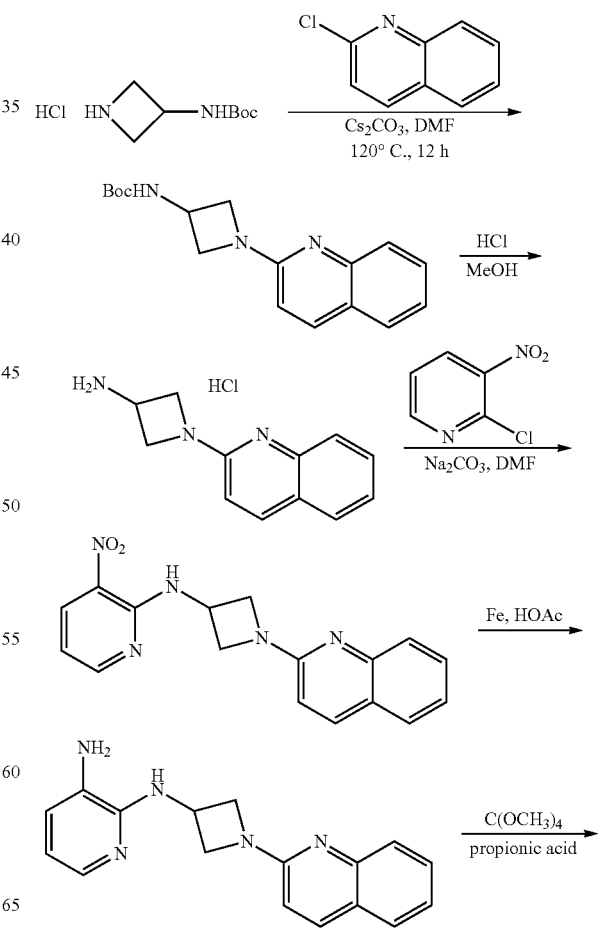

-continued

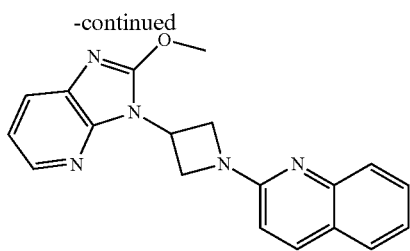

Step 1: tert-butyl(1-(quinolin2-yl)azetidin-3-yl)-carbamate

Cesium carbonate (4.68 g, 14.4 mmol), 2-chloroquinoline (0.782 g, 4.8 mmol) and tert-butyl azetidin-3-yl-carbamate hydrochloride (1.0 g, 4.8 mmol) were dissolved in dry dimethylformamide (15 mL) and the resulting mixture was heated at 120° C. overnight. The mixture was diluted with water (40 mL) and extracted with ethyl acetate (2×50 mL). The combined organic extracts were washed with water (30 mL) and brine (30 mL), then dried over sodium sulfate. The organic was evaporated in vacuo and the residue was purified by flash column chromatography on silica gel (20% to 40% ethyl acetate in petroleum ether) to give tert-butyl (1-(quinolin-2-yl)azetidin-3-yl)-carbamate (1.14 g, 3.84 mmol, 80% yield) as white solid.

Step 2: 1-(quinolin2-yl)azetidin-3-amine hydrochloride

To tert-butyl (1-(quinolin-2-yl)azetidin-3-yl)-carbamate (1.14 g, 3.84 mmol) was added hydrogen chloride (4 M solution in methanol, 20 mL). The reaction mixture was stirred at room temperature for 1 hour. It was concentrated to give 1-(quinolin-2-yl)azetidin-3-amine hydrochloride (0.90 g, 3.84 mmol, 100% yield) which was used in the next step without further purification.

Step 3: 3-nitro-N-(1-(quinolin2-yl)azetidin-3-yl)pyridin-2-amine

To a solution of 1-(quinolin-2-yl)azetidin-3-amine hydrochloride (0.90 g, 3.84 mmol) in dry dimethylformamide (15 mL) was added sodium carbonate (1.22 g, 11.5 mmol) and 2-chloro-3-nitro-pyridine (608 mg, 3.84 mmol). The reaction mixture was stirred and heated at reflux for 14 hours. The reaction mixture was diluted with water (25 mL) and extracted with ethyl acetate (2×30 mL). The combined organic extracts were washed with water (30 mL), brine (30 mL), and dried over sodium sulfate. The filtrate was evaporated in vacuo and the residue was purified by column chromatography on silica gel (20% to 50% ethyl acetate in petroleum ether) to give 3-nitro-N-(1-(quinolin-2-yl)azetidin-3-yl)pyridin-2-amine (1.05 g, 3.20 mmol, 85% yield) as yellow solid.

Step 4: $N^2$-(1-(quinolin2-yl)azetidin-3-yl)pyridine-2,3-diamine

To a solution of 3-nitro-N-(1-(quinolin-2-yl)azetidin-3-yl)pyridin-2-amine (1.05 g, 3.20 mmol) in ethanol (30 mL) and water (10 mL) was added iron (448 mg, 8.0 mmol) and acetic acid (240 mg, 4.0 mmol) slowly dropwise. The mixture was heated at 95° C. until TLC analysis confirmed the absence of starting materials. The reaction mixture was filtered through a plug of CELITE™ washing with methanol. The black filtrate was concentrated in vacuo, treated with brine (40 mL) and extracted with dichloromethane (3×60 mL). The combined organic extracts were washed with water (30 mL) and brine (30 mL) and then dried over sodium sulfate. The filtrate was evaporated in vacuo to give $N^2$-(1-(quinolin-2-yl)azetidin-3-yl)pyridine-2,3-diamine (0.744 g, 2.6 mmol, yield 80%).

Step 5: 2-(3-(2-methoxy-3H-imidazo[4,5-b]pyridin-3-yl)azetidin-1-yl)quinoline $N^2$-(1-Quinolin-2-yl-azetidin-3-yl)-pyridine-2,3-diamine (150 mg, 0.51 mmol) was combined with tetramethylorthocarbonate (1 mL) and propionic acid (8 mg) and heated at 90° C. for 2 hours. After that, the reaction solution was concentrated under reduced pressure and the residue was purified by column chromatography on silica gel to give 2-(3-(2-methoxy-3H-imidazo[4,5-b]pyridin-3-yl)azetidin-1-yl)quinoline (100 mg, 0.30 mmol, 59% yield). M+1: 332. $^1$H NMR (CDCl$_3$, 400 MHz): δ(ppm) 8.06-8.05 (m, 1 H); 7.87-7.85 (m, 1 H); 7.72-7.68 (m, 2 H); 7.58-7.47 (m, 2 H); 7.20-7.17 (m, 1 H); 7.06-7.03 (m, 1 H); 6.62-6.60 (m, 1 H); 5.62-5.55 (m, 1 H); 4.84-4.80 (m, 2 H); 4.61-4.57 (m, 2 H); 4.10 (s, 3 H).

Method F4

Example 133

N-(4-(2-methoxy-3H-imidazo[4,5-b]pyridin-3-yl)cyclohexyl)-1H-benzo[d]imidazol-2-amine

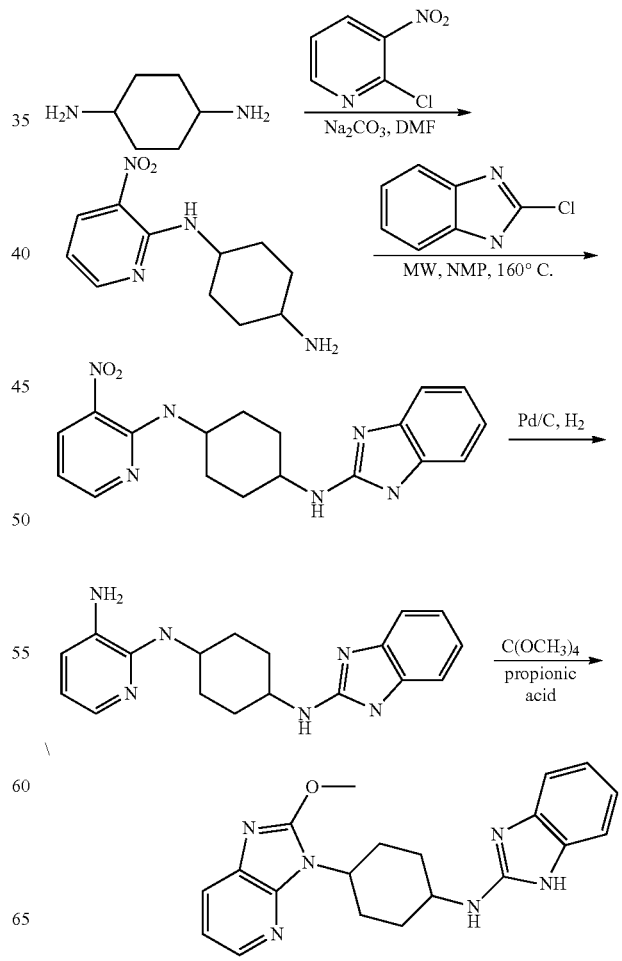

Step 1: N¹-(3-nitropyridin-2-yl)cyclohexane-1,4-diamine

2-Chloro-3-nitropyridine (10 g, 63.3 mmol), cyclohexane-1,4-diamine (7.2 g, 63.3 mmol), anhydrous dimethylformamide (100 mL) and anhydrous sodium carbonate (13.4 g, 126 mmol) were combined with stirring under nitrogen. The reaction mixture was stirred at room temperature for 14 hours. It was poured into water and the resulting orange solid was filtered off and found to be N¹-(3-nitropyridin-2-yl)cyclohexane-1,4-diamine (8.2 g, 34.7 mmol, 54.9% yield) which was used in the next step without further purification.

Step 2: N¹-(1H-benzo[d]imidazol-2-yl)-N⁴-(3-nitropyridin-2-yl)cyclohexane-1,4-diamine A mixture of N¹-(3-nitropyridin-2-yl)cyclohexane-1,4-diamine (500 mg, 2.11 mmol) and 2-chloro-1H-benzoimidazole (320 mg, 2.11 mmol) in N-methylpyrrolidinone (5 mL) was heated at 180° C. in microwave for 2 hours. The mixture was diluted with water (60 mL), and extracted with ethyl acetate (2×50 mL). The organic layer was dried over sodium sulfate and concentrated to give N¹-(1H-benzo[d]imidazol-2-yl)-N⁴-(3-nitropyridin-2-yl)cyclohexane-1,4-diamine (400 mg, 1.13 mmol, 53.8% yield) which was used in the next step without further purification.

Step 3: N²-[4-((1H-benzo[d]imidazol-2-yl)amino)cyclohexyl)pyridine-2,3-diamine A mixture of N¹-(1H-benzo[d]imidazol-2-yl)-N⁴-(3-nitropyridin-2-yl)cyclohexane-1,4-diamine (400 mg, 1.13 mmol) and palladium on activated carbon (50% by wt, 0.20 g) in methanol (10 mL) was stirred under hydrogen at 30 psi for 2 hours. The mixture was filtered through a pad of CELITE™ and the filtrate was concentrated to give N²-[4-((1H-benzo[d]imidazol-2-yl)amino)cyclohexyl)pyridine-2,3-diamine (320 mg, 0.99 mmol, 87.4% yield) which was used in the next step without further purification.

Step 4: N-(4-(2-methoxy-3H-imidazo[4,5-b]pyridin-3-yl)cyclohexyl)-1H-benzo[d]imidazol-2-amine N²-[4-((1H-Benzo[d]imidazol-2-yl)amino)cyclohexyl)pyridine-2,3-diamine (320 mg, 0.99 mmol) was combined with tetramethylorthocarbonate (2 mL) and propionic acid (8 mg), the mixture was heated at 90° C. for 2 hours. After that, the reaction solution was concentrated under reduced pressure and the residue was purified by silica chromatography to give N-(4-(2-methoxy-3H-imidazo[4,5-b]pyridin-3-yl)cyclohexyl)-1H-benzo[d]imidazol-2-amine (50 mg, 0.14 mmol, 14.4% yield). M+1: 380.

Method F5

Example 136

1H-benzo[d]imidazol-2-yl)(3-(2-methoxy-3H-imidazo[4,5-b]pyridin-3-yl)cyclobutyl)methanol

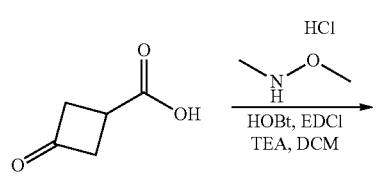

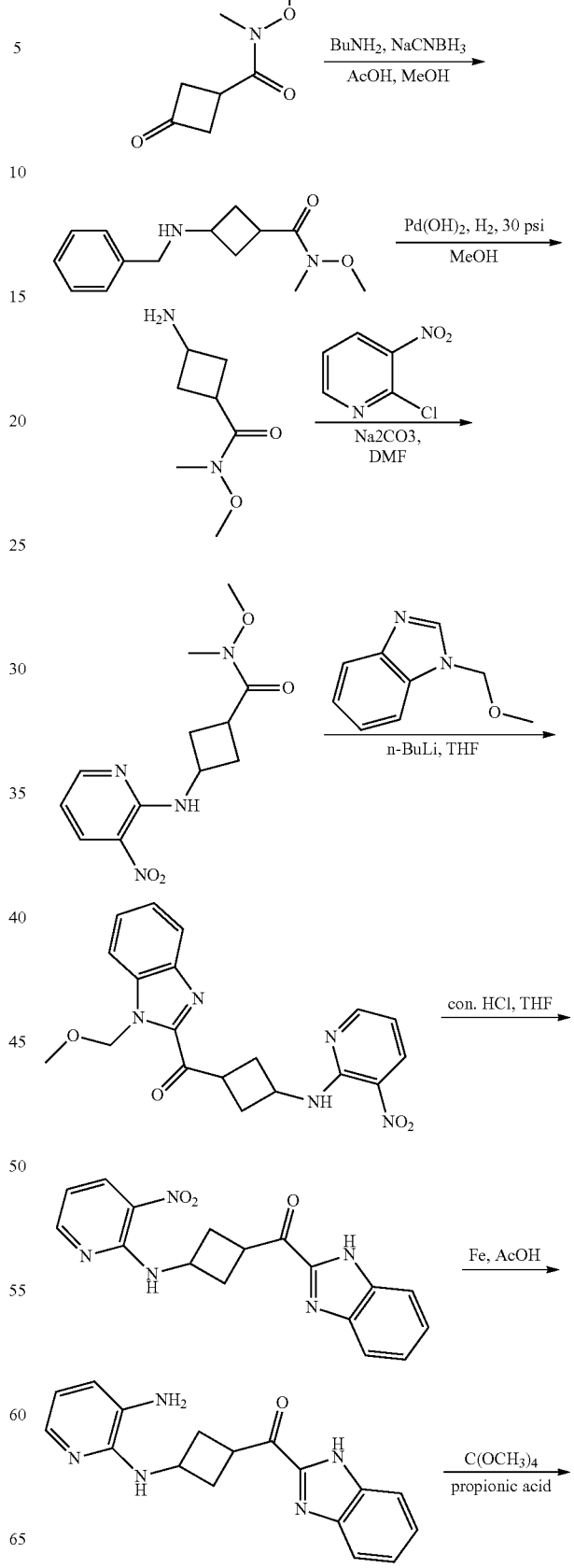

-continued

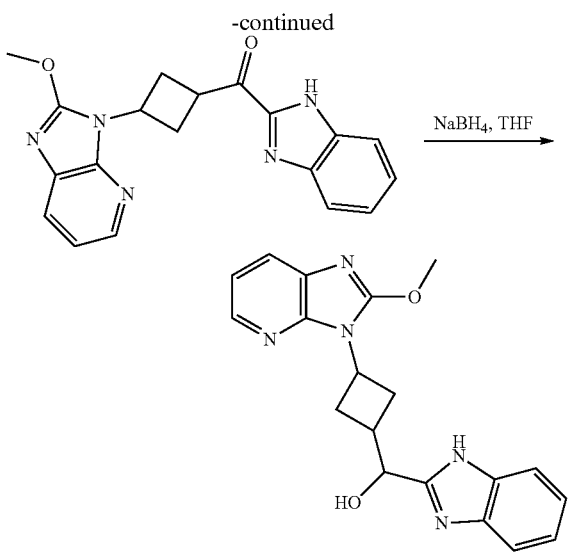

Step 1: N-methoxy-N-methyl-3-oxocyclobutanecarboxamide

A mixture of 3-oxo-cyclobutanecarboxylic acid (2.28 g, 20.0 mmol), O,N-dimethyl-hydroxylamine hydrochloride (1.94 g, 20.0 mmol), 1-hydroxybenzotriazole (2.99 g, 22.0 mmol), (3-dimethylamino-propyl)-ethyl-carbodiimide hydrochloride (4.22 g, 22.0 mmol) and triethylamine (4.04 g, 40.0 mmol) in dichloromethane (50 mL) was stirred at room temperature for 24 hours. The mixture was diluted with water (30 mL), and extracted with dichloromethane (2×30 mL). The combined organic extracts were washed with water (20 mL) and brine (20 mL), and dried over sodium sulfate. The filtrate was evaporated in vacuo and the residue was purified by silica chromatography to provide N-methoxy-N-methyl-3-oxocyclobutanecarboxamide (2.68 g, 17.0 mmol, yield: 85%).

Step 2: 3-(benzylamino)-N-methoxy-N-methylcyclobutanecarboxamide

Benzylamine (751 mg, 7.02 mmol), N-methoxy-N-methyl-3-oxocyclobutanecarboxamide (423 mg, 2.70 mmol), and sodium cyanoborohydride (237 mg, 3.78 mmol) were dissolved in 25 mL of anhydrous methanol. The pH of the solution was brought to 5 by addition of acetic acid, and the reaction was stirred for 24 hours at room temperature. The pH of the solution then was brought to 8 by addition of 1 M aqueous sodium bicarbonate. The solvents were removed under reduced pressure. The crude product was partitioned between ethyl acetate (80 mL) and water (25 mL). The organic layer was washed with water and brine and dried, purified using flash column chromatography with hexanes/ethyl acetate (2:1) as an eluant to give 3-(benzylamino)-N-methoxy-N-methylcyclobutanecarboxamide (498 mg, 2.00 mmol, 75% yield) as an oil.

Step 3: 3-amino-N-methoxy-N-methylcyclobutanecarboxamide

A mixture of 3-(benzylamino)-N-methoxy-N-methylcyclobutanecarboxamide (349 mg, 2.2 mmol) and wet palladium hydroxide on activated carbon (50 wt %, 200 mg) in methanol (30 mL) was stirred under hydrogen (30 psi) at room temperature for 13 hours then the reaction mixture was filtered through CELITE™ H and washed with methanol. The filtrate was concentrated in vacuo to give 3-amino-N-methoxy-N-methylcyclobutanecarboxamide (332 mg, 2.09 mmol, yield 95%).

Step 4: N-methoxy-N-methyl-3-((3-nitropyridin-2-yl)amino) cyclobutanecarboxamide To a solution of 3-amino-N-methoxy-N-methylcyclobutanecarboxamide (0.606 g, 3.84 mmol) in dry dimethylformamide (15 mL) was added sodium carbonate (1.22 g, 11.5 mmol) and 2-chloro-3-nitropyridine (608 mg, 3.84 mmol). The reaction mixture was stirred and heated at reflux for 14 hours. The reaction mixture was diluted with water (25 mL) and extracted with ethyl acetate (2×30 mL). The combined organic extracts were washed with water (30 mL), brine (30 mL) and dried over sodium sulfate. The filtrate was evaporated in vacuo and the residue was purified by column chromatography on silica gel (20% to 50% ethyl acetate in petroleum ether) to give N-methoxy-N-methyl-3-((3-nitropyridin-2-yl)amino)cyclobutanecarboxamide (0.86 g, 3.07 mmol, 80% yield) as yellow solid.

Step 5: (1-(methoxymethyl)-1H-benzo[d]imidazol-2-yl)-3-((3-nitropyridin-2-yl)amino)-cyclobutyl)methanone To a solution of 1-(methoxymethyl)-1H-benzo[d]imidazole (1.5 g, 9.04 mmol) in dry tetrahydrofuran (20 mL) at −78° C. was added butyllithium (2.5 M in hexane, 3.7 mL, 9.16 mmol). The solution was stirred at −78° C. for 30 min and a solution of N-methoxy-N-methyl-3-((3-nitropyridin-2-yl)amino)cyclobutanecarboxamide (1.92 g, 6.87 mmol) in dry tetrahydrofuran (20 mL) was added dropwise via cannula. The reaction mixture was stirred at −78° C. for 30 minutes and then warmed to room temperature and quenched with water. The reaction mixture was extracted with ethyl acetate (3×30 mL) and the organic phases were combined and washed with water (20 mL), then brine (20 mL). The organic was dried over magnesium sulfate and concentrated to get a residue, which was purified by flash column chromatography on silica gel (10% to 40% ethyl acetate in hexanes) to give (1-(methoxymethyl)-1H-benzo[d]imidazol-2-yl)(3-((3-nitropyridin-2-yl)amino)-cyclobutyl)methanone (1.17 g, 3.07 mmol, 80% yield) as solid.

Step 6: (1H-benzo[d]imidazol-2-yl)(3-((3-nitropyridin-2-yl)amino)cyclobutyl)methanone To a solution of (1-(methoxymethyl)-1H-benzo[d]imidazol-2-yl)(3-((3-nitropyridin-2-yl)amino)-cyclobutyl)methanone (534 mg, 1.40 mmol) in tetrahydrofuran (20 mL) at room temperature was added concentrated hydrochloric acid (20 mL). The reaction mixture was stirred at room temperature for 1 hour and then heated at 60° C. for 6 hours. The mixture was partially concentrated, neutralized with aqueous saturated sodium bicarbonate and diluted with ethyl acetate. The aqueous phase was extracted with ethyl acetate (2×40 mL) and the combined organic extracts were washed with brine (20 mL). The organic was dried over magnesium sulfate and concentrated to get a residue, which was purified by flash column chromatography on silica gel (10% to 40% ethyl acetate in petroleum ether) to give (1H-benzo[d]imidazol-2-yl)(3-((3-nitropyridin-2-yl)amino)cyclobutyl)methanone (0.57 g, 1.30 mmol, 92% yield) as solid.

Step 7: (3-((3-aminopyridin-2-yl)amino)cyclobutyl)(1H-benzo[d]imidazol-2-yl)methanone To a solution of (1H-benzo[d]imidazol-2-yl)-3-((3-nitropyridin-2-yl)amino)cyclobutyl)methanone (0.57 g, 1.30 mmol) in ethanol (30 mL) and water (10 mL) was added iron (364 mg, 6.5 mmol) and acetic acid (dropwise, 180 mg, 3.0 mmol). The mixture was heated at 95° C. until TLC analysis confirmed the absence of starting materials. The reaction mixture was filtered through a plug of CELITE™ washing with methanol. The black filtrate was concentrated in vacuo, treated with brine (40 mL) and extracted with dichloromethane (3×60 mL). The combined organic extracts were washed with water (30 mL) and brine (30 mL), then dried over sodium sulfate. The filtrate was evaporated in vacuo to give (3-((3-aminopyridin-2-yl)amino)cyclobutyl)(1H-benzo[d]imidazol-2-yl)methanone (0.319 g, 1.04 mmol, yield 80%).

Step 8: (1H-benzo[d]imidazol-2-yl)(3-(2-methoxy-3H-imidazo[4,5-b]pyridin-3-yl)cyclobutyl)methanone (3-((3-Aminopyridin-2-yl)amino)cyclobutyl)(1H-benzo[d]imidazol-2-yl)methanone (150 mg, 0.48 mmol) was combined with tetramethylorthocarbonate (1 mL) and propionic acid (8 mg) and heated at 90° C. for 2 hours. After that, the reaction solution was concentrated under reduced pressure and the residue was purified by column chromatography on silica gel to give (1H-benzo[d]imidazol-2-yl)-3-(2-methoxy-3H-imidazo[4,5-b]pyridin-3-yl)cyclobutyl)methanone (110 mg, 0.32 mmol, 65% yield).

Step 9: (1H-benzo[d]imidazol-2-yl)(3-(2-methoxy-3H-imidazo[4,5-b]pyridin-3-yl)cyclobutyl)methanol (1H-benzo[d]imidazol-2-yl)(3-(2-methoxy-3H-imidazo[4,5-b]pyridin-3-yl)cyclobutyl)methanone (60 mg, 0.17 mmol) was dissolved in dry tetrahydrofuran (10 mL) and treated with sodium borohydride (11 mg, 0.29 mmol). The reaction was stirred at room temperature until the starting material was consumed by TLC. After that, the reaction solution was concentrated under reduced pressure and the residue was purified by column chromatography on silica gel, followed by prep. TLC (dichloromethane:methanol=10:1) to give two isomers of (1H-benzo[d]imidazol-2-yl)-3-(2-methoxy-3H-imidazo[4,5-b]pyridin-3-yl)cyclobutyl)methanol as mixtures of diastereomers. M+1: 367.

Method F6

Example 137

N-(trans-3-(2-methoxy-3H-imidazo[4,5-b]pyridin-3-yl)cyclobutyl)-3,4-dihydroquinoxalin-2-amine

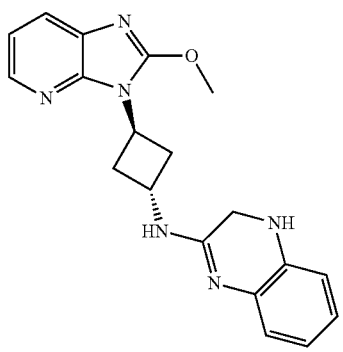 [SMILES: COc1nc2cccnc2n1[C@H]1C[C@H](NC2=Nc3ccccc3NC2)C1]

To a 15-mL round-bottomed flask was added 7-chloro-N-(−3-(2-methoxy-3H-imidazo[4,5-b]pyridin-3-yl)cyclobutyl)quinoxalin-2-amine (example 19, 118 mg, 0.310 mmol) and palladium on activated carbon (10 wt. %, 33.0 µl, 0.310 mmol) in methanol. The reaction mixture was stirred under a hydrogen balloon for 3 days. The solution was filtered and concentrated in vacuo to give the crude material as a yellow oil. The crude material was absorbed onto a plug of silica gel and purified by chromatography through a Redi-Sep prepacked silica gel column (4 g, 0-20% (2M ammonia in methanol) in dichloromethane gradient) to provide N-(trans-3-(2-methoxy-3H-imidazo[4,5-b]pyridin-3-yl)cyclobutyl)-3,4-dihydroquinoxalin-2-amine (80 mg, 0.230 mmol, 74.1% yield) as light-yellow glass. M+1: 349.1. $^1$H NMR (300 MHz, CHLOROFORM-d) δ ppm 1.68 (br. s, 1 H) 2.52 (d, J=2.05 Hz, 2 H) 3.33-3.52 (m, 2 H) 3.81 (s, 2 H) 4.25 (s, 3 H) 4.68-4.81 (m, 1 H) 5.40 (quin, J=8.59 Hz, 1 H) 6.58 (dd, J=7.53, 1.39 Hz, 1 H) 6.76 (td, J=7.50, 1.60 Hz, 1 H) 6.84 (td, J=7.50, 1.60 Hz, 1 H) 7.05 (d, J=7.16 Hz, 1 H) 7.10 (dd, J=7.82, 5.04 Hz, 1 H) 7.75 (dd, J=7.82, 1.39 Hz, 1 H) 8.16 (dd, J=4.97, 1.46 Hz, 1 H).

Examples 124-125, 127-132, and 134-135 were prepared according to methods analogous to the above methods F1-F6 as specified in Table 7 below:

TABLE 7

Preparation of Examples 124-125, 127-132, and 134-135

| Ex # | Method | Reagent | M + 1 | NMR |
|---|---|---|---|---|
| 124 | F1 | Intermediate 58, benzo[d]thiazole-2-carboxylic acid | 394 | |
| 125 | F2 | Intermediate 58, 2-chloro-1H-benzo[d]imidazole | 349 | |
| 127 | F3 | 2-Chloro-4-methylpyrimidine | 297 | $^1$H NMR (CD$_3$OD, 400 MHz): δ (ppm) 8.18-8.17 (m, 1 H); 8.08-8.06 (m, 1 H); 7.75-7.73 (m, 1 H); 7.17-7.13 (m, 1 H); 6.61-6.60 (m, 1 H); 5.61-5.55 (m, 1 H); 4.82-4.80 (m, 2 H); 4.56-4.50 (m, 2 H); 4.17 (s, 3 H); 2.36 (s, 3 H). |
| 128 | F3 | 2-Chloro-5-methylpyrimidine | 297 | $^1$H NMR (CDCl$_3$, 400 MHz): δ (ppm) 8.19 (s, 2 H); 8.10-8.08 (m, 1 H); 7.73-7.70 (m, 1 H); 7.09-7.06 (m, 1 H); 5.61-5.53 (m, 1 H); 4.81-4.77 (m, 2 H); 4.54-4.15 (m, 2 H); 4.15 (s, 3 H); 2.14 (s, 3 H). |
| 129 | F3 | 2-Chloroquinazoline | 333 | $^1$H NMR (CDCl$_3$, 400 MHz): δ (ppm) 9.00 (s, 1 H); 8.05-8.04 (m, 1 H); 7.70-7.58 (m, 4 H); 722-7.18 (m, 1 H); 7.05-7.02 (m, 1 H); 5.62-5.55 (m, 1 H); 4.90-4.87 (m, 2 H); 4.67-4.63 (m, 2 H); 4.11 (s, 3 H). |

TABLE 7-continued

Preparation of Examples 124-125, 127-132, and 134-135

| Ex # | Method | Reagent | M + 1 | NMR |
|------|--------|---------|-------|-----|
| 130 | F3 | Intermediate 59 | 374 | ¹H NMR (CDCl₃, 400 MHz): δ (ppm) 9.12-9.11 (m, 1 H); 8.43-8.42 (m, 1 H); 8.26-8.23 (m, 1 H); 8.13-8.11 (m, 1 H); 7.76-7.73 (m, 1 H); 7.24-7.23 (m, 1 H); 7.11-7.08 (m, 1 H); 7.02-7.01 (m, 1 H); 5.63-5.60 (m, 1 H); 4.91-4.85 (m, 2 H); 4.66-4.64 (m, 2 H); 4.18 (s, 3 H); 2.60 (s, 3 H). |
| 131 | F3 | 2-Chlorobenzo[d]thiazole | 338 | |
| 132 | F3 | 2-Chloro-1H-benzoidlimidazole | 321 | |
| 134 | F4 | 2-Chloro-1H-benzo[d]imidazole | 363 | |
| 135 | A4 | See example 5 | 352 | |

Example 138

3-(cis)-3-(benzo[d]thiazol-2-ylamino)cyclobutyl)-1-methyl-1H-imidazo[4,5-b]pyridin-2(3H)-one

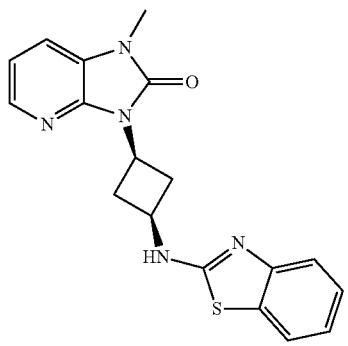 [SMILES: Cn1c(=O)n([C@H]2C[C@@H](Nc3nc4ccccc4s3)C2)c2ncccc21]

Following the procedure described for Example 87 (MethOD C3), using methyl (2-chloropyridin-3-yl)(methyl)carbamate, INTERMEDIATE 40, (0.196 g, 0.977 mmol), cis-N1-(benzo[d]thiazol-2-yl)cyclobutane-1,3-diamine dihydrochloride, (INTERMEDIATE 60), (0.285 g, 0.977 mmol), sodium tert-butoxide (0.478 mL, 3.91 mmol) and chloro(2-dicyclohexylphosphino-3,6-dimethoxy-2'-4'-6'-triisopropyl-1,1'-biphenyl)][2-(2-aminoethyl)Ph]Pd(II) (0.078 g, 0.098 mmol) in dioxane (3 mL) afforded the title compound (0.187 g, 0.532 mmol, 54.5% yield). m/z: 352.1 (M+1); ¹H NMR (400 MHz, CHLOROFORM-d) δ: ppm 8.10 (dd, J=5.18, 1.27 Hz, 1 H), 7.50-7.66 (m, 2 H), 7.24-7.36 (m, 1 H), 7.15-7.22 (m, 1 H), 6.98-7.13 (m, 2 H), 6.57 (br. s., 1 H), 4.95 (quin, J=8.36 Hz, 1 H), 4.31 (br. s., 1 H), 3.42 (s, 3 H), 2.98-3.21 (m, 4 H).

Example 139

7,7-dimethyl-5-(cis-3-((5-methylpyridin-2-yl)amino)cyclobutyl)-5H-pyrrolo[2,3-b]pyrazin-6(7H)-one

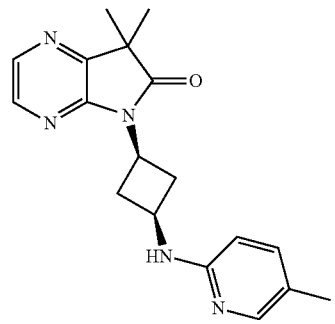 [SMILES: Cc1ccc(N[C@H]2C[C@@H](N3C(=O)C(C)(C)c4nccnc43)C2)nc1]

A solution of 2-(3-chloropyrazin-2-yl)-2-methylpropanoic acid (0.200 g, 0.997 mmol), (INTERMEDIATE 29), in DCE (2 mL) was treated with thionyl chloride (2 ml, 27.4 mmol) at room temperature and the resulting solution heated to 60° C. for 1 h and concentrated. The residue obtained was dissolved in THF (5 mL) and triethylamine (0.416 ml, 2.99 mmol) and cis-N1-(5-methylpyridin-2-yl)cyclobutane-1,3-diamine trihydrochloride (INTERMEDIATE 61) (0.314 g, 1.097 mmol) were added. After stirring at room temperature for 30 minutes, sodium tert-butoxide (0.610 ml, 4.98 mmol) was added. The reaction mixture was stirred at room temperature for another 1 h, then diluted with water and extracted with EtOAc. EtOAc was concentrated and residue purified with ISCO eluting with 0-80% EtOAc/hexanes to afford the title compound 7,7-dimethyl-5-(cis-3-((5-methylpyridin-2-yl)amino)cyclobutyl)-5H-pyrrolo[2,3-b]pyrazin-6(7H)-one (0.192 g, 0.594 mmol, 59.6% yield). m/z: 324.2 (M+1); ¹H NMR (400 MHz, CHLOROFORM-d) δ; ppm 8.02-8.16 (m, 2 H), 7.93 (d, J=0.78 Hz, 1 H), 7.25-7.31 (m, 2 H), 6.37 (d, J=8.41 Hz, 1 H), 4.99 (d, J=8.41 Hz, 1 H), 4.79 (quin, J=8.71 Hz, 1 H), 4.02-4.26 (m, 1 H), 2.92-3.06 (m, 3 H), 2.74-2.90 (m, 3 H), 2.18 (s, 4 H), 1.44 (s, 8 H).

Example 140

(R)-5-(1-(benzo[d]thiazol-2-yl)pyrrolidin-3-yl)-7,7-dimethyl-5H-pyrrolo[2,3-b]pyrazin-6(7H)-one

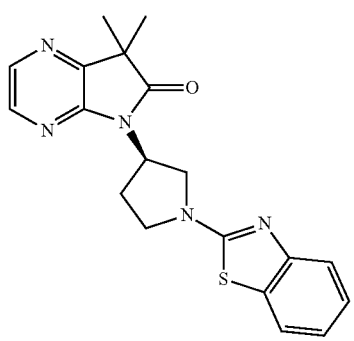 [SMILES: CC1(C)C(=O)N([C@@H]2CCN(c3nc4ccccc4s3)C2)c2nccnc21]

The title compound was synthesized following the procedure described for (S)-5-(1-(benzo[d]thiazol-2-yl)pyrrolidin-3-yl)-7,7-dimethyl-5H-pyrrolo[2,3-b]pyrazin-6(7H)-one (See EXAMPLE 141), using (R)-tert-butyl 3-(7,7-dimethyl-6-oxo-6,7-dihydro-5H-pyrrolo[2,3-b]pyrazin-5-yl)pyrrolidine-1-carboxylate (0.3 g, 0.903 mmol), hydrogen chloride, 4M in 1,4-dioxane (10 mL, 40.0 mmol), diisopropylethylamine (1 mL, 5.75 mmol), and 2-chlorobenzothiazole (0.153 mL, 0.903 mmol) to afford (R)-5-(1-(benzo[d]thiazol-2-yl)pyrrolidin-3-yl)-7,7-dimethyl-5H-pyrrolo[2,3-b]pyrazin-6(7H)-one (0.201 g, 0.550 mmol, 60.9% yield). m/z: 366.0 (M+1);
$^1$H NMR (400 MHz, CHLOROFORM-d) δ ppm 8.12 (br. s., 1 H), 8.02 (br. s., 1 H), 7.61 (d, J=16.43 Hz, 2 H), 7.23-7.37 (m, 1 H), 7.08 (t, J=7.43 Hz, 1 H), 5.25-5.42 (m, 1 H), 4.08-4.27 (m, 1 H), 3.84-4.06 (m, 2 H), 3.72 (q, J=8.22 Hz, 1 H), 2.82-3.06 (m, 1 H), 2.25-2.49 (m, 1 H), 1.47 (br. s., 6 H).

Example 141

(S)-5-(1-(benzo[d]thiazol-2-yl)pyrrolidin-3-yl)-7,7-dimethyl-5H-pyrrolo[2,3-b]pyrazin-6(7H)-one

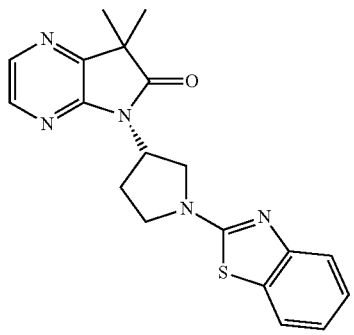

Thionyl chloride (2 ml, 27.4 mmol) was added slowly to 2-(3-chloropyrazin-2-yl)-2-methylpropanoic acid (0.200 g, 0.997 mmol) at room temperature and the solution warmed to 60° C. for 2 h. The reaction mixture was concentrated in vacuo and dried under high vacuum for 30 min. The residue obtained was dissolved in THF (10 mL) and triethylamine (0.416 ml, 2.99 mmol) and (S)-(−)-1-boc-3-aminopyrrolidine (0.200 ml, 1.097 mmol) were added. After stirring at room temperature for 30 minutes, sodium tert-butoxide (0.488 ml, 3.99 mmol) was added and the reaction mixture was stirred at room temperature for 1 h, diluted with water and extracted with EtOAc. EtOAc layer was separated and concentrated and residue purified with ISCO on silica gel column eluting with 0-50% EtOAc/hexanes to give the cyclized intermediate. To this was added hydrogen chloride, 4M in 1,4-dioxane (10 ml, 40.0 mmol) and resulting solution stirred for 1 h and concentrated. The HCl salt obtained was dissolved in DMSO (0.5 mL) and diisopropylethylamine (1 ml, 5.75 mmol) and 2-chlorobenzothiazole (0.254 ml, 1.495 mmol) were added. The mixture was heated to 110° C. for 2 h, diluted with water and extracted with EtOAc. EtOAc was concentrated and residue purified with ISCO eluting with 0-60% EtOAc/hexanes to give desired product (S)-5-(1-(benzo[d]thiazol-2-yl)pyrrolidin-3-yl)-7,7-dimethyl-5H-pyrrolo[2,3-b]pyrazin-6(7H)-one (0.121 g, 0.331 mmol, 33.2% yield). m/z 366.0 (M+1);
$^1$H NMR (400 MHz, CHLOROFORM-d) δ: ppm 8.11 (d, J=3.13 Hz, 1 H), 8.02 (s, 1 H), 7.53-7.69 (m, 2 H), 7.21-7.38 (m, 1 H), 7.07 (t, J=7.53 Hz, 1 H), 5.21-5.40 (m, 1 H), 4.09-4.26 (m, 1 H), 3.84-4.06 (m, 2 H), 3.64-3.81 (m, 1 H), 2.94 (dq, J=12.40, 8.65 Hz, 1 H), 2.37 (dtd, J=11.93, 7.82, 7.82, 3.72 Hz, 1 H), 1.46 (s, 6 H).

Example 142

3-(trans-3-(benzo[d]oxazol-2-ylamino)cyclobutyl)-1-methyl-1H-imidazo[4,5-b]pyridin-2(3H)-one

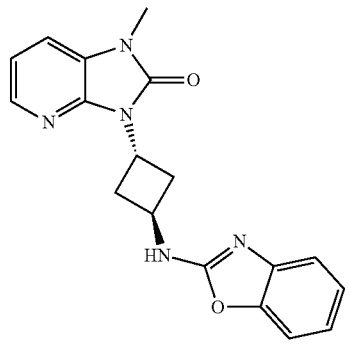 [SMILES: Cn1c(=O)n([C@H]2C[C@H](Nc3nc4ccccc4o3)C2)c2ncccc21]

The title compound was synthesized following the procedure described for INTERMEDIATE 10, using 3-(trans-3-aminocyclobutyl)-1-methyl-1H-imidazo[4,5-b]pyridin-2(3H)-one dihydrochloride (0.146 g, 0.501 mmol), diisopropylethylamine (1 ml, 5.75 mmol), 4-dimethylaminopyridine (6.13 mg, 0.050 mmol), and 2-chlorobenzoxazole (0.057 ml, 0.501 mmol) in DMSO (0.5 mL) to afford 3-(trans-3-(benzo[d]oxazol-2-ylamino)cyclobutyl)-1-methyl-1H-imidazo[4,5-b]pyridin-2(3H)-one (0.102 g, 0.304 mmol, 60.7% yield). m/z: 336.2 (M+1); $^1$H NMR (400 MHz, DMSO-d$_6$) δ: ppm 8.44 (d, J=5.87 Hz, 1 H), 8.04 (d, J=4.69 Hz, 1 H), 7.50 (d, J=7.43 Hz, 1 H), 7.37 (d, J=7.82 Hz, 1 H), 7.28 (d, J=7.63 Hz, 1 H), 7.05-7.19 (m, 2 H), 6.92-7.03 (m, 1 H), 5.26 (t, J=8.22 Hz, 1 H), 4.53 (br. s., 1 H), 3.23-3.46 (m, 5 H), 2.38-2.61 (m, 2 H).

Example 143

3-(trans-3-((5-fluorobenzo[d]thiazol-2-yl)amino)cyclobutyl)-1-methyl-1H-imidazo[4,5-b]pyridin-2(3H)-one

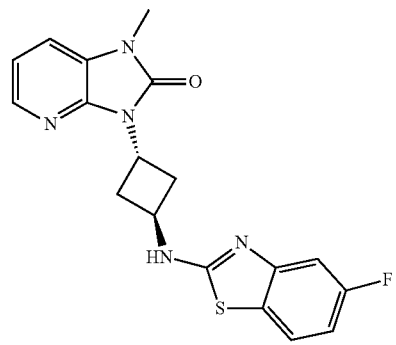 [SMILES: Cn1c(=O)n([C@H]2C[C@H](Nc3nc4cc(F)ccc4s3)C2)c2ncccc21]

The title compound was synthesized following the procedure described for INTERMEDIATE 10, using 3-(trans-3-aminocyclobutyl)-1-methyl-1H-imidazo[4,5-b]pyridin-2(3H)-one hydrochloride (0.147 g, 0.577 mmol), 2-chloro-5-fluorobenzo[d]thiazole (0.108 g, 0.577 mmol), diisopropylethylamine (1 ml, 5.75 mmol), and 4-dimethylaminopyridine (7.05 mg, 0.058 mmol) in DMSO (0.5 mL) and purified by ISCO on silica gel column using 0-80% EtOAc/hexanes to afford 3-(trans-3-((5-fluorobenzo[d]thiazol-2-yl)amino)cyclobutyl)-1-methyl-1H-imidazo[4,5-b]pyridin-2(3H)-one (0.030 g, 0.081 mmol, 14.07% yield). m/z: 370.1 (M+1); $^1$H NMR (400 MHz, CHLOROFORM-d) δ: ppm 8.07 (d, J=4.89 Hz, 1 H), 7.43-7.60 (m, 1 H), 7.23-7.34 (m, 1 H), 7.17 (d, J=7.43 Hz, 1 H), 6.98-7.10 (m, 1 H), 6.84 (t, J=8.71 Hz, 1 H), 6.18 (br. s., 1 H), 5.40 (quin, J=8.36 Hz, 1 H), 4.62 (br. s., 1 H), 3.50-3.67 (m, 2 H), 3.43 (s, 3 H), 2.55 (t, J=10.07 Hz, 2 H).

Example 144

1-methyl-3-(trans-3-((1-methyl-1H-benzo[d]imidazol-2-yl)oxy)cyclobutyl)-1H-imidazo[4,5-b]pyridin-2(3H)-one

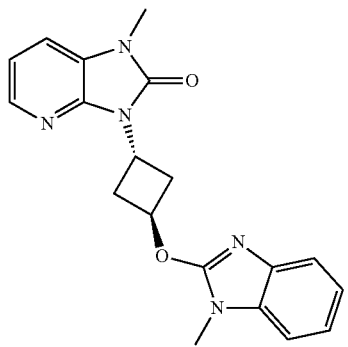 [SMILES: Cn1c(O[C@H]2C[C@H](n3c(=O)n(C)c4cccnc43)C2)nc2ccccc21]

The title compound was synthesized following the procedure described for EXAMPLE 87 (MethOD C3) using tert-butyl(trans-3-((1-methyl-1H-benzo[d]imidazol-2-yl)oxy)cyclobutyl)carbamate (0.150 g, 0.473 mmol), hydrogen chloride, 4N in 1,4-dioxane (8 ml, 32.0 mmol), methyl (2-chloropyridin-3-yl)(methyl)carbamate, INTERMEDIATE 40, (0.114 g, 0.567 mmol), sodium t-butoxide (0.289 ml, 2.363 mmol) and chloro(2-dicyclohexylphosphino-3,6-dimethoxy-2'-4'-6'-triisopropyl-1,1'-biphenyl)]2-(2-aminoethyl)Ph)Pd(II) (0.076 g, 0.095 mmol) to afford 1-methyl-3-(trans-3-((1-methyl-1H-benzo[d]imidazol-2-yl)oxy)cyclobutyl)-1H-imidazo[4,5-b]pyridin-2(3H)-one (0.070 g, 0.200 mmol, 42.4% yield). m/z: 350.1 (M+1); $^1$H NMR (400 MHz, CHLOROFORM-d) δ: ppm 8.06 (dd, J=5.18, 1.27 Hz, 1 H), 7.54-7.71 (m, 1 H), 7.19-7.30 (m, 3 H), 7.16 (dd, J=7.63, 1.17 Hz, 1 H), 7.01 (dd, J=7.73, 5.18 Hz, 1 H), 5.83 (t, J=6.75 Hz, 1 H), 5.47 (t, J=8.51 Hz, 1 H), 3.68-3.84 (m, 2 H), 3.66 (s, 3 H), 3.31-3.45 (m, 3 H), 2.65-2.84 (m, 2 H).

Example 145

1-methyl-3-(trans-3-((1-methyl-1H-benzo[d]imidazol-2-yl)amino)cyclobutyl)-1H-imidazo[4,5-b]pyridin-2(3H)-one

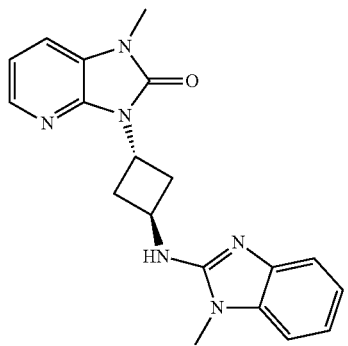 [SMILES: Cn1c(N[C@H]2C[C@H](n3c(=O)n(C)c4cccnc43)C2)nc2ccccc21]

The title compound was synthesized following the procedure described for INTERMEDIATE 10, using 3-(trans-3-aminocyclobutyl)-1-methyl-1H-imidazo[4,5-b]pyridin-2(3H)-one hydrochloride (0.147 g, 0.577 mmol), 2-chloro-1-methyl-1 h-benzoimidazole (0.096 g, 0.577 mmol), diisopropylethylamine (1 ml, 5.75 mmol) and 4-dimethylaminopyridine (7.05 mg, 0.058 mmol) in DMSO (0.5 mL) and purified by ISCO on silica gel column using 0-80% EtOAc/hexanes to afford 1-methyl-3-(trans-3-((1-methyl-1H-benzo[d]imidazol-2-yl)amino)cyclobutyl)-1H-imidazo[4,5-b]pyridin-2(3H)-one (0.103 g, 0.296 mmol, 51.2% yield). m/z: 366.0 (M+1); $^1$H NMR (400 MHz, DMSO-d$_6$) δ: ppm 8.04 (dd, J=5.28, 1.17 Hz, 1 H), 7.50 (dd, J=7.82, 1.17 Hz, 1 H), 7.19-7.24 (m, 1 H), 7.13-7.18 (m, 1 H), 7.10 (dd, J=7.73, 5.18 Hz, 1 H), 7.02 (d, J=6.46 Hz, 1 H), 6.88-6.98 (m, 2 H), 5.32 (t, J=8.41 Hz, 1 H), 4.51-4.69 (m, 1 H), 3.56 (s, 3 H), 3.26-3.40 (m, 5 H), 2.41-2.57 (m, 2 H).

Example 146

3-(trans-3-((5-chloropyridin-2-yl)amino)cyclobutyl)-1-methyl-1H-imidazo[4,5-b]pyridin-2(3H)-one

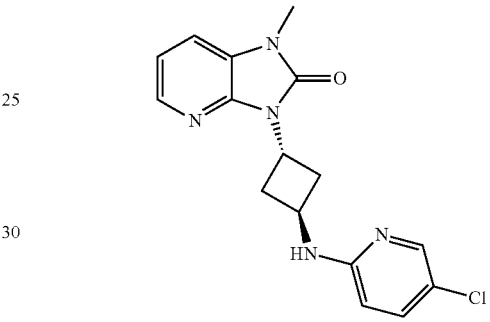

The title compound was synthesized following the procedure described for EXAMPLE 87 (MethOD C3), using 3-(trans-3-aminocyclobutyl)-1-methyl-1H-imidazo[4,5-b]pyridin-2(3H)-one (0.100 g, 0.458 mmol), 2-bromo-5-chloropyridine (0.097 g, 0.504 mmol), chloro(2-dicyclohexylphosphino-2',4',6'-triisopropyl-1,1'-biphenyl)[2-(2-aminoethyl)phenyl]pd(II), -methyl-tert-butyl ether adduct (0.034 g, 0.046 mmol), and cesium carbonate (0.073 mL, 0.916 mmol) in DMA (0.5 mL) and dioxane (2 mL) to afford 3-(trans-3-((5-chloropyridin-2-yl)amino)cyclobutyl)-1-methyl-1H-imidazo[4,5-b]pyridin-2(3H)-one (0.023 g, 0.070 mmol, 15.22% yield). m/z: 330.0; $^1$H NMR (400 MHz, CHLOROFORM-d) δ; ppm 8.06 (br. s., 2 H), 7.40 (d, J=8.61 Hz, 1 H), 7.16 (d, J=7.63 Hz, 1 H), 6.93-7.08 (m, 1 H), 6.29 (d, J=8.80 Hz, 1 H), 5.36 (quin, J=8.36 Hz, 1 H), 4.99 (br. s., 1 H), 4.43 (br. s., 1 H), 3.44-3.56 (m, 2 H), 3.42 (s, 3 H), 2.38 (t, J=10.07 Hz, 2 H).

Example 147

7-(trans-3-(benzo[d]thiazol-2-ylamino)cyclobutyl)-5,5-dimethyl-5H-pyrrolo[2,3-d]pyrimidin-6(7H)-one

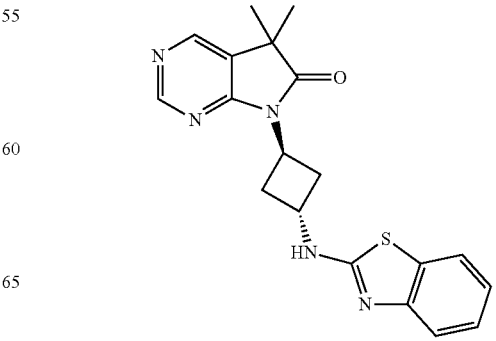

A solution of 7-(trans-3-aminocyclobutyl)-5,5-dimethyl-5H-pyrrolo[2,3-d]pyrimidin-6(7H)-one hydrochloride, INTERMEDIATE 62, (0.100 g, 0.372 mmol), 2-chlorobenzothiazole (0.095 mL, 0.558 mmol), and N,N-diisopropylethylamine (0.194 mL, 1.116 mmol) in DMSO (0.4 mL) was stirred at 120° C. for 4 h. The reaction was allowed to cool to room temperature, diluted with water and extracted with EtOAc. EtOAc was concentrated and residue purified with ISCO using silica gel column eluting with 0-60% EtOAc/hexane to give the title compound 7-(trans-3-(benzo[d]thiazol-2-ylamino)cyclobutyl)-5,5-dimethyl-5H-pyrrolo[2,3-d]pyrimidin-6(7H)-one (0.082 g, 0.224 mmol, 60.3% yield) as brown solid. m/z: 366.0 (M+1); $^1$H NMR (400 MHz, CHLOROFORM-d) δ ppm 8.84 (s, 1 H), 8.33 (s, 1 H), 7.60 (dd, J=13.11, 7.82 Hz, 2 H), 7.23-7.39 (m, 1 H), 6.99-7.18 (m, 1 H), 6.26 (br. s., 1 H), 5.15-5.40 (m, 1 H), 4.53-4.70 (m, 1 H), 3.33-3.55 (m, 2 H), 2.41-2.58 (m, 2 H), 1.36-1.55 (m, 6 H).

Example 148

Methyl 2-((trans-3-(3-cyclopropyl-2-oxo-2,3-dihydro-1H-imidazo[4,5-b]pyrazin-1-yl)cyclobutyl)amino)thiazole-5-carboxylate

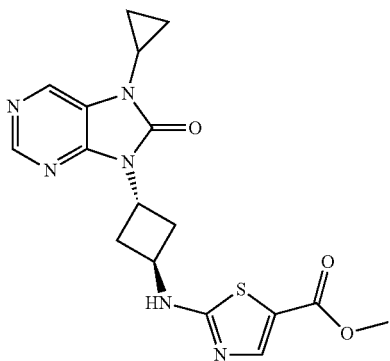 [SMILES: COC(=O)c1cnc(N[C@H]2C[C@H](n3c(=O)n(C4CC4)c4cncnc43)C2)s1]

A solution of 1-(trans-3-aminocyclobutyl)-3-cyclopropyl-1H-imidazo[4,5-b]pyrazin-2(3H)-one hydrochloride (Intermediate 79, 1.00 g, 3.55 mmol), methyl 2-chloro-4-thiazolecarboxylate (0.820 g, 4.61 mmol), and diisopropylethylamine (3.09 mL, 17.75 mmol) in DMSO (10 mL) was stirred at 120° C. for 18 h. The reaction was allowed to cool to room temperature, diluted with water and extracted with EtOAc. EtOAc was concentrated and residue purified with ISCO using silica gel column eluting with 0-70% EtOAc/hexane to give the title compound methyl 2-((trans-3-(3-cyclopropyl-2-oxo-2,3-dihydro-1H-imidazo[4,5-b]pyrazin-1-yl)cyclobutyl)amino)thiazole-5-carboxylate (0.380 g, 0.983 mmol, 27.7% yield). m/z: 387.0 (M+1); $^1$H NMR (400 MHz, DMSO-d$_6$) δ: ppm 8.38 (d, J=6.46 Hz, 1 H), 7.99 (q, J=3.26 Hz, 2 H), 7.60 (s, 1 H), 5.15 (t, J=8.31 Hz, 1 H), 4.28-4.47 (m, 1 H), 3.77 (s, 3 H), 3.18-3.30 (m, 2 H), 2.88-3.07 (m, 1 H), 2.34-2.47 (m, 2 H), 0.91-1.13 (m, 4 H).

Example 149

2-((trans-3-(3-cyclopropyl-2-oxo-2,3-dihydro-1H-imidazo[4,5-b]pyrazin-1-yl)cyclobutyl)amino)thiazole-5-carboxylic acid

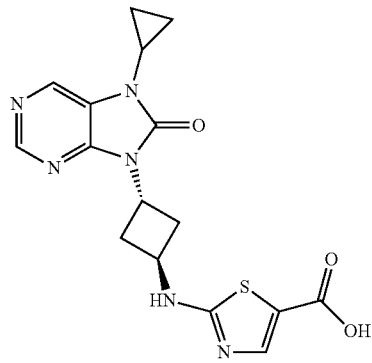 [SMILES: O=C(O)c1cnc(N[C@H]2C[C@H](n3c(=O)n(C4CC4)c4cncnc43)C2)s1]

To a suspension of methyl 2-((trans-3-(3-cyclopropyl-2-oxo-2,3-dihydro-1H-imidazo[4,5-b]pyrazin-1-yl)cyclobutyl)amino)thiazole-5-carboxylate, (EXAMPLE 148), (0.35 g, 0.906 mmol) in ethanol (5 mL) was added sodium hydroxide 1.0 N solution (2.72 mL, 2.72 mmol). The reaction mixture was heated to 80° C. for 1 h and concentrated. The residue was diluted with water and the pH of the resulting solution adjusted to 6 by the addition of 1N HCl (3.1 mL) solution. The precipitate formed was filtered and dried under high vacuum to give the title compound 2-((trans-3-(3-cyclopropyl-2-oxo-2,3-dihydro-1H-imidazo[4,5-b]pyrazin-1-yl)cyclobutyl)amino)thiazole-5-carboxylic acid (0.300 g, 0.806 mmol, 89% yield). m/z: 373.0 (M+1); $^1$H NMR (400 MHz, DMSO-d$_6$) δ: ppm 12.50 (br. s., 1 H), 8.18-8.51 (m, 1 H), 7.79-8.15 (m, 2 H), 7.35-7.66 (m, 1 H), 5.14 (quin, J=8.26 Hz, 1 H), 4.38 (br. s., 1 H), 3.16-3.31 (m, 2 H), 2.97 (tt, J=7.02, 3.64 Hz, 1 H), 2.31-2.47 (m, 2 H), 0.94-1.13 (m, 4 H).

Example 150

7-(trans-3-((1,5-naphthyridin-2-yl)amino)cyclobutyl)-5,5-dimethyl-5H-pyrrolo[2,3-d]pyrimidin-6(7H)-one

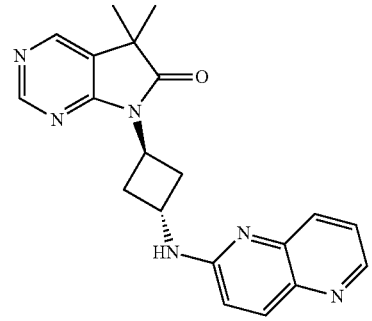 [SMILES: CC1(C)C(=O)N([C@H]2C[C@H](Nc3ccc4ncccc4n3)C2)c2ncncc21]

To suspension of 1,5-naphthyridin-2(1H)-one (0.200 g, 1.368 mmol) in Pyridine (1 mL) was added slowly trifluoromethanesulfonic anhydride (0.050 mL, 0.298 mmol). After the addition, the reaction mixture was stirred at room temperature for 18 h. The solvent was evaporated under high vacuum and residue diluted with water and extracted with EtOAc. EtOAc was washed with water, brine, dried over Na₂SO₄ and concentrated to give crude 1,5-naphthyridin-2-yl trifluoromethanesulfonate. To this crude 1,5-naphthyridin-2-yl trifluoromethanesulfonate (100 mg) in DMSO (0.5 mL) was added 7-(trans-3-aminocyclobutyl)-5,5-dimethyl-5H-pyrrolo[2,3-d]pyrimidin-6(7H)-one hydrochloride, INTERMEDIATE 62, (0.05 g, 0.186 mmol) and N,N-diisopropylethylamine (0.032 mL, 0.186 mmol). The mixture was heated to 100° C. for 2 hours, diluted with water and extracted with EtOAc. EtOAc was concentrated and residue purified with ISCO using silical gel column eluting with 0-100% EtOAc/hexanes to give the title compound 7-(trans-3-((1,5-naphthyridin-2-yl)amino)cyclobutyl)-5,5-dimethyl-5H-pyrrolo[2,3-d]pyrimidin-6(7H)-one (0.048 g, 0.133 mmol, 71.6% yield). m/z: 361.2; ¹H NMR (400 MHz, CHLOROFORM-d) δ ppm 8.85 (s, 1 H) 8.62 (dd, J=4.21, 1.27 Hz, 1 H) 8.33 (s, 1 H) 8.07 (d, J=9.00 Hz, 1 H) 7.98 (d, J=8.22 Hz, 1 H) 7.45 (dd, J=8.51, 4.21 Hz, 1 H) 6.88 (d, J=9.00 Hz, 1 H) 5.46 (d, J=4.50 Hz, 1 H) 5.17-5.35 (m, 1 H) 4.79 (dd, J=7.92, 3.62 Hz, 1 H) 3.32-3.58 (m, 2 H) 2.44 (tt, J=10.03, 3.08 Hz, 2 H) 1.45 (s, 6 H).

Example 151

N-(1-cyanocyclopropyl)-2-((trans-3-(3-cyclopropyl-2-oxo-2,3-dihydro-1H-imidazo[4,5-b]pyrazin-1-yl)cyclobutyl)amino)thiazole-5-carboxamide

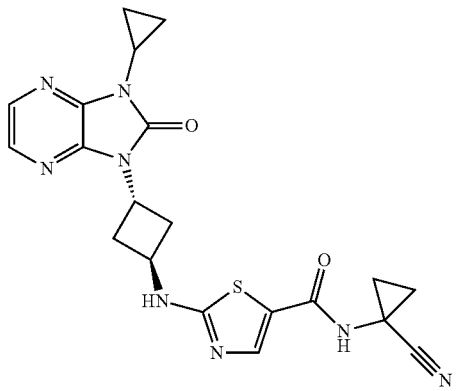 [SMILES: N#CC1(NC(=O)c2cnc(N[C@H]3C[C@H](n4c(=O)n(C5CC5)c5nccnc54)C3)s2)CC1]

A mixture of 2-((trans-3-(3-cyclopropyl-2-oxo-2,3-dihydro-1H-imidazo[4,5-b]pyrazin-1-yl)cyclobutyl)amino)thiazole-5-carboxylic acid, (EXAMPLE 149), (0.070 g, 0.188 mmol), (benzotriazol-1-yloxy)tripyrrolidinophosphonium hexafluorophosphate (0.147 g, 0.282 mmol), diisopropylethylamine (0.049 ml, 0.282 mmol), and 1-amino-1-cyclopropanecarbonitrile hydrochloride (0.033 g, 0.282 mmol) in DCM (5 mL) was stirred at room temperature for 12 hours. Purification of the reaction mixture using silica chromatography with ISCO eluting with 0-80% EtOAc/hexanes gave the title compound N-(1-cyanocyclopropyl)-2-((trans-3-(3-cyclopropyl-2-oxo-2,3-dihydro-1H-imidazo[4,5-b]pyrazin-1-yl)cyclobutyl)amino)thiazole-5-carboxamide (0.060 g, 0.137 mmol, 73.1% yield). m/z: 437 (M+1); ¹H NMR (400 MHz, DMSO-d₆) δ: ppm 8.78 (s, 1 H) 8.32 (d, J=6.65 Hz, 1 H) 7.93-8.05 (m, 2 H) 7.40 (s, 1 H) 5.18 (quin, J=8.51 Hz, 1 H) 4.31-4.53 (m, 1 H) 3.21-3.41 (m, 2 H) 2.88-3.05 (m, 1 H) 2.29-2.44 (m, 2 H) 1.44-1.60 (m, 2 H) 1.23-1.35 (m, 2 H) 0.93-1.10 (m, 4 H).

Example 152

1-cyclopropyl-3-(trans-3-((5-(morpholine-4-carbonyl)thiazol-2-yl)amino)cyclobutyl)-1H-imidazo[4,5-b]pyrazin-2(3H)-one

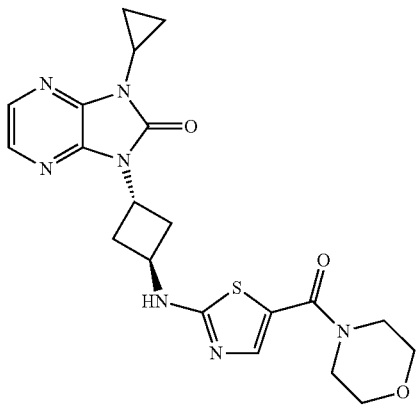 [SMILES: O=C(c1cnc(N[C@H]2C[C@H](n3c(=O)n(C4CC4)c4nccnc43)C2)s1)N1CCOCC1]

The title compound was prepared following the procedure for EXAMPLE 151, using a mixture of 2-((trans-3-(3-cyclopropyl-2-oxo-2,3-dihydro-1H-imidazo[4,5-b]pyrazin-1-yl)cyclobutyl)amino)thiazole-5-carboxylic acid, EXAMPLE 149, (0.07 g, 0.188 mmol), morpholine (0.025 ml, 0.282 mmol), diisopropylethylamine (0.049 ml, 0.282 mmol), and (benzotriazol-1-yloxy)tris(dimethylamino)phosphonium hexafluorophosphate (0.125 g, 0.282 mmol) to give 1-cyclopropyl-3-(trans-3-((5-(morpholine-4-carbonyl)thiazol-2-yl)amino)cyclobutyl)-1H-imidazo[4,5-b]pyrazin-2(3H)-one (0.025 g, 0.057 mmol, 30.1% yield). m/z: 442.0 (M+1); ¹H NMR (400 MHz, DMSO-d₆) δ: ppm 8.30 (d, J=5.67 Hz, 1 H), 7.81-8.10 (m, 2 H), 7.13 (s, 1 H), 5.13 (t, J=8.31 Hz, 1 H), 4.32 (d, J=4.50 Hz, 1 H), 3.77 (br. s., 2 H), 3.58 (br. s., 6 H), 3.12-3.27 (m, 2 H), 2.85-3.03 (m, 1 H), 2.28-2.46 (m, 2 H), 0.89-1.10 (m, 4 H).

Example 153

3-(trans-3-((6-fluorobenzo[d]thiazol-2-yl)amino)cyclobutyl)-1-methyl-1H-imidazo[4,5-b]pyridin-2(3H)-one

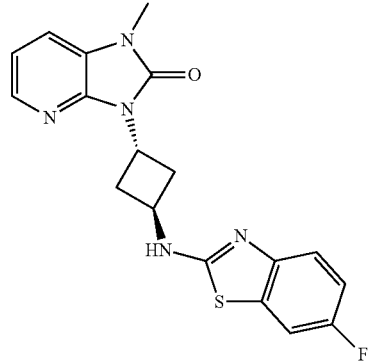 [SMILES: Cn1c(=O)n([C@H]2C[C@H](Nc3nc4ccc(F)cc4s3)C2)c2ncccc21]

A mixture of tert-butyl(trans-3-aminocyclobutyl)carbamate (0.099 g, 0.533 mmol), 2-chloro-6-fluoro-1,3-benzothiazole (0.100 g, 0.533 mmol) and diisopropylethylamine (0.185 ml, 1.066 mmol) in DMSO (0.5 mL) contained in a microwave vial was capped and heated to 120° C. for 2 hrs. The mixture was diluted with water and extracted with EtOAc. EtOAc extract was concentrated to give crude tert-butyl (trans-3-((6-fluorobenzo[d]thiazol-2-yl)amino)cyclobutyl) carbamate. To the crude tert-butyl(trans-3-((6-fluorobenzo[d]thiazol-2-yl)amino)cyclobutyl)carbamate was added hydrogen chloride, 4N in 1,4-dioxane (10 ml, 40.0 mmol) and the resulting solution stirred at room temperature for 2 h and concentrated to afford crude trans-N1-(6-fluorobenzo[d]thiazol-2-yl)cyclobutane-1,3-diamine hydrochloride. The crude trans-N1-(6-fluorobenzo[d]thiazol-2-yl)cyclobutane-1,3-diamine hydrochloride was added to mixture of methyl (2-chloropyridin-3-yl)(methyl)carbamate, INTERMEDIATE 40, (0.107 g, 0.533 mmol), chloro(2-dicyclohexylphosphino-3,6-dimethoxy-2'-4'-6'-triisopropyl-1,1'-biphenyl)]2-(2-aminoethyl)Ph)Pd(II) (0.021 g, 0.027 mmol), and sodium tert-butoxide (0.261 ml, 2.132 mmol) in dioxane (10 mL). The mixture was stirred at 100° C. for 2 h and concentrated. The residue was diluted with water and extracted with EtOAc. EtOAc extract was concentrated and residue purified with ISCO on silica gel column eluting with 0-80% EtOAc/hexanes to give the title compound 3-(trans-3-((6-fluorobenzo[d]thiazol-2-yl)amino)cyclobutyl)-1-methyl-1H-imidazo[4,5-b]pyridin-2(3H)-one (0.092 g, 0.249 mmol, 46.7% yield). m/z: 370.1 (M+1); $^1$H NMR (400 MHz, CHLOROFORM-d) δ: ppm 8.07 (dd, J=5.18, 1.27 Hz, 1 H), 7.49 (dd, J=8.90, 4.79 Hz, 1 H), 7.32 (dd, J=8.12, 2.64 Hz, 1 H), 7.17 (dd, J=7.73, 1.27 Hz, 1 H), 6.97-7.07 (m, 2 H), 5.90 (br. s., 1 H), 5.33-5.50 (m, 1 H), 4.48-4.74 (m, 1 H), 3.48-3.67 (m, 2 H), 3.43 (s, 3 H), 2.34-2.63 (m, 2 H).

Example 154

5-(trans-3-((5-fluorobenzo[d]thiazol-2-yl)amino)cyclobutyl)-7,7-dimethyl-5H-pyrrolo[2,3-b]pyrazin-6(7H)-one

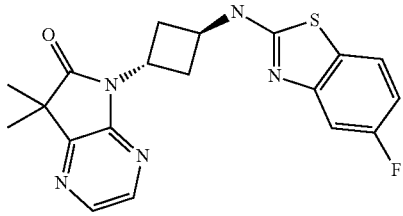 [SMILES: CC1(C)C(=O)N([C@H]2C[C@H](Nc3nc4cc(F)ccc4s3)C2)c2nccnc21]

2-(3-Chloropyrazin-2-yl)-2-methylpropanoic acid, INTERMEDIATE 29 (0.250 g, 1.246 mmol) was dissolved in a mixture of thionyl chloride (5 ml, 68.5 mmol) and dichloromethane (5 mL) and heated to reflux. After 20 minutes the solution was evaporated to dryness under reduced pressure. The crude was dissolved in carbon tetrachloride (20 mL) and evaporated to dryness once more. The crude was dried further under high vac then dissolved in dichloromethane (20 mL). The product was then added to an ice cooled solution of trans-N1-(5-fluorobenzo[d]thiazol-2-yl)cyclobutane-1,3-diamine, in the presence of INTERMEDIATE 73 (0.245 g, 1.032 mmol) and diisopropylethylamine (1.0 ml, 5.75 mmol) in dry tetrahydrofuran (30 mL). The mixture was stirred for 5 minutes then sodium tert-butoxide (0.50 g, 5.20 mmol) was added in one portion and the reaction stirred for an additional 20 minutes. Water (200 mL) and ethyl acetate (300 mL) were added and the phases mixed and separated. The organic was dried with magnesium sulfate and evaporated to dryness under reduced pressure. Purification using silica chromatography (dichloromethane to ethyl acetate gradient) gave the desired 5-(trans-3-((5-fluorobenzo[d]thiazol-2-yl)amino)cyclobutyl)-7,7-dimethyl-5H-pyrrolo[2,3-b]pyrazin-6(7H)-one (0.135 g, 0.352 mmol, 34.1% yield) m/z: 384.0 (M+1); $^1$H NMR (400 MHz, CHLOROFORM-d) δ: ppm 1.46 (s, 6 H) 2.45-2.55 (m, 2 H) 3.40-3.51 (m, 2 H) 4.53-4.63 (m, 1 H) 5.31 (quin, J=8.46 Hz, 1 H) 6.62 (br. s., 1 H) 6.84 (td, J=8.80, 2.15 Hz, 1 H) 7.27 (dd, J=9.98, 2.15 Hz, 1 H) 7.51 (dd, J=8.70, 5.38 Hz, 1 H) 8.11 (dd, J=13.99, 3.03 Hz, 2 H).

Example 155

1-(trans-3-(benzo[d]thiazol-2-ylamino)cyclobutyl)-3-methyl-1H-benzo[d]imidazol-2(3H)-one

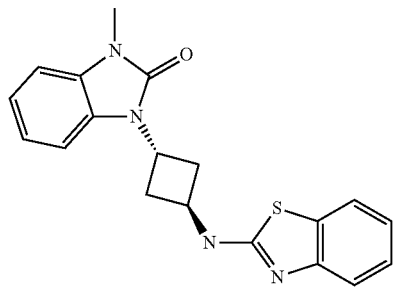 [SMILES: Cn1c(=O)n([C@H]2C[C@H](Nc3nc4ccccc4s3)C2)c2ccccc21]

Following the procedure described for Example 44 (MethOD B6), using methyl (2-bromophenyl)(methyl)carbamate, INTERMEDIATE 74 (0.510 g, 2.089 mmol), trans-N1-(benzo[d]thiazol-2-yl)cyclobutane-1,3-diamine, INTERMEDIATE 11 (0.400 g, 1.824 mmol), tris(dibenzylideneacetone)dipalladium (o) (0.042 g, 0.046 mmol), 2-(dicyclohexylphosphino)-3,6-dimethoxy-2'-4'-6'-triisopropyl-1,1'biphenyl (0.049 g, 0.091 mmol), and sodium tert-butoxide (0.351 g, 3.65 mmol) in dry dioxane (5 mL) afforded the title compound 1-(trans-3-(benzo[d]thiazol-2-ylamino)cyclobutyl)-3-methyl-1H-benzo[d]imidazol-2(3H)-one (0.0811 g, 0.231 mmol, 12.69% yield) m/z: 351.0 (M+1); $^1$H NMR (400 MHz, CHLOROFORM-d) δ: ppm 2.55-2.65 (m, 2 H) 3.38-3.47 (m, 5 H) 4.47-4.55 (m, 1 H) 5.22 (quin, J=8.51 Hz, 1 H) 6.97-7.01 (m, 1 H) 7.06-7.16 (m, 4 H) 7.27-7.33 (m, 1 H) 7.57 (d, J=8.02 Hz, 1 H) 7.60 (dd, J=7.92, 0.68 Hz, 1 H).

Example 156

7-(trans-3-((6-fluorobenzo[d]thiazol-2-yl)amino)cyclobutyl)-5,5-dimethyl-2-(methylthio)-5H-pyrrolo[2,3-d]pyrimidin-6(7H)-one

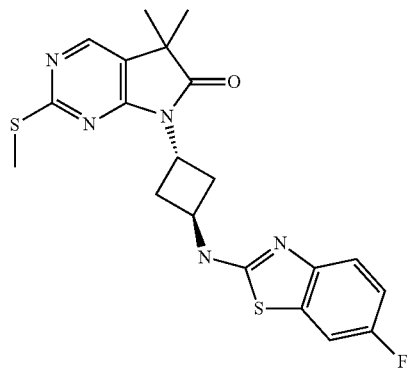 [SMILES: CSc1ncc2c(n1)N([C@H]1C[C@H](Nc3nc4ccc(F)cc4s3)C1)C(=O)C2(C)C]

Following the procedure described for Example 44 (MethOD B6), using trans-N1-(6-fluorobenzo[d]thiazol-2-yl)cyclobutane-1,3-diamine, INTERMEDIATE 72 (0.454 g, 1.913 mmol), ethyl 2-(4-chloro-2-(methylthio)pyrimidin-5-yl)-2-methylpropanoate (0.550 g, 2.002 mmol), dicyclohexyl(2',4',6'-triisopropyl-3,6-dimethoxy-[1,1'-biphenyl]-2-yl)phosphine (0.185 g, 0.344 mmol), tris(dibenzylideneacetone)dipalladium (0) (0.131 g, 0.143 mmol), sodium t-butoxide (0.460 g, 4.78 mmol) in dry dioxane (3 mL) afforded the title 7-(trans-3-((6-fluorobenzo[d]thiazol-2-yl)amino)cyclobutyl)-5,5-dimethyl-2-(methylthio)-5H-pyrrolo[2,3-d]pyrimidin-6(7H)-one (0.230 g, 0.535 mmol, 28.0% yield). m/z: 430.1 (M+1); $^1$H NMR (400 MHz, CHLOROFORM-d) δ: ppm 1.41 (s, 6H) 2.42-2.53 (m, 2 H) 2.61 (s, 3H) 3.38-3.53 (m, 2 H) 4.55-4.65 (m, 1 H) 5.15-5.27 (m, 1 H) 5.91 (br s, 1 H) 7.03 (td, J=9.0 Hz, 2.6 Hz, 1H) 7.32 (dd, J=8.2 Hz, 2.6 Hz, 1H) 7.49 (dd, J=8.9 Hz, 4.7 Hz, 1H) 8.12 (s, 1H).

Example 157

7-(trans-3-((6-fluorobenzo[d]thiazol-2-yl)amino)cyclobutyl)-5,5-dimethyl-5H-pyrrolo[2,3-d]pyrimidin-6(7H)-one

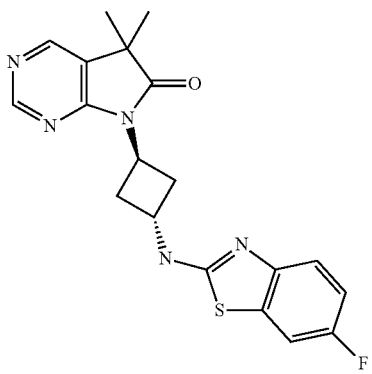 [SMILES: CC1(C)C(=O)N([C@H]2C[C@H](Nc3nc4ccc(F)cc4s3)C2)c2ncncc21]

7-(Trans-3-((6-fluorobenzo[d]thiazol-2-yl)amino)cyclobutyl)-5,5-dimethyl-2-(methylthio)-5H-pyrrolo[2,3-d]pyrimidin-6(7H)-one (EXAMPLE 156) (0.200 g, 0.466 mmol) was dissolved in dry tetrahydrofuran (10 mL) under nitrogen. Palladium (10 wt. % on activated carbon, 0.080 g, 0.075 mmol) was added followed by triethylsilane (0.200 ml, 1.252 mmol). The suspension was stirred at room temperature. After 40 minutes additional triethylsilane (0.5 mL) was added and the reaction stirred for another 4 hours. Additional palladium/carbon (0.122 g) and triethylsilane (0.25 mL) were added and the reaction stirred for another 55 minutes. The mixture was filtered through a pad of CELITE® and evaporated to dryness under reduced pressure. Purification using silica chromatography (0-5% methanol in dichloromethane gradient) gave 7-(trans-3-((6-fluorobenzo[d]thiazol-2-yl)amino)cyclobutyl)-5,5-dimethyl-5H-pyrrolo[2,3-d]pyrimidin-6(7H)-one (0.091 g, 0.237 mmol, 51.0% yield) as a white solid. m/z: 384.0 (M+1); $^1$H NMR (400 MHz, CHLOROFORM-d) δ: ppm 1.42 (s, 6H) 2.42-2.53 (m, 2 H) 3.38-3.53 (m, 2 H) 4.55-4.65 (m, 1 H) 5.15-5.27 (m, 1 H) 7.03 (td, J=9.0 Hz, 2.6 Hz, 1H) 7.32 (dd, J=8.2 Hz, 2.6 Hz, 1H) 7.49 (dd, J=8.9 Hz, 4.7 Hz, 1H) 8.33 (s, 1H) 8.84 (s, 1H).

Examples 158 and 159 are tabulated in Table 8 below.

Example 160

5-(trans-3-((5-bromopyridin-2-yl)amino)cyclobutyl)-7,7-dimethyl-5H-pyrrolo[2,3-b]pyrazin-6(7H)-one

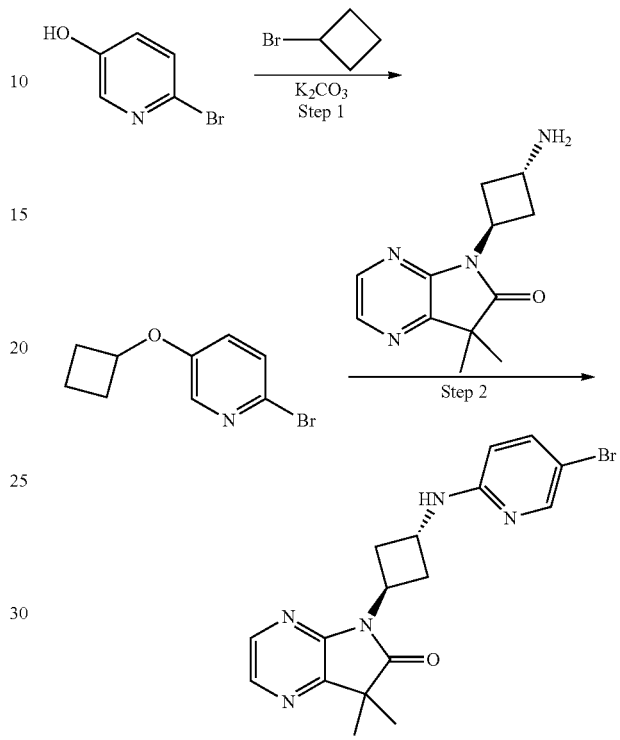

Step 1: 2-bromo-5-cyclobutoxypyridine

2-Bromo-5-hydroxypyridine (1.0 g, 5.75 mmol), bromocyclobutane (0.783 mL, 8.33 mmol), and potassium carbonate (1.59 g, 11.5 mmol) were mixed in DMF (11 mL) and stirred at 60° C. for 5 h, then at 80° C. for 14 h. The reaction mixture was diluted with EtOAc and washed with water, saturated NaHCO$_3$, and brine. The organic layer was dried (Na$_2$SO$_4$) and concentrated. The crude product was purified by ISCO (40 g), eluting with a gradient of EtOAc/hexane 0-10% to provide to give 2-bromo-5-cyclobutoxypyridine (0.92 g, 4.0 mmol, 70% yield) as white solid. ESI (M+1) 229.9.

Step 2: 5-(trans-3-((5-bromopyridin-2-yl)amino)cyclobutyl)-7,7-dimethyl-5H-pyrrolo[2,3-b]pyrazin-6(7H)-one 5-(trans-3-aminocyclobutyl)-7,7-dimethyl-5H-pyrrolo[2,3-b]pyrazin-6(7H)-one (Intermediate 30, 100 mg, 0.43 mmol), cesium acetate (512 mg, 2.67 mmol), 2-bromo-5-cyclobutoxypyridine (147 mg, 0.646 mmol), and copper (2.19 mg, 0.034 mmol) were weighed into a microwave vial. The vial was evacuated and flushed with nitrogen. DMSO (0.5 ml) was then added and the reaction mixture was heated to 100° C. for 20 h. The Reaction mixture was diluted with ethyl acetate and washed with aqueous ammonium hydroxide. The aqueous layer was back extracted with EtOAc (2×) and the combined organics was dried with magnesium sulfate and evaporated to dryness under reduced pressure. The crude product was purified by ISCO (12 g), eluting with a gradient of EtOAc/hexane 0-40%, followed by Gilson reverse-phase preparative HPLC using a Phenomenex Gemini column, 10 micron, C18, 110 Å, 150×30 mm, 0.1% TFA in CH$_3$CN:H$_2$O, gradient 30% to 95% over 10 min, then neutralized with NaHCO$_3$, to provide the title compound (34 mg, 0.09 mmol, 21% yield) as a white solid. $^1$H NMR (400 MHz, CHLOROFORM-d) d ppm 1.45 (s, 6 H) 1.62-1.77 (m, 1 H) 1.83-1.96 (m, 1 H) 2.06-2.22 (m, 2 H) 2.35-2.49 (m, 2 H) 2.52-2.64 (m, 2 H) 3.23-3.38 (m, 2 H) 4.39-4.54 (m, 2 H) 5.21-5.35 (m, 1 H) 6.57 (d, J=9.39 Hz, 1 H) 7.45 (dd, J=9.49, 2.64 Hz, 1 H) 8.09 (dd, J=18.98, 3.13 Hz, 2 H).

Example 161 is tabulated in Table 8 below.

Example 162

5-(trans-3-((1,8-naphthyridin-2-yl)amino)cyclobutyl)-7,7-dimethyl-5H-pyrrolo[2,3-b]pyrazin-6(7H)-one (method G1)

2-chloro-1,8-naphthyridine (89 mg, 0.54 mmol), 5-(trans-3-aminocyclobutyl)-7,7-dimethyl-5H-pyrrolo[2,3-b]pyrazin-6(7H)-one (100 mg, 0.431 mmol), and cesium carbonate (202 mg, 0.620 mmol) were suspended in dry dimethylformamide (0.86 mL) under nitrogen and heated to 100° C. for 18 h. The mixture was cooled and extracted with ethyl acetate and water. The phases were separated and the organic was dried with magnesium sulfate before evaporating to dryness under reduced pressure. Purification using the ISCO (0-100% EtOAc in hexane), gave the desired 5-(trans-3-((1,8-naphthyridin-2-yl)amino)cyclobutyl)-7,7-dimethyl-5H-pyrrolo[2,3-b]pyrazin-6(7H)-one (32 mg, 0.089 mmol, 21% yield) as a light yellow solid. $^1$H NMR (300 MHz, CHLOROFORM-d) δ: ppm 1.45 (s, 6 H) 2.42 (ddd, J=13.88, 9.28, 3.29 Hz, 2 H) 3.44-3.62 (m, 2 H) 5.22-5.38 (m, 2 H) 6.71 (d, J=8.92 Hz, 1 H) 7.16 (dd, J=7.82, 4.46 Hz, 1 H) 7.79-7.98 (m, 2 H) 8.11 (q, J=3.12 Hz, 2 H) 8.84 (dd, J=4.38, 1.90 Hz, 1 H).

Examples 163-164 are tabulated in Table 8 below.

Example 165

N-(trans-3-(1H-pyrrolo[2,3-b]pyridin-1-yl)cyclobutyl)benzo[d]thiazol-2-amine

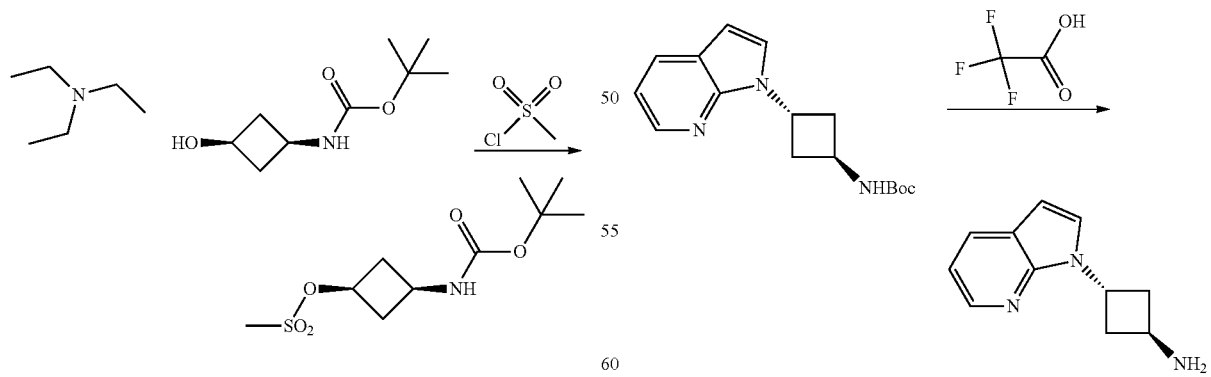

Step 1: cis-3-((tert-butoxycarbonyl)amino)cyclobutyl methanesulfonate

In a round-bottomed flask charged with tert-butyl(cis-3-hydroxycyclobutyl)carbamate (1.11 g, 5.93 mmol) and triethylamine (2.474 ml, 17.79 mmol) was added CH$_2$Cl$_2$ (12 ml). methanesulfonyl chloride (0.505 ml, 6.52 mmol) was added dropwise via syringe at −20° C. over 5 min. The reaction mixture was stirred at room temperature for 30 min, then diluted with water (15 mL) and extracted with CH$_2$Cl$_2$(2×). The organic extract was washed with saturated NH4Cl and dried over MgSO4. It was filtered and concentrated in vacuo to give cis-3-((tert-butoxycarbonyl)amino)cyclobutyl methanesulfonate (1.64 g, 6.1 mmol, 100% yield) as a off-white solid.

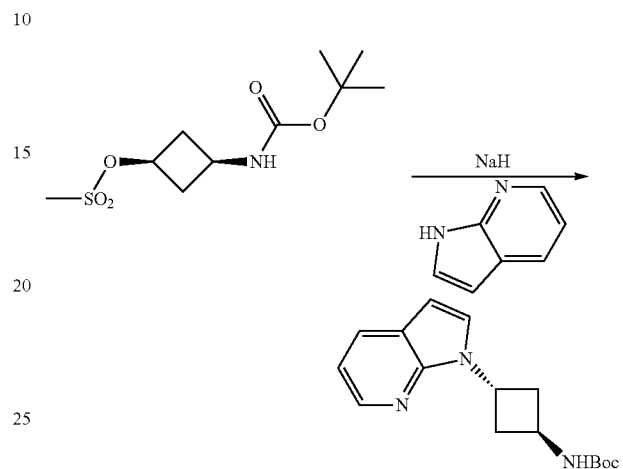

Step 2. Tert-butyl(trans-3-(1H-pyrrolo[2,3-b]pyridin-1-yl)cyclobutyl)carbamate

To a solution of 1H-pyrrolo[2,3-b]pyridine (44.5 mg, 0.377 mmol) in DMF (1.3 ml) at room temperature was added sodium hydride, 60% in oil (18 mg, 0.45 mmol), followed by cis-3-((tert-butoxycarbonyl)amino)cyclobutyl methanesulfonate (100 mg, 0.38 mmol). The reaction mixture was heated at 100° C. for 16 h. The reaction mixture was partitioned between EtOAc and water. The aqueous layer was back extracted with EtOAc (2×) and the combined organics was dried (MgSO$_4$) and concentrated. The crude product was purified by ISCO (12 g), eluting with a gradient of EtOAc/hexane 0-50% to provide tert-butyl(trans-3-(1H-pyrrolo[2,3-b]pyridin-1-yl)cyclobutyl)carbamate (10 mg, 0.035 mmol, 9.23% yield) as off-white solid. ESI (M+1) 288.0.

Step 3. Trans-3-(1H-pyrrolo[2,3-b]pyridin-1-yl)cyclobutanamine

To the solution of tert-butyl(trans-3-(1H-pyrrolo[2,3-b]pyridin-1-yl)cyclobutyl)carbamate (294 mg, 1.02 mmol) in DCM (2.0 ml) was added trifluoroacetic acid, 99% (760 μl, 10.2 mmol). The reaction mixture was stirred at room temperature under $N_2$ for 1 h. The solvent was evaporated and the residue was triturated with DCM three times, redissolved in DCM, and then treated with solid $NaHCO_3$. The solid was filtered off and the filtrate concentrated in vacuo. The crude material was purified by chromatography through a Redi-Sep pre-packed silica gel column (12 g), eluting with a gradient of 0% to 100% EtOAc in hexane, then 15% MeOH in EtOAc, to provide trans-3-(1H-pyrrolo[2,3-b]pyridin-1-yl)cyclobutanamine (75 mg, 0.401 mmol, 39.2% yield) as light-yellow oil. ESI (M+1) 188.0.

Step 4. N-(trans-3-(1H-pyrrolo[2,3-b]pyridin-1-yl)cyclobutyl)benzo[d]thiazol-2-amine trans-3-(1H-pyrrolo[2,3-b]pyridin-1-yl)cyclobutanamine (78 mg, 0.42 mmol), 4-dimethylaminopyridine (3.56 mg, 0.029 mmol), N,N-diisopropylethylamine (159 μl, 0.916 mmol) and 2-chlorobenzothiazole (81 μl, 0.625 mmol) were added in a round bottomed flask, followed by dry DMSO (833 μl). The mixture was sealed and heated at 110° C. for 16 h. The reaction mixture was partitioned between water, saturated ammonium chloride and ethyl acetate. The organic was dried with magnesium sulfate and evaporated to dryness under reduced pressure. Purification using ISCO (0-60% EtOAc in hexane), gave N-(trans-3-(1H-pyrrolo[2,3-b]pyridin-1-yl)cyclobutyl)benzo[d]thiazol-2-amine (23 mg, 0.072 mmol, 17% yield) as off-white solid. $^1$H NMR (400 MHz, CHLOROFORM-d) δ: ppm 2.77 (ddd, J=14.04, 8.46, 3.72 Hz, 2 H) 2.96-3.14 (m, 2 H) 4.56 (dt, J=7.43, 3.72 Hz, 1 H) 5.59-5.76 (m, 1 H) 6.54 (d, J=3.52 Hz, 1 H) 7.04-7.17 (m, 2 H) 7.28-7.36 (m, 1 H) 7.45 (d, J=3.72 Hz, 1 H) 7.60 (t, J=8.51 Hz, 2 H) 7.92 (dd, J=7.82, 1.37 Hz, 1 H) 8.32 (dd, J=4.69, 1.37 Hz, 1 H).

Example 166 is tabulated in Table 8 below.

Example 167

5-(trans-3-((5-(difluoromethoxy)pyridin-2-yl)amino)cyclobutyl)-7,7-dimethyl-5H-pyrrolo[2,3-b]pyrazin-6(7H)-one(trifluoroacetic acid salt)

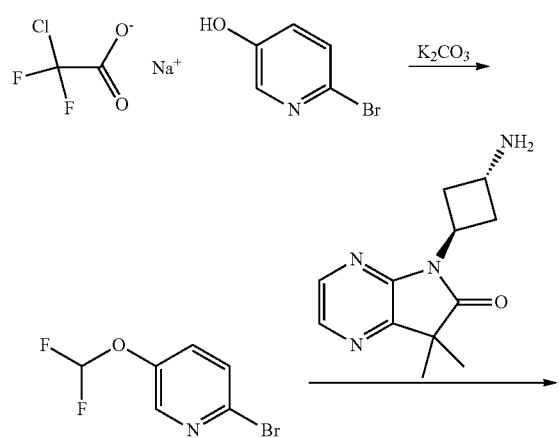

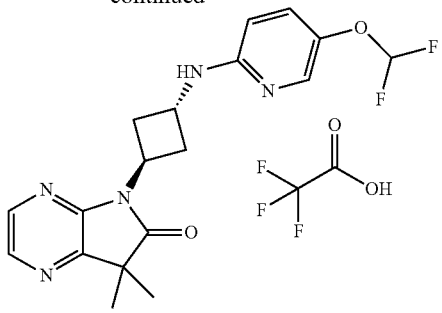

Step 1: 2-bromo-5-(difluoromethoxy)pyridine

A mixture of 2-bromo-5-hydroxypyridine (1.2 g, 6.9 mmol), sodium chlorodifluoroacetate (2.1 g, 13.8 mmol), and potassium carbonate (1.24 g, 8.97 mmol) in anhydrous DMF (10 ml) was stirred at 80° C. for 20 h. After cooling to room temperature, the reaction mixture was partitioned between EtOAc and water. The aqueous layer was back extracted with EtOAc and the combined organics was dried ($Na_2SO_4$) and concentrated. The crude material was purified by chromatography through a Redi-Sep pre-packed silica gel column (40 g), eluting with a gradient of 0% to 10% EtOAc in hexane, to provide 2-bromo-5-(difluoromethoxy)pyridine (0.89 g, 4.0 mmol, 58% yield) as colorless oil. ESI (M+1) 225.8.

Step 2: 5-(trans-3-((5-(difluoromethoxy)pyridin-2-yl)amino) cyclobutyl)-7,7-dimethyl-5H-pyrrolo[2,3-b]pyrazin-6(7H)-one 5-(trans-3-aminocyclobutyl)-7,7-dimethyl-5H-pyrrolo[2,3-b]pyrazin-6(7H)-one (Intermediate 83, 58 mg, 0.250 mmol), cesium acetate (297 mg, 1.548 mmol), 2-bromo-5-(difluoromethoxy)pyridine (115 mg, 0.513 mmol), and copper (1.269 mg, 0.020 mmol) were weighed into a microwave vial. The vial was evacuated and flushed with nitrogen. DMSO (312 μl) was then added and the mixture was heated to 100° C. for 20 h. The mixture was diluted with ethyl acetate and washed with aqueous ammonium hydroxide. The aqueous layer was back extracted with EtOAc two times and the combined organics were dried with magnesium sulfate and evaporated to dryness under reduced pressure. The crude product was purified by ISCO (12 g), eluting with a gradient of EtOAc/hexane 0-40%, followed by reverse-phase preparative HPLC using a Phenomenex Gemini column, 10 micron, C18, 110 Å, 150×30 mm, 0.1% TFA in $CH_3CN/H_2O$, gradient 30% to 95% over 15 min, to provide the title compound as a trifluoroacetic acid salt as a light-yellow oil. Yield: 1.6 mg, 3.27 μmol, 1.3% yield. $^1$H NMR (300 MHz, CHLOROFORM-d) δ 8.11-8.16 (d, J=3.22 Hz, 1H), 8.08 (d, J=3.22 Hz, 1H), 7.79 (d, J=2.12, Hz, 1H), 7.70 (dd, J=2.12, 9.57 Hz, 1H) 6.65 (d, J=9.65 Hz, 1H), 6.48 (t, J=46.00 Hz, 1H), 5.22-5.37 (m, 1H), 4.48-4.60 (m, 1H), 3.24-3.41 (m, 2H), 2.57-2.74 (m, 2H), 1.47 (s, 6H)

Examples 168-172 are tabulated in Table 8 below.

Example 173

7,7-dimethyl-5-(trans-3-(thiazolo[5,4-b]pyridin-2-ylamino)cyclobutyl)-5H-pyrrolo[2,3-b]pyrazin-6(7H)-one

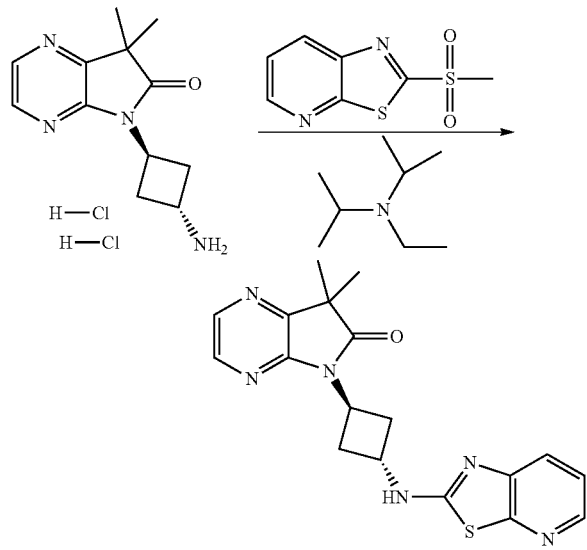

A mixture of 5-(trans-3-aminocyclobutyl)-7,7-dimethyl-5H-pyrrolo[2,3-b]pyrazin-6(7H)-one dihydrochloride (Intermediate 83, 51 mg, 0.167 mmol), N-ethyl-N-isopropylpropan-2-amine (102 µl, 0.585 mmol), and 2-(methylsulfonyl)thiazolo[5,4-b]pyridine (Intermediate 76) (43.0 mg, 0.201 mmol) in DMSO (0.3 ml) was stirred at 100° C. for 3 h. The mixture was diluted with EtOAc and water in a separatory funnel. The aqueous layer was extracted with EtOAc twice. The combined organic layer was dried over $Na_2SO_4$ and concentrated in vacuo. The crude solution was purified by silica gel chromatography (ISCO 12 g, 0-70% EtOAc-hexane) to give 7,7-dimethyl-5-(trans-3-(thiazolo[5,4-b]pyridin-2-ylamino)cyclobutyl)-5H-pyrrolo[2,3-b]pyrazin-6(7H)-one (37 mg, 0.101 mmol, 60.4% yield) as off-white solid. $^1$H NMR (300 MHz, CHLOROFORM-d) δ ppm 1.46 (s, 6 H) 2.50 (ddd, J=14.03, 9.35, 3.51 Hz, 2 H) 3.37-3.55 (m, 2 H) 5.30 (t, J=8.48 Hz, 1 H) 5.73 (br. s., 1 H) 7.17-7.25 (m, 1 H) 7.74 (dd, J=8.04, 1.46 Hz, 1 H) 8.05-8.16 (m, 2 H) 8.22 (dd, J=4.75, 1.53 Hz, 1 H).

Examples 174-179 are tabulated in Table 8 below.

Example 180

5-((1S,2R)-2-(3-methoxyphenyl)cyclopropyl)-7,7-dimethyl-5H-pyrrolo[2,3-b]pyrazin-6(7H)-one and 5-((1S,2S)-2-(3-methoxyphenyl)cyclopropyl)-7,7-dimethyl-5H-pyrrolo[2,3-b]pyrazin-6(7H)-one

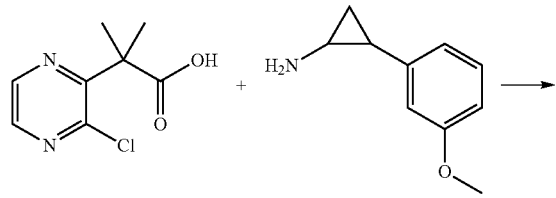

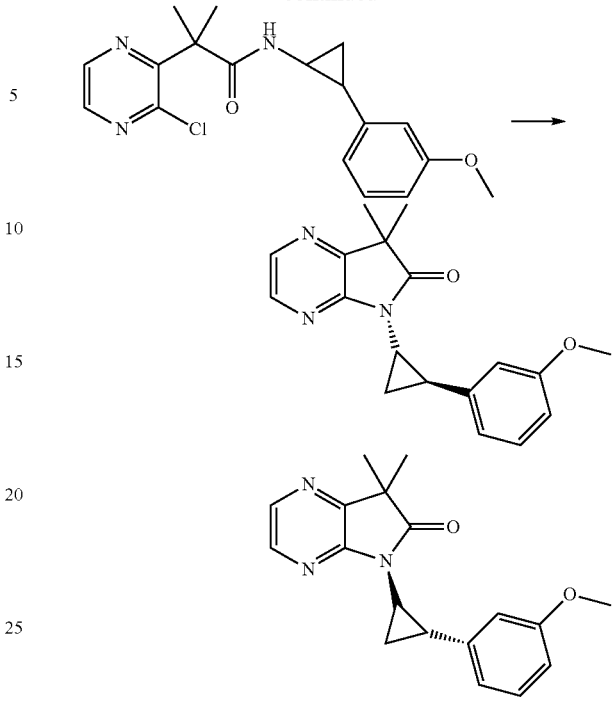

Step 1. 2-(3-chloropyrazin-2-yl)-N-(2-(3-methoxyphenyl)cyclopropyl)-2-methylpropanamide A mixture of Intermediate 29 (0.2 g, 0.997 mmol), 2-(3-methoxyphenyl)cyclopropanamine (FSSI, mixture of cis/trans, 0.163 g, 0.997 mmol), HATU (GenScript Corporation, 0.455 g, 1.196 mmol), hunig's base (Aldrich, 0.696 ml, 3.99 mmol) in DMF (0.997 ml) and DCM (0.997 ml) was stirred at room temperature overnight. Reaction mixture was diluted with DCM and washed with water and brine. The organic layer was loaded onto a Biotage samplet (25 g). Purification (0-100% EtOAc/hexane) produced 2-(3-chloropyrazin-2-yl)-N-(2-(3-methoxyphenyl)cyclopropyl)-2-methylpropanamide (0.183 g, 0.529 mmol, 53%). M+1: 346.0.

Step 2. 5-((1S,2R)-2-(3-methoxyphenyl)cyclopropyl)-7,7-dimethyl-5H-pyrrolo[2,3-b]pyrazin-6(7H)-one and 5-((1S,2S)-2-(3-methoxyphenyl)cyclopropyl)-7,7-dimethyl-5H-pyrrolo[2,3-b]pyrazin-6(7H)-one A mixture of 2-(3-chloropyrazin-2-yl)-N-(2-(3-methoxyphenyl)cyclopropyl)-2-methylpropanamide (0.183 g, 0.529 mmol), sodium tert-butoxide (Aldrich, 0.102 g, 1.058 mmol) in THF was stirred at room temperature overnight. Reaction mixture was directly loaded onto a Biotage samplet. Purification (0-100% EtOAc/hexane) produced mixture of products 5-((1S,2R)-2-(3-methoxyphenyl)cyclopropyl)-7,7-dimethyl-5H-pyrrolo[2,3-b]pyrazin-6(7H)-one and 5-((1S,2S)-2-(3-methoxyphenyl)cyclopropyl)-7,7-dimethyl-5H-pyrrolo[2,3-b]pyrazin-6(7H)-one (0.111 g, 0.359 mmol, 68% yield). M+1: 310.0. $^1$H NMR (300 MHz, CHLOROFORM-d) δ ppm 1.45 (d, J=1.90 Hz, 6 H) 1.54-1.63 (m, 1 H) 1.66-1.75 (m, 1 H) 2.62 (ddd, J=9.87, 6.72, 3.58 Hz, 1 H) 2.93-3.06 (m, 1 H) 3.82 (s, 3 H) 6.73-6.83 (m, 1 H) 6.86-6.97 (m, 2 H) 7.16-7.31 (m, 1 H) 8.11 (s, 2 H).

Example 181

(R)-1-(trans-3-(benzo[d]thiazol-2-ylamino)cyclobutyl)-3-hydroxy-3-methyl-1H-pyrrolo[2,3-b]pyridin-2(3H)-one and (S)-1-(trans-3-(benzo[d]thiazol-2-ylamino)cyclobutyl)-3-hydroxy-3-methyl-1H-pyrrolo[2,3-b]pyridin-2(3H)-one

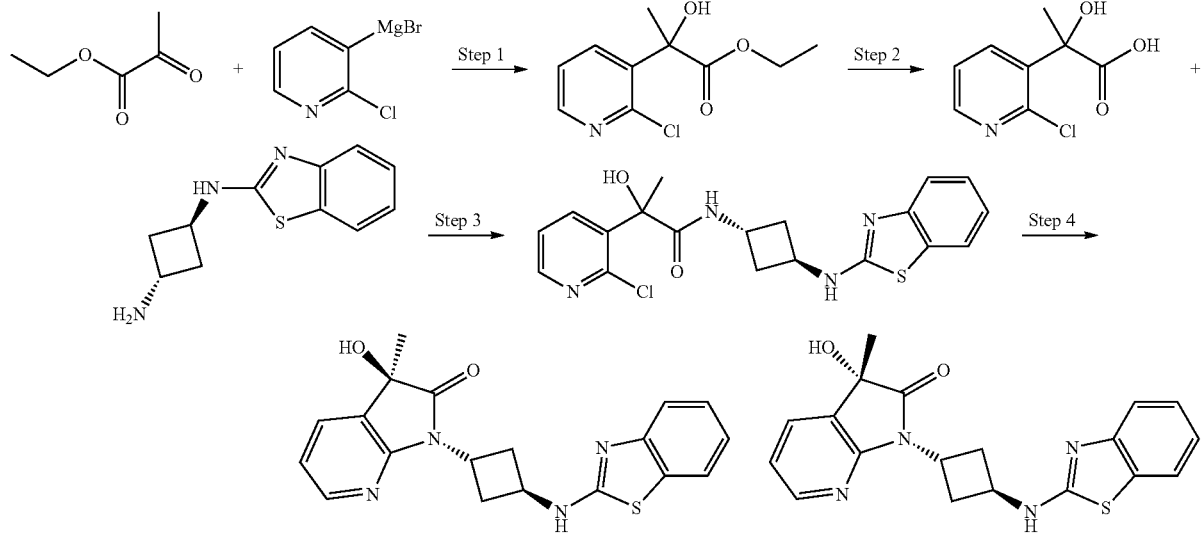

Step 1. ethyl 2-(2-chloropyridin-3-yl)-2-hydroxypropanoate

Preparation of Grignard solution of (2-chloropyridin-3-yl) magnesium bromide in THF: To a solution of 3-bromo-2-chloropyridine (Sigma Aldrich, 0.5 g, 2.60 mmol) in Tetrahydrofuran (10.39 ml) was added isopropylmagnesium chloride lithium chloride complex, 14% solution in THF (Acros Organics, 3.68 ml, 3.38 mmol). The resulting mixture was stirred at room temperature for 3 hr.

To the Grignard solution prepared above (approximately (2-chloropyridin-3-yl)magnesium bromide (0.564 g, 2.6 mmol) in THF) was added ethyl pyruvate (Sigma Aldrich, 0.289 ml, 2.60 mmol). The resulting mixture was stirred at room temperature for 2 hr. Reaction mixture was quenched with saturated NH₄Cl and extracted with EtOAc. Material was advanced to the next step. M: 229.9.

Step 2. 2-(2-chloropyridin-3-yl)-2-hydroxypropanoic acid

A solution of ethyl 2-(2-chloropyridin-3-yl)-2-hydroxypropanoate (0.2 g, 0.871 mmol) in hydrochloric acid, 37% (Sigma Aldrich, 2.75 ml, 33.5 mmol) was heated in a sealed tube at 60° C. overnight. Reaction mixture was rotovapped and dried by vacuum pump. The residue containing 2-(2-chloropyridin-3-yl)-2-hydroxypropanoic acid was advanced to next step. M: 201.9.

Step 3. N-(trans-3-(benzo[d]thiazol-2-ylamino)cyclobutyl)-2-(2-chloropyridin-3-yl)-2-hydroxypropanamide A mixture of Intermediate 11 (0.223 g, 0.870 mmol), 2-(2-chloropyridin-3-yl)-2-hydroxypropanoic acid hydrochloride (0.207 g, 0.87 mmol), HATU (GenScript, 0.662 g, 1.740 mmol), Hunig's base (Aldrich, 1.216 ml, 6.96 mmol) in DMF (0.870 ml) and DCM (0.870 ml) was stirred at room temperature for 3 days. The reaction mixture was diluted with DCM and washed with water and brine. The organic layer was loaded onto a Biotage samplet (25 g).

Purification (0-10% MeOH/DCM) produced N-(trans-3-(benzo[d]thiazol-2-ylamino)cyclobutyl)-2-(2-chloropyridin-3-yl)-2-hydroxypropanamide (0.094 g, 0.233 mmol, 27% yield). M: 402.9.

Step 4. (R)-1-(trans-3-(benzo[d]thiazol-2-ylamino)cyclobutyl)-3-hydroxy-3-methyl-1H-pyrrolo[2,3-b]pyridin-2(3H)-one and (S)-1-(trans-3-(benzo[d]thiazol-2-ylamino)cyclobutyl)-3-hydroxy-3-methyl-1H-pyrrolo[2,3-b]pyridin-2(3H)-one A mixture of N-(trans-3-(benzo[d]thiazol-2-ylamino)cyclobutyl)-2-(2-chloropyridin-3-yl)-2-hydroxypropanamide (0.094 g, 0.233 mmol), chloro-(2-dicyclohexylphosphino-2',6'-diisopropoxy-1,1'-biphenyl)[2-(2-aminoethyl)phenyl]palladium(II)-methyl-tert-butyl ether adduct (Sigma Aldrich, 0.011 g, 0.014 mmol), sodium tert-butoxide (Aldrich, 0.045 g, 0.467 mmol) in Dioxane (0.933 ml) in a microwave vial was heated to 80° C. overnight. The reaction mixture was directly loaded onto a Biotage samplet. Purification by Biotage (25 g column; 0-100% EtOAc/hexane) followed by a second purification by Gilson HPLC (Gemini Gradient 10-70 method, Gemini-NX 10 u C18 column, 100×50 mm, solvets: ACN/0.1% TFA and water/0.1% TFA) to produce mixtures (R)-1-(trans-3-(benzo[d]thiazol-2-ylamino)cyclobutyl)-3-hydroxy-3-methyl-1H-pyrrolo[2,3-b]pyridin-2(3H)-one and (S)-1-(trans-3-(benzo[d]thiazol-2-ylamino)cyclobutyl)-3-hydroxy-3-methyl-1H-pyrrolo[2,3-b]pyridin-2(3H)-one (0.0059 g, 0.016 mmol, 7% yield). M+1: 367.0. $^1$H NMR (300 MHz, CHLOROFORM-d) δ ppm 1.55 (s, 3 H) 2.53-2.72 (m, 2 H) 3.48-3.67 (m, 2 H) 4.63-4.77 (m, 1 H) 5.18-5.37 (m, 1 H) 7.03-7.18 (m, 1 H) 7.32-7.45 (m, 1 H) 7.46-7.61 (m, 2 H) 7.71-7.79 (m, 1 H) 7.79-7.88 (m, 1 H) 8.19-8.30 (m, 1 H).

Example 182

4-(trans-3-(benzo[d]thiazol-2-ylamino)cyclobutyl)-2H-pyrido[3,2-b][1,4]oxazin-3(4H)-one

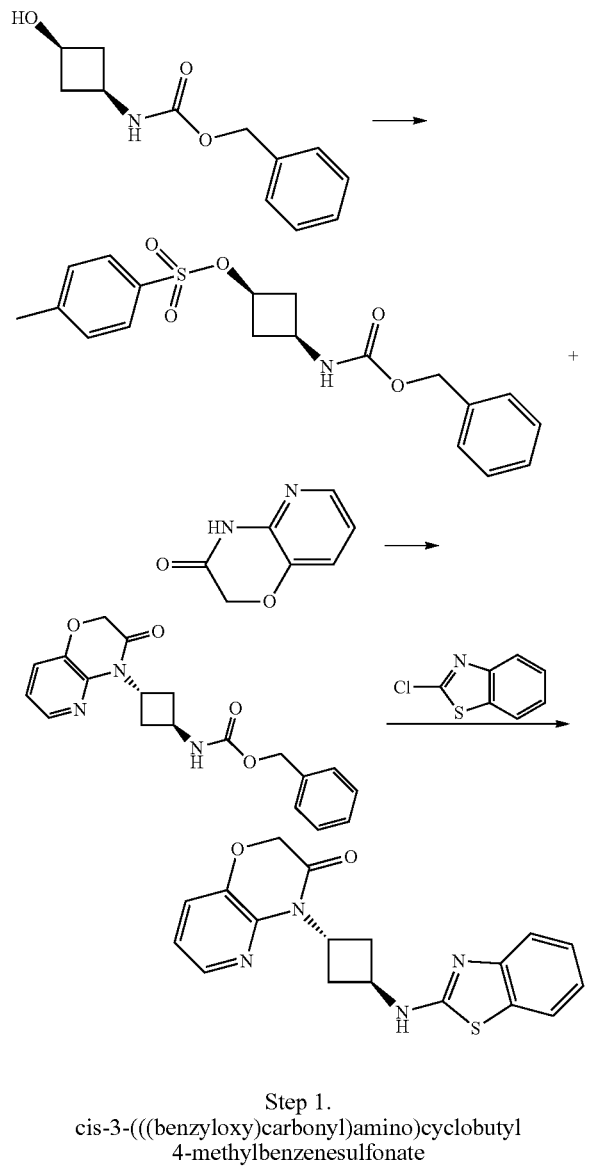

Step 1.
cis-3-(((benzyloxy)carbonyl)amino)cyclobutyl 4-methylbenzenesulfonate

A solution of Intermediate 47 (0.67 g, 3.03 mmol), p-toluenesulfonyl chloride (Sigma Aldrich, 1.155 g, 6.06 mmol), triethylamine (Aldrich, 1.688 ml. 12.11 mmol) in DCM (6.06 ml) was stirred at room temperature overnight. Reaction mixture was diluted with DCM and washed with saturated NaHCO$_3$ solution. Organic layer was dried over sodium sulfate to provide 1.4 g crude product upon rotovap. Material was advanced to next step before further purification.

Step 2. benzyl (trans-3-(3-oxo-2H-benzo[b][1,4]oxazin-4(3H)-yl)cyclobutyl)carbamate To a solution of cis-3-(((benzyloxy)carbonyl)amino)cyclobutyl 4-methylbenzenesulfonate (0.563 g, 1.5 mmol) in DMF (3.00 ml) was added 2H-pyrido[3,2-b][1,4]oxazin-3(4H)-one (FSSI, 0.225 g, 1.500 mmol) and potassium carbonate (EMD, 0.415 g, 3.00 mmol). The resulting mixture was heated to 50° C. overnight. Reaction mixture was heated to 85° C. for 3 hr then at 110° C. overnight. Reaction mixture was diluted with DCM and washed with water and brine. Purification by Biotage (0-10% MeOH/DCM) produced product. Material was advanced to the next step. M+1: 353.9

Step 3. 4-(trans-3-(benzo[d]thiazol-2-ylamino)cyclobutyl)-2H-pyrido[3,2-b][1,4]oxazin-3(4H)-one To a solution of benzyl (trans-3-(3-oxo-2H-pyrido[3,2-b][1,4]oxazin-4(3H)-yl)cyclobutyl)carbamate (0.154 g, 0.436 mmol) in Acetic Acid (1.2 ml) was added hydrogen bromide, 33 wt. % in acetic acid (Alfa Aesar, Avocado, Lancaster, 1.302 ml, 23.97 mmol). The resulting mixture was stirred at room temperature for 1 hr. The mixture was quenched with addition of 1N NaOH solution and rotovapped and dried by vacuum pump overnight.

The residual solid was suspended in DMSO (1.800 ml) and added Hunig's base (Aldrich, 0.304 ml, 1.743 mmol) and 2-chlorobenzothiazole (Alfa Aesar, 0.074 g, 0.436 mmol). The resulting mixture was heated to 120° C. for 24 hr. Reaction mixture was diluted with DCM and washed with water and brine. The crude was purified twice by Gilson HPLC (Gemini Gradient 10-70 method, Gemini-NX 10 u C18 column, 100×50 mm, solvets: ACN/0.1% TFA and water/0.1% TFA) then by prep-plate TLC (5% MeOH/DCM) to afford 4-(trans-3-(benzo[d]thiazol-2-ylamino)cyclobutyl)-2H-pyrido[3,2-b][1,4]oxazin-3(4H)-one (0.028 g, 0.079 mmol, 18% yield). M+1: 353.0. $^1$H NMR (300 MHz, CHLOROFORM-d) δ ppm 2.53 (br. s., 2 H) 3.31-3.44 (m, 3 H) 4.61 (s, 3 H) 5.55-5.77 (m, 1 H) 6.93-7.05 (m, 1 H) 7.05-7.19 (m, 1 H) 7.29 (s, 2 H) 7.39-7.48 (m, 1 H) 7.57-7.68 (m, 1 H) 7.94-8.09 (m, 1 H).

Example 183

3-(trans-3-(benzo[d]oxazol-2-ylamino)cyclobutyl)-1-cyclopropyl-1H-imidazo[4,5-b]pyridin-2(3H)-one

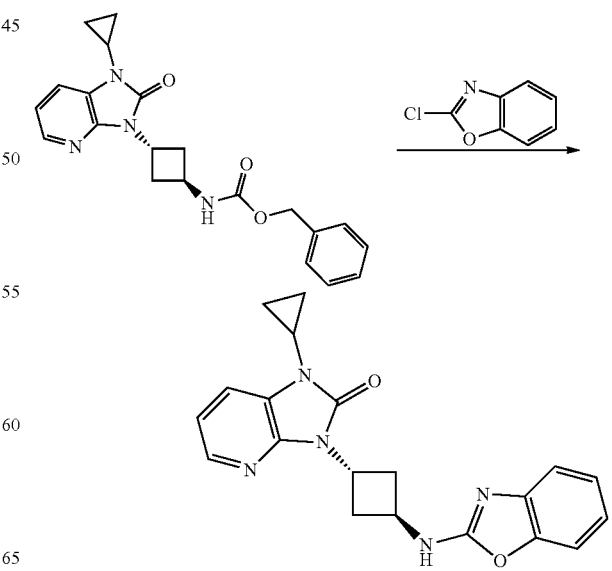

To a solution of Intermediate XX (0.22 g, 0.581 mmol) in Acetic Acid (1.550 ml) was added hydrogen bromide, 33 wt. % in acetic acid (Alfa Aesar, Avocado, Lancaster, 1.736 ml, 32.0 mmol). The resulting mixture was stirred at room temperature for 1 hr. The mixture was quenched with addition of 5 mL 1N NaOH solution and rotovapped and dried by vacuum pump. The residual solid was suspended in DMSO (2.325 ml) and added hunig's base (Aldrich, 0.406 ml, 2.325 mmol) and 2-chlorobenzoxazole (Sigma Aldrich, 0.066 ml, 0.581 mmol). The resulting mixture was heated to 120° C. overnight. Reaction mixture was diluted with DCM and washed with water and brine. The crude was purified by Biotage (0-10% MeOH/DCM, 25 g column) to afford 3-(trans-3-(benzo[d]oxazol-2-ylamino)cyclobutyl)-1-cyclopropyl-1H-imidazo[4,5-b]pyridin-2(3H)-one (0.105 g, 0.291 mmol, 50% yield). M+1: 362.0. $^1$H NMR (300 MHz, MeOH) δ ppm 0.96-1.06 (m, 2 H) 1.15 (d, J=5.70 Hz, 2 H) 2.45-2.62 (m, 2 H) 2.86-2.98 (m, 1 H) 3.47-3.63 (m, 2 H) 4.57-4.70 (m, 1 H) 5.22-5.39 (m, 1 H) 6.98-7.21 (m, 3 H) 7.24-7.34 (m, 2 H) 7.46-7.55 (m, 2 H) 8.02-8.10 (m, 1 H).

Example 184

1-cyclopropyl-3-(trans-3-(quinazolin-2-ylamino)cyclobutyl)-1H-imidazo[4,5-b]pyridin-2(3H)-one

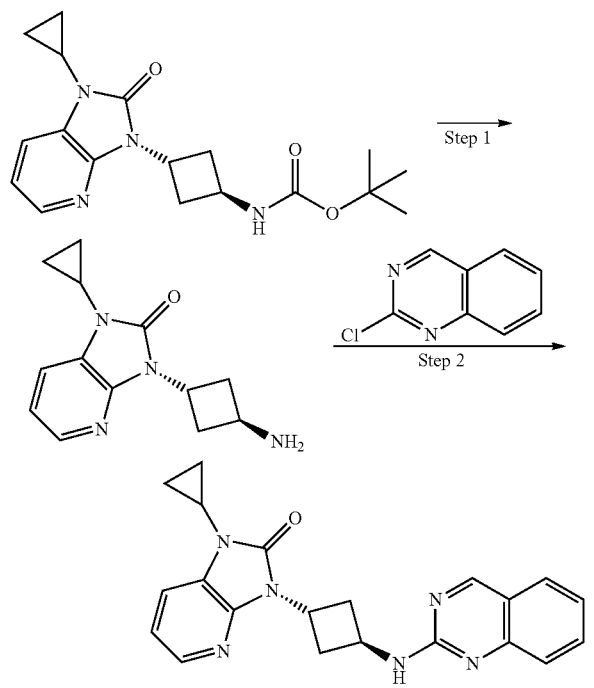

Step 1. 3-(trans-3-amnocyclobutyl)-1-cyclopropyl-1H-imidazo[4,5-b]pyridin-2(3H)-one hydrochloride To a solution of Intermediate 75 (0.56 g, 1.626 mmol) in dioxane (3.25 ml), was added hydrogen chloride, 4.0M solution in 1,4-dioxane (Sigma Aldrich, 2.032 ml, 8.13 mmol) at room temperature for 5 h. The reaction mixture was rotovapped to remove volatile solvents. The residue was dried on vacuum pump overnight and advanced to the next step. M+1: 245.0.

Step 2. 1-cyclopropyl-3-(trans-3-(quinazolin-2-ylamino)cyclobutyl)-1H-imidazo[4,5-b]pyridin-2(3H)-one A mixture of 3-(trans-3-aminocyclobutyl)-1-cyclopropyl-1H-imidazo[4,5-b]pyridin-2(3H)-one hydrochloride (0.458 g, 1.63 mmol), Hunig's base (Aldrich, 1.139 ml, 6.52 mmol), and 2-chloroquinazoline (Waterstone, 0.322 g, 1.956 mmol) in DMSO (3.26 ml) was heated to 120° C. overnight. The reaction mixture was diluted with EtOAc and washed with water and brine. Purification by Biotage (0-100% EtOAc/hexane, 25 g Biotage column) produced 1-cyclopropyl-3-(trans-3-(quinazolin-2-ylamino)cyclobutyl)-1H-imidazo[4,5-b]pyridin-2(3H)-one (0.244 g, 0.601 mmol, 37% yield). M+1: 373.0. $^1$H NMR (300 MHz, MeOH) δ ppm 0.93-1.03 (m, 3 H) 1.06-1.19 (m, 3 H) 2.47-2.64 (m, 2 H) 2.85-3.00 (m, 2 H) 3.42-3.60 (m, 2 H) 5.25-5.45 (m, 1 H) 7.04-7.20 (m, 1 H) 7.20-7.35 (m, 1 H) 7.48-7.64 (m, 3 H) 7.64-7.83 (m, 3 H) 7.99-8.14 (m, 1 H) 8.99-9.12 (m, 1 H).

Example 185

1-cyclopropyl-3-(trans-3-((5-fluorobenzo[d]thiazol-2-yl)amino)cyclobutyl)-1H-imidazo[4,5-b]pyridin-2(3H)-one

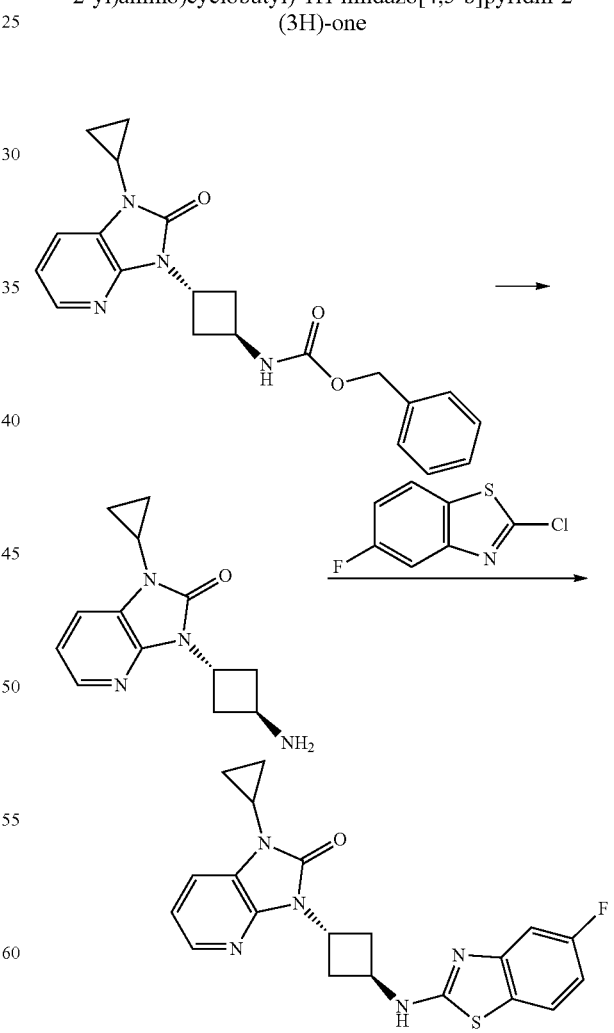

To a solution of Intermediate 75 (0.22 g, 0.581 mmol) in Acetic Acid (1.550 ml) was added hydrogen bromide, 33 wt. % in acetic acid (Alfa Aesar, Avocado, Lancaster, 1.736 ml, 32.0 mmol). The resulting mixture was stirred at room temperature for 1 hr. The mixture was quenched with addition of 5 mL 1N NaOH solution and rotovapped and dried by vacuum pump. The residual solid was suspended in DMSO (2.325 ml) and Hunig's base (Aldrich, 0.406 ml, 2.325 mmol) and 2-chloro-5-fluoro-benzothiazole (0.109 g, 0.581 mmol) were added. The resulting mixture was heated to 120° C. overnight. The reaction mixture was then diluted with DCM and washed with water and brine. The crude was purified by Biotage (0-100% EtOAc/hexane, 25 g column) to afford 1-cyclopropyl-3-(trans-3-((5-fluorobenzo[d]thiazol-2-yl)amino)cyclobutyl)-1H-imidazo[4,5-b]pyridin-2(3H)-one (0.126 g, 0.319 mmol, 55% yield). M: 395.9. $^1$H NMR (300 MHz, MeOH) δ ppm 0.90-1.07 (m, 2 H) 1.11-1.22 (m, 2 H) 2.45-2.62 (m, 2 H) 2.83-3.02 (m, 1 H) 3.46-3.63 (m, 2 H) 4.53-4.65 (m, 1 H) 5.21-5.39 (m, 1 H) 6.74-6.88 (m, 1 H) 7.03-7.14 (m, 1 H) 7.14-7.25 (m, 1 H) 7.43-7.59 (m, 3 H) 8.00-8.14 (m, 1 H).

Example 186

1-cyclopropyl-3-(trans-3-((6-fluorobenzo[d]thiazol-2-yl)amino)cyclobutyl)-1H-imidazo[4,5-b]pyridin-2(3H)-one

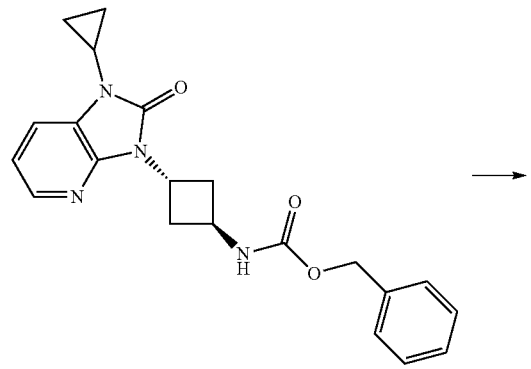

→

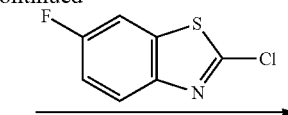

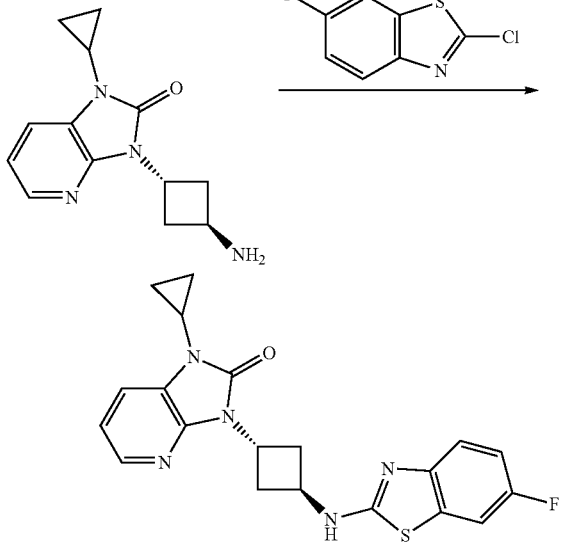

To a solution of Intermediate 75 (0.22 g, 0.581 mmol) in acetic acid (1.550 ml) was added hydrogen bromide, 33 wt. % in acetic acid (Alfa Aesar, Avocado, Lancaster, 1.736 ml, 32.0 mmol). The resulting mixture was stirred at room temperature for 1 h. The mixture was then quenched with addition of 5 mL 1N NaOH solution and rotovapped and dried by vacuum pump. The residual solid was suspended in DMSO (2.325 ml) and Hunig's base (Aldrich, 0.406 ml, 2.325 mmol) and 2-chloro-6-fluoro-1,3-benzothiazole (Sigma Aldrich, 0.109 g, 0.581 mmol) were added. The resulting mixture was heated to 120° C. overnight. The reaction mixture was diluted with DCM and washed with water and brine. The crude was purified by Biotage (0-100% EtOAc/hexane, 25 g column) to afford 1-cyclopropyl-3-(trans-3-((6-fluorobenzo[d]thiazol-2-yl)amino)cyclobutyl)-1H-imidazo[4,5-b]pyridin-2(3H)-one (0.075 g, 0.190 mmol, 32% yield). M: 395.9. $^1$H NMR (300 MHz, CHLOROFORM-d) δ ppm 0.97-1.08 (m, 2 H) 1.08-1.20 (m, 2 H) 2.44-2.60 (m, 2 H) 2.83-2.96 (m, 1 H) 3.43-3.65 (m, 2 H) 5.35 (dd, J=8.99, 7.97 Hz, 1 H) 5.58-5.67 (m, 1 H) 6.92-7.09 (m, 2 H) 7.29-7.41 (m, 2 H) 7.44-7.53 (m, 1 H) 7.99-8.12 (m, 1 H).

TABLE 8

Preparation of Examples 158-159, 161, 163-164, 166, 168-172, 174-179, 187-196, 207, 210-211, and 222-225.

| Ex # | Method | Reagent | MW* | NMR |
|---|---|---|---|---|
| 158 | B1 | Intermediate 30 | 383.9 | 1H NMR (300 MHz, CHLOROFORM-d) □ ppm 1.45 (s, 6 H) 2.40-2.55 (m, 2 H) 3.36-3.52 (m, 2 H) 5.28 (t, J = 8.70 Hz, 1 H) 5.48 (br. s., 1 H) 7.03 (td, J = 8.92, 2.63 Hz, 1 H) 7.32 (dd, J = 8.11, 2.56 Hz, 1 H) 7.49 (dd, J = 8.77, 4.82 Hz, 1 H) 8.04-8.17 (m, 2 H) |
| 159 | B1 | intermediate 30 | 389.9 | 1H NMR (300 MHz, CHLOROFORM-d) d ppm 1.44 (s, 6 H) 2.24-2.40 (m, 2 H) 3.30-3.46 (m, 2 H) 4.41 (dd, J = 8.04, 3.95 Hz, 1 H) 4.88 (d, J = 4.68 Hz, 1 H) 6.25 (d, J = 8.77 Hz, 1 H) 7.51 (dd, J = 8.77, 2.48 Hz, 1 H) 8.03-8.18 (m, 3 H) |
| 161 | B1 | intermediate 30 | 340.1 | 1H NMR (300 MHz, CHLOROFORM-d) d ppm 1.44 (s, 6 H) 2.23-2.39 (m, 2 H) 3.29-3.44 (m, 2 H) 3.78 (s, 3 H) 4.33-4.45 (m, 1 H) 5.17-5.35 (m, 1 H) 6.32 (d, J = 8.92 Hz, 1 H) 7.15 (dd, J = 8.92, 3.07 Hz, 1 H) 7.84 (d, J = 2.29 Hz, 1 H) 8.04-8.14 (m, 2 H) |

TABLE 8-continued

Preparation of Examples 158-159, 161, 163-164, 166, 168-172, 174-179, 187-196, 207, 210-211, and 222-225.

| Ex # | Method | Reagent | MW* | NMR |
|---|---|---|---|---|
| 163 | G1 | Intermediate 30 | 363 | 1H NMR (400 MHz, CHLOROFORM-d) d ppm 1.45 (s, 6 H) 2.43 (ddd, J = 13.74, 9.15, 2.74 Hz, 2 H) 3.48-3.62 (m, 5 H) 4.76 (d, J = 4.11 Hz, 1 H) 5.26-5.41 (m, 1 H) 7.05-7.17 (m, 3 H) 7.52 (d, J = 7.04 Hz, 1 H) 8.04-8.15 (m, 2 H) |
| 164 | G1 | Intermediates 3 and 30 | 361 | 1H NMR (300 MHz, CHLOROFORM-d) d ppm 1.46 (s, 6 H) 2.35- 2.53 (m, 2 H) 3.38-3.56 (m, 2 H) 4.69-4.86 (m, 1 H) 5.26-5.33 (m, 1 H) 6.87 (d, J = 9.06 Hz, 1 H) 7.44 (dd, J = 8.48, 4.24 Hz, 1 H) 7.97 (d, J = 8.04 Hz, 1 H) 8.03-8.16 (m, 3 H) 8.62 (dd, J = 4.24, 1.61 Hz, 1 H) |
| 166 | B1 | intermediate 30 | 376 | 1H NMR (400 MHz, CHLOROFORM-d) d ppm 1.43-1.48 (m, 6 H) 2.25-2.38 (m, 2 H) 3.24-3.42 (m, 2 H) 4.07-4.21 (m, 1 H) 5.21-5.36 (m, 1 H) 7.32-7.39 (m, 2 H) 7.43 (s, 1 H) 7.98 (ddd, J = 8.31, 2.64, 1.37 Hz, 1 H) 8.10 (dd, J = 13.40, 3.03 Hz, 3 H) 8.47 (dd, J = 4.79, 1.47 Hz, 1 H) 8.90 (d, J = 2.54 Hz, 1 H) |
| 168 | C4 | Intermediate 26 | 360 | 1H NMR (300 MHz, CHLOROFORM-d) d ppm 1.39 (s, 6 H) 2.31-2.52 (m, 2 H) 3.42-3.60 (m, 2 H) 4.76-4.95 (m, 1 H) 5.24 -5.43 (m, 1 H) 5.60 (d, J = 5.99 Hz, 1 H) 6.96 (dd, J = 7.16, 5.26 Hz, 1 H) 7.18-7.21 (m, 1 H) 7.42 (dd, J = 7.16, 1.61 Hz, 1 H) 7.56-7.73 (m, 3 H) 8.20 (dd, J = 5.26, 1.61 Hz, 1 H) 8.99 (s, 1 H) |
| 169 | C4 | Intermediate 26 | 349.1 | 1H NMR (300 MHz, CHLOROFORM-d) d ppm 1.39 (s, 6 H) 2.48 (ddd, J = 13.96, 9.35, 3.43 Hz, 2 H) 3.45-3.62 (m, 2 H) 5.16-5.39 (m, 2 H) 6.96 (dd, J = 7.31, 5.26 Hz, 1 H) 7.01-7.09 (m, 1 H) 7.17 (td, J = 7.67, 1.17 Hz, 1 H) 7.28 (s, 1 H) 7.36-7.47 (m, 2 H) 8.18 (dd, J = 5.26, 1.61 Hz, 1 H) |
| 170 | C4 | intermediate 30 | 401.9 | 1H NMR (300 MHz, CHLOROFORM-d) d ppm 1.45 (s, 6 H) 2.39-2.57 (m, 2 H) 3.32-3.55 (m, 2 H) 5.19-5.38 (m, 1 H) 5.62 (br. s., 1 H) 7.30-7.44 (m, 2 H) 8.03-8.17 (m, 2 H). |
| 171 | C4 | Intermediate 30 | 401.9 | 1H NMR (300 MHz, CHLOROFORM-d) d ppm 1.45 (s, 6 H) 2.38-2.56 (m, 2 H) 3.34-3.52 (m, 2 H) 5.20-5.36 (m, 1 H) 5.90 (br. s., 1 H) 6.86 (ddd, J = 10.49, 9.39, 2.48 Hz, 1 H) 7.14 ((ddd, J = 7.75, 2.34, 1.17 Hz, 1 H) 8.02-8.18 (m, 2 H) |
| 172 | C4 | Intermediate 30 | 396 | 1H NMR (300 MHz, CHLOROFORM-d) d ppm 1.45 (s, 6 H) 2.41-2.53 (m, 2 H) 3.38-3.51 (m, 2 H) 3.82 (s, 3 H) 4.54-4.63 (m, 1 H) 5.22-5.35 (m, 1 H) 6.92 (dd, J = 2.63, 1.2 Hz, 1 H) 7.15 (d, J = 2.63 Hz, 1 H) 7.48 (d, J = 8.77 Hz, 1 H) 8.07-8.14 (m, 2 H) |
| 174 | C4 | Intermediate 84 | 353 | 1H NMR (300 MHz, CHLOROFORM-d) d ppm 2.55 (ddd, J = 13.96, 9.13, 3.36 Hz, 2 H) 3.43 (s, 8 H) 3.50-3.64 (m, 5 H) 5.39 (dd, J = 8.99, 7.97 Hz, 2 H) 7.03 (dd, J = 7.67, 5.19 Hz, 1 H) 7.13-2.75 (m, 2 H) 7.74 (dd, J = 8.11, 1.53 Hz, 1 H) 8.07 (dd, J = 5.19, 1.39 Hz, 1 H) 8.21 (dd, J = 4.75, 1.53 Hz, 1 H) |
| 175 | C4 | Intermediate 79 | 392 | 1H NMR (300 MHz, CHLOROFORM-d) d ppm 1.08-1.22 (m, 4 H) 2.11-2.62 (m, 2 H) 2.96-3.07 (m, 1 H) 3.41-3.57 (m, 2 H) 4.81 (dd, J = 8.40, 3.29 Hz, 1 H) 5.26-5.43 (m, 1 H) 5.64 (d J = 5.85 Hz, 1 H) 7.00 (td, J = 8.66, 2.41 Hz, 1 H) 7.23 (dd, J = 10.74, 2.41 Hz, 1 H) 7.67 (dd, J = 8.84, 6.21 Hz, 1 H) 7.96 (s, 2 H) 8.94 (s, 1 H). |
| 176 | C4 | Intermediate 30 | 379.1 | 1H NMR (300 MHz, CHLOROFORM-d) d ppm 1.46 (s, 6 H) 2.36-2.56 (m, 2 H) 3.33-3.56(m, 2 H) 4.75-4.92 (m, 1 H) 5.19-5.40 (m, 1 H) 5.64 (d, J = 5.85 Hz, 1 H) 6.99 (td, J = 8.66, 2.41 Hz, 1 H) 7.22 (dd, |

TABLE 8-continued

Preparation of Examples 158-159, 161, 163-164, 166, 168-172, 174-179, 187-196, 207, 210-211, and 222-225.

| Ex # | Method | Reagent | MW* | NMR |
|---|---|---|---|---|
| | | | | J = 10.60, 2.27 Hz, 1 H) 7.67 (dd, J = 8.77, 6.14 Hz, 1 H) 8.06-8.17 (m, 2 H) 8.94 (s, 1 H) |
| 177 | C4 | Intermediate 79 | 381.1 | 1H NMR (300 MHz, CHLOROFORM-d) d ppm 1.10-1.21 (m, 4 H) 2.50-2.68 (m, 2 H) 2.93-3.07 (m, 2 H) 3.39-3.58 (m, 2 H) 5.18-5.42 (m, 2 H) 6.91 (ddd, J = 9.90, 8.66, 2.48 Hz, 1 H) 7.04 (dd, J = 7.97, 2.41 Hz, 1 H) 7.26-7.34 (m, 2 H) 7.89-8.01 (m, 2 H). |
| 178 | C4 | Intermediate 30 | 368.1 | 1H NMR (300 MHz, CHLOROFORM-d) d ppm 1.45 (s, 6 H) 2.43-2.59 (m, 2 H) 3.35-3.53 (m, 2 H) 5.14 (d, J = 5.70 Hz, 1 H) 5.22-5.39 (m, 1 H) 6.91 (ddd, J = 9.87, 8.70, 2.48 Hz, 1 H) 7.04 (dd, J = 8.11, 2.41 Hz, 1 H) 7.28-7.35 (m, 1 H) 8.02-8.16 (m, 2 H) |
| 179 | C4 | Intermediate 79 | 380 | 1H NMR (400 MHz, CHLOROFORM-d) d ppm 1.11-1.20 (m, 4 H) 2.50-2.64 (m, 2 H) 2.96-3.05 (m, 1 H) 3.44-3.59 (m, 2 H) 4.69 (dt, J = 7.92, 4.06 Hz, 1 H) 5.25-5.41 (m, 1 H) 7.23 (dd, J = 8.12, 4.79 Hz, 1 H) 7.75 (dd, J = 8.12, 1.47 Hz, 1 H) 7.91-8.02 (m, 2 H) 8.22 (dd, J = 4.69, 1.37 Hz, 1 H) |
| 187 | B7 | Intermediate 30, 2-chloroquinazoline (Waterstone) | 361 | 1H NMR (400 MHz, CHLOROFORM-d) d ppm 1.46 (s, 6 H) 2.37-2.59 (m, 2 H) 3.36-3.55 (m, 2 H) 4.76-4.94 (m, 1 H) 5.22-5.41 (m, 1 H) 5.73 (br. s., 1 H) 7.17-7.32 (m, 1 H) 7.56-7.77 (m, 3 H) 8.05-8.20 (m, 2 H) 9.01 (s, 1 H) |
| 188 | F7 | Intermediate 30, Intermediate 51 | 360 | 1H NMR (400 MHz, CHLOROFORM-d) d ppm 1.46 (s, 6 H) 2.37-2.49 (m, 2 H) 3.40-3.52 (m, 2 H) 4.73 (dd, J = 7.92, 3.62 Hz, 1 H) 5.25-5.38 (m, 1 H) 6.66 (d, J = 8.80 Hz, 1 H) 7.20-7.26 (m, 1 H) 7.51-7.58 (m, 1 H) 7.61 (d, J = 8.02 Hz, 1 H) 7.66-7.73 (m, 1 H) 7.88 (d, J = 9.00 Hz, 1 H) 8.09-8.15 (m, 2 H) |
| 189 | B7 | Intermediate 57, 2-chloroquinazoline (Waterstone) | 374 | 1H NMR (400 MHz, CHLOROFORM-d) d ppm 1.37 (s, 6 H) 1.82 (dd, J = 11.84, 2.05 Hz, 2 H) 2.77 (0, J = 12.58, 4.30 Hz, 2 H) 3.07 (td, J = 13.11, 2.35 Hz, 2 H) 4.64 (tt, J = 12.23, 4.01 Hz, 1 H) 5.20 (dt, J = 13.45, 2.08 Hz, 2 H) 6.92 (dd, J = 7.24, 5.28 Hz, 1 H) 7.22 (td, J = 7.38, 1.08 Hz, 1 H) 7.41 (dd, J = 7.24, 1.56 Hz, 1 H) 7.55-7.62 (m, 1 H) 7.63-7.72 (m, 2 H) 8.10 (dd, J = 5.28, 1,56 Hz, 1 H) 9.02 (d, J = 0.39 Hz, 1 H) |
| 190 | F7 | Intermediate 57, 2-chlorobenzo[d]thiazole (Alfa Aesar) | 379 | 1H NMR (400 MHz ,CHLOROFORM-d) d = 8.12 (dd, J = 1.6, 5.3 Hz, 1 H), 7.61 (dd, J = 0.8, 7.8 Hz, 1 H), 7.56 (dd, J = 0.6, 8.2 Hz, 1 H), 7.41 (dd, J = 1.8, 7.2 Hz, 1 H), 7.30 (ddd, J = 1.2, 7.3, 8.2 Hz, 1 H) 7.08 (dt, J = 1.1, 7.6 Hz, 1 H), 6.93 (dd, J = 5.3, 7.2 Hz, 1 H), 4.59 (tt, J = 3.9, 12.2 Hz, 1 H) 4.33 (td, J = 2.2, 13.2 Hz, 2 H), 3.25 (dt, J = 2.5, 13.1 Hz, 2 H), 2.88 (dq, J = 4.5, 12.7 Hz, 2 H), 1.82 (dd, J = 2.0, 11.5 Hz, 2 H), 1.38 (s, 6 H) |
| 191 | F7 | Intermediate 57, 2-chloroquinoline (Aldrich) | 373 | 1H NMR (400 MHz ,CHLOROFORM-d) d = 8.11 (dd, J =1.8, 5.3 Hz, 1 H), 7.89 (d, J = 9.2 Hz, 1 H), 7.70 (d, J = 8.4 Hz, 1 H), 7.60 (dd, J = 1.3, 7.9 Hz, 1 H), 7.53 (ddd, J = 1.6, 6.8, 8.4 Hz, 1 H), 7.41 (dd, J = 1.6, 7.2 Hz, 1 H), 7.22 (ddd, J = 1.0, 6.9, 8.0 Hz, 1 H), 7.05 (d, J =9.2 Hz, 1 H), 6.92 (dd, J = 5.3, 7.2 Hz, 1 H), 4.76 (td, J = 2.1, 13.3 Hz, 2 H), 4.62 (tt, J = 4.1, 12.2 Hz, 1 H), 3.06 (dt, J = 2.2, 13.1 Hz, 2 H), 2.81 (dq, J = 4.1, 12.5 Hz, 2 H), 1.88-1.77 (m, 2 H), 1.37 (s, 6 H) |
| 192 | F7 | Intermediate 57, 2-chloro-6-fluorobenzo[d]thiazole (see Step 1 of Example 213) | 397 | 1H NMR (400 MHz ,CHLOROFORM-d) d = 8.12 (dd, J = 1.4, 5.3 Hz, 1 H), 7.47 (dd, J = 4.7, 8.8 Hz, 1 H), 7.42 (dd, J = 1.4, 7.2 Hz, 1 H), 7.32 (dd, J = 2.5, 8.2, Hz, 1 H) 7.02 (dt, J = 2.6, 8.9 Hz, 1 H), 6.94 (dd, J = 5.5, 7.2 Hz, 1 H), 4.59 (tt, J = 3.9 , 12.3 Hz, 1 H), 4.28 (d, J = 13.1 Hz, 2 H), 3.25 (dt, J = 2.2, 13.1 Hz, 2 H), 2.99-2.79 (m, 2 H), 1.82 (d, J = 12.9 Hz, 2 H), 1.38 (s, 6 H) |

TABLE 8-continued

Preparation of Examples 158-159, 161, 163-164, 166, 168-172, 174-179, 187-196, 207, 210-211, and 222-225.

| Ex # | Method | Reagent | MW* | NMR |
|------|--------|---------|-----|-----|
| 193 | F7 | Intermediate 30, 6-fluoroquinolin-2-yl trifluoromethane sultbnate (commercially available) | 378 | 1H NMR (400 MHz, CHLOROFORM-d) d = 8.13-8.08 (m, 2 H), 7.81 (d, J = 8.8 Hz, 1 H), 7.66 (dd, J = 5.3, 9.2 Hz, 1 H), 7.34-7.22 (m, 2 H), 6.67 (d, J = 8.8 Hz, 1 H), 5.41-5.21 (m, 1 H), 5.05 (d, J = 5.5 Hz, 1 H), 4.72 (dt, J = 4.5, 8.1 Hz, 1 H), 3.55-3.37 (m, 2 H), 2.50-2.34 (m, 2 H), 1.45 (s, 6 H) |
| 194 | F7 | Intermediate 57, 2-chloro-7-fluoroquinoline (commercially available) | 391 | 1H NMR (400 MHz, CHLOROFORM-d) d = 8.11 (dd, J = 1.6, 5.3 Hz, 1 H), 7.85 (d, J = 9.2 Hz, 1 H), 7.55 (dd, J = 6.4, 8.7 Hz, 1 H), 7.41 (dd, J = 1.6, 7.2 Hz, 1 H), 7.32 (dd, J = 2.5, 11.2 Hz, 1 H), 7.01-6.90 (m, 3 H), 4.82-4.72 (m, 2 H), 4.62 (tt, J = 4.0, 12.2 Hz, 1 H), 3.06 (dt, J = 2.2, 13.1 Hz, 2 H), 2.79 (dq, J = 4.2, 12.6 Hz, 2 H), 1.88-1.77 (m, 2 H), 1.41-1.35 (m, 6 H) |
| 195 | F-7 | Intermediate 57, 6-fluoroquinolin-2-yl trifluoromethane sulfonate (commercially available) | 391 | 1H NMR (400 MHz, CHLOROFORM-d) d = 8.11 (dd, J = 1.6, 5.3 Hz, 1 H), 7.84 (d, J = 9.2 Hz, 1 H), 7.67 (dd, J = 5.3, 9.2 Hz, 1 H), 7.42 (dd, J = 1.6, 7.2 Hz, 1 H), 7.35-7.20 (m, 2 H), 7.08 (d, J = 9.2 Hz, 1 H), 6.93 (dd, J = 5.2, 7.3 Hz, 1 H), 4.76-4.67 (m, 2 H), 4.61 (tt, J = 4.0, 12.2 Hz, 1 H), 3.05 (dt, J = 2.2, 13.0 Hz, 2 H), 2.80 (dq, J = 4.1, 12.6 Hz, 2 H), 1.82 (dd, J = 2.0, 11.7 Hz, 2 H), 1.38 (s, 6 H) |
| 196 | B7 | Intermediate 30, 2-chloro-7-fluoroquinoline (commercially available) | 378 | 1H NMR (400 MHz, CHLOROFORM-d) d ppm 1.46 (s, 6 H) 2.35-2.49 (m, 2 H) 3.39-3.53 (m, 2 H) 4.73 (td, J = 8.22, 4.50 Hz, 1 H) 5.24-5.35 (m, 1 H) 6.59 (d, J = 9.00 Hz, 1 H) 6.95-7.03 (m, 1 H) 7.31 (dd, J = 10.95, 2.35 Hz, 1 H) 7.56 (dd, J = 8.80, 6.26 Hz, 1 H) 7.84 (d, J = 8.80 Hz, 1 H) 8.08-8.14 (m, 2 H) |
| 207 | G1 | 2-chlorobenzoxazole (in step 3) | M + 1 354.2 | $^1$H NMR (400 MHz, DMSO-d$_6$) δ ppm 2.45-2.55 (m, 2 H) 3.23-3.32 (m, 2 H) 3.35 (s, 3 H) 4.47-4.56 (m, 1 H) 5.23 (quin, J = 8.36 Hz, 1 H) 7.00 (td, J = 7.73, 1.17 Hz, 1 H) 7.12 (td, J = 7.63, 0.78 Hz, 1 H) 7.28 (d, J = 7.63 Hz, 1 H) 7.37 (d, J = 7.63 Hz, 1 H) 7.67 (dd, J = 8.90, 2.45 Hz, 1 H) 8.04 (t, J = 2.25 Hz, 1 H) 8.44 (d, J = 6.46 Hz, 1 H) |
| 210 | G3 | 2-chloro-5-fluorobenzothiazole (in step 4) | M + 1 388.1 | $^1$H NMR (400 MHz, DMSOd$_6$) δ ppm 2.42-2.50 (m, 2 H) 3.26-3.34 (m, 2 H) 3.36 (s, 3 H) 4.51-4.61 (m, 1 H) 5.21 (quin, J = 8.41 Hz, 1 H) 6.90 (td, J = 9.00, 2.54 Hz, 1 H) 7.25 (dd, J = 10.56, 2.54 Hz, 1 H) 7.66-7.75 (m, 2 H) 8.05 (t, J = 2.35 Hz, 1 H) 8.75 (d, J = 6.06 Hz, 1 H) |
| 211 | G2 | 2-amino-5-chloropyridine (in step 1) | M + 1 407.0 | 1H NMR (400 MHz, CHLQROFORM-d) δ ppm 2.46-2.57 (m, 2 H) 3.36-3.47 (m, 2 H) 4.54-4.62 (m, 1 H) 5.23 (quin, J = 8.46 Hz, 1 H) 5.76 (br, s. 1 H) 7.12 (t, J = 7.53 Hz, 1 H) 7.32 (t, J = 7.73 Hz, 1 H) 7.56-7.64 (m, 2 H) 7.82 (s, 1 H) 8.39 (br. s, 1 H) |
| 222 | H1 | 2-chloro-5-fluorobenzo[d]thiazole | 397.0 | $^1$H NMR (400 MHz, CHLOROFORM-d) δ ppm 1.05-1.36 (m, 4 H) 2.53-2.65 (m, 2 H) 2.97-3.06 (m, 1 H) 3.43-3.55 (m, 2 H) 4.63 (dt, J = 7.78, 4.03 Hz, 1 H) 5.27-5.40 (m, 1 H) 6.88 (td, J = 8.80, 2.54 Hz, 1 H) 7.29 (d, J = 2.35 Hz, 1 H) 7.52 (dd, J = 8.61, 5.28 Hz, 1 H) 7.93-7.97 (m, 1 H) 7.98 (s, 1 H) |
| 223 | H1 | 2-chloro-1,8-naphthyridine (Parkway Scientific LLC) | 374.0 | $^1$H NMR (400 MHz, CHLOROFORM-d) δ ppm 1.07-1.32 (m, 4 H) 2.52 (br. s., 2 H) 3.01 (br. s., 1 H) 3.56 (d, J = 8.02 Hz, 2 H) 4.93 (br. s., 1 H) 5.32 (d, J = 8.80 Hz, 1 H) 6.74 (d, J = 8.41 Hz, 1 H) 7.20 (br. s., 1 H) 7.86 (d, J = 9.19 Hz, 1 H) 7.96 (br. s. 3 H) 8.85 (br. s., 1 H) |
| 224 | H1 | 2-chloro-6-methoxybenzo[d]thiazole (TCI America) | 409.0 | $^1$H NMR (400 MHz, CHLOROFORM-d) δ ppm 1.18 (br. s., 4 H) 2.58 (t, J = 9.78 Hz, 2 H) 3.01 (t, J = 4.99 Hz, 1 H) 3.41-3.54 (m, 2 H) 3.84 (s, 3 H) 4.61 (br. s., 1 H) 5.33 (quin, J = 8.17 Hz, 1 H) 6.93 (d, J = 8.61 Hz, 1 H) 7.16 (s, 1 H) 7.49 (d, J = 8.61 Hz. 1 H) 7.91-8.01 (m, 2 H) |

TABLE 8-continued

Preparation of Examples 158-159, 161, 163-164, 166, 168-172, 174-179, 187-196, 207, 210-211, and 222-225.

| Ex # | Method | Reagent | MW* NMR |
|------|--------|---------|---------|
| 225 | H1 | quinolin-2-yl trifluoromethane sulfonate | 373.0 ¹H NMR (400 MHz, CHLOROFORM-d) δ ppm 1.10-1.22 (m, 4 H) 2.52 (t, J = 10.27 Hz, 2 H) 2.96-3.07 (m, 1 H) 3.43-3.55 (m, 2 H) 4.76 (br. s., 1 H) 5.34 (dd, J = 17.31, 8.71 Hz, 1 H) 6.68 (d, J = 8.80 Hz, 1 H) 7.24 (s, 1 H) 7.57 (t, J = 7.53 Hz, 1 H) 7.63 (d, J = 8.02 Hz, 1 H) 7.71 (d, J = 8.22 Hz, 1 H) 7.92 (d, J = 8.80 Hz, 1 H) 7.97 (s, 2 H) |

And are named as follows:

| Ex # | Chemical Name |
|------|---------------|
| 158 | 5-(trans-3-((5-bromopyridin-2-yl)amino)cyclobuty1)-7,7-dimethyl-5H-pyrrolo[2,3-b]pyrazin-6(7 H)-one |
| 159 | 5-(trans-3-((5-methoxypyrazin-2-yl)amino)cyclobulyl)-7,7-dimethyl-5H-pyrrolo[2,3-b]pyrazin-6(7 H)-one |
| 161 | 7,7-dimethyl-5-(trans-3-((1-methyl-1H-benzo[d]imidazol-2-yl)amino)cyclobutyl)-5H-pyrrolo-[2,3-b]pyrazin-6(7 H)-one |
| 163 | 5-(trans-3-((1,5-naphthyridin-2-yl)amino)cyclobutyl)-7,7-dimethyl-5H-pyrrolo[2,3-b]pyrazin-6(7 H)-one |
| 164 | 5-(trans-3-((5-(1H-pyrazol-1-yl)pyridin-2-yl)amino)cyclobutyl)-7,7-dimethyl-5H-pyrrolo[2,3-b]pyrazin-6(7 H)-one triacetate |
| 166 | 3,3-dimethyl-1-(trans-3-(quinazolin-2-ylamino)cyclobutyl)-1H-pyrrolo[2,3-b]pyridin-2(38)-one |
| 168 | 1-(trans-3-(benzo[d]oxazol-2-ylamino)cyclobutyl)-3,3-dimethyl-1H-pyrrolo[2,3-b]pyridin-2(3 H)-one |
| 169 | 5-(trans-3-((5,6-difluorobenzo[d]thiazole-2-yl)amino)cyclobutyl)7,7-dimethyl-5H-pyrrolo-[2,3-b]pyrazin-6(7 H)-one |
| 170 | 5-(trans-3-((4,6-difluorobenzo[d]thiazole-2-yl)amino)cyclobutyl)-7,7-dimethyl-5H-pyrrolo-[2,3-b]pyrazin-6(714)-one |
| 171 | 5-(trans-3-((6-methoxybenzo[d]thiazole-2-yl)amino)cyclobutyl)-7,7-dimethyl-5H-pyrrolo[2,3-b]pyrazin-6(7 H)-one |
| 172 | 1-methyl-3-(trans-3-(thiazolo[-5,4-b]pyridin-2-ylamino)cyclobutyl)-1H-imidazo[4,5-b]pyridin-2(3 H)-one |
| 174 | 1-cyclopropyl-3-(trans-3-((7-fluoroquinazoln-2-yl)amino)cyclobutyl)-1H-imidazo[4,5-b]pyrazin-2(3 H)-one |
| 175 | 5-(trans-3-((7-fluoroquinazolin-2-yl)amino)cyclobutyl)-7,7-dimethyl-5H-pyrrolo[2,3-b]pyrazin-6(7 H)-one |
| 176 | 1-cyclopropyl-3-(trans-3-((6-fluorobenzo[d]oxazol-2-yl)amino)cyclobutyl)-1H-imidazo[4,5-b]pyrazin-2(3 H)-one |
| 177 | 5-(trans-3-((6fluorobenzo[d]oxazol-2-yl)amino)cyclobutyl)-7,7-dimethyl-5H-pyrrolo[2,3-b]pyrazin- 6(7 H)-one |
| 178 | 1-cyclopropyl-3-(trans-3-(thiazolo[5,4-b]pyridin-2-ylamino)cyclobutyl)-1H-imidazo[4,5-b]pyrazin-2(3 H)-one |
| 179 | 7,7-dimethyl-5-(trans-3-(quinazolin-2-ylamino)cyclobutyl)-5H-pyrrolo[2,3-b]pyrazin-6(7 H)-one |
| 187 | 7,7-dimethyl-5-(3-(quinolin-2-ylamino)cyclobutyl)-5H-pyrrolo[2,3-b]pyrazin-6(7 H)-one |
| 188 | 3,3-dimethyl-1-(1-(quinazolin-2-yl)piperidin-4-yl)-1H-pyrrolo[2,3-b]pyridin-2(3 H)-one |
| 189 | 1-(1-(benzo[d]thiazol-2-yl)piperidin-4-yl)-3,3-dimethyl-1H-pyrrolo[2,3-b]pyridin-2(3 H)-one |
| 190 | 3,3-dimethyl-1-(1-(quinolin-2-yl)piperidin-4-yl)-1H-pyrrolo[2,3-b]pyridin-2(3 H)-one |
| 191 | 1-(1-(6-fluorobenzo[d]thiazol-2-yl)piperidin-4-yl)-3,3-dimethyl-1H-pyrrolo[2,3-b]pyridin-2(3 H)-one |
| 192 | 5-(trans-3-((6-fluoroquinolin-2-yl)amino)cyclobutyl)-7,7-dimethyl-5H-pyrrolo[2,3-b]pyrazin-6 7 H)-one |
| 193 | 1-(1-(7-fluoroquinolin-2-yl)piperidin-4-yl)-3,3-dimethyl-1H-pyrrolo[2,3-b]pyridin-2(3 H)-one |
| 194 | 1-(1-(6-fluoroquinolin-2-yl)piperidin-4-yl)-3,3-dimethyl-1H-pyrrolo[2,3-b]pyridin-2(3 H)-one |
| 195 | 3-(trans-3-((7-fluoroquinolin-2-yl)amino)cyclobutyl)-7,7-dimethyl-5H-pyrrolo[2,3-b]pyrazin- 6(7 H)-one |
| 196 | 3-(Trans-3-(benzo[d]oxazol-2-ylamino)cyclobutyl)-6-fluoro-1-methyl-1H-imidazo[4,5-b]pyridin-2(3 H)-one |
| 207 | 5-(trans-3-((5-bromopyridin-2-yl)amino)cyclobutyl)-7,7-dimethyl-5H-pyrrolo[2,3-b]pyrazin-6(7 H)-one |
| 210 | 6-fluoro-3-(trans-3-((5-fluorobenzo[d]thiazol-2-yl)amino)cyclobutyl)-1-methyl-1H-imidazo[4,5-b]pyridin-2(3 H)-one |
| 211 | 1-(trans-3-(benzo[d]thiazol-2-ylamino)cyclobutyl)-5-chloro-3,3-difluoro-1H-pyrrolo[2,3-b]pyridin-2(3 H)-one |
| 222 | 1-cyclopropyl-3-(trans-3-((5-fluorobenzo[d]thiazol-2-yl)amino)cyclobutyl)-1H-imidazo[4,5-b]pyrazin-2(3 H)-one |
| 223 | 1-(trans-3-((1,8-naphthyridin-2-yl)amino)cyclobutyl)-3-cyclopropyl-1H-imidazo[4,5-b]pyrazin-2(3 H)-one |
| 224 | 1-cyclopropyl-3-(trans-3-((6-methoxybenzo[d]thiazol-2-yl)amino)cyclobutyl)-1H-imidazo[4,5-b]pyrazin-2(3 H)-one |
| 225 | 1-cyclopropyl-3-(trans-3-((6-methoxy-1,3-benzothiazol-2-yl)amino)cyclobutyl)-1,3-dihydro-2H-imidazo[4,5-b]pyrazin-2-one |

Example 197

5-(trans-3-(benzo[d]thiazol-2-yloxy)cyclobutyl)-7,7-dimethyl-5H-pyrrolo[2,3-b]pyrazin-6(7H)-one

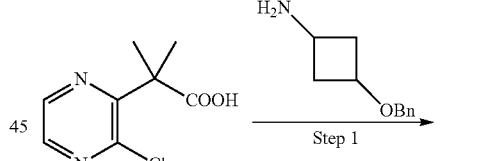

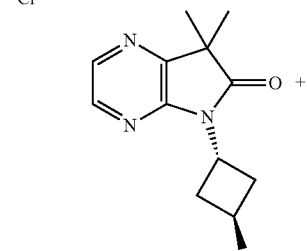

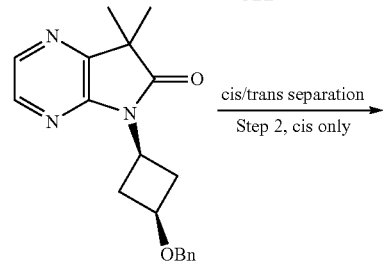

-continued

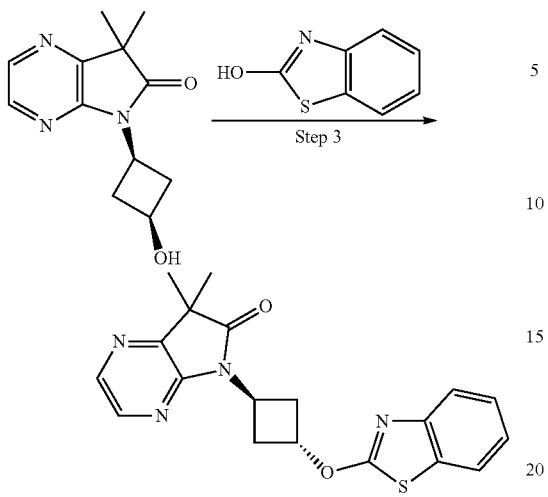

Step 1: 5-(trans-3-(benzyloxy)cyclobutyl)-7,7-dimethyl-5H-pyrrolo[2,3-b]pyrazin-6(7H)-one and 5-(cis-3-(benzyloxy)cyclobutyl)-7,7-dimethyl-5H-pyrrolo[2,3-b]pyrazin-6(7H)-one A mixture of 2-(3-chloropyrazin-2-yl)-2-methylpropanoic acid (Intermediate 29) (1.5 g, 7.48 mmol), 3-(benzyloxy)cyclobutanamine (1.458 g, 8.22 mmol), DIEA (1.698 ml, 9.72 mmol), and HATU (3.13 g, 8.22 mmol) in DMF (20 mL) was stirred at room temperature overnight. H$_2$O was added, and the mixture was extracted with DCM (3×). The extracts were dried over Na$_2$SO$_4$, filtered, concentrated. The crude material was dissolved in p-dioxane (20 mL), sodium tert-butoxide (3.59 g, 37.4 mmol) was added, and the reaction was stirred at room temperature for 3 h. H$_2$O was added and extracted with EtOAc (3×). The extracts were dried over MgSO$_4$, concentrated and purified by ISCO (20% EtOAc Hexanes) to give the title compounds the cis-isomer (450 mg, 18.5%) and trans-isomer (450 mg, 18%). MS (M+1): 324. The trans and cis isomers were separated by silica gel chromatography (0-20% EtOAc/Hexanes) and the cis isomer was used without further purification in the next step.

Step 2: 5-(cis-3-hydroxycyclobutyl)-7,7-dimethyl-5H-pyrrolo[2,3-b]pyrazin-6(7H)-one A mixture of 5-(cis-3-(benzyloxy)cyclobutyl)-7,7-dimethyl-5H-pyrrolo[2,3-b]pyrazin-6(7H)-one (0.205 g, 0.634 mmol), and dihydroxypalladium (0.092 g, 0.655 mmol) in MeOH (5 mL) was hydrogenated at room temperature under H, balloon overnight. The catalyst was filtered off, the filtrate was concentrated, and purified by ISCO (65% EtOAc/Hexanes) to give the title compound (55 mg, 37%). MS (M+1): 234.1.

Step 3: 5-(trans-3-(benzo[d]thiazol-2-yloxy)cyclobutyl)-7,7-dimethyl-5H-pyrrolo[2,3-b]pyrazin-6(7H)-one To a stirred mixture of 5-(cis-3-hydroxycyclobutyl)-7,7-dimethyl-5H-pyrrolo[2,3-b]pyrazin-6(7H)-one (0.022 g, 0.094 mmol), triphenylphosphine (0.030 g, 0.113 mmol), 2-hydroxybenzothiazole (0.017 g, 0.113 mmol) in THF (2 mL) at 0° C. was added DIAD (0.028 mL, 0.141 mmol). The reaction mixture was stirred at room temperature overnight, concentrated, purified by reverse phase HPLC. The pure fractions were concentrated to minimal H$_2$O, neutralized with saturated aqueous NaHCO$_3$, and the off white solid was collected and dried (18.5 mg, 53.5%). MS (M+1):367.1. $^1$H NMR (400 MHz, MeOH) δ ppm 8.20 (1 H, d, J=3.1 Hz), 8.15 (1 H, d, J=3.1 Hz), 7.76 (1 H, dd, J=7.9, 0.7 Hz), 7.66 (1 H, d, J=7.6 Hz), 7.39 (1 H, td, J=7.8, 1.3 Hz), 7.19-7.34 (1 H, m), 5.79 (1 H, dt, J=7.0, 3.5 Hz), 5.25-5.42 (1 H, m), 3.40-3.56 (2 H, m), 2.68-2.86 (2 H, m), 1.38-1.50 (6 H, m). MS (M+1): 367.1.

Example 198

5-(1-(benzo[d]thiazol-2-yl)piperidin-4-yl)-7,7-dimethyl-5H-pyrrolo[2,3-b]pyrazin-6(7H)-one

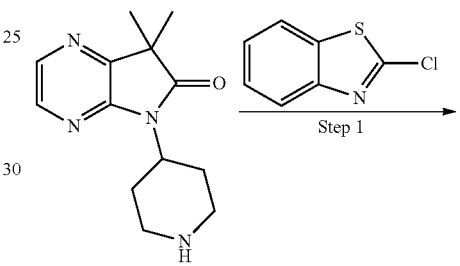

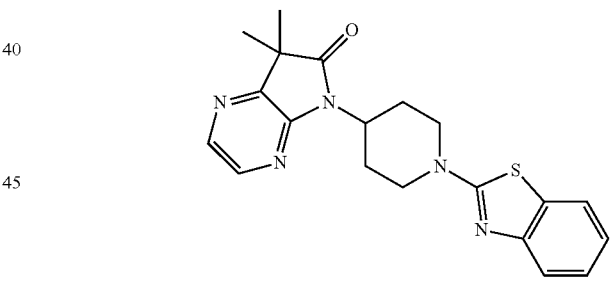

A mixture of 7,7-dimethyl-5-(piperidin-4-yl)-5H-pyrrolo[2,3-b]pyrazin-6(7H)-one hydrochloride (Intermediate 78) (0.107 g, 0.378 mmol), potassium carbonate (0.183 g, 1.324 mmol), and 2-chlorobenzo[d]thiazole (0.077 g, 0.454 mmol) in DMSO (3 mL) was heated at 110° C. in 2 h. The reaction mixture was cooled, H$_2$O was added, and extracted with DCM (3×). The organic extracts were dried over Na$_2$SO$_4$, filtered, concentrated, and purified by reverse phase HPLC. The pure fractions were concentrated to minimal H$_2$O, neutralized with saturated aqueous NaHCO$_3$. The white solid was collected, washed with H$_2$O, and dried to afford the title compound (67 mg, 47%). MS (M+1): 380. $^1$H NMR (400 MHz, DMSO-d$_6$) δ ppm 8.04-8.19 (2 H, m), 7.77 (1 H, d, J=7.4 Hz), 7.46 (1 H, d, J=8.0 Hz), 7.21-7.35 (1 H, m), 6.98-7.14 (3 H, m), 4.46-4.65 (1 H, m), 4.18 (2 H, d, J=13.1 Hz), 3.32-3.41 (2 H, m), 2.52-2.62 (2 H, m), 1.83 (2 H, d, J=10.8 Hz), 1.33 (6 H, s)

Example 199

5-(1-(6-fluoroquinolin-2-yl)piperidin-4-yl)-7,7-dimethyl-5H-pyrrolo[2,3-b]pyrazin-6(7H)-one

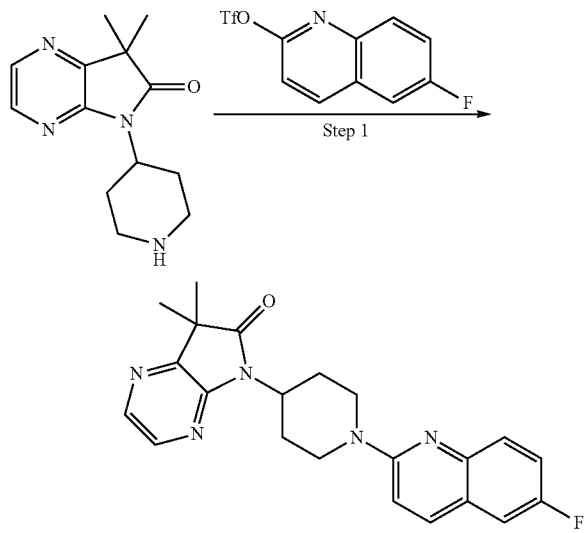

A mixture of 7,7-dimethyl-5-(piperidin-4-yl)-5H-pyrrolo[2,3-b]pyrazin-6(7H)-one hydrochloride (Intermediate 78) (0.117 g, 0.414 mmol), 6-fluoroquinolin-2-yl trifluoromethanesulfonate (0.134 g, 0.455 mmol), and DIEA (0.253 ml, 1.448 mmol) in DMSO (3 mL) was heated at 110° C. in 1 h. The reaction mixture was cooled, H$_2$O was added, and the mixture was extracted with DCM (3×). The organic extracts were dried over Na$_2$SO$_4$, filtered, concentrated, and purified by ISCO (0-30% EtOAc/DCM) to give the title compound (81 mg, 50%). MS (M+1): 392.1. $^1$H NMR (400 MHz, DMSO-d$_6$) δ ppm 8.11-8.13 (1 H, m), 8.08-8.10 (1 H, m), 8.05 (1 H, d, J=9.2 Hz), 7.60 (1 H, dd, J=9.2, 5.3 Hz), 7.52 (1 H, dd, J=9.4, 2.9 Hz), 7.40-7.45 (1 H, m), 7.35-7.40 (1 H, m), 4.71 (2 H, d, J=13.5 Hz), 4.48-4.63 (1 H, m), 3.02 (2 H, t, J=12.1 Hz), 2.36-2.48 (2 H, m), 1.79 (2 H, d, J=9.8 Hz), 1.27-1.36 (6 H, m).

Example 200

5-(1-(7-chloroquinazolin-2-yl)piperidin-4-yl)-7,7-dimethyl-5H-pyrrolo[2,3-b]pyrazin-6(7H)-one

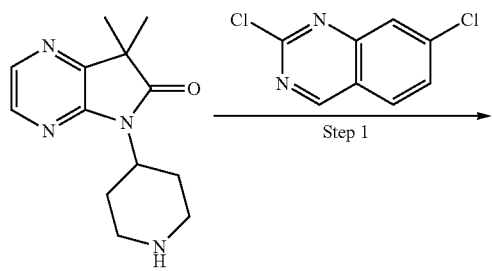

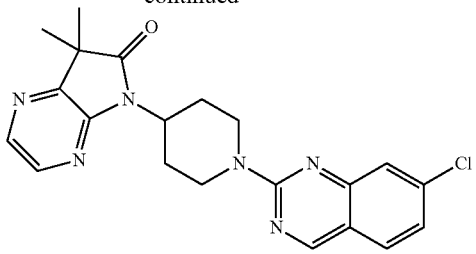

A mixture of 7,7-dimethyl-5-(piperidin-4-yl)-5H-pyrrolo[2,3-b]pyrazin-6(7H)-one hydrochloride (Intermediate 78) (0.150 g, 0.530 mmol, Intermediate 57), 2,7-dichloroquinazoline (0.127 g, 0.637 mmol), and potassium carbonate (0.257 g, 1.857 mmol) in DMSO (3 mL) was heated at 110° C. in 2 h. The reaction mixture was cooled, H$_2$O was added, and the solid was collected, purified by ISCO (30% EtOAc/Hexanes) to give the title compound (165 mg, 76%). MS (M+1): 409. $^1$H NMR (400 MHz, DMSO-d$_6$) δ ppm 9.25 (1 H, s), 8.08 (1 H, d, J=3.1 Hz), 8.12 (1 H, d, J=3.1 Hz), 7.89 (1 H, d, J=8.6 Hz), 7.54 (1 H, d, J=1.8 Hz), 7.29 (1 H, dd, J=8.6, 2.0 Hz), 5.02 (2 H, d, J=13.3 Hz), 4.60 (1 H, tt, J=12.2, 4.0 Hz), 2.92-3.15 (2 H, m), 2.42 (2 H, qd, J=12.6, 4.4 Hz), 1.82 (2 H, d, J=9.8 Hz), 1.32 (6 H, s).

Example 201

5-(1-(6-fluoroquinazolin-2-yl)piperidin-4-yl)-7,7-dimethyl-5H-pyrrolo[2,3-b]pyrazin-6(7H)-one

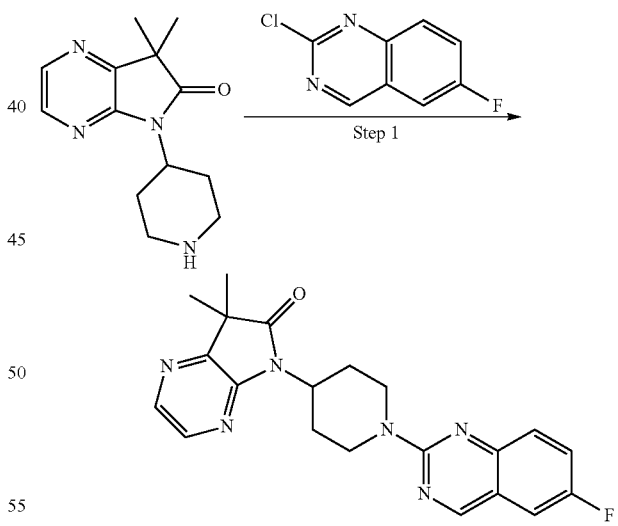

A mixture of 7,7-dimethyl-5-(piperidin-4-yl)-5H-pyrrolo[2,3-b]pyrazin-6(7H)-one hydrochloride (Intermediate 78) (0.088 g, 0.311 mmol), 2-chloro-6-fluoroquinazoline (0.063 g, 0.342 mmol), and potassium carbonate (0.129 g, 0.934 mmol) in DMSO (3 mL) was heated at 110° C. overnight. The mixture was cooled, H$_2$O was added, and the solid was collected, dried, and purified by ISCO (40% EtOAc/Hexanes) to give the title compound (43 mg, 35%). MS (M+1): 393. $^1$H NMR (400 MHz, DMSO-d$_6$) δ ppm 9.23 (1 H, s), 8.08 (1 H, d, J=3.1 Hz), 8.12 (1 H, d, J=3.1 Hz), 7.62-7.74 (2 H, m), 7.46-7.62 (1 H, m), 5.00 (2 H, d, J=13.5 Hz), 4.47-4.67 (1 H, m), 2.97-3.14 (2 H, m), 2.36-2.48 (2 H, m), 1.80 (2 H, d, J=9.6 Hz), 1.32 (6 H, s).

Example 202

7,7-dimethyl-5-(1-(6-(trifluoromethyl)benzo[d]thiazol-2-yl)piperidin-4-yl)-5H-pyrrolo[2,3-b]pyrazin-6(7H)-one

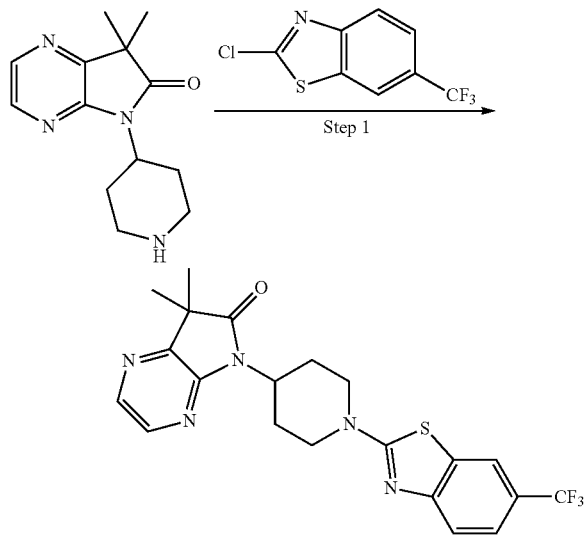

A mixture of 7,7-dimethyl-5-(piperidin-4-yl)-5H-pyrrolo[2,3-b]pyrazin-6(7H)-one hydrochloride (Intermediate 78) (0.088 g, 0.311 mmol), 2-chloro-6-(trifluoromethyl)benzo[d]thiazole (0.089 g, 0.373 mmol), and potassium carbonate (0.172 g, 1.245 mmol) in DMSO (3 mL) was heated at 110° C. overnight. The reaction mixture was cooled, H$_2$O was added, and the solid was collected, dried and purified by ISCO (35% EtOAc/Hexanes) to give the title compound (93.5 mg, 67%). MS (M+1): 448. $^1$H NMR (400 MHz, DMSO-d$_6$) δ ppm 8.27 (1 H, s), 8.03-8.18 (2 H, m), 7.52-7.68 (2 H, m), 4.51-4.68 (1 H, m), 4.23 (2 H, d, J=12.5 Hz), 3.36-3.49 (2 H, m), 2.52-2.61 (2 H, m), 1.86 (2 H, d, J=10.4 Hz), 1.33 (6 H, s).

Example 203

3,3-dimethyl-1-(trans-3-((4-methylthiazol-2-yl)amino)cyclobutyl)-1H-pyrrolo[2,3-b]pyridin-2(3H)-one

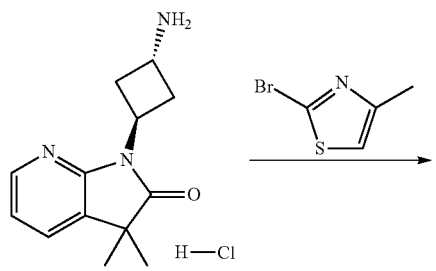

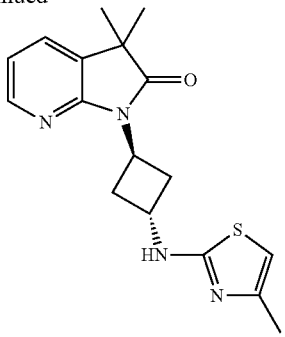

3,3-Dimethyl-1-(trans-3-((4-methylthiazol-2-yl)amino)cyclobutyl)-1h-pyrrolo[2,3-b]pyridin-2(3h)-one was prepared by Method B7 using starting materials 1-(trans-3-aminocyclobutyl)-3,3-dimethyl-1H-pyrrolo[2,3-b]pyridin-2(3H)-one hydrochloride (intermediate 26, 0.100 g, 0.329 mmol) and 2-bromo-4-methylthiazole (0.0585 g, 0.329 mmol) at 120° C. for 96 h. M+1: 329.1. $^1$H NMR (400 MHz, CHLOROFORM-d) δ ppm 1.38 (s, 6 H) 2.25 (s, 3 H) 2.33-2.42 (m, 2 H) 3.38-3.49 (m, 2 H) 4.35 (br. s., 1 H) 5.27 (quin, J=8.56 Hz, 1 H) 5.60 (br. s., 1 H) 6.09 (s, 1 H) 6.96 (t, J=6.16 Hz, 1 H) 7.43 (d, J=6.85 Hz, 1 H) 8.17 (d, J=5.30 Hz, 1 H).

Example 204

3,3-dimethyl-1-(trans-3-((5-phenylthiazol-2-yl)amino)cyclobutyl)-1H-pyrrolo[2,3-b]pyridin-2(3H)-one

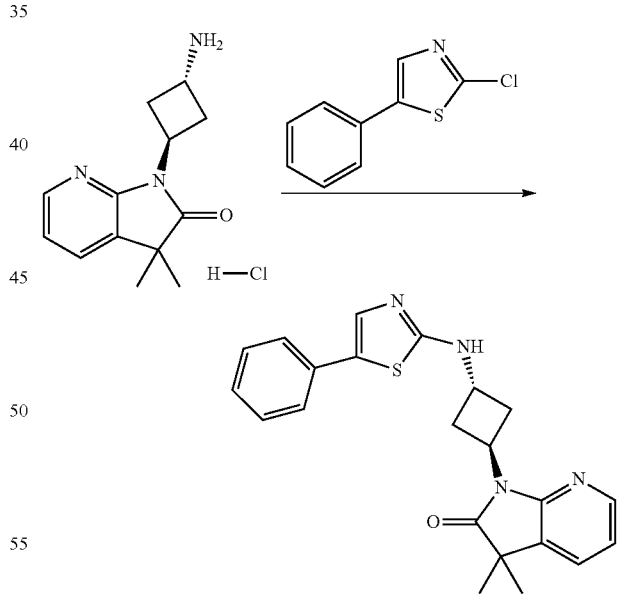

3,3-Dimethyl-1-(trans-3-((5-phenylthiazol-2-yl)amino)cyclobutyl)-1H-pyrrolo[2,3-b]pyridin-2(3h)-one was prepared by Method B7 using starting materials 1-(trans-3-aminocyclobutyl)-3,3-dimethyl-1H-pyrrolo[2,3-b]pyridin-2(3H)-one hydrochloride (intermediate 26, 0.100 g, 0.329 mmol) and 2-chloro-5-phenylthiazole (0.0643 g, 0.329 mmol) at 120° C. for 96 h. M+1: 391.1. $^1$H NMR (400 MHz, DMSO-d$_6$) δ ppm 1.31 (s, 6 H) 2.31-2.40 (m, 2 H) 3.21-3.31 (m, 2 H) 4.34-4.43 (m, 1 H) 5.17 (quin, J=8.46 Hz, 1 H) 7.08

(dd, J=7.24, 5.09 Hz, 1 H) 7.17-7.22 (m, 1 H) 7.35 (br. t, J=7.70, 7.70 Hz, 2 H) 7.45 (br. d, J=7.20 Hz, 2 H) 7.52 (s, 1 H) 7.76 (dd, J=7.24, 1.56 Hz, 1 H) 8.21 (dd, J=5.28, 1.56 Hz, 1 H) 8.30 (d, J=6.20 Hz, 1 H).

Example 205

3,3-dimethyl-1-(trans-3-((5-methylthiazol-2-yl)amino)cyclobutyl)-1H-pyrrolo[2,3-b]pyridin-2(3H)-one

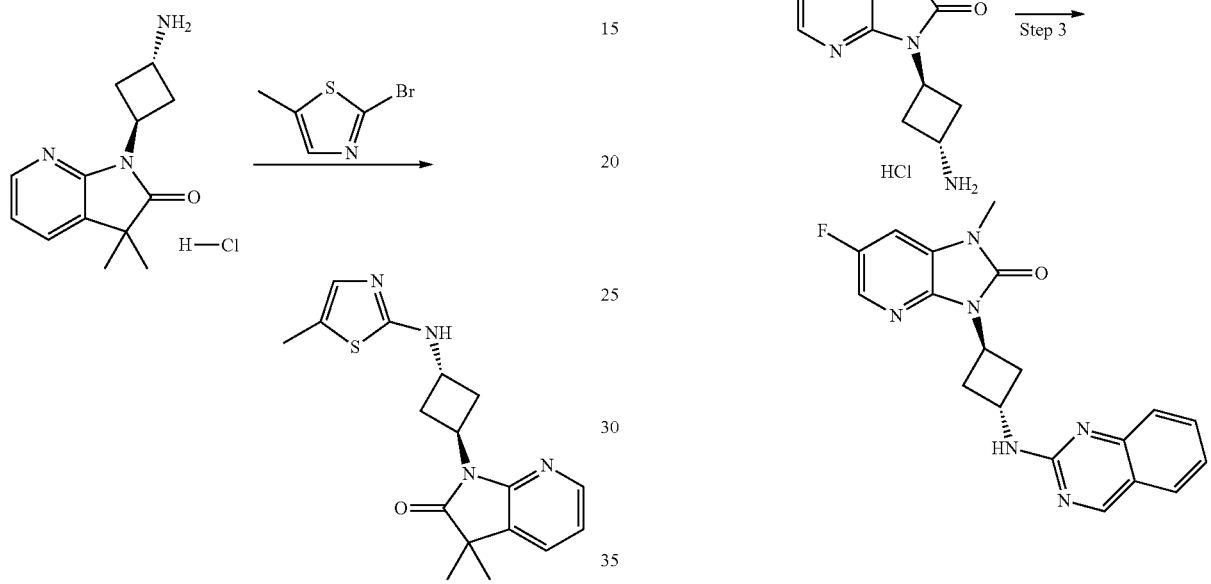

3,3-Dimethyl-1-(trans-3-((5-methylthiazol-2-yl)amino)cyclobutyl)-1H-pyrrolo[2,3-b]pyridin-2(3H)-one was prepared by Method B7 using starting materials 1-(trans-3-aminocyclobutyl)-3,3-dimethyl-1H-pyrrolo[2,3-b]pyridin-2(3H)-one hydrochloride (intermediate 26, 0.100 g, 0.329 mmol) and 2-bromo-5-methylthiazole (0.0585 g, 0.329 mmol) at 120° C. for 192 h. M+1: 329.1. $^1$H NMR (400 MHz, DMSO-$d_6$) δ ppm 1.31 (s, 6 H) 2.23 (d, J=1.17 Hz, 3 H) 2.24-2.33 (m, 2 H) 3.16-3.27 (m, 2 H) 4.23-4.33 (m, 1 H) 5.14 (quin, J=8.41 Hz, 1 H) 6.71 (br. d, J=1.20 Hz, 1 H) 7.08 (dd, J=7.24, 5.28 Hz, 1 H) 7.76 (dd, J=7.24, 1.56 Hz, 1 H) 7.81 (d, J=6.26 Hz, 1 H) 8.21 (dd, J=5.18, 1.66 Hz, 1 H).

Method G1

Example 206

6-fluoro-1-methyl-3-(trans-3-(quinazolin-2-ylamino)cyclobutyl)-1H-imidazo[4,5-b]pyridin-2(3H)-one

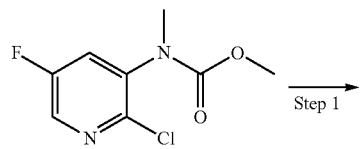

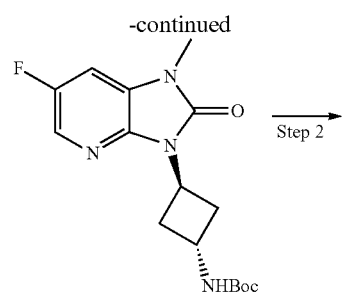

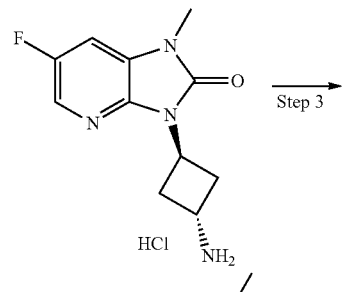

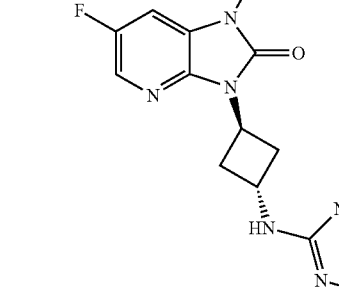

Step 1: tert-butyl(trans-3-(6-fluoro-1-methyl-2-oxo-1H-imidazo[4,5-b]pyridin-3(2H)-yl)cyclobutyl)carbamate Methyl (2-chloro-5-fluoropyridin-3-yl)(methyl)carbamate (intermediate 37, 0.343 g, 1.569 mmol), tert-butyl(trans-3-aminocyclobutyl)carbamate (0.292 g, 1.569 mmol), BrettPhos Precatalyst (0.125 g, 0.157 mmol), and sodium tert-butoxide (0.377 g, 3.92 mmol) were mixed in 1,4-dioxane (2 mL) under an argon atmosphere. The reaction mixture was heated to 50° C. and stirred for 30 min. The reaction mixture was diluted with water and extracted once with EtOAc. The organic layer was separated, washed with saturated aqueous sodium chloride, dried over magnesium sulfate, filtered, and concentrated in vacuo. The resulting crude product was purified by silica gel column chromatography eluting with EtOAc in hexanes to yield tert-butyl(trans-3-(6-fluoro-1-methyl-2-oxo-1 h-imidazo[4,5-b]pyridin-3(2h)-yl)cyclobutyl)carbamate (0.250 g, 0.743 mmol, 47.4% yield) as a white solid.

Step 2: 3-(trans-3-aminocyclobutyl)-6-fluoro-1-methyl-1H-imidazo[4,5-b]pyridin-2(3H)-one hydrochloride Hydrogen chloride (4.0 M in 1,4-dioxane, 1.843 mL, 7.37 mmol) was added to a stirred mixture of tert-butyl(trans-3-(6-fluoro-1-methyl-2-oxo-1H-imidazo[4,5-b]pyridin-3(2H)-yl)cyclobutyl)carbamate (0.248 g, 0.737 mmol) in 1,4-dioxane (3 mL). The reaction mixture was stirred at room temperature for 5 h. The reaction mixture was concentrated to yield 3-(trans-3-aminocyclobutyl)-6-fluoro-1-methyl-1 h-imidazo[4,5-b]pyridin-2(3h)-one hydrochloride (0.210 g, 0.770 mmol, 104% yield) as a white solid. M+1: 237.1.

Step 3: 6-fluoro-1-methyl-3-(trans-3-(quinazolin-2-ylamino)cyclobutyl)-1H-imidazo[4,5-b]pyridin-2(3H)-one 3-(Trans-3-aminocyclobutyl)-6-fluoro-1-methyl-1H-imidazo[4,5-b]pyridin-2(3H)-one hydrochloride (0.105 g, 0.385 mmol), 2-chloroquinazoline (0.076 g, 0.462 mmol), and N,N-diisopropylethylamine (0.268 mL, 1.540 mmol) were mixed in DMSO (0.5 mL). The reaction mixture was warmed to 120° C. and stirred for 3 h. The reaction mixture was cooled to room temperature, diluted with water, and extracted with EtOAc. The organic layer was separated, washed with saturated aqueous sodium chloride, dried over magnesium sulfate, filtered, and concentrated in vacuo. The resulting crude product was purified by silica gel column chromatography eluting with EtOAc in hexanes to yield 6-fluoro-1-methyl-3-(trans-3-(quinazolin-2-ylamino)cyclobutyl)-1H-imidazo[4,5-b]pyridin-2(3h)-one (0.054 g, 0.148 mmol, 38.5% yield) as a yellow solid. M+1: 365.1. $^1$H NMR (400 MHz, DMSO-d) δ ppm 2.42-2.50 (m, 2 H) 3.25-3.34 (m, 2 H) 3.35 (s, 3 H) 4.63-4.74 (m, 1 H) 5.25 (quin, J=8.51 Hz, 1 H) 7.22-7.27 (m, 1 H) 7.49 (d, J=8.41 Hz, 1 H) 7.64-7.73 (m, 2 H) 7.81 (dd, J=8.02, 0.78 Hz, 1 H) 7.99 (br. d, J=6.30 Hz, 1 H) 8.05 (t, J=2.25 Hz, 1 H) 9.15 (s, 1 H).

Method G2

Example 208

1-(trans-3-(benzo[d]thiazol-2-ylamino)cyclobutyl)-3,3,5-trifluoro-1H-pyrrolo[2,3-b]pyridin-2(3H)-one

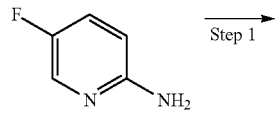

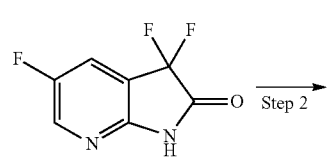

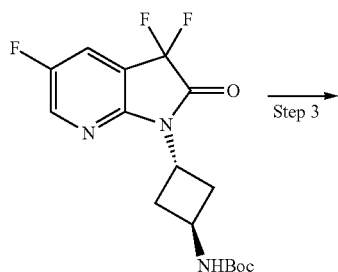

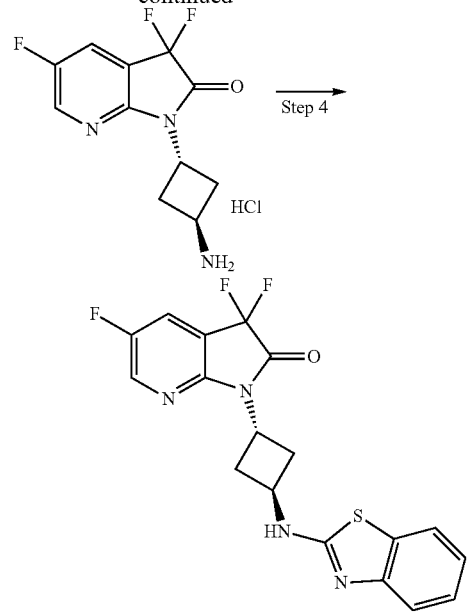

Step 1:
3,3,5-trifluoro-1H-pyrrolo[2,3-b]pyridin-2(3H)-one

Hydrogen peroxide (30% aqueous solution, 0.984 mL, 9.63 mmol) was added dropwise to a stirred mixture of 2-amino-5-fluoropyridine (0.540 g, 4.82 mmol), ferrocene (0.090 g, 0.482 mmol), and ethyl bromodifluoroacetate (1.862 mL, 14.45 mmol) in DMSO (24 mL) under an argon atmosphere. The mixture was stirred at room temperature for 18 h. Sulfuric acid (0.514 mL, 9.63 mmol) was added, and the reaction mixture was stirred at room temperature for another 24 h. The reaction mixture was diluted with water and extracted with EtOAc. The organic layer was separated, washed with saturated aqueous sodium chloride, dried over magnesium sulfate, filtered, and concentrated in vacuo. The resulting crude product was purified by silica gel column chromatography eluting with EtOAc in hexanes to yield the title compound (0.248 g, 1.318 mmol, 27.4% yield) as a brown solid. M+1: 189.1.

Step 2: tert-butyl(trans-3-(3,3,5-trifluoro-2-oxo-2,3-dihydro-1H-pyrrolo[2,3-b]pyridin-1-yl)cyclobutyl)carbamate 3,3,5-Trifluoro-1H-pyrrolo[2,3-b]pyridin-2(3H)-one (0.248 g, 1.318 mmol), tert-butyl(cis-3-hydroxycyclobutyl)carbamate (0.247 g, 1.318 mmol), and triphenylphosphine (0.519 g, 1.978 mmol) were mixed in THF (5 mL) under an argon atmosphere. The mixture was cooled to 0° C. before diisopropyl azodicarboxylate (0.389 mL, 1.978 mmol) was added dropwise via syringe. The reaction mixture was warmed to room temperature and stirred for 22 h. The reaction mixture was diluted with sat. NaHCO$_3$ and extracted with EtOAc. The organic layer was separated, washed with saturated aqueous sodium chloride, dried over magnesium sulfate, filtered, and concentrated in vacuo. The resulting crude product was purified by silica gel column chromatography eluting with EtOAc in hexanes to yield the title compound (0.241 g, 0.674 mmol, 51.2% yield) as a white solid.

Step 3: 1-(trans-3-aminocyclobutyl)-3,3,5-trifluoro-1H-pyrrolo[2,3-b]pyridin-2(3H)-one hydrochloride Hydrogen chloride (4.0 M in 1,4-dioxane, 1.686 mL, 6.74 mmol) was added to a stirred mixture of tert-butyl(trans-3-(3,3,5-trifluoro-2-oxo-2,3-dihydro-1H-pyrrolo[2,3-b]pyridin-1-yl)cyclobutyl)carbamate (0.241 g, 0.674 mmol) in 1,4-dioxane (3 mL). The reaction mixture was stirred at room temperature for 2.5 h. Additional 1,4-dioxane (3 mL) was added, and the reaction mixture was stirred for another 20 h. The reaction mixture was concentrated to yield the title compound (0.210 g, 0.715 mmol, 106% yield) as a white solid. M+1: 258.0.

Step 4: 1-(trans-3-(benzo[d]thiazol-2-ylamino)cyclobutyl)-3,3,5-trifluoro-1H-pyrrolo[2,3-b]pyridin-2(3H)-one 1-(Trans-3-aminocyclobutyl)-3,3,5-trifluoro-1H-pyrrolo[2,3-b]pyridin-2(3H)-one hydrochloride (0.105 g, 0.358 mmol), 2-chlorobenzothiazole (0.0728 g, 0.429 mmol), and N,N-diisopropylethylamine (0.249 mL, 1.430 mmol) were mixed in DMSO (0.5 mL) in a sealed tube. The reaction mixture was stirred at 120° C. for 1.5 h. The reaction mixture was cooled to room temperature, diluted with water, and extracted with EtOAc. The organic layer was separated, washed with saturated aqueous sodium chloride, dried over magnesium sulfate, filtered, and concentrated in vacuo. The resulting crude product was purified by silica gel column chromatography eluting with EtOAc in hexanes to yield the title compound (0.032 g, 0.082 mmol, 22.9% yield) as a white solid. M+1: 391.1 $^1$H NMR (400 MHz, CHLOROFORM-d) δ ppm 2.46-2.56 (m, 2 H) 3.37-3.48 (m, 2 H) 4.58 (m, J=3.50 Hz, 1 H) 5.23 (quin, J=8.61 Hz, 1 H) 5.76 (br. s., 1 H) 7.12 (t, J=7.53 Hz, 1 H) 7.32 (t, J=7.73 Hz, 1 H) 7.56-7.66 (m, 3 H) 8.30 (s, 1 H).

Method G3

Example 209

6-fluoro-3-(trans-3-((6-fluorobenzo[d]thiazol-2-yl)amino)cyclobutyl)-1-methyl-1H-imidazo[4,5-b]pyridin-2(3H)-one

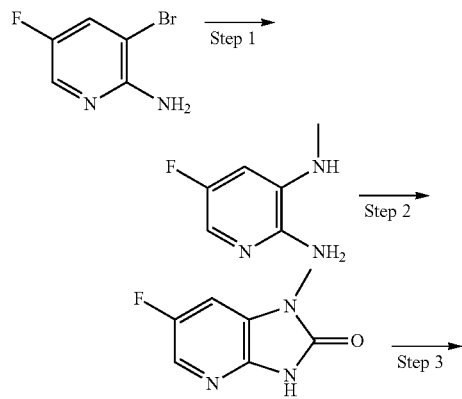

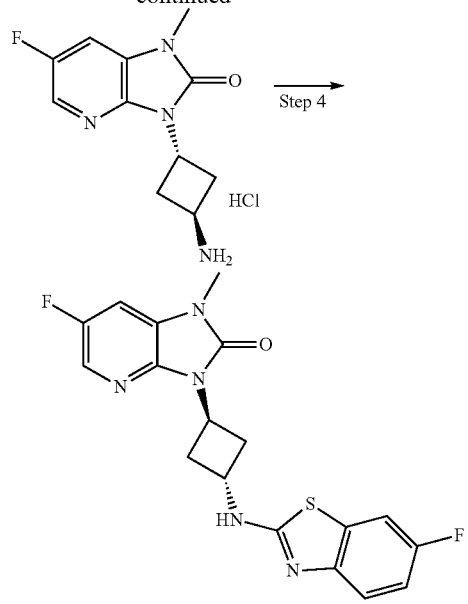

Step 1: 5-fluoro-N3-methylpyridine-2,3-diamine

2-Amino-3-bromo-5-fluoropyridine (1.127 g, 5.90 mmol) and BrettPhos Precatalyst (0.141 g, 0.177 mmol) were mixed under an argon atmosphere. Methylamine (2.0 M in THF, 4.43 ml, 8.85 mmol) and lithium bis(trimethylsilyl)amide (1.0 M in THF, 14.75 ml, 14.75 mmol) were added slowly via syringe, and the reaction mixture was stirred at room temperature for 3.5 h. The reaction mixture was quenched with saturated aqueous ammonium chloride and extracted three times with a 9:1 mixture of DCM to MeOH. The combined organic layers were dried over magnesium sulfate, filtered, and concentrated in vacuo. The resulting crude product was purified by silica gel column chromatography eluting with acetone in DCM to yield the title compound (0.497 g, 3.52 mmol, 59.7% yield) as a tan solid. M+1: 142.1.

Step 2: 6-fluoro-1-methyl-1H-imidazo[4,5-b]pyridin-2(3H)-one

5-Fluoro-N3-methylpyridine-2,3-diamine (0.399 g, 2.83 mmol) and 1,1'-carbonyldiimidazole (0.917 g, 5.65 mmol) were mixed in THF (12 mL). The reaction mixture was stirred at 60° C. for 3 h. The reaction mixture was diluted with saturated aqueous sodium bicarbonate and extracted three times with EtOAc. The combined organic layers were washed with saturated aqueous sodium chloride, dried over magnesium sulfate, filtered, and concentrated in vacuo. The resulting crude brown solid was triturated with DCM and filtered to yield the title compound (0.304 g, 1.819 mmol, 64.3% yield) as a gray solid. M+1: 168.1.

Step 3: 3-(trans-3-aminocyclobutyl)-6-fluoro-1-methyl-1H-imidazo[4,5-b]pyridin-2(3H)-one hydrochloride 6-Fluoro-1-methyl-H-imidazo[4,5-b]pyridin-2(3H)-one (0.377 g, 2.256 mmol), tert-butyl(cis-3-hydroxycyclobutyl)carbamate (0.422 g, 2.256 mmol), and triphenylphosphine (0.887 g, 3.38 mmol) were mixed in THF (8 mL) under an argon atmosphere. The mixture was cooled to 0° C. before diisopropyl azodicarboxylate (0.665 mL, 3.38 mmol) was added dropwise via syringe. The reaction mixture was warmed to room temperature and stirred for 4 h. The reaction mixture was diluted with saturated aqueous sodium bicarbonate and extracted with EtOAc. The organic layer was separated, washed with saturated aqueous sodium chloride, dried over magnesium sulfate, filtered, and concentrated in vacuo. The resulting crude product was purified by silica gel column chromatography eluting with acetone in hexanes to yield crude tert-butyl(trans-3-(6-fluoro-1-methyl-2-oxo-1H-imidazo[4,5-b]pyridin-3(2H)-yl)cyclobutyl)carbamate (1.136 g) as a white solid. The material was used without further purification.

Hydrogen chloride (4.0 M in 1,4-dioxane, 8.44 mL, 33.8 mmol) was added to a stirred mixture of crude tert-butyl (trans-3-(6-fluoro-1-methyl-2-oxo-H-imidazo[4,5-b]pyridin-3(2H)-yl)cyclobutyl)carbamate (1.136 g, 3.38 mmol) in 1,4-dioxane (15 mL). The reaction mixture was stirred at room temperature for 5 h. The reaction mixture was partially concentrated in vacuo. The resulting precipitate was filtered to yield 3-(trans-3-aminocyclobutyl)-6-fluoro-1-methyl-1H-imidazo[4,5-b]pyridin-2(3h)-one hydrochloride (0.469 g, 1.720 mmol, 76.2% yield) as an off-white solid. M+1: 237.1.

Step 4: 6-fluoro-3-(trans-3-((6-fluorobenzo[d]thiazol-2-yl)amino)cyclobutyl)-1-methyl-1H-imidazo[4,5-b]pyridin-2(3H)-one 3-(trans-3-aminocyclobutyl)-6-fluoro-1-methyl-1H-imidazo[4,5-b]pyridin-2(3H)-one hydrochloride (0.100 g, 0.367 mmol), 2-chloro-6-fluorobenzothiazole (0.083 g, 0.440 mmol), and N,N-diisopropylethylamine (0.255 mL, 1.467 mmol) were mixed in DMSO (0.5 mL) in a sealed tube. The reaction mixture was stirred at 120° C. for 5 h. The reaction mixture was cooled to room temperature, diluted with water, and extracted with EtOAc. The organic layer was separated, washed with saturated aqueous sodium chloride, dried over magnesium sulfate, filtered, and concentrated. The resulting crude product was purified by silica gel column chromatography eluting with EtOAc in hexanes to yield the title compound (0.062 g, 0.160 mmol, 43.6% yield) as an off-white solid. M+1: 388.1. $^1$H NMR (400 MHz, DMSO-$d_6$) δ ppm 2.40-2.49 (m, 2 H) 3.25-3.34 (m, 2 H) 3.36 (s, 3 H) 4.50-4.59 (m, 1 H) 5.21 (quin, J=8.36 Hz, 1 H) 7.08 (td, J=9.10, 2.74 Hz, 1 H) 7.41 (dd, J=8.80, 4.89 Hz, 1 H) 7.62-7.71 (m, 2 H) 8.05 (t, J=2.25 Hz, 1 H) 8.57 (d, J=6.26 Hz, 1 H).

Examples 210-211 are tabulated in Table 8 above.

Example 212

1-(trans-3-(benzo[d]thiazol-2-ylamino)cyclobutyl)-3,3-difluoro-1-H-pyrrolo[2,3-b]pyridin-2-(3H)-one

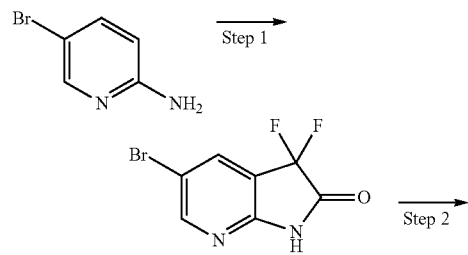

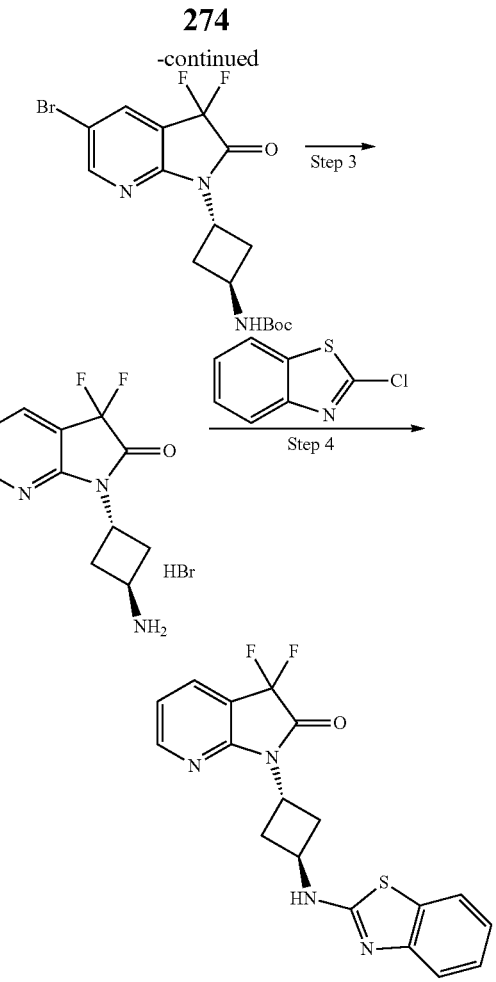

Step 1: 5-bromo-3,3-difluoro-1H-pyrrolo[2,3-b]pyridin-2(3H)-one

Hydrogen peroxide (30% aqueous, 2.019 mL, 19.77 mmol) was added dropwise to a stirred mixture of 2-amino-5-bromopyridine (1.71 g, 9.88 mmol), ferrocene (0.184 g, 0.988 mmol), and ethyl bromodifluoroacetate (3.82 mL, 29.7 mmol) in DMSO (50 mL) under an argon atmosphere. The reaction mixture was stirred at room temperature for 23 h. sulfuric acid (1.054 mL, 19.77 mmol) was added, and the reaction mixture was stirred at room temperature for 72 h. The reaction mixture was diluted with water and extracted with EtOAc. The organic layer was separated, washed with saturated aqueous sodium chloride, dried over magnesium sulfate, filtered, and concentrated in vacuo. The resulting crude product was purified by silica gel column chromatography eluting with EtOAc in hexanes to yield the title compound (1.19 g, 4.78 mmol, 48.4% yield) as a light purple solid. M+1: 248.9.

Step 2: tert-butyl(trans-3-(5-bromo-3,3-difluoro-2-oxo-2,3-dihydro-1H-pyrrolo[2,3-b]pyridin-1-yl)cyclobutyl)carbamate 5-Bromo-3,3-difluoro-1H-pyrrolo[2,3-b]pyridin-2(3H)-one (1.19 g, 4.78 mmol), tert-butyl(cis-3-hydroxycyclobutyl) carbamate (0.895 g, 4.78 mmol), and triphenylphosphine (1.88 g, 7.17 mmol) were mixed in THF (18 mL) under an argon atmosphere. The mixture was cooled to 0° C. before diisopropyl azodicarboxylate (1.409 mL, 7.17 mmol) was added dropwise via syringe. The reaction mixture was warmed to room temperature and stirred for 19 h. The reaction mixture was diluted with saturated aqueous sodium bicarbonate and extracted with EtOAc. The organic layer was separated, washed with saturated aqueous sodium chloride, dried over magnesium sulfate, filtered, and concentrated in vacuo. The resulting crude product was purified via silica gel column chromatography eluting with EtOAc in hexanes to yield the title compound (0.477 g, 1.141 mmol, 23.9% yield) as a white solid.

Step 3: 1-(trans-3-aminocyclobutyl)-3,3-difluoro-1H-pyrrolo[2,3-b]pyridin-2(3H)-one hydrobromide Palladium (10 weight percent on activated carbon, 0.0607 g, 0.057 mmol) was added to a mixture of tert-butyl(trans-3-(5-bromo-3,3-difluoro-2-oxo-2,3-dihydro-1H-pyrrolo[2,3-b]pyridin-1-yl)cyclobutyl)carbamate (0.477 g, 1.141 mmol) in EtOH (5 mL) under an argon atmosphere. The reaction mixture was placed under a hydrogen atmosphere (balloon) and stirred at room temperature for 7 h. The reaction mixture was filtered through CELITE®, and the filtrate was concentrated. The resulting white solid was triturated with DCM and filtered to yield the title compound (0.084 g, 0.262 mmol, 23.0% yield) as a white solid. M+1: 240.1.

Step 4: 1-(trans-3-(benzo[d]thiazol-2-ylamino)cyclobutyl)-3,3-difluoro-1H-pyrrolo[2,3-b]pyridin-2(3H)-one 1-(Trans-3-aminocyclobutyl)-3,3-difluoro-1H-pyrrolo[2,3-b]pyridin-2(3H)-one hydrobromide (0.084 g, 0.262 mmol), 2-chlorobenzothiazole (0.0534 g, 0.315 mmol), and N,N-diisopropylethylamine (0.183 mL, 1.050 mmol) were mixed in DMSO (0.5 mL) in a sealed tube. The reaction mixture was stirred at 120° C. for 2 hr. The reaction mixture was cooled to room temperature, diluted with water, and extracted with EtOAc. The organic layer was separated, washed with saturated aqueous sodium chloride, dried over magnesium sulfate, filtered, and concentrated in vacuo. The resulting crude product was purified by silica gel column chromatography eluting with EtOAc in hexanes to yield the title compound (0.030 g, 0.081, 30.7% yield) as a white solid. M+1: 373.1. $^1$H NMR (400 MHz, DMSO-$d_6$) δ ppm 2.39-2.49 (m, 2 H) 3.19-3.30 (m, 2 H) 4.48-4.58 (m, 1 H) 5.10 (quin, J=8.36 Hz, 1 H) 7.04 (t, J=7.53 Hz, 1 H) 7.21-7.26 (m, 1 H) 7.29 (dd, J=7.34, 5.38 Hz, 1 H) 7.43 (d, J=7.82 Hz, 1 H) 7.70 (d, J=7.24 Hz, 1 H) 8.20 (dd, J=7.43, 1.37 Hz, 1 H) 8.51-8.56 (m, 2 H).

Example 213

1-cyclopropyl-3-(trans-3-((6-fluorobenzo[d]thiazol-2-yl)amino)cyclobutyl)-1H-imidazo[4,5-b]pyrazin-2(3H)-one

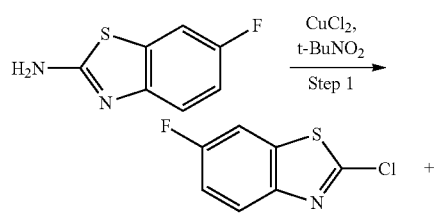

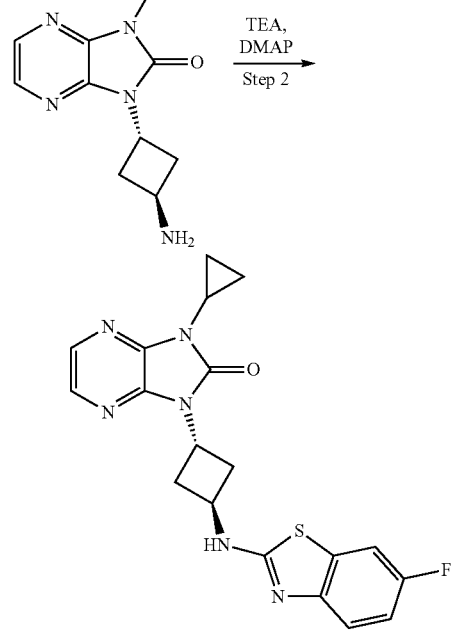

Step 1: 2-chloro-6-fluorobenzo[d]thiazole

To a round bottomed flask was added 2-amino-6-fluorobenzothiazole (1.0017 g, 5.96 mmol, Sigma-Aldrich Chemical Company, Inc.), copper (II) chloride (1.201 g, 8.93 mmol, Sigma-Aldrich Chemical Company, Inc.), and tert-butyl nitrite (1.063 ml, 8.93 mmol, Acros Organics) in ACN and was heated to 65° C. for 2 hours. The reaction mixture was diluted with 1N HCl and extracted with EtOAc. The organic extract was washed with water, satd NaCl, dried over MgSO$_4$, filtered and concentrated in vacuo to give the title compound (0.9249 g, 4.93 mmol, 83% yield). $^1$H NMR (400 MHz, DMSO-$d_6$) δ ppm s 7.45 (td, J=9.10, 2.74 Hz, 1 H) 7.97-8.07 (m, 2 H)

Step 2: 1-cyclopropyl-3-(trans-3-((6-fluorobenzo[d]thiazol-2-yl)amino)cyclobutyl)-1H-imidazo[4,5-b]pyrazin-2(3H)-one A glass microwave reaction vessel was charged with 1-(trans-3-aminocyclobutyl)-3-cyclopropyl-1H-imidazo[4,5-b]pyrazin-2(3H)-one hydrochloride (Intermediate 79, 0.1283 g, 0.455 mmol), 2-chloro-6-fluorobenzo[d]thiazole (0.094 g, 0.501 mmol, Step 1), DMAP (0.056 g, 0.455 mmol, Sigma-Aldrich Chemical Company, Inc.), and diisopropylamine (0.238 ml, 1.366 mmol, Sigma-Aldrich Chemical Company, Inc.) in DMSO (1.518 ml) and heated to 90° C. for 20 h. The crude product was purified by reverse-phase preparative HPLC using a Phenomenex Gemini column, 10 micron, C18, 110 Å, 100×50 mm, 0.1% TFA in CH$_3$CN/H$_2$O, gradient 10% to 90% over 12 min. Fractions containing product peak were concentrated in vacuo. The product was taken up in DCM and loaded onto a Silicyle Si-carbonate cartridge to remove any salts to give the title compound (61.2 mg, 0.154 mmol, 33.9% yield). LCMS showed product peak at 1.732 min (m+1=397.0).

$^1$H NMR (400 MHz, DMSO-d$_6$) δ ppm 0.96-1.09 (m, 4 H) 2.46 (t, J=9.78 Hz, 2 H) 2.97 (tt, J=7.09, 3.67 Hz, 1 H) 3.20-3.31 (m, 2 H) 4.49-4.61 (m, 1 H) 5.16 (quin, J=8.26 Hz, 1 H) 7.07 (td, J=9.10, 2.74 Hz, 1 H) 7.40 (dd, J=8.80, 4.89 Hz, 1 H) 7.64 (dd, J=8.80, 2.74 Hz, 1 H) 7.96-7.99 (m, 1 H) 7.99-8.01 (m, 1 H) 8.54 (d, J=6.26 Hz, 1 H)

Example 214

5-(trans-3-(benzo[d]oxazol-2-ylamino)cyclobutyl)-7,7-dimethyl-5H-pyrrolo[2,3-b]pyrazin-6(7H)-one

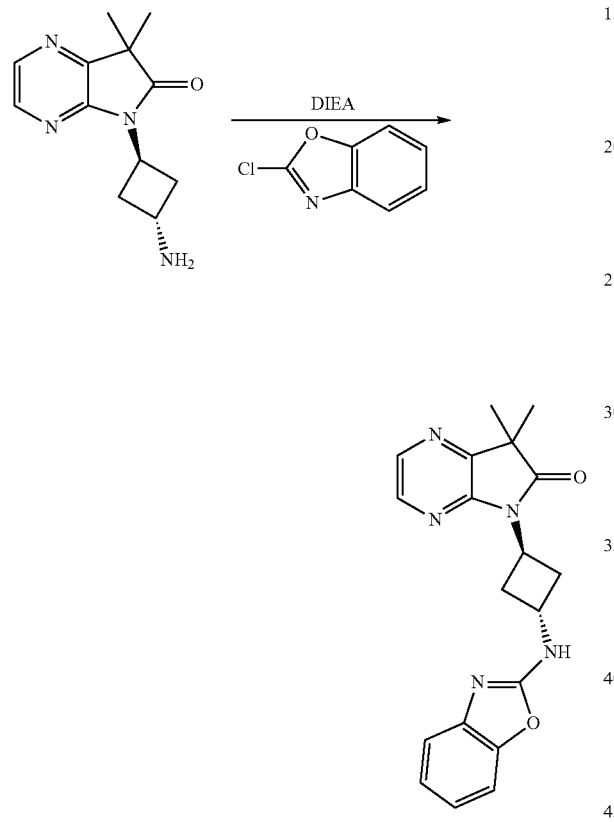

To a round bottomed flask was added 5-(trans-3-aminocyclobutyl)-7,7-dimethyl-5H-pyrrolo[2,3-b]pyrazin-6(7H)-one (Intermediate 30, 0.1663 g, 0.716 mmol, [00391]), 2-chlorobenzo[d]oxazole (0.132 g, 0.859 mmol, Sigma-Aldrich Chemical Company, Inc.), and diisopropylethylamine (0.249 ml, 1.432 mmol, Sigma-Aldrich Chemical Company, Inc.) in DMSO (2.386 ml) to stir at 90° C. for 17 hours. The crude product was purified by reverse-phase preparative HPLC using 0.1% TFA in CH$_3$CN/H$_2$O, gradient 10% to 90% over min. Product was taken up in DCM and loaded onto a Silicycle Si-carbonate cartridge to remove any salts to give 5-(trans-3-(benzo[d]oxazol-2-ylamino)cyclobutyl)-7,7-dimethyl-5H-pyrrolo[2,3-b]pyrazin-6(7H)-one (32.2 mg, 0.092 mmol, 12.87% yield). LCMS showed product peak at 1.625 min (m+1=350.0). $^1$H NMR (400 MHz, DMSO-d$_6$) δ ppm 1.34 (s, 6 H) 2.42-2.48 (m, 1 H) 3.18-3.29 (m, 2 H) 4.47-4.60 (m, 1 H) 5.17 (quin, J=8.31 Hz, 1 H) 6.95-7.04 (m, 1 H) 7.12 (td, J=7.63, 0.98 Hz, 1 H) 7.28 (d, J=7.24 Hz, 1 H) 7.37 (d, J=7.63 Hz, 1 H) 8.18 (d, J=3.33 Hz, 1 H) 8.23 (d, J=3.13 Hz, 1 H) 8.42 (d, J=6.65 Hz, 1 H).

Example 215

5-(cis-3-(benzo[d]thiazol-2-ylamino)cyclobutyl)-7,7-dimethyl-5H-pyrrolo[2,3-b]pyrazin-6(7H)-one

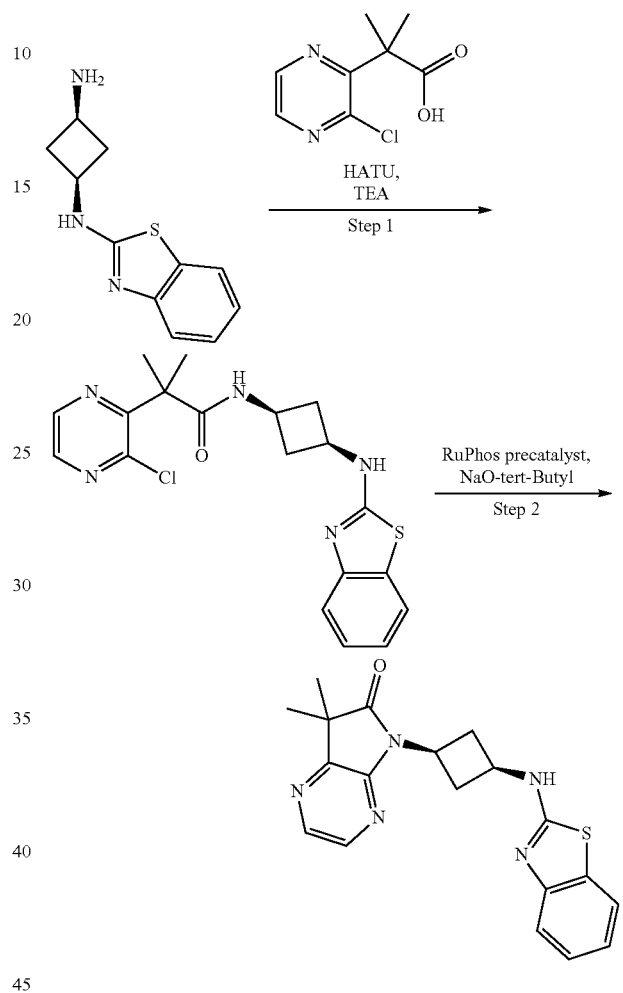

Step 1: N-(cis-3-(benzo[d]thiazol-2-ylamino)cyclobutyl)-2-(3-chloropyrazin-2-yl)-2-methylpropanamide To a round bottomed flask was added cis-N$^1$-(benzo[d]thiazol-2-yl)cyclobutane-1,3-diamine (Intermediate 32, 0.3010 g, 1.030 mmol), 2-(3-chloropyrazin-2-yl)-2-methylpropanoic acid (Intermediate 29, 0.248 g, 1.236 mmol), HATU (0.509 g, 1.339 mmol, GenScript Corp), and triethylamine (0.573 ml, 4.12 mmol, Sigma-Aldrich Chemical Company, Inc.) in DCM (2.060 ml) to stir at room temperature for 4 hours. The reaction mixture was diluted with water and extracted with CH$_2$Cl$_2$. The organic extract was washed with water, saturated NaHCO$_3$, saturated NaCl, dried over MgSO$_4$, filtered and concentrated in vacuo. The crude product (592.4 mg) was adsorbed onto a plug of silica gel and chromatographed through a Biotage SNAP HP-silica gel column (50 g), eluting with a gradient of 10% to 100% EtOAc in hexane, to provide the title compound (0.3181 g, 0.791 mmol, 77% yield). LCMS showed product peak at 1.536 min (m+1=401.9). $^1$H NMR (400 MHz, DMSO-d$_6$) δ ppm 1.52 (s, 4 H) 1.88-2.03 (m, 1 H) 2.60-2.69 (m, 1 H) 3.87-4.03 (m, 1 H) 6.97-7.07 (m, 1 H) 7.18-7.26 (m, 1 H) 7.39 (d, J=7.43 Hz, 1 H) 7.63-7.71 (m, 1 H) 7.76 (d, J=6.65 Hz, 1 H) 8.27 (d, J=6.26 Hz, 1 H) 8.45 (d, J=2.54 Hz, 1 H) 8.68 (d, J=2.54 Hz, 1 H)

Step 2: 5-(cis-3-(benzo[d]thiazol-2-ylamino)cyclobutyl)-7,7-dimethyl-5H-pyrrolo[2,3-b]pyrazin-6(7H)-one To a glass microwave reaction vessel was added N-(cis-3-(benzo[d]thiazol-2-ylamino)cyclobutyl)-2-(3-chloropyrazin-2-yl)-2-methylpropanamide (0.3181 g, 0.791 mmol), RuPhos Precatalyst (0.035 g, 0.047 mmol, Strem Chemicals, Inc.), and sodium tert-butoxide (0.152 g, 1.583 mmol, Sigma-Aldrich Chemical Company, Inc.) in dry dioxane (0.791 ml) to stir at 80° C. for 5 h. The crude product was purified by reverse-phase preparative HPLC using 0.1% TFA in CH$_3$CN/H$_2$O, gradient 10% to 90% over 12 min. The collected fractions were evaporated and the residue was taken up in DCM and filtered through a Silicycle Si-Carbonate cartridge to remove any salts to give the title compound (139.2 mg, 0.381 mmol, 48.1% yield). LCMS showed product peak at 1.607 min (m+1=366.0). $^1$H NMR (400 MHz, DMSO-d$_6$) δ ppm 1.35 (s, 6 H) 2.74 (qd, J=7.86, 2.64 Hz, 2 H) 3.00 (qd, J=9.13, 2.74 Hz, 2 H) 4.12-4.27 (m, 1 H) 4.55-4.69 (m, 1 H) 7.04 (td, J=7.58, 1.08 Hz, 1 H) 7.24 (td, J=7.68, 1.27 Hz, 1 H) 7.36-7.44 (m, 1 H) 7.69 (dd, J=7.83, 0.78 Hz, 1 H) 8.15-8.23 (m, 2 H) 8.49 (d, J=6.65 Hz, 1 H)

Example 216

1-(cis-3-(benzo[d]thiazol-2-ylamino)cyclobutyl)-3-methyl-1H-imidazo[4,5-b]pyrazin-2(3H)-one

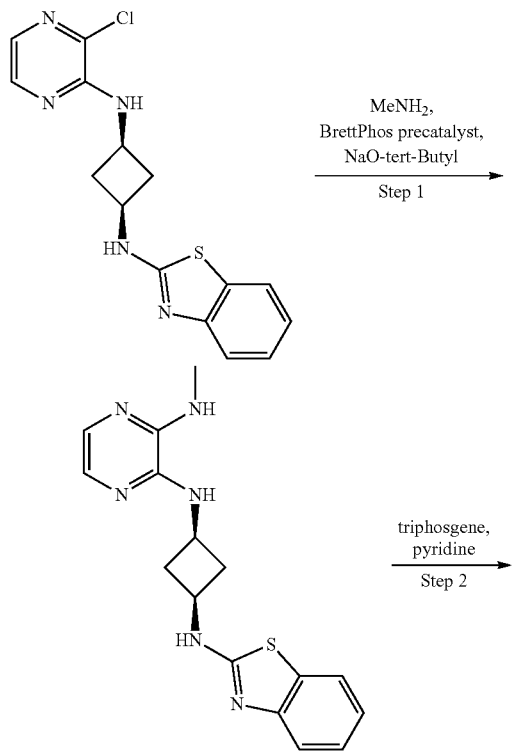

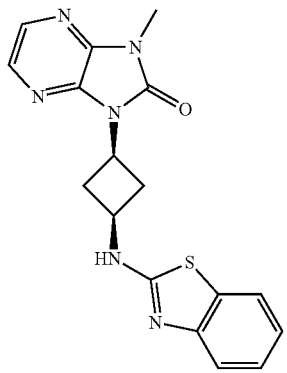

Step 1: N$^2$-(cis-3-(benzo[d]thiazol-2-ylamino)cyclobutyl)-N'-methylpyrazine-2,3-diamine To a glass microwave reaction vessel was added cis-N$^1$-(benzo[d]thiazol-2-yl)-N$^3$-(3-chloropyrazin-2-yl)cyclobutane-1,3-diamine (Intermediate 81, 0.1952 g, 0.588 mmol), sodium tert-butoxide (0.226 g, 2.353 mmol, Sigma-Aldrich Chemical Company, Inc.), and BrettPhos precatalyst (7.05 mg, 8.82 mol, Strem Chemicals, Inc.), and methanamine solution, 2.0 M in THF (1.471 ml, 2.94 mmol, Sigma-Aldrich Chemical Company, Inc.) in dioxane (1.177 ml) to stir at 50° C. for 3 h. The crude product was adsorbed onto a plug of silica gel and chromatographed through a Biotage SNAP HP-silica gel column (25 g), eluting with a gradient of 1% to 8% MeOH in CH$_2$Cl$_2$, to provide the title compound (110 mg, 0.337 mmol, 57.3% yield). LCMS showed product peak at 1.26 min (m+1=327.0). $^1$H NMR (400 MHz, DMSO-d$_6$) δ ppm 1.82-1.95 (m, 2 H) 2.80-2.91 (m, 5 H) 4.00-4.18 (m, 2 H) 6.31 (br. s., 1 H) 6.38 (d, J=6.06 Hz, 1 H) 7.03 (td, J=7.63, 1.17 Hz, 1 H) 7.20 (d, J=3.13 Hz, 1 H) 7.21-7.28 (m, 2 H) 7.41 (d, J=7.43 Hz, 1 H) 7.69 (dd, J=7.82, 0.78 Hz, 1 H) 8.36 (d, J=6.85 Hz, 1 H)

Step 2: 1-(cis-3-(benzo[d]thiazol-2-ylamino)cyclobutyl)-3-methyl-1H-imidazo[4,5-b]pyrazin-2(3H)-one To a round bottomed flask was added N$^2$-(cis-3-(benzo[d]thiazol-2-ylamino)cyclobutyl)-N3-methylpyrazine-2,3-diamine (0.1100 g, 0.337 mmol) and pyridine (0.082 mL, Sigma-Aldrich Chemical Company, Inc.) in DCM (1.1 mL) to stir at −40° C. for 30 mins. Triphosgene (0.120 g, 0.404 mmol, Sigma-Aldrich Chemical Company, Inc.) was added to stir for 30 mins. The temperature was brought to 0° C. and allowed to stir for 5 h. The reaction mixture was diluted with saturated sodium bicarbonate and extracted with CH$_2$Cl$_2$. The organic extract was washed with water, saturated NaCl, dried over MgSO$_4$, filtered and concentrated in vacuo. The crude product was adsorbed onto a plug of silica gel and chromatographed through a Biotage SNAP HP-silica gel column (25 g), eluting with a gradient of 40% to 100% EtOAc in hexane, to provide the title compound (0.0352 g, 0.100 mmol, 29.6% yield). LCMS showed product peak at 1.51 min (m+1=353.0). $^1$H NMR (400 MHz, DMSO-d$_6$) δ ppm 2.72-2.85 (m, 1 H) 2.94-3.08 (m, 1 H) 3.34 (s, 2 H) 4.14-4.28 (m, 1 H) 4.62-4.76 (m, 1 H) 6.98-7.07 (m, 1 H) 7.19-7.26 (m, 1 H) 7.40 (d, J=7.43 Hz, 1 H) 7.64-7.71 (m, 1 H) 7.98 (s, 1 H) 8.52 (d, J=6.65 Hz, 1 H)

Example 217

N-(cis-3-(7,7-dimethyl-6-oxo-6,7-dihydro-5H-pyrrolo[2,3-b]pyrazin-5-yl)cyclobutyl)-1H-benzo[d]imidazolE-2-carboxamide

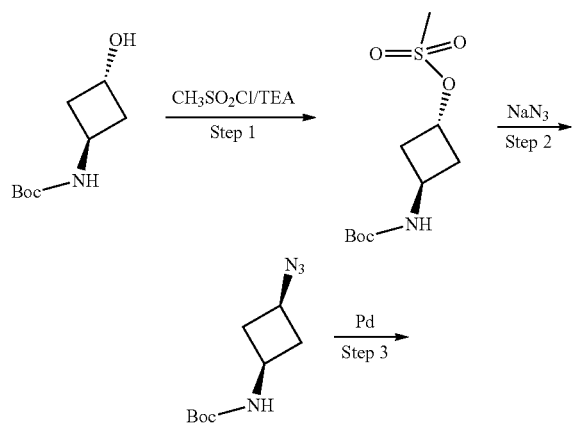

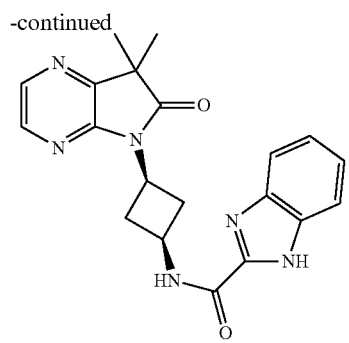

Step 1: trans-3-((tert-butoxycarbonyl)amino)cyclobutyl methanesulfonate

A solution of tert-butyl(trans-3-hydroxycyclobutyl)carbamate (20.05 g, 107 mmol, MC09PH1559, Pharmacore) and triethylamine (22.34 mL, 161 mmol, Sigma-Aldrich Chemical Company, Inc.) in DCM (200 mL) was cooled to −30° C. and methanesulfonyl chloride (9.94 mL, 129 mmol, Sigma-Aldrich Chemical Company, Inc.) was added dropwise over 20 min period. The mixture was stirred at room temperature for 12 h, washed with 200 mL water, then 200 mL 10% aq. citric acid followed by brine, dried over $Na_2SO_4$ and evaporated to give the title compound (29 g, 109 mmol, 102% yield). It was used in the next step without further purification.

Step 2: tert-butyl(trans-3-azidocyclobutyl)carbamate

To a solution of trans-3-((tert-butoxycarbonyl)amino)cyclobutyl methanesulfonate (29 g, 109 mmol) in DMF (100 mL) was added sodium azide (5.68 mL, 162 mmol, Sigma-Aldrich Chemical Company, Inc.) portionwise and the mixture stirred at 85° C. for 18 h. The reaction was diluted with water (200 mL) after cooling and extracted with EtOAc (3×100 mL). The combined organic was washed with water (2×100 mL) and brine, dried over $Na_2SO_4$ and evaporated in vacuo to give product tert-butyl(cis-3-azidocyclobutyl)carbamate (22 g, 104 mmol, 95% yield) that was used in the next step without further purification.

Step 3: tert-butyl(cis-3-aminocyclobutyl)carbamate

A mixture of tert-butyl(cis-3-azidocyclobutyl)carbamate (15.00 g, 70.7 mmol) and palladium 10 wt. % (dry basis) on activated carbon, wet (3.76 ml, 35.3 mmol, Sigma-Aldrich Chemical Company, Inc.) in three necked 1000 mL flask was flushed with $N_2$ and closed tightly and 2M ammonia in methanol solution (200 mL) was added. The flask was evacuated and a balloon filled with hydrogen was introduced. The mixture was stirred for 18 h, filtered, and the filtrate was evaporated under reduced pressure to give the title compound (11.1 g, 59.6 mmol, 84% yield), which was used in the next step without further purification.

Step 4: tert-butyl(cis-3-(2-(3-chloropyrazin-2-yl)-2-methylpropanamido)cyclobutyl)carbamate To a round bottomed flask was added tert-butyl(cis-3-aminocyclobutyl)carbamate (0.4903 g, 2.63 mmol), 2-(3-chloropyrazin-2-yl)-2-methylpropanoic acid (Intermediate 29, 0.634 g, 3.16 mmol), HATU (1.301 g, 3.42 mmol, GenScript Corp), and triethylamine (1.465 ml, 10.53 mmol, Sigma-Aldrich Chemical Company, Inc.) in DCM (5.26 ml) to stir at room temperature for 24 h. The crude product was adsorbed onto a plug of silica gel and chromatographed through a Biotage SNAP HP-silica gel column (50 g), eluting with a gradient of 10% to 100% EtOAc in hexane, to provide the title compound (0.8210 g, 2.226 mmol, 85% yield). LCMS showed product peak at 1.86 min (m+1=313.0, product-tbutyl group). $^1$H NMR (400 MHz, DMSO-d$_6$) δ ppm 1.36 (s, 7 H) 1.49 (s, 5 H) 1.82 (qd, J=9.00, 2.35 Hz, 2 H) 2.34-2.47 (m, 2 H) 2.69 (s, 3 H) 3.48-3.65 (m, 1 H) 3.72-3.87 (m, 1 H) 7.04 (d, J=6.85 Hz, 1 H) 7.63 (d, J=6.46 Hz, 1 H) 8.42 (d, J=2.54 Hz, 1 H) 8.65 (d, J=2.35 Hz, 1 H).

Step 5: tert-butyl(cis-3-(7,7-dimethyl-6-oxo-6,7-dihydro-5H-pyrrolo[2,3-b]pyrazin-5-yl)cyclobutyl) carbamate To a glass microwave reaction vessel was added tert-butyl (cis-3-(2-(3-chloropyrazin-2-yl)-2-methylpropanamido)cyclobutyl)carbamate (0.8210 g, 2.226 mmol), RuPhos Precatalyst (0.097 g, 0.134 mmol, Strem Chemicals), and sodium tert-butoxide (0.428 g, 4.45 mmol, Sigma-Aldrich Chemical Company, Inc.) in dry dioxane (2.226 ml) to stir at 80° C. for 24 h. The solvent was evaporated in vacuo. The crude product was adsorbed onto a plug of silica gel and chromatographed through a Biotage SNAP HP-silica gel column (50 g), eluting with a gradient of 40% to 100% EtOAc in hexane, to provide the title compound (0.1812 g, 0.545 mmol, 24.49% yield). LCMS showed product peak at 2.060 min (m+1=333.0). $^1$H NMR (400 MHz, DMSO-d$_6$) δ ppm 1.31 (s, 3 H) 1.39 (s, 5 H) 2.52-2.58 (m, 1 H) 2.80 (qd, J=9.16, 2.64 Hz, 1 H) 3.68-3.83 (m, 1 H) 4.34-4.47 (m, 1 H) 7.21 (d, J=6.85 Hz, 1 H) 8.13-8.18 (m, 1 H)

Step 6: 5-(cis-3-aminocyclobutyl)-7,7-dimethyl-5H-pyrrolo[2,3-b]pyrazin-6(7H)-one To a round bottomed flask was added tert-butyl(cis-3-(7,7-dimethyl-6-oxo-6,7-dihydro-5H-pyrrolo[2,3-b]pyrazin-5-yl)cyclobutyl)carbamate (0.1812 g, 0.545 mmol) and hydrogen chloride, 4.0M solution in 1,4-dioxane (0.136 ml, 0.545 mmol, Sigma-Aldrich Chemical Company, Inc.) to stir at room temperature for 1 h. Solvent was evaporated and carried on without further purification. LCMS showed product peak at 0.357 min (m+=233.0). $^1$H NMR (400 MHz, DMSO-d$_6$) δ ppm 1.33 (s, 5 H) 2.61-2.74 (m, 2 H) 2.91-3.04 (m, 2 H) 3.63-3.76 (m, 1 H) 4.50-4.64 (m, 1 H) 8.18 (s, 2 H)

Step 7: N-(cis-3-(7,7-dimethyl-6-oxo-6,7-dihydro-5H-pyrrolo[2,3-b]pyrazin-5-yl)cyclobutyl)-1H-benzo[d]imidazole-2-carboxamide To a round bottomed flask was added 5-(cis-3-aminocyclobutyl)-7,7-dimethyl-5H-pyrrolo[2,3-b]pyrazin-6(7H)-one (0.1518 g, 0.497 mmol), 1H-benzimidazole-2-carboxylic acid (0.097 g, 0.597 mmol, ChemBridge Corporation), 2-(3H-[1,2,3]triazolo[4,5-b]pyridin-3-yl)-1,1,3,3-tetramethylisouronium hexafluorophosphate(V) (0.246 g, 0.647 mmol, GenScript) and triethylamine (0.277 ml, 1.989 mmol, Sigma-Aldrich Chemical Company, Inc.) in DCM (1.658 ml) to stir at room temperature for 5 h. Solvent was evaporated in vacuo. The crude product was adsorbed onto a plug of silica gel and chromatographed through a Biotage SNAP HP-silica gel column (50 g), eluting with a gradient of 10% to 100% EtOAc in hexane. LCMS showed product was not isolated at ≥95%. The crude product was taken up in DCM and loaded onto an AccuBond SCX cartridge. The cartridge was rinsed with DCM followed by MeOH to remove impurities. The column was then rinsed with 2.0 ammonia in MeOH. The fractions were evaporated in vacuo. The residue was taken up in MeOH at which time a precipitate was noted to form. The round bottomed flask was placed in the freezer overnight. The solid was filtered from the filtrate and washed with cold MeOH to give the title compound (17.1 mg, 0.045 mmol, 9.13% yield). LCMS showed product peak at 1.757 min (m+1=377.0).

$^1$H NMR (400 MHz, DMSO-d) δ ppm 1.35 (s, 6 H) 2.71-2.85 (m, 2 H) 2.95-3.11 (m, 2 H) 4.35 (sxt, J=7.94 Hz, 1 H) 4.59 (quin, J=8.46 Hz, 1 H) 7.31 (br. s., 2 H) 7.55 (d, J=6.26 Hz, 1 H) 7.77 (d, J=6.65 Hz, 1 H) 8.20 (d, J=3.13 Hz, 1 H) 8.27 (d, J=3.13 Hz, 1 H) 9.28 (d, J=7.83 Hz, 1 H) 13.27 (s, 1 H)

Example 218

7,7-dimethyl-5-(cis-4-((5-methylpyridin-2-yl)amino)cyclohexyl)-5H-pyrrolo[2,3-b]pyrazin-6(7H)-one

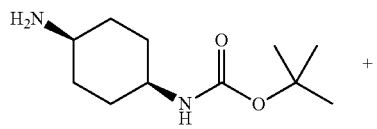

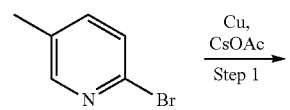

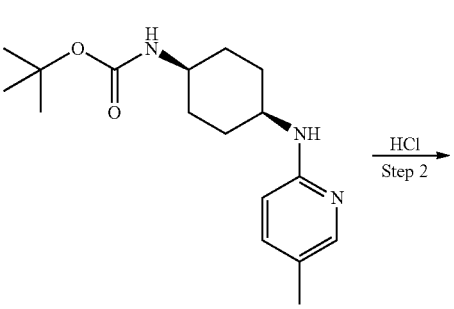

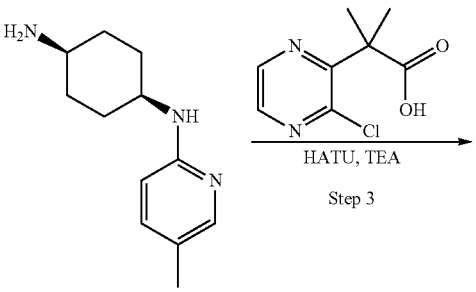

-continued

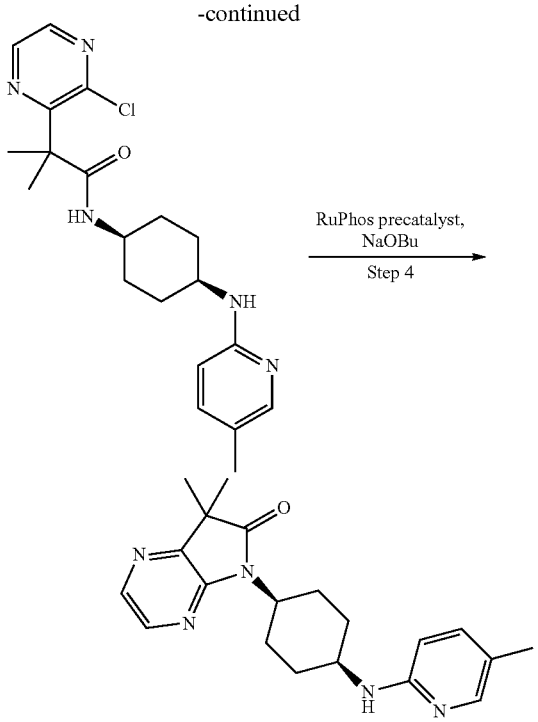

Step 1: tert-butyl(cis-4-((5-methylpyridin-2-yl)amino)cyclohexyl)carbamate

To a round bottomed flask was added cis tert-butyl 4-aminocyclohexylcarbamate (0.5020 g, 2.342 mmol, Matrix Scientific), 2-bromo-5-methylpyridine (0.484 g, 2.81 mmol, Acros Organics), copper (0.012 g, 0.187 mmol, Fisher Scientific), and cesium acetate (2.79 g, 14.52 mmol, Sigma-Aldrich Chemical Company, Inc.) in DMSO (2.93 ml) to stir at 100° C. for 17 h. The reaction mixture was diluted with water and extracted with $CH_2Cl_2$. The organic extract was washed with ammonium hydroxide, water, saturated NaCl, dried over $MgSO_4$, filtered and concentrated in vacuo. The crude product was adsorbed onto a plug of silica gel and chromatographed through a Biotage SNAP HP-silica gel column (50 g), eluting with a gradient of 10% to 100% EtOAc in hexane, to provide the title compound (279.5 mg, 0.915 mmol, 39.1% yield). LCMS showed product peak at 1.56 min (m+1=306.0).

Step 2: cis-$N^1$-(5-methylpyridin-2-yl)cyclohexane-1,4-diamine

To a round bottomed flask was added tert-butyl(cis-4-((5-methylpyridin-2-yl)amino)cyclohexyl)carbamate (0.2795 g, 0.915 mmol) and hydrogen chloride, 4.0M solution in 1,4-dioxane (1.144 ml, 4.58 mmol, Sigma-Aldrich Chemical Company, Inc.) to stir at room temperature for 6 h. Solvent was evaporated in vacuo to provide the title compound, which was carried on without further work up. LCMS showed product peak at 0.357 min (m+1=206.0).

Step 3: 2-(3-chloropyrazin-2-yl)-2-methyl-N-(cis-4-((5-methylpyridin-2-yl)amino)cyclohexyl)propanamide To a round bottomed flask was added 2-(3-chloropyrazin-2-yl)-2-methylpropanoic acid (0.267 g, 1.333 mmol, 00388), 2-(3H-[1,2,3]triazolo[4,5-b]pyridin-3-yl)-1,1,3,3-tetramethylisouronium hexafluorophosphate(V) (0.659 g, 1.733 mmol, GenScript) and triethylamine (0.743 ml, 5.33 mmol, Sigma-Aldrich Chemical Company, Inc.) in DCM (4.44 ml). cis-N1-(5-Methylpyridin-2-yl)cyclohexane-1,4-diamine (0.3709 g, 1.333 mmol) was added and the reaction was allowed to stir at room temperature for 4 h. Solvent was evaporated in vacuo. The crude product was adsorbed onto a plug of silica gel and chromatographed through a Biotage SNAP HP-silica gel column (50 g), eluting with a gradient of 10% to 100% EtOAc in hexane to give the title compound (105.0 mg, 0.271 mmol, 20.3% yield). Product peak was found at 1.438 min (m+1=388.0). $^1$H NMR (400 MHz, DMSO-$d_6$) δ ppm 1.45-1.67 (m, 12 H) 1.75 (d, J=4.89 Hz, 2 H) 2.08 (s, 3 H) 3.68 (br. s., 1 H) 3.76 (br. s., 1 H) 6.50 (d, J=8.41 Hz, 1 H) 7.14-7.28 (m, 2 H) 7.76 (s, 1 H) 8.42 (d, J=2.54 Hz, 1 H) 8.65 (d, J=2.54 Hz, 1 H)

Step 4: 7,7-dimethyl-5-(cis-4-((5-methylpyridin-2-yl)amino)cyclohexyl)-5H-pyrrolo[2,3-b]pyrazin-6(7H)-one To a glass microwave reaction vessel was added 2-(3-chloropyrazin-2-yl)-2-methyl-N-(cis-4-((5-methylpyridin-2-yl)amino)cyclohexyl)propanamide (0.1050 g, 0.271 mmol), RuPhos Precatalyst (0.012 g, 0.016 mmol, Strem Chemicals), and sodium tert-butoxide (0.052 g, 0.541 mmol, Sigma-Aldrich Chemical Company, Inc.) in dry dioxane (0.271 ml) to stir at 90° C. for 17 h. Solvent was evaporated in vacuo. The crude product was adsorbed onto a plug of silica gel and chromatographed through a Biotage SNAP HP-silica gel column (25 g), eluting with a gradient of 10% to 100% EtOAc in hexane, to provide the title compound (0.0313 g, 0.089 mmol, 32.9% yield). LCMS showed product peak at 1.526 min (m+1=352.1). $^1$H NMR (400 MHz, DMSO-$d_6$) δ ppm 1.33 (s, 6 H) 1.52 (d, J=11.93 Hz, 2 H) 1.64 (t, J=13.60 Hz, 2 H) 1.98-2.14 (m, 5 H) 2.58 (d, J=10.37 Hz, 2 H) 3.91 (br. s., 1 H) 4.16-4.30 (m, 1 H) 6.16 (br. s., 1 H) 6.58 (d, J=8.41 Hz, 1 H) 7.24 (dd, J=8.31, 2.05 Hz, 1 H) 7.81 (s, 1 H) 8.15 (d, J=3.13 Hz, 1 H) 8.16-8.21 (m, 1 H)

Method H1

Example 219

1-cyclopropyl-3-(trans-3-(quinazolin-2-ylamino)cyclobutyl)-1H-imidazo[4,5-b]pyrazin-2(3H)-one

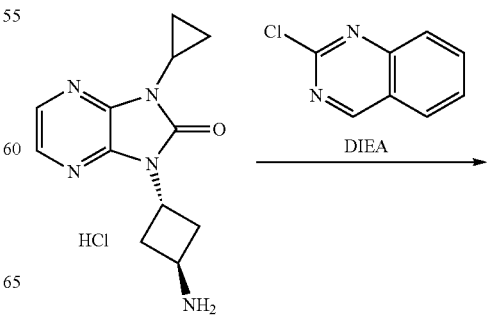

287

-continued

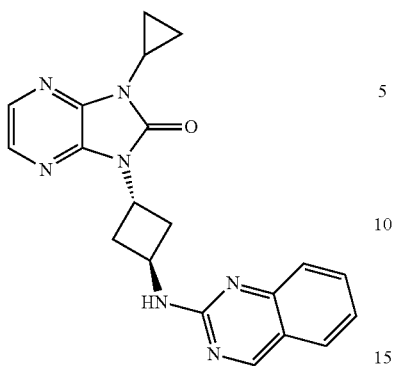

A glass microwave reaction vessel was charged with 1-(trans-3-aminocyclobutyl)-3-cyclopropyl-1H-imidazo[4,5-b]pyrazin-2(3H)-one hydrochloride (Intermediate 79, 0.1099 g, 0.390 mmol), 2-chloroquinazoline (0.128 g, 0.780 mmol, Waterstone), and diisopropylamine (0.204 ml, 1.170 mmol, Sigma-Aldrich Chemical Company, Inc.) in DMSO. The reaction was heated to 90° C. for 24 h. The reaction was taken up in DCM and loaded onto an Accubond SCX cartridge and washed with DCM (2×), MeOH (2×), and 2.0 ammonia in MeOH (2×). The ammonia fractions were combined and concentrated. The crude product was adsorbed onto a plug of silica gel and chromatographed through a Biotage SNAP HP-silica gel column (25 g), eluting with a gradient of 1% to 5% MeOH in $CH_2CL_2$, to provide the title compound (0.0445 g, 0.119 mmol, 30.6% yield). LCMS showed product peak at 1.511 min (m+1=374.0). $^1$H NMR (400 MHz, CHLOROFORM-d) δ ppm 1.12-1.23 (m, 4 H) 2.65 (t, J=9.29 Hz, 2 H) 2.97-3.08 (m, 1 H) 3.41-3.53 (m, 2 H) 5.30-5.42 (m, 1 H) 7.36 (t, J=6.85 Hz, 1 H) 7.69 (d, J=8.41 Hz, 1 H) 7.73-7.85 (m, 2 H) 7.92-7.99 (m, 2 H) 9.11 (br. s., 1 H)

Example 220

1-(trans-3-(benzo[d]oxazol-2-ylamino)cyclobutyl)-3-cyclopropyl-1H-imidazo[4,5-b]pyrazin-2(3H)-one

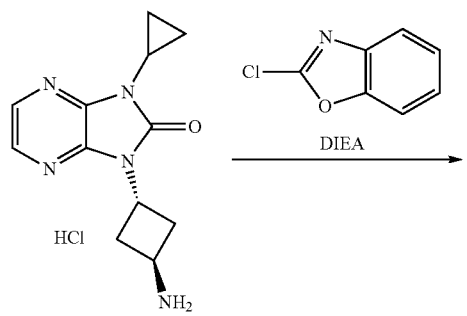

288

-continued

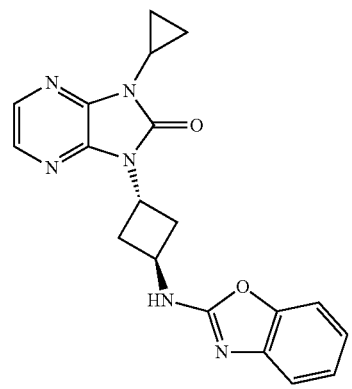

A glass microwave reaction vessel was charged with 1-(trans-3-aminocyclobutyl)-3-cyclopropyl-1H-imidazo[4,5-b]pyrazin-2(3H)-one hydrochloride (Intermediate 79, 0.1099 g, 0.390 mmol), 2-chlorobenzoxazole (0.088 ml, 0.768 mmol, Sigma-Aldrich Chemical Company, Inc.), and diisopropylamine (0.204 ml, 1.170 mmol, Sigma-Aldrich Chemical Company, Inc.) in DMSO. The reaction was heated to 90° C. for 24 h The crude product was purified by reverse-phase preparative HPLC using a Phenomenex Gemini column, 10 micron, C18, 110 Å, 100×50 mm, 0.1% TFA in $CH_3CN/H_2O$, gradient 10% to 909% over 15 min. LCMS showed product was not isolated at ≥95% purity. The crude product was adsorbed onto a plug of silica gel and chromatographed through a Biotage SNAP HP-silica gel column (25 g), eluting with a gradient of % to 5% MeOH in $CH_2Cl_2$, to provide the title compound (0.0590 g, 0.163 mmol, 42.4% yield). LCMS showed product peak at 1.604 min (m+1=362.9). $^1$H NMR (400 MHz, DMSO-$d_6$) δ ppm 0.96-1.02 (m, 2 H) 1.02-1.09 (m, 2 H) 2.52-2.58 (m, 1 H) 2.91-3.01 (m, 1 H) 3.18-3.30 (m, 2 H) 4.46-4.59 (m, 1 H) 5.11-5.23 (m, 1 H) 6.99 (td, J=7.73, 1.37 Hz, 1 H) 7.12 (td, J=7.63, 1.17 Hz, 1 H) 7.27 (dd, J=7.73, 0.68 Hz, 1 H) 7.36 (dd, J=7.82, 0.59 Hz, 1 H) 7.94-7.98 (m, 1 H) 7.99-8.02 (m, 1 H) 8.42 (d, J=6.46 Hz, 1 H)

Example 221

1-(trans-3-((5-chloropyridin-2-yl)amino)cyclobutyl)-3-cyclopropyl-1H-imidazo[4,5-b]pyrazin-2(3H)-one

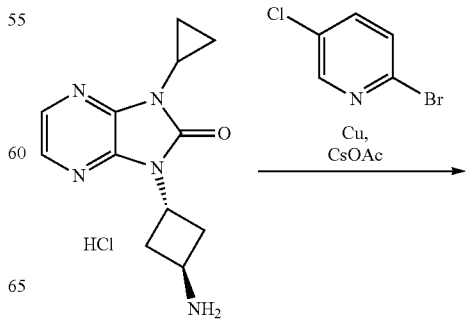

-continued

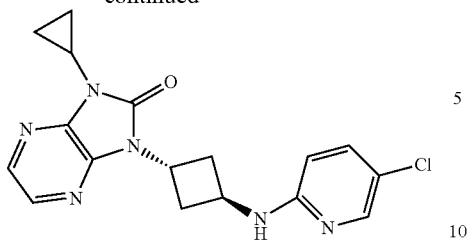

Step 7-1: 1-(trans-3-((5-chloropyridin-2-yl)amino)cyclobutyl)-3-cyclopropyl-1H-imidazo[4,5-b]pyrazin-2(3H)-one To a round bottomed flask was added 1-(trans-3-aminocyclobutyl)-3-cyclopropyl-1H-imidazo[4,5-b]pyrazin-2(3H)-one hydrochloride (Intermediate 79, 0.1128 g, 0.400 mmol), 2-bromo-5-chloropyridine (0.092 g, 0.480 mmol, Matrix Scientific), copper (2.035 mg, 0.032 mmol, Fisher Scientific), and cesium acetate (0.476 g, 2.482 mmol, Sigma-Aldrich Chemical Company, Inc.) in DMSO (0.500 ml) to stir at 100° C. for 2 days. The crude product was purified by reverse-phase preparative HPLC using a Phenomenex Gemini column, micron, C18, 110 Å, 100×50 mm, 0.1% TFA in CH$_3$CN/H$_2$O, gradient 10% to 900 over 12 min. Fractions containing product peak were concentrated in vacuo. The product was taken up in DCM and loaded onto a Silicyle Si-carbonate cartridge to remove any salts to give the title compound (5.4 mg, 0.015 mmol, 3.8% yield). LCMS showed product peak at 1.448 min (m+1=356.9). $^1$H NMR (400 MHz, DMSO-d$_6$) δ ppm 0.95-1.03 (m, 2 H) 1.02-1.09 (m, 2 H) 2.26-2.36 (m, 2 H) 2.96 (tt, J=7.09, 3.77 Hz, 1 H) 3.15-3.28 (m, 2 H) 4.42 (d, J=5.67 Hz, 1 H) 5.13 (quin, J=8.26 Hz, 1 H) 6.50 (d, J=9.00 Hz, 1 H) 7.30 (d, J=6.06 Hz, 1 H) 7.47 (dd, J=9.00, 2.54 Hz, 1 H) 7.92-8.03 (m, 3 H)

Examples 222-225 are tabulated in Table 8 below.

Example 226

1-cyclopropyl-3-(trans-3-((1-methyl-1H-benzo[d]imidazol-2-yl)amino)cyclobutyl)-1H-imidazo[4,5-b]pyrazin-2(3H)-one

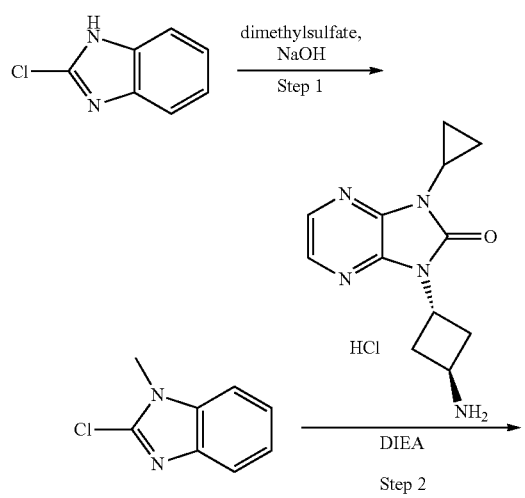

-continued

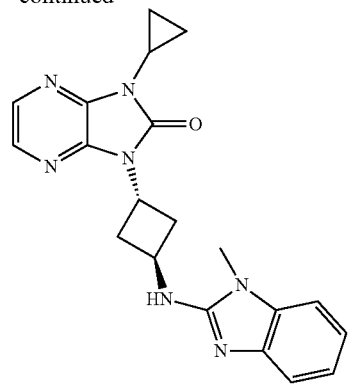

Step 1: 2-chloro-1-methyl-1H-benzo[d]imidazole

To a solution of 2-chloro-1H-benzo[d]imidazole (3.0019 g, 19.67 mmol, Sigma-Aldrich Chemical Company, Inc.) in 2.5 M sodium hydroxide solution (19.67 ml, 49.2 mmol, J. T. Baker) at 0° C. was added dimethyl sulfate (3.01 ml, 31.5 mmol, Riedel de Haen AG) dropwise. The reaction was allowed to stir for 1½ h. White precipitate was noted to form. The white precipitate was filtered, washed with water, and dried to give the title compound. LCMS showed product peak at 1.47 min (m+1=167.0). $^1$H NMR (400 MHz, DMSO-d$_6$) δ ppm 3.80 (s, 3 H) 7.21-7.28 (m, 1 H) 7.28-7.35 (m, 1 H) 7.59 (d, J=3.72 Hz, 1 H) 7.61 (d, J=3.72 Hz, 1 H)

Step 2: 1-cyclopropyl-3-(trans-3-((1-methyl-1H-benzo[d]imidazol-2-yl)amino)cyclobutyl)-1H-imidazo[4,5-b]pyrazin-2(3H)-one A glass microwave reaction vessel was charged with 1-(trans-3-aminocyclobutyl)-3-cyclopropyl-1H-imidazo[4,5-b]pyrazin-2(3H)-one hydrochloride (Intermediate 79, 0.1138 g, 0.404 mmol), 2-chloro-1-methyl-1H-benzo[d]imidazole (0.081 g, 0.485 mmol), and diisopropylamine (0.211 ml, 1.212 mmol, Sigma-Aldrich Chemical Company, Inc.) in DMSO (0.577 ml) and heated to 120° C. to stir for 2 days. The crude product was purified by reverse-phase preparative HPLC using a Phenomenex Gemini column, micron, C18, 110 Å, 100×50 mm, 0.1% TFA in CH$_3$CN/H$_2$O, gradient 10% to 100% over min. Fractions containing product were collected and concentrated. Residue taken up in DCM and loaded onto a Silicycle Si-carbonate cartridge to remove any salts to give the title compound (103 mg, 0.027 mmol, 6.79 yield). LCMS showed product peak at 1.57 min (m+1=376.0). $^1$H NMR (400 MHz, DMSO-d$_6$) δ ppm 0.97-1.03 (m, 2 H) 1.04-1.11 (m, 2 H) 2.47 (d, J=3.33 Hz, 1 H) 2.98 (tt, f=7.04, 3.72 Hz, 1 H) 3.27 (dt, J=13.30, 8.12 Hz, 2 H) 3.56 (s, 3 H) 4.53-4.66 (m, 1 H) 5.24 (quin, J=8.31 Hz, 1 H) 6.89-6.99 (m, 2 H) 7.02 (d, J=6.46 Hz, 1 H) 7.13-7.19 (m, 1 H) 7.19-7.25 (m, 1 H) 7.96-8.00 (m, 1 H) 8.00-8.04 (m, 1 H)

Example 227

1-(trans-4-aminocyclohexyl)-3-cyclopropyl-1H-imidazo[4,5-b]pyrazin-2(3H)-one

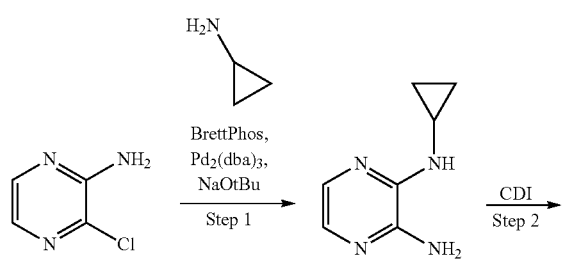

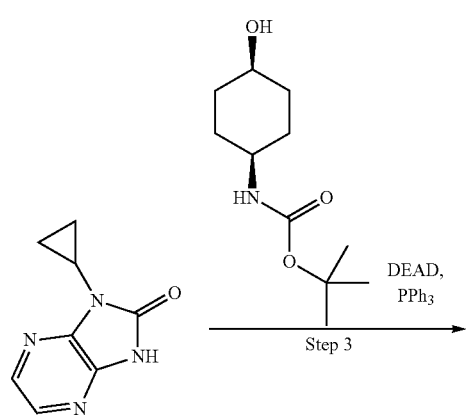

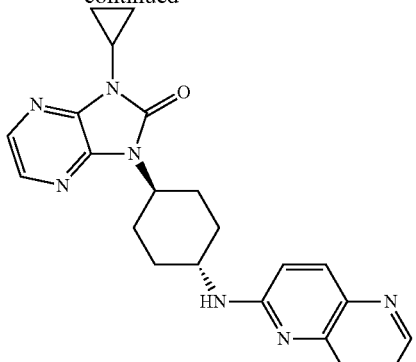

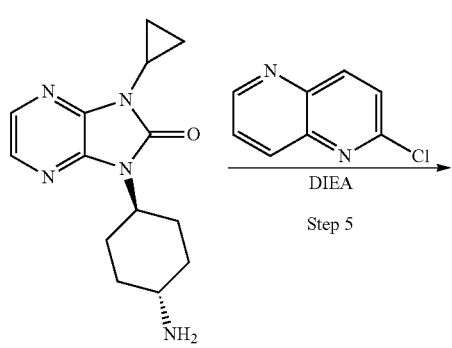

Step 1: N²-cyclopropylpyrazine-2,3-diamine

A glass microwave reaction vessel (20 mL) was charged with 3-chloropyrazin-2-amine (0.500 g, 3.86 mmol, FSSI), tris(dibenzylideneacetone)dipalladium(o) (0.070 g, 0.076 mmol, Strem Chemicals, Inc.) and BrettPhos (0.100 g, 0.186 mmol, Strem Chemicals, Inc.). The vessel was transferred to the glove-box where sodium tert-butoxide (0.700 g, 7.28 mmol, Sigma-Aldrich Chemical Company) was added. The vessel was capped and placed under an atmosphere of argon using 3 evacuation/backfill cycles. Dioxane (5 mL) and cyclopropylamine (0.410 mL, 5.85 mmol, Alfa Aesar) were added and the reaction mixture was heated at 45° C. for 1 h. The reaction was poured into water (100 mL, 0° C.) and the extracted with DCM (4×).

Step 2: 1-cyclopropyl-1H-imidazo[4,5-b]pyrazin-2(3H)-one

To a solution of N²-cyclopropylpyrazine-2,3-diamine (0.6690 g, 4.45 mmol) in THF (22.27 ml) at 50° C. was added CDI (2.89 g, 17.82 mmol, Fluka). The reaction was allowed to stir for 1½ h. The reaction flask was place in an ice bath until the temperature reached 0° C. The flask was raised and water (5 mL) was added dropwise to quench. (Note: if exothermic reaction was detected then flask was placed back into ice bath until it stopped.) The crude product was adsorbed onto a plug of silica gel and chromatographed through a Biotage SNAP HP-silica gel column (50 g), eluting with a gradient of 1% to 8% MeOH in $CH_2Cl_2$, to provide 1 the title compound (0.5578 g, 3.17 mmol, 71.1% yield). LCMS showed product peak at 0.999 min (m+1=177.1). $^1$H NMR (400 MHz, DMSO-$d_6$) δ ppm 0.95-1.07 (m, 4 H) 2.87-3.00 (m, 1 H) 7.84-7.89 (m, 1 H) 7.89-7.94 (m, 1 H) 11.87 (s, 1 H)

Step 3: tert-butyl(trans-4-(3-cyclopropyl-2-oxo-2,3-dihydro-1H-imidazo[4,5-b]pyrazin-1-yl)cyclohexyl) carbamate To a cooled solution (0° C.) of tert-butyl cis-4-hydroxycyclohexanecarbamate (0.682 g, 3.17 mmol, Biofine International), 1-cyclopropyl-1H-imidazo[4,5-b]pyrazin-2(3H)-one (0.5578 g, 3.17 mmol), and triphenylphosphine (1.100 ml, 4.75 mmol, Sigma-Aldrich Chemical Company) in THF (17.49 ml) was added diethyl azodicarboxylate, 40 wt. % solution in toluene (1.870 ml, 4.75 mmol, Chem Impex International) dropwise. After 10 mins, the round bottomed flask was removed from the ice bath and allowed to warm to room temperature to stir. Reaction was allowed to stir for 5 h and was then concentrated in vacuo. The crude product was adsorbed onto a plug of silica gel and chromatographed through a Biotage SNAP HP-silica gel column (50 g), eluting with a gradient of 10% to 100% EtOAc in hexane, to provide the title compound (0.7301 g, 1.955 mmol, 61.7% yield). LCMS showed product peak at 2.13 min (m+1=374.0). NMR showed some biproduct from DEAD reagent. Product was carried on without further purification.

Step 4: 1-(trans-4-aminocyclohexyl)-3-cyclopropyl-1H-imidazo[4,5-b]pyrazin-2(3H)-one To a round bottomed flask was added tert-butyl(trans-4-(3-cyclopropyl-2-oxo-2,3-dihydro-1H-imidazo[4,5-b]pyrazin-1-yl)cyclohexyl)carbamate (0.7301 g, 1.955 mmol, Step 3) and hydrogen chloride, 4.0M solution in 1,4-dioxane (4.89 ml, 19.55 mmol, Sigma-Aldrich Chemical Company, Inc.) to stir at room temperature for 7 h. Precipitate was noted to form. The reaction mixture was filtered and the solid was washed with diethyl ether to give the title compound (209.9 mg, 0.678 mmol, 34.7% yield). $^1$H NMR (400 MHz, DMSO-$d_6$) δ ppm 0.95-1.10 (m, 4 H) 1.47-1.62 (m, 2 H) 1.85 (d, J=11.15 Hz, 2 H) 2.10 (d, J=11.35 Hz, 2 H) 2.26-2.41 (m, 2 H) 2.93-3.02 (m, 1 H) 3.11 (t, J=11.93 Hz, 1 H) 4.22 (ddd, J=12.23, 8.51, 3.72 Hz, 1 H) 7.91-7.95 (m, 1 H) 7.95-7.99 (m, 1 H) 8.12 (br. s., 2 H)

Step 5: 1-(trans-4-((1,5-naphthyridin-2-yl)amino)cyclohexyl)-3-cyclopropyl-1H-imidazo[4,5-b]pyrazin-2(3H)-one A glass microwave reaction vessel was charged with 1-(trans-4-aminocyclohexyl)-3-cyclopropyl-1H-imidazo[4,5-b]pyrazin-2(3H)-one (0.1050 g, 0.339 mmol), 2-chloro-1,5-naphthyridine (0.067 g, 0.407 mmol, 00358), and diisopropylethylamine (0.177 ml, 1.017 mmol, Sigma-Aldrich Chemical Company, Inc.) in DMSO (0.484 ml) and heated to 120° C. for 2 days. The crude product was purified by reverse-phase preparative HPLC using a Phenomenex Gemini column, 10 micron, 100×50 mm, 0.1% TFA in CH$_3$CN/H$_2$O, gradient 10% to 90% over 15 min. Fractions containing product were collected and concentrated. The product was taken up in DCM and loaded onto a Silicycle Si-carbonate cartridge and washed with DCM and MeOH to remove any salts to give the title compound (6.4 mg, 0.016 mmol, 4.7% yield). LCMS showed product peak at 1.434 min (m+1=402.0). $^1$H NMR (400 MHz, CHLOROFORM-d) δ ppm 1.09-1.24 (m, 4 H) 1.37-1.53 (m, 2 H) 1.94 (d, J=11.93 Hz, 2 H) 2.39 (d, J=12.13 Hz, 2 H) 2.68 (qd, J=12.91, 3.13 Hz, 2 H) 2.97-3.09 (m, 1 H) 4.08-4.24 (m, 1 H) 4.47 (tt, J=12.32, 3.91 Hz, 1 H) 6.85 (d, J=9.19 Hz, 1 H) 7.45 (dd, J=8.41, 4.30 Hz, 1 H) 7.91-7.96 (m, 2 H) 7.97 (d, J=8.61 Hz, 1 H) 8.03 (d, J=9.19 Hz, 1 H) 8.60 (d, J=3.33 Hz, 1 H)

Example 228

1-(trans-3-((1,5-naphthyridin-2-yl)amino)cyclobutyl)-3-cyclopropyl-1H-imidazo[4,5-b]pyrazin-2(3H)-one

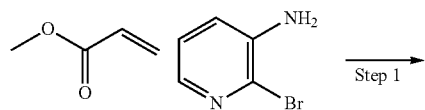

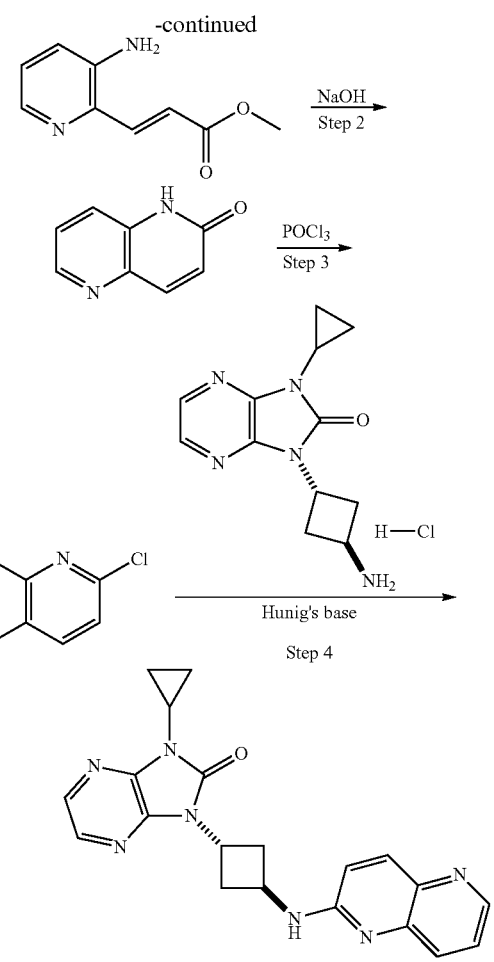

Step 1: (E)-methyl 3-(3-aminopyridin-2-yl)acrylate

The following reaction was performed in duplicate: A glass microwave reaction vessel was charged with 3-amino-2-bromopyridine (2.00 g, 11.56 mmol) and bis(di-tert-butyl(4-dimethylaminophenyl)phosphine)dichloropalladium(II) (0.250 g, 0.353 mmol). DMF (10 mL) was added followed by methyl acrylate (4.00 mL, 44.3 mmol) and triethylamine (4.00 mL, 28.7 mmol). The reaction mixture was sealed under argon and heated in an Initiator microwave reactor (Personal Chemistry, Biotage AB, Inc., Upssala, Sweden) at 145° C. for 40 min. The reaction mixtures were combined and the solvent was removed in vacuo. The residue was dissolved in DCM, evaporated onto silica gel and purified by flash chromatography (ISCO, (120 gram HP)) eluting with 2M NH$_3$ in MeOH:CH$_2$Cl$_2$ (0:1-1:39) to give 2.75 g (69%) of a yellow amorphous solid. ESI-MS 179.0 [M+1].

Step 2: 1,5-naphthyridin-2(1H)-one

To a room temperature solution of (E)-methyl 3-(3-aminopyridin-2-yl)acrylate (3.63 g, 20.37 mmol) in MeOH (40 mL) was added sodium methoxide, 25 wt % solution in methanol (20.00 mL, 90 mmol). The reaction was heated at 60° C. for 6 h, the mixture was cooled to room temperature and the solvent was removed in vacuo to give tan solid. ESI-MS 147.0 [M+1].

Step 3: 2-chloro-1,5-naphthyridine

A 250 mL round bottomed flask charged with 1,5-naphthyridin-2(1H)-one (2.98 g, 20.37 mmol) and phosphorus oxychloride (40 ml, 437 mmol) was heated at 100° C. for 3 h. The reaction was cooled to room temperature and excess POCl₃ was removed in vacuo. The residue was poured onto ice and neutralized with NaHCO₃. The mixture was extracted with DCM (4×) and the combined organic layers were evaporated onto silica gel and purified by flash chromatography (ISCO (80 gram)) eluting with EtOAc:DCM (0:1→1:4) to give 1.08 g (32%, 2 steps) of a light-yellow amorphous solid. ESI-MS 164.9, 166.9 [M+1].

Step 4: 1-(trans-3-((1,5-naphthyridin-2-yl)amino) cyclobutyl)-3-cyclopropyl-1H-imidazo[4,5-b] pyrazin-2(3H)-one A glass microwave reaction vessel was charged with 1-(trans-3-aminocyclobutyl)-3-cyclopropyl-1H-imidazo[4,5-b]pyrazin-2(3H)-one hydrochloride (Intermediate 79, 0.133 g, 0.472 mmol), 2-chloro-1,5-naphthyridine (0.100 g, 0.608 mmol) and DMSO (2 mL). N,N-Diisopropylethylamine (0.250 mL, 1.437 mmol) was added and the reaction mixture was sealed under argon and heated at 100° C. for 59 h. The reaction was cooled to room temperature and partitioned between water/DCM. The aqueous layer was extracted with DCM (3×) and the combined organic layers were evaporated onto silica gel and purified by flash chromatography (Isco, (25 gram)) eluting with 2M NH₃ in MeOH:CH₂Cl₂ (0:1→1:19) to give 67 mg (34%) of a white crystalline solid. ESI-MS 374.0 [M+1]. ¹H NMR (400 MHz, DMSO-d₆) δ ppm 8.49 (dd, J=4.30, 1.56 Hz, 1 H), 8.00 (d, J=3.33 Hz, 1 H), 7.97 (d, J=3.33 Hz, 1 H), 7.93 (d, J=9.19 Hz, 1 H), 7.81-7.89 (m, 2 H), 7.46 (dd, J=8.41, 4.11 Hz, 1 H), 7.02 (d, J=9.19 Hz, 1 H), 5.21 (m, 1 H), 4.64-4.76 (m, 1 H), 3.25-3.38 (m, 2 H), 2.91-3.02 (m, 1 H), 2.34-2.45 (m, 2 H), 0.94-1.11 (m, 4 H)

Example 229

1-(trans-3-((6-chlorobenzo[d]oxazol-2-yl)amino) cyclobutyl)-3-cyclopropyl-1H-imidazo[4,5-b] pyrazin-2(3H)-one

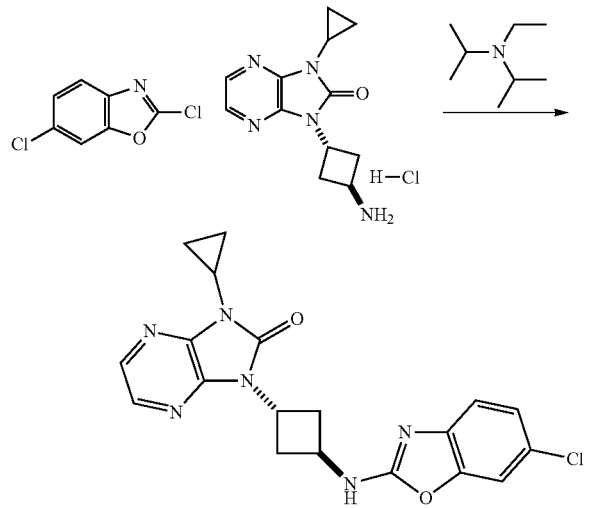

A glass microwave reaction vessel was charged with 1-(trans-3-aminocyclobutyl)-3-cyclopropyl-1H-imidazo[4,5-b]pyrazin-2(3H)-one hydrochloride (Intermediate 79, 0.100 g, 0.355 mmol) and 2,6-dichlorobenzoxazole (0.099 g, 0.527 mmol, TCI America). DMSO (2 mL) was added followed by N,N-diisopropylethylamine (0.250 mL, 1.437 mmol) and the reaction mixture was sealed under argon and heated at 100° C. for 30 h. The reaction was cooled to room temperature, diluted with MeOH and purified by reverse-phase HPLC (Gilson; Gemini-NX 10 m C18 110A AXIA, 100×50 mm column) eluting with 0.1% TFA-H₂O:0.1% TFA CH₃CN (9:1→1:9). The fractions containing the desired product were combined and concentrated in vacuo. The residue was dissolved in MeOH and loaded onto an SCX II cartridge eluting with MeOH then 2M NH₃ in MeOH to give 93 mg (66%) of a white crystalline solid. ESI-MS 397.0, 398.9 [M+1]. ¹H NMR (400 MHz, DMSO-d₆) δ ppm 8.62 (d, J=6.46 Hz, 1 H), 8.00 (d, J=3.33 Hz, 1 H), 7.98 (d, J=3.33 Hz, 1 H), 7.56 (d, J=1.96 Hz, 1 H), 7.26 (d, J=8.22 Hz, 1 H), 7.16 (dd, J=8.41, 1.96 Hz, 1 H), 5.17 (quin, J=8.22 Hz, 1 H), 4.44-4.61 (m, 1 H), 3.19-3.30 (m, 2 H), 2.91-3.02 (m, 1 H), 2.48-2.59 (m, 2 H), 0.94-1.12 (m, 4 H)

Example 230

1-(trans-3-(benzo[d]thiazol-2-ylamino)cyclobutyl)-5-bromo-3-cyclopropyl-1H-imidazo[4,5-b]pyrazin-2(3H)-one

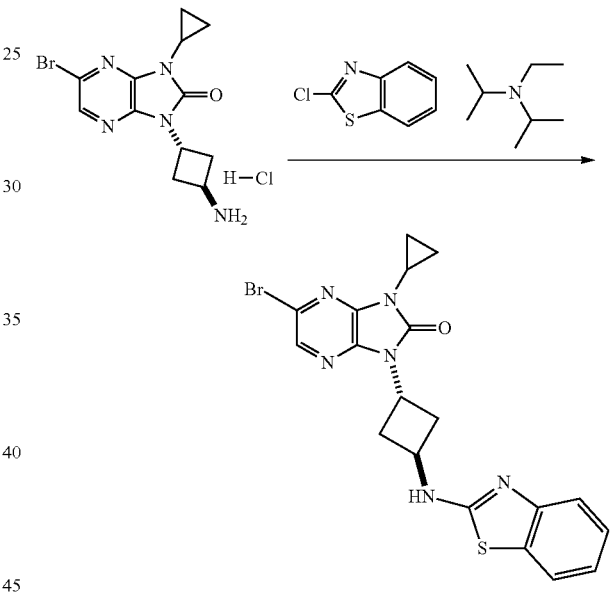

1-(trans-3-(benzo[d]thiazol-2-ylamino)cyclobutyl)-5-bromo-3-cyclopropyl-1H-imidazo[4,5-b]pyrazin-2(3H)-one A glass microwave reaction vessel was charged with 1-(trans-3-aminocyclobutyl)-5-bromo-3-cyclopropyl-1H-imidazo[4,5-b]pyrazin-2(3H)-one hydrochloride (Intermediate 82, 0.128 g, 0.355 mmol) and DMSO (2 mL). N,N-Diisopropylethylamine (0.250 ml, 1.437 mmol) was added followed by 2-chlorobenzothiazole (0.060 ml, 0.461 mmol) and the reaction mixture was sealed under argon and heated at 100° C. for 24 h. The reaction mixture was diluted with water and a small amount of MeOH. The resultant solid was filtered, washed with water and dried in vacuo to give 94 mg (58%) of an off-white crystalline solid. ESI MS 456.8, 458.8 [M+1]. ¹H NMR (300 MHz, DMSO-d₆) δ ppm 8.53 (d, J=6.28 Hz, 1 H), 8.16 (s, 1 H), 7.63-7.75 (m, 1 H), 7.42 (d, J=7.45 Hz, 1 H), 7.15-7.30 (m, 1 H), 6.96-7.09 (m, 1 H), 5.12 (quin, J=8.29 Hz, 1 H), 4.41-4.65 (m, 1 H), 3.14-3.29 (m, 2 H), 2.87-3.01 (m, 1 H), 2.39-2.57 (m, 2 H), 0.91-1.11 (m, 4 H)

Example 231

5-bromo-3-cyclopropyl-1-(trans-3-((7-fluoro-quinazolin-2-yl)amino)cyclobutyl)-1H-imidazo[4,5-b]pyrazin-2(3H)-one

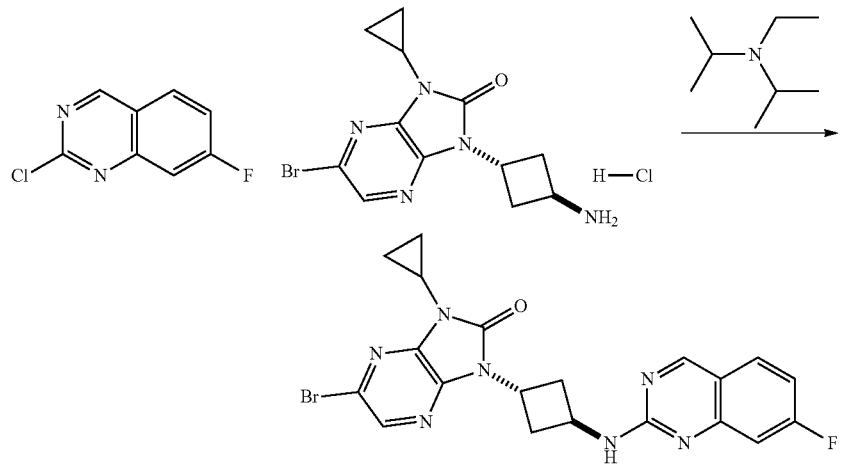

A glass microwave reaction vessel was charged with 1-(trans-3-aminocyclobutyl)-5-bromo-3-cyclopropyl-1H-imidazo[4,5-b]pyrazin-2(3H)-one hydrochloride (Intermediate 82, 0.143 g, 0.397 mmol) and 2-chloro-7-fluoroquinazoline (0.118 g, 0.646 mmol). DMSO (2 mL) was added followed by N,N-diisopropylethylamine (0.300 mL, 1.725 mmol) and the reaction mixture was sealed under argon and heated at 100° C. overnight. The reaction was cooled room temperature and diluted with water. The precipitate was filtered to give an off-white solid. The material was dissolved in 4M HCl in dioxane and purified by reverse-phase HPLC (Gilson; Gemini-NX 10 m C18 110A AXIA, 100×50 mm column) eluting with 0.1% TFA-$H_2O$:0.1% TFA $CH_3CN$ (9:1→1:9). The fractions containing the desired product were combined and concentrated in vacuo. The residue was dissolved in MeOH and loaded onto an Si-Carbonate (Silicycle) cartridge eluting with DCM/MeOH to give 50 mg (27%) of a white crystalline solid. ESI MS 469.9, 471.8 [M+1].

$^1$H NMR (300 MHz, DMSO-$d_6$) δ ppm 9.13 (s, 1 H), 8.16 (s, 1 H), 8.13 (d, J=6.43 Hz, 1 H), 7.90 (dd, J=8.92, 6.58 Hz, 1 H), 7.19 (d, J=10.67 Hz, 1 H), 7.12 (td, J=8.88, 2.56 Hz, 1 H), 5.16 (quin, J=8.40 Hz, 1 H), 4.56-4.82 (m, 1 H), 3.22 (dt, J=13.26, 8.20 Hz, 2 H), 2.87-3.02 (m, 1 H), 2.40-2.50 (d, J=3.51 Hz, 2 H), 0.92-1.14 (m, 4 H)

Additional Examples

The following compounds of Formula (I), wherein each D and E is nitrogen, G is —NH—$R^1$, and $R^{3a}$, $R^{3b}$, and $R^{3c}$ are hydrogens; as shown in Table 9 below, can be prepared according to methods analogous to the above General Schemes 1-12 by using Intermediate Compounds as prepared in the above Preparations or other analogous compounds that are commercially available, or can be made according to methods available to those skilled in the art.

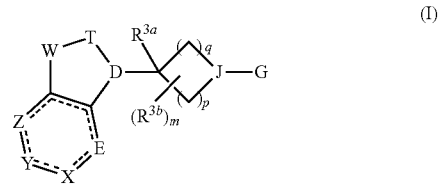

(I)

TABLE 9

| Ex. # | G | p | q | J | —X—Y—Z— | W | T |
|---|---|---|---|---|---|---|---|
| 232 | ![benzothiazole-HN] | 1 | 1 | CH | =CH—N=CH— | tBu | (C=O) |
| 233 | ![benzothiazole-HN] | 1 | 1 | CH | =CH—CH=CH— | iPr-N | (C=O) |

TABLE 9-continued
Examples 232-328
| Ex. # | G | p | q | J | —X—Y—Z— | W | T |
|---|---|---|---|---|---|---|---|
| 234 | 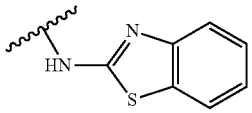 [SMILES: *Nc1nc2ccccc2s1] | 1 | 1 | CH | =CH—CH=N— | 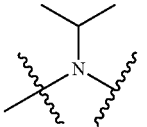 | (C=O) |
| 235 | 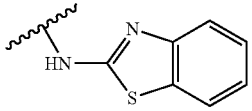 [SMILES: *Nc1nc2ccccc2s1] | 1 | 1 | CH | =CH—CH=N— | 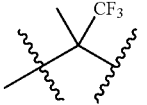 | (C=O) |
| 236 | 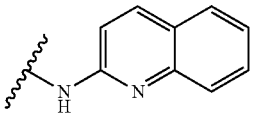 | 1 | 1 | CH | =CH—CH=CH— | 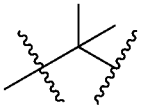 [SMILES: *C(*)(C)C] | (C=O) |
| 237 | 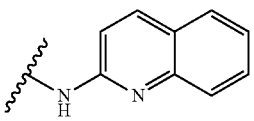 [SMILES: *Nc1ccc2ccccc2n1] | 1 | 1 | CH | =CH—N=CH— | 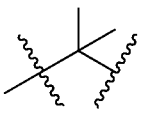 | (C=O) |
| 238 | 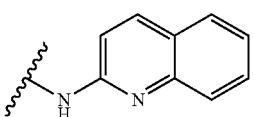 | 1 | 1 | CH | =CH—CH=CH— | 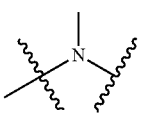 | (C=O) |
| 239 | 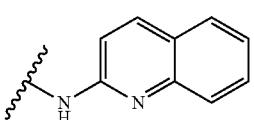 | 1 | 1 | CH | =CH—CH=N— | 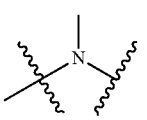 [SMILES: *N(*)C] | (C=O) |
| 240 | 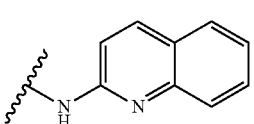 | 1 | 1 | CH | =CH—CH=CH— | 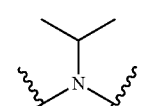 | (C=O) |
| 241 | 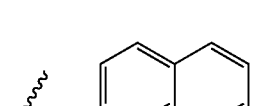 | 1 | 1 | CH | =CH—CH=N— | 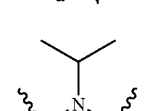 | (C=O) |
| 242 | 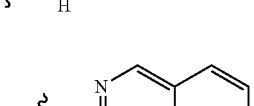 | 1 | 1 | CH | =CH—N=CH— |  | (C=O) |
| 243 | 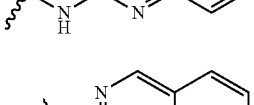 | 1 | 1 | CH | =CH—CH=CH— |  | (C=O) |
| 244 | 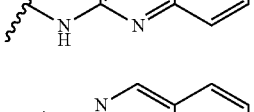 | 1 | 1 | CH | =CH—CH=N— |  | (C=O) |

TABLE 9-continued

Examples 232-328

| Ex. # | G | p | q | J | —X—Y—Z— | W | T |
|---|---|---|---|---|---|---|---|
| 245 | quinazolin-2-ylamino | 1 | 1 | CH | =CH—CH=CH— | N-iPr (di-substituted) | (C=O) |
| 246 | quinazolin-2-ylamino | 1 | 1 | CH | =CH—CH=N— | N-iPr (di-substituted) | (C=O) |
| 247 | quinoxalin-2-ylamino | 1 | 1 | CH | =CH—CH=CH— | N-tBu (di-substituted) | (C=O) |
| 248 | quinoxalin-2-ylamino | 1 | 1 | CH | =CH—CH=N— | N-tBu (di-substituted) | (C=O) |
| 249 | quinoxalin-2-ylamino | 1 | 1 | CH | =CH—N=CH— | N-tBu (di-substituted) | (C=O) |
| 250 | quinoxalin-2-ylamino | 1 | 1 | CH | =CH—CH=CH— | N-Me (di-substituted) | (C=O) |
| 251 | quinoxalin-2-ylamino | 1 | 1 | CH | =CH—CH=N— | N-Me (di-substituted) | (C=O) |
| 252 | quinoxalin-2-ylamino | 1 | 1 | CH | =CH—CH=CH— | N-iPr (di-substituted) | (C=O) |
| 253 | quinoxalin-2-ylamino | 1 | 1 | CH | =CH—CH=N— | N-iPr (di-substituted) | (C=O) |
| 254 | 1,5-naphthyridin-2-ylamino | 1 | 1 | CH | =CH—CH=CH— | N-tBu (di-substituted) | (C=O) |
| 255 | 1,5-naphthyridin-2-ylamino | 1 | 1 | CH | =CH—CH=CH— | N-Me (di-substituted) | (C=O) |

TABLE 9-continued
Examples 232-328
| Ex. # | G | p | q | J | —X—Y—Z— | W | T |
|---|---|---|---|---|---|---|---|
| 256 | 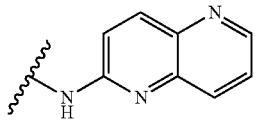 [SMILES: *Nc1ccc2ncccc2n1] | 1 | 1 | CH | =CH—CH=N— | 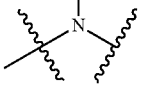 | (C=O) |
| 257 | 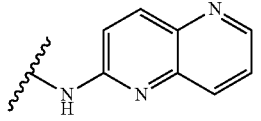 [SMILES: *Nc1ccc2ncccc2n1] | 1 | 1 | CH | =CH—CH=CH— | 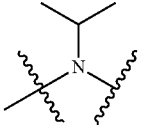 [SMILES: *N(*)C(C)C] | (C=O) |
| 258 | 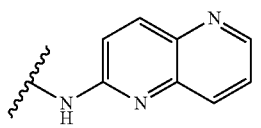 [SMILES: *Nc1ccc2ncccc2n1] | 1 | 1 | CH | =CH—CH=N— | 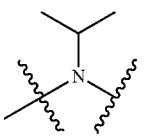 [SMILES: *N(*)C(C)C] | (C=O) |
| 259 | 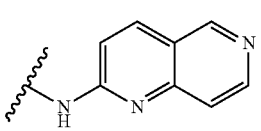 [SMILES: *Nc1ccc2cnccc2n1] | 1 | 1 | CH | =CH—CH=CH— | 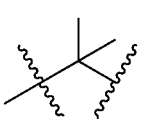 [SMILES: *C(*)(C)C] | (C=O) |
| 260 | 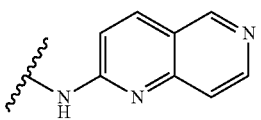 [SMILES: *Nc1ccc2cnccc2n1] | 1 | 1 | CH | =CH—CH=N— | 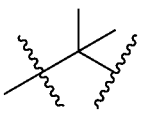 [SMILES: *C(*)(C)C] | (C=O) |
| 261 | 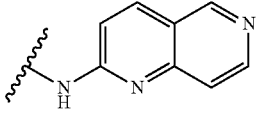 [SMILES: *Nc1ccc2cnccc2n1] | 1 | 1 | CH | =CH—N=CH— | 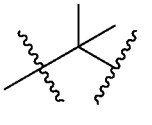 | (C=O) |
| 262 | 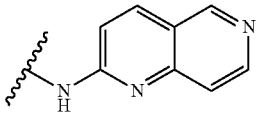 | 1 | 1 | CH | =CH—CH=CH— | 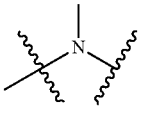 [SMILES: *N(*)C] | (C=O) |
| 263 | 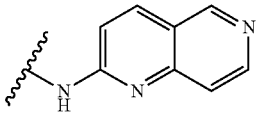 | 1 | 1 | CH | =CH—CH=N— | 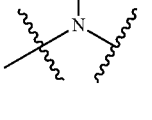 | (C=O) |
| 264 | 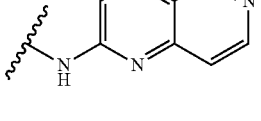 | 1 | 1 | CH | =CH—CH=CH— | 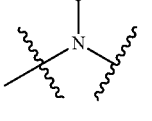 [SMILES: *N(*)C] | (C=O) |
| 265 | 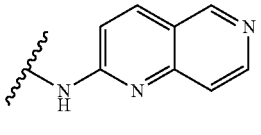 [SMILES: *Nc1ccc2cnccc2n1] | 1 | 1 | CH | =CH—CH=N— | 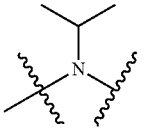 [SMILES: *N(*)C(C)C] | (C=O) |
| 266 | 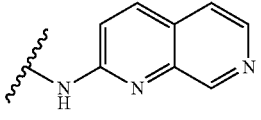 [SMILES: *Nc1ccc2ccncc2n1] | 1 | 1 | CH | =CH—CH=CH— | 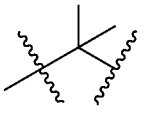 [SMILES: *C(*)(C)C] | (C=O) |

TABLE 9-continued

Examples 232-328

| Ex. # | G | p | q | J | —X—Y—Z— | W | T |
|---|---|---|---|---|---|---|---|
| 267 | NH-[1,7-naphthyridin-2-yl] | 1 | 1 | CH | =CH—CH=N— | t-Bu (C quaternary) | (C=O) |
| 268 | NH-[1,7-naphthyridin-2-yl] | 1 | 1 | CH | =CH—N=CH— | t-Bu (C quaternary) | (C=O) |
| 269 | NH-[1,7-naphthyridin-2-yl] | 1 | 1 | CH | =CH—CH=CH— | N-Me | (C=O) |
| 270 | NH-[1,7-naphthyridin-2-yl] | 1 | 1 | CH | =CH—CH=N— | N-Me | (C=O) |
| 271 | NH-[1,7-naphthyridin-2-yl] | 1 | 1 | CH | =CH—CH=CH— | N-iPr | (C=O) |
| 272 | NH-[1,7-naphthyridin-2-yl] | 1 | 1 | CH | =CH—CH=N— | N-iPr | (C=O) |
| 273 | NH-[1,8-naphthyridin-2-yl] | 1 | 1 | CH | =CH—CH=CH— | t-Bu (C quaternary) | (C=O) |
| 274 | NH-[1,8-naphthyridin-2-yl] | 1 | 1 | CH | =CH—N=CH— | t-Bu (C quaternary) | (C=O) |
| 275 | NH-[1,8-naphthyridin-2-yl] | 1 | 1 | CH | =CH—CH=CH— | N-Me | (C=O) |
| 276 | NH-[1,8-naphthyridin-2-yl] | 1 | 1 | CH | =CH—CH=N— | N-Me | (C=O) |
| 277 | NH-[1,8-naphthyridin-2-yl] | 1 | 1 | CH | =CH—CH=CH— | N-iPr | (C=O) |

TABLE 9-continued

Examples 232-328

| Ex. # | G | p | q | J | —X—Y—Z— | W | T |
|---|---|---|---|---|---|---|---|
| 278 | (1,8-naphthyridin-2-yl)NH— | 1 | 1 | CH | =CH—CH=N— | isopropyl-N< | (C=O) |
| 279 | (thiazolo[5,4-b]pyridin-2-yl)HN— | 1 | 1 | CH | =CH—CH=CH— | tert-butyl-N< | (C=O) |
| 280 | (thiazolo[5,4-b]pyridin-2-yl)HN— | 1 | 1 | CH | =CH—CH=N— | tert-butyl-N< | (C=O) |
| 281 | (thiazolo[5,4-b]pyridin-2-yl)HN— | 1 | 1 | CH | =CH—N=CH— | tert-butyl-N< | (C=O) |
| 282 | (thiazolo[5,4-b]pyridin-2-yl)HN— | 1 | 1 | CH | =CH—CH=CH— | Me-N< | (C=O) |
| 283 | (thiazolo[5,4-b]pyridin-2-yl)HN— | 1 | 1 | CH | =CH—CH=N— | Me-N< | (C=O) |
| 284 | (thiazolo[5,4-b]pyridin-2-yl)HN— | 1 | 1 | CH | =CH—CH=CH— | isopropyl-N< | (C=O) |
| 285 | (thiazolo[5,4-b]pyridin-2-yl)HN— | 1 | 1 | CH | =CH—CH=N— | isopropyl-N< | (C=O) |
| 286 | (thiazolo[4,5-b]pyridin-2-yl)HN— | 1 | 1 | CH | =CH—CH=CH— | tert-butyl-N< | (C=O) |
| 287 | (thiazolo[4,5-b]pyridin-2-yl)HN— | 1 | 1 | CH | =CH—N=CH— | tert-butyl-N< | (C=O) |
| 288 | (thiazolo[4,5-b]pyridin-2-yl)HN— | 1 | 1 | CH | =CH—CH=N— | Me-N< | (C=O) |

TABLE 9-continued

Examples 232-328

| Ex. # | G | p | q | J | —X—Y—Z— | W | T |
|---|---|---|---|---|---|---|---|
| 289 | thiazolo[5,4-b]pyridin-2-ylamino | 1 | 1 | CH | =CH—CH=CH— | N(iPr)(—)(—) | (C=O) |
| 290 | thiazolo[5,4-b]pyridin-2-ylamino | 1 | 1 | CH | =CH—CH=N— | N(iPr)(—)(—) | (C=O) |
| 291 | quinolin-2-ylamino | 2 | 2 | CH | =CH—N=CH— | N(Me)(—)(CH2—) | (C=O) |
| 292 | benzothiazol-2-ylamino | 1 | 1 | CH | =CH—CH=CH— | N(Me)(—)(CH2—) | (C=O) |
| 293 | benzothiazol-2-yl-C(O)— | 1 | 1 | N | =CH—CH=N— | N(Me)(—)(CH2—) | (C=O) |
| 294 | benzothiazol-2-ylamino | 1 | 1 | CH | =CH—N=CH— | N(—)(CH(Me)—)(—) | (C=O) |
| 295 | benzothiazol-2-ylamino | 2 | 1 | CH | =CH—CH=CH— | N(—)(CH(Me)—)(—) | (C=O) |
| 296 | benzothiazol-2-ylamino | 1 | 1 | CH | =CH—CH=N— | N(—)(CH(Me)—)(—) | (C=O) |
| 297 | benzothiazol-2-ylamino | 1 | 1 | CH | =CH—N=CH— | N(—)(C(Me)2—)(—) | (C=O) |
| 298 | 5-methoxypyridin-2-yl | 2 | 2 | N | =CH—CH=CH— | N(—)(C(Me)2—)(—) | (C=O) |
| 299 | benzothiazol-2-ylamino | 1 | 1 | CH | =CH—CH=N— | N(—)(C(Me)2—)(—) | (C=O) |

TABLE 9-continued
Examples 232-328
| Ex. # | G | p | q | J | —X—Y—Z— | W | T |
|---|---|---|---|---|---|---|---|
| 300 | 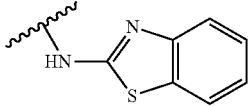 [SMILES: *Nc1nc2ccccc2s1] | 1 | 1 | CH | =CH—N=CH— | 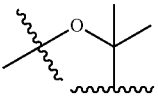 [SMILES: *OC(*)(C)C] | (C=O) |
| 301 | 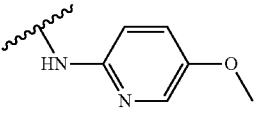 [SMILES: *Nc1ccc(OC)cn1] | 1 | 1 | CH | =CH—CH=CH— | 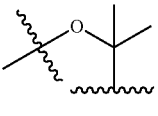 [SMILES: *OC(*)(C)C] | (C=O) |
| 302 | 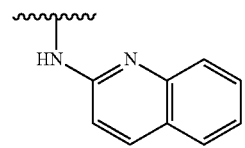 [SMILES: *Nc1ccc2ccccc2n1] | 1 | 1 | CH | =CH—CH=N— | 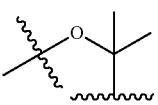 [SMILES: *OC(*)(C)C] | (C=O) |
| 303 | 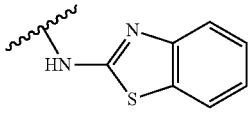 [SMILES: *Nc1nc2ccccc2s1] | 1 | 2 | CH | =CH—CH=CH— | 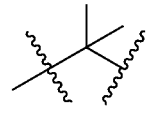 [SMILES: *C(*)(C)C] | (C=O) |
| 304 | 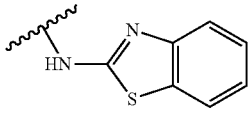 [SMILES: *Nc1nc2ccccc2s1] | 1 | 2 | CH | =CH—CH=N— | 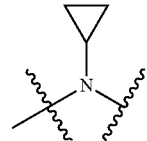 | (C=O) |
| 305 | 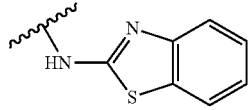 | 1 | 2 | CH | =CH—N=CH— | 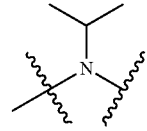 [SMILES: *N(*)C(C)C] | (C=O) |
| 306 | 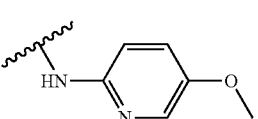 | 1 | 2 | CH | =CH—CH=CH— | 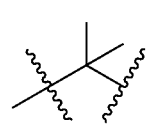 [SMILES: *C(*)(C)C] | (C=O) |
| 307 | 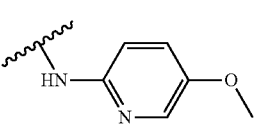 | 1 | 2 | CH | =CH—CH=N— | 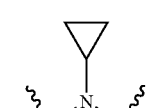 | (C=O) |
| 308 |  | 1 | 2 | CH | =CH—N=CH— | 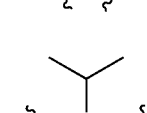 | (C=O) |
| 309 | 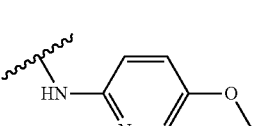 | 1 | 3 | CH | =CH—CH=CH— | 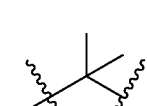 | (C=O) |

TABLE 9-continued
Examples 232-328
| Ex. # | G | p | q | J | —X—Y—Z— | W | T |
|---|---|---|---|---|---|---|---|
| 310 | 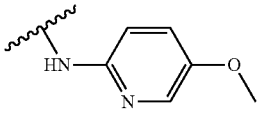 | 1 | 3 | CH | =CH—CH=N— | 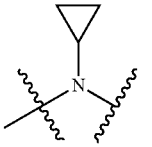 [SMILES: *N(*)C1CC1] | (C=O) |
| 311 | 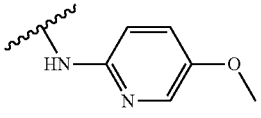 [SMILES: *Nc1ccc(OC)cn1] | 1 | 3 | CH | =CH—N=CH— | 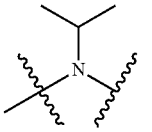 | (C=O) |
| 312 | 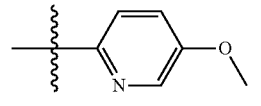 | 1 | 2 | N | =CH—CH=CH— | 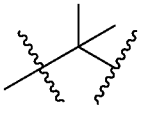 [SMILES: *C(*)(C)C] | (C=O) |
| 313 | 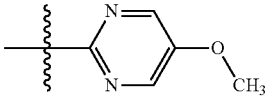 | 1 | 1 | N | =CH—CH=CH— | 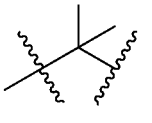 | (C=O) |
| 314 | 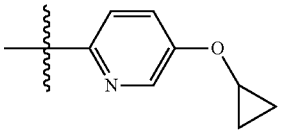 [SMILES: *c1ccc(OC2CC2)cn1] | 2 | 2 | N | =CH—CH=N— | 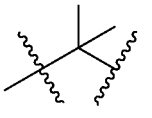 [SMILES: *C(*)(C)C] | (C=O) |
| 315 | 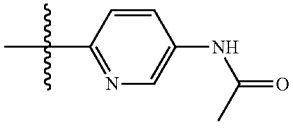 | 2 | 2 | N | =CH—CH=N— | 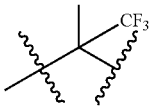 [SMILES: *C(*)(C)C(F)(F)F] | (C=O) |
| 316 | 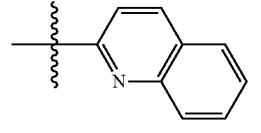 | 1 | 1 | N | =CH—CH=CH— | 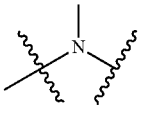 [SMILES: *N(*)C] | (C=O) |
| 317 | 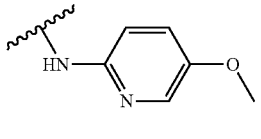 | 1 | 1 | CH | =CH—CH=CH— | 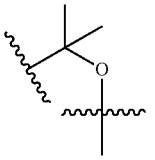 [SMILES: *OC(*)(C)C] | (C=O) |
| 318 | 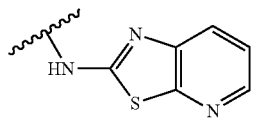 | 1 | 1 | CH | =CH—CH=N— | 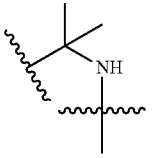 [SMILES: *NC(*)(C)C] | (C=O) |
| 319 | 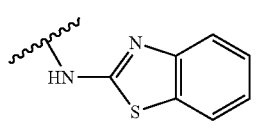 [SMILES: *Nc1nc2ccccc2s1] | 2 | 1 | CH | =CH—N=CH— | 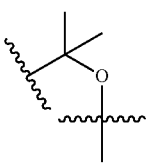 [SMILES: *OC(*)(C)C] | (C=O) |

TABLE 9-continued
Examples 232-328
| Ex. # | G | p | q | J | —X—Y—Z— | W | T |
|---|---|---|---|---|---|---|---|
| 320 | 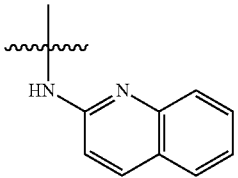 [SMILES: *Nc1ccc2ccccc2n1] | 2 | 1 | CH | =CH—CH=N— | 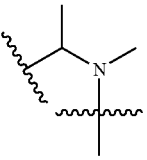 [SMILES: *C(C)N(*)C] | (C=O) |
| 321 | 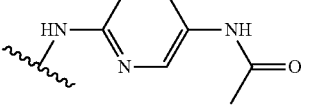 | 2 | 2 | CH | =CH—CH=N— | 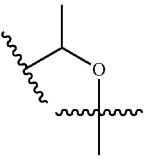 [SMILES: *OC(*)C] | (C=O) |
| 322 | 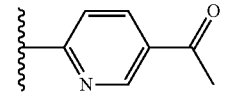 | 2 | 2 | N | =CH—CH=N— | 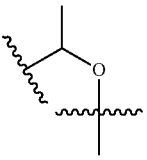 [SMILES: *OC(*)C] | (C=O) |
| 323 | 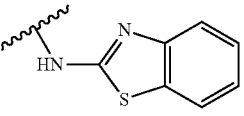 [SMILES: *Nc1nc2ccccc2s1] | 1 | 1 | CH | =CH—CH=CH— | 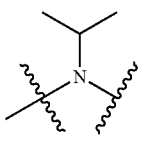 [SMILES: *N(*)C(C)C] | (SO$_2$) |
| 324 | 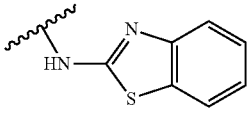 [SMILES: *Nc1nc2ccccc2s1] | 1 | 1 | CH | =CH—CH=CH— | 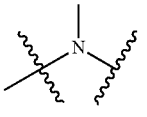 [SMILES: *N(*)C] | (SO$_2$) |
| 325 | 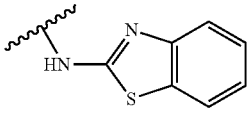 [SMILES: *Nc1nc2ccccc2s1] | 1 | 1 | CH | =CH—CH=CH— | 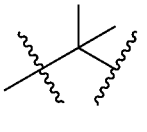 [SMILES: *C(*)(C)C] | (SO$_2$) |
| 326 | 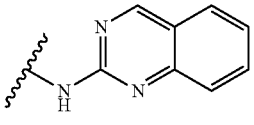 [SMILES: *Nc1ncc2ccccc2n1] | 1 | 1 | CH | =CH—CH=N— | 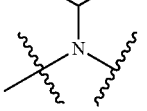 | (SO$_2$) |
| 327 | 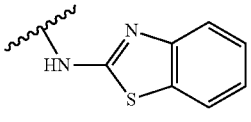 [SMILES: *Nc1nc2ccccc2s1] | 1 | 1 | CH | =CH—CH=N— | 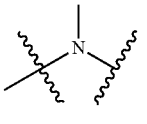 [SMILES: *N(*)C] | (SO$_2$) |
| 328 | 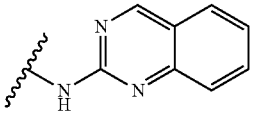 [SMILES: *Nc1ncc2ccccc2n1] | 1 | 1 | CH | =CH—CH=N— | 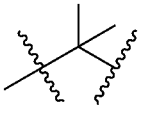 | (SO$_2$) |

And are named as:

| Ex. # | Name |
|---|---|
| 232 | 7-(trans-3-(benzo[d]thiazol-2-ylamino)cyclobutyl)-5,5-dimethyl-5H-pyrrolo[2,3-d]pyrimidin-6(7 H)-one |
| 233 | 3-(trans-3-(benzo[d]thiazol-2-ylamino)cyclobutyl)-1-isopropyl-1H-imidazo[4,5-b]pyradin-2(3 H)-one |
| 234 | 1-(trans-3-(benzo[d]thiazol-2-ylamino)cyclobutyl)-3-isopropyl-1H-imidazo[4,5-b]pyrazin-2(3 H)-one |
| 235 | 5-(trans-3-(benzo[d]thiazol-2-ylamino)cyclobutyl)-7-methyl-7-(trifluoromethyl)-5H-pyrrolo[2,3-b]pyrazin-6(7 H)-one |
| 236 | 3,3-dimethyl-1-(trans-3-(quinolin-2-ylamino)cyclobutyl)-1H-pyrrolo[2,3-b]pyridin-2(3 H)-one |
| 237 | 5,5-dimethyl-7-(trans-3-(quinolin-2-ylamino)cyclobutyl)-5H-pyrrolo[2,3-d]pyrimidin-6(7 H)-one |
| 238 | 1-methyl-3-(trans-3-(quinolin-2-ylamino)cyclobutyl)-1H-imidazo[4,5-b]pyridin-2(3 H)-one |
| 239 | 1-methyl-3-(trans-3-(quinolin-2-ylamino)cyclobutyl)-1H-imdiazo[4,5-b]pyrazin-2(3 H)-one |
| 240 | 1-isopropyl-3-(trans-3- quinolin-2-ylamino)cyclobutyl)-1H-imidazo[4,5-b]pyridin-2(3 H)-one |
| 241 | 1- isopropyl-3-(trans-3-(quinolin-2-ylamino)cyclobutyl)-1H-imidazo[4,5-b]pyrazin-2(3 H)-one |
| 242 | 5,5-dimethyl-7-(trans-3-(quinazolin-2-ylamino)cyclobutyl)-5H-pyrrolo[2,3-d]pyrimidin-6(7 H)-one |
| 243 | 1-methyl-3-(trans-3-(quinazolin-2-ylamino)cyclobutyl)-1H-imidazo[4,5-b]pyridin-2(3 H)-one |
| 244 | 1-methyl-3-(trans-3-(quinazolin-2-ylamino)cyclobutyl)-1H-imidazol[4,5-b]pyrazin-2(3 H)-one |
| 245 | 1-isopropyl-3-(trans-3-(quinazolin-2-ylamino)cyclobutyl)-1H-imidazo[4,5-b]pyridin-2(3 H)-one |
| 246 | 1- isopropyl-3-(trans-3-(quinazolin-2-ylamino)cyclobutyl)-1H-imidazo[4,5-b]pyrazin-2(3 H)-one |
| 247 | 3,3-dimethyl-1-(trans-3-(quinoxalin-2-ylamino)cyclobutyl)-1H-pyrrolo[2,3-b]pyridin-2(3 H)-one |
| 248 | 7,7-dimethyl-5-(trans-3-(quinoxalin-2-ylamino)cyclobutyl)-5H-pyrrolo[2,3-b]pyrazin-6(7 H)-one |
| 249 | 5,5-dimethyl-7-(trans-3-(quinoxlin-2-ylamino)cyclobutyl)-5H-pyrrolo[2,3-d]primidin-6(7 H)-one |
| 250 | 1-methyl-3-(trans-3-(quinoxalin-2-ylamino)cyclobutyl)-1H-imidazo[4,5-b]pyridin-2(3 H)-one |
| 251 | 1-methyl-3-(trans-3-(quinoxalin-2-ylamino)cyclobutyl-1H-imidazo[4,5-b]pyrazin-2(3 H)-one |
| 252 | 1-isopropyl-3-(trans-3-(quinoxalin-2-ylamino)cyclobutyl-1H-imidazo[4,5-b]pyridin-2(3 H)-one |
| 253 | 1-isopropyl-3-(trans-3-(quinoxalin-2-ylamino)cyclobutyl-1H-imidazo[4,5-b]pyrazin-2(3 H)-one |
| 254 | 7-(trans-3-(1,5-napthyridin-2-ylamino)cyclobutyl)-5,5-dimethyl-5H-pyrrolo[2,3-d]pyrimidin-6(7 H)-one |
| 255 | 3-(trans-3-(1,5-napthyridin-2-ylamino)cyclobutyl)-1-methyl-1H-imidazo[4,5-b]pyridin-2(3 H)-one |
| 256 | 3-(trans-3-(1,5-napthyridin-2-ylamino)cyclobutyl)-1-methyl-1H-imidazo[4,5-b]pyrazin-2(3 H)-one |
| 257 | 3-(trans-3-(1,5-napthyridin-2-ylamino)cyclobutyl)-1-isopropyl-1H-imidazo[4,5-b]pyridin-2(3 H)-one |
| 258 | 3-(trans-3-(1,5-napthyridin-2-ylamino)cyclobutyl)-1- isopropyl-1H-imidazo[4,5-b]pyrazin-2(3 H)-one |
| 259 | 1-(trans-3-(1,6-napthyridin-2-ylamino)cyclobutyl)-3,3-dimethyl-1H-pyrrolo[2,3-b]pyridin-2(3 H)-one |
| 260 | 5-(trans-3-(1,6-napthyridin-2-ylamino)cyclobutyl)-7,7-dimethyl-5H-pyrrolo[2,3-b]pyridin-6(7 H)-one |
| 261 | 7-(trans-3-(1,6-napthyridin-2-ylamino)cyclobutyl)-5,5-dimethyl-5H-pyrrolo[2,3-d]pyridin-6(7 H)-one |
| 262 | 3-(trans-3-(1,6-napthyridin-2-ylamino)cyclobutyl)-1-methyl-1H-imidazo[4,5-b]pyridin-2(3 H)-one |
| 263 | 3-(trans-3-(1,6-napthyridin-2-ylamino)cyclobutyl)-1-methyl-1H-imidazo[4,5-b]pyrazin-2(3 H)-one |
| 264 | 3-(trans-3-(1,6-napthyridin-2-ylamino)cyclobutyl)-1-isopropyl-1H-imidazo[4,5-b]pyridin-2(3 H)-one |
| 265 | 3-(trans-3-(1,6-napthyridin-2-ylamino)cyclobutyl)-1- isopropyl-1H-imidazo[4,5-b]pyrazin-2(3 H)-one |
| 266 | 1-(trans-3-(1,7-napthyridin-2-ylamino)cyclobutyl)-3,3-dimethyl-1H-pyrrolo[2,3-b]pyridin-2(3 H)-one |
| 267 | 5-(trans-3-(1,7-napthyridin-2-ylamino)cyclobutyl)-7,7-dimethyl-5H-pyrrolo[2,3-b]pyrazin-6(7 H)-one |
| 268 | 7-(trans-3-(1,7-napthyridin-2-ylamino)cyclobutyl)-5,5-dimethyl-5H-pyrrolo[2,3-d]pyrimidin-6(7 H)-one |
| 269 | 3-(trans-3-(1,7-napthyridin-2-ylamino)cyclobutyl)-1-methyl-1H-imidazo[4,5-b]pyridin-2(3 H)-one |
| 270 | 3-(trans-3-(1,7-napthyridin-2-ylamino)cyclobutyl)-1-methyl-1H-imidazo[4,5-b]pyrazin-2(3 H)-one |
| 271 | 3-(trans-3-(1,7-napthyridin-2-ylamino)cyclobutyl)-1-isopropyl-1H-imidazo[4,5-b]pyridin-2(3 H)-one |
| 272 | 3-(trans-3-(1,7-napthyridin-2-ylamino)cyclobutyl)-1- isopropyl-1H-imidazo[4,5-b]pyrazin-2(3 H)-one |
| 273 | 1-(trans-3-(1,8-napthyridin-2-ylamino)cyclobutyl)-3,3-dimethyl-1H-pyrrolo[2,3-b]pyridin-2(3 H)-one |
| 274 | 7-(trans-3-(1,8-napthyridin-2-ylamino)cyclobutyl)-5,5-dimethyl-5H-pyrrolo[2,3-b]pyridin-6(7 H)-one |
| 275 | 3-(trans-3-(1,8-napthyridin-2-ylamino)cyclobutyl)-1-methyl-1H-imidazo[4,5-b]pyridin-2(3 H)-one |
| 276 | 3-(trans-3-(1,8-napthyridin-2-ylamino)cyclobutyl)-1-methyl-1H-imidazo[4,5-b]pyrazin-2(3 H)-one |
| 277 | 3-(trans-3-(1,8-napthyridin-2-ylamino)cyclobutyl)-1-isopropyl-1H-imidazo[4,5-b]pyridin-2(3 H)-one |
| 278 | 3-(trans-3-(1,8-napthyridin-2-ylamino)cyclobutyl)-1- isopropyl-1H-imidazo[4,5-b]pyrazin-2(3 H)-one |
| 279 | 3,3-dimethyl-1-(trans-3-(thiazolo[4,5-b]pyridin-2-ylamino)cyclobutyl)-1H-pyrrolo[2,3-b]pyridin-2(3 H)-one |
| 280 | 7,7-dimethyl-5-(trans-3-(thiazolo[4,5-b]pyridin-2-ylamino)cyclobutyl)-5H-pyrrolo[2,3-b]pyrazin-6(7 H)-one |
| 281 | 5,5-dimethyl-7-(trans-3-(thiazolo[4,5-b]pyridin-2-ylamino)cyclobutyl)-5H-pyrrolo[2,3-b]pyrimidin-6(7 H)-one |
| 282 | 1-methyl-3-(trans-3-(thiazolo[4,5-b]pyridin-2-ylamino)cyclobutyl)-1H-imidazo[4,5-b]pyridin-2(3 H)-one |
| 283 | 1-methyl-3-(trans-3-(thiazolo[4,5-b]pyridin-2-ylamino)cyclobutyl)-1H-imidazo[4,5-b]pyrazin-2(3 H)-one |
| 284 | 1-isopropyl-3-(trans-3-(thiazolo[4,5-b]pyridin-2-ylamino)cyclobutyl)-1H-imidazo[4,5-b]pyridin-2(3 H)-one |
| 285 | 1- isopropyl-3-(trans-3-(thiazolo[4,5-b]pyridin-2-ylamino)cyclobutyl)-1H-imidazo[4,5-b]pyrazin-2(3 H)-one |
| 286 | 3,3-dimethyl-1-(trans-3-(thiazolo[5,4-b]pyridin-2-ylamino)cyclobutyl)-1H-pyrrolo[2,3-b]pyridin-2(3 H)-one |
| 287 | 5,5-dimethyl-7-(trans-3-(thiazolo[5,4-b]pyridin-2-ylamino)cyclobutyl)-5H-pyrrolo[2,3-b]pyrimidin-6(7 H)-one |
| 288 | 1-methyl-3-(trans-3-(thiazolo[5,4-b]pyridin-2-ylamino)cyclobutyl)-1H-imidazo[4,5-b]pyrazin-2(3 H)-one |
| 289 | 1-isopropyl-3-(trans-3-(thiazolo[5,4-b]pyridin-2-ylamino)cyclobutyl)-1H-imidazo[4,5-b]pyridin-2(3 H)-one |
| 290 | 1- isopropyl-3-(trans-3-(thiazolo[5,4-b]pyridin-2-ylamino)cyclobutyl)-1H-imidazo[4,5-b]pyridin-2(3 H)-one |
| 291 | 8-(trans-4-((1,5-napthyridin-2-yl)amino)cyclohexyl)-5-methyl-5,6-dihydropteridin-7(8 H)-one |
| 292 | 4-(trans-3-(benzo[d]thiazol-2-ylamino)cyclobutyl)-1-methyl-1,2-dihydropyrido[2,3-b]pyrazin-3(4 H)-one |
| 293 | 1-(1-(benzo[d]thiazole-2-carbonyl)azetidin-3-yl)-4-methyl-3,4-dihydropyrazino[2,3-b]pyrazin-2(1 H)-one |
| 294 | 8-(trans-3-(benzo[d]thiazol-2-ylamino)cyclobutyl)-5,6-dimethyl-5,6-dihydropteridin-7(8 H)-one |
| 295 | 4-(3-(benzo[d]thiazol-2-ylamino)cyclopentyl)-1,2-dimethyl-1,2-dihydropyrido[2,3-b]pyrazin-3(4 H)-one |
| 296 | 1-(trans-3-(benzo[d]thiazol-2-ylamino)cyclobutyl)-3,4-dimethyl-3,4-dihydropyrazino[2,3-b]pyrazin-3(1 H)-one |
| 297 | 8-(trans-3-(benzo[d]thiazol-2-ylamino)cyclobutyl)-5,6,6-trimethyl-5,6-dihydropteridin-7(8 H)-one |
| 298 | 4-(1-(5-methoxypyridin-2-yl)piperidin-4-yl)-1,2,2-trimethyl-1,2-dihydropyrido[2,3-b]pyrazin-3(4 H)-one |
| 299 | 1-(trans-3-(benzo[d]thiazol-2-ylamino)cyclobutyl)-3,3,4-trimethyl-3,4-dihydropyrazino[2,3-b]pyrazin-2(1 H)-one |
| 300 | 8-(trans-3-(benzo[d]thiazol-2-ylamino)cyclobutyl)-6,6-dimethyl-6H-pyrimido[5,4-b][1,4]oxazin-7(8 H)-one |
| 301 | 4-(trans)-3-((5-methoxypyridin-2-yl)amino)cyclobutyl)-2,2-dimethyl-2H-pyrido[3,2-b][1,4]oxazin-3(4 H)-one |
| 302 | 2,2-dimethyl-4-(trans-3-(quinolin-2-ylamino)cyclobutyl)-2H-pyrazino[2,3-b][1,4]oxazin-3(4 H)-one |
| 303 | 1-(3-(benzo[d]thiazol-2-ylamino)cyclopentyl)-3,3-dimethyl-1H-pyrrolo[2,3-b]pyridin-2(3 H)-one |
| 304 | 1-(3-(benzo[d]thiazol-2-ylamino)cyclopentyl)-3-cyclopropyl-1H-imidazo[4,5-b]pyrazin-2(3 H)-one |
| 305 | 9-(3-(benzo[d]thiazol-2-ylamino)cyclopentyl)-7-isopropyl-7H-purin-8(9 H)-one |
| 306 | 1-(3-((5-methoxypyridin-2-yl)amino)cyclopentyl)3,3-dimethyl-1H-pyrrolo[2,3-b]pyridin-2(3 H)-one |
| 307 | 1-(3-((5-methoxypyridin-2-yl)amino)cyclopentyl)-3-cyclopropyl-1H-imidazo[4,5-b]pyrazin-2(3 H)-one |

| Ex. # | Name |
|---|---|
| 308 | 9-(3-((5-methoxypyridin-2-yl)amino)cyclopentyl)-7-isopropyl-7H-purin-8(9 H)-one |
| 309 | 1-(3-((5-methoxypyridin-2-yl)amino)cyclohexyl)-3,3-dimethyl-1H-pyrrolo[2,3-b]pyridin-2(3 H)-one |
| 310 | 1-(3((5-methoxypyridin-2-yl)amino)cyclopentyl)-3-cyclopropyl-1H-imidazo[4,5]pyrazin-2(3 H)-one |
| 311 | 9-(3((5methoxypyridin-2-yl)amino)cyclopentyl)-7-isopropyl-7H-purin-8(9 H)-one |
| 312 | 1-(1-(5-methoxypyridin-2-yl)pyrrolidin-3-yl)-3,3-dimethyl-1H-pyrrolo[2,3-b]pyridin-2(3 H)-one |
| 313 | 3,3-dimethyl-1-(1-(5-(trifluormethoxy)pyrimidin-2-yl)azetidin-3-yl-1H-pyrrolo[2,3-b]pyridin-2(3 H)-one |
| 314 | 5-(1-(5-cyclopropoxypyridin-2-yl)piperidin-4-yl)-7,7-dimethyl-5H-pyrrolo[2,3-b]pyrazin-6(7 H)-one |
| 315 | N-(6-(4-(7-methyl-6-oxo-7-(trifluoromethyl)-6,7-dihydro-5H-pyrrolo[2,3-b]pyrazin-5-yl)piperidin-1-yl)pyridine-3-yl)acetamide |
| 316 | 1-methyl-3-(1-quinolin-2-yl)azetidin-3-yl)-1H-imidazo[4,5-b]pyridine-2(3 H)-one |
| 317 | 1-(3-((5-methoxypyridin-2-yl)amino)cyclobutyl)-4,4-dimethyl-1H-pyrido[2,3-d][1,3]oxazin-2(4 H)-one |
| 318 | 4,4-dimethyl-1-(3-(thiazolo[5,4-b]pyridine-2-ylamino)cyclobutyl)-3,4-dihydropteridin-2(1 H)-one |
| 319 | 1-(3-(benzo[d]thiazol-2-ylamino)cyclopentyl)-4,4-dimethyl-1H-pyrimido[4,5-d][1,3]oxazin-2(4 H)-one |
| 320 | 3,4-dimethyl-1-(3-(quinolin-2-ylamino)cyclopentyl)-3,4-dihydropteridin-2(1 H)-one |
| 321 | N-(6-((4-(4-methyl-2-oxo-2,4-dihydro-1H-pyrazino[2,3-d][1,3]oxazin-1-yl)cyclohexyl)amino)pyridin-3-yl)acetamide |
| 322 | 1-(1-(5-acetylpyridin-2-yl)piperidin-4-yl)-4-methyl-1H-pyrazino[2,3-d][1,3]oxazin-2(4 H)-one |
| 323 | 3-(trans-3-(benzo[d]thiazol-2-ylamino)cyclobutyl)-1-isopropyl-1,3-dihydro-[1,2,5]thiadiazolo[3,4-b]pyridine 2,2dioxide |
| 324 | 3-(trans-3-(benzo[d]thiazol-2-ylamino)cyclobutyl)-1-methyl-1,3-dihydro-[1,2,5]thiadiazolo[3,4-b]pyridine 2,2dioxide |
| 325 | 1-(trans-3-(benzo[d]thiazol-2-ylamino)cyclobutyl)-3,3-dimethyl-1,3-dihydroisothiazolo[3,4-b]pyridine 2,2dioxide |
| 326 | 1-isopropyl-3-((trans)-3-(quinazolin-2-ylamino)cyclobutyl)-1,3-dihydro-[1,2,5]thiadiazolo[3,4-b]pyrazine 2,2dioxide |
| 327 | 1-(trans-3-(benzo[dthiazol-2-ylamino)cyclobutyl)-3-methyl-1,3-dihydro[1,2,5]thiadiazolo[3,4-b]pyrazine 2,2dioxide |
| 328 | 3,3-dimethyl-1-(trans-3-(quinazolin-2-ylamino)cyclobutyl)-1,3-dihydroisothiazolo[3,4-b]pyridine 2,2dioxide |

BIOLOGICAL EXAMPLES

Example A

MPDE10A7 Enzyme Activity and Inhibition

Enzyme Activity. An IMAP TR-FRET assay was used to analyze the enzyme activity (Molecular Devices Corp., Sunnyvale Calif.). 10 µL of serial diluted PDE10A (BPS Bioscience, San Diego, Calif.) or tissue homogenate was incubated with equal volumes of diluted fluorescein labeled cAMP or cGMP for 90 min in 384-well Polypropylene assay plates (Greiner, Monroe, N.C.) at room temperature. After incubation, the reaction was stopped by adding 55 µL of diluted binding reagents and was incubated for 4 hours to overnight at room temperature. The plates were read on an Envision (Perkin Elmer, Waltham, Mass.) for time resolved fluorescence resonance energy transfer. The data were analyzed with Genedata Screener® (Lexington, Mass.).

Enzyme Inhibition. To check the inhibition profile, 0.2 µL of serial diluted compounds were incubated with 10 µL of diluted PDE10 enzyme (BPS Bioscience, San Diego, Calif.) or tissue homogenate in a 384-well Polypropylene assay plate (Greiner, Monroe, N.C.) for 60 min at room temperature. After incubation, 10 µL of diluted fluorescein labeled cAMP or cGMP substrate were added and incubated for 90 min at room temperature. The reaction was stopped by adding 55 µL of diluted binding reagents and plates were read on an Envision (Perkin Elmer, Waltham, Mass.) for time resolved fluorescence resonance energy transfer. The data were analyzed with Genedata Screener® (Lexington, Mass.).

Example B

Apomorphine Induced Deficits in Prepulse Inhibition of the Startle Response in Rats, an In Vivo Test for Antipsychotic Activity The thought disorders that are characteristic of schizophrenia may result from an inability to filter, or gate, sensorimotor information. The ability to gate sensorimotor information can be tested in many animals as well as in humans. A test that is commonly used is the reversal of apomorphine-induced deficits in the prepulse inhibition of the startle response. The startle response is a reflex to a sudden intense stimulus such as a burst of noise. In this example, rats can be exposed to a sudden burst of noise, at a level of 120 db for 40 msec, e.g., the reflex activity of the rats can be measured. The reflex of the rats to the burst of noise may be attenuated by preceding the startle stimulus with a stimulus of lower intensity, at 3 db to 12 db above background (65 db), which attenuates the startle reflex by 20% to 80%.

The prepulse inhibition of the startle reflex, described above, may be attenuated by drugs that affect receptor signaling pathways in the CNS. One commonly used drug is the dopamine receptor agonist apomorphine. Administration of apomorphine reduces the inhibition of the startle reflex produced by the prepulse. Antipsychotic drugs such as haloperidol prevents apomorphine from reducing the prepulse inhibition of the startle reflex. This assay can be used to test the antipsychotic efficacy of PDE10 inhibitors, as they reduce the apomorphine-induced deficit in the prepulse inhibition of startle.

Example C

Conditioned Avoidance Responding (CAR) in Rats, an In Vivo Test for Antipsychotic Activity Conditioned avoidance responding (CAR) occurs, for instance, when an animal learns that a tone and light predict the onset of a mild foot shock. The subject learns that when the tone and light are on, it must leave the chamber and enter a safe area. All known antipsychotic drugs reduce this avoidance response at doses which do not cause sedation. Examining the ability of test compounds to suppress the conditioned avoidance has been widely used for close to fifty years to screen for drugs with useful antipsychotic properties.

In this example, an animal can be placed in a two-chambered shuttle box and presented with a neutral conditioned stimulus (CS) consisting of a light and tone, followed by an aversive unconditioned stimulus (US) consisting of a mild foot shock through a floor grid in the shuttle box chamber. The animal can be free to escape the US by running from one chamber to the other, where the grid is not electrified. After several presentations of the CS-US pair, the animal typically learns to leave the chamber during the presentation of the CS and avoid the US altogether. Animals treated with clinically-relevant doses of antipsychotic drugs have a suppression of their rate of avoidances in the presence of the CS even though their escape response to the shock itself is unaffected.

Specifically, conditioned avoidance training can be conducted using a shuttle box (Med Associates, St. Albans, Vt.). The shuttle box is typically divided into 2 equal compartments that each contain a light source, a speaker that emits an 85 dB tone when activated and an electrified grid that can deliver a scrambled foot shock. Sessions can consist of trials per day (intertrial interval of 25-40 sec) during which a 10 sec illumination and a concurrent 10 sec tone signals the subsequent delivery of a 0.5 mA shock applied for a maximum of 10 sec. Active avoidance, defined as the crossing into the opposite compartment during the 10 sec conditioning stimuli (light and tone) prevents the delivery of the shock. Crossing over to the other compartment after the delivery of the shock terminates shock delivery and may be recorded as an escape response. If an animal does not leave the conditioning chamber during the delivery of the shock it is recorded as an escape failure. Training can be continued daily until the avoidance of 16 or more shocks out of 20 trials (80% avoidance) on 2 consecutive days is achieved. After this criterion is reached the rats may be given one day of pharmacological testing. On test day, rats can be randomly assigned to experimental groups, weighed and injected intraperitoneally (i.p.) (1 cc tuberculin syringe, 26⅜ gauge needle) or per os (p.o.) (18 gauge feeding needle) with either control or compound solutions. Compounds can be injected at 1.0 ml/kg for i.p. and 10 mL/kg for p.o. administration. Compounds can be administered either acutely or chronically. For testing, each rat may be placed in the shuttle box, and given 20 trials with the same parameters as described above for training trials. The number of avoidances, escapes, and escape failures can be recorded.

Example D

PCP-Induced Hyperactivity (PCP-LMA)

Equipment Used: 4×8 home cage photobeam activity system (PAS) frame from San Diego Instruments. Open PAS program and prepare an experimental session using the following variables:
Multiphase Experiment
  300 sec/interval (5 min)
  12 intervals (1 h)
  Individual on screen switches.
  Start recording after first beam break.
  End session after end of interval.
  Cage Preparation: Techniplast™ rat cage with filter top, but no wire lid. Place ~400 mL bedding and one food pellet in cage and place 250 mL techniplast water bottle in holder on filter top. Place the prepped cage in the PAS frame. Make sure bedding or pellet doesn't block the photobeams.
  Animal preparation: Mark rats and record their weights. Bring rats to testing room.
Phase I: Habituation
  Start the experiment session. Place the rat in the enclosure. The computer should start recording when it detects the rat breaking the beam. The computer will record for 1 h. During the habituation phase, prepare risperidone (positive control): Measure out risperidone, calculate final volume at 1 mg/mL concentration and add 1% glacial acetic acid of the final volume to dissolve risperidone. When risperidone is dissolved, add saline to final volume to make a concentration of 1 mg/mL. Fill syringes (3 mL syringes with 23g ½ needle) with solution of compound of Formula (I) (5 mL/kg) or RISPERIDONE® (1 mL syringe with 23g ½ needle) control (1 mL/kg) s.c.
Phase II: Compound Pre-Treatment
  Make sure Phase I has ended. Remove rat from enclosure, start the next phase using on-screen individual switch, administer compound p.o or i.p. and control s.c. and place rat back in the enclosure. The computer should start recording when it detects the rat breaking the beam. The computer will record for 1 h.
  During phase II, prepare PCP: Dissolve PCP in saline to a concentration of 5 mg/mL.
  Fill syringes (1 mL syringes with 26g ⅜ needle) with PCP solution (1 mL/kg).
Phase III: PCP Administration.
  Make sure phase II is ended. Remove rat from enclosure, start the next phase using on-screen individual switch, administer PCP s.c. and place rat back in the enclosure. The computer will record for 1 h.
  Clean-up: End-session to terminate experiment and so that computer will compile data. Export raw data to excel file for data analysis. Euthanize rats and take necessary tissue/sample for PK.
  Data Generation: Export raw data to excel file for data analysis. Total time of movement is recorded as the number of photobeam breaks by the computer. Total time of movement (seconds) is combined into 5 minute bins and averaged for each treatment group for an N of 7-10 animals. Data are analyzed for statistical significance using a two-way ANOVA followed by a Bonferroni's post-hoc test for multiple comparisons.
  $IC_{50}$ curves were generated from the raw data collected from the TopCount and fitted with a four-parameter logistic equation using in-house data analysis tool, Activity Base.
  In approximate $IC_{50}$ value of a representative number of compounds of Formula (I) in the above assay of Biological Example 1 is provided in the table 10 below.

| Ex. # | $IC_{50}$ (nM) |
|---|---|
| 1 | 0.113 |
| 2 | 0.373 |
| 3 | 0.622 |
| 4 | 0.67 |
| 5 | 0.836 |
| 6 | 0.944 |
| 7 | 1.41 |
| 8 | 1.68 |
| 9 | 3.37 |
| 10 | 4.82 |
| 11 | 5.53 |
| 12 | 6.9 |
| 13 | 7.94 |
| 14 | 14.2 |
| 15 | 19.8 |
| 16 | 23.7 |
| 17 | 28.4 |
| 18 | 28.4 |
| 19 | 35.7 |
| 20 | 68 |
| 21 | 88.4 |
| 22 | 178 |
| 23 | 440 |
| 24 | 487 |
| 25 | 735 |
| 26 | 3630 |
| 27 | 11 |
| 28 | 77.9 |
| 29 | 76.7 |
| 30 | 0.0125 |
| 31 | 0.0151 |
| 32 | 0.0402 |
| 33 | 0.0768 |
| 34 | 0.107 |
| 35 | 0.115 |
| 36 | 0.134 |
| 37 | 0.14 |
| 38 | 0.166 |
| 39 | 0.212 |
| 40 | 0.263 |
| 41 | 0.329 |
| 42 | 0.856 |
| 43 | 1.57 |
| 44 | 2.44 |
| 45 | 2.52 |
| 46 | 2.53 |
| 47 | 2.64 |
| 48 | 3.46 |

| Ex. # | IC$_{50}$ (nM) |
|---|---|
| 49 | 3.88 |
| 50 | 4.63 |
| 51 | 4.85 |
| 52 | 5.69 |
| 53 | 5.7 |
| 54 | 6.47 |
| 55 | 7.43 |
| 56 | 8.42 |
| 57 | 11 |
| 58 | 13 |
| 59 | 15.9 |
| 60 | 19.3 |
| 61 | 30.4 |
| 67 | 35.6 |
| 63 | 38.6 |
| 64 | 43.3 |
| 65 | 44.8 |
| 66 | 51.1 |
| 67 | 59 |
| 68 | 158 |
| 69 | 167 |
| 70 | 180 |
| 71 | 244 |
| 72 | 352 |
| 73 | 1.54 |
| 74 | 2.88 |
| 75 | 5.02 |
| 76 | 51.1 |
| 77 | 1.29 |
| 78 | 4.2 |
| 79 | 6.15 |
| 80 | 1.43 |
| 81 | 1.26 |
| 82 | 2.83 |
| 83 | 7.72 |
| 84 | 23.1 |
| 85 | 0.0254 |
| 86 | 0.0655 |
| 87 | 0.0794 |
| 88 | 0.0911 |
| 89 | 0.131 |
| 90 | 0.388 |
| 91 | 0.469 |
| 92 | 0.664 |
| 93 | 0.878 |
| 94 | 0.91 |
| 95 | 0.971 |
| 96 | 1.09 |
| 97 | 3.03 |
| 98 | 4.82 |
| 99 | 7.7 |
| 100 | 10.3 |
| 101 | 17.9 |
| 102 | 25.6 |
| 103 | 26.6 |
| 104 | 31.4 |
| 105 | 35.5 |
| 106 | 43.1 |
| 107 | 152 |
| 108 | 266 |
| 109 | 339 |
| 110 | 461 |
| 111 | 1770 |
| 112 | >10.0 |
| 113 | 77.1 |
| 114 | 0.152 |
| 115 | 1.7 |
| 116 | 3.38 |
| 117 | 3.26 |
| 118 | 1.69 |
| 119 | 8.85 |
| 120 | 0.315 |
| 121 | 0.049 |
| 122 | 1.13 |
| 123 | 2.24 |
| 124 | 2.64 |
| 125 | 3.79 |
| 126 | 0.13 |
| 127 | 4.77 |
| 128 | 23.0 |
| 129 | 1.13 |
| 130 | 2.84 |
| 131 | 1.35 |
| 132 | 1.69 |
| 133 | 0.505 |
| 134 | 1.04 |
| 135 | 0.002 |
| 136 | 0.228 |
| 137 | 0.009 |
| 138 | 4.74 |
| 139 | 157 |
| 140 | 656 |
| 141 | 295 |
| 142 | 1.31 |
| 143 | 0.947 |
| 144 | 1.12 |
| 145 | 0.305 |
| 146 | 3.32 |
| 147 | 0.0406 |
| 148 | 193 |
| 149 | 8480 |
| 150 | 0.906 |
| 151 | 2490 |
| 152 | 9040 |
| 153 | 0.255 |
| 154 | 0.136 |
| 155 | 1.67 |
| 156 | 9.08 |
| 157 | 4.45 |
| 158 | 0.189 |
| 159 | 2.73 |
| 160 | 90.5 |
| 161 | 2.73 |
| 162 | 6.77 |
| 163 | 0.459 |
| 164 | 0.921 |
| 165 | 38.5 |
| 166 | 1120 |
| 167 | 98.4 |
| 168 | 0.116 |
| 169 | 0.416 |
| 170 | 2.71 |
| 171 | 4.16 |
| 172 | 2.15 |
| 173 | 1.49 |
| 174 | 0.896 |
| 175 | 18.4 |
| 176 | 7.75 |
| 177 | 2.82 |
| 178 | 2.22 |
| 179 | 2.01 |
| 180 | 0.378 |
| 181 | 2.86 |
| 182 | >9750 |
| 138 | 2.62 |
| 184 | 34.7 |
| 185 | 0.839 |
| 186 | 0.669 |
| 187 | 1.06 |
| 188 | 0.127 |
| 189 | 1.99 |
| 190 | 0.695 |
| 191 | 3.46 |
| 192 | 14.8 |
| 193 | 2.1 |
| 194 | 15.1 |
| 195 | 0.938 |
| 196 | 4.2 |
| 197 | 1.77 |
| 198 | 2.36 |
| 199 | 15.1 |
| 200 | 86.3 |
| 201 | 3.48 |
| 202 | 68.8 |

-continued

| Ex. # | IC$_{50}$ (nM) |
|---|---|
| 203 | 109 |
| 204 | 2910 |
| 205 | 13.2 |
| 206 | 7.65 |
| 207 | 2.39 |
| 208 | 0.626 |
| 209 | 0.88 |
| 210 | 0.892 |
| 211 | 0.111 |
| 212 | 0.449 |
| 213 | 1.57 |
| 214 | 2.87 |
| 215 | 0.978 |
| 216 | 16.9 |
| 217 | 38.3 |
| 218 | 1410 |
| 219 | 554 |
| 220 | 2.35 |
| 221 | 2.77 |
| 222 | 7.61 |
| 223 | 18.4 |
| 224 | 57.7 |
| 225 | 10.8 |
| 226 | 1.2 |
| 227 | 1.87 |
| 228 | 246 |
| 229 | 10.1 |
| 230 | 0.393 |
| 231 | 31.5 |

The foregoing invention has been described in some detail by way of illustration and example, for purposes of clarity and understanding. Those skilled in the art understand that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited herein are hereby incorporated by reference in their entirety for all purposes to the same extent as if each individual patent, patent application or publication were so individually denoted.

What is claimed is:

1. A compound of Formula (I):

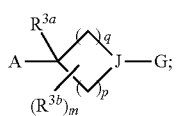

(I)

or a pharmaceutically-acceptable salt, tautomer, or stereoisomer thereof, wherein:

each p and q is independently 1; wherein the sum of p and q is 2;

m is 0, 1, 2, 3, or 4;

A is a 9- to 10-membered heterocyclic ring having the formula:

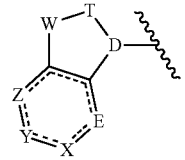

wherein the group —W-T-D< is selected from the group consisting of: —N=CR$^5$—N<; NR$^7$—N=C<; —NR$^7$—(C=O)—N<; NR$^7$—CR$^6$R$^7$—(C=O)—N<; —NR$^7$—(SO$_2$)—N<; —CR$^5$=CR$^5$—N<; —CR$^8$=N—N<; —CR$^6$R$^7$—(C=O)—N<; —CR$^6$R$^7$—NR$^7$—(C=O)—N<; —CR$^6$R$^7$—O—(C=O)—N<; —CR$^6$R$^7$—(SO$_2$)—N<; —O—(C=O)—N<; and —O—CR$^6$R$^7$—(C=O)—N<;

J is CR$^{3c}$; wherein each E, X, Y, and Z is independently N or CR$^4$; wherein 1, 2, or 3 of E, X, Y, and Z are N;

G is R$^1$, —NR$^1$R$^2$; —NH(C=O)R$^1$; —OR$^1$, —(C=O)R$^1$; or —CHR$^1$R$^2$;

R$^1$ is a carbon-linked or nitrogen-linked saturated, partially-saturated or unsaturated 9- or 10-membered bicyclic ring, wherein each said ring contains 0, 1, 2, 3, or 4 N atoms and 0, 1, or 2 O or S atoms; wherein each R$^1$ is independently substituted by 0, 1, 2 or 3 R$^9$ groups;

R$^2$ is independently H, OH, C$_{1-4}$alk, a carbon-linked or nitrogen-linked saturated, partially-saturated, or unsaturated 5- or 6-membered monocyclic ring, wherein each said ring contains 0, 1, 2, 3, or 4 N atoms and 0, 1, or 2 O or S atoms; wherein each R$^2$ C$_{1-4}$alk or monocyclic ring is independently substituted by 0, 1, 2 or 3 R$^9$ groups;

each R$^{3a}$ and R$^{3c}$ is independently H, F, OH, C$_{1-4}$alk, or C$_{1-4}$haloalk;

R$^{3b}$ is independently F, Cl, Br, CN, OH, OC$_{1-4}$alk, C$_{1-4}$alk, C$_{1-4}$haloalk, or oxo;

R$^4$ is halo, R$^{4a}$, —SR$^{4a}$, —OR$^{4a}$, —NHR$^{4a}$, or —N(C$_{1-4}$alk)R$^{4a}$, wherein —R$^{4a}$ is H, C$_{1-4}$alk, a saturated, partially-saturated or unsaturated 3-, 4-, 5- or 6-membered monocyclic ring, wherein each said ring contains 0, 1, 2, 3, or 4 N atoms and 0, 1, or 2 O or S atoms; wherein each R$^4$ C$_{1-4}$alk or monocyclic ring is independently substituted by 0, 1, 2 or 3 R$^9$ groups;

each R$^5$ is independently R$^{5a}$, —OR$^{5b}$, —NHR$^{5a}$, or —N(C$_{1-4}$alk)R$^{5a}$, wherein R$^{5a}$ is H or C$_{1-4}$alk; R$^{5b}$ is C$_{1-4}$alk, a saturated, partially-saturated or unsaturated 3-, 4-, 5- or 6-membered monocyclic ring, wherein each said ring contains 0, 1, 2, 3, or 4 N atoms and 0, 1, or 2 O or S atoms; wherein each R$^5$ C$_{1-4}$alk or monocyclic ring is independently substituted by 0, 1, 2 or 3 R$^9$ groups;

each R$^6$ and R$^7$ is independently H, halo, OH, C$_{1-4}$alk, OC$_{1-4}$alk, a saturated, partially-saturated or unsaturated 3-, 4-, 5- or 6-membered monocyclic ring, wherein each said ring contains 0, 1, 2, 3, or 4 N atoms and 0, 1, or 2 O or S atoms; wherein each R$^6$ and R$^7$ C$_{1-4}$alk or monocyclic ring is independently substituted by 0, 1, 2 or 3 R$^9$ groups;

or R$^6$ and R$^7$ may optionally form a saturated or partially-saturated 3-, 4-, 5- or 6-membered monocyclic ring, wherein each said ring contains 0, 1, 2, 3, or 4 N atoms and 0, 1, or 2 O or S atoms; wherein said monocyclic ring is independently substituted by 0, 1, 2 or 3 R$^9$ groups;

R$^8$ is R$^{8a}$, —O—R$^{8a}$, —NHR$^{8a}$, or —N(C$_{1-4}$alk)R$^{8a}$, wherein R$^{8a}$ is H, C$_{1-4}$alk, a saturated, partially-saturated or unsaturated 3-, 4-, 5- or 6-membered monocyclic ring, wherein each said ring contains 0, 1, 2, 3, or 4

N atoms and 0, 1, or 2 O or S atoms; wherein each $R^8$ $C_{1-4}$alk or monocyclic ring is independently substituted by 0, 1, 2 or 3 $R^9$ groups;

$R^9$ is independently F, Cl, Br, $C_{1-6}$alk, $C_{1-4}$haloalk, —$OR^a$, $OR^c$, —$OC_{1-4}$haloalk, CN, —C(=O)$R^b$, —C(=O)$R^c$, —C(=O)$OR^a$, —C(=O)$NR^aR^a$, —C(=O)$NR^aR^c$, —C(=$NR^a$)$NR^aR^a$, —OC(=O)$R^b$, —OC(=O)$NR^aR^a$, —O$C_{1-6}$alk$NR^aR^a$, —O$C_{1-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{1-6}$alk$NR^aR^a$, —$NR^aC_{1-6}$alk$OR^a$, —$C_{1-6}$alk$NR^aR^a$, —$C_{1-6}$alk$OR^a$, —$C_{1-6}$ alk$N(R^a)C$(=O)$R^b$, —$C_{1-6}$ alkOC(=O)$R^b$, —$C_{1-6}$alkC(=O)$NR^aR^a$, —$C_{1-6}$ alkC(=O)$OR^a$, or oxo;

$R^{10}$ is halo, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —O$C_{1-6}$alk$NR^aR^a$, —O$C_{1-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{1-6}$alk$NR^aR^a$, —$NR^aC_{1-6}$alk$OR^a$, —$C_{1-6}$alk$NR^aR^a$, —$C_{1-6}$alk$OR^a$, —$C_{1-6}$alk$N(R^a)C$(=O)$R^b$, —$C_{1-6}$ alkOC(=O)$R^b$, —$C_{1-6}$alkC(=O))$NR^aR^a$, —$C_{1-6}$alkC(=O)$OR^a$, or oxo;

$R^a$ is independently H or $R^b$;

$R^b$ is independently phenyl, benzyl, or $C_{1-6}$alk, wherein said phenyl, benzyl, and $C_{1-6}$alk are substituted by 0, 1, 2 or 3 substituents which are $C_{1-4}$alk, $C_{1-3}$haloalk, —OH, —$OC_{1-4}$alk, —$NH_2$, —$NHC_{1-4}$alk, —OC(=O)$C_{1-4}$alk, or —N($C_{1-4}$alk)$C_{1-4}$alk; and $R^c$ is independently a carbon-linked or nitrogen-linked saturated, partially-saturated or unsaturated 3-, 4-, 5-, 6-, or 7-membered monocyclic ring or a saturated, partially-saturated or unsaturated 6-, 7-, 8-, 9-, 10-, 11-, or 12-membered bicyclic ring, said ring contains 0, 1, 2, 3, or 4 N atoms and 0, 1, or 2 atoms which are O or S; $R^c$ is independently substituted by 0, 1, 2 or 3 $R^{10}$ groups.

2. The compound as in claim 1 wherein the group

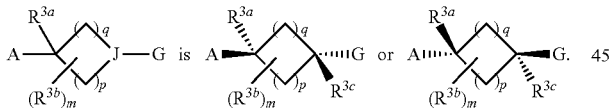

3. The compound as in claim 1 wherein E, X, Y, and Z is independently N or $CR^4$; wherein 1 or 2 of E, X, Y, and Z are N; selected from the group consisting of

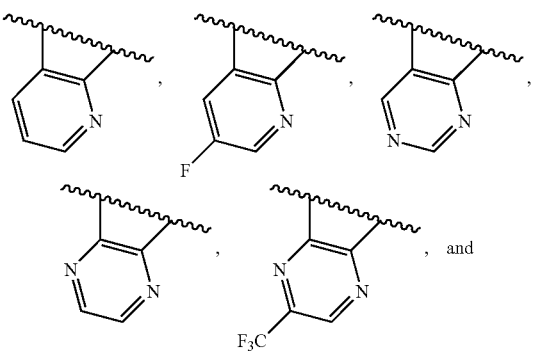

, and

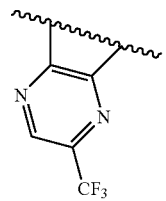

4. The compound as in claim 1 wherein the group —W-T-D< is selected from the group consisting of —N=$CR^5$—N<; $NR^7$—N=C<; $NR^7$—(C=O)—N<; $NR^7$—$CR^6R^7$—(C=O)—N<; and —$NR^7$—(SO$_2$)—N<.

5. The compound as in claim 1 wherein the group —W-T-D< is —$NR^7$—(C=O)—N<.

6. The compound as in claim 5 wherein $R^7$ is H, $C_{1-4}$alk or a saturated 3-, 4-, 5- or 6-membered monocyclic ring; or unsaturated 5- or 6-membered monocyclic ring; wherein each said ring contains 0, 1, or 2 N atoms and 0, 1, or 2 O or S atoms; wherein said $R^7$ $C_{1-4}$alk or monocyclic ring is independently substituted by 0, 1, 2 or 3 $R^9$ groups.

7. The compound as in claim 1 wherein the sum of p and q is 2.

8. The compound as in claim 1 wherein $R^1$ is a saturated, partially-saturated or unsaturated 9- or 10-membered bicyclic ring wherein each $R^1$ is selected from

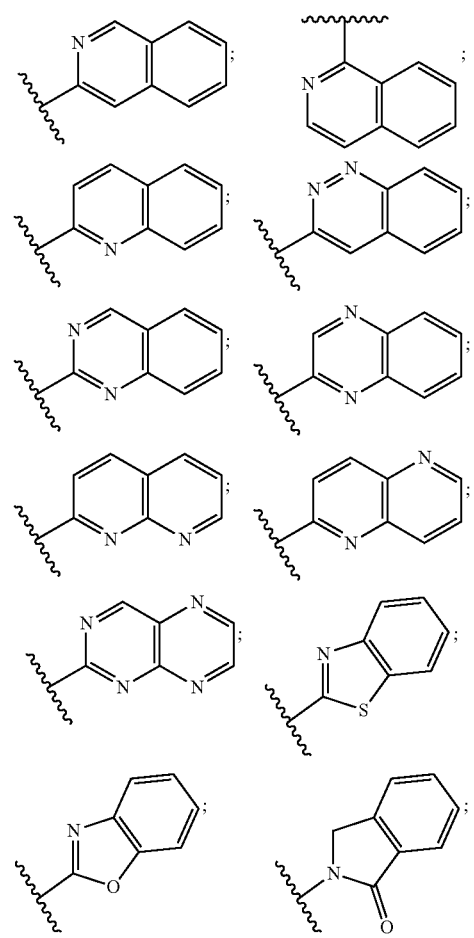

-continued

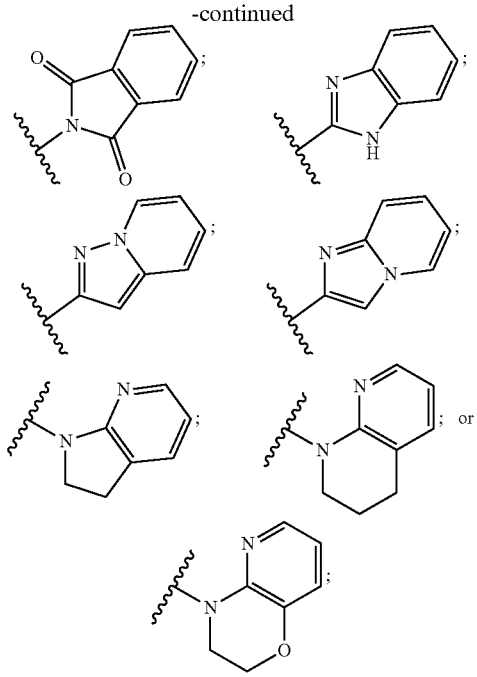

and wherein each R¹ is independently substituted by 0, 1, 2 or 3 R⁹ groups.

9. The compound as in claim 1 wherein R¹ is unsaturated 9- or 10-membered bicyclic ring, wherein each said ring contains 0, 1, 2, 3, or 4 N atoms and 0, 1, or 2 O or S atoms; wherein each R¹ is independently substituted by 0, 1, 2 or 3 R⁹ groups.

10. The compound as in claim 1 wherein R¹ is pyridothiazolyl, pyridooxazolyl, pyridimidazolyl, pyrazimidazolyl, pyrimidimidazolyl, benzimidazolyl, benzoxazolyl, benzthiazolyl, quinolinyl, isoquinolinyl, quinazolinyl, quinaxolinyl, naphthyridinyl, pyridimidazolyl, pyridopyrazolyl, or thiazolo[5,4-b]pyridinyl.

11. The compound as in claim 1 wherein R¹ is benzoxazolyl, quinazolinyl, quinolinyl, benzimidazolyl, benzthiazolyl, 1,5-naphthyridinyl, 1,6-naphthyridinyl, 1,7-naphthyridinyl, or 1,8-naphthyridinyl.

12. The compound as in claim 1 wherein R² is H or methyl.

13. The compound as in claim 1 wherein m is 0.

14. The compound as in claim 1 wherein each R³ᵃ and R³ᶜ is H and m is 0.

15. The compound as in claim 1 wherein J is —CH or —CCH₃; and G is R¹ or —NR¹R².

16. A pharmaceutical composition comprising a compound, or a pharmaceutically-acceptable salt, tautomer, or stereoisomer thereof, as in claim 1 and a pharmaceutically-acceptable excipient.

17. The compound, or a pharmaceutically-acceptable salt thereof, as in claim 1, selected from the group consisting of:
N-(trans-3-(2-ethyl-3H-imidazo[4,5-b]pyridin-3-yl)cyclobutyl)benzo[d]thiazol-2-amine;
N-(trans-3-(2-cyclopropyl-3H-imidazo[4,5-b]pyridin-3-yl)cyclobutyl)benzo[d]thiazol-2-amine;
N-(Trans-3-(2-cyclopropyl-3h-imidazo[4,5-b]pyridin-3-yl)cyclobutyl)-1,5-naphthyridin-2-amine;
N-(Trans-3-(2-cyclopropyl-3h-imidazo[4,5-b]pyridin-3-yl)cyclobutyl)thiazolo[5,4-b]pyridin -2-amine;
N-(Trans-3-(2-methoxy-3H-imidazo[4,5-b]pyridin-3-yl)cyclobutyl)benzo[d]thiazol-2-amine;
N-(Trans-3-(2-cyclopropyl-3h-imidazo[4,5-b]pyridin-3-yl)cyclobutyl)quinolin-2-amine;
N-(Trans-3-(2-cyclopropyl-3H-imidazo[4,5-b]pyridin-3-yl)cyclobutyl)-6-fluoroquinolin-2-amine;
N-(Trans-3-(2-cyclopropyl-3H-imidazo[4,5-b]pyridin-3-yl)cyclobutyl)quinazolin-2-amine;
N-(Cis-3-(2-methoxy-3H-imidazo[4,5-b]pyridin-3-yl)cyclobutyl)benzo[d]thiazol-2-amine;
N-(trans-3-(2-(trifluoromethyl)-3H-imidazo[4,5-b]pyridin-3-yl)cyclobutyl)benzo[d]thiazol-2-amine;
N-(Trans-3-(2-cyclopropyl-3h-imidazo[4,5-b]pyridin-3-yl)cyclobutyl)-1,8-naphthyridin-2-amine;
N-(Trans-3-(2-(trifluoromethyl)-3H-imidazo[4,5-b]pyridin-3-yl)cyclobutyl)quinazolin-2-amine;
N-(trans-3-(8-cyclopropyl-9H-purin-9-yl)cyclobutyl) quinazolin-2-amine;
N-(trans-3-(3H-imidazo[4,5-b]pyridin-3-yl)cyclobutyl) benzo[d]thiazol-2-amine;
N-(Trans-3-(2-cyclopropyl-3H-imidazo[4,5-b]pyridin-3-yl)cyclobutyl)benzo[d]oxazol-2-amine;
N-(Trans-3-(2-cyclopropyl-3h-imidazo[4,5-b]pyridin-3-yl)cyclobutyl)-1,7-naphthyridin-2-amine;
7-Chloro-N-(trans-3-(2-(tetrahydro-2H-pyran-4-yl)-3H-imidazo[4,5-b]pyridin-3-yl)cyclobutyl)quinoxalin-2-amine;
N-(Trans-3-(2-cyclopropyl-3H-imidazo[4,5-b]pyridin-3-yl)cyclobutyl)-1,7-naphthyridin-2-amine;
7-Chloro-N-(trans-3-(2-methoxy-3H-imidazo[4,5-b]pyridin-3-yl)cyclobutyl)quinoxalin-2-amine;
7-Chloro-N-(trans-3-(2-cyclopropyl-3H-imidazo[4,5-b]pyridin-3-yl)cyclobutyl)quinolin-2-amine;
N-(Trans-3-(6-chloro-9H-purin-9-yl)cyclobutyl)quinazolin-2-amine;
N-(Trans-3-(3H-imidazo[4,5-b]pyridin-3-yl)cyclobutyl) quinazolin -2-amine;
9-(Trans-3-(quinazolin-2-ylamino)cyclobutyl)-8-(trifluoromethyl)-9H-purin-6-ol;
N-(Trans-3-(6-morpholino-9H-purin-9-yl)cyclobutyl) quinazolin-2-amine;
Methyl 4-(9-(trans-3-(quinazolin-2-ylamino)cyclobutyl)-8-(trifluoromethyl)-9H-purin-6-yl)benzoate;
Methyl 4-(9-(trans-3-(quinazolin-2-ylamino)cyclobutyl)-9H -purin-6-yl)benzoate;
N-(Trans-3-(2-cyclopropyl-3H-imidazo[4,5-b]pyridin-3-yl)cyclobutyl)thiazolo[4,5-b]pyridin-2-amine;
7-Chloro-N-(trans-3-(2-methoxy-3H-imidazo[4,5-b]pyridin-3-yl)cyclobutyl)quinazolin-2-amine;
1-(trans-3-(benzo[d]thiazol-2-ylamino)cyclobutyl)-3,3-dimethyl-1H-pyrrolo[2,3-b]pyridin-2(3H)-one;
1'-(Trans-3-(benzo[d]thiazol-2-ylamino)cyclobutyl)spiro [cyclopropane-1,3'-pyrrolo[2,3-b]pyridin]-2'(1'H)-one;
1-(trans-3-((6-fluorobenzo[d]thiazol-2-yl)amino)cyclobutyl)-3,3-dimethyl-1H-pyrrolo[2,3-b]pyridin-2 (3H)-one;
1'-(trans-3-(1,3-benzothiazol-2-ylamino)cyclobutyl)-5'-fluorospiro[cyclopropane-1,3'-pyrrolo[2,3-b]pyridin]-2'(1'H)-one;
5-(trans-3-(benzo[d]thiazol-2-ylamino)cyclobutyl)-7,7-dimethyl-5H-pyrrolo[2,3-b]pyrazin-6(7H)-one;
1'-(trans-3-(benzo[d]thiazol-2-ylamino)cyclobutyl)spiro [cyclobutane-1,3'-pyrrolo[2,3-b]pyridin]-2'(1'H)-one;
1'-(Trans-3-(benzo[d]thiazol-2-ylamino)cyclobutyl)spiro [cyclopentane-1,3'-pyrrolo[2,3-b]pyridin]-2'(1'H)-one;
1'-(Trans-3-(benzo[d]thiazol-2-ylamino)cyclobutyl)-2,3, 5,6-tetrahydrospiro[pyran-4,3'-pyrrolo[2,3-b]pyridin]-2'(1'H)-one;
1-(trans-3-(benzo[d]thiazol-2-ylamino)cyclobutyl)-1H-pyrrolo[2,3-b]pyridin-2(3H)-one;
1-(Cis-3-(benzo[d]thiazol-2-ylamino)cyclobutyl)-3,3-dimethyl-1H pyrrolo[2,3-b]pyridin-2(3H)-one;
3-(trans-3-(benzo[d]thiazol-2-ylamino)cyclobutyl)-1-cyclopropyl-1H-imidazo[4,5-b]pyridin-2(3H)-one;

3-(trans-3-(benzo[d]thiazol-2-ylamino)cyclobutyl)-6-fluoro-1-methyl-1H-imidazo[4,5-b]pyridin-2(3H)-one;

3-(trans-3-(benzo[d]thiazol-2-ylamino)cyclobutyl)-1-cyclopropyl-6-fluoro-1H-imidazo[4,5-b]pyridin-2(3H)-one;

3-(trans-3-(benzo[d]thiazol-2-ylamino)cyclobutyl)-1-methyl-1H-imidazo[4,5-b]pyridin-2(3H)-one;

3-(trans-3-(benzo[d]thiazol-2-ylamino)cyclobutyl)-1-cyclopentyl-1H-imidazo[4,5-b]pyridin-2(3H)-one;

1-(trans-3-(benzo[d]thiazol-2-ylamino)cyclobutyl)-3-cyclopropyl-1H-imidazo[4,5-b]pyrazin-2(3H)-one;

9-(trans-3-(benzo[d]thiazol-2-ylamino)cyclobutyl)-7-cyclopropyl-7H-purin-8(9H)-one;

3-(trans-3-((6-fluorobenzo[d]thiazol-2-yl)amino)cyclobutyl)-1H-imidazo[4,5-b]pyridin-2(3H)-one;

9-(trans-3-(benzo[d]thiazol-2-ylamino)cyclobutyl)-7-methyl-7H-purin-8(9H)-one;

3-(trans-3-(benzo[d]thiazol-2-ylamino)cyclobutyl)-1H-imidazo[4,5-b]pyridin-2(3H)-one;

1-(trans-3-(benzo[d]thiazol-2-ylamino)cyclobutyl)-3-methyl-1H-imidazo[4,5-b]pyrazin-2(3H)-one;

3-(trans-3-(quinolin-2-ylamino)cyclobutyl)-1H-imidazo[4,5-b]pyridin-2(3H)-one;

9-(trans-3-(benzo[d]thiazol-2-ylamino)cyclobutyl)-7H-purin-8(9H)-one;

3-(trans-3-((4-fluorobenzo[d]thiazol-2-yl)amino)cyclobutyl)-1H-imidazo[4,5-b]pyridin-2(3H)-one;

3-(trans-3-((5-fluorobenzo[d]thiazol-2-yl)amino)cyclobutyl)-1H-imidazo[4,5-b]pyridin-2(3H)-one;

3-(trans-3-(benzo[d]thiazol-2-ylamino)cyclobutyl)oxazolo[4,5-b]pyridin-2(3H)-one;

3-(trans-3-((7-fluoroquinolin-2-yl)amino)cyclobutyl)-1H-imidazo[4,5-b]pyridin-2(3H)-one;

3-(trans-3-(quinazolin-2-ylamino)cyclobutyl)-1H-imidazo[4,5-b]pyridin-2(3H)-one;

3-(cis-3-(benzo[d]thiazol-2-ylamino)cyclobutyl)-1H-imidazo[4,5-b]pyridin-2(3H)-one;

3-(trans-3-((7-methoxyquinolin-2-yl)amino)cyclobutyl)-1H-imidazo[4,5-b]pyridin-2(3H)-one;

3-(cis-3-(benzo[d]thiazol-2-yl(methyl)amino)cyclobutyl)-1-methyl-1H-imidazo[4,5-b]pyridin-2(3H)-one;

3-(trans-3-((7-fluoroquinazolin-2-yl)amino)cyclobutyl)-1H-imidazo[4,5-b]pyridin-2(3H)-one;

N-(trans-3-(3-amino-1H-pyrazolo[3,4-b]pyridin-1-yl)cyclobutyl)benzo[d]thiazol-2-amine;

N-(trans-3-(3-cyclopropyl-1H-pyrazolo[3,4-b]pyridin-1-yl)cyclobutyl)benzo[d]thiazol-2-amine;

N-(trans-3-(3-(trifluoromethyl)-1H-pyrazolo[3,4-b]pyridin-1-yl)cyclobutyl)benzo[d]thiazol-2-amine;

1-(4-((1-(trans-3-(benzo[d]thiazol-2-ylamino)cyclobutyl)-1H-pyrazolo[3,4-b]pyridin-3-yl)amino)piperidin-1-yl)ethanone;

N-(3-(2-methoxy-3H-imidazo[4,5-b]pyridin-3-yl)cyclobutyl)-1,3-benzothiazol-2-amine;

1H-benzimidazol-2-yl(3-(2-methoxy-3H-imidazo[4,5-b]pyridin-3-yl)cyclobutyl)methanol;

N-(cis-3-(2-methoxy-3H-imidazo[4,5-b]pyridin-3-yl)cyclobutyl)-1,3-benzothiazol-2-amine;

N-(trans-3-(2-methoxy-3H-imidazo[4,5-b]pyridin-3-yl)cyclobutyl)-1,3-benzothiazol-2-amine;

N-(trans-3-(2-methoxy-3H-imidazo[4,5-b]pyridin-3-yl)cyclobutyl)-3,4-dihydro-2-quinoxalinamine;

4-(trans-3-(benzo[d]thiazol-2-ylamino)cyclobutyl)-2H-pyrido[3,2-b][1,4]oxazin-3(4H)-one;

7,7-dimethyl-5-(trans-3-(thiazolo[5,4-b]pyridin-2-ylamino)cyclobutyl)-5h-pyrrolo[2,3-b]pyrazin-6(7h)-one;

3-(cis)-3-(benzo[d]thiazol-2-ylamino)cyclobutyl-1-methyl-1H-imidazo[4,5-b]pyridin-2(3H)-one;

3-(trans-3-(benzo[d]oxazol-2-ylamino)cyclobutyl)-1-methyl-1H-imidazo[4,5-b]pyridin-2(3H)-one;

3-(trans-3-((5-fluorobenzo[d]thiazol-2-yl)amino)cyclobutyl)-1-methyl-1H-imidazo[4,5-b]pyridin-2(3H)-one;

1-methyl-3-(trans-3-((1-methyl-1H-benzo[d]imidazol-2-yl)oxy)cyclobutyl)-1H-imidazo[4,5-b]pyridin-2(3H)-one;

1-methyl-3-(trans-3-((1-methyl-1H-benzo[d]imidazol-2-yl)amino)cyclobutyl)-1H-imidazo[4,5-b]pyridin-2(3H)-one;

7-(trans-3-(1,3-benzothiazol-2-ylamino)cyclobutyl)-5,5-dimethyl-5,7-dihydro-6H-pyrrolo[2,3-d]pyrimidin-6-one;

5,5-dimethyl-7-(trans-3-(1,5-naphthyridin-2-ylamino)cyclobutyl)-5,7-dihydro-6H-pyrrolo[2,3-d]pyrimidin-6-one;

3-(trans-3-((6-fluorobenzo[d]thiazol-2-yl)amino)cyclobutyl)-1-methyl-1H-imidazo[4,5-b]pyridin-2(3H)-one;

5-(trans-3-((5-fluorobenzo[d]thiazol-2-yl)amino)cyclobutyl)-7,7-dimethyl-5H-pyrrolo[2,3-b]pyrazin-6(7H)-one;

5-(trans-3-((5-fluoro-1,3-benzothiazol-2-yl)amino)cyclobutyl)-7,7-dimethyl-5,7-dihydro-6H-pyrrolo[2,3-b]pyrazin-6-one;

1-(trans-3-(1,3-benzothiazol-2-ylamino)cyclobutyl)-3-methyl-1,3-dihydro-2H-benzimidazol-2-one;

7-(trans-3-((6-fluoro-1,3-benzothiazol-2-yl)amino)cyclobutyl)-5,5-dimethyl-2-(methylsulfanyl)-5,7-dihydro-6H-pyrrolo[2,3-d]pyrimidin-6-one;

7-(trans-3((6-fluoro-1,3-benzothiazol-2-yl)amino)cyclobutyl)-5,5-dimethyl-5,7-dihydro-6H-pyrrolo[2,3-d]pyrimidin-6-one;

7,7-dimethyl-5-(trans-3-((1-methyl-1H-benzo[d]imidazol-2-yl)amino)cyclobutyl)-5H-pyrrolo[2,3-b]pyrazin-6(7H)-one;

5-(trans-3-((1,8-naphthyridin-2-yl)amino)cyclobutyl)-7,7-dimethyl-5H-pyrrolo[2,3-b]pyrazin-6(7H)-one;

5-(trans-3-((1,5-naphthyridin-2-yl)amino)cyclobutyl)-7,7-dimethyl-5H-pyrrolo[2,3-b]pyrazin-6(7H)-one;

3,3-dimethyl-1-(trans-3-(2-quinazolinylamino)cyclobutyl)-1,3-dihydro-2H-pyrrolo[2,3-b]pyridin-2-one;

1-(trans-3-(1,3-benzoxazol-2-ylamino)cyclobutyl)-3,3-dimethyl-1,3-dihydro-2H-pyrrolo[2,3-b]pyridin-2-one;

5-(trans-3-((5,6-difluoro-1,3-benzothiazol-2-yl)amino)cyclobutyl)-7,7-dimethyl-5,7-dihydro-6H-pyrrolo[2,3-b]pyrazin-6-one;

5-(trans-3-((4,6-difluoro-1,3-benzothiazol-2-yl)amino)cyclobutyl)-7,7-dimethyl-5,7-dihydro-6H-pyrrolo[2,3-b]pyrazin-6-one;

5-(trans-3-((6-methoxy-1,3-benzothiazol-2-yl)amino)cyclobutyl)-7,7-dimethyl-5,7-dihydro-6H-pyrrolo[2,3-b]pyrazin-6-one;

7,7-dimethyl-5-(trans-3-([1,3]thiazolo[5,4-b]pyridin-2-ylamino)cyclobutyl)-5,7-dihydro-6H-pyrrolo[2,3-b]pyrazin-6-one;

1-methyl-3-(trans-3-([1,3]thiazolo[5,4-b]pyridin-2-ylamino)cyclobutyl)-1,3-dihydro-2H-imidazo[4,5-b]pyridin-2-one;

1-cyclopropyl-3-(trans-3-((7-fluoro-2-quinazolinyl)amino)cyclobutyl)-1,3-dihydro-2H-imidazo[4,5-b]pyrazin-2-one;

5-(trans-3-((7-fluoro-2-quinazolinyl)amino)cyclobutyl)-7,7-dimethyl-5,7-dihydro-6H-pyrrolo[2,3-b]pyrazin-6-one;

1-cyclopropyl-3-(trans-3-((6-fluoro-1,3-benzoxazol-2-yl)amino)cyclobutyl)-1,3-dihydro-2H-imidazo[4,5-b]pyrazin-2-one;

5-(trans-3-((6-fluoro-1,3-benzoxazol-2-yl)amino)cyclobutyl)-7,7-dimethyl-5,7-dihydro-6H-pyrrolo[2,3-b]pyrazin-6-one;
1-cyclopropyl-3-(trans-3-([1,3]thiazolo[5,4-b]pyridin-2-ylamino)cyclobutyl)-1,3-dihydro-2H-imidazo[4,5-b]pyrazin-2-one;
1-cyclopropyl-3-(trans-3-((6-fluoro-1,3-benzothiazol-2-yl)amino)cyclobutyl)-1,3-dihydro-2H-imidazo[4,5-b]pyrazin-2-one;
(R)-1-(trans-3-(benzo[d]thiazol-2-ylamino)cyclobutyl)-3-hydroxy-3-methyl-1H-pyrrolo[2,3-b]pyridin-2(3H)-one;
(S)-1-(trans-3-(benzo[d]thiazol-2-ylamino)cyclobutyl)-3-hydroxy-3-methyl-1H-pyrrolo[2,3-b]pyridin-2(3H)-one;
(3R)-1-(trans-3-(1,3-benzothiazol-2-ylamino)cyclobutyl)-3-hydroxy-3-methyl-1,3-dihydro-2H-pyrrolo[2,3-b]pyridin-2-one;
(3s)-1-(trans-3-(1,3-benzothiazol-2-ylamino)cyclobutyl)-3-hydroxy-3-methyl-1,3-dihydro-2H-pyrrolo[2,3-b]pyridin-2-one;
1-cyclopropyl-3-(trans-3-(quinazolin-2-ylamino)cyclobutyl)-1H-imidazo[4,5-b]pyridin-2(3H)-one;
1-cyclopropyl-3-(trans-3-((5-fluorobenzo[d]thiazol-2-yl)amino)cyclobutyl)-1H-imidazo[4,5-b]pyridin-2(3H)-one;
1-cyclopropyl-3-(trans-3-((6-fluorobenzo[d]thiazol-2-yl)amino)cyclobutyl)-1H-imidazo[4,5-b]pyridin-2(3H)-one;
7,7-dimethyl-5-(3-(quinolin-2-ylamino)cyclobutyl)-5H-pyrrolo[2,3-b]pyrazin-6(7H)-one;
7,7-dimethyl-5-(trans-3-(2-quinolinylamino)cyclobutyl)-5,7-dihydro-6H-pyrrolo[2,3-b]pyrazin-6-one;
5-(trans-3-((6-fluoro-2-quinolinyl)amino)cyclobutyl)-7,7-dimethyl-5,7-dihydro-6H-pyrrolo[2,3-b]pyrazin-6-one;
5-(trans-3-((7-fluoro-2-quinolinyl)amino)cyclobutyl)-7,7-dimethyl-5,7-dihydro-6H-pyrrolo[2,3-b]pyrazin-6-one;
5-(trans-3-(1,3-benzothiazol-2-yloxy)cyclobutyl)-7,7-dimethyl-5,7-dihydro-6H-pyrrolo[2,3-b]pyrazin-6-one;
6-fluoro-1-methyl-3-(trans-3-(quinazolin-2-ylamino)cyclobutyl)-1H-imidazo[4,5-b]pyridin-2(3H)-one;
1-(trans-3-(benzo[d]thiazol-2-ylamino)cyclobutyl)-3,3,5-trifluoro-1H-pyrrolo[2,3-b]pyridin-2(3H)-one;
6-fluoro-3-(trans-3-((6-fluorobenzo[d]thiazol-2-yl)amino)cyclobutyl)-1-methyl-1H-imidazo[4,5-b]pyridin-2(3H)-one;
6-fluoro-3-(trans-3-((5-fluorobenzo[d]thiazol-2-yl)amino)cyclobutyl)-1-methyl-1H-imidazo[4,5-b]pyridin-2(3H)-one;
1-(trans-3-(benzo[d]thiazol-2-ylamino)cyclobutyl)-5-chloro-3,3-difluoro-1H-pyrrolo[2,3-b]pyridin-2(3H)-one;
1-(trans-3-(benzo[d]thiazol-2-ylamino)cyclobutyl)-3,3-difluoro-1H-pyrrolo[2,3-b]pyridin-2(3H)-one;
1-cyclopropyl-3-(trans-3((6-fluorobenzo[d]thiazol-2-yl)amino)cyclobutyl)-1H-imidazo[4,5-b]pyrazin-2(3H)-one;
1-(trans-3-(1,3-benzothiazol-2-ylamino)cyclobutyl)-3,3-difluoro-1,3-dihydro-2H-pyrrolo[2,3-b]pyridin-2-one;
5-(cis-3-(benzo[d]thiazol-2-ylamino)cyclobutyl)-7,7-dimethyl-5H-pyrrolo[2,3-b]pyrazin-6(7H)-one;
1-(cis-3-(benzo[d]thiazol-2-ylamino)cyclobutyl)-3-methyl-1H-imidazo[4,5-b]pyrazin-2(3H)-one;
n-(cis-3-(7,7-dimethyl-6-oxo-6,7-dihydro-5H-pyrrolo[2,3-b]pyrazin-5-yl)cyclobutyl)-1H-benzo[d]imidazole-2-carboxamide;
1-cyclopropyl-3-(trans-3-(quinazolin-2-ylamino)cyclobutyl)-1H-imidazo[4,5-b]pyrazin-2(3H)-one;
1-(trans-3-(benzo[d]oxazol-2-ylamino)cyclobutyl)-3-cyclopropyl-1H-imidazo[4,5-b]pyrazin-2(3H)-one;
1-cyclopropyl-3-(trans-3-((5-fluoro-1,3-benzothiazol-2-yl)amino)cyclobutyl)-1,3-dihydro-2H-imidazo[4,5-b]pyrazin-2-one;
1-cyclopropyl-3-(trans-3-(1,8-naphthyridin-2-ylamino)cyclobutyl)-1,3-dihydro-2H-imidazo[4,5-b]pyrazin-2-one;
1-cyclopropyl-3-(trans-3-((6-methoxy-1,3-benzothiazol-2-yl)amino)cyclobutyl)-1,3-dihydro-2H-imidazo[4,5-b]pyrazin-2-one;
1-cyclopropyl-3-(trans-3-(2-quinolinylamino)cyclobutyl)-1,3-dihydro-2H-imidazo[4,5-b]pyrazin-2-one;
1-cyclopropyl-3-(trans-3-((1-methyl-1H-benzimidazol-2-yl)amino)cyclobutyl)-1,3-dihydro-2H-imidazo[4,5-b]pyrazin-2-one;
1-(trans-3-((6-chlorobenzo[d]oxazol-2-yl)amino)cyclobutyl)-3-cyclopropyl-1H-imidazo[4,5-b]pyrazin-2(3H)-one;
1-(trans-3-(1,3-benzothiazol-2-ylamino)cyclobutyl)-5-bromo-3-cyclopropyl-1,3-dihydro-2H-imidazo[4,5-b]pyrazin-2-one; and
5-bromo-3-cyclopropyl-1-(trans-3-((7-fluoro-2-quinazolinyl)amino)cyclobutyl)-1,3-dihydro-2H-imidazo[4,5-b]pyrazin-2-one.

* * * * *